United States Patent
Erion et al.

(10) Patent No.: US 6,756,360 B1
(45) Date of Patent: Jun. 29, 2004

(54) COMBINATION OF FBPASE INHIBITORS AND INSULIN SENSITIZERS FOR THE TREATMENT OF DIABETES

(75) Inventors: Mark D. Erion, Del Mar, CA (US); Paul D. van Poelje, La Jolla, CA (US)

(73) Assignee: Metabasis Therapeutics, Inc., San Diego, CA (US)

(*) Notice: Subject to any disclaimer, the term of this patent is extended or adjusted under 35 U.S.C. 154(b) by 0 days.

(21) Appl. No.: 09/470,649

(22) Filed: Dec. 22, 1999

Related U.S. Application Data

(60) Provisional application No. 60/114,718, filed on Dec. 23, 1998.

(51) Int. Cl.$^7$ .......................... A01N 43/04; A61K 31/70
(52) U.S. Cl. .......................... 514/43; 514/369; 514/364; 514/376; 514/277; 514/299; 514/367; 514/370; 514/569; 514/725
(58) Field of Search .................. 514/369, 364, 514/376, 277, 299, 367, 370, 569, 725, 43

(56) References Cited

U.S. PATENT DOCUMENTS

| | | | |
|---|---|---|---|
| 4,728,739 A | 3/1988 | Kees et al. | 548/183 |
| 4,791,125 A | 12/1988 | Clark | 514/369 |
| 4,968,790 A | 11/1990 | De Vries et al. | 536/117 |
| 5,236,941 A | 8/1993 | Zask et al. | 514/369 |
| 5,457,109 A | 10/1995 | Antonucci et al. | 514/252 |
| 5,468,762 A | 11/1995 | Malamas et al. | 514/376 |
| 5,478,853 A | 12/1995 | Regnier et al. | 514/369 |
| 5,532,256 A | 7/1996 | Malamas et al. | 514/361 |
| 5,658,889 A | 8/1997 | Gruber et al. | 514/43 |
| 6,008,237 A * | 12/1999 | Sahoo et al. | |
| 6,028,052 A * | 2/2000 | Heyman et al. | |
| 6,054,587 A * | 4/2000 | Reddy et al. | |
| 6,200,998 B1 * | 3/2001 | Sahoo et al. | |
| 6,312,662 B1 * | 11/2001 | Erion et al. | |

FOREIGN PATENT DOCUMENTS

| | | |
|---|---|---|
| CA | 2 173 660 A1 | 4/1996 |
| EP | 0 129 747 A2 | 6/1984 |
| EP | 0 177 353 A2 | 10/1985 |
| EP | 0 091 761 B1 | 11/1987 |
| EP | 0 283 035 A1 | 3/1988 |
| EP | 0 427 799 B1 | 1/1990 |
| EP | 0 489 663 A1 | 12/1991 |
| EP | 0 506 273 A2 | 3/1992 |
| EP | 0 543 662 A2 | 11/1992 |
| EP | 0 559 571 A1 | 3/1993 |
| EP | 0 708 098 A1 | 10/1995 |
| EP | 0 745 600 A1 | 12/1996 |
| EP | 0 787 727 A1 | 8/1997 |
| EP | 0 861 666 A2 | 9/1998 |
| JP | 07-002852 A2 | 1/1995 |
| WO | 92/14719 A1 | 9/1992 |
| WO | 94/01433 A1 | 1/1994 |
| WO | 95/026347 A1 | 10/1995 |
| WO | 96/11196 A1 | 4/1996 |
| WO | 96/26207 A1 | 8/1996 |
| WO | 96/38427 A1 | 12/1996 |
| WO | 96/38428 A1 | 12/1996 |
| WO | 96/39401 A1 | 12/1996 |
| WO | 97/10819 | 3/1997 |
| WO | 97/37688 A2 | 10/1997 |
| WO | 97/40051 A1 | 10/1997 |
| WO | 98/39342 A1 | 9/1998 |
| WO | 98/39343 A1 | 9/1998 |
| WO | 98/39344 A1 | 9/1998 |

OTHER PUBLICATIONS

Maryanoff, et al., "Stereoselective Synthesis and Biological Activity of β– and α–D–Arabinose 1,5–Diphosphate: Analogues of a Potent Metabolic Regulator," *J. Am. Chem. Soc.*, 106:7851–7853 (1984).

Mathisen, et al., "The Effect of Pioglitazone on Glucose Control and Lipid Profile in Patients With Type 2 Diabetes," *Diabetes*, 48(Suppl.1):0441 (1998).

Patel, et al., "Rosiglitazone Monotherapy Improves Glycaemic Control in Patients with Type 2 Diabetes: A Twelve–Week, Randomized, Placebo–Controlled Study," *Diabetes, Obesity and Metabolism*, 1:165–172 (1999).

Riddle, "New Tactics for Type 2 Diabetes: Regimens Based on Intermediate–Acting Insulin Taken at Bedtime," *The Lancet*, 192–195 (1985).

Saltiel & Olefsky, "Thiazolidinediones in the Treatment of Insulin Resistance and Type II Diabetes," *Diabetes*, 45:1661–1669 (1996).

Schmitz–Peiffer, et al., "Reversal of Chronic Alterations of Skeletal Muscle Protein Kinase C From Fat–Fed Rats by BRL–49653," *Am. J. Physiol.*, 273:E915–E921 (1997).

Sreenan, et al., "Prevention of Hyperglycemia in the Zucker Diabetic Fatty Rat by Treatment with Metformin or Troglitazone," *Am. J. Physiol.*, 271:E742–747 (1996).

Torlone, et al., "Improved Insulin Action and Glycemic Control After Long–Term Angiotensin–Converting Enzyme Inhibition in Subjects with Arterial Hypertension and Type II Diabetes," *Diabetes Care*, 16(10):1347–1355 (1993).

U.K. Prospective Diabetes Study Group, "U.K. Prospective Diabetes Study 16: Overview of 6 Years' Therapy of Type II Diabetes: A Progressive Disease," *Diabetes*, 44:1249–1258 (1995).

(List continued on next page.)

*Primary Examiner*—James O. Wilson
*Assistant Examiner*—Patrick Lewis
(74) *Attorney, Agent, or Firm*—Paul Hastings Janofsky & Walker

(57) ABSTRACT

Pharmaceutical compositions containing an FBPase inhibitor and an insulin sensitizer are provided as well as methods for treating diabetes and diseases responding to increased glycemic control, an improvement in insulin sensitivity, a reduction in insulin levels, or an enhancement of insulin secretion.

74 Claims, No Drawings

OTHER PUBLICATIONS

Valiquett, et al., "Troglitazone Dose–Response Study in Patients with NIDDM," *Diabetes*, 44(Suppl.1):406 (1995).

Willson, et al., "The Structure–Activity Realtionship Between Peroxisome Proliferator–Activated Receptor γ Agonism and the Antihyperglycemic Activity of Thiazolidinediones," *J. Med. Chem.*, 39:665–668 (1996).

Brown, et al., "A Novel N–Aryl Tyrosine Activator of Peroxisome Proliferator–Activated Receptor–γ Reverses the Diabetic Phenotype of the Zucker Diabetic Fatty Rat," *Diabetes*, 48:1415–1424 (1999).

Folli, et al., "Angiotensin II Inhibits Insulin Signaling in Aortic Smooth Muscle Cells at Multiple Levels," *J. Clin. Invest.*, 100(9):2158–2169 (1997).

Fujiwara, et al., "Characterization of New Oral Antidiabetic Agent CS–045: Studies in *KK* and *ob/ob* Mice and Zucker Fatty Rats," *Diabetes*, 37:1549–1558 (1988).

Glucksmann, et al., "Novel Mutations and a Mutational Hotspot in the MODY3 Gene," *Diabetes*, 46:1081–1086 (1997).

Howard, et al., "Insulin Sensitivity and Atherosclerosis," *Circulation*, 93(10):1809–1817 (1996).

Lehmann, et al., "An Antidiabetic Thiazolidinedione Is a High Affinity Ligand for Peroxisome Proliferator–Activated Receptor γ (PPARγ)," *J. Biol. Chem.*, 270(22):12953–12956 (1995).

Amri, et al., "Regulation of adipose cell differentiation. I. Fatty acids are inducers of the aP2 gene expression," *J. Lipid Res.* 32:1449–1456 (1991).

Clark, et al., "Substituted dihydrobenzopyran and dihydrobenzofuran thiazolidine–2,4–diones as hypoglycemic agents" *J. Med. Chem.* (1991) 34:319–325.

Grimaldi, et al., "Induction of a P2 gene expression by nonmetabolized long–chain fatty acids," *Proc. Natl. Sci. USA* 89:10930–10934 (1992).

Hulin, et al., "Novel Thiazolidine–2,4–diones as Potent Euglycemic Agents," *J. Med. Chem.* 35:1853–1864 (1992).

Lehmann, et al., "An antidiabetic thiazolidinedione is a high affinity ligand for peroxisome proliferator–activated receptor gamma (PPAR gamma)." *JBC* (1995);270(22):12953–6.

Maryanoff, et al., "Stereoselective Synthesis and Biological Activity of β– and α–D–Arabinose 1,5–Diphosphate: Analogues of a Potent Metabolic Regulator," *J. Am. Chem. Soc.* 106:7851–7853 (1984).

Scheen, et al., "Oral antidiabetic agents: a guide to selection" *Drugs* (1998) 55:225–236.

Tontonoz, et al., "Stimulation of Adipogenesis in Fibroblasts by PPARγ2, a Lipid–Activated Transcription Factor," *Cell* 79:1147–1159 (1994).

Tontonoz, et al., "mPPARγ2: tissue specific regulator of an adipocyte enhancer," *Gene and Development* (1994) 8:1224–1234.

Zask, et al., "Synthesis and Antihyperglycemic Activity of Novel 5–(Naphthalenylsulfonyl)–2, 4–thiazolidinediones," J. Med. Chem.(1990) 33:1418–1423.

*Diabetologia* (1993) 36(Suppl):182A.

*Diabetes* (1993) 42(Suppl):79A.

*Diabetes* (1996) 45(Suppl 2):141A.

\* cited by examiner

COMBINATION OF FBPASE INHIBITORS AND INSULIN SENSITIZERS FOR THE TREATMENT OF DIABETES

RELATED APPLICATIONS

This application is a continuation-in-part of Provisional Application Serial No. 60/114,718, filed Dec. 23, 1998 and is hereby incorporated by reference in its entirety.

BACKGROUND OF THE INVENTION

A combination therapy of an insulin sensitizer and an FBPase inhibitor is disclosed for the treatment of diabetes, and other diseases where the control of blood glucose levels or an improvement in insulin sensitivity, reduction in insulin levels or an enhancement of insulin secretion is beneficial. Compositions used in the therapy are also disclosed.

BACKGROUND OF THE INVENTION

Diabetes mellitus (or diabetes) is one of the most prevalent diseases in the world today. Diabetes patients have been divided into two classes, namely type I or insulin-dependent diabetes mellitus and type II or non-insulin dependent diabetes mellitus (NIDDM). NIDDM accounts for approximately 90% of all diabetics and is estimated to affect 12–14 million adults in the U.S. alone (6.6% of the population). NIDDM is characterized by both fasting hyperglycemia and exaggerated postprandial increases in plasma glucose levels. NIDDM is associated with a variety of long-term complications, including microvascular diseases such as retinopathy, nephropathy and neuropathy, and macrovascular diseases such as coronary heart disease. Numerous studies in animal models demonstrate a causal relationship between long term hyperglycemia and complications. Results from the Diabetes Control and Complications Trial (DCCT) and the Stockholm Prospective Study demonstrate this relationship for the first time in man by showing that insulin-dependent diabetics with tighter glycemic control are at substantially lower risk for the development and progression of these complications. Tighter control is also expected to benefit NIDDM patients.

Current therapies used to treat NIDDM patients entail both controlling lifestyle risk factors and pharmaceutical intervention. First-line therapy for NIDDM is typically a tightly-controlled regimen of diet and exercise since an overwhelming number of NIDDM patients are overweight or obese (67%) and since weight loss can improve insulin secretion, insulin sensitivity and lead to normoglycemia. Normalization of blood glucose occurs in less than 30% of these patients due to poor compliance and poor response. Patients with hyperglycemia not controlled by diet alone are subsequently treated with oral hypoglycemics or insulin. Until recently, the sulfonylureas were the only class of oral hypoglycemic agents available for NIDDM. Treatment with sulfonylureas leads to effective blood glucose lowering in only 70% of patients and only 40% after 10 years of therapy. Patients that fail to respond to diet and sulfonylureas are subsequently treated with daily insulin injections to gain adequate glycemic control.

Although the sulfonylureas represent a major therapy for NIDDM patients, four factors limit their overall success. First, as mentioned above, a large segment of the NIDDM population do not respond adequately to sulfonylurea therapy (i.e. primary failures) or become resistant (i.e. secondary failures). This is particularly true in NIDDM patients with advanced NIDDM since these patients have severely impaired insulin secretion. Second, sulfonylurea therapy is associated with an increased risk of severe hypoglycemic episodes. Third, chronic hyperinsulinemia has been associated with increased cardiovascular disease although this relationship is considered controversial and unproven. Last, sulfonylureas are associated with weight gain, which leads to worsening of peripheral insulin sensitivity and thereby can accelerate the progression of the disease.

Results from the U.K. Diabetes Prospective Study also showed that patients undergoing maximal therapy of a sulfonylurea, metformin, or a combination of the two, were unable to maintain normal fasting glycemia over the six year period of the study.

U.K. Prospective Diabetes Study 16. *Diabetes*, 44:1249–158 (1995). These results further illustrate the great need for alternative therapies.

Another drug therapy recently developed for NIDDM patients acts on the underlying mechanisms of insulin resistance and thereby lower glucose by enhancing insulin action at both peripheral and hepatic sites. Saltiel & Olefsky *Diabetes* 45: 1661–1669 (1996). Accordingly, these agents are reported to increase insulin-dependent glucose disposal and to inhibit HGO. These agents are commonly referred to as "insulin sensitizers".

One class of insulin sensitizers are compounds containing a thiazolidinedione. These compounds are reported to enhance insulin action without directly stimulating insulin secretion. Thiazolidinediones markedly decrease glucose levels in a variety of obese, insulin-resistant diabetic animal models including the KK-mouse, ob/ob mouse, Zucker Diabetic Fatty rat and db/db mouse. Similar effects are found in non-genetic diabetic animal models, including the fructose fed rat and high fat fed rat. Animal models characterized by severe hypoinsulinemia, e.g. the STZ rat, fail to respond to these agents unless treated with insulin. Thiazolidinediones are also reported to restore the ability of insulin to suppress HGO.

Although the molecular target of insulin sensitizers and more specifically thiazolidinedione analogs is unknown, several studies suggest that peroxisome proliferator-activated receptors (PPAR γs) may be the target and therefore that ligands to these receptors will be useful antihyperglycemic agents. Lehmann et al. *J. Biol. Chem.* 270: 12953–12956 (1995). PPAR γs are members of the steroid/thyroid hormone receptor superfamily of transcription factors. At least three PPAR γs exist, namely the α, β and γ receptors and thiazolidinediones have been identified as ligands that activate the β and γ receptors. Binding occurs at a concentration achieved in vivo and some data suggests that there is a correlation between PPAR γ binding affinity and in vivo activity. Wilson et al. *J. Med. Chem.* 39: 665–668 (1996).

PPAR γs exist as a heterodimer with the retinoic acid X receptor (RXR). A co-repressor protein has been postulated to maintain the receptor in an inactive state similar to other nuclear receptors. Binding of molecules to the complex, i.e. PPAR γ ligands and/or RXR ligands may lead to dissociation of the co-repressor protein and activation of the receptor, which in turn is postulated to interact with specific DNA sequences, PPRE's, and to activate or repress gene transcription. Accordingly, RXR ligands are thought to enhance insulin sensitivity and therefore be useful as antidiabetics either alone or in combination with PPAR γ agonists such as a thiazolidinedione. Heyman et al., WO 97/10819. In db/db mice, the combination of an RXR ligand and a PPAR γ agonist reduces glucose levels more than either component alone.

Other classes of insulin sensitizers (i.e. non-thiazolidinediones) have been identified. For example, the insulin sensitizers SB 236636 and SB 219994 are 3-aryl-2-alkoxy propanoic acids. These compounds are reported to bind to human PPAR γ with high affinity. SB 236636 is equipotent with thiazolidinedione BRL 49653 in stimulation of glucose transport in differentiated 3T3-L1 adipocytes and in glucose lowering activity in ob/ob mice. Young et al. *Diabetes* (1997). Relative to other thiazolidinediones, SB 236636 was shown to bind with higher affinity to crude extracts of Sf9 cells transfected with full length hPPAR γ and rat adipocytes. This higher binding affinity correlated well with in vivo potency.

Some data suggests that chronic activation of PKC isoenzymes is involved in the generation of muscle insulin resistance and that insulin sensitizers may decrease the translocation of PKC isoenzymes from the cytosolic to particulate fractions in red skeletal muscle and therefore PKC activation. Schmitz-Peiffer et al. *Am. J. Physiol.* 273: E915–E921 (1997)

Angiotensin II antagonists and angiotensin converting enzyme inhibitors may be useful in enhancing insulin sensitivity based on potential interactions between angiotensin II and insulin signaling systems. Torlone et al. Diabetes Care 16: 1347–1355 (1993); Howard G. et al., Circulation 93: 1809–1817 (1996); Folli et al. J. Clin. Invest. 100: 2158–2169 (1997); Tamura et al., WO9737688 A2.

Thus, there are several mechanisms by which agents may act as insulin sensitizers.

Gluconeogenesis from pyruvate is a highly regulated biosynthetic pathway requiring eleven enzymes. Seven enzymes catalyze reversible reactions and are common to both gluconeogenesis and glycolysis. Four enzymes catalyze reactions unique to gluconeogenesis, namely pyruvate carboxylase, phosphoenolpyruvate carboxykinase, fructose-1,6-bisphosphatase and glucose-6-phosphatase. Overall flux through the pathway is controlled by the specific activities of these enzymes, the enzymes that catalyzed the corresponding steps in the glycolytic direction, and by substrate availability. Dietary factors (glucose, fat) and hormones (insulin, glucagon, glucocorticoids, epinephrine) coordinatively regulate enzyme activities in the gluconeogenesis and glycolysis pathways through gene expression and post-translational mechanisms.

Synthetic inhibitors of fructose-1,6-bisphosphatase (hereinafter "FBPase") have been reported. McNiel reported that fructose-2,6-bisphosphate analogs inhibit FBPase by binding to the substrate site. *J. Am. Chem. Soc.*, 106:7851–7853 (1984); U.S. Pat. No. 4,968,790 (1984). These compounds, however, were relatively weak and did not inhibit glucose production in hepatocytes presumably due to poor cell penetration.

Gruber reported that some nucleosides can lower blood glucose in the whole animal through inhibition of FBPase. These compounds exert their activity by first undergoing phosphorylation to the corresponding monophosphate. EP 0 427 799 B 1.

Gruber et al. U.S. Pat. No. 5,658,889 described the use of inhibitors of the AMP site of FBPase to treat diabetes. WO 98/39344, WO 98/39343, and WO 98/39342 describe the use of FBPase inhibitors to treat diabetes.

SUMMARY OF THE INVENTION

The instant invention is a combination therapy and a composition for the treatment for diabetes and diseases responding to improved glycemic control or to improve peripheral insulin sensitivity. The therapy requires administration of a insulin sensitizer agent, e.g. PPAR γ agonist, RXR ligand, or another agent known to enhance insulin action and an FBPase inhibitor either together or at a different time such that improved glycemic control is achieved. In another aspect of the invention, the combined therapy results in decreases in hepatic glucose output beyond that observed for glucose lowering doses of the insulin sensitizer agent. Furthermore, the combined therapy can result in improvements in insulin resistance and/or insulin secretion beyond that observed for either agent alone. Yet another aspect of the invention is that a combination therapy achieves similar benefits as observed with one or the other therapies alone but at significantly lower doses.

The present invention relates to methods and compositions for treating an animal having NIDDM or a condition associated with insulin resistance by administering to the animal a composition containing a pharmaceutically effective amount of an agent that enhances insulin sensitivity and a pharmaceutically effective amount of an FBPase inhibitor. The compositions of this invention are adapted to cure, improve or prevent one or more symptoms of NIDDM. A preferred drug combination will have high potency and low toxicity.

Another object of the invention relates to methods and compositions for treating insulin-requiring NIDDM patients. The combination therapy decreases the insulin requirement and associated safety risks.

Another object of the invention relates to methods and compositions for treating diseases or conditions characterized by insulin resistance, including obesity, hypertension, impaired glucose tolerance, and polycystic ovarian syndrome. Individuals with syndrome X, renal disease, or pancreatitis are also effectively treated with the combination therapy.

Another object of the invention is the use of insulin sensitizer to attenuate certain potentially adverse effects that could be associated with FBPase inhibitor therapy such as lactate and triglyceride elevation.

Another object of the invention is the use of FBPase inhibitors to attenuate certain potentially adverse effects that could be associated with insulin sensitizers such as weight gain.

Another aspect of the invention is to use FBPase inhibitors in combination with insulin sensitizer therapies that include administration of agents that enhance endogenous or exogenous insulin levels, such as sulfonylureas, insulin, or insulin mimetics.

Definitions

In accordance with the present invention and as used herein, the following terms are defined with the following meanings, unless explicitly stated otherwise.

X and $X^3$ group nomenclature as used herein in formulae I and X describes the group attached to the phosphonate and ends with the group attached to the heteroaromatic ring. For example, when X is alkylamino, the following structure is intended:

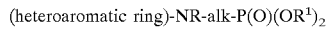

(heteroaromatic ring)-NR-alk-P(O)(OR$^1$)$_2$

Likewise, A, B, C, D, E, A", B", C"', D", E", $A^2$, $L^2$, $E^2$, and $J^2$ groups and other substituents of the heteroaromatic ring are described in such a way that the term ends with the group attached to the heteroaromatic ring. Generally, substituents are named such that the term ends with the group at the point of attachment.

The term "aryl" refers to aromatic groups which have 5–14 ring atoms and at least one ring having a conjugated pi electron system and includes carbocyclic aryl, heterocyclic aryl and biaryl groups, all of which may be optionally substituted. Suitable aryl groups include phenyl and furan-2,5-diyl.

Carbocyclic aryl groups are groups wherein the ring atoms on the aromatic ring are carbon atoms. Carbocyclic aryl groups include monocyclic carbocyclic aryl groups and polycyclic or fused compounds such as optionally substituted naphthyl groups.

Heterocyclic aryl or heteroaryl groups are groups having from 1 to 4 heteroatoms as ring atoms in the aromatic ring and the remainder of the ring atoms being carbon atoms. Suitable heteroatoms include oxygen, sulfur, nitrogen, and selendum. Suitable heteroaryl groups include furanyl, thienyl, pyridyl, pyrrolyl, N-lower alkyl pyrrolyl, pyridyl-N-oxide, pyrimidyl, pyrazinyl, imidazolyl, and the like, all optionally substituted.

The term "annulation" or "annulated" refers to the formation of an additional cyclic moiety onto an existing aryl or heteroaryl group. The newly formed ring may be carbocyclic or heterocyclic, saturated or unsaturated, and contains 2–9 new atoms of which 0–3 may be heteroatoms taken from the group of N, O, and S. The annulation may incorporate atoms from the X group as part of the newly formed ring. For example, the phrase "together $L^2$ and $E^2$ form an annulated cyclic group," includes

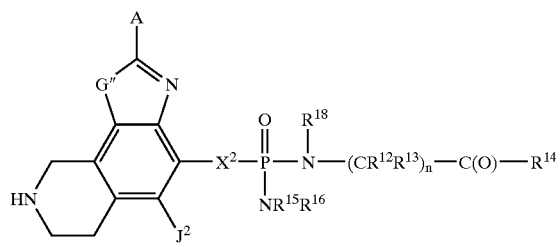

The term "biaryl" represents aryl groups containing more than one aromatic ring including both fused ring systems and aryl groups substituted with other aryl groups. Such groups may be optionally substituted. Suitable biaryl groups include naphthyl and biphenyl.

The term "alicyclic" means compounds which combine the properties of aliphatic and cyclic compounds. Such cyclic compounds include but are not limited to, aromatic, cycloalkyl and bridged cycloalkyl compounds. The cyclic compound includes heterocycles. Cyclohexenylethyl and cyclohexylethyl are suitable alicyclic groups. Such groups may be optionally substituted.

The term "optionally substituted" or "substituted" includes groups substituted by one to four substituents, independently selected from lower alkyl, lower aryl, lower aralkyl, lower alicyclic, hydroxy, lower alkoxy, lower aryloxy, perhaloalkoxy, aralkoxy, heteroaryl, heteroaryloxy, heteroarylalkyl, heteroaralkoxy, azido, amino, guanidino, amidino, halo, lower alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, aralkylamino, phosphono, sulfonyl, -carboxamidoalkylaryl, -carboxamidoaryl, hydroxyalkyl, haloalkyl, alkylarninoalkylcarboxy-, aminocarboxamidoalkyl-, cyano, lower alkoxyalkyl, lower perhaloalkyl, and arylalkyloxyalkyl. "Substituted aryl" and "substituted heteroaryl" preferably refers to aryl and heteroaryl groups substituted with 1–3 substituents. Preferably these substituents are selected from the group consisting of lower alkyl, lower alkoxy, lower perhaloalkyl, halo, hydroxy, and amino. "Substituted" when describing an $R^5$ group does not include annulation.

The term "aralkyl" refers to an alkyl group substituted with an aryl group. Suitable aralkyl groups include benzyl, picolyl, and the like, and may be optionally substituted. The term "-aralkyl-" refers to a divalent group -aryl-alkylene-. "Heteroarylalkyl" refers to an alkylene group substituted with a heteroaryl group.

The term "-alkylaryl-" refers to the group -alk-aryl- where "alk" is an alkylene group. "Lower -alkylaryl-" refers to such groups where alkylene is lower alkylene.

The term "lower" referred to herein in connection with organic radicals or compounds respectively defines such as with up to and including 10, preferably up to and including 6, and advantageously one to four carbon atoms. Such groups may be straight chain, branched, or cyclic.

The terms "arylamino" (a), and "aralkylamino" (b), respectively, refer to the group —NRR' wherein respectively, (a) R is aryl and. R' is hydrogen, alkyl, aralkyl or aryl, and (b) R is aralkyl and R' is hydrogen or aralkyl, aryl, alkyl.

The term "acyl" refers to —C(O)R where R is alkyl and aryl.

The term "carboxy esters" refers to —C(O)OR where R is alkyl, aryl, aralkyl, and alicyclic, all optionally substituted.

The term "carboxyl" refers to —C(O)OH.

The term "oxo" refers to =O in an alkyl group.

The term "amino" refers to —NRR' where R and R' are independently selected from hydrogen, alkyl, aryl, aralkyl and alicyclic, all except H are optionally substituted; and R and $R^1$ can form a cyclic ring system.

The term "carbonylamino" and "-carbonylamino-" refers to RCONR— and —CONR—, respectively, where each R is independently hydrogen or alkyl.

The term "halogen" or "halo" refers to —F, —Cl, —Br and —I.

The term "-oxyalkylamino-" refers to —O-alk-NR—, where "alk" is an alkylene group and R is H or alkyl.

The term "-alkylaminoalkylcarboxy-" refers to the group -alk-NR-alk-C(O)—O— where "alk" is an alkylene group, and R is a H or lower alkyl.

The term "-alkylaminocarbonyl-" refers to the group -alk-NR—C(O)— where "alk" is an alkylene group, and R is a H or lower alkyl.

The term "-oxyalkyl-" refers to the group —O-alk- where "alk" is an alkylene group.

The term "-alkylcarboxyalkyl-" refers to the group -alk-C(O)—O-alk- where each alk is independently an alkylene group.

The term "alkyl" refers to saturated aliphatic groups including straight-chain, branched chain and cyclic groups. Alkyl groups may be optionally substituted. Suitable alkyl groups include methyl, isopropyl, and cyclopropyl.

The term "cyclic alkyl" or "cycloalkyl" refers to alkyl groups that are cyclic. Suitable cyclic groups include norbornyl and cyclopropyl. Such groups may be substituted.

The term "heterocyclic" and "heterocyclic alkyl" refer to cyclic groups of 3 to 10 atoms, more preferably 3 to 6 atoms, containing at least one heteroatom, preferably 1 to 3 heteroatoms. Suitable heteroatoms include oxygen, sulfur, and nitrogen. Heterocyclic groups may be attached through a nitrogen or through a carbon atom in the ring. Suitable heterocyclic groups include pyrrolidinyl, morpholino, morpholinoethyl, and pyridyl.

The term "phosphono" refers to —PO₃R₂, where R is selected from the group consisting of —H, alkyl, aryl, aralkyl, and alicyclic.

The term "sulphonyl" or "sulfonyl" refers to —SO₃R, where R is H, alkyl, aryl, aralkyl, and alicyclic.

The term "alkenyl" refers to unsaturated groups which contain at least one carbon-carbon double bond and includes straight-chain, branched-chain and cyclic groups. Alkenyl groups may be optionally substituted. Suitable alkenyl groups include allyl. "1-alkenyl" refers to alkenyl groups where the double bond is between the first and second carbon atom. If the 1-alkenyl group is attached to another group, e.g. it is a W substituent attached to the cyclic phosph(oramid)ate, it is attached at the first carbon.

The term "alkynyl" refers to unsaturated groups which contain at least one carbon-carbon triple bond and includes straight-chain, branched-chain and cyclic groups. Alkynyl groups may be optionally substituted. Suitable alkynyl groups include ethynyl. "1-alkynyl" refers to alkynyl groups where the triple bond is between the first and second carbon atom. If the 1-alkynyl group is attached to another group, e.g. it is a W substituent attached to the cyclic phosph (oramid)ate, it is attached at the first carbon.

The term "alkylene" refers to a divalent straight chain, branched chain or cyclic saturated aliphatic group.

The term "-cycloalkylene-COOR³" refers to a divalent cyclic alkyl group or heterocyclic group containing 4 to 6 atoms in the ring, with 0–1 heteroatoms selected from O, N, and S. The cyclic alkyl or heterocyclic group is substituted with —COOR³.

The term "acyloxy" refers to the ester group —O—C(O)R, where R is H, alkyl, alkenyl, alkynyl, aryl, aralkyl, or alicyclic.

The term "aminoalkyl-" refers to the group NR₂-alk- wherein "alk" is an alkylene group and R is selected from H, alkyl, aryl, aralkyl, and alicyclic.

The term "-alkyl(hydroxy)-" refers to an —OH off the alkyl chain. When this term is an X group, the —OH is at the position a to the phosphorus atom.

The term "alkylaminoalkyl-" refers to the group alkyl-NR-alk- wherein each "alk" is an independently selected alkylene, and R is H or lower alkyl. "Lower alkylaminoalkyl-" refers to groups where each alkylene group is lower alkylene.

The term "arylaminoalkyl-" refers to the group aryl-NR-alk- wherein "alk" is an alkylene group and R is H, alkyl, aryl, aralkyl, and alicyclic. In "lower arylaminoalkyl-", the alkylene group is lower alkylene.

The term "alkylaminoaryl-" refers to the group alkyl-NR-aryl- wherein "aryl" is a divalent group and R is H, alkyl, aralkyl, and alicyclic. In "lower alkylaminoaryl-", the alkylene group is lower alkyl.

The term "alkyloxyaryl-" refers to an aryl group substituted with an alkyloxy group. In "lower alkyloxyaryl-", the alkyl group is lower alkyl.

The term "aryloxyalkyl-" refers to an alkyl group substituted with an aryloxy group.

The term "aralkyloxyalkyl-" refers to the group aryl-alk-O-alk- wherein "alk" is an alkylene group. "Lower aralkyloxyalkyl-" refers to such groups where the alkylene groups are lower alkylene.

The term "-alkoxy-" or "-alkyloxy-" refers to the group -alk-O— wherein "alk" is an alkylene group. The term "alkoxy-" refers to the group alkyl-O—.

The term "-alkoxyalkyl-" or "-alkyloxyalkyl-" refer to the group -alk-O-alk- wherein each "alk" is an independently selected alkylene group. In "lower -alkoxyalkyl-", each alkylene is lower alkylene.

The terms "alkylthio-" and "-alkylthio-" refer to the groups alkyl-S—, and -alk-S—, respectively, wherein "alk" is alkylene group.

The term "-alkylthioalkyl-" refers to the group -alk-S-alk- wherein each "alk" is an independently selected alkylene group. In "lower -alkylthioalkyl-" each alkylene is lower alkylene.

The term "alkoxycarbonyloxy-" refers to alkyl-O—C(O)—O—.

The term "aryloxycarbonyloxy-" refers to aryl-O—C(O)—O—.

The term "alkylthiocarbonyloxy-" refers to alkyl-S—C(O)—O—.

The term "-alkoxycarbonylamino-" refers to -alk-O—C(O)—NR¹—, where "alk" is alkylene and R¹ includes —H, alkyl, aryl, alicyclic, and aralkyl.

The term "-alkylaminocarbonylamino-" refers to -alk-NR¹—C(O)—NR¹—, where "alk" is alkylene and R¹ is independently selected from H, alkyl, aryl, aralkyl, and alicyclic.

The terms "amido" or "carboxamido" refer to NR₂—C(O)— and RC(O)—NR¹—, where R and R¹ include H, alkyl, aryl, aralkyl, and alicyclic. The term does not include urea, —NR—C(O)—NR—.

The terms "carboxamidoalkylaryl" and "carboxamidoaryl" refers to an aryl-alk-NR¹—C(O)—, and an —NR¹—C(O)-alk-, respectively, where "ar" is aryl, and "alk" is alkylene, R¹ and R include H, alkyl, aryl, aralkyl, and aliyclic.

The term "-alkylcarboxamido-" or "-alkylcarbonylamino-" refers to the group -alk-C(O)N(R)— wherein "alk" is an alkylene group and R is H or lower alkyl.

The term "-alkylaminocarbonyl-" refers to the group -alk-NR—C(O)— wherein "alk" is an alkylene group and R is H or lower alkyl.

The term "aminocarboxamidoalkyl-" refers to the group NR₂—C(O)—N(R)-alk- wherein R is an alkyl group or H and "alk" is an alkylene group. "Lower aminocarboxamidoalkyl-" refers to such groups wherein "alk" is lower alkylene.

The term "thiocarbonate" refers to —O—C(S)—O— either in a chain or in a cyclic group.

The term "hydroxyalkyl" refers to an alkyl group substituted with one —OH.

The term "haloalkyl" refers to an alkyl group substituted with one halo, selected from the group I, Cl, Br, F.

The term "cyano" refers to —C≡N.

The term "nitro" refers to —NO₂.

The term "acylalkyl" refers to an alkyl-C(O)-alk-, where "alk" is alkylene.

The term "heteroarylalkyl" refers to an alkyl group substituted with a heteroaryl group.

The term "-1,1-dihaloalkyl-" refers to an X group where the 1 position and therefore halogens are α to the phosphorus atom.

The term "perhalo" refers to groups wherein every C—H bond has been replaced with a C-halo bond on an aliphatic or aryl group. Suitable perhaloalkyl groups include —CF₃ and —CFCl₂.

The term "guanidino" refers to both —NR—C(NR)—NR₂ as well as —N=C(NR₂)₂ where each R group is independently selected from the group of —H, alkyl, alkenyl, alkynyl, aryl, and alicyclic, all except —H are optionally substituted.

The term "amidino" refers to —C(NR)—NR₂ where each R group is independently selected from the group of —H, alkyl, alkenyl, alkynyl, aryl, and alicyclic, all except —H are optionally substituted.

The term "2-thiazolyl-" or "2-oxazolyl-" or "2-selenozoly" refers to the corresponding base and its attachment of the X group at the 2-position of the heterocycle.

The term "pharmaceutically acceptable salt" includes salts of compounds of formula I and its prodrugs derived from the combination of a compound of this invention and an organic or inorganic acid or base. Suitable acids include HCl.

The term "prodrug" as used herein refers to any compound that when administered to a biological system generates the "drug" substance (a biologically active compound) as a result of spontaneous chemical reaction(s), enzyme catalyzed chemical reaction(s), and/or metabolic chemical reaction(s). Standard prodrugs are formed using groups attached to functionality, e.g. HO—, HS—, HOOC—, $R_2N$—, associated with the FBPase inhibitor, that cleave in vivo. Standard prodrugs include but are not limited to carboxylate esters where the group is alkyl, aryl, aralkyl, acyloxyalkyl, alkoxycarbonyloxyalkyl as well as esters of hydroxyl, thiol and amines where the group attached is Ian acyl group, an alkoxycarbonyl, aminocarbonyl, phosphate or sulfate. The groups illustrated are exemplary, not exhaustive, and one skilled in the art could prepare other known varieties of prodrugs. Such prodrugs of the compounds of formulae I and X, fall within the scope of the present invention. Prodrugs must undergo some form of a chemical transformation to produce the compound that is biologically active or is a precursor of the biologically active compound. In some cases, the prodrug is biologically active usually less than the drug itself, and serves to improve efficacy or safety through improved oral bioavailability, pharmacodynamic half-life, etc.

The term "prodrug ester" as employed herein includes, but is not limited to, the following groups and combinations of these groups:

[1] Acyloxyalkyl esters which are well described in the literature (Farquhar et al., *J. Pharm. Sci.* 72, 324–325 (1983)) and are represented by formula A

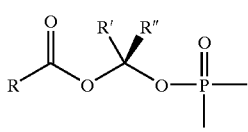

Formula A wherein R, R', and R" are independently H, alkyl, aryl, alkylaryl, and alicyclic; (see WO 90/08155; WO 90/10636).

[2] Other acyloxyalkyl esters are possible in which an alicyclic ring is formed such as shown in formula B. These esters have been shown to generate phosphorus-containing nucleotides inside cells through a postulated sequence of reactions beginning with deesterification and followed by a series of elimination reactions (e.g. Freed et al., *Biochem. Pharm.* 38: 3193–3198 (1989)).

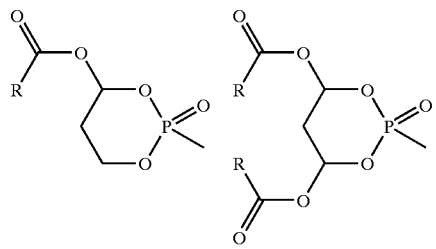

Formula B wherein R is —H, alkyl, aryl, alkylaryl, alkoxy, aryloxy, alkylthio, arylthio, alkylamino, arylamino, cycloalkyl, or alicyclic.

[3] Another class of these double esters known as alkyloxycarbonyloxymethyl esters, as shown in formula A, where R is alkoxy, aryloxy, alkylthio, arylthio, alkylamino, and arylamino; R', and R" are independently H, alkyl, aryl, alkylaryl, and alicyclic, have been studied in the area of β-lactam antibiotics (Tatsuo Nishimura et al. *J. Antibiotics*, 1987, 40(1), 81–90; for a review see Ferres, H., *Drugs of Today*, 1983,19, 499.). More recently Cathy, M. S., et al. (Abstract from AAPS Western Regional Meeting, April, 1997) showed that these alkyloxycarbonyloxymethyl ester prodrugs on (9-[(R)-2-phosphonomethoxy)propyl]adenine (PMPA) are bioavailable up to 30% in dogs.

[4] Aryl esters have also been used as phosphonate prodrugs (e.g. Erion, DeLambert et al., *J. Med. Chem.* 37: 498, 1994; Serafinowska et al., *J. Med. Chem.* 38: 1372, 1995). Phenyl as well as mono and poly-substituted phenyl proesters have generated the parent phosphonic acid in studies conducted in animals and in man (Formula C). Another approach has been described where Y is a carboxylic ester ortho to the phosphate. Khamnei and Torrence, *J. Med. Chem.*; 39:4109–4115 (1996).

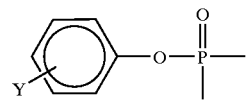

Formula C wherein Y is H, alkyl, aryl, alkylaryl, alkoxy, acyloxy, halogen, amino, alkoxycarbonyl, hydroxy, cyano, and alicyclic.

[5] Benzyl esters have also been reported to generate the parent phosphonic acid. In some cases, using substituents at the para-position can accelerate the hydrolysis. Benzyl analogs with 4-acyloxy or 4-alkyloxy group [Formula D, X=H, OR or O(CO)R or O(CO)OR] can generate the 4-hydroxy compound more readily through the action of enzymes, e.g. oxidases, esterases, etc. Examples of this class of prodrugs are described in Mitchell et al., *J. Chem. Soc. Perkin Trans.* I 2345 (1992); Brook, et al. WO 91/19721.

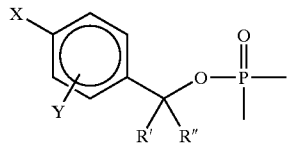

Formula D wherein X and Y are independently H, alkyl, aryl, alkylaryl, alkoxy, acyloxy, hydroxy, cyano, nitro, perhaloalkyl, halo, or alkyloxycarbonyl; and R' and R" are independently H, alkyl, aryl, alkylaryl, halogen, and alicyclic.

[6] Thio-containing phosphonate proesters have been described that are useful in the delivery of FBPase inhibitors to hepatocytes. These proesters contain a protected thioethyl moiety as shown in formula E. One or more of the oxygens of the phosphonate can be esterified. Since the mechanism that results in de-esterification requires the generation of a free thiolate, a variety of thiol protecting groups are possible. For example, the disulfide is reduced by a reductase-mediated process (Puech et al., *Antiviral Res.*, 22: 155–174 (1993)). Thioesters will also generate free thiolates after esterase-mediated hydrolysis. Benzaria, et al., *J. Med. Chem.*, 39:4958 (1996). Cyclic analogs are also possible and were shown to liberate phosphonate in isolated rat hepatocytes. The cyclic disulfide shown below has not been previously described and is novel.

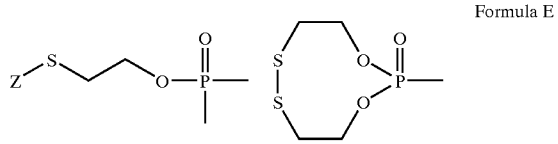

Formula E wherein Z is alkylcarbonyl, alkoxycarbonyl, arylcarbonyl, aryloxycarbonyl, or alkylthio.

Other examples of suitable prodrugs include proester classes exemplified by Biller and Magnin (U.S. Pat. No. 5,157,027); Serafinowska et al. (*J. Med. Chem.* 38, 1372 (1995)); Starrett et al. (*J. Med. Chem.* 37, 1857 (1994)); Martin et al. *J. Pharm. Sci.* 76, 180 (1987); Alexander et al., *Collect. Czech. Chem. Commun*, 59, 1853 (1994)); and EPO patent application 0 632 048 A1. Some of the structural classes described are optionally substituted, including fused lactones attached at the omega position (formulae E-1 and E-2) and optionally substituted 2-oxo-1,3-dioxolenes attached through a methylene to the phosphorus oxygen (formula E-3) such as:

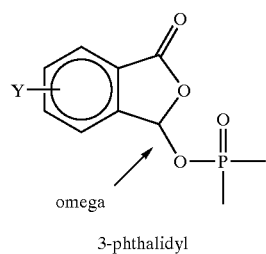

E-1

3-phthalidyl

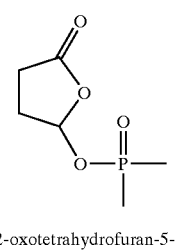

E-2

2-oxotetrahydrofuran-5-yl

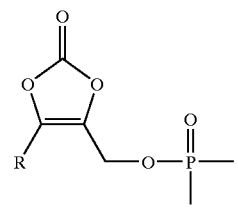

E-3

2-oxo-4,5-didehydro-1,3-dioxolanemethyl wherein R is —H, alkyl, cycloalkyl, or alicyclic; and wherein Y is —H, alkyl, aryl, atkylaryl, cyano, alkoxy, acyloxy, halogen, amino, alicyclic, and alkoxycarbonyl.

The prodrugs of Formula E-3 are an example of "optionally substituted alicyclic where the cyclic moiety contains a carbonate or thiocarbonate."

[7] Propyl phosphonate proesters can also be used to deliver FBPase inhibitors into hepatocytes. These proesters may contain a hydroxyl and hydroxyl group derivatives at the 3-position of the propyl group as shown in formula F. The R and X groups can form a cyclic ring system as shown in formula F. One or more of the oxygens of the phosphonate can be esterified.

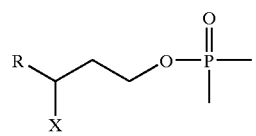

Formula F

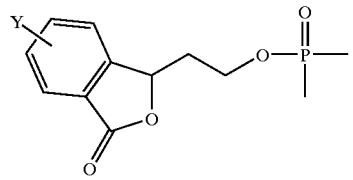

wherein R is alkyl, aryl, heteroaryl;

X is hydrogen, alkylcarbonyloxy, alkyloxycarbonyloxy; and

Y is alkyl, aryl, heteroaryl, alkoxy, alkylamino, alkylthio, halogen, hydrogen, hydroxy, acyloxy, amino.

[8] Phosphoramidate derivatives have been explored as phosphate prodrugs (e.g. McGuigan et al., *J. Med. Chem.*, 1999, 42: 393 and references cited therein) and phosphonate prodrugs (Bischofberger, et al., U.S. Pat. No. 5,798,340 and references cited therein) .as shown in Formulae G and H.

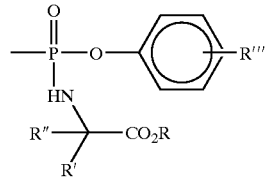

Formula G

Formula H

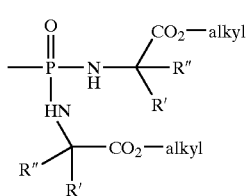

Cyclic phosphoramidates have also been studied as phosphonate prodrugs because of their speculated higher stability compared to non-cyclic phosphoramidates (e.g. Starrett et al., *J. Med. Chem.*, 1994, 37: 1857).

Another type of nucleotide prodrug was reported as the combination of S-acyl-2-thioethyl ester and phosphoramidate (Egron et al., *Nucleosides & Nucleotides*, 1999, 18, 981) as shown in Formula J.

Formula J

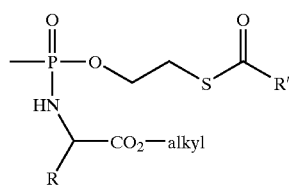

Other prodrugs are possible based on literature reports such as substituted ethyls for example, bis(trichloroethyl) esters as disclosed by McGuigan, et al. *Bioorg Med. Chem. Lett.*, 3:1207–1210 (1993), and the phenyl and benzyl combined nucleotide esters reported by Meier, C. et al. *Bioorg. Med. Chem. Lett.*, 7:99–104 (1997).

The structure

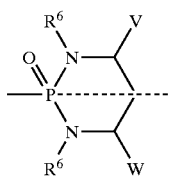

has a plane of symmetry running through the phosphorus-oxygen double bond when $R^6=R^6$, V=W, W'=H, and V and W are either both pointing up or both pointing down. The same is true of structures where each —$NR^6$ is replaced with —O—.

The term "cyclic 1',3'-propane ester", "cyclic 1,3-propane ester", "cyclic 1',3'-propanyl ester", and "cyclic 1,3-propanyl ester" refers to the following:

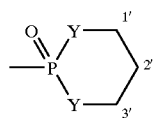

The phrase "together V and Z are connected via an additional 3–5 atoms to form a cyclic group containing 5–7 atoms, optionally containing 1 heteroatom, substituted with hydroxy, acyloxy, alkoxycarbonyloxy, or aryloxycarbonyloxy attached to a carbon atom that is three atoms from both Y groups attached to the phosphorus" includes the following:

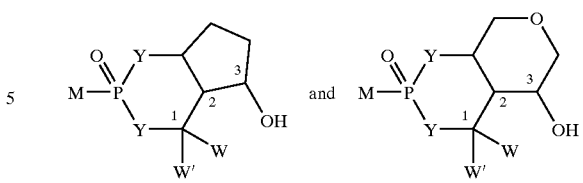

The structure shown above (left) has an additional 3 carbon atoms that forms a five member cyclic group. Such cyclic groups must possess the listed substitution to be oxidized.

The phrase "together V and Z are connected via an additional 3–5 atoms to form a cyclic group, optionally containing one heteroatom, that is fused to an aryl group attached at the beta and gamma position to the Y attached to the phosphorus" includes the following:

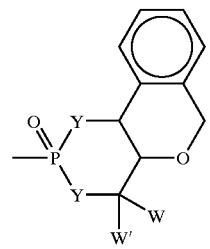

The phrase "together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said additional carbon atoms that is three atoms from a Y attached to the phosphorus" includes the following:

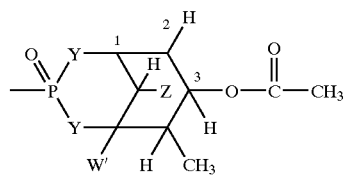

The structure above has an acyloxy substituent that is three carbon atoms from a Y, and an optional substituent, —$CH_3$, on the new 6-membered ring. There has to be at least one hydrogen at each of the following positions: the carbon attached to Z; both carbons alpha to the carbon labelled "3"; and the carbon attached to "$OC(O)CH_3$" above.

The phrase "together W and W' are connected via an additional 2–5 atoms to form a cyclic group, optionally containing 0–2 heteroatoms, and V must be aryl, substituted aryl, heteroaryl, or substituted heteroaryl" includes the following:

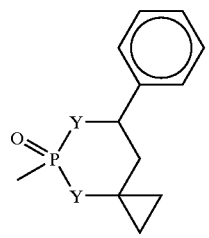

The structure above has V=aryl, and a spiro-fused cyclopropyl group for W and W'.

The term "cyclic phosph(oramid)ate" refers to

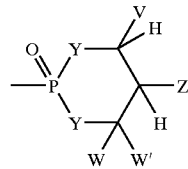

where Y is independently —O— or —NR⁶—. The carbon attached to V must have a C—H bond. The carbon attached to Z must also have a C—H bond.

The term "enhancing" refers to increasing or improving a specific property.

The term "enhanced oral bioavailability" refers to an increase of at least 50% of the absorption of the dose of the parent drug or prodrug(not of this invention) from the gastrointestinal tract. More preferably it is at least 100%. Measurement of oral bioavailability usually refers to measurements of the prodrug, drug, or drug metabolite in blood, tissues, or urine following oral administration compared to measurements following systemic administration.

The term "parent drug" refers to any compound which delivers the same biologically active compound. The parent drug form is M—X—P(O)(OH)$_2$ and standard prodrugs, such as esters.

The term "drug metabolite" refers to any compound produced in vivo or in vitro from the parent drug, which can include the biologically active drug.

The term "pharmacodynamic half-life" refers to the time after administration of the drug or prodrug to observe a diminution of one half of the measured pharmacological response. Pharmacodynamic half-life is enhanced when the half-life is increased by preferably at least 50%.

The term "pharmacokinetic half-life" refers to the time after administration of the drug or prodrug to observe a diminution of one half of the drug concentration in plasma or tissues.

The term "therapeutic index" refers to the ratio of the dose of a drug or prodrug that produces a therapeutically beneficial response relative to the dose that produces an undesired response such as death, an elevation of markers that are indicative of toxicity, and/or pharmacological side effects.

The term "biologically active drug or agent" refers to the chemical entity that produces a biological effect. Thus, active drugs or agents include compounds which as M—X—P(O)(OH)$_2$ are biologically active.

The term "therapeutically effective amount" refers to an amount that has any beneficial effect in treating a disease or condition.

FBPase inhibitors used in the invention are compounds that inhibit human FBPase activity (Example A), inhibit glucose production from hepatocytes (Examples C and D), lower glucose levels in fasted animals (Examples E–F), and decrease blood glucose levels in diabetic animal models (Examples N–T).

Insulin sensitizers used in this invention are compounds that alter the body's response to endogenous or exogeneous insulin or insulin-like molecules. This reponse can include an improvement in whole-body glucose disposal, a reduction in hepatic glucose output, an increase in insulin-mediated glycogenesis, and other manifestations of improved peripheral insulin resistance. In some instances, the insulin sensitizers used in this invention may also lower circulating triglycerides and/or free fatty acids, may increase HDL cholesterol levels, may reduce hyperinsulinemia, or may improve the pancreatic insulin secretory response. Examples of insulin sensitizers include compounds that activate or are agonists of the PPARγ receptor, are ligands of RXR that activate transcriptional activity of the RXR:PPAR γ heterodimer, or are compounds that achieve enhanced insulin sensitivity through modulation of enzyme activities in cell signalling pathways associated with insulin receptor activation. Enzymes in the latter pathways include protein kinase C, tyrosine phosphatase, PI-3-kinase, MAP kinase, and others. The insulin sensitizers used in this invention have affinity for PPARγ1, PPARγ2, and/or other isoforms of the PPARγ family, and contain either a thiazolidinedione ring structure, a modified thiazolidinedione ring structure, or have a structure that is unrelated to the thiazolidinediones (eg. the 3-aryl-2-alkoxy propanoic acids). The insulin sensitizers also include compounds with affinity for RXRα, RXRβ, RXRγ and/or other RXR receptor isoforms, and are either retinoids such as 9-cis-retinoic acid and its analogs, rexinoids such as (tetramethyltetrahydronaphthyl) carbonylbenzoic acid analogs, or are of other structural classes. Insulin sensitizers used in this invention typically exhibit activity in assays known to be useful for characterizing compounds that act as insulin sensitizers. The assays include but are not limited to: (a) PPARγ binding assays; (b) RXR or RXR-PPARγ activation assays (eg. co-transfection or cis-trans assays); (c) insulin signaling assays such as those measuring receptor or signaling protein phosphorylation/expression (d) adipocyte binding assays; (e) glucose uptake assays in adipocytes or L6 myocytes; (f) adipocyte differentiation assays using triglyceride accumulation, glucose oxidation, or fat/carbohydrate metabolism gene expression as indeces; (g) insulin secretion assays in beta cell islets or the perfused pancreas; (h) pancreatic islet histology assays; (i) in vivo glucose disposal assays; (j) whole body insulin sensitivity assays using the in vivo hyperinsulinemic-glucose clamp technique; (k) hepatic glucose output assays utilizing labeling or NMR techniques; and (l) antihyperglycemic and/or triglyceride/free fatty acid lowering activity in animal models of diabetes such as the KK, ob/ob, or db/db mouse or the ZDF rat.

DETAILED DESCRIPTION OF THE INVENTION

The instant invention is a combination therapy and a composition for the treatment for diabetes and diseases responding to increased glycemic control or to decreased insulin levels. The combination therapy consists of administering one or more FBPase inhibitors and one or more agents known to enhance insulin action, i.e. an insulin sensitizer agent. Known insulin sensitizers include thiazolidinediones, PPAR γ agonists, RXR ligands and inhibitors of the RAX system or angiotensin II action. The therapy is useful for treating diseases characterized by hyperglycemia, impaired glucose tolerance or insulin resistance. Such diseases include diabetes, obesity, hypertension, impaired glucose tolerance and polycystic ovarian syndrome, pancreatitis and renal disease.

In some cases, the combined therapy provides a method for improved glycemic control. The combined therapy will provide improved therapy for one or more of these conditions relative to either agent alone. The combined therapy provides a method for improved glycemic control in NIDDM subjects beyond that achievable by either agent alone. The combined therapy can result in decreases in hepatic glucose output beyond that observed for glucose-lowering doses of the insulin sensitizer agent. Furthermore, the combined therapy can result in improvements in insulin resistance and/or insulin secretion beyond that observed for FBPase inhibitors. In other cases, combining an insulin sensitizer with an FBPase inhibitor or visa versa has an insignificant effect on glycemia but instead results in an improved therapy by minimizing potential adverse pharmacologies sometimes associated with FBPase and insulin sensitizer therapies. For example, FBPase therapy may be associated with elevations of lactate, tryglicerides, free fatty acids or potential side-effects resulting from the renal clearance of the inhibitor. Insulin sensitizer therapy is known to be associated with weight gain, elevation of liver enzymes, and reductions in heamatocrit. In still another aspect of the invention is that the combination therapy achieves similar benefits as observed with one or the other therapies alone but at significantly lower doses. The lower doses improve or eliminate side effects and/or toxicologies associated with the individual drug treatment. The combined therapy entails administration to the host the agents either separately or simultaneously.

Most preferred would be the administration of both agents simultaneously in either the same capsule or as separate pills. Another preferred embodiment is the administration of both agents during meal time (just prior to feeding or just after feeding). Another preferred embodiment is the administration of the insulin sensitizer during meal time and the FBPase inhibitor during times of fasting such as at bed time.

The compounds of the invention may be administered for therapy by any suitable route including, oral, rectal, nasal, topical, vaginal, parenteral (including subcutaneous, intramuscular, intravenous and intradermal) and transdermal. The preferred route is oral.

The present invention relates to methods and compositions for treating a host having NIDDM or a condition associated with insulin resistance by administering to the host a composition containing a pharmaceutically effective amount of an agent that enhances insulin sensitivity and a pharmaceutically effective amount of an FBPase inhibitor. The compositions of this invention are adapted to cure, improve or prevent one or more symptoms of NIDDM. A preferred drug combination will have high potency and low toxicity as can be determined by standard pharmaceutical procedures in cell cultures or experimental animal models, e.g. by determining the LD50 and the ED50.

Preferred FBPase inhibitors encompassed by the instant invention are compounds that inhibit enzyme activity as determined by conducting in vitro inhibition studies (Examples A–D). In some cases, in vivo metabolic activation of a compound may be required to generate the FBPase inhibitor. This class of compounds may be inactive in the enzyme inhibition screen (Example A), may or may not be active in hepatocytes (Examples C and D), but is active in vivo as evidenced by glucose lowering in the normal, fasted rat (Examples E and F) and/or in animal models of diabetes (Examples N–T).

Although the present invention is not limited to the following structures, the FBPase inhibitors generally are of the following formulae:

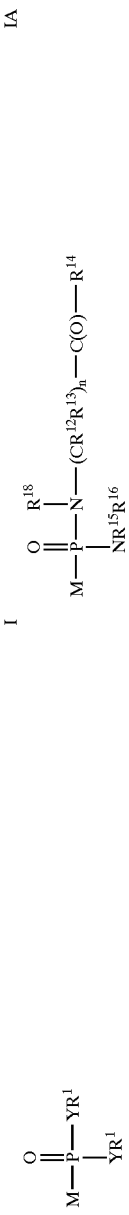
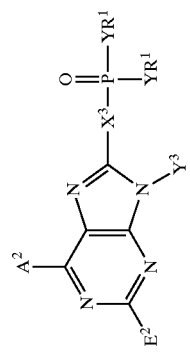
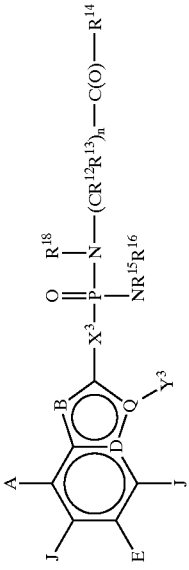
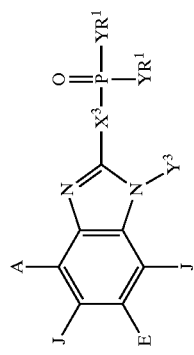
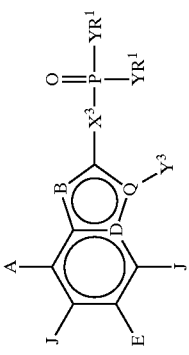

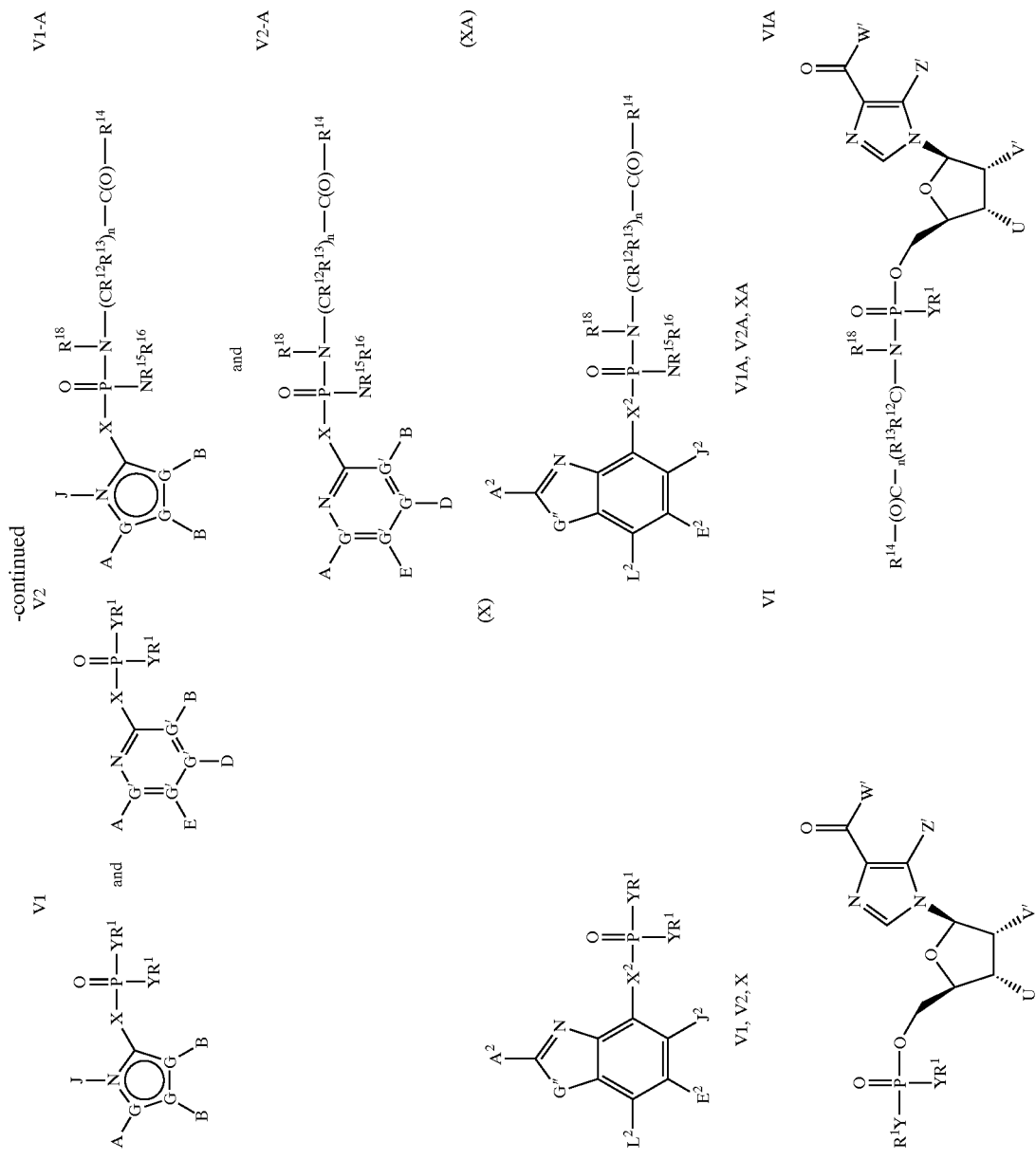

Preferred Compounds

Suitable alkyl groups include groups having from 1 to about 20 carbon atoms. Suitable aryl groups include groups having from 1 to about 20 carbon atoms. Suitable aralkyl groups include groups having from 2 to about 21 carbon atoms. Suitable acyloxy groups include groups having from 1 to about 20 carbon atoms. Suitable alkylene groups include groups having from 1 to about 20 carbon atoms. Suitable alicyclic groups include groups having from 3 to about 20 carbon atoms. Suitable heteroaryl groups include groups having from 1 to about 20 carbon atoms and from 1 to 4 heteroatoms, preferably independently selected from nitrogen, oxygen, phosphorous, and sulfur. Suitable heteroalicyclic groups include groups having from 2 to about twenty carbon atoms and from 1 to 5 heteroatoms, preferably independently selected from nitrogen, oxygen, phosphorous, and sulfur.

Preferred are the following compounds of formula IA

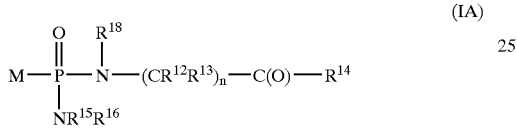

(IA)

wherein in vivo or in vitro compounds of formula IA are converted to M—PO$_3^{2-}$ which is an inhibitor of fructose-1,6-bisphosphatase and n is an integer from 1 to 3;

R$^{18}$ is independently selected from the group consisting of H, lower alkyl, aryl, aralkyl, or together with R$^{12}$ is connected via 1–4 carbon atoms to form a cyclic group;

each R$^{12}$ and R$^{13}$ is independently selected from the group consisting of H, lower alkyl, lower aryl, lower aralkyl, all optionally substituted, or R$^{12}$ and R$^{13}$ together are connected via 2–6 carbon atoms to form a cyclic group;

each R$^{14}$ is independently selected from the group consisting of —OR$^{17}$, —N(R$^{17}$)$_2$, —NHR$^{17}$, and —SR$^{17}$;

R$^{15}$ is selected from the group consisting of —H, lower alkyl, lower aryl, lower arakyl, or together with R$^{16}$ is connected via 2–6 atoms, optionally including 1 heteroatom selected from the group consisting of O, N, and S;

R$^{16}$ R is selected from the group consisting of —(CR$^{12}$R$^{13}$)$_n$, —C(O)—R$^{14}$, lower alkyl, lower aryl, lower aralkyl, or together with R$^{15}$ is connected via 2–6 atoms, optionally including 1 heteroatom selected from the group consisting of O, N, and S;

each R$^{17}$ is independently selected from the group consisting of lower alkyl, lower aryl, and lower aralkyl, or together R$^{17}$ and R$^{17}$ on N is connected via 2–6 atoms, optionally including 1 heteroatom selected from the group consisting of O, N, and S;

and pharmaceutically acceptable salts thereof.

More preferred are FBPase inhibitors where M—PO$_3^{2-}$ has an IC$_{50}$ on isolated human FBPase enzyme of less than or equal to 5 μM. Especially preferred are such compounds that bind to the AMP site of FBPase.

In one aspect, preferred are compounds of formula IA or formula I wherein M is R$^5$—X—
wherein
R$^5$ is selected from the group consisting of:

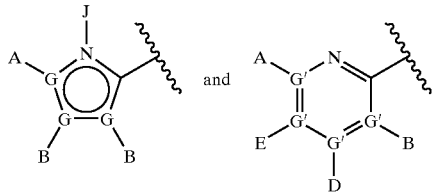

wherein:
each G is independently selected from the group consisting of C, N, O, S, and Se, and wherein only one G may be O, S, or Se, and at most one G is N;

each G' is independently selected from the group consisting of C and N and wherein no more than two G' groups are N;

A is selected from the group consisting of —H, —NR$^4_2$, —CONR$^4_2$, —CO$_2$R$^3$, halo, —S(O)R$^3$, —SO$_2$R$^3$, alkyl, alkenyl, alkynyl, perhaloalkyl, haloalkyl, aryl, —CH$_2$OH, —CH$_2$NR$^4_2$, —CH$_2$CN, —CN, —C(S)NH$_2$, —OR$^3$, —SR$^3$, —N$_3$, —NHC(S)NR$^4_2$, —NHAc, and null;

each B and D are independently selected from the group consisting of —H, alkyl, alkenyl, alkynyl, aryl, alicyclic, aralkyl, alkoxyalkyl, —C(O)R$^{11}$, —C(O)SR$^3$, —SO$_2$R$^{11}$, —S(O)R$^3$, —CN, —NR$^9_2$, —OR$^3$, —SR$^3$, perhaloalkyl, halo, —NO$_2$, and null, all except —H, —CN, perhaloalkyl, —NO$_2$, and halo are optionally substituted;

E is selected from the group consisting of —H, alkyl, alkenyl, alkynyl, aryl, alicyclic, alkoxyalkyl, —C(O)OR$^3$, —CONR$^4_2$, —CN, —NR$^9_2$, —NO$_2$, —OR$^3$, —SR$^3$, perhaloalkyl halo, and null, all except —H, —CN, perhaloalkyl, and halo are optionally substituted;

J is selected from the group consisting of —H and null;

X is an optionally substituted linking group that links R$^5$ to the phosphorus atom via 2–4 atoms, including 0–1 heteroatoms selected from N, O, and S, except that if X is urea or carbamate there is 2 heteroatoms, measured by the shortest path between R$^5$ and the phosphorus atom, and wherein the atom attached to the phosphorus is a carbon atom, and wherein X is selected from the group consisting of -alkyl(hydroxy)-, -alkynyl-, -heteroaryl-, -carbonylalkyl-, -1,1-dihaloalkyl-, -alkoxyalkyl-, -alkyloxy-, -alkylthioalkyl-, -alkylthio-, -alkylaminocarbonyl-, -alkylcarbonylamino-, -alkoxycarbonyl-, -carbonyloxyalkyl-, -alkoxycarbonylamino-, and -alkylaminocarbonylamino-, all optionally substituted; with the proviso that X is not substituted with —COOR$^2$, —SO$_3$H, or —PO$_3$R$^2_2$;

R$^2$ is selected from the group consisting of R$^3$ and —H;

R$^3$ is selected from the group consisting of alkyl, aryl, alicyclic, and aralkyl;

each R$^4$ is independently selected from the group consisting of —H, and alkyl, or together R$^4$ and R$^4$ form a cyclic alkyl group;

each R$^9$ is independently selected from the group consisting of —H, alkyl, aralkyl, and alicyclic, or together R$^9$ and R$^9$ form a cyclic alkyl group;

$R^{11}$ is selected from the group consisting of alkyl, aryl, —$NR^2_2$, and —$OR^2$; and with the proviso that:
1) when G' is N, then the respective A, B, D, or E is null;
2) at least one of A and B, or A, B, D, and E is not selected from the group consisting of —H or null;
3) when $R^5$ is a six-membered ring, then X is not any 2 atom linker, an optionally substituted -alkyloxy-, or an optionally substituted -alkylthio-;
4) when G is N, then the respective A or B is not halogen or a group directly bonded to G via a heteroatom;
5) when X is not a -heteroaryl- group, then $R^5$ is not substituted with two or more aryl groups;

and pharmaceutically acceptable prodrugs and salts thereof.

More preferred are such compounds wherein when $R^5$ is 2-thiazolyl, 2-oxazolyl, or 2-selenazolyl, and X is -alkoxyalkyl-, -alkylthioalkyl-, -alkyloxy-, or -alkylthio-, then A is not —$CONH_2$ and B is not —H. Also more preferred are such compounds wherein when $R^5$ is 2-thiazolyl, 2-oxazolyl, or 2-selenazolyl, then X is not -alkyloxyalkyl-, -alkylthioalkyl-, -alkyloxy-, or -alkylthio-.

Preferably, compounds of formula IA have an $IC_{50}$ of $\leq 50$ $\mu$M on glucose production in isolated rat hepatocytes.

More preferred $R^5$ groups include pyrrolyl, imidazolyl, oxazolyl, thiazolyl, isothiazolyl, 1,2,4-thiadiazolyl, pyrazolyl, isoxazolyl, 1,2,3-oxadiazolyl, 1,2,4-oxadiazolyl, 1,2,5-oxadiazolyl, 1,3,4-oxadiazolyl, 1,2,4-thiadiazolyl, 1,3,4-thiadiazolyl, pyridinyl, pyrimidinyl, pyrazinyl, pyridazinyl, 1,3,5-triazinyl, 1,2,4-triazinyl, and 1,3-selenazolyl, all of which contain at least one substituent. Preferably, $R^5$ is not 2-thiazolyl, or 2-oxazolyl.

In one aspect, preferred $R^5$ groups are substituted with the following groups:

A is selected from the group consisting of —H, —$NR^4_2$, —$CONR^4_2$, —$CO_2R^3$, halo, C1–C6 alkyl, C2–C6 alkenyl, C2–C6 alkynyl, C1–C6 perhaloalkyl, C1–C6 haloalkyl, aryl, —$CH_2OH$, —$CH_2NR^4_2$, —$CH_2CN$, —CN, —$C(S)NH_2$, —$OR^4$, —$SR^4$, —$N_3$, —$NHC(S)NR^4_2$, —NHAc, and null;

each B and D are independently selected from the group consisting of —H, alkyl, alkenyl, alkynyl, aryl, alicyclic, aralkyl, alkoxyalkyl, —$C(O)R^{11}$, —$C(O)SR^3$, —$SO_2R^{11}$, —$S(O)R^3$, —CN, —$NR^2_2$, —$OR^3$, —$SR^3$, perhaloalkyl, halo, and null, all except —H, —CN, perhaloalkyl, and halo are optionally substituted;

E is selected from the group consisting of —H, C1–C6 alkyl, C2–C6 alkenyl, C2–C6 alkynyl, aryl, C4–C6 alicyclic, alkoxyalkyl, —$C(O)OR^3$, —$CONR^4_2$, —CN, —$NR^9_2$, —$OR^3$, —$SR^3$, C1–C6 perhaloalkyl, halo, and null, all except —H, —CN, perhaloalkyl, and halo are optionally substituted; and each $R^4$ is independently selected from the group consisting of —H, and C1–C2 alkyl.

In another aspect, preferred are compounds wherein $R^5$ is:

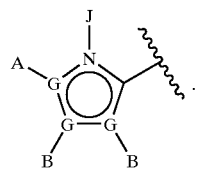

In another aspect, preferred are compounds wherein $R^5$ is:

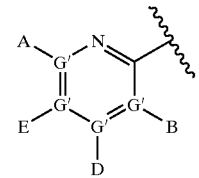

More preferred are compounds wherein $R^5$ is selected from the group consisting of:

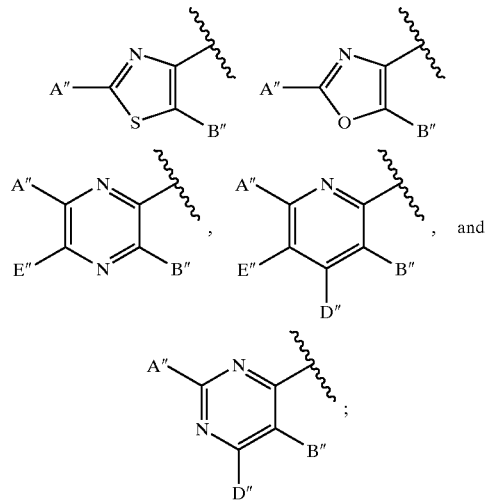

wherein

A" is selected from the group consisting of —H, —$NR^4_2$, —$CONR^4_2$, —$CO_2R^3$, halo, C1–C6 alkyl, C2–C6 alkenyl, C2–C6 alkynyl, C1–C6 perhaloalkyl, C1–C6 haloalkyl, aryl, —$CH_2OH$, —$CH_2NR^4_2$, —$CH_2CN$, —CN, —$C(S)NH_2$, —$OR^3$, —$SR^1$, —$N_3$, —$NHC(S)NR^4_2$, and —NHAc;

B" and D" are independently selected from the group consisting of —H, alkyl, alkenyl, alkynyl, aryl, alicyclic, aralkyl, alkoxyalkyl, —$C(O)R^{11}$, —$C(O)SR^3$, —$SO_2R^{11}$, —$S(O)R^3$, —CN, —$NR^9_2$, —$OR^3$, —$SR^3$, perhaloalkyl, and halo, all except —H, —CN, perhaloalkyl, and halo are optionally substituted;

E" is selected from the group consisting of —H, C1–C6 alkyl, C2–C6 alkenyl, C2–C6 alkynyl, C4–C6 alicyclic, alkoxyalkyl, —$C(O)OR^3$, —$CONR^4_2$, —CN, —$NR^9_2$, —$OR^3$, —$SR^3$, C1–C6 perhaloalkyl, and halo, all except H, —CN, perhaloalkyl, and halo are optionally substituted; and each $R^4$ is independently selected from the group consisting of —H and C1–C2 alkyl.

Especially preferred are those compounds of formula V-1A and formula V-2A wherein A" is selected from the group consisting of —$NH_2$, —$CONH_2$, halo, —$CH_3$, —$CF_3$, —$CH_2$-halo, —CN, —$OCH_3$, —$SCH_3$, and —H;

B" is selected from the group consisting of —H, —$C(O)R^{11}$, —$C(O)SR^3$, alkyl, aryl, alicyclic, halo, —CN, —$SR^3$, $OR^3$ and —$NR^9_2$;

D" is selected from the group consisting of —H, —$C(O)R^{11}$, —$C(O)SR^3$, —$NR^9_2$, alkyl, aryl, alicyclic, halo, and —$SR^3$;

E" is selected from the group consisting of —H, C1–C6 alkyl, lower alicyclic, halo, —CN, —C(O)OR$^3$, and —SR$^3$.

E" is selected from the group consisting of -heteroaryl-, -alkoxycarbonyl-, and -alkylaminocarbonyl-, all optionally substituted;

R$^{18}$ and R$^{15}$ are selected from the group consisting of H, and methyl;

R$^2$ is selected from the group consisting of R$^3$ and —H;

R$^3$ is selected from the group consisting of alkyl, aryl, alicyclic, and aralkyl;

each R$^{12}$ and R$^{13}$ is independently selected from the group consisting of —H, methyl, i-propyl, i-butyl, and benzyl, or together R$^{12}$ and R$^{13}$ are connected via 2–5 carbon atoms to form a cycloalkyl group;

n is 1;

R$^{14}$ is —OR$^{17}$;

R$^{16}$ is —(CR$^{12}$R$^{13}$)$_n$—C(O)—R$^{14}$; and

R$^{17}$ is selected from the group consisting of methyl, ethyl, propyl, phenyl, and benzyl. Most preferred are such compounds with

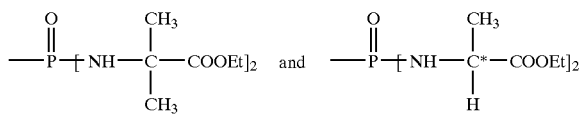

wherein C* has S stereochemistry.

Also particularly preferred are such compounds wherein R$^5$ is selected from the group consisting of:

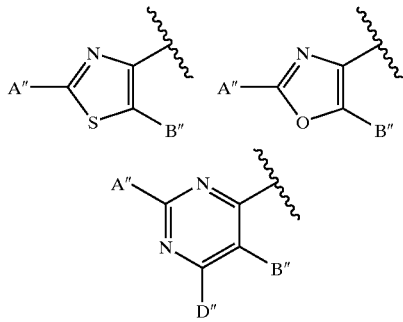

Also particularly preferred are such compounds wherein R$^5$ is selected from the group consisting of:

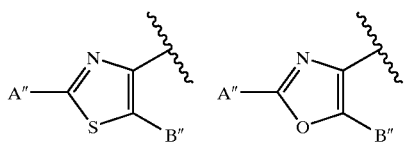

Also particularly preferred are such compounds wherein R$^5$ is selected from the group consisting of:

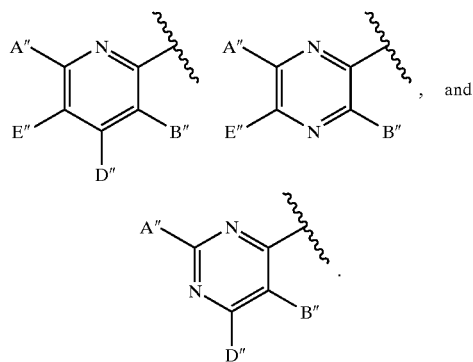

In one especially preferred aspect, R$^5$ is

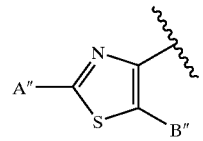

X is selected from the group consisting of methylenoxycarbonyl, and furan-2,5-diyl, and pharmaceutically acceptable salts and prodrugs thereof. More preferred are such compounds wherein A" is —NH2, X is furan-2,5-diyl, and B" is —S(CH$_2$)$_2$CH$_3$; wherein A" is —NH$_2$, X is furan-2,5-diyl, and B" is —CH$_2$—CH(CH$_3$)$_2$; wherein A" is —NH$_2$, X is furan-2,5-diyl, and B" is —COOEt; wherein A" is —NH$_2$, X is furan-2,5-diyl, and B" is —SMe; or wherein A" is —NH$_2$, X is methyleneoxycarbonyl, and B" is —CH(CH$_3$)$_2$.

Most preferred are such thiazoles where A" is —NH$_2$, X is furan-2,5-diyl, B" is —S(CH$_2$)$_2$CH$_3$ and wherein

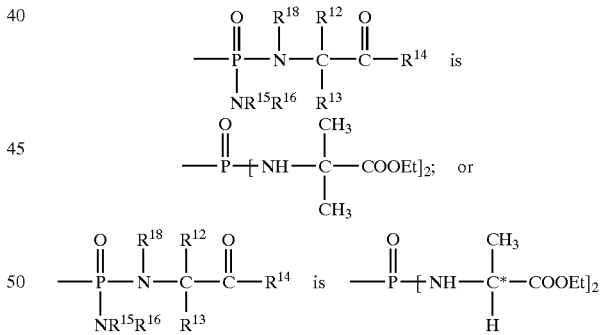

wherein C* has S stereochemistry.

Also most preferred are such thiazoles where A" is —NH$_2$, X is furan-2,5-diyl, B" is —CH$_2$—CH(CH$_3$)$_2$, and wherein

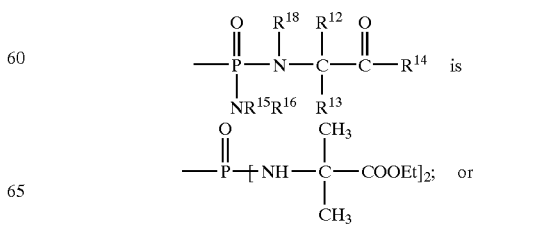

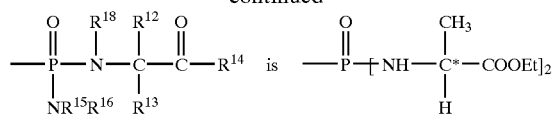

wherein C* has S stereochemistry.
In another preferred aspect, $R^5$ is

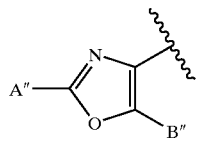

X is selected from the group consisting of furan-2,5-diyl, and methyleneoxycarbonyl, A" is —$NH_2$, and pharmaceutically acceptable salts and prodrugs thereof. More preferred are such compounds wherein X is furan-2,5-diyl, and B" is —$SCH_2CH_2CH_3$.

In another preferred aspect, $R^5$ is

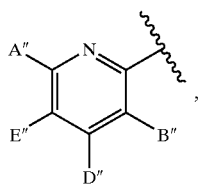

A" is —$NH_2$, E" and D" are —H, B" is selected from the group consisting of cyclopropyl, and n-propyl, X is selected from the group consisting of methyleneoxycarbonyl, and furan-2,5-diyl, and pharmaceutically acceptable salts and prodrugs thereof.

In another preferred aspect, $R^5$ is

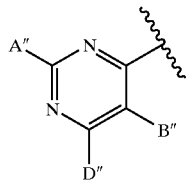

A" is —$NH_2$, D" is —H, B" is selected from the group consisting of n-propyl, and cyclopropyl, X is selected from the group consisting of furan-2,5-diyl, and methyleneoxycarbonyl, and pharmaceutically acceptable salts and prodrugs thereof.

Preferred groups include -heteroaryl-, -alkylcarbonylamino-, -alkylaminocarbonyl-, and -alkoxycarbonyl-. More preferred is -heteroaryl-, and -alkoxycarbonyl-.

The compounds of formula 1A are preferred.

(VII)

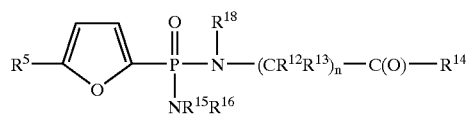

(VIII)

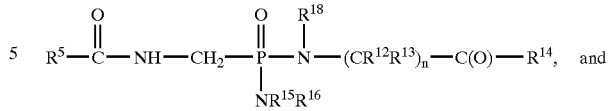

(IX)

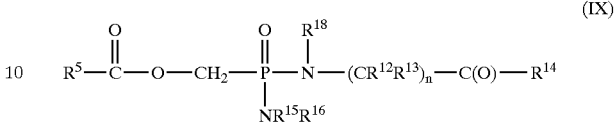

More preferred are compounds of formulae VII or IX:

(VII)

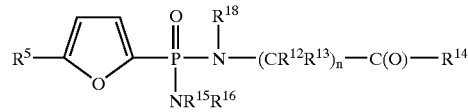

(IX)

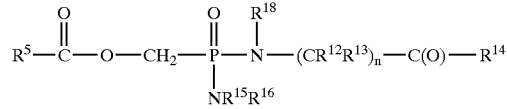

Preferred A" groups include —$NH_2$, —$CONH_2$, halo, —$CH_3$, —$CF_3$, —$CH_2$-halo, —CN, —$OCH_3$, —$SCH_3$, and —H.

More preferred A" groups include —$NH_2$, —Cl, —Br, and —$CH_3$.

Preferred B" groups include —H, —C(O)$R^{11}$, —C(O)S$R^3$, alkyl, aryl, alicyclic, halo, —CN, —S$R^3$, —N$R^9_2$, and —O$R^3$. More preferred is —H, —C(O)O$R^3$, —C(O)S$R^3$, C1–C6 alkyl, alicyclic, halo, heteroaryl, and —SR.

Preferred D" groups include —H, —C(O)$R^{11}$, —C(O)S$R^3$, alkyl, aryl, alicyclic, halo, —N$R^9_2$, and —S$R^3$. More preferred is —H, —C(O)O$R^3$, lower alkyl, alicyclic, and halo.

Preferred E" groups include —H, C1–C6 alkyl, lower alicyclic, halogen, —CN, —C(O)O$R^3$, —S$R^3$, and —CON$R^4_2$. More preferred is —H, —Br, and —Cl.

Preferred $R^{18}$ groups include —H, methyl, and ethyl. More preferred is —H and methyl. Especially preferred is —H.

Preferred compounds include those wherein each $R^{12}$ and $R^{13}$ is independently selected from the group consisting of —H, methyl, ethyl, n-propyl, i-propyl, n-butyl, i-butyl, —$CH_2CH_2$—$SCH_3$, phenyl, and benzyl, or together $R^{12}$ and $R^{13}$ are connected via 2–5 carbon atoms to form a cycloalkyl group. More preferred is each $R^{12}$ and $R^{13}$ is independently selected from the group consisting of —H, methyl, i-propyl, i-butyl, and benzyl, or together $R^{12}$ and $R^{13}$ are connected via 2–5 carbon atoms to form a cycloalkyl group. Also more preferred are such compounds wherein each $R^{12}$ and $R^{13}$ is independently selected from the group consisting of —H, methyl, i-propyl, and benzyl, or together $R^{12}$ and $R^{13}$ are connected via 4 carbon atoms to form a cyclopentyl group. Especially preferred are those compounds wherein $R^{12}$ and $R^{13}$ are both —H, both methyl, or $R^{12}$ is H and $R^{13}$ is selected from the group consisting of methyl, i-propyl, and benzyl. Most preferred are such compounds wherein n is 1, and R is —H, then the carbon attached to $R^{12}$ and $R^{13}$ has S stereochemistry.

Preferably, n is an integer of from 1–2. More preferred is when n is 1.

Preferred compounds include those wherein each $R^{14}$ is independently selected from the group consisting of —OR$^{17}$, and —SR$^{17}$; and R$^{17}$ is selected from the group consisting of optionally substituted methyl, ethyl, propyl, t-butyl, and benzyl. More preferred are such compounds wherein each R$^{14}$ is independently selected from the group consisting of —OR$^{17}$; and R$^{17}$ is selected from the group consisting of methyl, ethyl, propyl, and benzyl. Most preferred are such compounds wherein R$^{17}$ is selected from the group consisting of ethyl, and benzyl.

Preferred are compounds wherein R$^{15}$ is not H. More preferred are compounds wherein R$^{15}$ and R$^{16}$ are independently selected from the group consisting of lower alkyl, and lower aralkyl, or together R$^{15}$ and R$^{16}$ are connected via 2–6 atoms, optionally including 1 heteroatom selected from the group consisting of O, N, and S. Also more preferred are compounds wherein R$^{15}$ and R$^{16}$ are independently selected from the group consisting of C1–C6 alkyl, or together R$^{15}$ and R$^{16}$ are connected via 2–6 atoms, optionally including 1 heteroatom selected from the group consisting of O, N, and S. In one aspect, particularly preferred are compounds wherein —N$^{15}$R$^{16}$ is a cyclic amine. Especially preferred are such compounds wherein —NR$^{15}$R$^{16}$ is selected from the group consisting of morpholinyl and pyrrolidinyl.

Preferred are compounds where R$^{16}$ is —(CR$^{12}$R$^{13}$)$_n$—C(O)—R$^{14}$. Particularly preferred are such compounds that are of the formula:

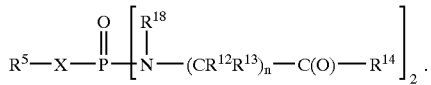

More preferred are such compounds wherein n is 1. Especially preferred are such compounds wherein when R$^{12}$ and R$^{13}$ are not the same, then H$_2$N—CR$^{12}$R$^{13}$—C(O)—R$^{14}$ is an ester, or thioester of a naturally occurring amino acid; and R$^{14}$ is selected from the group consisting of —OR$^{17}$ and —SR$^{17}$.

More preferred are compounds where n is 1 and wherein
R$^{18}$ is selected from the group consisting of —H, methyl, and ethyl;
R$^{12}$ and R$^{13}$ are independently selected from the group consisting of —H, methyl, i-propyl, i-butyl, and benzyl, or together are connected via 2–5 carbon atoms to form a cycloalkyl group;
R$^{14}$ is OR$^{17}$;
R$^{17}$ is selected from the group consisting of methyl, ethyl, propyl, t-butyl, and benzyl; and
R$^{15}$ and R$^{16}$ are independently selected from the group consisting of lower alkyl, and lower aralkyl, or together R$^{15}$ and R$^{16}$ are connected via 2–6 atoms, optionally including 1 heteroatom selected from the group consisting of O, and N.

In one aspect, preferred are compounds of Formula IA wherein M is

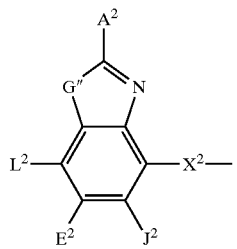

wherein:
G″ is selected from the group consisting of —O— and —S—;
A$^2$, L$^2$, E$^2$, and J$^2$ are selected from the group consisting of —N$^4$$_2$, —NO$_2$, —H, —OR$^2$, —SR$^2$, —C(O)NR$^4$$_2$, halo, —COR$^{11}$, —SO$_2$R$^3$, guanidinyl, amidinyl, aryl, aralkyl, alkyoxyalkyl, —SCN, —NHSO$_2$R$^9$, —SO$_2$NR$^4$$_2$, —CN, —S(O)R$^3$, perhaloacyl, perhaloalkyl, perhaloalkoxy, C1–C5 alkyl, C2–C5 alkenyl, C2–C5 alkynyl, and lower alicyclic, or together L$^2$ and E$^2$ or E$^2$ and J$^2$ form an annulated cyclic group;
X$^2$ is selected from the group consisting of —CR$^2$$_2$—, —CF$_2$—, —OCR$^2$$_2$—, —SCR$^2$$_2$—, —O—C(O)—, —S—C(O)—, —O—C(S)—; and —NR$^{19}$CR$^2$$_2$—, and wherein in the atom attached to the phosphorus is a carbon atom; with the proviso that X$^2$ is not substituted with —COOR$^2$, —SO$_3$H, or —PO$_3$R$^2$$_2$;
R is selected from the group consisting of R$^3$ and —H;
R$^3$ is selected from the group consisting of alkyl, aryl, alicyclic, and aralkyl;
each R$^4$ is independently selected from the group consisting of —H, and alkyl, or together R$^4$ and R$^4$ form a cyclic alkyl group;
each R$^9$ is independently selected from the group consisting of —H, alkyl, aralkyl, and alicyclic, or together R$^9$ and R$^9$ form a cyclic alkyl group;
R$^{11}$ is selected from the group consisting of alkyl, aryl, —NR$^2$$_2$, and —OR$^2$;
R$^{19}$ is selected from the group consisting of lower alkyl, —H, and —COR$^2$; and
pharmaceutically acceptable prodrugs and salts thereof. More preferred are compounds wherein G″ is —S—. Most preferred are compounds wherein A$^2$, L$^2$, E$^2$, and J$^2$ are independently selected from the group consisting of —H, —NR$^4$$_2$, —S—C≡N, halogen, —OR$^3$, hydroxy, -alkyl(OH), aryl, alkyloxycarbonyl, —SR$^3$, lower perhaloalkyl, and C1–C5 alkyl, or together L$^2$ and E$^2$ form an annulated cyclic group. More preferably A$^2$, L$^2$, E$^2$ and J$^2$ are independently selected from the group consisting of —H, —NR$^4$$_2$, —S—C≡N, halogen, lower alkoxy, hydroxy, lower alkyl(hydroxy), lower aryl, and C1–C5 alkyl, or together L$^2$ and E$^2$ form an annulated cyclic group.

Most preferred A$^2$ groups include —NH$_2$, —H, halo, and C1–C5 alkyl.

Most preferred L$^2$ and E$^2$ groups are those independently selected from the group consisting of —H, —S—C≡N, lower alkoxy, C1–C5 alkyl, lower alkyl(hydroxy), lower aryl, and halogen or together L$^2$ and E$^2$ form an annulated cyclic group containing an additional 4 carbon atoms.

Most preferred J$^2$ groups include —H, and C1–C5 alkyl.

Preferred X$^2$ groups include —CF$_2$—, —CH$_2$—, —OC(O)—, —OCH$_2$—, —SCH$_2$—, —NHCH$_2$—, and —N(C(O)CH$_3$)—CH$_2$—. More preferred are —OCH$_2$—, —SCH$_2$—, and —N(C(O)CH$_3$)—CH$_2$—. Most preferred is —OCH$_2$—.

One preferred aspect include compound wherein A$^2$ is selected from the group consisting of —H, —NH$_2$, —CH$_3$, —Cl, and —Br;
L$^2$ is —H, lower alkyl, halogen, lower alkyloxy, hydroxy, -alkenylene-OH, or together with E$^2$ forms a cyclic group including aryl, cyclic alkyl, heteroaryls, heterocyclic alkyl;
E$^2$ is selected from the groups consisting of H, lower alkyl, halogen, SCN, lower alkyloxycarbonyl, lower alkyloxy, or together with $L^2$ forms a cyclic group including aryl, cyclic alkyl, heteroaryl, or heterocyclic alkyl;

$J^2$ is selected from the groups consisting of H, halogen, and lower alkyl;

G″ is —S—;

$X^2$ is —OCH$_2$—;

and pharmaceutically acceptable salts and prodrugs thereof. More preferred are such compounds wherein $R^{18}$ is selected from the group consisting of —H, methyl, and ethyl;

$R^{12}$ and $R^{13}$ are independently selected from the group consisting of —H, methyl, i-propyl, i-butyl, and benzyl, or together are connected via 2–5 carbon atoms to form a cycloalkyl group;

$R^{14}$ is —OR$^{17}$;

$R^{17}$ is selected from the group consisting of methyl, ethyl, propyl, t-butyl, and benzyl; and $R^{15}$ and $R^{16}$ are independently selected from the group consisting of lower alkyl, and lower aralkyl, or together $R^{15}$ and $R^{16}$ are connected via 2–6 atoms, optionally including 1 heteroatom selected from the group consisting of O, and N.

Also more preferred are such compounds where $A^2$ is NH$_2$, $L^2$ is selected from the group consisting of —Et and —Cl, $E^2$ is selected from the group consisting of —SCN, —Et, and —Br, and $J^2$ is —H. Particularly preferred are such compounds wherein

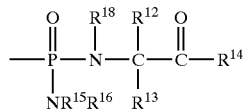

is selected from the group consisting of

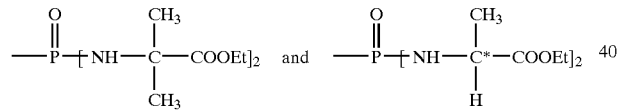

wherein C* has S stereochemistry.

Preferred $R^{18}$ groups include —H, methyl, and ethyl. More preferred is —H and methyl. Especially preferred is —H.

Preferred compounds include those wherein each $R^{12}$ and $R^{13}$ is independently selected from the group consisting of —H, methyl, ethyl, n-propyl, i-propyl, n-butyl, i-butyl, —CH$_2$CH$_2$—SCH$_3$, phenyl, and benzyl, or together $R^{12}$ and $R^{13}$ are connected via 2–5 carbon atoms to form a cycloalkyl group. More preferred is each $R^{12}$ and $R^{13}$ is independently, selected from the group consisting of —H, methyl, i-propyl, i-butyl, and benzyl, or together $R^{12}$ and $R^{13}$ are connected via 2–5 carbon atoms to form a cycloalkyl group. Also more preferred are such compounds wherein each $R^{12}$ and $R^{13}$ is independently selected from the group consisting of —H, methyl, i-propyl, and benzyl, or together $R^{12}$ and $R^{13}$ are connected via 4 carbon atoms to form a cyclopentyl group. Especially preferred are those compounds wherein $R^{12}$ and $R^3$ are both —H, both methyl, or $R^{12}$ is H and $R^3$ is selected from the group consisting of methyl, i-propyl, and benzyl. Most preferred are such compounds wherein n is 1, and $R^{12}$ is —H, then the carbon attached to $R^{12}$ and $R^{13}$ has S stereochemistry.

Preferably, n is an integer of from 1–2. More preferred is when n is 1.

Preferred compounds include those wherein each $R^{14}$ is independently selected from the group consisting of —OR$^{17}$, and —SR$^{17}$; and $R^{17}$ is selected from the group consisting of optionally substituted methyl, ethyl, propyl, t-butyl, and benzyl. More preferred are such compounds wherein each $R^{14}$ is independently selected from the group consisting of —OR$^{17}$; and $R^{17}$ is selected from the group consisting of methyl, ethyl, propyl, and benzyl. Most preferred are such compounds wherein $R^{17}$ is selected from the group consisting of ethyl, and benzyl.

Preferred are compounds wherein $R^{15}$ is not H. More preferred are compounds wherein $R^{15}$ and $R^{16}$ are independently selected from the group consisting of lower alkyl, and lower aralkyl, or together $R^{15}$ and $R^{16}$ are connected via 2–6 atoms, optionally including 1 heteroatom selected from the group consisting of O, N, and S. Also more preferred are compounds wherein $R^{15}$ and $R^{16}$ are independently selected from the group consisting of C1–C6 alkyl, or together $R^{15}$ and $R^{16}$ are connected via 2–6 atoms, optionally including 1 heteroatom selected from the group consisting of O, N, and S. In one aspect, particularly preferred are compounds wherein —NR$^{15}$R$^{16}$ is a cyclic amine. Especially preferred are such compounds wherein —NR$^{15}$R$^{16}$ is selected from the group consisting of morpholinyl and pyrrolidinyl.

Preferred are compounds $R^{16}$ is —(CR$^{12}$R$^{13}$)$_n$—C(O)—R$^{14}$.

More preferred are compounds where n is 1, and wherein $R^{18}$ is selected from the group consisting of —H, methyl, and ethyl;

$R^{12}$ and $R^{13}$ are independently selected from the group consisting of —H, methyl, i-propyl, i-butyl, and benzyl, or together are connected via 2–5 carbon atoms to form a cycloalkyl group;

$R^{14}$ is —OR$^{17}$;

$R^{17}$ is selected from the group consisting of methyl, ethyl, propyl, t-butyl, and benzyl; and $R^{15}$ and $R^{16}$ are independently selected from the group consisting of lower alkyl, and lower aralkyl, or together $R^{15}$ and $R^{16}$ are connected via 2–6 atoms, optionally including 1 heteroatom selected from the group consisting of O, and N. Particularly preferred are such compounds that are of the formula:

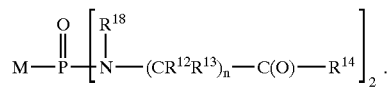

More preferred are such compounds wherein n is 1. Especially preferred are such compounds wherein when $R^{12}$ and $R^{13}$ are not the same, then H$_2$N—CR$^{12}$R$^{13}$—C(O)—R$^{14}$ is an ester, or thioester of a naturally occurring amino acid; and $R^{14}$ is selected from the group consisting of —OR$^{17}$ and —SR$^{17}$.

In one aspect, preferred are compounds of formula IA or formula I wherein M is

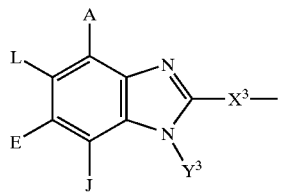

wherein:
- A, E, and L are selected from the group consisting of —NR$^8_2$, —NO$_2$, —H, —OR, —SR$^7$, —C(O)NR$^4_2$, halo, —COR$^{11}$, —SO$_2$R$^3$, guanidine, amidine, —NHSO$_2$R$^5$, —SO$_2$NR$^4_2$, —CN, sulfoxide, perhaloacyl, perhaloalkyl, perhaloalkoxy, C1–C5 alkyl, C2–C5 alkenyl, C2–C5 alkynyl, and lower alicyclic, or together A and L form a cyclic group, or together L and E form a cyclic group, or together E and J form a cyclic group including aryl, cyclic alkyl, and heterocyclic;
- J is selected from the group consisting of —NR$^8_2$, —NO$_2$, —H, —OR$^7$, —SR$^7$, —C(O)NR$^4_2$, halo, —C(O)R$^{11}$, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y forms a cyclic group including aryl, cyclic alkyl and heterocyclic alkyl;
- X$^3$ is selected from the group consisting of -alkyl (hydroxy)-, -alkyl-, -alkynyl-, -aryl-, -carbonylalkyl-, -1,1-dihaloalkyl-, -alkoxyalkyl-, -alkyloxy-, -alkylthioalkyl-, -alkylthio-, -alkylaminocarbonyl-, -alkylcarbonylamino-, -alicyclic-, -aralkyl-, -alkylaryl-, -alkoxycarbonyl-, -carbonyloxyalkyl-, -alkoxycarbonylamino-, and -alkylaminocarbonylamino-, all optionally substituted; with the proviso that X$^3$ is not substituted with —COOR$^2$, —SO$_3$H, or —PO$_3$R$^2_2$;
- —Y$^3$ is selected from the group consisting of —H, alkyl, alkenyl, alkynyl, aryl, alicyclic, aralkyl, aryloxyalkyl, alkoxyalkyl, —C(O)R$^3$, —S(O)$_2$R$^3$, —C(O)—R$^{11}$, —CONHR$^3$, —NR$^2_2$, and —OR, all except H are optionally substituted;
- R$^2$ is selected from the group consisting of R$^3$ and —H;
- R$^3$ is selected from the group consisting of alkyl, aryl, alicyclic, and aralkyl;
- each R$^4$ is independently selected from the group consisting of —H, and alkyl, or together R$^4$ and R$^4$ form a cyclic alkyl group;
- R$^5$ is selected from the group consisting of lower alkyl, lower aryl, lower aralkyl, and lower alicyclic;
- R$^7$ is independently selected from the group consisting of —H, lower alkyl, lower alicyclic, lower aralkyl, lower aryl, and —C(O)R$^{10}$;
- R$^8$ is independently selected from the group consisting of —H, lower alkyl, lower aralkyl, lower aryl, lower alicyclic, —C(O)R$^{10}$, or together they form a bidentate alkyl;
- each R$^9$ is independently selected from the group consisting of —H, alkyl, aralkyl, and alicyclic, or together R$^9$ and R$^9$ form a cyclic alkyl group;
- R$^{10}$ is selected from the group consisting of —H, lower alkyl, —NH$_2$, lower aryl, and lower perhaloalkyl;
- R$^{11}$ is selected from the group consisting of alkyl, aryl, —NR$^2_2$, and —OR$^2$; and pharmaceutically acceptable prodrugs and salts thereof; with the provisos that:

a) when X$^3$ is alkyl or alkene, then A is —N(R$^8_2$);
b) X$^3$ is not alkylamine and alkylaminoalkyl substituted with phosphonic esters and acids; and
c) A, L, E, J, and Y$^3$ together may only form 0–2 cyclic groups.

More preferred are such compounds wherein X$^3$ is not -alkoxyalkyl-, -alkyloxy-, alkythioalkyl-, and -alkylthio-. Particularly preferred are such compounds with the additional proviso that when X$^3$ is aryl or alkylaryl, said aryl or alkylaryl group is not linked 1,4 through a six-membered aromatic ring.

Especially preferred benzimidazole compounds include those wherein A, L, and E are independently selected from the group consisting of —H, —NR$^8_2$, —NO$_2$, hydroxy, halogen, —OR$^7$, alkylaminocarbonyl, —SR$^7$, lower perhaloalkyl, and C1–C5 alkyl, or together E and J together form a cyclic group; and wherein J is selected from the group consisting of —H, halogen, lower alkyl, lower hydroxyalkyl, —NR$^8_2$, lower R$^8_2$N-alkyl, lower haloalkyl, lower perhaloalkyl, lower alkenyl, lower alkynyl, lower aryl, heterocyclic, and alicyclic; and wherein Y is selected from the group consisting of alicyclic and lower alkyl; wherein X$^3$ is selected from the group consisting of -heteroaryl-, -alkylcarbonylamino-, -alkylaminocarbonyl-, and -alkoxycarbonyl-. More preferred are such compounds wherein

- R$^{18}$ is selected from the group consisting of —H, methyl, and ethyl;
- R$^{12}$ and R$^{13}$ are independently selected from the group consisting of —H, methyl, i-propyl, i-butyl, and benzyl, or together are connected via 2–5 carbon atoms to form a cycloalkyl group;
- R$^{14}$ is —OR$^{17}$;
- R$^{17}$ is selected from the group consisting of methyl, ethyl, propyl, t-butyl, and benzyl; and
- R$^{15}$ and R$^{16}$ are independently selected from the group consisting of lower alkyl, and lower aralkyl, or together R$^{15}$ and R$^{16}$ are connected via 2–6 atoms, optionally including 1 heteroatom selected from the group consisting of O, and N. Most preferred are such compounds wherein A is selected from the group consisting of —H, —NH$_2$, —F, and —CH$_3$;
- L is selected from the group consisting of —H, —F, —OCH$_3$, Cl and —CH$_3$;
- E is selected from the group consisting of —H, and —Cl;
- J is selected from the group consisting of —H, halo, C1–C5 hydroxyalkyl, C1–C5 haloalkyl, C1–C5 R$^8_2$N-alkyl, C1–C5 alicyclic, and C1–C5 alkyl;
- X$^3$ is selected from the group consisting of —CH$_2$OCH$_2$—, -methyleneoxycarbonyl-, and -furan-2,5-diyl-; and
- Y is lower alkyl.

Also more preferred are such benzimidazoles where A is —NH$_2$, L is —F, E is —H, J is ethyl, Y is isobutyl, and X$^3$ is -furan-2,5-diyl-; or where A is —NH$_2$, L is —F, E is —H, J is N,N-dimethylaminopropyl, Y is isobutyl, and X$^3$ is -furan-2,5-diyl-.

37

Particularly preferred are those compounds wherein

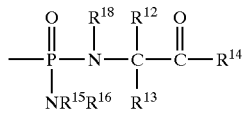

is selected from the group consisting of

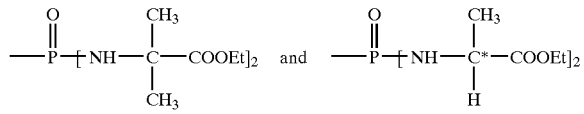

wherein C* has S stereochemistry.

Preferably, oral bioavailability is at least 5%. More preferably, oral bioavailability is at least 10%.

The prodrugs of formula IA may have two isomeric forms around the phosphorus. Preferred is when the phosphorus is not chiral. Also preferred is when there is no chiral center in the amino groups attached to the phosphorus. Also preferred is when n is 1 and $R^{12}$ is —H, then the carbon attached to $R^{12}$ and $R^{13}$ has S stereochemistry.

In another aspect preferred are compounds of formula I or I—A where M is

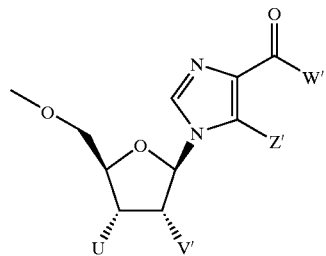

wherein

Z' is selected from the group consisting of alkyl or halogen,

U and V' are independently selected from the group consisting of hydrogen, hydroxy, acyloxy or when taken together form a lower cyclic ring containing at least one oxygen;

W' is selected from the group consisting of amino and lower alkyl amino;

and pharmaceutically acceptable salts thereof

In another aspect, preferred are compounds of formula II

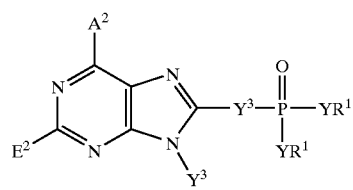

II wherein $A^2$ is selected from the group consisting of —$NR^8{}_2$, $NHSO_2R^3$, —$OR^5$, —$SR^5$, halogen, lower alkyl, —$CON(R^4)_2$, guanidine, amidine, —H, and perhaloalkyl;

$E^2$ is selected from the group consisting of —H, halogen, lower alkylthio, lower perhaloalkyl, lower alkyl, lower alkenyl, lower alkynyl, lower alkoxy, —CN, and —$NR^7{}_2$;

38

$X^3$ is selected from the group consisting of -alkyl (hydroxy)-, -alkyl-, -alkynyl-, -aryl-, -carbonylalkyl-, -1,1-dihaloalkyl-, -alkoxyalkyl-, -alkyloxy-, -alkylthioalkyl-, -alkylthio-, -alkylaminocarbonyl-, -alkylcarbonylamino-, -alicyclic-, -aralkyl-, -alkylaryl-, -alkoxycarbonyl-, -carbonyloxyalkyl-, -alkoxycarbonylamino-, and -alkylaminocarbonylamino-, all optionally substituted; with the proviso that $X^3$ is not substituted with —$COOR^2$, —$SO_3H$, or —$PO_3R^2{}_2$;

$Y^3$ is selected from the group consisting of —H, alkyl, alkenyl, alkynyl, aryl, alicyclic, aralkyl, aryloxyalkyl, alkoxyalkyl, —$C(O)R^3$, —$S(O)_2R^3$, —$C(O)$—$R^{11}$, —$CONHR^3$, —$NR^2{}_2$, and —$OR^3$, all except H are optionally substituted;

Y is independently selected from the group consisting of —O—, and —$NR^6$—;

when Y is —O—, then $R^1$ attached to —O— is independently selected from the group consisting of —H, alkyl, optionally substituted aryl, optionally substituted alicyclic where the cyclic moiety contains a carbonate or thiocarbonate, optionally substituted -alkylaryl, —$C(R^2)_2OC(O)NR^2{}_2$, —$NR^2$—$C(O)$—$R^3$, —$C(R^2)_2$—$OC(O)R^3$, —$C(R^2)_2$—$O$—$C(O)OR^3$, —$C(R^2)_2OC(O)SR^3$, -alkyl-S—$C(O)R^3$, -alkyl-S—S-alkylhydroxy, and -alkyl-S—S—S-alkylhydroxy, when Y is —$NR^6$—, then $R^1$ attached to —$NR^6$— is independently selected from the group consisting of —H, —$[C(R^2)_2]_q$—$COOR^3$, —$C(R^4)_2COOR^3$, —$[C(R^2)_2]_q$—$C(O)SR^3$, and -cycloalkylene-$COOR^3$;

or when either Y is independently selected from —O— and —$NR^6$—, then together $R^1$ and $R^1$ are -alkyl-S—S-alkyl- to form a cyclic group, or together $R^1$ and $R^1$ are

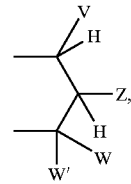

wherein

V, W, and W' are independently selected from the group consisting of —H, alkyl, aralkyl, alicyclic, aryl, substituted aryl, heteroaryl, substituted heteroaryl, 1-alkenyl, and 1-alkynyl; or together V and Z are connected via an additional 3–5 atoms to form a cyclic group containing 5–7 atoms, optionally 1 heteroatom, substituted with hydroxy, acyloxy, alkoxycarbonyloxy, or aryloxycarbonyloxy attached to a carbon atom that is three atoms from both Y groups attached to the phosphorus; or together V and Z are connected via an additional 3–5 atoms to form a cyclic group, optionally containing 1 heteroatom, that is fused to an aryl group at the beta and gamma position to the Y attached to the phosphorus;

together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3–5 atoms to form a cyclic group, optionally containing one heteroatom, and V must be aryl, substituted aryl, heteroaryl, or substituted heteroaryl;

together W and W' are connected via an additional 2–5 atoms to form a cyclic group, optionally containing 0–2 heteroatoms, and V must be aryl, substituted aryl, heteroaryl, or substituted heteroaryl;

Z is selected from the group consisting of —CHR$^2$OH, —CHR$^2$OC(O)R$^3$, —CHR$^2$OC(S)R$^3$, —CHR$^2$OC(S)OR, —CHR$^2$OC(O)SR$^3$, —CHR$^2$OCO$_2$R$^3$, —OR$^2$, —SR$^2$, —CHR$^2$N$_3$, —CH$_2$aryl, —CH(aryl)OH, —CH(CH=CR$^2{}_2$)OH, —CH(C≡CR$^2$)OH, —R$^2$, —NR$^2{}_2$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—OR$^2$, and —(CH$_2$)$_p$—SR$^2$;

p is an integer 2 or 3;

q is an integer 1 or 2;

with the provisos that:
a) V, Z, W, W' are not all —H; and
b) when Z is —R$^2$ then at least one of V, W, and W' is not —H, alkyl, aralkyl, or alicyclic;

R$^2$ is selected from the group consisting of R$^3$ and —H;

R$^3$ is selected from the group consisting of alkyl, aryl, alicyclic, and aralkyl;

each R$^4$ is independently selected from the group consisting of —H, and alkyl, or together R$^4$ and R$^4$ form a cyclic alkyl group;

R$^6$ is selected from the group consisting of —H, lower alkyl, acyloxyalkyl, alkoxycarbonyloxyalkyl, and lower acyl;

R$^5$ is selected from the group consisting of lower alkyl, lower aryl, lower aralkyl, and lower alicyclic;

R$^9$ is independently selected from the group consisting of —H, lower alkyl, lower alicyclic, lower aralkyl, lower aryl, and —(CO)R$^{10}$;

R$^8$ is independently selected from the group consisting of —H, lower alkyl, lower aralkyl, lower aryl, lower alicyclic, —C(O)R$^{10}$, or together they form a bidendate alkyl;

R$^9$ is selected from the group consisting of alkyl, aralkyl, and alicyclic;

R$^{10}$ is selected from the group consisting of —H, lower alkyl, —NH$_2$, lower aryl, and lower perhaloalkyl; and R$^{11}$ is selected from the group consisting of alkyl, aryl, —NR$_2{}^2$, and —OR$^2$; and pharmaceutically acceptable prodrugs and salts thereof.

Preferred A$^2$ groups for formula II include —NR$^8{}_2$, lower alkyl, lower perhaloalkyl, lower alkoxy, and halogen. Particularly preferred are —NR$^8{}_2$, and halogen. Especially preferred is —NR$^8{}_2$. Most preferred is —NH$_2$.

Preferred E$^2$ groups for formula II include —H, halogen, lower perhaloalkyl, —CN, lower alkyl, lower alkoxy, and lower alkylthio. Particularly preferred E$^2$ groups include —H, —SMe, —Et, and —Cl. Especially preferred is —H and —SCH$_3$.

Preferred X$^3$ groups for formula II include -alkyl-, -alkynyl-, -alkoxyalkyl-, -alkylthio-, -aryl-, -1,1-dihaloalkyl-, -carbonylalkyl-, -heteroaryl-, -alkylcarbonylamino-, and -alkylaminocarbonyl. Particularly preferred is -alkyl- substituted with 1 to 3 substituents selected from halogen, and —OH. Particularly preferred are -alkylaminocarbonyl-, -alkoxyalkyl-, and -heteroaryl-. Preferred -alkoxyalkyl- groups include -methoxymethyl-. Preferred -heteroaryl- groups include -furan-2,5-diyl-, optionally substituted.

Preferred Y$^3$ groups for formula II include aralkyl, alicyclic, alkyl, and aryl, all optionally substituted. Particularly preferred is lower alkyl. Particularly preferred Y$^3$ groups include (2-naphthyl)methyl, cyclohexylethyl, phenylethyl, nonyl, cyclohexylpropyl, ethyl, cyclopropylmethyl, cyclobutylmethylphenyl, (2-methyl)propyl, neopentyl, cyclopropyl, cyclopentyl, (1-imidozolyl)propyl, 2-ethoxybenzyl, 1-hydroxy-2,2-dimethylpropyl, 1-chloro-2,2-dimethylpropyl, 2,2-dimethylbutyl, 2-(spiro-3,3-dimethylcyclohex-4-enyl)propyl, and 1-methylneopentyl. Especially preferred is neopentyl and isobutyl.

Preferred R$^4$ and R$^7$ groups are —H, and lower alkyl. Particularly preferred are —H, and methyl.

In another preferred aspect, A$^2$ is —NR$^8{}_2$ or halogen, E$^2$ is —H, halogen, —CN, lower alkyl, lower perhaloalkyl, lower alkoxy, or lower alkylthio, X$^3$ is -alkyl-, -alkoxyalkyl-, -alkynyl-, 1,1-dihaloalkyl-, -carbonylakyl-, -alkyl(OH)—, -alkylcarbonylamino-, -alkylaminocarbonyl-, -alkylthio-, -aryl-, or -heteroaryl-, and R$^4$ and R$^7$ is —H or lower alkyl. Particularly preferred are such compounds where Y$^3$ is aralkyl, aryl, alicyclic, or alkyl.

In another preferred aspect, A$^2$ is —NR$^8{}_2$, E$^2$ is —H, Cl—, or methylthio, and X$^3$ is optionally substituted -furan-2,5-diyl-, or -alkoxyalkyl-. Particularly preferred are such compounds where A$^2$ is —NH$_2$, X$^3$ is -furan-2,5-diyl-, or -methoxymethyl-, and Y$^3$ is lower alkyl. Most preferred are such compounds where E$^2$ is H, X$^3$ is -furan-2,5-diyl-, and Y$^3$ is neopentyl; those where E$^2$ is —SCH$_3$, X$^3$ is -furan-2,5-diyl-, and Y$^3$ is isobutyl; and those where E$^2$ is —H, X$^3$ is -furan-2,5-diyl-, and Y$^3$ is 1-(3-chloro-2,2-dimethyl)propyl. Especially preferred are such compounds where R$^1$ is —CH$_2$O—C(O)—C(CH$_3$)$_3$.

In another aspect, preferred are compounds of formula III

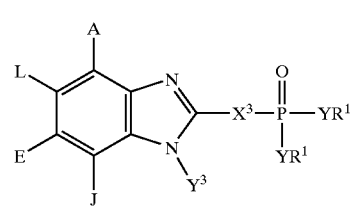

III wherein:

A, E, and L are selected from the group consisting of —NR$^8{}_2$, —NO$_2$, —H, —OR, —SR$^7$, —C(O)NR$^4{}_2$, halo, —COR$^{11}$, —SO$_2$R$^3$, guanidine, amidine, —NHSO$_2$R$^5$, —SO$_2$NR$^4{}_2$, —CN, sulfoxide, perhaloacyl, perhaloalkyl, perhaloalkoxy, C1–C5 alkyl, C2–C5 alkenyl, C2–C5 alkynyl, and lower alicyclic, or together A and L form a cyclic group, or together L and E form a cyclic group, or together E and J form a cyclic group including aryl, cyclic alkyl, and heterocyclic;

J is selected from the group consisting of —NR$^8{}_2$, —NO$_2$, —H, —OR$^7$, —SR$^7$, —C(O)NR$^4{}_2$, halo, —C(O)R$^{11}$, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y forms a cyclic group including aryl, cyclic alkyl and heterocyclic alkyl;

X$^3$ is selected from the group consisting of -alkyl(hydroxy)-, -alkyl-, -alkynyl-, -aryl-, -carbonylalkyl-, -1,1-dihaloalkyl-, -alkoxyalkyl-, -alkyloxy-, -alkylthioalkyl-, -alkylthio-, -alkylaminocarbonyl-, -alkylcarbonylamino-, -alicyclic-, -aralkyl-, -alkylaryl-, -alkoxycarbonyl-, -carbonyloxyalkyl-, -alkoxycarbonylamino-, and -alkylaminocarbonylamino-, all optionally substituted; with the proviso that $X^3$ is not substituted with —$COOR^2$, —$SO_3H$, or —$PO_3RR^2{}_2$;

$Y^3$ is selected from the group consisting of —H, alkyl, alkenyl, alkynyl, aryl, alicyclic, aralkyl, aryloxyalkyl, alkoxyalkyl, —$C(O)R^3$, —$S(O)_2R^3$, —$C(O)$—$R^{11}$, —$CONHR^3$, —$NR^2{}_2$, and —$OR^3$, all except H are optionally substituted;

Y is independently selected from the group consisting of —O—, and —$NR^6$—;

when Y is —O—, then $R^1$ attached to —O— is independently selected from the group consisting of —H, alkyl, optionally substituted aryl, optionally substituted alicyclic where the cyclic moiety contains a carbonate or thiocarbonate, optionally substituted -alkylaryl, —$C(R^2)_2OC(O)NR^2{}_2$, —$NR^2$—$C(O)$—$R^3$, —$C(R^2)_2$—$OC(O)R^3$, —$C(R^2)_2$—O—$C(O)OR^3$, —$C(R^2)_2OC(O)SR^3$, -alkyl-S—$C(O)R^3$, -alkyl-S—S-alkylhydroxy, and -alkyl-S—S—S-alkylhydroxy, when Y is —$NR^6$—, then $R^1$ attached to —$NR^6$— is independently selected from the group consisting of —H, —$[C(R^2)_2]_q$—$COOR^3$, —$C(R^4)_2COOR^3$, —$[C(R^2)_2]_q$—$C(O)SR^3$ and -cycloalkylene-$COOR^3$;

or when either Y is independently selected from —O— and —$NR^6$—, then together $R^1$ and $R^1$ are -alkyl-S—S-alkyl- to form a cyclic group, or together $R^1$ and $R^1$ are

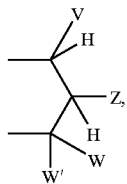

wherein

V, W, and W' are independently selected from the group consisting of —H, alkyl, aralkyl, alicyclic, aryl, substituted aryl, heteroaryl, substituted heteroaryl, 1-alkenyl, and 1-alkynyl; or together V and Z are connected via an additional 3–5 atoms to form a cyclic group containing 5–7 atoms, optionally 1 heteroatom, substituted with hydroxy, acyloxy, alkoxycarbonyloxy, or aryloxycarbonyloxy attached to a carbon atom that is three atoms from both Y groups attached to the phosphorus; or together V and Z are connected via an additional 3–5 atoms to form a cyclic group, optionally containing 1 heteroatom, that is fused to an aryl group at the beta and gamma position to the Y attached to the phosphorus;

together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3–5 atoms to form a cyclic group, optionally containing one heteroatom, and V must be aryl, substituted aryl, heteroaryl, or substituted heteroaryl;

together W and W' are connected via an additional 2–5 atoms to form a cyclic group, optionally containing 0–2 heteroatoms, and V must be aryl, substituted aryl, heteroaryl, or substituted heteroaryl;

Z is selected from the group consisting of —$CHR^2OH$, —$CHR^2OC(O)R^3$, —$CHR^2OC(S)R^3$, —$CHR^2OC(S)OR^3$, —$CHR^2OC(O)SR^3$, —$CHR^2OCO_2R^3$, —$OR^2$, —$SR^2$, —$CHR^2N_3$, —$CH_2aryl$, —$CH(aryl)OH$, —$CH(CH=CR^2{}_2)OH$, —$CH(C\equiv CR^2)OH$, —$R^2$, —$NR^2{}_2$, —$OCOR^3$, —$OCO_2R^3$, —$SCOR^3$, —$SCO_2R^3$, —$NHCOR^2$, —$NHCO_2R^3$, —$CH_2NHaryl$, —$(CH_2)_p$—$OR^2$, and —$(CH_2)_p$—$SR^2$;

p is an integer 2 or 3;

q is an integer 1 or 2;

with the provisos that:
a) V, Z, W, W' are not all —H; and
b) when Z is —$R^2$, then at least one of V, W, and W' is not —H, alkyl, aralkyl, or alicyclic;

$R^2$ is selected from the group consisting of $R^3$ and —H;

$R^3$ is selected from the group consisting of alkyl, aryl, alicyclic, and aralkyl;

each $R^4$ is independently selected from the group consisting of —H, and alkyl, or together $R^4$ and $R^4$ form a cyclic alkyl group;

$R^6$ is selected from the group consisting of —H, lower alkyl, acyloxyalkyl, alkoxycarbonyloxyalkyl, and lower acyl;

$R^5$ is selected from the group consisting of lower alkyl, lower aryl, lower aralkyl, and lower alicyclic;

$R^7$ is independently selected from the group consisting of —H, lower alkyl, lower alicyclic, lower aralkyl, lower aryl, and —$C(O)R^{10}$;

$R^8$ is independently selected from the group consisting of —H, lower alkyl, lower aralkyl, lower aryl, lower alicyclic, —$C(O)R^{10}$, or together they form a bidendate alkyl;

$R^9$ is selected from the group consisting of alkyl, aralkyl, and alicyclic;

$R^{10}$ is selected from the group consisting of —H, lower alkyl, —$NH_2$, lower aryl, and lower perhaloalkyl;

$R^{11}$ is selected from the group consisting of alkyl, aryl, —$NR^2{}_2$, and —$OR^2$, and pharmaceutically acceptable prodrugs and salts thereof Preferred A, L, and E groups for formula III include —H, —$NR^8{}_2$, —$NO^2$, hydroxy, alkylaminocarbonyl, halogen, —$OR^7$, —$SR^7$, lower perhaloalkyl, and C1–C5 alkyl, or together E and J form a cyclic group. Such a cyclic group may be aromatic, cyclic alkyl, or heterocyclic alkyl, and may be optionally substituted. Suitable aromatic groups include thiazole. Particularly preferred A, L and E groups are —$NR^8{}_2$, —H, hydroxy, halogen, lower alkoxy, lower perhaloalkyl, and lower alkyl.

Preferred A groups for formula III include, —$NR^8{}_2$, —H, halogen, lower perhaloalkyl, and lower alkyl.

Preferred L and E groups for formula III include —H, lower alkoxy, lower alkyl, and halogen.

Preferred J groups for formula III include —H, halogen, lower alkyl, lower hydroxylalkyl, —$NR^8{}_2$, lower $R^8{}_2N$-alkyl, lower haloalkyl, lower perhaloalkyl, lower alkenyl, lower alkynyl, lower aryl, heterocyclic, and alicyclic, or together with Y forms a cyclic group. Such a cyclic group may be aromatic, cyclic alkyl, or heterocyclic, and may be optionally substituted. Particularly preferred J groups include —H, halogen, and lower alkyl, lower hydroxyalkyl, —NR$^8_2$, lower R$^8_2$N-alkyl, lower haloalkyl, lower alkenyl, alicyclic, and aryl. Especially preferred are alicyclic and lower alkyl.

Preferred X$^3$ groups for formula III include -alkyl-, -alkynyl-, -aryl-, -alkoxyalkyl-, -alkylthio-, -alkylaminocarbonyl-, -alkylcarbonylamino-, -1,1-dihaloalkyl-, -carbonylalkyl-, and -alkyl(OH)—. Particularly preferred is -heteroaryl-, -alkylaminocarbonyl-, -1,1-dihaloalkyl-, and -alkoxyalkyl-. Also particularly preferred are -heteroaryl-, -alkylaminocarbonyl-, and -alkoxyalkyl-. Especially preferred are -methylaminocarbonyl-, -methoxymethyl-, and -furan-2,5-diyl-.

In another preferred aspect, when X$^3$ is aryl or alkylaryl, these groups are not linked 1,4 through a 6-membered aromatic ring.

Preferred Y$^3$ groups for formula III include —H, alkyl, aralkyl, aryl, and alicyclic, all except —H may be optionally substituted. Particularly preferred are lower alkyl, and alicyclic.

Preferred R$^4$ and R$^7$ groups include —H, and lower alkyl.

In one preferred aspect of compounds of formula III, A, L, and E are independently —H, lower alkyl, hydroxy, halogen, lower alkoxy, lower perhaloalkyl, and —NR$^8_2$; X$^3$ is -aryl-, -alkoxyalkyl-, -alkyl-, -alkylthio-, -1,1-dihaloalkyl-, -carbonylalkyl-, -alkyl(hydroxy)-, -alkylaminocarbonyl-, and -alkylcarbonylamino-; and each R$^4$ and R$^7$ is independently —H, and lower alkyl. Particularly preferred are such compounds where A, L, and E are independently —H, lower alkyl, halogen, and —NR$^8_2$; J is —H, halogen, haloalkyl, hydroxyalkyl, R$^8_2$N-alkyl, lower alkyl, lower aryl, heterocyclic, and alicyclic, or together with Y$^3$ forms a cyclic group; and X$^3$ is -heteroaryl-, -alkylaminocarbonyl-, -1,1-dihaloalkyl-, and -alkoxyalkyl-. Especially preferred are such compounds where A is —H, —NH$_2$, —F, and —CH$_3$, L is —H, —F, —OCH$_3$, —Cl, and —CH$_3$, E is —H and —Cl, J is —H, halo, C1–C5 hydroxyalkyl, C1–C5 haloalkyl, C1–C5 R$^8_2$N-alkyl, C1–C5 alicyclic, and C1–C5 alkyl, X$^3$ is —CH$_2$OCH$_2$—, and -furan-2,5-diyl-, and Y$^3$ is lower alkyl. Most preferred are the following such compounds and their salts, and prodrug and their salts:

1) A is —NH$_2$, L is —F, E is —H, J is —H, Y$^3$ is isobutyl, and X$^3$ is -furan-2,5-diyl-;
2) A, L, and J are —H, E is —Cl, Y$^3$ is isobutyl, and X$^3$ is -furan-2,5-diyl-;
3) A is —NH$_2$, L is —F, E and J are —H, Y$^3$ is cyclopropylmethyl, and X$^3$ is -furan-2,5-diyl-;
4) A is —NH$_2$, L is —F, E is —H, J is ethyl, Y$^3$ is isobutyl, and X$^3$ is -furan-2,5-diyl-;
5) A is —CH$_3$, L is —Cl, E and J are —H, Y$^3$ is isobutyl, and X$^3$ is -furan-2,5-diyl-;
6) A is —NH$_2$, L is —F, E is —H, J is —Cl, Y$^3$ is isobutyl, and X$^3$ is -furan-2,5-diyl-;
7) A is —NH$_2$, L is —F, E is —H, J is —Br, Y$^3$ is isobutyl, and X$^3$ is —CH$_2$OCH$_2$—; and
8) A, L, E, and J are —CH$_3$, Y$^3$ is cyclopropylmethyl, and X$^3$ is -furan-2,5-diyl-.

Also especially preferred are compounds where A is —NH$_2$, L is —F, E is —H, J is bromopropyl, bromobutyl, chlorobutyl, cyclopropyl, hydroxypropyl, or N,N-dimethylaminopropyl, and X$^3$ is -furan-2,5-diyl-. The preferred prodrug is where R$^1$ is pivaloyloxymethyl or its HCl salt.

In another aspect, preferred are compounds of formula IV

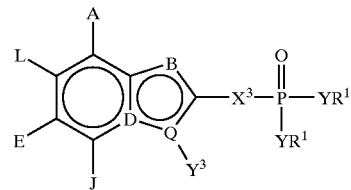

IV wherein:
B is selected from the group consisting of —NH—, —N= and —CH=;
D is selected from the group consisting of —C= and —N—;
Q is selected from the group consisting of

and

with the proviso that when B is —NH— then Q is —C= and D is

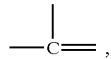

when B is —CH= then Q is —N— and D is

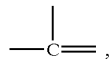

when B is —N=, then D is

and Q is —C=;

A, E, and L are selected from the group consisting of —NR$^8_2$, —NO$_2$, —H, —OR$^1$, —SR$^1$, —C(O)NR$^4_2$, halo, —COR$^{11}$, —SO$_2$R$^3$, guanidino, amidino, —NHSO$_2$R$^5$, —SO$_2$NR$^4_2$, —CN, sulfoxide, perhaloacyl, perhaloalkyl, perhaloalkoxy, C1–C5 alkyl, C2–C5 alkenyl, C2–C5 alkynyl, and lower alicyclic, or together A and L form a cyclic group, or together L and E form a cyclic group, or together E and J form a cyclic group including aryl, cyclic alkyl, and heterocyclic;

J is selected from the group consisting of —NR$^8_2$, —NO$_2$, —H, —OR$^7$, —SR$^7$, —C(O)NR$^4_2$, halo, —C(O)R$^{11}$, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y forms a cyclic group including aryl, cyclic alkyl and heterocyclic alkyl;

X$^3$ is selected from the group consisting of -alkyl(hydroxy)-, -alkyl-, -alkynyl-, -aryl-, -carbonylalkyl-, -1,1-dihaloalkyl-, -alkoxyalkyl-, -alkyloxy-, -alkylthioalkyl-, -alkylthio-, -alkylaminocarbonyl-, -alkylcarbonylamino-, -alicyclic-, -aralkyl-, -alkylaryl-, -alkoxycarbonyl-, -carbonyloxyalkyl-, -alkoxycarbonylamino-, and -alkylaminocarbonylamino-, all optionally substituted; with the proviso that $X^3$ is not substituted with —$COOR^2$, —$SO_3H$, or —$PO_3R^2{}_2$;

$Y^3$ is selected from the group consisting of —H, alkyl, alkenyl, alkynyl, aryl, alicyclic, aralkyl, aryloxyalkyl, alkoxyalkyl, —$C(O)R^3$, —$S(O)_2R^3$, —$C(O)$—$R^{11}$, —$CONHR^3$, —$NR^2{}_2$, and —$OR^3$, all except H are optionally substituted;

Y is independently selected from the group consisting of —O—, and —$NR^6$—;

when Y is —O—, then $R^1$ attached to —O— is independently selected from the group consisting of —H, alkyl, optionally substituted aryl, optionally substituted alicyclic where the cyclic moiety contains a carbonate or thiocarbonate, optionally substituted -alkylaryl, —$C(R^2)_2OC(O)NR^2{}_2$, —$NR^2$—$C(O)$—$R^3$, —$C(R^2)_2$—$OC(O)R^3$, —$C(R^2)_2$—$O$—$C(O)OR^3$, —$C(R^2)_2OC(O)SR^3$, -alkyl-S—$C(O)R^3$, -alkyl-S—S-alkylhydroxy, and -alkyl-S—S—S-alkylhydroxy, when Y is —$NR^6$—, then $R^1$ attached to —$NR^6$— is independently selected from the group consisting of —H, —$[C(R^2)_2]_q$—$COOR^3$, —$C(R^4)_2COOR^3$, —$[C(R^2)_2]_q$—$C(O)SR$ and -cycloalkylene-$COOR^3$;

or when either Y is independently selected from —O— and —$NR^6$—, then together $R^1$ and $R^1$ are -alkyl-S—S-alkyl- to form a cyclic group, or together $R^1$ and $R^1$ are

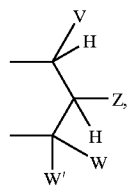

wherein

V, W, and W' are independently selected from the group consisting of —H, alkyl, aralkyl, alicyclic, aryl, substituted aryl, heteroaryl, substituted heteroaryl, 1-alkenyl, and 1-alkynyl; or together V and Z are connected via an additional 3–5 atoms to form a cyclic group containing 5–7 atoms, optionally 1 heteroatom, substituted with hydroxy, acyloxy, alkoxycarbonyloxy, or aryloxycarbonyloxy attached to a carbon atom that is three atoms from both Y groups attached to the phosphorus; or together V and Z are connected via an additional 3–5 atoms to form a cyclic group, optionally containing 1 heteroatom, that is fused to an aryl group at the beta and gamma position to the Y attached to the phosphorus;

together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3–5 atoms to form a cyclic group, optionally containing one heteroatom, and V must be aryl, substituted aryl, heteroaryl, or substituted heteroaryl;

together W and W' are connected via an additional 2–5 atoms to form a cyclic group, optionally containing 0–2 heteroatoms, and V must be aryl, substituted aryl, heteroaryl, or substituted heteroaryl;

Z is selected from the group consisting of —$CHR^2OH$, —$CHR^2OC(O)R^3$, —$CHR^2OC(S)R^3$, —$CHR^2OC(S)OR^3$, —$CHR^2OC(O)SR^3$, —$CHR^2OCO_2R^3$, —$OR^2$, —$SR^2$, —$CHR^2N_3$, —$CH_2aryl$, —$CH(aryl)OH$, —$CH(CH=CR^2{}_2)OH$, —$CH(C\equiv CR^2)OH$, —$R^2$, —$NR^2{}_2$, —$OCOR^3$, —$OCO_2R^3$, —$SCOR^3$, —$SCO_2R^3$, —$NHCOR^2$, —$NHCO_2R^3$, —$CH_2NHaryl$, —$(CH_2)_p$—$OR^2$, and —$(CH_2)_p$—$SR^2$;

p is an integer 2 or 3;

q is an integer 1 or 2;

with the provisos that:
a) V, Z, W, W' are not all —H; and
b) when Z is —$R^2$, then at least one of V, W, and W' is not —H, alkyl, aralkyl, or alicyclic;

$R^2$ is selected from the group consisting of $R^3$ and —H;

$R^3$ is selected from the group consisting of alkyl, aryl, alicyclic, and aralkyl;

each $R^4$ is independently selected from the group consisting of —H, and alkyl, or together $R^4$ and $R^4$ form a cyclic alkyl group;

$R^6$ is selected from the group consisting of —H, lower alkyl, acyloxyalkyl, alkoxycarbonyloxyalkyl, and lower acyl;

$R^5$ is selected from the group consisting of lower alkyl, lower aryl, lower aralkyl, and lower alicyclic;

$R^7$ is independently selected from the group consisting of —H, lower alkyl, lower alicyclic, lower aralkyl, lower aryl, and —$C(O)R^{10}$;

$R^8$ is independently selected from the group consisting of —H, lower alkyl, lower aralkyl, lower aryl, lower alicyclic, —$C(O)R^{10}$, or together they form a bidentate alkyl;

$R^9$ is selected from the group consisting of alkyl, aralkyl, and alicyclic;

$R^{10}$ is selected from the group consisting of —H, lower alkyl, —$NH_2$, lower aryl, and lower perhaloalkyl;

$R^{11}$ is selected from the group consisting of alkyl, aryl, —$NR_2{}^2$ and —$OR^2$; and pharmaceutically acceptable prodrugs and salts thereof.

Preferred A, L, and E groups in formula IV include —H, —$NR^8{}_2$, —$NO_2$, hydroxy, halogen, —$OR^7$, alkylaminocarbonyl, —$SR^7$, lower perhaloalkyl, and C1–C5 alkyl, or together E and J form a cyclic group. Such a cyclic group may be aromatic or cyclic alkyl, and may be optionally substituted. Suitable aromatic groups include thiazole. Particularly preferred A, L and E groups are —$NR^8{}_2$, —H, hydroxy, halogen, lower alkoxy, lower perhaloalkyl, and lower alkyl.

Preferred A groups in formula IV include —$NR^8{}_2$, lower alkyl, —H, halogen, and lower perhaloalkyl.

Preferred L and E groups in formula IV include —H, lower alkoxy, lower alkyl, and halogen.

Preferred J groups in formula IV include —H, halogen, lower alkyl, lower hydroxyalkyl, —$NR^8{}_2$, lower $R^8{}_2N$-alkyl, lower haloalkyl, lower perhaloalkyl, lower alkenyl, lower alkynyl, lower aryl, heterocyclic, and alicyclic or together with $Y^3$ forms a cyclic group. Such a cyclic group may be aromatic or cyclic alkyl, and may be optionally substituted. Particularly preferred J groups —H, halogen, lower alkyl, lower hydroxyalkyl, —$NR^8{}_2$, lower $R^8{}_2N$-alkyl, lower haloalkyl, lower alkenyl, alicyclic, and aryl.

Preferred $X^3$ groups in formula IV include -alkyl-, -alkynyl-, -alkoxyalkyl-, -alkylthio-, -aryl-, -alkylaminocarbonyl-, -alkylcarbonylamino-, -1,1-dihaloalkyl-, -carbonylalkyl-, and -alkyl(OH)—. Particularly preferred is -1,1-dihaloalkyl-, -alkylaminocarbonyl-, -alkoxyalkyl-, and -heteroaryl-. Such compounds that are especially preferred are -heteroaryl-, -alkylaminocarbonyl-, and -alkoxyalkyl-. Most preferred is -methylaminocarbonyl-, -methoxymethyl-, and -furan-2,5-diyl.

In one preferred aspect, $X^3$ is not -(C2–C3 alkyl)aminocarbonyl-.

Preferred $Y^3$ groups for formula IV include —H, alkyl, aryl, aralkyl, and alicyclic, all except —H may be optionally substituted. Particularly preferred $Y^3$ groups include lower alkyl, and alicyclic.

Preferred $R^4$ and $R^7$ groups include —H, and lower alkyl.

In one preferred aspect of formula IV, B is NH, D is

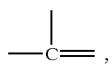

and Q is —C≡. In another preferred aspect, B is —N≡, D is

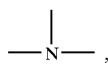

and Q is —C≡.

In another preferred aspect of formula IV, A, L, and E are independently —NR$^8{}_2$, lower alkyl, lower perhaloalkyl, lower alkoxy, halogen, —OH, or —H, $X^3$ is -aryl-, -alkoxyalkyl-, -alkyl-, -alkylthio-, -1,1-dihaloalkyl-, -carbonylalkyl-, -alkyl(hydroxy)-, -alkylaminocarbonyl-, and -alkylcarbonylamino-, and each $R^4$ and $R^7$ is independently —H, or lower alkyl. Particularly preferred are such compounds where A, L, and E are independently —H, lower alkyl, halogen, and —NR$^8{}_2$; J is —H, halogen, haloalkyl, hydroxyalkyl, —R$^8{}_2$N-alkyl, lower alkyl, lower aryl, heterocyclic, and alicyclic, or together with $Y^3$ forms a cyclic group; and $X^3$ is -heteroaryl-, -alkylaminocarbonyl-, -1,1-dihaloalkyl-, and -alkoxyalkyl-. Especially preferred are such compounds where A is —H, —NH$_2$, —F, or —CH$_3$, L is —H, —F, —OCH$_3$, or —CH$_3$, E is —H, or —Cl, J is —H, halo, C1–C5 hydroxyalkyl, C1–C5 haloalkyl, C1–C5 R$^8{}_2$N-alkyl, C1–C5 alicyclic or C1–C5 alkyl, $X^3$ is —CH$_2$OCH$_2$—, or -furan-2,5-diyl-; and $Y^3$ is lower alkyl. Preferred are such compounds where B is NH, D is

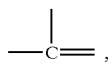

and Q is —C≡ or where B is —N≡, D is

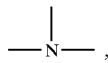

and Q is —C≡.

Most preferred are compounds where:
1) A is —NH$_2$, L is —F, E is —H, J is —H, $Y^3$ is isobutyl, and $X^3$ is -furan-2,5-diyl-;
2) A is —NH$_2$, L is —F, E is —H, J is —Cl, $Y^3$ is isobutyl, and $X^3$ is -furan-2,5-diyl-.

3) A is —H, L is —H, E is —Cl, J is —H, B is —NH, D is

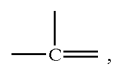

Q is —C≡, and $Y^3$ is isobutyl; and
4) A is —CH$_3$, L is —H, E is —H, J is —H, B is —N≡, D is

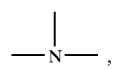

Q is —C≡, and $Y^3$ is isobutyl.

Particularly preferred are such compounds where $R^1$ is —CH$_2$OC(O)—C(CH$_3$)$_3$.

Another especially preferred aspect are such compounds where A, L, and E are —H, lower alkyl, halogen, or —NR$^8{}_2$, J is —H, halogen, lower alkyl, lower aryl, heterocyclic, or alicyclic, or together with $Y^3$ forms a cyclic group, and $X^3$ is -heteroaryl-, -alkylaminocarbonyl-, or -alkoxyalkyl-.

In another aspect, preferred are compounds of formula V wherein M is R$^5$—X—
wherein
R$^5$ is selected from the group consisting of:

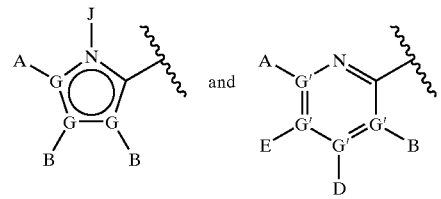

wherein:
each G is independently selected from the group consisting of C, N, O, S, and Se, and wherein only one G may be O, S, or Se, and at most one G is N;
each G' is independently selected from the group consisting of C and N and wherein no more than two G' groups are N;
A is selected from the group consisting of —H, —NR$^4{}_2$, —CONR$^4{}_2$, —CO$_2$R$^3$, halo, —S(O)R$^3$, —SO$_2$R$^3$, alkyl, alkenyl, alkynyl, perhaloalkyl, haloalkyl, aryl, —CH$_2$OH, —CH$_2$NR$^4{}_2$, —CH$_2$CN, —CN, —C(S)NH$_2$, —OR$^3$, —SR$^3$, —N$_3$, —NHC(S)NR$^4{}_2$, —NHAc, and null;
each B and D are independently selected from the group consisting of —H, alkyl, alkenyl, alkynyl, aryl, alicyclic, aralkyl, alkoxyalkyl, —C(O)R$^{11}$, —C(O)SR$^3$, —SO$_2$R$^{11}$, —S(O)R$^3$, —CN, —NR$^9{}_2$, —OR$^3$, —SR$^3$, perhaloalkyl, halo, —NO$_2$, and null, all except —H, —CN, perhaloalkyl, —NO$_2$, and halo are optionally substituted;
E is selected from the group consisting of —H, alkyl, alkenyl, alkynyl, aryl, alicyclic, alkoxyalkyl, —C(O)OR$^3$, —CONR$^4{}_2$, —CN, —NR$^9{}_2$, —NO$_2$, —OR$^3$, —SR$^3$, perhaloalkyl, halo, and null, all except —H, —CN, perhaloalkyl, and halo are optionally substituted;
J is selected from the group consisting of —H and null;
X is an optionally substituted linking group that links R$^5$ to the phosphorus atom via 2–4 atoms, including 0–1 heteroatoms selected from N, O, and S, except that if X is urea or carbamate there is 2 heteroatoms, measured by the shortest path between $R^5$ and the phosphorus atom, and wherein the atom attached to the phosphorus is a carbon atom, and wherein X is selected from the group consisting of -alkyl(hydroxy)-, -alkynyl-, -heteroaryl-, -carbonylalkyl-, 1,1-dihaloalkyl-, -alkoxyalkyl-, -alkyloxy-, -alkylthioalkyl-, -alkylthio-, -alkylaminocarbonyl-, -alkylcarbonylamino-, -alkoxycarbonyl-, -carbonyloxyalkyl-, -alkoxycarbonylamino-, and -alkylaminocarbonylamino-, all optionally substituted; with the proviso that X is not substituted with —$COOR^2$, —$SO_3H$, or —$PO_3R^2_2$;

$R^2$ is selected from the group consisting of $R^3$ and —H;

$R^3$ is selected from the group consisting of alkyl, aryl, alicyclic, and aralkyl;

each $R^4$ is independently selected from the group consisting of —H, and alkyl, or together $R^4$ and $R^4$ form a cyclic alkyl group;

each $R^9$ is independently selected from the group consisting of —H, alkyl, aralkyl, and alicyclic, or together $R^9$ and $R^9$ form a cyclic alkyl group;

$R^{11}$ is selected from the group consisting of alkyl, aryl, —$NR^2_2$, and —$OR^2$; and with the proviso that:

1) when G' is N, then the respective A, B, D, or E is null;
2) at least one of A and B, or A, B, D, and E is not selected from the group consisting of —H or null;
3) when $R^5$ is a six-membered ring, then X is not any 2 atom linker, an optionally substituted -alkyloxy-, or an optionally substituted -alkylthio-;
4) when G is N, then the respective A or B is not halogen or a group directly bonded to G via a heteroatom;
5) when X is not a -heteroaryl- group, then $R^5$ is not substituted with two or more aryl groups;

Y is independently selected from the group consisting of —O—, and —$NR^6$—;

when Y is —O—, then $R^1$ attached to —O— is independently selected from the group consisting of —H, alkyl, optionally substituted aryl, optionally substituted alicyclic where the cyclic moiety contains a carbonate or thiocarbonate, optionally substituted -alkylaryl, —$C(R^2)_2OC(O)NR^2_2$, —$NR^2$—$C(O)$—$R^3$, —$C(R^2)_2$—$OC(O)R^3$, —$C(R^2)_2$—O—$C(O)OR^3$, —$C(R^2)_2OC(O)SR^3$, -alkyl-S—$C(O)R^3$, -alkyl-S—S-alkylhydroxy, and -alkyl-S—S—S-alkylhydroxy, when Y is —$NR^6$—, then $R^1$ attached to —$NR^6$— is independently selected from the group consisting of —H, —$[C(R^2)_2]_q$—$COOR^3$, —$C(R^4)_2COOR^3$, —$[C(R^2)_2]_q$—$C(O)SR$, and -cycloalkylene-$COOR^3$;

or when either Y is independently selected from —O— and —$NR^6$—, then together $R^1$ and $R^1$ are -alkyl-S—S-alkyl- to form a cyclic group, or together $R^1$ and $R^1$ are

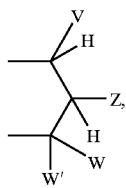

wherein

V, W, and W' are independently selected from the group consisting of —H, alkyl, aralkyl, alicyclic, aryl, substituted aryl, heteroaryl, substituted heteroaryl, 1-alkenyl, and 1-alkynyl; or together V and Z are connected via an additional 3–5 atoms to form a cyclic group containing 5–7 atoms, optionally 1 heteroatom, substituted with hydroxy, acyloxy, alkoxycarbonyloxy, or aryloxycarbonyloxy attached to a carbon atom that is three atoms from both Y groups attached to the phosphorus; or together V and Z are connected via an additional 3–5 atoms to form a cyclic group, optionally containing 1 heteroatom, that is fused to an aryl group at the beta and gamma position to the Y attached to the phosphorus;

together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3–5 atoms to form a cyclic group, optionally containing one heteroatom, and V must be aryl, substituted aryl, heteroaryl, or substituted heteroaryl;

together W and W' are connected via an additional 2–5 atoms to form a cyclic group, optionally containing 0–2 heteroatoms, and V must be aryl, substituted aryl, heteroaryl, or substituted heteroaryl;

Z is selected from the group consisting of —$CHR^2OH$, —$CHR^2OC(O)R^3$, —$CHR^2OC(S)R^3$, —$CHR^2OC(S)OR^3$, —$CHR^2OC(O)SR^3$, —$CHR^2OCO_2R^3$, —$OR^2$, —$SR^2$, —$CHR^2N_3$, —$CH_2aryl$, —$CH(aryl)OH$, —$CH(CH=CR^2_2)OH$, —$CH(C\equiv CR^2)OH$, —$R^2$, $NR^2_2$, —$OCOR^3$, —$OCO_2R^3$, —$SCOR^3$, —$SCO_2R^3$, —$NHCOR^2$, —$NHCO_2R^3$, —$CH_2NHaryl$, —$(CH_2)_p$—$OR^2$, and —$(CH_2)_p$—$SR^2$;

p is an integer 2 or 3;

is an integer 1 or 2;

with the provisos that:
a) V, Z, W, W' are not all —H; and
b) when Z is —$R^2$, then at least one of V, W, and W' is not —H, alkyl, aralkyl, or alicyclic;

$R^2$ is selected from the group consisting of $R^3$ and —H;

$R^3$ is selected from the group consisting of alkyl, aryl, alicyclic, and aralkyl;

each $R^4$ is independently selected from the group consisting of —H, and alkyl, or together $R^4$ and $R^4$ form a cyclic alkyl group;

$R^6$ is selected from the group consisting of —H, lower alkyl, acyloxyalkyl, alkoxycarbonyloxyalkyl, and lower acyl;

In one preferred aspect of formula V-1 and formula V-2 compounds,

A" is selected from the group consisting of —$NH_2$, —$CONH_2$, halo, —$CH_3$, —$CF_3$, —$CH_2$-halo, —CN, —$OCH_3$, —$SCH_3$, and —H;

B" is selected from the group consisting of —H, —$C(O)R^{11}$, —$C(O)SR^3$, alkyl, aryl, alicyclic, halo, —CN, —$SR^3$, $OR^3$ and —$NR^9_2$;

D" is selected from the group consisting of —H, —$C(O)R^{11}$, —$C(O)SR^3$, —$NR^9_2$, alkyl, aryl, alicyclic, halo, and —$SR^3$;

E" is selected from the group consisting of —H, C1–C6 alkyl, lower alicyclic, halo, —CN, —C(O)OR³, and —SR³.

X is selected from the group consisting of -alkyl (hydroxy)-, -alkyl-, -alkynyl-, -aryl-, -carbonylalkyl-, -1,1-dihaloalkyl-, -alkoxyalkyl-, -alkyloxy-, -alkylthioalkyl-, -alkylthio-, -alkylaminocarbonyl-, -alkylcarbonylamino-, -alicyclic-, -aralkyl-, -alkylaryl-, -alkoxycarbonyl-, -carbonyloxyalkyl-, -alkoxycarbonylamino-, and -alkylaminocarbonylamino-, all optionally substituted;

when both Y groups are —O—, then R¹ is independently selected from the group consisting of optionally substituted aryl, optionally substituted benzyl, —C(R²)₂OC(O)R³, —C(R²)₂OC(O)OR³, and —H; or when one Y is —O—, then R¹ attached to —O— is optionally substituted aryl; and the other Y is —NR⁶—, then R¹ attached to —NR⁶— is selected from the group consisting of —C(R⁴)₂COOR³, and —C(R²)₂COOR³; or when Y is —O— or —NR⁶—, then together R¹ and R¹ are

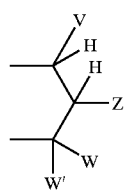

wherein

V, W, and W' are independently selected from the group consisting of —H, alkyl, aralkyl, alicyclic, aryl, substituted aryl, heteroaryl, substituted heteroaryl, 1-alkenyl, and 1-alkynyl, or together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3–5 atoms to form a cyclic group, optionally containing one heteroatom, and V must be aryl, substituted aryl, heteroaryl, or substituted heteroaryl;

together W and W' are connected via an additional 2–5 atoms to form a cyclic group, optionally containing 0–2 heteroatoms, and V must be aryl, substituted aryl, heteroaryl, or substituted heteroaryl;

Z is selected from the group consisting of —CHR²OH, —CHR²OC(O)R³, —CHR²OC(S)R³, —CHR²OC(S)OR³, —CHR²OC(O)SR³, —CHR²OCO₂R³, —OR², —SR², —R², —NHCOR², —NHCO₂R³, —(CH₂)ₚ—OR², and —(CH₂)ₚ—SR²;

with the provisos that:
a) V, Z, W, W' are not all —H;
b) when Z is —R², then at least one of V, W, and W' is not —H, alkyl, aralkyl, or alicyclic; and
c) both Y groups are not —NR⁶—;

R² is selected from the group consisting of R³ and —H;

R³ is selected from the group consisting of alkyl, aryl, alicyclic, and aralkyl;

R⁶ is selected from the group consisting of —H, and lower alkyl.

In one particularly preferred aspect of formula I where M is R⁵—X— and R⁵ is

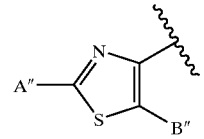

X is selected from the group consisting of methylenoxycarbonyl, and furan-2,5-diyl; at least one Y group is —O—; and pharmaceutically acceptable salts and prodrugs thereof. More preferred are such compounds wherein when Y is —O—, then R¹ attached to —O— is independently selected from the group consisting of —H, optionally substituted phenyl, —CH₂OC(O)-tBu, —CH₂OC(O)Et and —CH₂OC(O)-iPr;

when Y is —NR⁶—, then R¹ is attached to —NR⁶— independently selected from the group consisting of —C(R²)₂COOR³, —C(R⁴)₂COOR³, or when Y is —O— or —NR⁶—, and at least one Y is —O—, then together R¹ and R¹ are

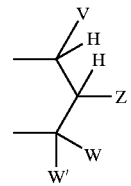

wherein

V is selected from the group consisting of optionally substituted aryl, and optionally substituted heteroaryl; and Z, W', and W are H; and R⁶ is selected from the group consisting of —H, and lower alkyl.

The following such compounds and their salts are most preferred:
1) A" is —NH₂, X is furan-2,5-diyl, and B" is —CH₂—CH(CH₃)₂;
2) A" is —NH₂, X is furan-2,5-diyl, and B" is —COOEt;
3) A" is —NH₂, X is furan-2,5-diyl, and B" is —SCH₃;
4) A" is —NH₂, X is furan-2,5-diyl, and B" is —SCH₂CH₂SCH₃;
5) A" is —NH₂, X is methyleneoxycarbonyl, and B" is —CH(CH₃)₂.

In another particularly preferred aspect of formula I where M is R⁵—X—, R⁵ is

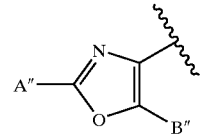

X is furan-2,5-diyl, and methyleneoxycarbonyl, and A" is —NH₂; at least one Y group is —O—; and pharmaceutically acceptable salts and prodrugs thereof. Especially preferred are such compounds when Y is —O—, then each R¹ is independently selected from the group consisting of —H, optionally substituted phenyl, —CH$_2$OC(O)-tBu, —CH$_2$OC(O)Et, and, —CH$_2$OC(O)-iPr;

or when Y is —NR$^6$—, then each R$^1$ is independently selected from the group consisting of —C(R$^2$)$_2$C(O)OR$^3$, and —C(R$^4$)$_2$COOR$^3$;

or when Y is independently selected from —O— and —NR$^6$—, then together R$^1$ and R$^1$ are

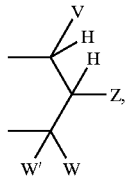

wherein

V selected from the group consisting of optionally substituted aryl and optionally substituted heteroaryl; and Z, W', and W are H. Also especially preferred are such compounds wherein B" is —SCH$_2$CH$_2$CH$_3$.

In another particularly preferred aspect of formula I where M is R$^5$—X— and R$^5$ is

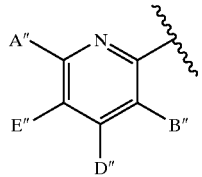

A" is —NH$_2$, E" and D" are —H, B" is n-propyl and cyclopropyl, X is furan-2,5-diyl and methyleneoxycarbonyl; at least one Y group is —O—; and pharmaceutically acceptable salts and prodrugs thereof. Especially preferred are such compounds wherein R$^1$ is selected from the group consisting of —H, optionally substituted phenyl —CH$_2$OC(O)-tBu, —CH$_2$OC(O)Et, and —CH$_2$OC(O)-iPr, or when Y is —NR$^6$—, then each R$^1$ is independently selected from the group consisting of —C(R$^2$)$_2$C(O)OR$^3$, and —C(R$^4$)$_2$COOR$^3$;

or when either Y is independently selected from —O— and —NR$^6$—, and at least one Y is —O—, then together R$^1$ and R$^1$ are

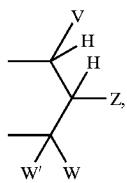

wherein

V is selected from the group consisting of optionally substituted aryl and optionally substituted heteroaryl; and Z, W', and W are H.

In another particularly preferred aspect of formula, I where M is R$^5$—X— and R$^5$ is

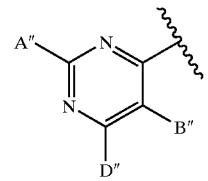

A" is —NH$_2$, D" is —H, B" is n-propyl and cyclopropyl, X is furan-2,5-diyl and methyleneoxycarbonyl; at least one, Y group is —O—; and pharmaceutically acceptable salts and prodrugs thereof. Especially preferred are such compounds wherein when Y is —O— then R$^1$ is selected from the group consisting of —H, optionally substituted phenyl, —CH$_2$OC(O)-tBu, —CH$_2$OC(O)Et, and —CH$_2$OC(O)-iPr;

or when one Y is —O— and its corresponding R$^1$ is -phenyl while the other Y is —NH— and its corresponding R$^1$ is —CH(Me)C(O)OEt, or when at least one Y group is —O—, then together R$^1$ and R$^1$ are

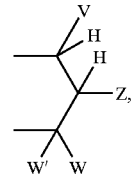

wherein

V is selected from the group, consisting of optionally substituted aryl and optionally substituted heteroaryl; and Z, W', and W are H.

Preferred are compounds of formula (X):

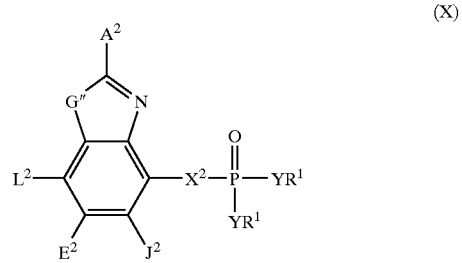

(X)

wherein:

G" is selected from the group consisting of —O— and —S—;

A$^2$, L$^2$, E$^2$, and J$^2$ are selected from the group consisting of —NR$^4$$_2$, —NO$_2$, —H, —OR$^2$, —SR$^2$, —C(O)NR$^4$$_2$, halo, —COR$^{11}$, —SO$_2$R$^3$, guanidinyl, amidinyl, aryl, aralkyl, alkyoxyalkyl, —SCN, —NHSO$_2$R$^9$, —SO$^2$NR$^4$$_2$, —CN, —S(O)R$^3$, perhaloacyl, perhaloalkyl, perhaloalkoxy, C1–C5 alkyl, C2–C5 alkenyl, C2–C5 alkynyl, and lower alicyclic, or together L$^2$ and E$^2$ or E$^2$ and J$^2$ form an annulated cyclic group;

X$^2$ is selected from the group consisting of —CR$^2$—, —CF$_2$—, —OCR$^2$$_2$—, —SCR$^2$$_2$—, —O—C(O)—, —S—C(O)—, —O—C(S)—, and —NR$^{19}$CR$^2$$_2$—, and wherein in the atom attached to the phosphorus is a carbon atom; with the proviso that X$^2$ is not substituted with —COOR$^2$, —SO$_3$H, or —PO$_3$R$^2$$_2$;

$R^{19}$ is selected from the group consisting of lower alkyl, —H, and —COR²; and Y is independently selected from the group consisting of —O—, and —NR⁶—;

when Y is —O—, then R¹ attached to —O— is independently selected from the group consisting of —H, alkyl, optionally substituted aryl, optionally substituted alicyclic where the cyclic moiety contains a carbonate or thiocarbonate, optionally substituted -alkylaryl, —C(R²)₂OC(O)NR²₂, —NR²—C(O)—R³, —C(R²)₂—OC(O)R³, —C(R²)₂—O—C(O)OR³, —C(R²)₂OC(O)SR³, -alkyl-S—C(O)R³, -alkyl-S—S-alkylhydroxy, and -alkyl-S—S—S-alkylhydroxy, when Y is —NR⁶—, then R¹ attached to —NR⁶— is independently selected from the group consisting of —H, —[C(R²)₂]_q—COOR³, —C(R⁴)₂COOR³, —[C(R²)₂]_q—C(O)SR, and -cycloalkylene-COOR³;

or when either Y is independently selected from —O— and —NR⁶—, then together R¹ and R¹ are -alkyl-S—S-alkyl- to form a cyclic group, or together R¹ and R¹ are

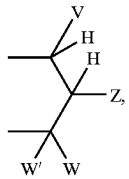

wherein

V, W, and W' are independently selected from the group consisting of —H, alkyl, aralkyl, alicyclic, aryl, substituted aryl, heteroaryl, substituted heteroaryl, 1-alkenyl, and 1-alkynyl; or together V and Z are connected via an additional 3–5 atoms to form a cyclic group containing 5–7 atoms, optionally 1 heteroatom, substituted with hydroxy, acyloxy, alkoxycarbonyloxy, or aryloxycarbonyloxy attached to a carbon atom that is three atoms from both Y groups attached to the phosphorus; or together V and Z are connected via an additional 3–5 atoms to form a cyclic group, optionally containing 1 heteroatom, that is fused to an aryl group at the beta and gamma position to the Y attached to the phosphorus;

together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3–5 atoms to form a cyclic group, optionally containing one heteroatom, and V must be aryl, substituted aryl, heteroaryl, or substituted heteroaryl;

together W and W' are connected via an additional 2–5 atoms to form a cyclic group, optionally containing 0–2 heteroatoms, and V must be aryl, substituted aryl, heteroaryl, or substituted heteroaryl;

Z is selected from the group consisting of —CHR²OH, —CHR²OC(O)R³, —CHR²OC(S)R³, —CHR²OC(S)OR³, —CHR²OC(O)SR³, —CHR²OCO₂R³, —OR², —SR², —CHR²N₃, —CH₂aryl, —CH(aryl)OH, —CH(CH=CR²₂)OH, —CH(C≡CR²)OH, —R², —NR²₂, —OCOR³, —OCO₂R³, —SCOR³, —SCO₂R³, —NHCOR², —NHCO₂R³, —CH₂NHaryl, —(CH₂)_p—OR², and —(CH₂)_p—SR²;

p is an integer 2 or 3;

q is an integer 1 or 2;

with the provisos that:
a) V, Z, W, W' are not all —H; and
b) when Z is —R², then at least one of V, W, and W' is not —H, alkyl, aralkyl, or licyclic;

R² is selected from the group consisting of R³ and —H;

R³ is selected from the group consisting of alkyl, aryl, alicyclic, and aralkyl;

each R⁴ is independently selected from the group consisting of —H, alkyl, or together R⁴ and R⁴ form a cyclic alkyl;

R⁶ is selected from the group consisting of —H, lower alkyl, acyloxyalkyl, alkoxycarbonyloxyalkyl, and lower acyl;

each R⁹ is independently selected from the group consisting of —H, alkyl, aralkyl, and alicyclic, or together R⁹ and R⁹ form a cyclic alkyl group;

R¹¹ is selected from the group consisting of alky, aryl, NR²₂, and —OR²; and pharmaceutically acceptable prodrugs and salts thereof More preferred are compounds wherein G" is —S—. Most preferred are compounds wherein A², L², E², and J² are independently selected from the group consisting of —H, —NR⁴₂, —S—C≡N, halogen, —OR³, hydroxy, -alkyl(OH), aryl, alkyloxycarbonyl, —SR³, lower perhaloalkyl, and C1–C5 alkyl, or together L² and E² form an annulated cyclic group. More preferably A², L², E² and J² are independently selected from the group consisting of —H, —NR⁴₂, —S—C≡N, halogen, lower alkoxy, hydroxy, lower alkyl(hydroxy), lower aryl, and C1–C5 alkyl, or together L² and E² form an annulated cyclic group.

Most preferred A² groups include —NH₂, —H, halo, and C1–C5 alkyl.

Most preferred L² and E² groups are those independently selected from the group consisting of —H, —S—C≡N, lower alkoxy, C1–C5 alkyl, lower alkyl(hydroxy), lower aryl, and halogen or together L² and E² form an annulated cyclic group containing an additional 4 carbon atoms.

Most preferred J² groups include —H, and C1–C5 alkyl.

Preferred X² groups include —CF₂—, —CH₂—, —OC(O)— —OCH₂—, —SCH₂—, —NHCH₂—, and —N(C(O)CH₃)—CH₂—. More preferred are —OCH₂—, —SCH₂—, and —N(C(O)CH₃)—CH₂—. Most preferred is —OCH₂—.

One preferred aspect include compound wherein A² is selected from the group consisting of —H, —NH₂, —CH₃, —Cl, and —Br;

L² is —H, lower alkyl, halogen, lower alkyloxy, hydroxy, -alkenylene-OH, or together with E² forms a cyclic group including aryl, cyclic alkyl, heteroaryls, heterocyclic alkyl;

E² is selected from the groups consisting of H, lower alkyl, halogen, SCN, lower alkyloxycarbonyl, lower alkyloxy, or together with L² forms a cyclic group including aryl, cyclic alkyl, heteroaryl, or heterocyclic alkyl;

J² is selected from the groups consisting of H, halogen, and lower alkyl;

G" is —S—;

X² is —OCH₂—;

and pharmaceutically acceptable salts and prodrugs thereof. More preferred are such compounds wherein $R^{18}$ is selected from the group consisting of —H, methyl, and ethyl;

$R^{12}$ and $R^{13}$ are independently selected from the group consisting of —H, methyl, i-propyl, i-butyl, and benzyl, or together are connected via 2–5 carbon atoms to form a cycloalkyl group;

$R^{14}$ is —$OR^{17}$;

$R^{17}$ is selected from the group consisting of methyl, ethyl, propyl, t-butyl, and benzyl; and $R^{15}$ and $R^{16}$ are independently selected from the group consisting of lower alkyl, and lower aralkyl, or together $R^{15}$ and $R^{16}$ are connected via 2–6 atoms, optionally including 1 heteroatom selected from the group consisting of O, and N.

Also more preferred are such compounds where $A^2$ is $NH_2$, $L^2$ is selected from the group consisting of —Et and —Cl, $E^2$ is selected from the group consisting of —SCN, —Et, and —Br, and $J^2$ is —H. Particularly preferred are such compounds wherein

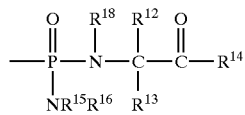

is selected from the group consisting of

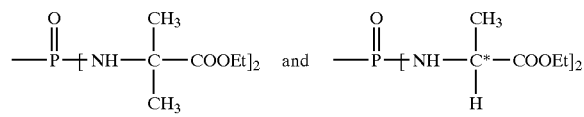

wherein C* has S stereochemistry.

Preferred $R^{18}$ groups include —H, methyl, and ethyl. More preferred is —H and methyl. Especially preferred is —H.

Preferred compounds include those wherein each $R^{12}$ and $R^{13}$ is independently selected from the group consisting of —H, methyl, ethyl, n-propyl, i-propyl, n-butyl, i-butyl, —$CH_2CH_2$—$SCH_3$, phenyl, and benzyl, or together $R^{12}$ and $R^{13}$ are connected via 2–5 carbon atoms to form a cycloalkyl group. More preferred is each $R^{12}$ and $R^{13}$ is independently selected from the group consisting of —H, methyl, i-propyl, i-butyl, and benzyl, or together $R^{12}$ and $R^{13}$ are connected via 2–5 carbon atoms to form a cycloalkyl group. Also more preferred are such compounds wherein each $R^{12}$ and $R^{13}$ is independently selected from the group consisting of —H, methyl, i-propyl, and benzyl, or together $R^{12}$ and $R^{13}$ are connected via 4 carbon atoms to form a cyclopentyl group. Especially preferred are those compounds wherein $R^{12}$ and $R^{13}$ are both —H, both methyl, or $R^{12}$ is H and $R^{13}$ is selected from the group consisting of methyl, i-propyl, and benzyl. Most preferred are such compounds wherein is 1, and $R^{12}$ is —H, then the carbon attached to $R^{12}$ and $R^{13}$ has S stereochemistry.

Preferably, n is an integer of from 1–2. More preferred is when n is 1.

Preferred compounds include those wherein each $R^{14}$ is independently selected from the group consisting of —$OR^{17}$, and —$SR^{17}$; and $R^{17}$ is selected from the group consisting of optionally substituted methyl, ethyl, propyl, t-butyl, and benzyl. More preferred are such compounds wherein each $R^{14}$ is independently selected from the group consisting of —$OR^{17}$; and $R^{17}$ is selected from the group consisting of methyl, ethyl, propyl, and benzyl. Most preferred are such compounds wherein $R^{17}$ is selected from the group consisting of ethyl, and benzyl.

Preferred are compounds wherein $R^{15}$ is not H. More preferred are compounds wherein $R^{15}$ and $R^{16}$ are independently selected from the group consisting of lower alkyl, and lower aralkyl, or together $R^{15}$ and $R^{16}$ are connected via 2–6 atoms, optionally including 1 heteroatom selected from the group consisting of O, N, and S. Also more preferred are compounds wherein $R^{15}$ and $R^{16}$ are independently selected from the group consisting of C1–C6 alkyl, or together $R^{15}$ and $R^{16}$ are connected via 2–6 atoms, optionally including 1 heteroatom selected from the group consisting of O, N, and S. In one aspect, particularly preferred are compounds wherein —$NR^{15}R^{16}$ is a cyclic amine. Especially preferred are such compounds wherein —$NR^{15}R^{16}$ is selected from the group consisting of morpholinyl and pyrrolidinyl.

Preferred are compounds $R^{16}$ is —$(CR^{12}R^{13})_n$—C(O)—$R^{14}$;

More preferred are compounds where n is 1, and wherein $R^{18}$ is selected from the group consisting of —H, methyl, and ethyl;

$R^{12}$ and $R^{13}$ are independently selected from the group consisting of —H, methyl, i-propyl, i-butyl, and benzyl, or together are connected via 2–5 carbon atoms to form a cycloalkyl group;

$R^{14}$ is —$OR^{17}$;

$R^{17}$ is selected from the group consisting of methyl, ethyl, propyl, t-butyl, and benzyl; and $R^{15}$ and $R^{16}$ are independently selected from the group consisting of lower alkyl, and lower aralkyl, or together $R^{15}$ and $R^{16}$ are connected via 2–6 atoms, optionally including 1 heteroatom selected from the group consisting of O, and N. Particularly preferred are such compounds that are of the formula:

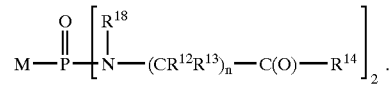

More preferred are such compounds wherein n is 1. Especially preferred are such compounds wherein when $R^{12}$ and $R^{13}$ are not the same, then $H_2N$—$CR^{12}R^{13}$—C(O)—$R^{14}$ is an ester, or thioester of a naturally occurring amino acid; and $R^{14}$ selected from the group consisting of —$OR^{17}$ and —$SR^{17}$.

In one aspect, preferred are compounds of formula IA or formula I wherein M is

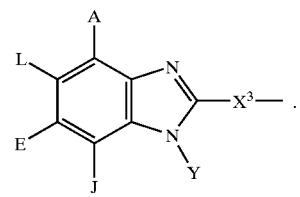

wherein:

A, E, and L are selected from the group consisting of —$NR^8_2$, —$NO_2$, —H, —$OR^7$, —$SR^7$, —$C(O)NR^4_2$, halo, —$COR^{11}$, —$SO_2R^3$, guanidine, amidine, —$NHSO_2R^5$, —$SO_2NR^4_2$, —CN, sulfoxide, perhaloacyl, perhaloalkyl, perhaloalkoxy, C1–C5 alkyl, C2–C5 alkenyl, C2–C5 alkynyl, and lower alicyclic, or together A and L form a cyclic group, or together L and E form a cyclic group, or together E and J form a cyclic group including aryl, cyclic alkyl, and heterocyclic;

J is selected from the group consisting of —NR$^8_2$, —NO$_2$, —H, —OR$^7$, —SR$^7$, —C(O)NR$^4_2$, halo, —C(O)R$^{11}$, —CN, sulfonyl, sulfoxide, perhaloalkyl, hydroxyalkyl, perhaloalkoxy, alkyl, haloalkyl, aminoalkyl, alkenyl, alkynyl, alicyclic, aryl, and aralkyl, or together with Y forms a cyclic group including aryl, cyclic alkyl and heterocyclic alkyl;

X$^3$ is selected from the group consisting of -alkyl (hydroxy)-, -alkyl-, -alkynyl-, -aryl-, -carbonylalkyl-, -1,1-dihaloalkyl-, -alkoxyalkyl-, -alkyloxy-, -alkylthioalkyl-, -alkylthio-, -alkylaminocarbonyl-, -alkylcarbonylamino-, -alicyclic-, -aralkyl-, -alkylaryl-, -alkoxycarbonyl-, -carbonyloxyalkyl-, -alkoxycarbonylamino-, and -alkylaminocarbonylamino-, all optionally substituted; with the proviso that X$^3$ is not substituted with —COOR$^2$, —SO$_3$H, or —PO$_3$R$^2_2$;

Y$^3$ is selected from the group consisting of —H, alkyl, alkenyl, alkynyl, aryl, alicyclic, aralkyl, aryloxyalkyl, alkoxyalkyl, —C(O)R$^3$, —S(O)$_2$R$^3$, —C(O)—R$^{11}$, —CONHR$^3$, —NR$^2_2$, and —OR$^3$, all except H are optionally substituted;

R$^2$ is selected from the group consisting of R$^3$ and —H;

R$^3$ is selected from the group consisting of alkyl, aryl, alicyclic, and aralkyl;

each R$^4$ is independently selected from the group consisting of —H, and alkyl, or Together R$^4$ and R$^4$ form a cyclic alkyl group;

R$^5$ is selected from the group consisting of lower alkyl, lower aryl, lower aralkyl, and lower alicyclic;

R$^7$ is independently selected from the group consisting of —H, lower alkyl, lower alicyclic, lower aralkyl, lower aryl, and —C(O)R$^{10}$;

R$^8$ is independently selected from the group consisting of —H, lower alkyl, lower aralkyl, lower aryl, lower alicyclic, —C(O)R$^{10}$, or together they form a bidendate alkyl;

each R$^9$ is independently selected from the group consisting of —H, alkyl, aralkyl, and alicyclic, or together R$^9$ and R$^9$ form a cyclic alkyl group;

R$^{10}$ is selected from the group consisting of —H, lower alkyl, —NH$_2$, lower aryl, and lower perhaloalkyl;

R$^{11}$ is selected from the group consisting of alkyl, aryl, —NR$^2_2$, and —OR$^2$; and pharmaceutically acceptable prodrugs and salts thereof; with the provisos that:
a) when X$^3$ is alkyl or alkene, then A is —N(R$^8_2$);
b) X$^3$ is not alkylamine and alkylaminoalkyl substituted with phosphonic esters and acids; and
c) A, L, E, J, and Y$^3$ together may only form 0–2 cyclic groups.

More preferred are such compounds wherein X$^3$ is not -alkoxyalkyl-, -alkyloxy-, -alkythioalkyl-, and -alkylthio-. Particularly preferred are such compounds with the additional proviso that when X$^3$ is aryl or alkylaryl, said aryl or alkylaryl group is not linked 1,4 through a six-membered aromatic ring.

Especially preferred benzimidazole compounds include those wherein A, L, and E are independently selected from the group consisting of —H, —NR$^8_2$, —NO$_2$, hydroxy, halogen, —OR$^7$, alkylaminocarbonyl, —SR$^7$, lower perhaloalkyl, and C1–C5 alkyl, or together E and J together form a cyclic group; and wherein J is selected from the group consisting of —H, halogen, lower alkyl, lower hydroxyalkyl, —NR$^8_2$, lower R$^8_2$N-alkyl, lower haloalkyl, lower perhaloalkyl, lower alkenyl, lower alkynyl, lower aryl, heterocyclic, and alicyclic; and wherein Y is selected from the group consisting of alicyclic and lower alkyl; wherein X$^3$ is selected from the group consisting of -heteroaryl-, -alkylcarbonylamino-, -alkylaminocarbonyl-, and -alkoxycarbonyl-. More preferred are such compounds wherein R$^{18}$ is selected from the group consisting of —H, methyl, and ethyl;

R$^{12}$ and R$^{13}$ are independently selected from the group consisting of —H, methyl, i-propyl, i-butyl, and benzyl, or together are connected via 2–5 carbon atoms to form a cycloalkyl group;

R$^{14}$ is —OR$^{17}$;

R$^{17}$ is selected from the group consisting of methyl, ethyl, propyl, t-butyl, and benzyl; and R$^{15}$ and R$^{16}$ are independently selected from the group consisting of lower alkyl, and lower aralkyl, or together R$^{15}$ and R$^{16}$ are connected via 2–6 atoms, optionally including 1 heteroatom selected from the group consisting of O, and N. Most preferred are such compounds wherein A is selected from the group consisting of —H, —NH$_2$, —F, and —CH$_3$;

L is selected from the group consisting of —H, —F, —OCH$_3$, Cl and —CH$_3$;

E is selected from the group consisting of —H, and —Cl;

J is selected from the group consisting of —H, halo, C1–C5 hydroxyalkyl, C1–C5 haloalkyl, C1–C5 R$^8_2$N-alkyl, C1–C5 alicyclic, and C1–C5 alkyl;

X$^3$ is selected from the group consisting of —CH$_2$OCH$_2$—, -methyleneoxycarbonyl-, and -furan-2,5-diyl-; and Y is lower alkyl.

Also more preferred are such benzimidazoles where A is —NH$_2$, L is —F, E is —H, J is ethyl, Y is isobutyl, and X$^3$ is -furan-2,5-diyl-; or
where A is —NH$_2$, L is —F, E is —H, J is N,N-dimethylaminopropyl, Y is isobutyl, and X$^3$ is -furan-2,5-diyl-.

Particularly preferred are those compounds wherein

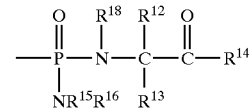

is selected from the group consisting of

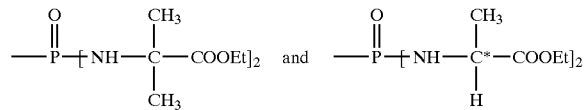

wherein C* has S stereochemistry.

Preferably, oral bioavailability is at least 5%. More preferably, oral bioavailability is at least 10%.

The prodrugs of formula IA may have two isomeric forms around the phosphorus. Preferred is when the phosphorus is not chiral. Also preferred is when there is no chiral center in the amino groups attached to the phosphorus. Also preferred is when n is 1 and R$^{12}$ is —H, then the carbon attached to R$^{12}$ and R$^{13}$ has,S stereochemistry.

In one aspect, preferred are compounds of formula X wherein A$^2$ is selected from the group consisting of —H, —NH$_2$, —CH$_3$, —Cl, and —Br;

$L^2$ is, —H, lower alkyl, halogen, lower alkyloxy, hydroxy, -alkenylene-OH, or together with $E^2$ forms a cyclic group including aryl, cyclic alkyl, heteroaryls, heterocyclic alkyl;

$E^2$ is selected from the groups consisting of H, lower alkyl, halogen, SCN, lower alkyloxycarbonyl, lower alkyloxy, or together with $L^2$ forms a cyclic group including aryl, cyclic alkyl, heteroaryl, or heterocyclic alkyl;

$J^2$ is selected from the groups consisting of H, halogen, and lower alkyl;

G" is —S—;

$X^2$ is —OCH$_2$—; and at least one Y group is —O—; and pharmaceutically acceptable salts and prodrugs thereof. Also particularly preferred are such compounds where $A^2$ is NH$_2$, G" is —S—, $L^2$ is Et, $E^2$ is SCN, and $J^2$ is H. More preferred are such compounds wherein one Y is —O— and its corresponding $R^1$ is optionally substituted phenyl, while the other Y is —NH—, and its corresponding $R^1$ is —C(R$^2$)$_2$—COOR$^3$. When $R^1$ is —CHR$^3$COOR$^3$, then the corresponding —NR$^6$—*CHR$^3$COOR$^3$, preferably has L stereochemistry.

Also more preferred are such compounds wherein one Y is —O—, and its corresponding $R^1$ is -phenyl, while the other Y is —NH— and its corresponding $R^1$ is —CH(Me) CO$_2$Et.

In compounds of formula I, II, III, IV, V-1, V-2, VI, or X, preferably both Y groups are —O—; or one Y is —O— and one Y is —NR$^6$—. When only one Y is —NR$^6$—, preferably the Y closest to W and W' is —O—. Most preferred are prodrugs where both Y groups are —O—;

In another particularly preferred aspect, both Y groups are —O—, and $R^1$ and $R^1$ together are

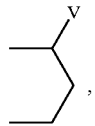

and V is phenyl substituted with 1–3 halogens. Especially preferred are such 3-bromo-4-fluorophenyl, 3-chlorophenyl, 3-bromophenyl, and 3,5-dichlorophenyl.

In another particularly preferred aspect, one Y is —O— and its corresponding $R^1$ is phenyl, or phenyl substituted with 1–2 substituents selected from —NHC(O)CH$_3$, —F, —Cl, —Br, —C(O)OCH$_2$CH$_3$, and —CH$_3$; while the other Y is —NR$^6$— and its corresponding $R^1$ is —C(R$^2$)COOR$^3$; each $R^2$ is independently selected from —H, —CH$_3$, and —CH$_2$CH$_3$. More preferred $R^6$ is —H, and $R^1$ attached to —NH— is —CH(Me)CO$_2$Et.

In general, preferred substituents, V, Z, W, and W' of formulae I, II, III, IV, V-1, V-2, VI or X are chosen such that they exhibit one or more of the following properties:

(1) enhance the oxidation reaction since this reaction is likely to be the rate determining step and therefore must compete with drug elimination processes.

(2) enhance stability in aqueous solution and in the presence of other non-p450 enzymes;

(3) enhance cell penetration, e.g. substituents are not charged or of high molecular weight since both properties can limit oral bioavailability as well as cell penetration;

(4) promote the (β-elimination reaction following the initial oxidation by producing ring-opened products that have one or more of the following properties:

a) fail to recyclize;

b) undergo limited covalent hydration;

c) promote β-elimination by assisting in the proton abstraction;

d) impede addition reactions that form stable adducts, e.g. thiols to the initial hydroxylated product or nucleophilic addition to the carbonyl generated after ring opening; and e) limit metabolism of reaction intermediates (e.g. ring-opened ketone);

(5) lead to a non-toxic and non-mutagenic by-product with one or more of the following characteristics. Both properties can be minimized by using substituents that limit Michael additions, reactions, e.g.

a) electron donating Z groups that decrease double bond polarization;

b) W groups that sterically block nucleophilic addition to β-carbon;

c) Z groups that eliminate the double bond after the elimination reaction either through retautomerization (enol→keto) or hydrolysis (e.g. enamine);

d) V groups that contain groups that add to the α,β-unsaturated ketone to form a ring;

e) Z groups that form a stable ring via Michael addition to double bond; and f) groups that enhance detoxification of the by-product by one or more of the following characteristics:

(i) confine to liver; and (ii) make susceptible to detoxification reactions (e.g. ketone reduction); and (6) capable of generating a pharmacologically active product.

In another aspect, it is preferred when Y is —O—, then $R^1$ attached to —O— is independently selected from the group consisting of —H, optionally substituted aryl, optionally substituted alicyclic where the cyclic moiety contains a carbonate or thiocarbonate, optionally substituted -alkylaryl, —C(R$^2$)$_2$OC(O)R$^3$, —C(R$^2$)$_2$—O—C(O)OR$^3$, —C(R$^2$)$_2$OC(O)SR$^3$, -alkyl-S—C(O)R$^3$, and -alkyl-S—S-alkylhydroxy;

when Y is —NR$^6$, then $R^1$ attached to NR$^6$ is independently selected from the group consisting of —H, —[C(R$^2$)$_2$]$_q$—COOR$^3$, —[C(R$^2$)$_2$]$_q$—C (O)SR$^3$; —C(R$^4$)$_2$COOR$^3$, and -cycloalkylene-COOR$^3$; or when either Y is independently selected from —O— and —NR$^6$—, then together $R^1$ and $R^1$ are

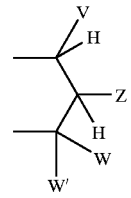

wherein

V, W, and W' are independently selected from the group consisting of —H, alkyl, aralkyl, alicyclic, aryl, substituted aryl, heteroaryl, substituted heteroaryl, 1-alkenyl, and 1-alkynyl, or together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3–5 atoms to form a cyclic group, optionally containing one heteroatom, and V must be aryl, substituted aryl, heteroaryl, or substituted heteroaryl;

together W and W' are connected via an additional 2–5 atoms to form a cyclic group, optionally containing 0–2 heteroatoms, and V must be aryl, substituted aryl, heteroaryl, or substituted heteroaryl;

Z is selected from the group consisting of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —R$^2$, —NHCOR$^2$, —NHCO$_2$R$^3$, —(CH$_2$)$_p$—OR$^2$, and —(CH$_2$)$_p$—SR$^2$;

p is an integer 2 or 3;

q is an integer 1 or 2;

with the provisos that:
a) V, Z, W, W' are not all —H;
b) when Z is —R$^2$, then at least one of V, W, and W' is not —H, alkyl, aralkyl, or alicyclic; and
c) both Y groups are not —NR$^6$—;

R$^2$ is selected from the group consisting of R$^3$ and —H;

R$^3$ is selected from the group consisting of alkyl, aryl, alicyclic, and aralkyl;

R$^6$ is selected from the group consisting of —H, and lower alkyl.

More preferred are such compounds wherein when both Y groups are —O—, then R$^1$ is independently selected from the group consisting of optionally substituted aryl, optionally substituted benzyl, —C(R$^2$)$_2$OC(O)R$^3$, —C(R$^2$)$_2$OC(O)OR$^3$, and —H; and when Y is —NR$^6$—, then the R$^1$ attached to said —NR$^6$— group is selected from the group consisting of —C(R$^4$)$_2$—COOR$^3$, and —C(R$^2$)$_2$COOR$^3$; and the other Y group is —O— and then R$^1$ attached to said —O— is selected from the group consisting of optionally substituted aryl, —C(R$^2$)$_2$OC(O)R$^3$, and —C(R$^2$)$_2$OC(O)OR$^3$.

In another aspect, when one Y is —O—, then its corresponding R$^1$ is phenyl, and the other Y is —NH—, and its corresponding R$^1$ is —CH$_2$CO$_2$Et.

In another preferred aspect, when one Y is —O—, its corresponding R$^1$ is phenyl, and the other Y is —NH— and its corresponding R$^1$ is —C(Me)$_2$CO$_2$Et.

In another preferred aspect, when one Y is —O—, its corresponding R$^1$ is 4-NHC(O)CH$_3$-phenyl, and the other Y is —NH—, and its corresponding R$^1$ is —CH$_2$COOEt.

In another preferred aspect, when one Y is —O—, its corresponding R$^1$ is 2-CO$_2$Et-phenyl, and the other Y is —NH— and its corresponding R$^1$ is —CH$_2$CO$_2$Et.

In another preferred aspect, when one Y is —O—, then its corresponding R$^1$ is 2-CH$_3$-phenyl, and the other Y is —NH, and its corresponding, R$^1$ is —CH$_2$CO$_2$Et.

In another aspect, preferred are compounds wherein both Y groups are —O—, and R$^1$ is aryl, or —C(R$^2$)$_2$-aryl.

Also preferred are compounds wherein both Y groups are O—, and at least one R$^1$ is selected from the group consisting of —C(R$^2$)$_2$—OC(O)R$^3$, and —C(R$^2$)$_2$—OC(O)OR$^3$.

In another aspect, preferred are compounds wherein both Y groups are —O— and at least one R$^1$ is -alkyl-S—S-alkylhydroxyl, -alkyl-S—C(O)R$^3$, and -alkyl-S—S-alkylhydroxy, or together R$^1$ and R$^1$ are -alkyl-S—S-alkyl- to form a cyclic group.

In one aspect, particularly preferred are compounds wherein both Y groups are —O—, and R$^1$ is H.

In another aspect, particularly preferred are compounds where both Y groups are —O—, and R$^1$ is —CH$_2$OC(O)OEt.

More preferred are compounds wherein at least one Y is —O—, and together R$^1$ and R$^1$ are

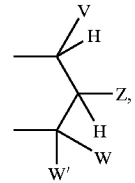

wherein

V, W, and W' are independently selected from the group consisting of —H, alkyl, aralkyl, alicyclic, aryl, substituted aryl, heteroaryl; substituted heteroaryl, 1-alkenyl, and 1-alkynyl, or together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3–5 atoms to form a cyclic group, optionally containing one heteroatom, and V must be aryl, substituted aryl, heteroaryl, or substituted heteroaryl;

together W and W' are connected via an additional 2–5 atoms to form a cyclic group, optionally containing 0–2 heteroatoms, and V must be aryl, substituted aryl, heteroaryl, or substituted heteroaryl;

Z is selected from the group consisting of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —R$^2$, —NHCOR$^2$, NHCO$_2$R$^3$, —(CH$_2$)$_p$—OR$^2$, and —(CH$_2$)$_p$—SR$^2$;

p is an integer 2 or 3;

with the provisos that:
a) V, Z, W, W' are not all —H;
b) when Z is —R$^2$, then at least one of V, W, and W' is not —H, alkyl, aralkyl, or alicyclic; and
c) both Y groups are not —NR$^6$—;

R$^2$ is selected from the group consisting of R$^3$ and —H;

R$^3$ is selected from the group consisting of alkyl, aryl, alicyclic, and aralkyl;

R$^6$ is selected from the group consisting of —H, and lower alkyl.

In an other aspect, more preferred are compounds wherein one Y is —O—, and R$^1$ is optionally substituted aryl; and the other Y is —NR where R$^1$ on said —NR$^6$— is selected from the group consisting of —C(R$^4$)$_2$COOR$^3$, and —C(R$^2$)$_2$C(O)OR$^3$. Particularly preferred are such compounds where R$^1$ attached to —O— is -phenyl, and R1 to —NH— is —CH(Me)CO$_2$Et, and —NH*CH(Me)CO$_2$Et is in the L configuration.

Especially preferred are such compounds where R¹ attached to —O— is selected from the group consisting of phenyl and phenyl substituted with 1–2 substituents selected from the group consisting of —NHAc, —F, —Cl, —Br, —COOEt, and —CH₃; and R¹ attached to NR⁶ is —C(R²)₂COOR³ where R² and R³ independently is —H, —CH₃, and —Et. Of such compounds, when R¹ attached to —O— is phenyl substituted with —NHAc or —COOEt, then preferably any —NHAc is at the 4-position, and any —COOEt is at the 2-position. More preferred are such compounds where the substituents on the substituted phenyl is 4-NHC(O)CH₃, —Cl, —Br, 2-C(O)OCH₃CH₃, or —CH₃.

More preferred V groups of formula 6-i are aryl, substituted aryl, heteroaryl, and substituted heteoaryl. Preferably Y is. —O—. Particularly preferred aryl and substituted aryl groups include phenyl, and phenyl substituted with 1–3 halogens. Especially preferred are 3,5-dichlorophenyl, 3-bromo-4-fluorophenyl, 3-chlorophenyl, and 3-bromophenyl.

It is also especially preferred when V is selected from the group consisting of monocyclic heteroaryl and monocyclic substituted heteroaryl containing at least one nitrogen atom. Most preferred is when such heteroaryl and substituted heteroaryl is 4-pyridyl, and 3-bromopyridyl, respectively.

It is also preferred when together V and Z are connected via an additional 3–5 atoms to form a cyclic group, optionally containing 1 heteroatom, that is fused to an aryl group at the beta and gamma positions to the Y attached to phosphorus. In such compounds preferably said aryl group is an optionally substituted monocyclic aryl group and the connection between Z and the gamma position of the aryl group is selected from the group consisting of O, CH₂, CH₂CH₂, OCH₂ or CH₂O.

In another aspect, it is preferred when together V and W are connected via an additional 3 carbon atoms to form an optionally substituted cyclic group containing 6 carbon atoms and monosubstituted with one substituent selected from the group consisting of hydroxy, acyloxy, alkosycarbonyloxy, alkylthiocarbonyloxy, and aryloxycarbonyloxy attached to one of said additional carbon atoms that is three atoms from a Y attached to the phosphorus. In such compounds, it is more preferred when together V and W form a cyclic group selected from the group consisting of —CH₂—CH(OH)—CH₂—, CH₂CH(OCOR³)—CH2—, and —CH₂CH(OC0₂)R³)—CH₂—.

Another preferred V group is 1-alkene. Oxidation by p450 enzymes is known to occur at benzylic and allylic carbons.

In one aspect, a preferred V group is —H, when Z is selected from the group consisting of —CHR²OH, —CHR²OCOR³, and —CHR²OCO₂R³.

In another aspect, when V is aryl, substituted aryl, heteroaryl, or substituted heteroaryl, preferred Z groups include -OR², —SR², —CHR²N₃, —R², —NR²₂, —OCOR², —OCO₂R³, —SCOR³, —SCO₂R³, —NHCOR², —NHCO₂R³, —CH₂NHaryl, —(CH₂)ₚOR², and —(CH₂)ₚ—SR². More preferred Z groups include-OR², —R², —OCOR², —OCO₂R³, —CH₃, —NHCOR², —NHCO₂R³, —(CH₂ₚ—OR², and, —(CH₂)ₚ—SR². Most preferred Z groups include —OR², —H , —OCOR², —OCO₂R³, and —NHCOR².

Preferred W and W' groups include H, R³, aryl, substituted aryl, heteroaryl, and substituted aryl. Preferably, W and W' are the same group. More preferred is when W and W' are H.

In one aspect, prodrugs of formula 6-i are preferred:

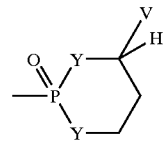

6-i wherein

V is selected from the group consisting of aryl, substituted aryl, heteroaryl, and substituted heteroaryl, 1-alkenyl, and 1-alkynyl. More preferred V groups of formula VI are aryl, substituted, heteroaryl, and substituted heteoaryl. Preferably Y is —O—. Particularly preferred aryl and substituted aryl groups include phenyl and substituted phenyl. Particularly preferred heteroaryl groups include monocyclic substiutted and unsubstituted heteroaryl groups. Especially preferred are 4-pyridyl and 3-bromopyridyl.

In one aspect, the compounds of formula VI preferably have a group Z which is H, alkyl, alicyclic, hydroxy, alkoxy,

or NHCOR. Preferred are such groups in which Z decreases the propensity of the byproduct, vinyl aryl ketone to undergo Michael additions. Preferred Z groups are groups that donate electrons to the vinyl group which is a known strategy for decreasing the propensity of α,β-unsaturated carbonyl compounds to undergo a Michael addition. For example, a methyl group in a similar position on acrylamide results in no mutagenic activity whereas the unsubstituted vinyl analog is highly mutagenic. Other groups could serve a similar function, e.g. Z=OR, NHAc, etc. Other groups may also prevent the Michael addition especially groups that result in removal of the double bond altogether such as Z=OH, —OC(O)R, —OCO₂R, and NH₂, which will rapidly undergo retautomerization after the elimination reaction. Certain W and W' groups are also advantageous in this role since the group(s) impede the addition reaction to the β-carbon or destabilize the product. Another preferred Z group is one that contains a nucleophilic group capable of adding to the α,β-unsaturated double bond after the elimination reaction i.e. (CH₂)ₚSH or (CH₂)ₙOH where p is 2 or 3. Yet another preferred group is a group attached to V which is capable of adding to the α,β-unsaturated double bond after the elimination reaction:

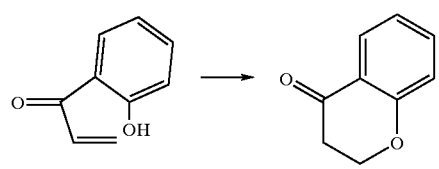

In another aspect, prodrugs of formula 7-i are preferred:

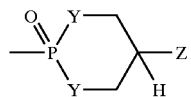
7-i wherein
Z is selected from the group consisting of: —CHR$^2$OH, —CHR$^2$OCOR$^3$, —CHR$^2$OC(S)R$^3$, —CHR$^2$OCO$_2$R$^3$, —CHR$^2$OC(O)SR$^3$, and —CHR$^2$OC(S)OR$^3$. Preferably Y is —O—. More preferred groups include —CHR$^2$OH, —CHR$^2$OC(O)R$^3$, and —CHR$^2$OCO$_2$R$^3$.

In another aspect, prodrugs of formula 8-i are preferred:

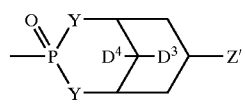
8-i wherein
Z' is selected from the group consisting of —OH, —OC(O)R$^3$, —OCO$_2$ R$^3$, and —OC(O)S R$^3$;
D$^4$ and D$^3$ are independently selected from the group consisting of —H, alkyl, OR$^2$, —OH, and —OC(O)R$^3$; with the proviso that at least one of D$^4$ and D$^3$ are —H. Preferably Y is —O—.

In one preferred embodiment, W' and Z are —H, W and V are both the same aryl, substituted aryl, heteroaryl, or substituted heteroaryl such that the phosphonate prodrug moiety:

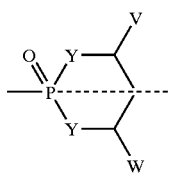

has a plane of symmetry. Preferably Y is —O—.

In another preferred embodiment, W and W' are H, V is selected from the group consisting of aryl, substituted aryl, heteroaryl, substituted heteroaryl, and Z is selected from the group consisting of —H, OR$^2$, and —NHCOR$^2$. More preferred are such compounds where Z is —H.

p450 oxidation can be sensitive to stereochemistry which might either be at phosphorus or at the carbon bearing the aromatic group. The prodrugs of the present invention have two isomeric forms around the phosphorus. Preferred is the stereochemistry that enables both oxidation and the elimination reaction. Preferred is the cis-stereochemistry.

The preferred compounds of formula 8-i utilize a Z' group that is capable of undergoing an oxidative reaction that yields an unstable intermediate which via elimination reactions breaks down to the corresponding R$^5$—X—PO$_3{}^{2-}$, R$^5$—X—P(O)(NHR$^6$)$_2$, or R$^5$—X—P(O)(O$^-$)NHR$^6$). Especially preferred Z' groups is OH. Groups D$^4$ and D$^3$ are preferably hydrogen, alkyl, and —OR$^2$, —OC(O)R$^3$, but at least one of D$^4$ or D$^3$ must be H.

The following prodrugs of formulae I, II, III, IV, V-1, V-2, VI, and X are preferred:
Acyloxyalkyl esters;
Alkoxycarbonyloxyalkyl esters;
Aryl esters;
Benzyl and substituted benzyl esters;
Disulfide containing esters;
Substituted (1,3-dioxolen-2-one)methyl esters;
Substituted 3-phthalidyl esters;
Cyclic-[5-hydroxycyclohexan-1,3-diyl) diesters and hydroxy protected forms;
Cyclic-[2-hydroxymethylpropan-1,3-diyl] diesters and hydroxy protected forms;
Cyclic-(1-arylpropan-1,3-diyl);
Bis Omega substituted lactone esters; and all mixed esters resulted from possible combinations of above esters;
More preferred are the following:
Bis-pivaloyloxymethyl esters;
Bis-isobutyryloxymethyl esters;
Cyclic-[2-hydroxymethylpropan-1,3-diyl] diester;
Cyclic-[2-acetoxymethylpropan-1,3-diyl] diester;
Cyclic-[2-methyloxycarbonyloxymethylpropan-1,3-diyl] diester;
Cyclic-[1-phenylpropan-1,3-diyl] diesters;
Cyclic-[1-(2-pyridyl)propan-1,3-diyl)] diesters;
Cyclic-[1-(3-pyridyl)propan-1,3-diyl] diesters;
Cyclic-[1-(4-pyridyl)propan-1,3-diyl] diesters;
Cyclic-[5-hydroxycyclohexan-1,3-diyl] diesters and hydroxy protected forms;
Bis-benzoylthiomethyl esters;
Bis-benzoylthioethyl esters;
Bis-benzoyloxyethyl esters;
Bis-p-fluorobenzoyloxymethyl esters;
Bis-6-chloronicotinoyloxymethyl esters;
Bis-5-bromonicotinoyloxymethyl esters;
Bis-thiophenecarbonyloxymethyl esters;
Bis-2-furoyloxymethyl esters;
Bis-3-furoyloxymethyl esters;
Diphenyl esters;
Bis-(4-methoxyphenyl) esters
Bis-(2-methoxyphenyl) esters;
Bis-(2-ethoxyphenyl) esters;
Mono-(2-ethoxyphenyl) esters;
Bis-(4-acetamidophenyl) esters;
Bis-(4-acetoxyphenyl) esters;
Bis-(4-hydroxyphenyl) esters;
Bis-(2-acetoxyphenyl) esters;
Bis-(3-acetoxyphenyl) esters;
Bis-(4-morpholinophenyl) esters;
Bis[4-(1-triazolophenyl) esters;
Bis-(3-N,N-dimethylaminophenyl) esters;
Bis-(1,2,3,4-tetrahydronapthalen-2-yl) esters;
Bis-(3-chloro-4-methoxy)benzyl esters;
Bis-(3-bromo-4-methoxy)benzyl esters;
Bis-(3-cyano-4-methoxy)benzyl esters;
Bis-(3-chloro-4-acetoxy)benzyl esters;
Bis-(3-bromo-4-acetoxy)benzyl esters;
Bis-(3-cyano-4-acetoxy)benzyl esters;
Bis-(4-chloro)benzyl esters;
Bis-(4-acetoxy)benzyl esters;
Bis-(3,5-dimethoxy-4-acetoxy)benzyl esters;
Bis-(3-methyl-4-acetoxy)benzyl esters;

Bis-(benzyl)esters;
Bis-(3-methoxy-4-acetoxy)benzyl esters;
Bis-(6'-hydroxy-3',4'-dithia)hexyl esters;
Bis-(6'-acetoxy-3',4'-dithia)hexyl esters;
(3,4-dithiahexan-1,6-diyl) esters;
Bis-(5-methyl-1,3-dioxolen-2-one-4-yl)methyl esters;
Bis-(5-ethyl-1,3-dioxolen-2-one-4-yl)methyl esters;
Bis-(5-tert-butyl-1,3-dioxolen-2-one-4-yl)methyl esters;
Bis-3-(5,6,7-trimethoxy)phthalidyl esters;
Bis-(cyclohekyloxycarbonyloxymethyl) esters;
Bis-(isopropyloxycarbonyloxymethyl) esters;
Bis-(ethyloxycarbonyloxymethyl) esters;
Bis-(methyloxycarbonyloxymethyl) esters;
Bis-(isopropylthiocarbonyloxymethyl) esters;
Bis-(phenyloxycarbonyloxymethyl) esters;
Bis-(benzyloxycarbonyloxymethyl) esters;
Bis-(phenylthiocarbonyloxymethyl) esters;
Bis-(p-methoxyphenoxycarbonyloxymethyl) esters;
Bis-(m-methoxyphenoxycarbonyloxymethyl) esters;
Bis-(o-methoxyphenoxycarbonyloxymethyl) esters;
Bis-(o-methylphenoxycarbonyloxymethyl) esters;
Bis-(p-chlorophenoxycarbonyloxymethyl) esters;
Bis-(1,4-biphenoxycarbonyloxymethyl) esters;
Bis-[(2-phthalimidoethyl)oxycarbonyloxymethyl]esters;
Bis-(N-phenyl-N-methylcarbamoyloxymethyl) esters;
Bis-(2,2,2-trichloroethyl) esters;
Bis-(2-bromoethyl) esters;
Bis-(2-iodoethyl) esters;
Bis-(2-azidoethyl) esters;
Bis-(2-acetoxyethyl) esters;
Bis-(2-aminoethyl) esters;
Bis-(2-N,N-dimethylaminoethyl) esters;
Bis-(2-aminoethyl) esters;
Bis-(methoxycarbonylmethyl) esters;
Bis-(2-aminoethyl) esters;
Bis-[N,N-di(2-hydroxyethyl)]carbamoylmethylesters;
Bis-(2-aminoethyl) esters;
Bis-(2-methyl-5-thiazolomethyl) esters;
Bis-(bis-2-hydroxyethylcarbamoylmethyl) esters.
O-phenyl-[N-(1-ethoxycarbonyl)ethyl]phosphoramidates (—P(O)(OPh)(N(H)—CH(Me)CO$_2$Et)
O-phenyl-[N-(1-methoxycarbonyl)ethyl] phosphoramidates (—P(O)(OPh)(N(H)—CH(Me)CO$_2$Me)
O-(3-chlorophenyl)-[N-(1-ethoxycarbonyl)ethyl] phosphoramidates (—P(O)(OPh-3-Cl)(NH-CH(Me)CO$_2$Et)
O-(2-chlorophenyl)-[N-(1-ethoxycarbonyl)ethyl] phosphoramidates (—P(O)(OPh-2-Cl)(NH—CH(Me)CO$_2$Et)
O-(4-chlorophenyl)-[N-(1-ethoxycarbonyl)ethyl] phosphoramidates (—P(O)(OPh-4-Cl)(NH—CH(Me)CO$_2$Et)
O-(4-acetamidophenyl)-[N-(1-ethoxycarbonyl)ethyl] phosphoramidates (—P(O)(OPh-4-NHAc)(NH—CH(Me)CO$_2$Et)
O-(2-ethoxycarbonylphenyl)-[N-(1-ethoxycarbonyl) ethyl]phosphoramidates (—P(O)(OPh-2-CO$_2$Et) (NH—CH(Me)CO$_2$Et)
O-phenyl-[N-(1-ethoxycarbonyl-1-methyl)ethyl] phosphoramidates (—P(O)(OPh)(NH—C(Me)$_2$CO$_2$Et)
O-phenyl-[N-(1-methoxycarbonyl-1-methyl)ethyl] phosphoramidates (—P(O)(OPh)(NH—C(Me)$_2$CO$_2$Me)
O-(3-chlorophenyl)-[N-(1-ethoxycarbonyl-1-methyl) ethyl]phosphoramidates (—P(O)(OPh-3-Cl)(NH-C(Me)$_2$CO$_2$Et)
O-(2-chlorophenyl)-[N-(1-ethoxycarbonyl-1-methyl) ethyl]phosphoramidates (—P(O)(OPh-2-Cl)(NH-C(Me)$_2$CO$_2$Et)
O-(4-chlorophenyl)-[N-(1-ethoxycarbonyl-1-methyl) ethyl]phosphoramidates (—P(O)(OPh-4-Cl)(NH—C(Me)$_2$CO$_2$Et).
O-(4-acetamidophenyl)-[N-(1-ethoxycarbonyl-1-methyl) ethyl]phosphoramidates (—P(O)(OPh-4-NHAc)(NH—C(Me)$_2$CO$_2$Et)
O-(2-ethoxycarbonylphenyl)-[N-(1-ethoxycarbonyl-1-methyl)ethyl]phosphoramidates (-P(O)(OPh-2-CO$_2$Et) (NH—C(Me)$_2$CO$_2$Et)
O-phenyl-[N-(ethoxycarbonyl)methyl]phosphoramidates (—P(O)(OPh)(NH—CH$_2$CO$_2$Et)
O-phenyl-[N-(methoxycarbonyl)methyl] phosphoramidates (—P(O)(OPh)(NH—CH2CO2Me)
O-(3-chlorophenyl)-[N-(ethoxycarbonyl)methyl] phosphoramidates (—P(O)(OPh-3-Cl)(NH—CH$_2$CO$_2$Et)
O-(2-chlorophenyl)-[N-(ethoxycarbonyl)methyl] phosphoramidates (—P(O)(OPh-2-Cl)(NH—CH$_2$CO$_2$Et)
O-(4-chlorophenyl)-[N-(ethoxycarbonyl)methyl] phosphoramidates (—P(O)(OPh-4-Cl)(NH—CH$_2$CO$_2$Et)
O-(4-acetamidophenyl)-[N-(ethoxycarbonyl)methyl] phosphoramidates (—P(O)(OPh-4-NHAc)(NH—CH$_2$C$_2$Et)
O-(2-ethoxycarbonylphenyl)-[N-(ethoxycarbonyl) methyl]phosphoramidates (—P(Q)(OPh-2-CO$_2$Et) (NH—CH$_2$CO$_2$Et)
Most preferred are the following:
Bis-pivaloyloxymethyl esters;
Bis-isobutyryloxymethyl esters;
Cyclic-(2-hydroxymethylpropan-1,3-diyl) ester;
Cyclic-(2-acetoxymethylpropan-1,3-diyl) ester;
Cyclic-(2-methyloxycarbonyloxymethylpropan-1,3-diyl) ester;
Cyclic-(2-cyclohexylcarbonyloxymethylpropan-1,3-diyl) ester;
Cyclic-[phenylpropan-1,3-diyl] diesters;
Cyclic-[1-(2-pyridyl)propan-1,3-diyl)] diesters;
Cyclic-[1-(3-pyridyl)propan-1,3-diyl] diesters;
Cyclic-[1-(4-pyridyl)propan-1,3-diyl] diesters;
Cyclic-[5-hydroxycyclohexan-1,3-diyl] diesters and hydroxy protected forms;
Bis-benzoylthiomethyl esters;
Bis-benzoylthioethylesters;
Bis-benzoyloxymethyl esters;
Bis-p-fluorobenzoyloxymethyl esters;
Bis-6-chloronicotinoyloxymethyl esters;
Bis-5-bromonicotinoyloxymethyl esters;

Bis-thiophenecarbonyloxymethyl esters;
Bis-2-furoyloxymethyl esters;
Bis-3-furoyloxymethyl esters;
Diphenyl esters;
Bis-(2-methylphenyl) esters;
Bis-(2-methoxyphenyl) esters;
Bis-(2-ethoxyphenyl) esters;
Bis-(4-methoxyphenyl) esters;
Bis-(3-bromo-4-methoxy benzyl) esters;
Bis-(4-acetoxybenzyl) esters;
Bis-(3,5-dimethoxy-4-acetoxybenzyl) esters;
Bis-(3-methyl-4-acetoxybenzyl) esters;
Bis-(3-methoxy-4-acetoxybenzyl) esters;
Bis-(3-chloro-4-acetoxybenzyl) esters;
Bis-(cyclohekyloxycarbonyloxymethyl) esters;
Bis-(isopropyloxycarbonyloxymethyl) esters;
Bis-(ethyloxycarbonyloxymethyl) esters,
Bis-(methyloxycarbonyloxymethyl) esters;
Bis-(isopropylthiocarbonyloxymethyl) esters;
Bis-(phenyloxycarbonyloxymethyl) esters;
Bis-(benzyloxycarbonyloxymethyl) esters;
Bis-(phenylthiocarbonyloxymethyl) esters;
Bis-(p-methoxyphenoxycarbonyloxymethyl) esters;
Bis-(m-methoxyphenoxycarbonyloxymethyl) esters;
Bis-(o-methoxyphenoxycarbonyloxymethyl) esters;
Bis-(o-methylphenoxycarbonyloxymethyl) esters;
Bis-(p-chlorophenoxycarbonyloxymethyl) esters;
Bis-(1,4-biphenoxycarbonyloxymethyl) esters;
Bis-[(2-phthalimidoethyl)oxycarbonyloxymethyl]esters;
Bis-(6-hydroxy-3,4-dithia)hexyl esters;
Cyclic-(3,4-dithiahexan-1,6-diyl) esters;
Bis-(2-bromoethyl) esters;
Bis-(2-aminoethyl) esters;
Bis-(2-N,N-diaminoethyl) esters;
O-phenyl-[N-(1-ethoxycarbonyl)ethyl]phosphoramidates (—P(O)(OPh)(NH—*CH(Me)CO$_2$Et)
O-phenyl-[N-(1-methoxycarbonyl)ethyl] phosphoramidates (—P(O)(OPh)(NH—*CH(Me)CO$_2$Me)
O-(3-chlorophenyl)-[N-(1-ethoxycarbonyl)ethyl] phosphoramidates (—P(O)(OPh-3-Cl)(NH—*CH(Me)CO$_2$Et)
O-(2-chlorophenyl)-[N-(1-ethoxycarbonyl)ethyl] phosphoramidates (—P(O)(OPh-2-Cl)(NH—*CH(Me)CO$_2$Et)
O-(4-chlorophenyl)-[N-(1-ethoxycarbonyl)ethyl] phosphoramidates (—P(O)(OPh-4-Cl)(NH—*CH(Me)CO$_2$Et)
O-(4-acetamidophenyl)-[N-(1-ethoxycarbonyl)ethyl] phosphoramidates (—P(O)(OPh-4-NHAc)(NH—*CH(Me)CO$_2$Et)
O-(2-ethoxycarbonylphenyl)-[N-(1-ethoxycarbonyl) ethyl]phosphoramidates (—P(O)(OPh-2-CO$_2$Et) (NH—*CH(Me)CO$_2$Et)
O-phenyl-[N-(1-ethoxycarbonyl-1-methyl)ethyl] phosphoramidates (—P(O)(OPh)(NH—C(Me)$_2$CO$_2$Et)
O-phenyl-[N-(1-methoxycarbonyl-1-methyl)ethyl] phosphoramidates (—P(O)(OPh)(NH—C(Me)$_2$CO$_2$Me)
O-(3-chlorophenyl)-[N-(1-ethoxycarbonyl-1-methyl) ethyl]phosphoramidates (—P(O)(OPh-3-Cl)(NH—C(Me)$_2$CO$_2$Et)
O-(2-chlorophenyl)-[N-(1-ethoxycarbonyl-1-methyl) ethyl]phosphoramidates (—P(O)(OPh-2-Cl)(NH—C(Me)$_2$CO$_2$Et)
O-(4-chlorophenyl)-[N-(1-ethoxycarbonyl-1-methyl) ethyl]phosphoramidates (—P(O)(OPh-4-Cl)(NH—O(Me)$_2$CO$_2$Et)
O-(4-acetamidophenyl)-[N-(1-ethoxycarbonyl-1-methyl) ethyl]phosphoramidates (—P(O)(OPh-4-NHAc) (NH—C(Me)$_2$CO$_2$Et)
O-(2-ethoxycarbonylphenyl)-[N-(1-ethoxycarbonyl-1-methyl)ethyl]phosphoramidates (—P(O)(OPh-2-CO$_2$Et)(NH—C(Me)$_2$CO$_2$Et)

In the above prodrugs an asterisk (*) on a carbon refers to the L-configuration.

O-phenyl-[N-(ethoxycarbonyl)methyl]phosphoramidates (—P(O)(OPh)(NH—CH$_2$CO$_2$Et)
O-phenyl-[N-(methoxycarbonyl)methyl] phosphoramidates (—P(O)(OPh)(NH—CH$_2$CO$_2$Me)
O-(3-chlorophenyl)-[N-(ethoxycarbonyl)methyl] phosphoramidates (—P(O)(OPh-3-Cl)(NH—CH$_2$CO$_2$Et)
O-(2-chlorophenyl)-[N-(ethoxycarbonyl)methyl] phosphoramidates (—P(O)(OPh-2-Cl)(NH—CH$_2$C02Et)
O-(4-chlorophenyl)-[N-(ethoxycarbonyl)methyl] phosphoramidates (—P(O)(OPh-4-Cl)(NH—CH$_2$CO$_2$Et)
O-(4-acetamidophenyl)-[N-(ethoxycarbonyl)methyl] phosphoramidates (—P(O)(OPh-4-NHAc)(NH—CH$_2$CO$_2$Et)
O-(2-ethoxycarbonylphenyl)-[N-(ethoxycarbonyl) methyl]phosphoramidates(—P(O)(OPh-2-CO$_2$Et) (NH—CH$_2$CO$_2$Et)

The compounds designated in Table 1 refer to preferred compounds of formula I-A where M is $R^5$—X— as defined in the following formulae: formula i, formula ii, and formula iii.

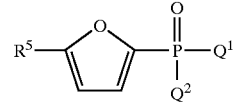

Formula i

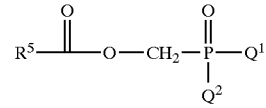

Formula ii

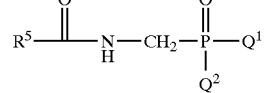

Formula iii

In the above formulae i, ii, and iii, $R^5$ may be substituted by A and B. The preferred compounds of formulae i, ii, and iii are listed in Table 1 by designated numbers assigned to $R^5$, A, B, $Q^1$, and $Q^2$ in the above formulae i, ii, and iii according to the following convention: $Q^1.Q^2$. $R^5$.B.A. For each moiety, structures assigned to a number shown in the following tables for $R^5$, A, B, $Q^1$ and $Q^2$.

Variable $R^5$ is divided into two groups, each listing four different structures.

Compounds named in Table 1 of formulae i, ii, and iii wherein the $R^5$ moieties are assigned the following numbers:

Group 1:

| | 1 | 2 | 3 | 4 |
|---|---|---|---|---|

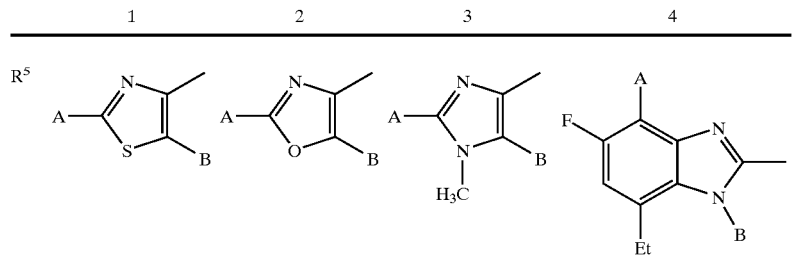

Group 2:

| | 1 | 2 | 3 | 4 |
|---|---|---|---|---|

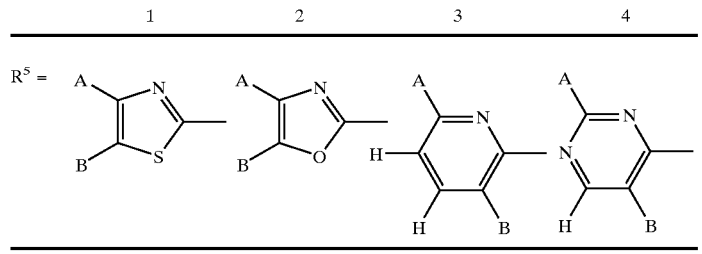

Variable A moieties are assigned the following numbers:

| | 1 | 2 | 3 | 4 |
|---|---|---|---|---|
| A = | NH2 | H | Me | Cl |

Variable B moieties are assigned the following numbers:

| | 1 | 2 | 3 | 4 | 5 | 6 | 7 | 8 |
|---|---|---|---|---|---|---|---|---|
| B = | —SCH3 | -iBu | -cPr | —S-nPr | —SEt | -iPr | -nPr | —CH2cPr |

Variables $Q^1$ and $Q^2$ are divided into three groups, each listing eight different substituents.

$Q^1$ and $Q^2$ moieties are assigned the following numbers:

Group 1:
$Q^1$ and $Q^2$
1. —NH—CH2-C(O)R14
2. —NH—CH(CH3)—C(O)R14
3. —NH—C(CH3)2-C(O)R14
4. —NH—C(CH3)2CH2-C(O)R14
5. —NH—CH(CH(CH3)2))—C(O)R14
6. —NH—CH(CH2(CH(CH3)2)))—C(O)R14
7. —NH—CH(CH2CH2SCH3)—C(O)R14
8. —NH—CH(CH2SCH2Ph)—C(O)R14

Group 2:
$Q^1$ and $Q^2$
1. —NH—CH2CH2-C(O)R14
2. —NH—CH(CH2CH2COR14)—C(O)R14
3. —NH—CH(CH2COR14)—C(O)R14
4. —NH—CH(CH2CONH2)—C(O)R14
5. —NH—CH(COR14)CH2-C(O)R:4
6. —NH—CH(CH2OR17)—C(O)R14
7. —NH—CH(CH2CH2COR14)—C(O)R14
8. —NH—CH(CH2OH)—C(O)R14

Group 3:
$Q^1$ and $Q^2$
1. —NH—CH(CH2-C6H5OH)—C(O)R14
2. —NH—C(c-propyl)—C(O)R14
3. —NH—C(c-pentyl)—C(O)R14
4. —NH—C(c-hexyl)—C(O)R14
5. —NH—CH(CH2Ph)—C(O)R14
6. —N(CH3)—CH2CO)—C(O)R14

7. 

8. —NR18R19
where $R^4$ is selected from the groups consisting of OMe, OEt, OBn, O-tBu, O-nPr, OPh, —N(Me)$_2$, Morpholine, SMe, SEt; $R^{17}$ is methyl, ethyl, benzyl, and propyl; $R^{18}$ is H, Me, Et, Bn, Pr and Ph and R19 is Me, Et, Bn, Pr and Ph; R18 and R19 is morpholinyl and pyrrolidinyl.

Thus, the compound 3.3.1.2.1 in Group 1 corresponds to the structure below for formula i:

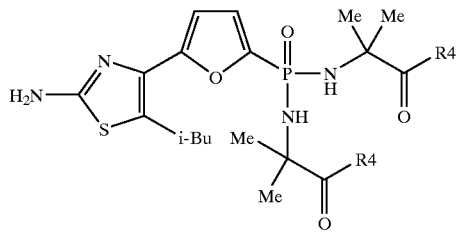

and when $R^4$ is ethoxy the structure would be

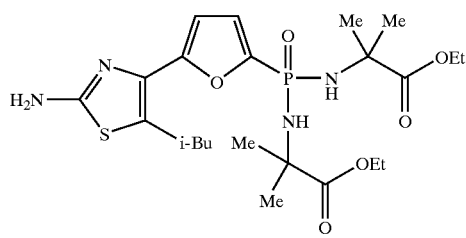

The numbers designated in Table 1 also refer to preferred benzothiazole and benzoxazole compounds of formula X. These preferred compounds are shown in formulae iv and v.

Formula iv

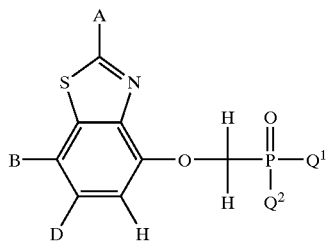

Formula v

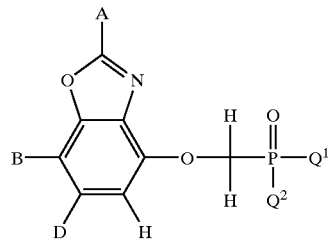

The preferred compounds of formulae iv and formula v are listed in Table 1 by designated numbers assigned to A, B, D, $Q^1$, and $Q^2$ in the above formulae iv and v, according to the following convention: $Q^1.Q^2.A.B.D$. For each moiety, structures assigned to a number shown in the following tables for A, B, D, $Q^1$ and $Q^2$.

Variables $Q^1$ and $Q^2$ are divided into three groups, each listing eight different substituents.

Group 1:
$Q^1$ and $Q^2$ moieties are assigned the following numbers:
$Q^1$ and $Q^2$ 1. —NH—CH2-C(O)R14
2. —NH—CH(CH3)—C(O)R14
3. —NH—C(CH3)2-C(O)R14
4. —NH—C(CH3)2CH2-C(O)R14
5. —NH—CH(CH(CH3)2))—C(O)R14
6. —NH—CH(CH2(CH(CH3)2)))—C(O)R14
7. —NH—CH(CH2CH2SCH3)—C(O)R14
8. —NH—CH(CH2SCH2Ph)—C(O)R14

Group 2:

$Q^1$ and $Q^2$

1. —NH—CH2CH2-C(O)R14
2. —NH—CH(CH2CH2COR14)—C(O)R14
3. —NH—CH(CH2COR14)—C(O)R14
4. —NH—CH(CH2CONH2)—C(O)R14
5. —NH—CH(COR14)CH2-C(O)R14
6. —NH—CH(CH2OR17)—C(O)R14
7. —NH—CH(CH2CH2COR14)—C(O)R14
8. —NH—CH(CH2OH)—C(O)R14

Group 3:

$Q^1$ and $Q^2$

1. —NH—CH(CH2-C6H5OH)—C(O)R14
2. —NH—C(c-propyl)—C(O)R14
3. —NH—C(c-pentyl)—C(O)R14
4. —NH—C(c-hexyl)—C(O)R14
5. —NH—CH(CH2Ph)—C(O)R14
6. —N(CH3)—CH2-C(O)R14

7. —N⟨△⟩—COR14

8. —NR18R19

Variable B is divided into three groups, each listing eight different substituents.

| Group 1: B moieties are assigned the following numbers: | | | | | | | |
|---|---|---|---|---|---|---|---|
| 1 | 2 | 3 | 4 | 5 | 6 | 7 | 8 |
| B = H | Me | Et | nPr | Br | iPr | Cl | cPr |

| Group 2: | | | | | | | |
|---|---|---|---|---|---|---|---|
| 1 | 2 | 3 | 4 | 5 | 6 | 7 | 8 |
| B = CN | F | OMe | OEt | SMe | SEt | 2-furanyl | C(O)OEt |

| | Group 3: | | | | | | |
|---|---|---|---|---|---|---|---|
| 1 | 2 | 3 | 4 | 5 | 6 | 7 | 8 |
| B = B & D are connected to form cyclo-hexyl ring | B & D are connected to form phenyl ring | B & D are connected to form furanyl ring (O attached at B) | B & D are connected to form furanyl ring (O attached at D) | B & D are connected to form cyclo-hexyl ring | B & D are connected to form phenyl ring | B & D are connected to form furanyl ring (O attached at B) | B & D are connected to form furanyl ring (O attached at D) |

Group 3 for Variable B can only be combined with Group 3 variable for D.

Variable D is divided into three groups, each listing four different substituents.

| | 1 | 2 | 3 | 4 |
|---|---|---|---|---|
| | | Group 1: | | |
| D = | H | Me | Et | SCN |
| | | Group 2: | | |
| Variable D is replaced with the moieties assigned in the following numbers: | | | | |
| D = | SMe | SEt | CH2OMe | OMe |
| | | Group 3: | | |
| D = | null | null | null | null |

Compounds named in Table 1 of formulae iv and v wherein the A moieties are assigned the following numbers:

| | 1 | 2 | 3 | 4 |
|---|---|---|---|---|
| A = | NH2 | H | Me | Cl | where $R^4$ is selected from the groups consisting of OMe, OEt, OBn, O-tBu, O-nPr, OPh, —N(Me)2, morpholine, SMe, SEt; R17 is methyl, ethyl, benzyl, and propyl; R18 is H, Me, Et, Bn, Pr and Ph and R19 is Me, Et, Bn, Pr and Ph; R18 and R19 is morpholinyl and pyrrolidinyl Thus, the compound 2.2.1.7.4 from Group 1 for B, D, $Q^1$ and $Q^2$ corresponds to the structure below for formula iv

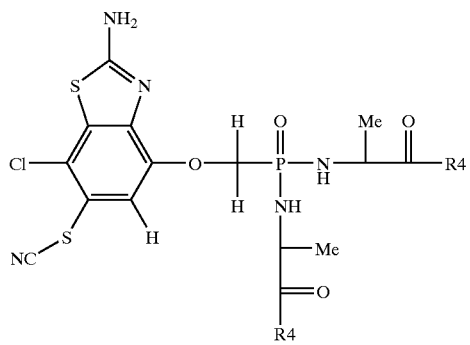

and when $R^4$ is ethoxy the structure would be

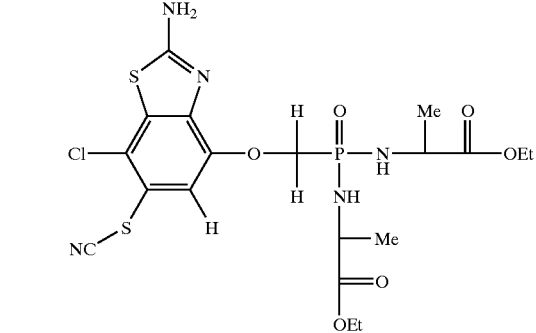

Similarly, in group 3 for variable B, the compound 2.2.1.7.4 corresponds to the structure below for formula iv

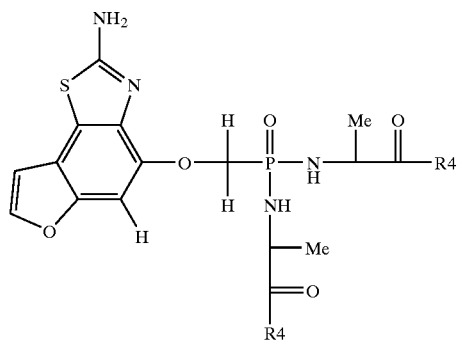

and when $R^4$ is ethoxy the structure would be

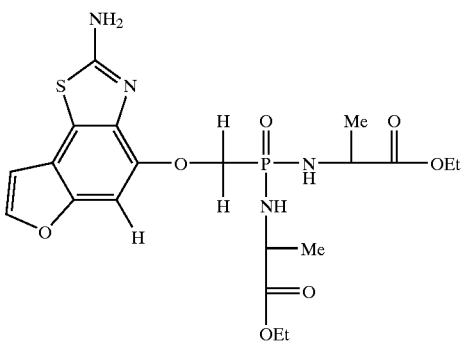

TABLE 1

| | | | | | | | |
|---|---|---|---|---|---|---|---|
| 1.1.1.1.1 | 1.1.1.1.2 | 1.1.1.1.3 | 1.1.1.1.4 | 1.1.1.2.1 | 1.1.1.2.2 | 1.1.1.2.3 | 1.1.1.2.4 |
| 1.1.1.3.1 | 1.1.1.3.2 | 1.1.1.3.3 | 1.1.1.3.4 | 1.1.1.4.1 | 1.1.1.4.2 | 1.1.1.4.3 | 1.1.1.4.4 |
| 1.1.1.5.1 | 1.1.1.5.2. | 1.1.1.5.3 | 1.1.1.5.4 | 1.1.1.6.1 | 1.1.1.6.2 | 1.1.1.6.3 | 1.1.1.6.4 |
| 1.1.1.7.1 | 1.1.1.7.2 | 1.1.1.7.3 | 1.1.1.7.4 | 1.1.1.8.1 | 1.1.1.8.2 | 1.1.1.8.3 | 1.1.1.8.4 |
| 1.1.2.1.1 | 1.1.2.1.2 | 1.1.2.1.3 | 1.1.2.1.4 | 1.1.2.2.1 | 1.1.2.2.2 | 1.1.2.2.3 | 1.1.2.2.4 |
| 1.1.2.3.1 | 1.1.2.3.2 | 1.1.2.3.3 | 1.1.2.3.4 | 1.1.2.4.1 | 1.1.2.4.2 | 1.1.2.4.3 | 1.1.2.4.4 |
| 1.1.2.5.1 | 1.1.2.5.2 | 1.1.2.5.3 | 1.1.2.5.4 | 1.1.2.6.1 | 1.1.2.6.2 | 1.1.2.6.3 | 1.1.2.6.4 |
| 1.1.2.7.1 | 1.1.2.7.2 | 1.1.2.7.3 | 1.1.2.7.4 | 1.1.2.8.1 | 1.1.2.8.2 | 1.1.2.8.3 | 1.1.2.8.4 |
| 1.1.3.1.1 | 1.1.3.1.2 | 1.1.3.1.3 | 1.1.3.1.4 | 1.1.3.2.1 | 1.1.3.2.2 | 1.1.3.2.3 | 1.1.3.2.4 |
| 1.1.3.3.1 | 1.1.3.3.2 | 1.1.3.3.3 | 1.1.3.3.4 | 1.1.3.4.1 | 1.1.3.4.2 | 1.1.3.4.3 | 1.1.3.4.4 |
| 1.1.3.5.1 | 1.1.3.5.2 | 1.1.3.5.3 | 1.1.3.5.4 | 1.1.3.6.1 | 1.1.3.6.2 | 1.1.3.6.3 | 1.1.3.6.4 |
| 1.1.3.7.1 | 1.1.3.7.2 | 1.1.3.7.3 | 1.1.3.7.4 | 1.1.3.8.1 | 1.1.3.8.2 | 1.1.3.8.3 | 1.1.3.8.4 |
| 1.1.4.1.1 | 1.1.4.1.2 | 1.1.4.1.3 | 1.1.4.1.4 | 1.1.4.2.1 | 1.1.4.2.2 | 1.1.4.2.3 | 1.1.4.2.4 |
| 1.1.4.3.1 | 1.1.4.3.2 | 1.1.4.3.3 | 1.1.4.3.4 | 1.1.4.4.1 | 1.1.4.4.2 | 1.1.4.4.3 | 1.1.4.4.4 |
| 1.1.4.5.1 | 1.1.4.5.2 | 1.1.4.5.3 | 1.1.4.5.4 | 1.1.4.6.1 | 1.1.4.6.2 | 1.1.4.6.3 | 1.1.4.6.4 |
| 1.1.4.7.1 | 1.1.4.7.2 | 1.1.4.7.3 | 1.1.4.7.4 | 1.1.4.8.1 | 1.1.4.8.2 | 1.1.4.8.3 | 1.1.4.8.4 |
| 1.2.1.1.1 | 1.2.1.1.2 | 1.2.1.1.3 | 1.2.1.1.4 | 1.2.1.2.1 | 1.2.1.2.2 | 1.2.1.2.3 | 1.2.1.2.4 |
| 1.2.1.3.1 | 1.2.1.3.2 | 1.2.1.3.3 | 1.2.1.3.4 | 1.2.1.4.1 | 1.2.1.4.2 | 1.2.1.4.3 | 1.2.1.4.4 |
| 1.2.1.5.1 | 1.2.1.5.2 | 1.2.1.5.3 | 1.2.1.5.4 | 1.2.1.6.1 | 1.2.1.6.2 | 1.2.1.6.3 | 1.2.1.6.4 |
| 1.2.1.7.1 | 1.2.1.7.2 | 1.2.1.7.3 | 1.2.1.7.4 | 1.2.1.8.1 | 1.2.1.8.2 | 1.2.1.8.3 | 1.2.1.8.4 |
| 1.2.2.1.1 | 1.2.2.1.2 | 1.2.2.1.3 | 1.2.2.1.4 | 1.2.2.2.1 | 1.2.2.2.2 | 1.2.2.2.3 | 1.2.2.2.4 |
| 1.2.2.3.1 | 1.2.2.3.2 | 1.2.2.3.3 | 1.2.2.3.4 | 1.2.2.4.1 | 1.2.2.4.2 | 1.2.2.4.3 | 1.2.2.4.4 |
| 1.2.2.5.1 | 1.2.2.5.2 | 1.2.2.5.3 | 1.2.2.5.4 | 1.2.2.6.1 | 1.2.2.6.2 | 1.2.2.6.3 | 1.2.2.6.4 |
| 1.2.2.7.1 | 1.2.2.7.2 | 1.2.2.7.3 | 1.2.2.7.4 | 1.2.2.8.1 | 1.2.2.8.2 | 1.2.2.8.3 | 1.2.2.8.4 |
| 1.2.3.1.1 | 1.2.3.1.2 | 1.2.3.1.3 | 1.2.3.1.4 | 1.2.3.2.1 | 1.2.3.2.2 | 1.2.3.2.3 | 1.2.3.2.4 |
| 1.2.3.3.1 | 1.2.3.3.2 | 1.2.3.3.3 | 1.2.3.3.4 | 1.2.3.4.1 | 1.2.3.4.2 | 1.2.3.4.3 | 1.2.3.4.4 |
| 1.2.3.5.1 | 1.2.3.5.2 | 1.2.3.5.3 | 1.2.3.5.4 | 1.2.3.6.1 | 1.2.3.6.2 | 1.2.3.6.3 | 1.2.3.6.4 |
| 1.2.3.7.1 | 1.2.3.7.2 | 1.2.3.7.3 | 1.2.3.7.4 | 1.2.3.8.1 | 1.2.3.8.2 | 1.2.3.8.3 | 1.2.3.8.4 |
| 1.2.4.1.1 | 1.2.4.1.2 | 1.2.4.1.3 | 1.2.4.1.4 | 1.2.4.2.1 | 1.2.4.2.2 | 1.2.4.2.3 | 1.2.4.2.4 |
| 1.2.4.3.1 | 1.2.4.3.2 | 1.2.4.3.3 | 1.2.4.3.4 | 1.2.4.4.1 | 1.2.4.4.2 | 1.2.4.4.3 | 1.2.4.4.4 |
| 1.2.4.5.1 | 1.2.4.5.2 | 1.2.4.5.3 | 1.2.4.5.4 | 1.2.4.6.1 | 1.2.4.6.2 | 1.2.4.6.3 | 1.2.4.6.4 |
| 1.2.4.7.1 | 1.2.4.7.2 | 1.2.4.7.3 | 1.2.4.7.4 | 1.2.4.8.1 | 1.2.4.8.2 | 1.2.4.8.3 | 1.2.4.8.4 |
| 1.3.1.1.1 | 1.3.1.1.2 | 1.3.1.1.3 | 1.3.1.1.4 | 1.3.1.2.1 | 1.3.1.2.2 | 1.3.1.2.3 | 1.3.1.2.4 |
| 1.3.1.3.1 | 1.3.1.3.2 | 1.3.1.3.3 | 1.3.1.3.4 | 1.3.1.4.1 | 1.3.1.4.2 | 1.3.1.4.3 | 1.3.1.4.4 |
| 1.3.1.5.1 | 1.3.1.5.2 | 1.3.1.5.3 | 1.3.1.5.4 | 1.3.1.6.1 | 1.3.1.6.2 | 1.3.1.6.3 | 1.3.1.6.4 |
| 1.3.1.7.1 | 1.3.1.7.2 | 1.3.1.7.3 | 1.3.1.7.4 | 1.3.1.8.1 | 1.3.1.8.2 | 1.3.1.8.3 | 1.3.1.8.4 |
| 1.3.2.1.1 | 1.3.2.1.2 | 1.3.2.1.3 | 1.3.2.1.4 | 1.3.2.2.1 | 1.3.2.2.2 | 1.3.2.2.3 | 1.3.2.2.4 |
| 1.3.2.3.1 | 1.3.2.3.2 | 1.3.2.3.3 | 1.3.2.3.4 | 1.3.2.4.1 | 1.3.2.4.2 | 1.3.2.4.3 | 1.3.2.4.4 |
| 1.3.2.5.1 | 1.3.2.5.2 | 1.3.2.5.3 | 1.3.2.5.4 | 1.3.2.6.1 | 1.3.2.6.2 | 1.3.2.6.3 | 1.3.2.6.4 |
| 1.3.2.7.1 | 1.3.2.7.2 | 1.3.2.7.3 | 1.3.2.7.4 | 1.3.2.8.1 | 1.3.2.8.2 | 1.3.2.8.3 | 1.3.2.8.4 |
| 1.3.3.1.1 | 1.3.3.1.2 | 1.3.3.1.3 | 1.3.3.1.4 | 1.3.3.2.1 | 1.3.3.2.2 | 1.3.3.2.3 | 1.3.3.2.4 |
| 1.3.3.3.1 | 1.3.3.3.2 | 1.3.3.3.3 | 1.3.3.3.4 | 1.3.3.4.1 | 1.3.3.4.2 | 1.3.3.4.3 | 1.3.3.4.4 |
| 1.3.3.5.1 | 1.3.3.5.2 | 1.3.3.5.3 | 1.3.3.5.4 | 1.3.3.6.1 | 1.3.3.6.2 | 1.3.3.6.3 | 1.3.3.6.4 |
| 1.3.3.7.1 | 1.3.3.7.2 | 1.3.3.7.3 | 1.3.3.7.4 | 1.3.3.8.1 | 1.3.3.8.2 | 1.3.3.8.3 | 1.3.3.8.4 |
| 1.3.4.1.1 | 1.3.4.1.2 | 1.3.4.1.3 | 1.3.4.1.4 | 1.3.4.2.1 | 1.3.4.2.2 | 1.3.4.2.3 | 1.3.4.2.4 |
| 1.3.4.3.1 | 1.3.4.3.2 | 1.3.4.3.3 | 1.3.4.3.4 | 1.3.4.4.1 | 1.3.4.4.2 | 1.3.4.4.3 | 1.3.4.4.4 |
| 1.3.4.5.1 | 1.3.4.5.2 | 1.3.4.5.3 | 1.3.4.5.4 | 1.3.4.6.1 | 1.3.4.6.2 | 1.3.4.6.3 | 1.3.4.6.4 |
| 1.3.4.7.1 | 1.3.4.7.2 | 1.3.4.7.3 | 1.3.4.7.4 | 1.3.4.8.1 | 1.3.4.8.2 | 1.3.4.8.3 | 1.3.4.8.4 |
| 1.4.1.1.1 | 1.4.1.1.2 | 1.4.1.1.3 | 1.4.1.1.4 | 1.4.1.2.1 | 1.4.1.2.2 | 1.4.1.2.3 | 1.4.1.2.4 |
| 1.4.1.3.1 | 1.4.1.3.2 | 1.4.1.3.3 | 1.4.1.3.4 | 1.4.1.4.1 | 1.4.1.4.2 | 1.4.1.4.3 | 1.4.1.4.4 |
| 1.4.1.5.1 | 1.4.1.5.2 | 1.4.1.5.3 | 1.4.1.5.4 | 1.4.1.6.1 | 1.4.1.6.2 | 1.4.1.6.3 | 1.4.1.6.4 |
| 1.4.1.7.1 | 1.4.1.7.2 | 1.4.1.7.3 | 1.4.1.7.4 | 1.4.1.8.1 | 1.4.1.8.2 | 1.4.1.8.3 | 1.4.1.8.4 |
| 1.4.2.1.1 | 1.4.2.1.2 | 1.4.2.1.3 | 1.4.2.1.4 | 1.4.2.2.1 | 1.4.2.2.2 | 1.4.2.2.3 | 1.4.2.2.4 |
| 1.4.2.3.1 | 1.4.2.3.2 | 1.4.2.3.3 | 1.4.2.3.4 | 1.4.2.4.1 | 1.4.2.4.2 | 1.4.2.4.3 | 1.4.2.4.4 |
| 1.4.2.5.1 | 1.4.2.5.2 | 1.4.2.5.3 | 1.4.2.5.4 | 1.4.2.6.1 | 1.4.2.6.2 | 1.4.2.6.3 | 1.4.2.6.4 |
| 1.4.2.7.1 | 1.4.2.7.2 | 1.4.2.7.3 | 1.4.2.7.4 | 1.4.2.8.1 | 1.4.2.8.2 | 1.4.2.8.3 | 1.4.2.8.4 |
| 1.4.3.1.1 | 1.4.3.1.2 | 1.4.3.1.3 | 1.4.3.1.4 | 1.4.3.2.1 | 1.4.3.2.2 | 1.4.3.2.3 | 1.4.3.2.4 |
| 1.4.3.3.1 | 1.4.3.3.2 | 1.4.3.3.3 | 1.4.3.3.4 | 1.4.3.4.1 | 1.4.3.4.2 | 1.4.3.4.3 | 1.4.3.4.4 |
| 1.4.3.5.1 | 1.4.3.5.2 | 1.4.3.5.3 | 1.4.3.5.4 | 1.4.3.6.1 | 1.4.3.6.2 | 1.4.3.6.3 | 1.4.3.6.4 |
| 1.4.3.7.1 | 1.4.3.7.2 | 1.4.3.7.3 | 1.4.3.7.4 | 1.4.3.8.1 | 1.4.3.8.2 | 1.4.3.8.3 | 1.4.3.8.4 |
| 1.4.4.1.1 | 1.4.4.1.2 | 1.4.4.1.3 | 1.4.4.1.4 | 1.4.4.2.1 | 1.4.4.2.2 | 1.4.4.2.3 | 1.4.4.2.4 |
| 1.4.4.3.1 | 1.4.4.3.2 | 1.4.4.3.3 | 1.4.4.3.4 | 1.4.4.4.1 | 1.4.4.4.2 | 1.4.4.4.3 | 1.4.4.4.4 |
| 1.4.4.5.1 | 1.4.4.5.2 | 1.4.4.5.3 | 1.4.4.5.4 | 1.4.4.6.1 | 1.4.4.6.2 | 1.4.4.6.3 | 1.4.4.6.4 |
| 1.4.4.7.1 | 1.4.4.7.2 | 1.4.4.7.3 | 1.4.4.7.4 | 1.4.4.8.1 | 1.4.4.8.2 | 1.4.4.8.3 | 1.4.4.8.4 |
| 1.5.1.1.1 | 1.5.1.1.2 | 1.5.1.1.3 | 1.5.1.1.4 | 1.5.1.2.1 | 1.5.1.2.2 | 1.5.1.2.3 | 1.5.1.2.4 |
| 1.5.1.3.1 | 1.5.1.3.2 | 1.5.1.3.3 | 1.5.1.3.4 | 1.5.1.4.1 | 1.5.1.4.2 | 1.5.1.4.3 | 1.5.1.4.4 |
| 1.5.1.5.1 | 1.5.1.5.2 | 1.5.1.5.3 | 1.5.1.5.4 | 1.5.1.6.1 | 1.5.1.6.2 | 1.5.1.6.3 | 1.5.1.6.4 |
| 1.5.1.7.1 | 1.5.1.7.2 | 1.5.1.7.3 | 1.5.1.7.4 | 1.5.1.8.1 | 1.5.1.8.2 | 1.5.1.8.3 | 1.5.1.8.4 |
| 1.5.2.1.1 | 1.5.2.1.2 | 1.5.2.1.3 | 1.5.2.1.4 | 1.5.2.2.1 | 1.5.2.2.2 | 1.5.2.2.3 | 1.5.2.2.4 |
| 1.5.2.3.1 | 1.5.2.3.2 | 1.5.2.3.3 | 1.5.2.3.4 | 1.5.2.4.1 | 1.5.2.4.2 | 1.5.2.4.3 | 1.5.2.4.4 |
| 1.5.2.5.1 | 1.5.2.5.2 | 1.5.2.5.3 | 1.5.2.5.4 | 1.5.2.6.1 | 1.5.2.6.2 | 1.5.2.6.3 | 1.5.2.6.4 |
| 1.5.2.7.1 | 1.5.2.7.2 | 1.5.2.7.3 | 1.5.2.7.4 | 1.5.2.8.1 | 1.5.2.8.2 | 1.5.2.8.3 | 1.5.2.8.4 |
| 1.5.3.1.1 | 1.5.3.1.2 | 1.5.3.1.3 | 1.5.3.1.4 | 1.5.3.2.1 | 1.5.3.2.2 | 1.5.3.2.3 | 1.5.3.2.4 |
| 1.5.3.3.1 | 1.5.3.3.2 | 1.5.3.3.3 | 1.5.3.3.4 | 1.5.3.4.1 | 1.5.3.4.2 | 1.5.3.4.3 | 1.5.3.4.4 |
| 1.5.3.5.1 | 1.5.3.5.2 | 1.5.3.5.3 | 1.5.3.5.4 | 1.5.3.6.1 | 1.5.3.6.2 | 1.5.3.6.3 | 1.5.3.6.4 |
| 1.5.3.7.1 | 1.5.3.7.2 | 1.5.3.7.3 | 1.5.3.7.4 | 1.5.3.8.1 | 1.5.3.8.2 | 1.5.3.8.3 | 1.5.3.8.4 |
| 1.5.4.1.1 | 1.5.4.1.2 | 1.5.4.1.3 | 1.5.4.1.4 | 1.5.4.2.1 | 1.5.4.2.2 | 1.5.4.2.3 | 1.5.4.2.4 |
| 1.5.4.3.1 | 1.5.4.3.2 | 1.5.4.3.3 | 1.5.4.3.4 | 1.5.4.4.1 | 1.5.4.4.2 | 1.5.4.4.3 | 1.5.4.4.4 |
| 1.5.4.5.1 | 1.5.4.5.2 | 1.5.4.5.3 | 1.5.4.5.4 | 1.5.4.6.1 | 1.5.4.6.2 | 1.5.4.6.3 | 1.5.4.6.4 |

TABLE 1-continued

| | | | | | | | |
|---|---|---|---|---|---|---|---|
| 1.5.4.7.1 | 1.5.4.7.2 | 1.5.4.7.3 | 1.5.4.7.4 | 1.5.4.8.1 | 1.5.4.8.2 | 1.5.4.8.3 | 1.5.4.8.4 |
| 1.6.1.1.1 | 1.6.1.1.2 | 1.6.1.1.3 | 1.6.1.1.4 | 1.6.1.2.1 | 1.6.1.2.2 | 1.6.1.2.3 | 1.6.1.2.4 |
| 1.6.1.3.1 | 1.6.1.3.2 | 1.6.1.3.3 | 1.6.1.3.4 | 1.6.1.4.1 | 1.6.1.4.2 | 1.6.1.4.3 | 1.6.1.4.4 |
| 1.6.1.5.1 | 1.6.1.5.2 | 1.6.1.5.3 | 1.6.1.5.4 | 1.6.1.6.1 | 1.6.1.6.2 | 1.6.1.6.3 | 1.6.1.6.4 |
| 1.6.1.7.1 | 1.6.1.7.2 | 1.6.1.7.3 | 1.6.1.7.4 | 1.6.1.8.1 | 1.6.1.8.2 | 1.6.1.8.3 | 1.6.1.8.4 |
| 1.6.2.1.1 | 1.6.2.1.2 | 1.6.2.1.3 | 1.6.2.1.4 | 1.6.2.2.1 | 1.6.2.2.2 | 1.6.2.2.3 | 1.6.2.2.4 |
| 1.6.2.3.1 | 1.6.2.3.2 | 1.6.2.3.3 | 1.6.2.3.4 | 1.6.2.4.1 | 1.6.2.4.2 | 1.6.2.4.3 | 1.6.2.4.4 |
| 1.6.2.5.1 | 1.6.2.5.2 | 1.6.2.5.3 | 1.6.2.5.4 | 1.6.2.6.1 | 1.6.2.6.2 | 1.6.2.6.3 | 1.6.2.6.4 |
| 1.6.2.7.1 | 1.6.2.7.2 | 1.6.2.7.3 | 1.6.2.7.4 | 1.6.2.8.1 | 1.6.2.8.2 | 1.6.2.8.3 | 1.6.2.8.4 |
| 1.6.3.1.1 | 1.6.3.1.2 | 1.6.3.1.3 | 1.6.3.1.4 | 1.6.3.2.1 | 1.6.3.2.2 | 1.6.3.2.3 | 1.6.3.2.4 |
| 1.6.3.3.1 | 1.6.3.3.2 | 1.6.3.3.3 | 1.6.3.3.4 | 1.6.3.4.1 | 1.6.3.4.2 | 1.6.3.4.3 | 1.6.3.4.4 |
| 1.6.3.5.1 | 1.6.3.5.2 | 1.6.3.5.3 | 1.6.3.5.4 | 1.6.3.6.1 | 1.6.3.6.2 | 1.6.3.6.3 | 1.6.3.6.4 |
| 1.6.3.7.1 | 1.6.3.7.2 | 1.6.3.7.3 | 1.6.3.7.4 | 1.6.3.8.1 | 1.6.3.8.2 | 1.6.3.8.3 | 1.6.3.8.4 |
| 1.6.4.1.1 | 1.6.4.1.2 | 1.6.4.1.3 | 1.6.4.1.4 | 1.6.4.2.1 | 1.6.4.2.2 | 1.6.4.2.3 | 1.6.4.2.4 |
| 1.6.4.3.1 | 1.6.4.3.2 | 1.6.4.3.3 | 1.6.4.3.4 | 1.6.4.4.1 | 1.6.4.4.2 | 1.6.4.4.3 | 1.6.4.4.4 |
| 1.6.4.5.1 | 1.6.4.5.2 | 1.6.4.5.3 | 1.6.4.5.4 | 1.6.4.6.1 | 1.6.4.6.2 | 1.6.4.6.3 | 1.6.4.6.4 |
| 1.6.4.7.1 | 1.6.4.7.2 | 1.6.4.7.3 | 1.6.4.7.4 | 1.6.4.8.1 | 1.6.4.8.2 | 1.6.4.8.3 | 1.6.4.8.4 |
| 1.7.1.1.1 | 1.7.1.1.2 | 1.7.1.1.3 | 1.7.1.1.4 | 1.7.1.2.1 | 1.7.1.2.2 | 1.7.1.2.3 | 1.7.1.2.4 |
| 1.7.1.3.1 | 1.7.1.3.2 | 1.7.1.3.3 | 1.7.1.3.4 | 1.7.1.4.1 | 1.7.1.4.2 | 1.7.1.4.3 | 1.7.1.4.4 |
| 1.7.1.5.1 | 1.7.1.5.2 | 1.7.1.5.3 | 1.7.1.5.4 | 1.7.1.6.1 | 1.7.1.6.2 | 1.7.1.6.3 | 1.7.1.6.4 |
| 1.7.1.7.1 | 1.7.1.7.2 | 1.7.1.7.3 | 1.7.1.7.4 | 1.7.1.8.1 | 1.7.1.8.2 | 1.7.1.8.3 | 1.7.1.8.4 |
| 1.7.2.1.1 | 1.7.2.1.2 | 1.7.2.1.3 | 1.7.2.1.4 | 1.7.2.2.1 | 1.7.2.2.2 | 1.7.2.2.3 | 1.7.2.2.4 |
| 1.7.2.3.1 | 1.7.2.3.2 | 1.7.2.3.3 | 1.7.2.3.4 | 1.7.2.4.1 | 1.7.2.4.2 | 1.7.2.4.3 | 1.7.2.4.4 |
| 1.7.2.5.1 | 1.7.2.5.2 | 1.7.2.5.3 | 1.7.2.5.4 | 1.7.2.6.1 | 1.7.2.6.2 | 1.7.2.6.3 | 1.7.2.6.4 |
| 1.7.2.7.1 | 1.7.2.7.2 | 1.7.2.7.3 | 1.7.2.7.4 | 1.7.2.8.1 | 1.7.2.8.2 | 1.7.2.8.3 | 1.7.2.8.4 |
| 1.7.3.1.1 | 1.7.3.1.2 | 1.7.3.1.3 | 1.7.3.1.4 | 1.7.3.2.1 | 1.7.3.2.2 | 1.7.3.2.3 | 1.7.3.2.4 |
| 1.7.3.3.1 | 1.7.3.3.2 | 1.7.3.3.3 | 1.7.3.3.4 | 1.7.3.4.1 | 1.7.3.4.2 | 1.7.3.4.3 | 1.7.3.4.4 |
| 1.7.3.5.1 | 1.7.3.5.2 | 1.7.3.5.3 | 1.7.3.5.4 | 1.7.3.6.1 | 1.7.3.6.2 | 1.7.3.6.3 | 1.7.3.6.4 |
| 1.7.3.7.1 | 1.7.3.7.2 | 1.7.3.7.3 | 1.7.3.7.4 | 1.7.3.8.1 | 1.7.3.8.2 | 1.7.3.8.3 | 1.7.3.8.4 |
| 1.7.4.1.1 | 1.7.4.1.2 | 1.7.4.1.3 | 1.7.4.1.4 | 1.7.4.2.1 | 1.7.4.2.2 | 1.7.4.2.3 | 1.7.4.2.4 |
| 1.7.4.3.1 | 1.7.4.3.2 | 1.7.4.3.3 | 1.7.4.3.4 | 1.7.4.4.1 | 1.7.4.4.2 | 1.7.4.4.3 | 1.7.4.4.4 |
| 1.7.4.5.1 | 1.7.4.5.2 | 1.7.4.5.3 | 1.7.4.5.4 | 1.7.4.6.1 | 1.7.4.6.2 | 1.7.4.6.3 | 1.7.4.6.4 |
| 1.7.4.7.1 | 1.7.4.7.2 | 1.7.4.7.3 | 1.7.4.7.4 | 1.7.4.8.1 | 1.7.4.8.2 | 1.7.4.8.3 | 1.7.4.8.4 |
| 1.8.1.1.1 | 1.8.1.1.2 | 1.8.1.1.3 | 1.8.1.1.4 | 1.8.1.2.1 | 1.8.1.2.2 | 1.8.1.2.3 | 1.8.1.2.4 |
| 1.8.1.3.1 | 1.8.1.3.2 | 1.8.1.3.3 | 1.8.1.3.4 | 1.8.1.4.1 | 1.8.1.4.2 | 1.8.1.4.3 | 1.8.1.4.4 |
| 1.8.1.5.1 | 1.8.1.5.2 | 1.8.1.5.3 | 1.8.1.5.4 | 1.8.1.6.1 | 1.8.1.6.2 | 1.8.1.6.3 | 1.8.1.6.4 |
| 1.8.1.7.1 | 1.8.1.7.2 | 1.8.1.7.3 | 1.8.1.7.4 | 1.8.1.8.1 | 1.8.1.8.2 | 1.8.1.8.3 | 1.8.1.8.4 |
| 1.8.2.1.1 | 1.8.2.1.2 | 1.8.2.1.3 | 1.8.2.1.4 | 1.8.2.2.1 | 1.8.2.2.2 | 1.8.2.2.3 | 1.8.2.2.4 |
| 1.8.2.3.1 | 1.8.2.3.2 | 1.8.2.3.3 | 1.8.2.3.4 | 1.8.2.4.1 | 1.8.2.4.2 | 1.8.2.4.3 | 1.8.2.4.4 |
| 1.8.2.5.1 | 1.8.2.5.2 | 1.8.2.5.3 | 1.8.2.5.4 | 1.8.2.6.1 | 1.8.2.6.2 | 1.8.2.6.3 | 1.8.2.6.4 |
| 1.8.2.7.1 | 1.8.2.7.2 | 1.8.2.7.3 | 1.8.2.7.4 | 1.8.2.8.1 | 1.8.2.8.2 | 1.8.2.8.3 | 1.8.2.8.4 |
| 1.8.3.1.1 | 1.8.3.1.2 | 1.8.3.1.3 | 1.8.3.1.4 | 1.8.3.2.1 | 1.8.3.2.2 | 1.8.3.2.3 | 1.8.3.2.4 |
| 1.8.3.3.1 | 1.8.3.3.2 | 1.8.3.3.3 | 1.8.3.3.4 | 1.8.3.4.1 | 1.8.3.4.2 | 1.8.3.4.3 | 1.8.3.4.4 |
| 1.8.3.5.1 | 1.8.3.5.2 | 1.8.3.5.3 | 1.8.3.5.4 | 1.8.3.6.1 | 1.8.3.6.2 | 1.8.3.6.3 | 1.8.3.6.4 |
| 1.8.3.7.1 | 1.8.3.7.2 | 1.8.3.7.3 | 1.8.3.7.4 | 1.8.3.8.1 | 1.8.3.8.2 | 1.8.3.8.3 | 1.8.3.8.4 |
| 1.8.4.1.1 | 1.8.4.1.2 | 1.8.4.1.3 | 1.8.4.1.4 | 1.8.4.2.1 | 1.8.4.2.2 | 1.8.4.2.3 | 1.8.4.2.4 |
| 1.8.4.3.1 | 1.8.4.3.2 | 1.8.4.3.3 | 1.8.4.3.4 | 1.8.4.4.1 | 1.8.4.4.2 | 1.8.4.4.3 | 1.8.4.4.4 |
| 1.8.4.5.1 | 1.8.4.5.2 | 1.8.4.5.3 | 1.8.4.5.4 | 1.8.4.6.1 | 1.8.4.6.2 | 1.8.4.6.3 | 1.8.4.6.4 |
| 1.8.4.7.1 | 1.8.4.7.2 | 1.8.4.7.3 | 1.8.4.7.4 | 1.8.4.8.1 | 1.8.4.8.2 | 1.8.4.8.3 | 1.8.4.8.4 |
| 2.1.1.1.1 | 2.1.1.1.2 | 2.1.1.1.3 | 2.1.1.1.4 | 2.1.1.2.1 | 2.1.1.2.2 | 2.1.1.2.3 | 2.1.1.2.4 |
| 2.1.1.3.1 | 2.1.1.3.2 | 2.1.1.3.3 | 2.1.1.3.4 | 2.1.1.4.1 | 2.1.1.4.2 | 2.1.1.4.3 | 2.1.1.4.4 |
| 2.1.1.5.1 | 2.1.1.5.2 | 2.1.1.5.3 | 2.1.1.5.4 | 2.1.1.6.1 | 2.1.1.6.2 | 2.1.1.6.3 | 2.1.1.6.4 |
| 2.1.1.7.1 | 2.1.1.7.2 | 2.1.1.7.3 | 2.1.1.7.4 | 2.1.1.8.1 | 2.1.1.8.2 | 2.1.1.8.3 | 2.1.1.8.4 |
| 2.1.2.1.1 | 2.1.2.1.2 | 2.1.2.1.3 | 2.1.2.1.4 | 2.1.2.2.1 | 2.1.2.2.2 | 2.1.2.2.3 | 2.1.2.2.4 |
| 2.1.2.3.1 | 2.1.2.3.2 | 2.1.2.3.3 | 2.1.2.3.4 | 2.1.2.4.1 | 2.1.2.4.2 | 2.1.2.4.3 | 2.1.2.4.4 |
| 2.1.2.5.1 | 2.1.2.5.2 | 2.1.2.5.3 | 2.1.2.5.4 | 2.1.2.6.1 | 2.1.2.6.2 | 2.1.2.6.3 | 2.1.2.6.4 |
| 2.1.2.7.1 | 2.1.2.7.2 | 2.1.2.7.3 | 2.1.2.7.4 | 2.1.2.8.1 | 2.1.2.8.2 | 2.1.2.8.3 | 2.1.2.8.4 |
| 2.1.3.1.1 | 2.1.3.1.2 | 2.1.3.1.3 | 2.1.3.1.4 | 2.1.3.2.1 | 2.1.3.2.2 | 2.1.3.2.3 | 2.1.3.2.4 |
| 2.1.3.3.1 | 2.1.3.3.2 | 2.1.3.3.3 | 2.1.3.3.4 | 2.1.3.4.1 | 2.1.3.4.2 | 2.1.3.4.3 | 2.1.3.4.4 |
| 2.1.3.5.1 | 2.1.3.5.2 | 2.1.3.5.3 | 2.1.3.5.4 | 2.1.3.6.1 | 2.1.3.6.2 | 2.1.3.6.3 | 2.1.3.6.4 |
| 2.1.3.7.1 | 2.1.3.7.2 | 2.1.3.7.3 | 2.1.3.7.4 | 2.1.3.8.1 | 2.1.3.8.2 | 2.1.3.8.3 | 2.1.3.8.4 |
| 2.1.4.1.1 | 2.1.4.1.2 | 2.1.4.1.3 | 2.1.4.1.4 | 2.1.4.2.1 | 2.1.4.2.2 | 2.1.4.2.3 | 2.1.4.2.4 |
| 2.1.4.3.1 | 2.1.4.3.2 | 2.1.4.3.3 | 2.1.4.3.4 | 2.1.4.4.1 | 2.1.4.4.2 | 2.1.4.4.3 | 2.1.4.4.4 |
| 2.1.4.5.1 | 2.1.4.5.2 | 2.1.4.5.3 | 2.1.4.5.4 | 2.1.4.6.1 | 2.1.4.6.2 | 2.1.4.6.3 | 2.1.4.6.4 |
| 2.1.4.7.1 | 2.1.4.7.2 | 2.1.4.7.3 | 2.1.4.7.4 | 2.1.4.8.1 | 2.1.4.8.2 | 2.1.4.8.3 | 2.1.4.8.4 |
| 2.2.1.1.1 | 2.2.1.1.2 | 2.2.1.1.3 | 2.2.1.1.4 | 2.2.1.2.1 | 2.2.1.2.2 | 2.2.1.2.3 | 2.2.1.2.4 |
| 2.2.1.3.1 | 2.2.1.3.2 | 2.2.1.3.3 | 2.2.1.3.4 | 2.2.1.4.1 | 2.2.1.4.2 | 2.2.1.4.3 | 2.2.1.4.4 |
| 2.2.1.5.1 | 2.2.1.5.2 | 2.2.1.5.3 | 2.2.1.5.4 | 2.2.1.6.1 | 2.2.1.6.2 | 2.2.1.6.3 | 2.2.1.6.4 |
| 2.2.1.7.1 | 2.2.1.7.2 | 2.2.1.7.3 | 2.2.1.7.4 | 2.2.1.8.1 | 2.2.1.8.2 | 2.2.1.8.3 | 2.2.1.8.4 |
| 2.2.2.1.1 | 2.2.2.1.2 | 2.2.2.1.3 | 2.2.2.1.4 | 2.2.2.2.1 | 2.2.2.2.2 | 2.2.2.2.3 | 2.2.2.2.4 |
| 2.2.2.3.1 | 2.2.2.3.2 | 2.2.2.3.3 | 2.2.2.3.4 | 2.2.2.4.1 | 2.2.2.4.2 | 2.2.2.4.3 | 2.2.2.4.4 |
| 2.2.2.5.1 | 2.2.2.5.2 | 2.2.2.5.3 | 2.2.2.5.4 | 2.2.2.6.1 | 2.2.2.6.2 | 2.2.2.6.3 | 2.2.2.6.4 |
| 2.2.2.7.1 | 2.2.2.7.2 | 2.2.2.7.3 | 2.2.2.7.4 | 2.2.2.8.1 | 2.2.2.8.2 | 2.2.2.8.3 | 2.2.2.8.4 |
| 2.2.3.1.1 | 2.2.3.1.2 | 2.2.3.1.3 | 2.2.3.1.4 | 2.2.3.2.1 | 2.2.3.2.2 | 2.2.3.2.3 | 2.2.3.2.4 |
| 2.2.3.3.1 | 2.2.3.3.2 | 2.2.3.3.3 | 2.2.3.3.4 | 2.2.3.4.1 | 2.2.3.4.2 | 2.2.3.4.3 | 2.2.3.4.4 |
| 2.2.3.5.1 | 2.2.3.5.2 | 2.2.3.5.3 | 2.2.3.5.4 | 2.2.3.6.1 | 2.2.3.6.2 | 2.2.3.6.3 | 2.2.3.6.4 |
| 2.2.3.7.1 | 2.2.3.7.2 | 2.2.3.7.3 | 2.2.3.7.4 | 2.2.3.8.1 | 2.2.3.8.2 | 2.2.3.8.3 | 2.2.3.8.4 |
| 2.2.4.1.1 | 2.2.4.1.2 | 2.2.4.1.3 | 2.2.4.1.4 | 2.2.4.2.1 | 2.2.4.2.2 | 2.2.4.2.3 | 2.2.4.2.4 |
| 2.2.4.3.1 | 2.2.4.3.2 | 2.2.4.3.3 | 2.2.4.3.4 | 2.2.4.4.1 | 2.2.4.4.2 | 2.2.4.4.3 | 2.2.4.4.4 |

TABLE 1-continued

| | | | | | | | |
|---|---|---|---|---|---|---|---|
| 2.2.4.5.1 | 2.2.4.5.2 | 2.2.4.5.3 | 2.2.4.5.4 | 2.2.4.6.1 | 2.2.4.6.2 | 2.2.4.6.3 | 2.2.4.6.4 |
| 2.2.4.7.1 | 2.2.4.7.2 | 2.2.4.7.3 | 2.2.4.7.4 | 2.2.4.8.1 | 2.2.4.8.2 | 2.2.4.8.3 | 2.2.4.8.4 |
| 2.3.1.1.1 | 2.3.1.1.2 | 2.3.1.1.3 | 2.3.1.1.4 | 2.3.1.2.1 | 2.3.1.2.2 | 2.3.1.2.3 | 2.3.1.2.4 |
| 2.3.1.3.1 | 2.3.1.3.2 | 2.3.1.3.3 | 2.3.1.3.4 | 2.3.1.4.1 | 2.3.1.4.2 | 2.3.1.4.3 | 2.3.1.4.4 |
| 2.3.1.5.1 | 2.3.1.5.2 | 2.3.1.5.3 | 2.3.1.5.4 | 2.3.1.6.1 | 2.3.1.6.2 | 2.3.1.6.3 | 2.3.1.6.4 |
| 2.3.1.7.1 | 2.3.1.7.2 | 2.3.1.7.3 | 2.3.1.7.4 | 2.3.1.8.1 | 2.3.1.8.2 | 2.3.1.8.3 | 2.3.1.8.4 |
| 2.3.2.1.1 | 2.3.2.1.2 | 2.3.2.1.3 | 2.3.2.1.4 | 2.3.2.2.1 | 2.3.2.2.2 | 2.3.2.2.3 | 2.3.2.2.4 |
| 2.3.2.3.1 | 2.3.2.3.2 | 2.3.2.3.3 | 2.3.2.3.4 | 2.3.2.4.1 | 2.3.2.4.2 | 2.3.2.4.3 | 2.3.2.4.4 |
| 2.3.2.5.1 | 2.3.2.5.2 | 2.3.2.5.3 | 2.3.2.5.4 | 2.3.2.6.1 | 2.3.2.6.2 | 2.3.2.6.3 | 2.3.2.6.4 |
| 2.3.2.7.1 | 2.3.2.7.2 | 2.3.2.7.3 | 2.3.2.7.4 | 2.3.2.8.1 | 2.3.2.8.2 | 2.3.2.8.3 | 2.3.2.8.4 |
| 2.3.3.1.1 | 2.3.3.1.2 | 2.3.3.1.3 | 2.3.3.1.4 | 2.3.3.2.1 | 2.3.3.2.2 | 2.3.3.2.3 | 2.3.3.2.4 |
| 2.3.3.3.1 | 2.3.3.3.2 | 2.3.3.3.3 | 2.3.3.3.4 | 2.3.3.4.1 | 2.3.3.4.2 | 2.3.3.4.3 | 2.3.3.4.4 |
| 2.3.3.5.1 | 2.3.3.5.2 | 2.3.3.5.3 | 2.3.3.5.4 | 2.3.3.6.1 | 2.3.3.6.2 | 2.3.3.6.3 | 2.3.3.6.4 |
| 2.3.3.7.1 | 2.3.3.7.2 | 2.3.3.7.3 | 2.3.3.7.4 | 2.3.3.8.1 | 2.3.3.8.2 | 2.3.3.8.3 | 2.3.3.8.4 |
| 2.3.4.1.1 | 2.3.4.1.2 | 2.3.4.1.3 | 2.3.4.1.4 | 2.3.4.2.1 | 2.3.4.2.2 | 2.3.4.2.3 | 2.3.4.2.4 |
| 2.3.4.3.1 | 2.3.4.3.2 | 2.3.4.3.3 | 2.3.4.3.4 | 2.3.4.4.1 | 2.3.4.4.2 | 2.3.4.4.3 | 2.3.4.4.4 |
| 2.3.4.5.1 | 2.3.4.5.2 | 2.3.4.5.3 | 2.3.4.5.4 | 2.3.4.6.1 | 2.3.4.6.2 | 2.3.4.6.3 | 2.3.4.6.4 |
| 2.3.4.7.1 | 2.3.4.7.2 | 2.3.4.7.3 | 2.3.4.7.4 | 2.3.4.8.1 | 2.3.4.8.2 | 2.3.4.8.3 | 2.3.4.8.4 |
| 2.4.1.1.1 | 2.4.1.1.2 | 2.4.1.1.3 | 2.4.1.1.4 | 2.4.1.2.1 | 2.4.1.2.2 | 2.4.1.2.3 | 2.4.1.2.4 |
| 2.4.1.3.1 | 2.4.1.3.2 | 2.4.1.3.3 | 2.4.1.3.4 | 2.4.1.4.1 | 2.4.1.4.2 | 2.4.1.4.3 | 2.4.1.4.4 |
| 2.4.1.5.1 | 2.4.1.5.2 | 2.4.1.5.3 | 2.4.1.5.4 | 2.4.1.6.1 | 2.4.1.6.2 | 2.4.1.6.3 | 2.4.1.6.4 |
| 2.4.1.7.1 | 2.4.1.7.2 | 2.4.1.7.3 | 2.4.1.7.4 | 2.4.1.8.1 | 2.4.1.8.2 | 2.4.1.8.3 | 2.4.1.8.4 |
| 2.4.2.1.1 | 2.4.2.1.2 | 2.4.2.1.3 | 2.4.2.1.4 | 2.4.2.2.1 | 2.4.2.2.2 | 2.4.2.2.3 | 2.4.2.2.4 |
| 2.4.2.3.1 | 2.4.2.3.2 | 2.4.2.3.3 | 2.4.2.3.4 | 2.4.2.4.1 | 2.4.2.4.2 | 2.4.2.4.3 | 2.4.2.4.4 |
| 2.4.2.5.1 | 2.4.2.5.2 | 2.4.2.5.3 | 2.4.2.5.4 | 2.4.2.6.1 | 2.4.2.6.2 | 2.4.2.6.3 | 2.4.2.6.4 |
| 2.4.2.7.1 | 2.4.2.7.2 | 2.4.2.7.3 | 2.4.2.7.4 | 2.4.2.8.1 | 2.4.2.8.2 | 2.4.2.8.3 | 2.4.2.8.4 |
| 2.4.3.1.1 | 2.4.3.1.2 | 2.4.3.1.3 | 2.4.3.1.4 | 2.4.3.2.1 | 2.4.3.2.2 | 2.4.3.2.3 | 2.4.3.2.4 |
| 2.4.3.3.1 | 2.4.3.3.2 | 2.4.3.3.3 | 2.4.3.3.4 | 2.4.3.4.1 | 2.4.3.4.2 | 2.4.3.4.3 | 2.4.3.4.4 |
| 2.4.3.5.1 | 2.4.3.5.2 | 2.4.3.5.3 | 2.4.3.5.4 | 2.4.3.6.1 | 2.4.3.6.2 | 2.4.3.6.3 | 2.4.3.6.4 |
| 2.4.3.7.1 | 2.4.3.7.2 | 2.4.3.7.3 | 2.4.3.7.4 | 2.4.3.8.1 | 2.4.3.8.2 | 2.4.3.8.3 | 2.4.3.8.4 |
| 2.4.4.1.1 | 2.4.4.1.2 | 2.4.4.1.3 | 2.4.4.1.4 | 2.4.4.2.1 | 2.4.4.2.2 | 2.4.4.2.3 | 2.4.4.2.4 |
| 2.4.4.3.1 | 2.4.4.3.2 | 2.4.4.3.3 | 2.4.4.3.4 | 2.4.4.4.1 | 2.4.4.4.2 | 2.4.4.4.3 | 2.4.4.4.4 |
| 2.4.4.5.1 | 2.4.4.5.2 | 2.4.4.5.3 | 2.4.4.5.4 | 2.4.4.6.1 | 2.4.4.6.2 | 2.4.4.6.3 | 2.4.4.6.4 |
| 2.4.4.7.1 | 2.4.4.7.2 | 2.4.4.7.3 | 2.4.4.7.4 | 2.4.4.8.1 | 2.4.4.8.2 | 2.4.4.8.3 | 2.4.4.8.4 |
| 2.5.1.1.1 | 2.5.1.1.2 | 2.5.1.1.3 | 2.5.1.1.4 | 2.5.1.2.1 | 2.5.1.2.2 | 2.5.1.2.3 | 2.5.1.2.4 |
| 2.5.1.3.1 | 2.5.1.3.2 | 2.5.1.3.3 | 2.5.1.3.4 | 2.5.1.4.1 | 2.5.1.4.2 | 2.5.1.4.3 | 2.5.1.4.4 |
| 2.5.1.5.1 | 2.5.1.5.2 | 2.5.1.5.3 | 2.5.1.5.4 | 2.5.1.6.1 | 2.5.1.6.2 | 2.5.1.6.3 | 2.5.1.6.4 |
| 2.5.1.7.1 | 2.5.1.7.2 | 2.5.1.7.3 | 2.5.1.7.4 | 2.5.1.8.1 | 2.5.1.8.2 | 2.5.1.8.3 | 2.5.1.8.4 |
| 2.5.2.1.1 | 2.5.2.1.2 | 2.5.2.1.3 | 2.5.2.1.4 | 2.5.2.2.1 | 2.5.2.2.2 | 2.5.2.2.3 | 2.5.2.2.4 |
| 2.5.2.3.1 | 2.5.2.3.2 | 2.5.2.3.3 | 2.5.2.3.4 | 2.5.2.4.1 | 2.5.2.4.2 | 2.5.2.4.3 | 2.5.2.4.4 |
| 2.5.2.5.1 | 2.5.2.5.2 | 2.5.2.5.3 | 2.5.2.5.4 | 2.5.2.6.1 | 2.5.2.6.2 | 2.5.2.6.3 | 2.5.2.6.4 |
| 2.5.2.7.1 | 2.5.2.7.2 | 2.5.2.7.3 | 2.5.2.7.4 | 2.5.2.8.1 | 2.5.2.8.2 | 2.5.2.8.3 | 2.5.2.8.4 |
| 2.5.3.1.1 | 2.5.3.1.2 | 2.5.3.1.3 | 2.5.3.1.4 | 2.5.3.2.1 | 2.5.3.2.2 | 2.5.3.2.3 | 2.5.3.2.4 |
| 2.5.3.3.1 | 2.5.3.3.2 | 2.5.3.3.3 | 2.5.3.3.4 | 2.5.3.4.1 | 2.5.3.4.2 | 2.5.3.4.3 | 2.5.3.4.4 |
| 2.5.3.5.1 | 2.5.3.5.2 | 2.5.3.5.3 | 2.5.3.5.4 | 2.5.3.6.1 | 2.5.3.6.2 | 2.5.3.6.3 | 2.5.3.6.4 |
| 2.5.3.7.1 | 2.5.3.7.2 | 2.5.3.7.3 | 2.5.3.7.4 | 2.5.3.8.1 | 2.5.3.8.2 | 2.5.3.8.3 | 2.5.3.8.4 |
| 2.5.4.1.1 | 2.5.4.1.2 | 2.5.4.1.3 | 2.5.4.1.4 | 2.5.4.2.1 | 2.5.4.2.2 | 2.5.4.2.3 | 2.5.4.2.4 |
| 2.5.4.3.1 | 2.5.4.3.2 | 2.5.4.3.3 | 2.5.4.3.4 | 2.5.4.4.1 | 2.5.4.4.2 | 2.5.4.4.3 | 2.5.4.4.4 |
| 2.5.4.5.1 | 2.5.4.5.2 | 2.5.4.5.3 | 2.5.4.5.4 | 2.5.4.6.1 | 2.5.4.6.2 | 2.5.4.6.3 | 2.5.4.6.4 |
| 2.5.4.7.1 | 2.5.4.7.2 | 2.5.4.7.3 | 2.5.4.7.4 | 2.5.4.8.1 | 2.5.4.8.2 | 2.5.4.8.3 | 2.5.4.8.4 |
| 2.6.1.1.1 | 2.6.1.1.2 | 2.6.1.1.3 | 2.6.1.1.4 | 2.6.1.2.1 | 2.6.1.2.2 | 2.6.1.2.3 | 2.6.1.2.4 |
| 2.6.1.3.1 | 2.6.1.3.2 | 2.6.1.3.3 | 2.6.1.3.4 | 2.6.1.4.1 | 2.6.1.4.2 | 2.6.1.4.3 | 2.6.1.4.4 |
| 2.6.1.5.1 | 2.6.1.5.2 | 2.6.1.5.3 | 2.6.1.5.4 | 2.6.1.6.1 | 2.6.1.6.2 | 2.6.1.6.3 | 2.6.1.6.4 |
| 2.6.1.7.1 | 2.6.1.7.2 | 2.6.1.7.3 | 2.6.1.7.4 | 2.6.1.8.1 | 2.6.1.8.2 | 2.6.1.8.3 | 2.6.1.8.4 |
| 2.6.2.1.1 | 2.6.2.1.2 | 2.6.2.1.3 | 2.6.2.1.4 | 2.6.2.2.1 | 2.6.2.2.2 | 2.6.2.2.3 | 2.6.2.2.4 |
| 2.6.2.3.1 | 2.6.2.3.2 | 2.6.2.3.3 | 2.6.2.3.4 | 2.6.2.4.1 | 2.6.2.4.2 | 2.6.2.4.3 | 2.6.2.4.4 |
| 2.6.2.5.1 | 2.6.2.5.2 | 2.6.2.5.3 | 2.6.2.5.4 | 2.6.2.6.1 | 2.6.2.6.2 | 2.6.2.6.3 | 2.6.2.6.4 |
| 2.6.2.7.1 | 2.6.2.7.2 | 2.6.2.7.3 | 2.6.2.7.4 | 2.6.2.8.1 | 2.6.2.8.2 | 2.6.2.8.3 | 2.6.2.8.4 |
| 2.6.3.1.1 | 2.6.3.1.2 | 2.6.3.1.3 | 2.6.3.1.4 | 2.6.3.2.1 | 2.6.3.2.2 | 2.6.3.2.3 | 2.6.3.2.4 |
| 2.6.3.3.1 | 2.6.3.3.2 | 2.6.3.3.3 | 2.6.3.3.4 | 2.6.3.4.1 | 2.6.3.4.2 | 2.6.3.4.3 | 2.6.3.4.4 |
| 2.6.3.5.1 | 2.6.3.5.2 | 2.6.3.5.3 | 2.6.3.5.4 | 2.6.3.6.1 | 2.6.3.6.2 | 2.6.3.6.3 | 2.6.3.6.4 |
| 2.6.3.7.1 | 2.6.3.7.2 | 2.6.3.7.3 | 2.6.3.7.4 | 2.6.3.8.1 | 2.6.3.8.2 | 2.6.3.8.3 | 2.6.3.8.4 |
| 2.6.4.1.1 | 2.6.4.1.2 | 2.6.4.1.3 | 2.6.4.1.4 | 2.6.4.2.1 | 2.6.4.2.2 | 2.6.4.2.3 | 2.6.4.2.4 |
| 2.6.4.3.1 | 2.6.4.3.2 | 2.6.4.3.3 | 2.6.4.3.4 | 2.6.4.4.1 | 2.6.4.4.2 | 2.6.4.4.3 | 2.6.4.4.4 |
| 2.6.4.5.1 | 2.6.4.5.2 | 2.6.4.5.3 | 2.6.4.5.4 | 2.6.4.6.1 | 2.6.4.6.2 | 2.6.4.6.3 | 2.6.4.6.4 |
| 2.6.4.7.1 | 2.6.4.7.2 | 2.6.4.7.3 | 2.6.4.7.4 | 2.6.4.8.1 | 2.6.4.8.2 | 2.6.4.8.3 | 2.6.4.8.4 |
| 2.7.1.1.1 | 2.7.1.1.2 | 2.7.1.1.3 | 2.7.1.1.4 | 2.7.1.2.1 | 2.7.1.2.2 | 2.7.1.2.3 | 2.7.1.2.4 |
| 2.7.1.3.1 | 2.7.1.3.2 | 2.7.1.3.3 | 2.7.1.3.4 | 2.7.1.4.1 | 2.7.1.4.2 | 2.7.1.4.3 | 2.7.1.4.4 |
| 2.7.1.5.1 | 2.7.1.5.2 | 2.7.1.5.3 | 2.7.1.5.4 | 2.7.1.6.1 | 2.7.1.6.2 | 2.7.1.6.3 | 2.7.1.6.4 |
| 2.7.1.7.1 | 2.7.1.7.2 | 2.7.1.7.3 | 2.7.1.7.4 | 2.7.1.8.1 | 2.7.1.8.2 | 2.7.1.8.3 | 2.7.1.8.4 |
| 2.7.2.1.1 | 2.7.2.1.2 | 2.7.2.1.3 | 2.7.2.1.4 | 2.7.2.2.1 | 2.7.2.2.2 | 2.7.2.2.3 | 2.7.2.2.4 |
| 2.7.2.3.1 | 2.7.2.3.2 | 2.7.2.3.3 | 2.7.2.3.4 | 2.7.2.4.1 | 2.7.2.4.2 | 2.7.2.4.3 | 2.7.2.4.4 |
| 2.7.2.5.1 | 2.7.2.5.2 | 2.7.2.5.3 | 2.7.2.5.4 | 2.7.2.6.1 | 2.7.2.6.2 | 2.7.2.6.3 | 2.7.2.6.4 |
| 2.7.2.7.1 | 2.7.2.7.2 | 2.7.2.7.3 | 2.7.2.7.4 | 2.7.2.8.1 | 2.7.2.8.2 | 2.7.2.8.3 | 2.7.2.8.4 |
| 2.7.3.1.1 | 2.7.3.1.2 | 2.7.3.1.3 | 2.7.3.1.4 | 2.7.3.2.1 | 2.7.3.2.2 | 2.7.3.2.3 | 2.7.3.2.4 |
| 2.7.3.3.1 | 2.7.3.3.2 | 2.7.3.3.3 | 2.7.3.3.4 | 2.7.3.4.1 | 2.7.3.4.2 | 2.7.3.4.3 | 2.7.3.4.4 |
| 2.7.3.5.1 | 2.7.3.5.2 | 2.7.3.5.3 | 2.7.3.5.4 | 2.7.3.6.1 | 2.7.3.6.2 | 2.7.3.6.3 | 2.7.3.6.4 |
| 2.7.3.7.1 | 2.7.3.7.2 | 2.7.3.7.3 | 2.7.3.7.4 | 2.7.3.8.1 | 2.7.3.8.2 | 2.7.3.8.3 | 2.7.3.8.4 |
| 2.7.4.1.1 | 2.7.4.1.2 | 2.7.4.1.3 | 2.7.4.1.4 | 2.7.4.2.1 | 2.7.4.2.2 | 2.7.4.2.3 | 2.7.4.2.4 |

TABLE 1-continued

| | | | | | | | |
|---|---|---|---|---|---|---|---|
| 2.7.4.3.1 | 2.7.4.3.2 | 2.7.4.3.3 | 2.7.4.3.4 | 2.7.4.4.1 | 2.7.4.4.2 | 2.7.4.4.3 | 2.7.4.4.4 |
| 2.7.4.5.1 | 2.7.4.5.2 | 2.7.4.5.3 | 2.7.4.5.4 | 2.7.4.6.1 | 2.7.4.6.2 | 2.7.4.6.3 | 2.7.4.6.4 |
| 2.7.4.7.1 | 2.7.4.7.2 | 2.7.4.7.3 | 2.7.4.7.4 | 2.7.4.8.1 | 2.7.4.8.2 | 2.7.4.8.3 | 2.7.4.8.4 |
| 2.8.1.1.1 | 2.8.1.1.2 | 2.8.1.1.3 | 2.8.1.1.4 | 2.8.1.2.1 | 2.8.1.2.2 | 2.8.1.2.3 | 2.8.1.2.4 |
| 2.8.1.3.1 | 2.8.1.3.2 | 2.8.1.3.3 | 2.8.1.3.4 | 2.8.1.4.1 | 2.8.1.4.2 | 2.8.1.4.3 | 2.8.1.4.4 |
| 2.8.1.5.1 | 2.5.1.5.2 | 2.8.1.5.3 | 2.8.1.5.4 | 2.8.1.6.1 | 2.8.1.6.2 | 2.8.1.6.3 | 2.8.1.6.4 |
| 2.8.1.7.1 | 2.8.1.7.2 | 2.8.1.7.3 | 2.8.1.7.4 | 2.8.1.8.1 | 2.8.1.8.2 | 2.8.1.8.3 | 2.8.1.8.4 |
| 2.8.2.1.1 | 2.8.2.1.2 | 2.8.2.1.3 | 2.8.2.1.4 | 2.8.2.2.1 | 2.8.2.2.2 | 2.8.2.2.3 | 2.8.2.2.4 |
| 2.8.2.3.1 | 2.8.2.3.2 | 2.8.2.3.3 | 2.8.2.3.4 | 2.8.2.4.1 | 2.8.2.4.2 | 2.8.2.4.3 | 2.8.2.4.4 |
| 2.8.2.5.1 | 2.8.2.5.2 | 2.8.2.5.3 | 2.8.2.5.4 | 2.8.2.6.1 | 2.8.2.6.2 | 2.8.2.6.3 | 2.8.2.6.4 |
| 2.8.2.7.1 | 2.8.2.7.2 | 2.8.2.7.3 | 2.8.2.7.4 | 2.8.2.8.1 | 2.8.2.8.2 | 2.8.2.8.3 | 2.8.2.8.4 |
| 2.8.3.1.1 | 2.8.3.1.2 | 2.8.3.1.3 | 2.8.3.1.4 | 2.8.3.2.1 | 2.8.3.2.2 | 2.8.3.2.3 | 2.8.3.2.4 |
| 2.8.3.3.1 | 2.8.3.3.2 | 2.8.3.3.3 | 2.8.3.3.4 | 2.8.3.4.1 | 2.8.3.4.2 | 2.8.3.4.3 | 2.8.3.4.4 |
| 2.8.3.5.1 | 2.8.3.5.2 | 2.8.3.5.3 | 2.8.3.5.4 | 2.8.3.6.1 | 2.8.3.6.2 | 2.8.3.6.3 | 2.8.3.6.4 |
| 2.8.3.7.1 | 2.8.3.7.2 | 2.8.3.7.3 | 2.8.3.7.4 | 2.8.3.8.1 | 2.8.3.8.2 | 2.8.3.8.3 | 2.8.3.8.4 |
| 2.8.4.1.1 | 2.8.4.1.2 | 2.8.4.1.3 | 2.8.4.1.4 | 2.8.4.2.1 | 2.8.4.2.2 | 2.8.4.2.3 | 2.8.4.2.4 |
| 2.8.4.3.1 | 2.8.4.3.2 | 2.8.4.3.3 | 2.8.4.3.4 | 2.8.4.4.1 | 2.8.4.4.2 | 2.8.4.4.3 | 2.8.4.4.4 |
| 2.8.4.5.1 | 2.8.4.5.2 | 2.8.4.5.3 | 2.8.4.5.4 | 2.8.4.6.1 | 2.8.4.6.2 | 2.8.4.6.3 | 2.8.4.6.4 |
| 2.8.4.7.1 | 2.8.4.7.2 | 2.8.4.7.3 | 2.8.4.7.4 | 2.8.4.8.1 | 2.8.4.8.2 | 2.8.4.8.3 | 2.8.4.8.4 |
| 3.1.1.1.1 | 3.1.1.1.2 | 3.1.1.1.3 | 3.1.1.1.4 | 3.1.1.2.1 | 3.1.1.2.2 | 3.1.1.2.3 | 3.1.1.2.4 |
| 3.1.1.3.1 | 3.1.1.3.2 | 3.1.1.3.3 | 3.1.1.3.4 | 3.1.1.4.1 | 3.1.1.4.2 | 3.1.1.4.3 | 3.1.1.4.4 |
| 3.1.1.5.1 | 3.1.1.5.2 | 3.1.1.5.3 | 3.1.1.5.4 | 3.1.1.6.1 | 3.1.1.6.2 | 3.1.1.6.3 | 3.1.1.6.4 |
| 3.1.1.7.1 | 3.1.1.7.2 | 3.1.1.7.3 | 3.1.1.7.4 | 3.1.1.8.1 | 3.1.1.8.2 | 3.1.1.8.3 | 3.1.1.8.4 |
| 3.1.2.1.1 | 3.1.2.1.2 | 3.1.2.1.3 | 3.1.2.1.4 | 3.1.2.2.1 | 3.1.2.2.2 | 3.1.2.2.3 | 3.1.2.2.4 |
| 3.1.2.3.1 | 3.1.2.3.2 | 3.1.2.3.3 | 3.1.2.3.4 | 3.1.2.4.1 | 3.1.2.4.2 | 3.1.2.4.3 | 3.1.2.4.4 |
| 3.1.2.5.1 | 3.1.2.5.2 | 3.1.2.5.3 | 3.1.2.5.4 | 3.1.2.6.1 | 3.1.2.6.2 | 3.1.2.6.3 | 3.1.2.6.4 |
| 3.1.2.7.1 | 3.1.2.7.2 | 3.1.2.7.3 | 3.1.2.7.4 | 3.1.2.8.1 | 3.1.2.8.2 | 3.1.2.8.3 | 3.1.2.8.4 |
| 3.1.3.1.1 | 3.1.3.1.2 | 3.1.3.1.3 | 3.1.3.1.4 | 3.1.3.2.1 | 3.1.3.2.2 | 3.1.3.2.3 | 3.1.3.2.4 |
| 3.1.3.3.1 | 3.1.3.3.2 | 3.1.3.3.3 | 3.1.3.3.4 | 3.1.3.4.1 | 3.1.3.4.2 | 3.1.3.4.3 | 3.1.3.4.4 |
| 3.1.3.5.1 | 3.1.3.5.2 | 3.1.3.5.3 | 3.1.3.5.4 | 3.1.3.6.1 | 3.1.3.6.2 | 3.1.3.6.3 | 3.1.3.6.4 |
| 3.1.3.7.1 | 3.1.3.7.2 | 3.1.3.7.3 | 3.1.3.7.4 | 3.1.3.8.1 | 3.1.3.8.2 | 3.1.3.8.3 | 3.1.3.8.4 |
| 3.1.4.1.1 | 3.1.4.1.2 | 3.1.4.1.3 | 3.1.4.1.4 | 3.1.4.2.1 | 3.1.4.2.2 | 3.1.4.2.3 | 3.1.4.2.4 |
| 3.1.4.3.1 | 3.1.4.3.2 | 3.1.4.3.3 | 3.1.4.3.4 | 3.1.4.4.1 | 3.1.4.4.2 | 3.1.4.4.3 | 3.1.4.4.4 |
| 3.1.4.5.1 | 3.1.4.5.2 | 3.1.4.5.3 | 3.1.4.5.4 | 3.1.4.6.1 | 3.1.4.6.2 | 3.1.4.6.3 | 3.1.4.6.4 |
| 3.1.4.7.1 | 3.1.4.7.2 | 3.1.4.7.3 | 3.1.4.7.4 | 3.1.4.8.1 | 3.1.4.8.2 | 3.1.4.8.3 | 3.1.4.8.4 |
| 3.2.1.1.1 | 3.2.1.1.2 | 3.2.1.1.3 | 3.2.1.1.4 | 3.2.1.2.1 | 3.2.1.2.2 | 3.2.1.2.3 | 3.2.1.2.4 |
| 3.2.1.3.1 | 3.2.1.3.2 | 3.2.1.3.3 | 3.2.1.3.4 | 3.2.1.4.1 | 3.2.1.4.2 | 3.2.1.4.3 | 3.2.1.4.4 |
| 3.2.1.5.1 | 3.2.1.5.2 | 3.2.1.5.3 | 3.2.1.5.4 | 3.2.1.6.1 | 3.2.1.6.2 | 3.2.1.6.3 | 3.2.1.6.4 |
| 3.2.1.7.1 | 3.2.1.7.2 | 3.2.1.7.3 | 3.2.1.7.4 | 3.2.1.8.1 | 3.2.1.8.2 | 3.2.1.8.3 | 3.2.1.8.4 |
| 3.2.2.1.1 | 3.2.2.1.2 | 3.2.2.1.3 | 3.2.2.1.4 | 3.2.2.2.1 | 3.2.2.2.2 | 3.2.2.2.3 | 3.2.2.2.4 |
| 3.2.2.3.1 | 3.2.2.3.2 | 3.2.2.3.3 | 3.2.2.3.4 | 3.2.2.4.1 | 3.2.2.4.2 | 3.2.2.4.3 | 3.2.2.4.4 |
| 3.2.2.5.1 | 3.2.2.5.2 | 3.2.2.5.3 | 3.2.2.5.4 | 3.2.2.6.1 | 3.2.2.6.2 | 3.2.2.6.3 | 3.2.2.6.4 |
| 3.2.2.7.1 | 3.2.2.7.2 | 3.2.2.7.3 | 3.2.2.7.4 | 3.2.2.8.1 | 3.2.2.8.2 | 3.2.2.8.3 | 3.2.2.8.4 |
| 3.2.3.1.1 | 3.2.3.1.2 | 3.2.3.1.3 | 3.2.3.1.4 | 3.2.3.2.1 | 3.2.3.2.2 | 3.2.3.2.3 | 3.2.3.2.4 |
| 3.2.3.3.1 | 3.2.3.3.2 | 3.2.3.3.3 | 3.2.3.3.4 | 3.2.3.4.1 | 3.2.3.4.2 | 3.2.3.4.3 | 3.2.3.4.4 |
| 3.2.3.5.1 | 3.2.3.5.2 | 3.2.3.5.3 | 3.2.3.5.4 | 3.2.3.6.1 | 3.2.3.6.2 | 3.2.3.6.3 | 3.2.3.6.4 |
| 3.2.3.7.1 | 3.2.3.7.2 | 3.2.3.7.3 | 3.2.3.7.4 | 3.2.3.8.1 | 3.2.3.8.2 | 3.2.3.8.3 | 3.2.3.8.4 |
| 3.2.4.1.1 | 3.2.4.1.2 | 3.2.4.1.3 | 3.2.4.1.4 | 3.2.4.2.1 | 3.2.4.2.2 | 3.2.4.2.3 | 3.2.4.2.4 |
| 3.2.4.3.1 | 3.2.4.3.2 | 3.2.4.3.3 | 3.2.4.3.4 | 3.2.4.4.1 | 3.2.4.4.2 | 3.2.4.4.3 | 3.2.4.4.4 |
| 3.2.4.5.1 | 3.2.4.5.2 | 3.2.4.5.3 | 3.2.4.5.4 | 3.2.4.6.1 | 3.2.4.6.2 | 3.2.4.6.3 | 3.2.4.6.4 |
| 3.2.4.7.1 | 3.2.4.7.2 | 3.2.4.7.3 | 3.2.4.7.4 | 3.2.4.8.1 | 3.2.4.8.2 | 3.2.4.8.3 | 3.2.4.8.4 |
| 3.3.1.1.1 | 3.3.1.1.2 | 3.3.1.1.3 | 3.3.1.1.4 | 3.3.1.2.1 | 3.3.1.2.2 | 3.3.1.2.3 | 3.3.1.2.4 |
| 3.3.1.3.1 | 3.3.1.3.2 | 3.3.1.3.3 | 3.3.1.3.4 | 3.3.1.4.1 | 3.3.1.4.2 | 3.3.1.4.3 | 3.3.1.4.4 |
| 3.3.1.5.1 | 3.3.1.5.2 | 3.3.1.5.3 | 3.3.1.5.4 | 3.3.1.6.1 | 3.3.1.6.2 | 3.3.1.6.3 | 3.3.1.6.4 |
| 3.3.1.7.1 | 3.3.1.7.2 | 3.3.1.7.3 | 3.3.1.7.4 | 3.3.1.8.1 | 3.3.1.8.2 | 3.3.1.8.3 | 3.3.1.8.4 |
| 3.3.2.1.1 | 3.3.2.1.2 | 3.3.2.1.3 | 3.3.2.1.4 | 3.3.2.2.1 | 3.3.2.2.2 | 3.3.2.2.3 | 3.3.2.2.4 |
| 3.3.2.3.1 | 3.3.2.3.2 | 3.3.2.3.3 | 3.3.2.3.4 | 3.3.2.4.1 | 3.3.2.4.2 | 3.3.2.4.3 | 3.3.2.4.4 |
| 3.3.2.5.1 | 3.3.2.5.2 | 3.3.2.5.3 | 3.3.2.5.4 | 3.3.2.6.1 | 3.3.2.6.2 | 3.3.2.6.3 | 3.3.2.6.4 |
| 3.3.2.7.1 | 3.3.2.7.2 | 3.3.2.7.3 | 3.3.2.7.4 | 3.3.2.8.1 | 3.3.2.8.2 | 3.3.2.8.3 | 3.3.2.8.4 |
| 3.3.3.1.1 | 3.3.3.1.2 | 3.3.3.1.3 | 3.3.3.1.4 | 3.3.3.2.1 | 3.3.3.2.2 | 3.3.3.2.3 | 3.3.3.2.4 |
| 3.3.3.3.1 | 3.3.3.3.2 | 3.3.3.3.3 | 3.3.3.3.4 | 3.3.3.4.1 | 3.3.3.4.2 | 3.3.3.4.3 | 3.3.3.4.4 |
| 3.3.3.5.1 | 3.3.3.5.2 | 3.3.3.5.3 | 3.3.3.5.4 | 3.3.3.6.1 | 3.3.3.6.2 | 3.3.3.6.3 | 3.3.3.6.4 |
| 3.3.3.7.1 | 3.3.3.7.2 | 3.3.3.7.3 | 3.3.3.7.4 | 3.3.3.8.1 | 3.3.3.8.2 | 3.3.3.8.3 | 3.3.3.8.4 |
| 3.3.4.1.1 | 3.3.4.1.2 | 3.3.4.1.3 | 3.3.4.1.4 | 3.3.4.2.1 | 3.3.4.2.2 | 3.3.4.2.3 | 3.3.4.2.4 |
| 3.3.4.3.1 | 3.3.4.3.2 | 3.3.4.3.3 | 3.3.4.3.4 | 3.3.4.4.1 | 3.3.4.4.2 | 3.3.4.4.3 | 3.3.4.4.4 |
| 3.3.4.5.1 | 3.3.4.5.2 | 3.3.4.5.3 | 3.3.4.5.4 | 3.3.4.6.1 | 3.3.4.6.2 | 3.3.4.6.3 | 3.3.4.6.4 |
| 3.3.4.7.1 | 3.3.4.7.2 | 3.3.4.7.3 | 3.3.4.7.4 | 3.3.4.8.1 | 3.3.4.8.2 | 3.3.4.8.3 | 3.3.4.8.4 |
| 3.4.1.1.1 | 3.4.1.1.2 | 3.4.1.1.3 | 3.4.1.1.4 | 3.4.1.2.1 | 3.4.1.2.2 | 3.4.1.2.3 | 3.4.1.2.4 |
| 3.4.1.3.1 | 3.4.1.3.2 | 3.4.1.3.3 | 3.4.1.3.4 | 3.4.1.4.1 | 3.4.1.4.2 | 3.4.1.4.3 | 3.4.1.4.4 |
| 3.4.1.5.1 | 3.4.1.5.2 | 3.4.1.5.3 | 3.4.1.5.4 | 3.4.1.6.1 | 3.4.1.6.2 | 3.4.1.6.3 | 3.4.1.6.4 |
| 3.4.1.7.1 | 3.4.1.7.2 | 3.4.1.7.3 | 3.4.1.7.4 | 3.4.1.8.1 | 3.4.1.8.2 | 3.4.1.8.3 | 3.4.1.8.4 |
| 3.4.2.1.1 | 3.4.2.1.2 | 3.4.2.1.3 | 3.4.2.1.4 | 3.4.2.2.1 | 3.4.2.2.2 | 3.4.2.2.3 | 3.4.2.2.4 |
| 3.4.2.3.1 | 3.4.2.3.2 | 3.4.2.3.3 | 3.4.2.3.4 | 3.4.2.4.1 | 3.4.2.4.2 | 3.4.2.4.3 | 3.4.2.4.4 |
| 3.4.2.5.1 | 3.4.2.5.2 | 3.4.2.5.3 | 3.4.2.5.4 | 3.4.2.6.1 | 3.4.2.6.2 | 3.4.2.6.3 | 3.4.2.6.4 |
| 3.4.2.7.1 | 3.4.2.7.2 | 3.4.2.7.3 | 3.4.2.7.4 | 3.4.2.8.1 | 3.4.2.8.2 | 3.4.2.8.3 | 3.4.2.8.4 |
| 3.4.3.1.1 | 3.4.3.1.2 | 3.4.3.1.3 | 3.4.3.1.4 | 3.4.3.2.1 | 3.4.3.2.2 | 3.4.3.2.3 | 3.4.3.2.4 |
| 3.4.3.3.1 | 3.4.3.3.2 | 3.4.3.3.3 | 3.4.3.3.4 | 3.4.3.4.1 | 3.4.3.4.2 | 3.4.3.4.3 | 3.4.3.4.4 |
| 3.4.3.5.1 | 3.4.3.5.2 | 3.4.3.5.3 | 3.4.3.5.4 | 3.4.3.6.1 | 3.4.3.6.2 | 3.4.3.6.3 | 3.4.3.6.4 |
| 3.4.3.7.1 | 3.4.3.7.2 | 3.4.3.7.3 | 3.4.3.7.4 | 3.4.3.8.1 | 3.4.3.8.2 | 3.4.3.8.3 | 3.4.3.8.4 |

TABLE 1-continued

| | | | | | | | |
|---|---|---|---|---|---|---|---|
| 3.4.4.1.1 | 3.4.4.1.2 | 3.4.4.1.3 | 3.4.4.1.4 | 3.4.4.2.1 | 3.4.4.2.2 | 3.4.4.2.3 | 3.4.4.2.4 |
| 3.4.4.3.1 | 3.4.4.3.2 | 3.4.4.3.3 | 3.4.4.3.4 | 3.4.4.4.1 | 3.4.4.4.2 | 3.4.4.4.3 | 3.4.4.4.4 |
| 3.4.4.5.1 | 3.4.4.5.2 | 3.4.4.5.3 | 3.4.4.5.4 | 3.4.4.6.1 | 3.4.4.6.2 | 3.4.4.6.3 | 3.4.4.6.4 |
| 3.4.4.7.1 | 3.4.4.7.2 | 3.4.4.7.3 | 3.4.4.7.4 | 3.4.4.8.1 | 3.4.4.8.2 | 3.4.4.8.3 | 3.4.4.8.4 |
| 3.5.1.1.1 | 3.5.1.1.2 | 3.5.1.1.3 | 3.5.1.1.4 | 3.5.1.2.1 | 3.5.1.2.2 | 3.5.1.2.3 | 3.5.1.2.4 |
| 3.5.1.3.1 | 3.5.1.3.2 | 3.5.1.3.3 | 3.5.1.3.4 | 3.5.1.4.1 | 3.5.1.4.2 | 3.5.1.4.3 | 3.5.1.4.4 |
| 3.5.1.5.1 | 3.5.1.5.2 | 3.5.1.5.3 | 3.5.1.5.4 | 3.5.1.6.1 | 3.5.1.6.2 | 3.5.1.6.3 | 3.5.1.6.4 |
| 3.5.1.7.1 | 3.5.1.7.2 | 3.5.1.7.3 | 3.5.1.7.4 | 3.5.1.8.1 | 3.5.1.8.2 | 3.5.1.8.3 | 3.5.1.8.4 |
| 3.5.2.1.1 | 3.5.2.1.2 | 3.5.2.1.3 | 3.5.2.1.4 | 3.5.2.2.1 | 3.5.2.2.2 | 3.5.2.2.3 | 3.5.2.2.4 |
| 3.5.2.3.1 | 3.5.2.3.2 | 3.5.2.3.3 | 3.5.2.3.4 | 3.5.2.4.1 | 3.5.2.4.2 | 3.5.2.4.3 | 3.5.2.4.4 |
| 3.5.2.5.1 | 3.5.2.5.2 | 3.5.2.5.3 | 3.5.2.5.4 | 3.5.2.6.1 | 3.5.2.6.2 | 3.5.2.6.3 | 3.5.2.6.4 |
| 3.5.2.7.1 | 3.5.2.7.2 | 3.5.2.7.3 | 3.5.2.7.4 | 3.5.2.8.1 | 3.5.2.8.2 | 3.5.2.8.3 | 3.5.2.8.4 |
| 3.5.3.1.1 | 3.5.3.1.2 | 3.5.3.1.3 | 3.5.3.1.4 | 3.5.3.2.1 | 3.5.3.2.2 | 3.5.3.2.3 | 3.5.3.2.4 |
| 3.5.3.3.1 | 3.5.3.3.2 | 3.5.3.3.3 | 3.5.3.3.4 | 3.5.3.4.1 | 3.5.3.4.2 | 3.5.3.4.3 | 3.5.3.4.4 |
| 3.5.3.5.1 | 3.5.3.5.2 | 3.5.3.5.3 | 3.5.3.5.4 | 3.5.3.6.1 | 3.5.3.6.2 | 3.5.3.6.3 | 3.5.3.6.4 |
| 3.5.3.7.1 | 3.5.3.7.2 | 3.5.3.7.3 | 3.5.3.7.4 | 3.5.3.8.1 | 3.5.3.8.2 | 3.5.3.8.3 | 3.5.3.8.4 |
| 3.5.4.1.1 | 3.5.4.1.2 | 3.5.4.1.3 | 3.5.4.1.4 | 3.5.4.2.1 | 3.5.4.2.2 | 3.5.4.2.3 | 3.5.4.2.4 |
| 3.5.4.3.1 | 3.5.4.3.2 | 3.5.4.3.3 | 3.5.4.3.4 | 3.5.4.4.1 | 3.5.4.4.2 | 3.5.4.4.3 | 3.5.4.4.4 |
| 3.5.4.5.1 | 3.5.4.5.2 | 3.5.4.5.3 | 3.5.4.5.4 | 3.5.4.6.1 | 3.5.4.6.2 | 3.5.4.6.3 | 3.5.4.6.4 |
| 3.5.4.7.1 | 3.5.4.7.2 | 3.5.4.7.3 | 3.5.4.7.4 | 3.5.4.8.1 | 3.5.4.8.2 | 3.5.4.8.3 | 3.5.4.8.4 |
| 3.6.1.1.1 | 3.6.1.1.2 | 3.6.1.1.3 | 3.6.1.1.4 | 3.6.1.2.1 | 3.6.1.2.2 | 3.6.1.2.3 | 3.6.1.2.4 |
| 3.6.1.3.1 | 3.6.1.3.2 | 3.6.1.3.3 | 3.6.1.3.4 | 3.6.1.4.1 | 3.6.1.4.2 | 3.6.1.4.3 | 3.6.1.4.4 |
| 3.6.1.5.1 | 3.6.1.5.2 | 3.6.1.5.3 | 3.6.1.5.4 | 3.6.1.6.1 | 3.6.1.6.2 | 3.6.1.6.3 | 3.6.1.6.4 |
| 3.6.1.7.1 | 3.6.1.7.2 | 3.6.1.7.3 | 3.6.1.7.4 | 3.6.1.8.1 | 3.6.1.8.2 | 3.6.1.8.3 | 3.6.1.8.4 |
| 3.6.2.1.1 | 3.6.2.1.2 | 3.6.2.1.3 | 3.6.2.1.4 | 3.6.2.2.1 | 3.6.2.2.2 | 3.6.2.2.3 | 3.6.2.2.4 |
| 3.6.2.3.1 | 3.6.2.3.2 | 3.6.2.3.3 | 3.6.2.3.4 | 3.6.2.4.1 | 3.6.2.4.2 | 3.6.2.4.3 | 3.6.2.4.4 |
| 3.6.2.5.1 | 3.6.2.5.2 | 3.6.2.5.3 | 3.6.2.5.4 | 3.6.2.6.1 | 3.6.2.6.2 | 3.6.2.6.3 | 3.6.2.6.4 |
| 3.6.2.7.1 | 3.6.2.7.2 | 3.6.2.7.3 | 3.6.2.7.4 | 3.6.2.8.1 | 3.6.2.8.2 | 3.6.2.8.3 | 3.6.2.8.4 |
| 3.6.3.1.1 | 3.6.3.1.2 | 3.6.3.1.3 | 3.6.3.1.4 | 3.6.3.2.1 | 3.6.3.2.2 | 3.6.3.2.3 | 3.6.3.2.4 |
| 3.6.3.3.1 | 3.6.3.3.2 | 3.6.3.3.3 | 3.6.3.3.4 | 3.6.3.4.1 | 3.6.3.4.2 | 3.6.3.4.3 | 3.6.3.4.4 |
| 3.6.3.5.1 | 3.6.3.5.2 | 3.6.3.5.3 | 3.6.3.5.4 | 3.6.3.6.1 | 3.6.3.6.2 | 3.6.3.6.3 | 3.6.3.6.4 |
| 3.6.3.7.1 | 3.6.3.7.2 | 3.6.3.7.3 | 3.6.3.7.4 | 3.6.3.8.1 | 3.6.3.8.2 | 3.6.3.8.3 | 3.6.3.8.4 |
| 3.6.4.1.1 | 3.6.4.1.2 | 3.6.4.1.3 | 3.6.4.1.4 | 3.6.4.2.1 | 3.6.4.2.2 | 3.6.4.2.3 | 3.6.4.2.4 |
| 3.6.4.3.1 | 3.6.4.3.2 | 3.6.4.3.3 | 3.6.4.3.4 | 3.6.4.4.1 | 3.6.4.4.2 | 3.6.4.4.3 | 3.6.4.4.4 |
| 3.6.4.5.1 | 3.6.4.5.2 | 3.6.4.5.3 | 3.6.4.5.4 | 3.6.4.6.1 | 3.6.4.6.2 | 3.6.4.6.3 | 3.6.4.6.4 |
| 3.6.4.7.1 | 3.6.4.7.2 | 3.6.4.7.3 | 3.6.4.7.4 | 3.6.4.8.1 | 3.6.4.8.2 | 3.6.4.8.3 | 3.6.4.8.4 |
| 3.7.1.1.1 | 3.7.1.1.2 | 3.7.1.1.3 | 3.7.1.1.4 | 3.7.1.2.1 | 3.7.1.2.2 | 3.7.1.2.3 | 3.7.1.2.4 |
| 3.7.1.3.1 | 3.7.1.3.2 | 3.7.1.3.3 | 3.7.1.3.4 | 3.7.1.4.1 | 3.7.1.4.2 | 3.7.1.4.3 | 3.7.1.4.4 |
| 3.7.1.5.1 | 3.7.1.5.2 | 3.7.1.5.3 | 3.7.1.5.4 | 3.7.1.6.1 | 3.7.1.6.2 | 3.7.1.6.3 | 3.7.1.6.4 |
| 3.7.1.7.1 | 3.7.1.7.2 | 3.7.1.7.3 | 3.7.1.7.4 | 3.7.1.8.1 | 3.7.1.8.2 | 3.7.1.8.3 | 3.7.1.8.4 |
| 3.7.2.1.1 | 3.7.2.1.2 | 3.7.2.1.3 | 3.7.2.1.4 | 3.7.2.2.1 | 3.7.2.2.2 | 3.7.2.2.3 | 3.7.2.2.4 |
| 3.7.2.3.1 | 3.7.2.3.2 | 3.7.2.3.3 | 3.7.2.3.4 | 3.7.2.4.1 | 3.7.2.4.2 | 3.7.2.4.3 | 3.7.2.4.4 |
| 3.7.2.5.1 | 3.7.2.5.2 | 3.7.2.5.3 | 3.7.2.5.4 | 3.7.2.6.1 | 3.7.2.6.2 | 3.7.2.6.3 | 3.7.2.6.4 |
| 3.7.2.7.1 | 3.7.2.7.2 | 3.7.2.7.3 | 3.7.2.7.4 | 3.7.2.8.1 | 3.7.2.8.2 | 3.7.2.8.3 | 3.7.2.8.4 |
| 3.7.3.1.1 | 3.7.3.1.2 | 3.7.3.1.3 | 3.7.3.1.4 | 3.7.3.2.1 | 3.7.3.2.2 | 3.7.3.2.3 | 3.7.3.2.4 |
| 3.7.3.3.1 | 3.7.3.3.2 | 3.7.3.3.3 | 3.7.3.3.4 | 3.7.3.4.1 | 3.7.3.4.2 | 3.7.3.4.3 | 3.7.3.4.4 |
| 3.7.3.5.1 | 3.7.3.5.2 | 3.7.3.5.3 | 3.7.3.5.4 | 3.7.3.6.1 | 3.7.3.6.2 | 3.7.3.6.3 | 3.7.3.6.4 |
| 3.7.3.7.1 | 3.7.3.7.2 | 3.7.3.7.3 | 3.7.3.7.4 | 3.7.3.8.1 | 3.7.3.8.2 | 3.7.3.8.3 | 3.7.3.8.4 |
| 3.7.4.1.1 | 3.7.4.1.2 | 3.7.4.1.3 | 3.7.4.1.4 | 3.7.4.2.1 | 3.7.4.2.2 | 3.7.4.2.3 | 3.7.4.2.4 |
| 3.7.4.3.1 | 3.7.4.3.2 | 3.7.4.3.3 | 3.7.4.3.4 | 3.7.4.4.1 | 3.7.4.4.2 | 3.7.4.4.3 | 3.7.4.4.4 |
| 3.7.4.5.1 | 3.7.4.5.2 | 3.7.4.5.3 | 3.7.4.5.4 | 3.7.4.6.1 | 3.7.4.6.2 | 3.7.4.6.3 | 3.7.4.6.4 |
| 3.7.4.7.1 | 3.7.4.7.2 | 3.7.4.7.3 | 3.7.4.7.4 | 3.7.4.8.1 | 3.7.4.8.2 | 3.7.4.8.3 | 3.7.4.8.4 |
| 3.8.1.1.1 | 3.8.1.1.2 | 3.8.1.1.3 | 3.8.1.1.4 | 3.8.1.2.1 | 3.8.1.2.2 | 3.8.1.2.3 | 3.8.1.2.4 |
| 3.8.1.3.1 | 3.8.1.3.2 | 3.8.1.3.3 | 3.8.1.3.4 | 3.8.1.4.1 | 3.8.1.4.2 | 3.8.1.4.3 | 3.8.1.4.4 |
| 3.8.1.5.1 | 3.8.1.5.2 | 3.8.1.5.3 | 3.8.1.5.4 | 3.8.1.6.1 | 3.8.1.6.2 | 3.8.1.6.3 | 3.8.1.6.4 |
| 3.8.1.7.1 | 3.8.1.7.2 | 3.8.1.7.3 | 3.8.1.7.4 | 3.8.1.8.1 | 3.8.1.8.2 | 3.8.1.8.3 | 3.8.1.8.4 |
| 3.8.2.1.1 | 3.8.2.1.2 | 3.8.2.1.3 | 3.8.2.1.4 | 3.8.2.2.1 | 3.8.2.2.2 | 3.8.2.2.3 | 3.8.2.2.4 |
| 3.8.2.3.1 | 3.8.2.3.2 | 3.8.2.3.3 | 3.8.2.3.4 | 3.8.2.4.1 | 3.8.2.4.2 | 3.8.2.4.3 | 3.8.2.4.4 |
| 3.8.2.5.1 | 3.8.2.5.2 | 3.8.2.5.3 | 3.8.2.5.4 | 3.8.2.6.1 | 3.8.2.6.2 | 3.8.2.6.3 | 3.8.2.6.4 |
| 3.8.2.7.1 | 3.8.2.7.2 | 3.8.2.7.3 | 3.8.2.7.4 | 3.8.2.8.1 | 3.8.2.8.2 | 3.8.2.8.3 | 3.8.2.8.4 |
| 3.8.3.1.1 | 3.8.3.1.2 | 3.8.3.1.3 | 3.8.3.1.4 | 3.8.3.2.1 | 3.8.3.2.2 | 3.8.3.2.3 | 3.8.3.2.4 |
| 3.8.3.3.1 | 3.8.3.3.2 | 3.8.3.3.3 | 3.8.3.3.4 | 3.8.3.4.1 | 3.8.3.4.2 | 3.8.3.4.3 | 3.8.3.4.4 |
| 3.8.3.5.1 | 3.8.3.5.2 | 3.8.3.5.3 | 3.8.3.5.4 | 3.8.3.6.1 | 3.8.3.6.2 | 3.8.3.6.3 | 3.8.3.6.4 |
| 3.8.3.7.1 | 3.8.3.7.2 | 3.8.3.7.3 | 3.8.3.7.4 | 3.8.3.8.1 | 3.8.3.8.2 | 3.8.3.8.3 | 3.8.3.8.4 |
| 3.8.4.1.1 | 3.8.4.1.2 | 3.8.4.1.3 | 3.8.4.1.4 | 3.8.4.2.1 | 3.8.4.2.2 | 3.8.4.2.3 | 3.8.4.2.4 |
| 3.8.4.3.1 | 3.8.4.3.2 | 3.8.4.3.3 | 3.8.4.3.4 | 3.8.4.4.1 | 3.8.4.4.2 | 3.8.4.4.3 | 3.8.4.4.4 |
| 3.8.4.5.1 | 3.8.4.5.2 | 3.8.4.5.3 | 3.8.4.5.4 | 3.8.4.6.1 | 3.8.4.6.2 | 3.8.4.6.3 | 3.8.4.6.4 |
| 3.8.4.7.1 | 3.8.4.7.2 | 3.8.4.7.3 | 3.8.4.7.4 | 3.8.4.8.1 | 3.8.4.8.2 | 3.8.4.8.3 | 3.8.4.8.4 |
| 4.1.1.1.1 | 4.1.1.1.2 | 4.1.1.1.3 | 4.1.1.1.4 | 4.1.1.2.1 | 4.1.1.2.2 | 4.1.1.2.3 | 4.1.1.2.4 |
| 4.1.1.3.1 | 4.1.1.3.2 | 4.1.1.3.3 | 4.1.1.3.4 | 4.1.1.4.1 | 4.1.1.4.2 | 4.1.1.4.3 | 4.1.1.4.4 |
| 4.1.1.5.1 | 4.1.1.5.2 | 4.1.1.5.3 | 4.1.1.5.4 | 4.1.1.6.1 | 4.1.1.6.2 | 4.1.1.6.3 | 4.1.1.6.4 |
| 4.1.1.7.1 | 4.1.1.7.2 | 4.1.1.7.3 | 4.1.1.7.4 | 4.1.1.8.1 | 4.1.1.8.2 | 4.1.1.8.3 | 4.1.1.8.4 |
| 4.1.2.1.1 | 4.1.2.1.2 | 4.1.2.1.3 | 4.1.2.1.4 | 4.1.2.2.1 | 4.1.2.2.2 | 4.1.2.2.3 | 4.1.2.2.4 |
| 4.1.2.3.1 | 4.1.2.3.2 | 4.1.2.3.3 | 4.1.2.3.4 | 4.1.2.4.1 | 4.1.2.4.2 | 4.1.2.4.3 | 4.1.2.4.4 |
| 4.1.2.5.1 | 4.1.2.5.2 | 4.1.2.5.3 | 4.1.2.5.4 | 4.1.2.6.1 | 4.1.2.6.2 | 4.1.2.6.3 | 4.1.2.6.4 |
| 4.1.2.7.1 | 4.1.2.7.2 | 4.1.2.7.3 | 4.1.2.7.4 | 4.1.2.8.1 | 4.1.2.8.2 | 4.1.2.8.3 | 4.1.2.8.4 |
| 4.1.3.1.1 | 4.1.3.1.2 | 4.1.3.1.3 | 4.1.3.1.4 | 4.1.3.2.1 | 4.1.3.2.2 | 4.1.3.2.3 | 4.1.3.2.4 |
| 4.1.3.3.1 | 4.1.3.3.2 | 4.1.3.3.3 | 4.1.3.3.4 | 4.1.3.4.1 | 4.1.3.4.2 | 4.1.3.4.3 | 4.1.3.4.4 |
| 4.1.3.5.1 | 4.1.3.5.2 | 4.1.3.5.3 | 4.1.3.5.4 | 4.1.3.6.1 | 4.1.3.6.2 | 4.1.3.6.3 | 4.1.3.6.4 |

TABLE 1-continued

| | | | | | | | |
|---|---|---|---|---|---|---|---|
| 4.1.3.7.1 | 4.1.3.7.2 | 4.1.3.7.3 | 4.1.3.7.4 | 4.1.3.8.1 | 4.1.3.8.2 | 4.1.3.8.3 | 4.1.3.8.4 |
| 4.1.4.1.1 | 4.1.4.1.2 | 4.1.4.1.3 | 4.1.4.1.4 | 4.1.4.2.1 | 4.1.4.2.2 | 4.1.4.2.3 | 4.1.4.2.4 |
| 4.1.4.3.1 | 4.1.4.3.2 | 4.1.4.3.3 | 4.1.4.3.4 | 4.1.4.4.1 | 4.1.4.4.2 | 4.1.4.4.3 | 4.1.4.4.4 |
| 4.1.4.5.1 | 4.1.4.5.2 | 4.1.4.5.3 | 4.1.4.5.4 | 4.1.4.6.1 | 4.1.4.6.2 | 4.1.4.6.3 | 4.1.4.6.4 |
| 4.1.4.7.1 | 4.1.4.7.2 | 4.1.4.7.3 | 4.1.4.7.4 | 4.1.4.8.1 | 4.1.4.8.2 | 4.1.4.8.3 | 4.1.4.8.4 |
| 4.2.1.1.1 | 4.2.1.1.2 | 4.2.1.1.3 | 4.2.1.1.4 | 4.2.1.2.1 | 4.2.1.2.2 | 4.2.1.2.3 | 4.2.1.2.4 |
| 4.2.1.3.1 | 4.2.1.3.2 | 4.2.1.3.3 | 4.2.1.3.4 | 4.2.1.4.1 | 4.2.1.4.2 | 4.2.1.4.3 | 4.2.1.4.4 |
| 4.2.1.5.1 | 4.2.1.5.2 | 4.2.1.5.3 | 4.2.1.5.4 | 4.2.1.6.1 | 4.2.1.6.2 | 4.2.1.6.3 | 4.2.1.6.4 |
| 4.2.1.7.1 | 4.2.1.7.2 | 4.2.1.7.3 | 4.2.1.7.4 | 4.2.1.8.1 | 4.2.1.8.2 | 4.2.1.8.3 | 4.2.1.8.4 |
| 4.2.2.1.1 | 4.2.2.1.2 | 4.2.2.1.3 | 4.2.2.1.4 | 4.2.2.2.1 | 4.2.2.2.2 | 4.2.2.2.3 | 4.2.2.2.4 |
| 4.2.2.3.1 | 4.2.2.3.2 | 4.2.2.3.3 | 4.2.2.3.4 | 4.2.2.4.1 | 4.2.2.4.2 | 4.2.2.4.3 | 4.2.2.4.4 |
| 4.2.2.5.1 | 4.2.2.5.2 | 4.2.2.5.3 | 4.2.2.5.4 | 4.2.2.6.1 | 4.2.2.6.2 | 4.2.2.6.3 | 4.2.2.6.4 |
| 4.2.2.7.1 | 4.2.2.7.2 | 4.2.2.7.3 | 4.2.2.7.4 | 4.2.2.8.1 | 4.2.2.8.2 | 4.2.2.8.3 | 4.2.2.8.4 |
| 4.2.3.1.1 | 4.2.3.1.2 | 4.2.3.1.3 | 4.2.3.1.4 | 4.2.3.2.1 | 4.2.3.2.2 | 4.2.3.2.3 | 4.2.3.2.4 |
| 4.2.3.3.1 | 4.2.3.3.2 | 4.2.3.3.3 | 4.2.3.3.4 | 4.2.3.4.1 | 4.2.3.4.2 | 4.2.3.4.3 | 4.2.3.4.4 |
| 4.2.3.5.1 | 4.2.3.5.2 | 4.2.3.5.3 | 4.2.3.5.4 | 4.2.3.6.1 | 4.2.3.6.2 | 4.2.3.6.3 | 4.2.3.6.4 |
| 4.2.3.7.1 | 4.2.3.7.2 | 4.2.3.7.3 | 4.2.3.7.4 | 4.2.3.8.1 | 4.2.3.8.2 | 4.2.3.8.3 | 4.2.3.8.4 |
| 4.2.4.1.1 | 4.2.4.1.2 | 4.2.4.1.3 | 4.2.4.1.4 | 4.2.4.2.1 | 4.2.4.2.2 | 4.2.4.2.3 | 4.2.4.2.4 |
| 4.2.4.3.1 | 4.2.4.3.2 | 4.2.4.3.3 | 4.2.4.3.4 | 4.2.4.4.1 | 4.2.4.4.2 | 4.2.4.4.3 | 4.2.4.4.4 |
| 4.2.4.5.1 | 4.2.4.5.2 | 4.2.4.5.3 | 4.2.4.5.4 | 4.2.4.6.1 | 4.2.4.6.2 | 4.2.4.6.3 | 4.2.4.6.4 |
| 4.2.4.7.1 | 4.2.4.7.2 | 4.2.4.7.3 | 4.2.4.7.4 | 4.2.4.8.1 | 4.2.4.8.2 | 4.2.4.8.3 | 4.2.4.8.4 |
| 4.3.1.1.1 | 4.3.1.1.2 | 4.3.1.1.3 | 4.3.1.1.4 | 4.3.1.2.1 | 4.3.1.2.2 | 4.3.1.2.3 | 4.3.1.2.4 |
| 4.3.1.3.1 | 4.3.1.3.2 | 4.3.1.3.3 | 4.3.1.3.4 | 4.3.1.4.1 | 4.3.1.4.2 | 4.3.1.4.3 | 4.3.1.4.4 |
| 4.3.1.5.1 | 4.3.1.5.2 | 4.3.1.5.3 | 4.3.1.5.4 | 4.3.1.6.1 | 4.3.1.6.2 | 4.3.1.6.3 | 4.3.1.6.4 |
| 4.3.1.7.1 | 4.3.1.7.2 | 4.3.1.7.3 | 4.3.1.7.4 | 4.3.1.8.1 | 4.3.1.8.2 | 4.3.1.8.3 | 4.3.1.8.4 |
| 4.3.2.1.1 | 4.3.2.1.2 | 4.3.2.1.3 | 4.3.2.1.4 | 4.3.2.2.1 | 4.3.2.2.2 | 4.3.2.2.3 | 4.3.2.2.4 |
| 4.3.2.3.1 | 4.3.2.3.2 | 4.3.2.3.3 | 4.3.2.3.4 | 4.3.2.4.1 | 4.3.2.4.2 | 4.3.2.4.3 | 4.3.2.4.4 |
| 4.3.2.5.1 | 4.3.2.5.2 | 4.3.2.5.3 | 4.3.2.5.4 | 4.3.2.6.1 | 4.3.2.6.2 | 4.3.2.6.3 | 4.3.2.6.4 |
| 4.3.2.7.1 | 4.3.2.7.2 | 4.3.2.7.3 | 4.3.2.7.4 | 4.3.2.8.1 | 4.3.2.8.2 | 4.3.2.8.3 | 4.3.2.8.4 |
| 4.3.3.1.1 | 4.3.3.1.2 | 4.3.3.1.3 | 4.3.3.1.4 | 4.3.3.2.1 | 4.3.3.2.2 | 4.3.3.2.3 | 4.3.3.2.4 |
| 4.3.3.3.1 | 4.3.3.3.2 | 4.3.3.3.3 | 4.3.3.3.4 | 4.3.3.4.1 | 4.3.3.4.2 | 4.3.3.4.3 | 4.3.3.4.4 |
| 4.3.3.5.1 | 4.3.3.5.2 | 4.3.3.5.3 | 4.3.3.5.4 | 4.3.3.6.1 | 4.3.3.6.2 | 4.3.3.6.3 | 4.3.3.6.4 |
| 4.3.3.7.1 | 4.3.3.7.2 | 4.3.3.7.3 | 4.3.3.7.4 | 4.3.3.8.1 | 4.3.3.8.2 | 4.3.3.8.3 | 4.3.3.8.4 |
| 4.3.4.1.1 | 4.3.4.1.2 | 4.3.4.1.3 | 4.3.4.1.4 | 4.3.4.2.1 | 4.3.4.2.2 | 4.3.4.2.3 | 4.3.4.2.4 |
| 4.3.4.3.1 | 4.3.4.3.2 | 4.3.4.3.3 | 4.3.4.3.4 | 4.3.4.4.1 | 4.3.4.4.2 | 4.3.4.4.3 | 4.3.4.4.4 |
| 4.3.4.5.1 | 4.3.4.5.2 | 4.3.4.5.3 | 4.3.4.5.4 | 4.3.4.6.1 | 4.3.4.6.2 | 4.3.4.6.3 | 4.3.4.6.4 |
| 4.3.4.7.1 | 4.3.4.7.2 | 4.3.4.7.3 | 4.3.4.7.4 | 4.3.4.8.1 | 4.3.4.8.2 | 4.3.4.8.3 | 4.3.4.8.4 |
| 4.4.1.1.1 | 4.4.1.1.2 | 4.4.1.1.3 | 4.4.1.1.4 | 4.4.1.2.1 | 4.4.1.2.2 | 4.4.1.2.3 | 4.4.1.2.4 |
| 4.4.1.3.1 | 4.4.1.3.2 | 4.1.1.3.3 | 4.4.1.3.4 | 4.4.1.4.1 | 4.4.1.4.2 | 4.4.1.4.3 | 4.4.1.4.4 |
| 4.4.1.5.1 | 4.4.1.5.2 | 4.4.1.5.3 | 4.4.1.5.4 | 4.4.1.6.1 | 4.4.1.6.2 | 4.4.1.6.3 | 4.4.1.6.4 |
| 4.4.1.7.1 | 4.4.1.7.2 | 4.4.1.7.3 | 4.4.1.7.4 | 4.4.1.8.1 | 4.4.1.8.2 | 4.4.1.8.3 | 4.4.1.8.4 |
| 4.4.2.1.1 | 4.4.2.1.2 | 4.4.2.1.3 | 4.4.2.1.4 | 4.4.2.2.1 | 4.4.2.2.2 | 4.4.2.2.3 | 4.4.2.2.4 |
| 4.4.2.3.1 | 4.4.2.3.2 | 4.4.2.3.3 | 4.4.2.3.4 | 4.4.2.4.1 | 4.4.2.4.2 | 4.4.2.4.3 | 4.4.2.4.4 |
| 4.4.2.5.1 | 4.4.2.5.2 | 4.4.2.5.3 | 4.4.2.5.4 | 4.4.2.6.1 | 4.4.2.6.2 | 4.4.2.6.3 | 4.4.2.6.4 |
| 4.4.2.7.1 | 4.4.2.7.2 | 4.4.2.7.3 | 4.4.2.7.4 | 4.4.2.8.1 | 4.4.2.8.2 | 4.4.2.8.3 | 4.4.2.8.4 |
| 4.4.3.1.1 | 4.4.3.1.2 | 4.4.3.1.3 | 4.4.3.1.4 | 4.4.3.2.1 | 4.4.3.2.2 | 4.4.3.2.3 | 4.4.3.2.4 |
| 4.4.3.3.1 | 4.4.3.3.2 | 4.4.3.3.3 | 4.4.3.3.4 | 4.4.3.4.1 | 4.4.3.4.2 | 4.4.3.4.3 | 4.4.3.4.4 |
| 4.4.3.5.1 | 4.4.3.5.2 | 4.4.3.5.3 | 4.4.3.5.4 | 4.4.3.6.1 | 4.4.3.6.2 | 4.4.3.6.3 | 4.4.3.6.4 |
| 4.4.3.7.1 | 4.4.3.7.2 | 4.4.3.7.3 | 4.4.3.7.4 | 4.4.3.8.1 | 4.4.3.8.2 | 4.4.3.8.3 | 4.4.3.8.4 |
| 4.4.4.1.1 | 4.4.4.1.2 | 4.4.4.1.3 | 4.4.4.1.4 | 4.4.4.2.1 | 4.4.4.2.2 | 4.4.4.2.3 | 4.4.4.2.4 |
| 4.4.4.3.1 | 4.4.4.3.2 | 4.4.4.3.3 | 4.4.4.3.4 | 4.4.4.4.1 | 4.4.4.4.2 | 4.4.4.4.3 | 4.4.4.4.4 |
| 4.4.4.5.1 | 4.4.4.5.2 | 4.4.4.5.3 | 4.4.4.5.4 | 4.4.4.6.1 | 4.4.4.6.2 | 4.4.4.6.3 | 4.4.4.6.4 |
| 4.4.4.7.1 | 4.4.4.7.2 | 4.4.4.7.3 | 4.4.4.7.4 | 4.4.4.8.1 | 4.4.4.8.2 | 4.4.4.8.3 | 4.4.4.8.4 |
| 4.5.1.1.1 | 4.5.1.1.2 | 4.5.1.1.3 | 4.5.1.1.4 | 4.5.1.2.1 | 4.5.1.2.2 | 4.5.1.2.3 | 4.5.1.2.4 |
| 4.5.1.3.1 | 4.5.1.3.2 | 4.5.1.3.3 | 4.5.1.3.4 | 4.5.1.4.1 | 4.5.1.4.2 | 4.5.1.4.3 | 4.5.1.4.4 |
| 4.5.1.5.1 | 4.5.1.5.2 | 4.5.1.5.3 | 4.5.1.5.4 | 4.5.1.6.1 | 4.5.1.6.2 | 4.5.1.6.3 | 4.5.1.6.4 |
| 4.5.1.7.1 | 4.5.1.7.2 | 4.5.1.7.3 | 4.5.1.7.4 | 4.5.1.8.1 | 4.5.1.8.2 | 4.5.1.8.3 | 4.5.1.8.4 |
| 4.5.2.1.1 | 4.5.2.1.2 | 4.5.2.1.3 | 4.5.2.1.4 | 4.5.2.2.1 | 4.5.2.2.2 | 4.5.2.2.3 | 4.5.2.2.4 |
| 4.5.2.3.1 | 4.5.2.3.2 | 4.5.2.3.3 | 4.5.2.3.4 | 4.5.2.4.1 | 4.5.2.4.2 | 4.5.2.4.3 | 4.5.2.4.4 |
| 4.5.2.5.1 | 4.5.2.5.2 | 4.5.2.5.3 | 4.5.2.5.4 | 4.5.2.6.1 | 4.5.2.6.2 | 4.5.2.6.3 | 4.5.2.6.4 |
| 4.5.2.7.1 | 4.5.2.7.2 | 4.5.2.7.3 | 4.5.2.7.4 | 4.5.2.8.1 | 4.5.2.8.2 | 4.5.2.8.3 | 4.5.2.8.4 |
| 4.5.3.1.1 | 4.5.3.1.2 | 4.5.3.1.3 | 4.5.3.1.4 | 4.5.3.2.1 | 4.5.3.2.2 | 4.5.3.2.3 | 4.5.3.2.4 |
| 4.5.3.3.1 | 4.5.3.3.2 | 4.5.3.3.3 | 4.5.3.3.4 | 4.5.3.4.1 | 4.5.3.4.2 | 4.5.3.4.3 | 4.5.3.4.4 |
| 4.5.3.5.1 | 4.5.3.5.2 | 4.5.3.5.3 | 4.5.3.5.4 | 4.5.3.6.1 | 4.5.3.6.2 | 4.5.3.6.3 | 4.5.3.6.4 |
| 4.5.3.7.1 | 4.5.3.7.2 | 4.5.3.7.3 | 4.5.3.7.4 | 4.5.3.8.1 | 4.5.3.8.2 | 4.5.3.8.3 | 4.5.3.8.4 |
| 4.5.4.1.1 | 4.5.4.1.2 | 4.5.4.1.3 | 4.5.4.1.4 | 4.5.4.2.1 | 4.5.4.2.2 | 4.5.4.2.3 | 4.5.4.2.4 |
| 4.5.4.3.1 | 4.5.4.3.2 | 4.5.4.3.3 | 4.5.4.3.4 | 4.5.4.4.1 | 4.5.4.4.2 | 4.5.4.4.3 | 4.5.4.4.4 |
| 4.5.4.5.1 | 4.5.4.5.2 | 4.5.4.5.3 | 4.5.4.5.4 | 4.5.4.6.1 | 4.5.4.6.2 | 4.5.4.6.3 | 4.5.4.6.4 |
| 4.5.4.7.1 | 4.5.4.7.2 | 4.5.4.7.3 | 4.5.4.7.4 | 4.5.4.8.1 | 4.5.4.8.2 | 4.5.4.8.3 | 4.5.4.8.4 |
| 4.6.1.1.1 | 4.6.1.1.2 | 4.6.1.1.3 | 4.6.1.1.4 | 4.6.1.2.1 | 4.6.1.2.2 | 4.6.1.2.3 | 4.6.1.2.4 |
| 4.6.1.3.1 | 4.6.1.3.2 | 4.6.1.3.3 | 4.6.1.3.4 | 4.6.1.4.1 | 4.6.1.4.2 | 4.6.1.4.3 | 4.6.1.4.4 |
| 4.6.1.5.1 | 4.6.1.5.2 | 4.6.1.5.3 | 4.6.1.5.4 | 4.6.1.6.1 | 4.6.1.6.2 | 4.6.1.6.3 | 4.6.1.6.4 |
| 4.6.1.7.1 | 4.6.1.7.2 | 4.6.1.7.3 | 4.6.1.7.4 | 4.6.1.8.1 | 4.6.1.8.2 | 4.6.1.8.3 | 4.6.1.8.4 |
| 4.6.2.1.1 | 4.6.2.1.2 | 4.6.2.1.3 | 4.6.2.1.4 | 4.6.2.2.1 | 4.6.2.2.2 | 4.6.2.2.3 | 4.6.2.2.4 |
| 4.6.2.3.1 | 4.6.2.3.2 | 4.6.2.3.3 | 4.6.2.3.4 | 4.6.2.4.1 | 4.6.2.4.2 | 4.6.2.4.3 | 4.6.2.4.4 |
| 4.6.2.5.1 | 4.6.2.5.2 | 4.6.2.5.3 | 4.6.2.5.4 | 4.6.2.6.1 | 4.6.2.6.2 | 4.6.2.6.3 | 4.6.2.6.4 |
| 4.6.2.7.1 | 4.6.2.7.2 | 4.6.2.7.3 | 4.6.2.7.4 | 4.6.2.8.1 | 4.6.2.8.2 | 4.6.2.8.3 | 4.6.2.8.4 |
| 4.6.3.1.1 | 4.6.3.1.2 | 4.6.3.1.3 | 4.6.3.1.4 | 4.6.3.2.1 | 4.6.3.2.2 | 4.6.3.2.3 | 4.6.3.2.4 |
| 4.6.3.3.1 | 4.6.3.3.2 | 4.6.3.3.3 | 4.6.3.3.4 | 4.6.3.4.1 | 4.6.3.4.2 | 4.6.3.4.3 | 4.6.3.4.4 |

TABLE 1-continued

| | | | | | | | |
|---|---|---|---|---|---|---|---|
| 4.6.3.5.1 | 4.6.3.5.2 | 4.6.3.5.3 | 4.6.3.5.4 | 4.6.3.6.1 | 4.6.3.6.2 | 4.6.3.6.3 | 4.6.3.6.4 |
| 4.6.3.7.1 | 4.6.3.7.2 | 4.6.3.7.3 | 4.6.3.7.4 | 4.6.3.8.1 | 4.6.3.8.2 | 4.6.3.8.3 | 4.6.3.8.4 |
| 4.6.4.1.1 | 4.6.4.1.2 | 4.6.4.1.3 | 4.6.4.1.4 | 4.6.4.2.1 | 4.6.4.2.2 | 4.6.4.2.3 | 4.6.4.2.4 |
| 4.6.4.3.1 | 4.6.4.3.2 | 4.6.4.3.3 | 4.6.4.3.4 | 4.6.4.4.1 | 4.6.4.4.2 | 4.6.4.4.3 | 4.6.4.4.4 |
| 4.6.4.5.1 | 4.6.4.5.2 | 4.6.4.5.3 | 4.6.4.5.4 | 4.6.4.6.1 | 4.6.4.6.2 | 4.6.4.6.3 | 4.6.4.6.4 |
| 4.6.4.7.1 | 4.6.4.7.2 | 4.6.4.7.3 | 4.6.4.7.4 | 4.6.4.8.1 | 4.6.4.8.2 | 4.6.4.8.3 | 4.6.4.8.4 |
| 4.7.1.1.1 | 4.7.1.1.2 | 4.7.1.1.3 | 4.7.1.1.4 | 4.7.1.2.1 | 4.7.1.2.2 | 4.7.1.2.3 | 4.7.1.2.4 |
| 4.7.1.3.1 | 4.7.1.3.2 | 4.7.1.3.3 | 4.7.1.3.4 | 4.7.1.4.1 | 4.7.1.4.2 | 4.7.1.4.3 | 4.7.1.4.4 |
| 4.7.1.5.1 | 4.7.1.5.2 | 4.7.1.5.3 | 4.7.1.5.4 | 4.7.1.6.1 | 4.7.1.6.2 | 4.7.1.6.3 | 4.7.1.6.4 |
| 4.7.1.7.1 | 4.7.1.7.2 | 4.7.1.7.3 | 4.7.1.7.4 | 4.7.1.8.1 | 4.7.1.8.2 | 4.7.1.8.3 | 4.7.1.8.4 |
| 4.7.2.1.1 | 4.7.2.1.2 | 4.7.2.1.3 | 4.7.2.1.4 | 4.7.2.2.1 | 4.7.2.2.2 | 4.7.2.2.3 | 4.7.2.2.4 |
| 4.7.2.3.1 | 4.7.2.3.2 | 4.7.2.3.3 | 4.7.2.3.4 | 4.7.2.4.1 | 4.7.2.4.2 | 4.7.2.4.3 | 4.7.2.4.4 |
| 4.7.2.5.1 | 4.7.2.5.2 | 4.7.2.5.3 | 4.7.2.5.4 | 4.7.2.6.1 | 4.7.2.6.2 | 4.7.2.6.3 | 4.7.2.6.4 |
| 4.7.2.7.1 | 4.7.2.7.2 | 4.7.2.7.3 | 4.7.2.7.4 | 4.7.2.8.1 | 4.7.2.8.2 | 4.7.2.8.3 | 4.7.2.8.4 |
| 4.7.3.1.1 | 4.7.3.1.2 | 4.7.3.1.3 | 4.7.3.1.4 | 4.7.3.2.1 | 4.7.3.2.2 | 4.7.3.2.3 | 4.7.3.2.4 |
| 4.7.3.3.1 | 4.7.3.3.2 | 4.7.3.3.3 | 4.7.3.3.4 | 4.7.3.4.1 | 4.7.3.4.2 | 4.7.3.4.3 | 4.7.3.4.4 |
| 4.7.3.5.1 | 4.7.3.5.2 | 4.7.3.5.3 | 4.7.3.5.4 | 4.7.3.6.1 | 4.7.3.6.2 | 4.7.3.6.3 | 4.7.3.6.4 |
| 4.7.3.7.1 | 4.7.3.7.2 | 4.7.3.7.3 | 4.7.3.7.4 | 4.7.3.8.1 | 4.7.3.8.2 | 4.7.3.8.3 | 4.7.3.8.4 |
| 4.7.4.1.1 | 4.7.4.1.2 | 4.7.4.1.3 | 4.7.4.1.4 | 4.7.4.2.1 | 4.7.4.2.2 | 4.7.4.2.3 | 4.7.4.2.4 |
| 4.7.4.3.1 | 4.7.4.3.2 | 4.7.4.3.3 | 4.7.4.3.4 | 4.7.4.4.1 | 4.7.4.4.2 | 4.7.4.4.3 | 4.7.4.4.4 |
| 4.7.4.5.1 | 4.7.4.5.2 | 4.7.4.5.3 | 4.7.4.5.4 | 4.7.4.6.1 | 4.7.4.6.2 | 4.7.4.6.3 | 4.7.4.6.4 |
| 4.7.4.7.1 | 4.7.4.7.2 | 4.7.4.7.3 | 4.7.4.7.4 | 4.7.4.8.1 | 4.7.4.8.2 | 4.7.4.8.3 | 4.7.4.8.4 |
| 4.8.1.1.1 | 4.8.1.1.2 | 4.8.1.1.3 | 4.8.1.1.4 | 4.8.1.2.1 | 4.8.1.2.2 | 4.8.1.2.3 | 4.8.1.2.4 |
| 4.8.1.3.1 | 4.8.1.3.2 | 4.8.1.3.3 | 4.8.1.3.4 | 4.8.1.4.1 | 4.8.1.4.2 | 4.8.1.4.3 | 4.8.1.4.4 |
| 4.8.1.5.1 | 4.8.1.5.2 | 4.8.1.5.3 | 4.8.1.5.4 | 4.8.1.6.1 | 4.8.1.6.2 | 4.8.1.6.3 | 4.8.1.6.4 |
| 4.8.1.7.1 | 4.8.1.7.2 | 4.8.1.7.3 | 4.8.1.7.4 | 4.8.1.8.1 | 4.8.1.8.2 | 4.8.1.8.3 | 4.8.1.8.4 |
| 4.8.2.1.1 | 4.8.2.1.2 | 4.8.2.1.3 | 4.8.2.1.4 | 4.8.2.2.1 | 4.8.2.2.2 | 4.8.2.2.3 | 4.8.2.2.4 |
| 4.8.2.3.1 | 4.8.2.3.2 | 4.8.2.3.3 | 4.8.2.3.4 | 4.8.2.4.1 | 4.8.2.4.2 | 4.8.2.4.3 | 4.8.2.4.4 |
| 4.8.2.5.1 | 4.8.2.5.2 | 4.8.2.5.3 | 4.8.2.5.4 | 4.8.2.6.1 | 4.8.2.6.2 | 4.8.2.6.3 | 4.8.2.6.4 |
| 4.8.2.7.1 | 4.8.2.7.2 | 4.8.2.7.3 | 4.8.2.7.4 | 4.8.2.8.1 | 4.8.2.8.2 | 4.8.2.8.3 | 4.8.2.8.4 |
| 4.8.3.1.1 | 4.8.3.1.2 | 4.8.3.1.3 | 4.8.3.1.4 | 4.8.3.2.1 | 4.8.3.2.2 | 4.8.3.2.3 | 4.8.3.2.4 |
| 4.8.3.3.1 | 4.8.3.3.2 | 4.8.3.3.3 | 4.8.3.3.4 | 4.8.3.4.1 | 4.8.3.4.2 | 4.8.3.4.3 | 4.8.3.4.4 |
| 4.8.3.5.1 | 4.8.3.5.2 | 4.8.3.5.3 | 4.8.3.5.4 | 4.8.3.6.1 | 4.8.3.6.2 | 4.8.3.6.3 | 4.8.3.6.4 |
| 4.8.3.7.1 | 4.8.3.7.2 | 4.8.3.7.3 | 4.8.3.7.4 | 4.8.3.8.1 | 4.8.3.8.2 | 4.8.3.8.3 | 4.8.3.8.4 |
| 4.8.4.1.1 | 4.8.4.1.2 | 4.8.4.1.3 | 4.8.4.1.4 | 4.8.4.2.1 | 4.8.4.2.2 | 4.8.4.2.3 | 4.8.4.2.4 |
| 4.8.4.3.1 | 4.8.4.3.2 | 4.8.4.3.3 | 4.8.4.3.4 | 4.8.4.4.1 | 4.8.4.4.2 | 4.8.4.4.3 | 4.8.4.4.4 |
| 4.8.4.5.1 | 4.8.4.5.2 | 4.8.4.5.3 | 4.8.4.5.4 | 4.8.4.6.1 | 4.8.4.6.2 | 4.8.4.6.3 | 4.8.4.6.4 |
| 4.8.4.7.1 | 4.8.4.7.2 | 4.8.4.7.3 | 4.8.4.7.4 | 4.8.4.8.1 | 4.8.4.8.2 | 4.8.4.8.3 | 4.8.4.8.4 |
| 5.1.1.1.1 | 5.1.1.1.2 | 5.1.1.1.3 | 5.1.1.1.4 | 5.1.1.2.1 | 5.1.1.2.2 | 5.1.1.2.3 | 5.1.1.2.4 |
| 5.1.1.3.1 | 5.1.1.3.2 | 5.1.1.3.3 | 5.1.1.3.4 | 5.1.1.4.1 | 5.1.1.4.2 | 5.1.1.4.3 | 5.1.1.4.4 |
| 5.1.1.5.1 | 5.1.1.5.2 | 5.1.1.5.3 | 5.1.1.5.4 | 5.1.1.6.1 | 5.1.1.6.2 | 5.1.1.6.3 | 5.1.1.6.4 |
| 5.1.1.7.1 | 5.1.1.7.2 | 5.1.1.7.3 | 5.1.1.7.4 | 5.1.1.8.1 | 5.1.1.8.2 | 5.1.1.8.3 | 5.1.1.8.4 |
| 5.1.2.1.1 | 5.1.2.1.2 | 5.1.2.1.3 | 5.1.2.1.4 | 5.1.2.2.1 | 5.1.2.2.2 | 5.1.2.2.3 | 5.1.2.2.4 |
| 5.1.2.3.1 | 5.1.2.3.2 | 5.1.2.3.3 | 5.1.2.3.4 | 5.1.2.4.1 | 5.1.2.4.2 | 5.1.2.4.3 | 5.1.2.4.4 |
| 5.1.2.5.1 | 5.1.2.5.2 | 5.1.2.5.3 | 5.1.2.5.4 | 5.1.2.6.1 | 5.1.2.6.2 | 5.1.2.6.3 | 5.1.2.6.4 |
| 5.1.2.7.1 | 5.1.2.7.2 | 5.1.2.7.3 | 5.1.2.7.4 | 5.1.2.8.1 | 5.1.2.8.2 | 5.1.2.8.3 | 5.1.2.8.4 |
| 5.1.3.1.1 | 5.1.3.1.2 | 5.1.3.1.3 | 5.1.3.1.4 | 5.1.3.2.1 | 5.1.3.2.2 | 5.1.3.2.3 | 5.1.3.2.4 |
| 5.1.3.3.1 | 5.1.3.3.2 | 5.1.3.3.3 | 5.1.3.3.4 | 5.1.3.4.1 | 5.1.3.4.2 | 5.1.3.4.3 | 5.1.3.4.4 |
| 5.1.3.5.1 | 5.1.3.5.2 | 5.1.3.5.3 | 5.1.3.5.4 | 5.1.3.6.1 | 5.1.3.6.2 | 5.1.3.6.3 | 5.1.3.6.4 |
| 5.1.3.7.1 | 5.1.3.7.2 | 5.1.3.7.3 | 5.1.3.7.4 | 5.1.3.8.1 | 5.1.3.8.2 | 5.1.3.8.3 | 5.1.3.8.4 |
| 5.1.4.1.1 | 5.1.4.1.2 | 5.1.4.1.3 | 5.1.4.1.4 | 5.1.4.2.1 | 5.1.4.2.2 | 5.1.4.2.3 | 5.1.4.2.4 |
| 5.1.4.3.1 | 5.1.4.3.2 | 5.1.4.3.3 | 5.1.4.3.4 | 5.1.4.4.1 | 5.1.4.4.2 | 5.1.4.4.3 | 5.1.4.4.4 |
| 5.1.4.5.1 | 5.1.4.5.2 | 5.1.4.5.3 | 5.1.4.5.4 | 5.1.4.6.1 | 5.1.4.6.2 | 5.1.4.6.3 | 5.1.4.6.4 |
| 5.1.4.7.1 | 5.1.4.7.2 | 5.1.4.7.3 | 5.1.4.7.4 | 5.1.4.8.1 | 5.1.4.8.2 | 5.1.4.8.3 | 5.1.4.8.4 |
| 5.2.1.1.1 | 5.2.1.1.2 | 5.2.1.1.3 | 5.2.1.1.4 | 5.2.1.2.1 | 5.2.1.2.2 | 5.2.1.2.3 | 5.2.1.2.4 |
| 5.2.1.3.1 | 5.2.1.3.2 | 5.2.1.3.3 | 5.2.1.3.4 | 5.2.1.4.1 | 5.2.1.4.2 | 5.2.1.4.3 | 5.2.1.4.4 |
| 5.2.1.5.1 | 5.2.1.5.2 | 5.2.1.5.3 | 5.2.1.5.4 | 5.2.1.6.1 | 5.2.1.6.2 | 5.2.1.6.3 | 5.2.1.6.4 |
| 5.2.1.7.1 | 5.2.1.7.2 | 5.2.1.7.3 | 5.2.1.7.4 | 5.2.1.8.1 | 5.2.1.8.2 | 5.2.1.8.3 | 5.2.1.8.4 |
| 5.2.2.1.1 | 5.2.2.1.2 | 5.2.2.1.3 | 5.2.2.1.4 | 5.2.2.2.1 | 5.2.2.2.2 | 5.2.2.2.3 | 5.2.2.2.4 |
| 5.2.2.3.1 | 5.2.2.3.2 | 5.2.2.3.3 | 5.2.2.3.4 | 5.2.2.4.1 | 5.2.2.4.2 | 5.2.2.4.3 | 5.2.2.4.4 |
| 5.2.2.5.1 | 5.2.2.5.2 | 5.2.2.5.3 | 5.2.2.5.4 | 5.2.2.6.1 | 5.2.2.6.2 | 5.2.2.6.3 | 5.2.2.6.4 |
| 5.2.2.7.1 | 5.2.2.7.2 | 5.2.2.7.3 | 5.2.2.7.4 | 5.2.2.8.1 | 5.2.2.8.2 | 5.2.2.8.3 | 5.2.2.8.4 |
| 5.2.3.1.1 | 5.2.3.1.2 | 5.2.3.1.3 | 5.2.3.1.4 | 5.2.3.2.1 | 5.2.3.2.2 | 5.2.3.2.3 | 5.2.3.2.4 |
| 5.2.3.3.1 | 5.2.3.3.2 | 5.2.3.3.3 | 5.2.3.3.4 | 5.2.3.4.1 | 5.2.3.4.2 | 5.2.3.4.3 | 5.2.3.4.4 |
| 5.2.3.5.1 | 5.2.3.5.2 | 5.2.3.5.3 | 5.2.3.5.4 | 5.2.3.6.1 | 5.2.3.6.2 | 5.2.3.6.3 | 5.2.3.6.4 |
| 5.2.3.7.1 | 5.2.3.7.2 | 5.2.3.7.3 | 5.2.3.7.4 | 5.2.3.8.1 | 5.2.3.8.2 | 5.2.3.8.3 | 5.2.3.8.4 |
| 5.2.4.1.1 | 5.2.4.1.2 | 5.2.4.1.3 | 5.2.4.1.4 | 5.2.4.2.1 | 5.2.4.2.2 | 5.2.4.2.3 | 5.2.4.2.4 |
| 5.2.4.3.1 | 5.2.4.3.2 | 5.2.4.3.3 | 5.2.4.3.4 | 5.2.4.4.1 | 5.2.4.4.2 | 5.2.4.4.3 | 5.2.4.4.4 |
| 5.2.4.5.1 | 5.2.4.5.2 | 5.2.4.5.3 | 5.2.4.5.4 | 5.2.4.6.1 | 5.2.4.6.2 | 5.2.4.6.3 | 5.2.4.6.4 |
| 5.2.4.7.1 | 5.2.4.7.2 | 5.2.4.7.3 | 5.2.4.7.4 | 5.2.4.8.1 | 5.2.4.8.2 | 5.2.4.8.3 | 5.2.4.8.4 |
| 5.3.1.1.1 | 5.3.1.1.2 | 5.3.1.1.3 | 5.3.1.1.4 | 5.3.1.2.1 | 5.3.1.2.2 | 5.3.1.2.3 | 5.3.1.2.4 |
| 5.3.1.3.1 | 5.3.1.3.2 | 5.3.1.3.3 | 5.3.1.3.4 | 5.3.1.4.1 | 5.3.1.4.2 | 5.3.1.4.3 | 5.3.1.4.4 |
| 5.3.1.5.1 | 5.3.1.5.2 | 5.3.1.5.3 | 5.3.1.5.4 | 5.3.1.6.1 | 5.3.1.6.2 | 5.3.1.6.3 | 5.3.1.6.4 |
| 5.3.1.7.1 | 5.3.1.7.2 | 5.3.1.7.3 | 5.3.1.7.4 | 5.3.1.8.1 | 5.3.1.8.2 | 5.3.1.8.3 | 5.3.1.8.4 |
| 5.3.2.1.1 | 5.3.2.1.2 | 5.3.2.1.3 | 5.3.2.1.4 | 5.3.2.2.1 | 5.3.2.2.2 | 5.3.2.2.3 | 5.3.2.2.4 |
| 5.3.2.3.1 | 5.3.2.3.2 | 5.3.2.3.3 | 5.3.2.3.4 | 5.3.2.4.1 | 5.3.2.4.2 | 5.3.2.4.3 | 5.3.2.4.4 |
| 5.3.2.5.1 | 5.3.2.5.2 | 5.3.2.5.3 | 5.3.2.5.4 | 5.3.2.6.1 | 5.3.2.6.2 | 5.3.2.6.3 | 5.3.2.6.4 |
| 5.3.2.7.1 | 5.3.2.7.2 | 5.3.2.7.3 | 5.3.2.7.4 | 5.3.2.8.1 | 5.3.2.8.2 | 5.3.2.8.3 | 5.3.2.8.4 |
| 5.3.3.1.1 | 5.3.3.1.2 | 5.3.3.1.3 | 5.3.3.1.4 | 5.3.3.2.1 | 5.3.3.2.2 | 5.3.3.2.3 | 5.3.3.2.4 |

TABLE 1-continued

| | | | | | | | |
|---|---|---|---|---|---|---|---|
| 5.3.3.3.1 | 5.3.3.3.2 | 5.3.3.3.3 | 5.3.3.3.4 | 5.3.3.4.1 | 5.3.3.4.2 | 5.3.3.4.3 | 5.3.3.4.4 |
| 5.3.3.5.1 | 5.3.3.5.2 | 5.3.3.5.3 | 5.3.3.5.4 | 5.3.3.6.1 | 5.3.3.6.2 | 5.3.3.6.3 | 5.3.3.6.4 |
| 5.3.3.7.1 | 5.3.3.7.2 | 5.3.3.7.3 | 5.3.3.7.4 | 5.3.3.8.1 | 5.3.3.8.2 | 5.3.3.8.3 | 5.3.3.8.4 |
| 5.3.4.1.1 | 5.3.4.1.2 | 5.3.4.1.3 | 5.3.4.1.4 | 5.3.4.2.1 | 5.3.4.2.2 | 5.3.4.2.3 | 5.3.4.2.4 |
| 5.3.4.3.1 | 5.3.4.3.2 | 5.3.4.3.3 | 5.3.4.3.4 | 5.3.4.4.1 | 5.3.4.4.2 | 5.3.4.4.3 | 5.3.4.4.4 |
| 5.3.4.5.1 | 5.3.4.5.2 | 5.3.4.5.3 | 5.3.4.5.4 | 5.3.4.6.1 | 5.3.4.6.2 | 5.3.4.6.3 | 5.3.4.6.4 |
| 5.3.4.7.1 | 5.3.4.7.2 | 5.3.4.7.3 | 5.3.4.7.4 | 5.3.4.8.1 | 5.3.4.8.2 | 5.3.4.8.3 | 5.3.4.8.4 |
| 5.4.1.1.1 | 5.4.1.1.2 | 5.4.1.1.3 | 5.4.1.1.4 | 5.4.1.2.1 | 5.4.1.2.2 | 5.4.1.2.3 | 5.4.1.2.4 |
| 5.4.1.3.1 | 5.4.1.3.2 | 5.4.1.3.3 | 5.4.1.3.4 | 5.4.1.4.1 | 5.4.1.4.2 | 5.4.1.4.3 | 5.4.1.4.4 |
| 5.4.1.5.1 | 5.4.1.5.2 | 5.4.1.5.3 | 5.4.1.5.4 | 5.4.1.6.1 | 5.4.1.6.2 | 5.4.1.6.3 | 5.4.1.6.4 |
| 5.4.1.7.1 | 5.4.1.7.2 | 5.4.1.7.3 | 5.4.1.7.4 | 5.4.1.8.1 | 5.4.1.8.2 | 5.4.1.8.3 | 5.4.1.8.4 |
| 5.4.2.1.1 | 5.4.2.1.2 | 5.4.2.1.3 | 5.4.2.1.4 | 5.4.2.2.1 | 5.4.2.2.2 | 5.4.2.2.3 | 5.4.2.2.4 |
| 5.4.2.3.1 | 5.4.2.3.2 | 5.4.2.3.3 | 5.4.2.3.4 | 5.4.2.4.1 | 5.4.2.4.2 | 5.4.2.4.3 | 5.4.2.4.4 |
| 5.4.2.5.1 | 5.4.2.5.2 | 5.4.2.5.3 | 5.4.2.5.4 | 5.4.2.6.1 | 5.4.2.6.2 | 5.4.2.6.3 | 5.4.2.6.4 |
| 5.4.2.7.1 | 5.4.2.7.2 | 5.4.2.7.3 | 5.4.2.7.4 | 5.4.2.8.1 | 5.4.2.8.2 | 5.4.2.8.3 | 5.4.2.8.4 |
| 5.4.3.1.1 | 5.4.3.1.2 | 5.4.3.1.3 | 5.4.3.1.4 | 5.4.3.2.1 | 5.4.3.2.2 | 5.4.3.2.3 | 5.4.3.2.4 |
| 5.4.3.3.1 | 5.4.3.3.2 | 5.4.3.3.3 | 5.4.3.3.4 | 5.4.3.4.1 | 5.4.3.4.2 | 5.4.3.4.3 | 5.4.3.4.4 |
| 5.4.3.5.1 | 5.4.3.5.2 | 5.4.3.5.3 | 5.4.3.5.4 | 5.4.3.6.1 | 5.4.3.6.2 | 5.4.3.6.3 | 5.4.3.6.4 |
| 5.4.3.7.1 | 5.4.3.7.2 | 5.4.3.7.3 | 5.4.3.7.4 | 5.4.3.3.1 | 5.4.3.8.2 | 5.4.3.8.3 | 5.4.3.8.4 |
| 5.4.4.1.1 | 5.4.4.1.2 | 5.4.4.1.3 | 5.4.4.1.4 | 5.4.4.2.1 | 5.4.4.2.2 | 5.4.4.2.3 | 5.4.4.2.4 |
| 5.4.4.3.1 | 5.4.4.3.2 | 5.4.4.3.3 | 5.4.4.3.4 | 5.4.4.4.1 | 5.4.4.4.2 | 5.4.4.4.3 | 5.4.4.4.4 |
| 5.4.4.5.1 | 5.4.4.5.2 | 5.4.4.5.3 | 5.4.4.5.4 | 5.4.4.6.1 | 5.4.4.6.2 | 5.4.4.6.3 | 5.4.4.6.4 |
| 5.4.4.7.1 | 5.4.4.7.2 | 5.4.4.7.3 | 5.4.4.7.4 | 5.4.4.8.1 | 5.4.4.8.2 | 5.4.4.8.3 | 5.4.4.8.4 |
| 5.5.1.1.1 | 5.5.1.1.2 | 5.5.1.1.3 | 5.5.1.1.4 | 5.5.1.2.1 | 5.5.1.2.2 | 5.5.1.2.3 | 5.5.1.2.4 |
| 5.5.1.3.1 | 5.5.1.3.2 | 5.5.1.3.3 | 5.5.1.3.4 | 5.5.1.4.1 | 5.5.1.4.2 | 5.5.1.4.3 | 5.5.1.4.4 |
| 5.5.1.5.1 | 5.5.1.5.2 | 5.5.1.5.3 | 5.5.1.5.4 | 5.5.1.6.1 | 5.5.1.6.2 | 5.5.1.6.3 | 5.5.1.6.4 |
| 5.5.1.7.1 | 5.5.1.7.2 | 5.5.1.7.3 | 5.5.1.7.4 | 5.5.1.8.1 | 5.5.1.8.2 | 5.5.1.8.3 | 5.5.1.8.4 |
| 5.5.2.1.1 | 5.5.2.1.2 | 5.5.2.1.3 | 5.5.2.1.4 | 5.5.2.2.1 | 5.5.2.2.2 | 5.5.2.2.3 | 5.5.2.2.4 |
| 5.5.2.3.1 | 5.5.2.3.2 | 5.5.2.3.3 | 5.5.2.3.4 | 5.5.2.4.1 | 5.5.2.4.2 | 5.5.2.4.3 | 5.5.2.4.4 |
| 5.5.2.5.1 | 5.5.2.5.2 | 5.5.2.5.3 | 5.5.2.5.4 | 5.5.2.6.1 | 5.5.2.6.2 | 5.5.2.6.3 | 5.5.2.6.4 |
| 5.5.2.7.1 | 5.5.2.7.2 | 5.5.2.7.3 | 5.5.2.7.4 | 5.5.2.8.1 | 5.5.2.8.2 | 5.5.2.8.3 | 5.5.2.8.4 |
| 5.5.3.1.1 | 5.5.3.1.2 | 5.5.3.1.3 | 5.5.3.1.4 | 5.5.3.2.1 | 5.5.3.2.2 | 5.5.3.2.3 | 5.5.3.2.4 |
| 5.5.3.3.1 | 5.5.3.3.2 | 5.5.3.3.3 | 5.5.3.3.4 | 5.5.3.4.1 | 5.5.3.4.2 | 5.5.3.4.3 | 5.5.3.4.4 |
| 5.5.3.5.1 | 5.5.3.5.2 | 5.5.3.5.3 | 5.5.3.5.4 | 5.5.3.6.1 | 5.5.3.6.2 | 5.5.3.6.3 | 5.5.3.6.4 |
| 5.5.3.7.1 | 5.5.3.7.2 | 5.5.3.7.3 | 5.5.3.7.4 | 5.5.3.8.1 | 5.5.3.8.2 | 5.5.3.8.3 | 5.5.3.8.4 |
| 5.5.4.1.1 | 5.5.4.1.2 | 5.5.4.1.3 | 5.5.4.1.4 | 5.5.4.2.1 | 5.5.4.2.2 | 5.5.4.2.3 | 5.5.4.2.4 |
| 5.5.4.3.1 | 5.5.4.3.2 | 5.5.4.3.3 | 5.5.4.3.4 | 5.5.4.4.1 | 5.5.4.4.2 | 5.5.4.4.3 | 5.5.4.4.4 |
| 5.5.4.5.1 | 5.5.4.5.2 | 5.5.4.5.3 | 5.5.4.5.4 | 5.5.4.6.1 | 5.5.4.6.2 | 5.5.4.6.3 | 5.5.4.6.4 |
| 5.5.4.7.1 | 5.5.4.7.2 | 5.5.4.7.3 | 5.5.4.7.4 | 5.5.4.8.1 | 5.5.4.8.2 | 5.5.4.8.3 | 5.5.4.8.4 |
| 5.6.1.1.1 | 5.6.1.1.2 | 5.6.1.1.3 | 5.6.1.1.4 | 5.6.1.2.1 | 5.6.1.2.2 | 5.6.1.2.3 | 5.6.1.2.4 |
| 5.6.1.3.1 | 5.6.1.3.2 | 5.6.1.3.3 | 5.6.1.3.4 | 5.6.1.4.1 | 5.6.1.4.2 | 5.6.1.4.3 | 5.6.1.4.4 |
| 5.6.1.5.1 | 5.6.1.5.2 | 5.6.1.5.3 | 5.6.1.5.4 | 5.6.1.6.1 | 5.6.1.6.2 | 5.6.1.6.3 | 5.6.1.6.4 |
| 5.6.1.7.1 | 5.6.1.7.2 | 5.6.1.7.3 | 5.6.1.7.4 | 5.6.1.8.1 | 5.6.1.8.2 | 5.6.1.8.3 | 5.6.1.8.4 |
| 5.6.2.1.1 | 5.6.2.1.2 | 5.6.2.1.3 | 5.6.2.1.4 | 5.6.2.2.1 | 5.6.2.2.2 | 5.6.2.2.3 | 5.6.2.2.4 |
| 5.6.2.3.1 | 5.6.2.3.2 | 5.6.2.3.3 | 5.6.2.3.4 | 5.6.2.4.1 | 5.6.2.4.2 | 5.6.2.4.3 | 5.6.2.4.4 |
| 5.6.2.5.1 | 5.6.2.5.2 | 5.6.2.5.3 | 5.6.2.5.4 | 5.6.2.6.1 | 5.6.2.6.2 | 5.6.2.6.3 | 5.6.2.6.4 |
| 5.6.2.7.1 | 5.6.2.7.2 | 5.6.2.7.3 | 5.6.2.7.4 | 5.6.2.8.1 | 5.6.2.8.2 | 5.6.2.8.3 | 5.6.2.8.4 |
| 5.6.3.1.1 | 5.6.3.1.2 | 5.6.3.1.3 | 5.6.3.1.4 | 5.6.3.2.1 | 5.6.3.2.2 | 5.6.3.2.3 | 5.6.3.2.4 |
| 5.6.3.3.1 | 5.6.3.3.2 | 5.6.3.3.3 | 5.6.3.3.4 | 5.6.3.4.1 | 5.6.3.4.2 | 5.6.3.4.3 | 5.6.3.4.4 |
| 5.6.3.5.1 | 5.6.3.5.2 | 5.6.3.5.3 | 5.6.3.5.4 | 5.6.3.6.1 | 5.6.3.6.2 | 5.6.3.6.3 | 5.6.3.6.4 |
| 5.6.3.7.1 | 5.6.3.7.2 | 5.6.3.7.3 | 5.6.3.7.4 | 5.6.3.8.1 | 5.6.3.8.2 | 5.6.3.8.3 | 5.6.3.8.4 |
| 5.6.4.1.1 | 5.6.4.1.2 | 5.6.4.1.3 | 5.6.4.1.4 | 5.6.4.2.1 | 5.6.4.2.2 | 5.6.4.2.3 | 5.6.4.2.4 |
| 5.6.4.3.1 | 5.6.4.3.2 | 5.6.4.3.3 | 5.6.4.3.4 | 5.6.4.4.1 | 5.6.4.4.2 | 5.6.4.4.3 | 5.6.4.4.4 |
| 5.6.4.5.1 | 5.6.4.5.2 | 5.6.4.5.3 | 5.6.4.5.4 | 5.6.4.6.1 | 5.6.4.6.2 | 5.6.4.6.3 | 5.6.4.6.4 |
| 5.6.4.7.1 | 5.6.4.7.2 | 5.6.4.7.3 | 5.6.4.7.4 | 5.6.4.8.1 | 5.6.4.8.2 | 5.6.4.8.3 | 5.6.4.8.4 |
| 5.7.1.1.1 | 5.7.1.1.2 | 5.7.1.1.3 | 5.7.1.1.4 | 5.7.1.2.1 | 5.7.1.2.2 | 5.7.1.2.3 | 5.7.1.2.4 |
| 5.7.1.3.1 | 5.7.1.3.2 | 5.7.1.3.3 | 5.7.1.3.4 | 5.7.1.4.1 | 5.7.1.4.2 | 5.7.1.4.3 | 5.7.1.4.4 |
| 5.7.1.5.1 | 5.7.1.5.2 | 5.7.1.5.3 | 5.7.1.5.4 | 5.7.1.6.1 | 5.7.1.6.2 | 5.7.1.6.3 | 5.7.1.6.4 |
| 5.7.1.7.1 | 5.7.1.7.2 | 5.7.1.7.3 | 5.7.1.7.4 | 5.7.1.8.1 | 5.7.1.8.2 | 5.7.1.8.3 | 5.7.1.8.4 |
| 5.7.2.1.1 | 5.7.2.1.2 | 5.7.2.1.3 | 5.7.2.1.4 | 5.7.2.2.1 | 5.7.2.2.2 | 5.7.2.2.3 | 5.7.2.2.4 |
| 5.7.2.3.1 | 5.7.2.3.2 | 5.7.2.3.3 | 5.7.2.3.4 | 5.7.2.4.1 | 5.7.2.4.2 | 5.7.2.4.3 | 5.7.2.4.4 |
| 5.7.2.5.1 | 5.7.2.5.2 | 5.7.2.5.3 | 5.7.2.5.4 | 5.7.2.6.1 | 5.7.2.6.2 | 5.7.2.6.3 | 5.7.2.6.4 |
| 5.7.2.7.1 | 5.7.2.7.2 | 5.7.2.7.3 | 5.7.2.7.4 | 5.7.2.8.1 | 5.7.2.8.2 | 5.7.2.8.3 | 5.7.2.8.4 |
| 5.7.3.1.1 | 5.7.3.1.2 | 5.7.3.1.3 | 5.7.3.1.4 | 5.7.3.2.1 | 5.7.3.2.2 | 5.7.3.2.3 | 5.7.3.2.4 |
| 5.7.3.3.1 | 5.7.3.3.2 | 5.7.3.3.3 | 5.7.3.3.4 | 5.7.3.4.1 | 5.7.3.4.2 | 5.7.3.4.3 | 5.7.3.4.4 |
| 5.7.3.5.1 | 5.7.3.5.2 | 5.7.3.5.3 | 5.7.3.5.4 | 5.7.3.6.1 | 5.7.3.6.2 | 5.7.3.6.3 | 5.7.3.6.4 |
| 5.7.3.7.1 | 5.7.3.7.2 | 5.7.3.7.3 | 5.7.3.7.4 | 5.7.3.8.1 | 5.7.3.8.2 | 5.7.3.8.3 | 5.7.3.8.4 |
| 5.7.4.1.1 | 5.7.4.1.2 | 5.7.4.1.3 | 5.7.4.1.4 | 5.7.4.2.1 | 5.7.4.2.2 | 5.7.4.2.3 | 5.7.4.2.4 |
| 5.7.4.3.1 | 5.7.4.3.2 | 5.7.4.3.3 | 5.7.4.3.4 | 5.7.4.4.1 | 5.7.4.4.2 | 5.7.4.4.3 | 5.7.4.4.4 |
| 5.7.4.5.1 | 5.7.4.5.2 | 5.7.4.5.3 | 5.7.4.5.4 | 5.7.4.6.1 | 5.7.4.6.2 | 5.7.4.6.3 | 5.7.4.6.4 |
| 5.7.4.7.1 | 5.7.4.7.2 | 5.7.4.7.3 | 5.7.4.7.4 | 5.7.4.8.1 | 5.7.4.8.2 | 5.7.4.8.3 | 5.7.4.8.4 |
| 5.8.1.1.1 | 5.8.1.1.2 | 5.8.1.1.3 | 5.8.1.1.4 | 5.8.1.2.1 | 5.8.1.2.2 | 5.8.1.2.3 | 5.8.1.2.4 |
| 5.8.1.3.1 | 5.8.1.3.2 | 5.8.1.3.3 | 5.8.1.3.4 | 5.8.1.4.1 | 5.8.1.4.2 | 5.8.1.4.3 | 5.8.1.4.4 |
| 5.8.1.5.1 | 5.8.1.5.2 | 5.8.1.5.3 | 5.8.1.5.4 | 5.8.1.6.1 | 5.8.1.6.2 | 5.8.1.6.3 | 5.8.1.6.4 |
| 5.8.1.7.1 | 5.8.1.7.2 | 5.8.1.7.3 | 5.8.1.7.4 | 5.8.1.8.1 | 5.8.1.8.2 | 5.8.1.8.3 | 5.5.1.8.4 |
| 5.8.2.1.1 | 5.8.2.1.2 | 5.8.2.1.3 | 5.8.2.1.4 | 5.8.2.2.1 | 5.8.2.2.2 | 5.8.2.2.3 | 5.8.2.2.4 |
| 5.8.2.3.1 | 5.8.2.3.2 | 5.8.2.3.3 | 5.8.2.3.4 | 5.8.2.4.1 | 5.8.2.4.2 | 5.8.2.4.3 | 5.8.2.4.4 |
| 5.8.2.5.1 | 5.8.2.5.2 | 5.8.2.5.3 | 5.8.2.5.4 | 5.8.2.6.1 | 5.8.2.6.2 | 5.8.2.6.3 | 5.8.2.6.4 |
| 5.8.2.7.1 | 5.8.2.7.2 | 5.8.2.7.3 | 5.8.2.7.4 | 5.8.2.8.1 | 5.8.2.8.2 | 5.8.2.8.3 | 5.8.2.8.4 |

TABLE 1-continued

| | | | | | | | |
|---|---|---|---|---|---|---|---|
| 5.8.3.1.1 | 5.8.3.1.2 | 5.8.3.1.3 | 5.8.3.1.4 | 5.8.3.2.1 | 5.8.3.2.2 | 5.8.3.2.3 | 5.8.3.2.4 |
| 5.8.3.3.1 | 5.8.3.3.2 | 5.8.3.3.3 | 5.8.3.3.4 | 5.8.3.4.1 | 5.8.3.4.2 | 5.8.3.4.3 | 5.8.3.4.4 |
| 5.8.3.5.1 | 5.8.3.5.2 | 5.8.3.5.3 | 5.8.3.5.4 | 5.8.3.6.1 | 5.8.3.6.2 | 5.8.3.6.3 | 5.8.3.6.4 |
| 5.8.3.7.1 | 5.8.3.7.2 | 5.8.3.7.3 | 5.8.3.7.4 | 5.8.3.8.1 | 5.8.3.8.2 | 5.8.3.8.3 | 5.8.3.8.4 |
| 5.8.4.1.1 | 5.8.4.1.2 | 5.8.4.1.3 | 5.8.4.1.4 | 5.8.4.2.1 | 5.8.4.2.2 | 5.8.4.2.3 | 5.8.4.2.4 |
| 5.8.4.3.1 | 5.8.4.3.2 | 5.8.4.3.3 | 5.8.4.3.4 | 5.8.4.4.1 | 5.8.4.4.2 | 5.8.4.4.3 | 5.8.4.4.4 |
| 5.8.4.5.1 | 5.8.4.5.2 | 5.8.4.5.3 | 5.8.4.5.4 | 5.8.4.6.1 | 5.8.4.6.2 | 5.8.4.6.3 | 5.8.4.6.4 |
| 5.8.4.7.1 | 5.8.4.7.2 | 5.8.4.7.3 | 5.8.4.7.4 | 5.8.4.8.1 | 5.8.4.8.2 | 5.8.4.8.3 | 5.8.4.8.4 |
| 6.1.1.1.1 | 6.1.1.1.2 | 6.1.1.1.3 | 6.1.1.1.4 | 6.1.1.2.1 | 6.1.1.2.2 | 6.1.1.2.3 | 6.1.1.2.4 |
| 6.1.1.3.1 | 6.1.1.3.2 | 6.1.1.3.3 | 6.1.1.3.4 | 6.1.1.4.1 | 6.1.1.4.2 | 6.1.1.4.3 | 6.1.1.4.4 |
| 6.1.1.5.1 | 6.1.1.5.2 | 6.1.1.5.3 | 6.1.1.5.4 | 6.1.1.6.1 | 6.1.1.6.2 | 6.1.1.6.3 | 6.1.1.6.4 |
| 6.1.1.7.1 | 6.1.1.7.2 | 6.1.1.7.3 | 6.1.1.7.4 | 6.1.1.8.1 | 6.1.1.8.2 | 6.1.1.8.3 | 6.1.1.8.4 |
| 6.1.2.1.1 | 6.1.2.1.2 | 6.1.2.1.3 | 6.1.2.1.4 | 6.1.2.2.1 | 6.1.2.2.2 | 6.1.2.2.3 | 6.1.2.2.4 |
| 6.1.2.3.1 | 6.1.2.3.2 | 6.1.2.3.3 | 6.1.2.3.4 | 6.1.2.4.1 | 6.1.2.4.2 | 6.1.2.4.3 | 6.1.2.4.4 |
| 6.1.2.5.1 | 6.1.2.5.2 | 6.1.2.5.3 | 6.1.2.5.4 | 6.1.2.6.1 | 6.1.2.6.2 | 6.1.2.6.3 | 6.1.2.6.4 |
| 6.1.2.7.1 | 6.1.2.7.2 | 6.1.2.7.3 | 6.1.2.7.4 | 6.1.2.8.1 | 6.1.2.8.2 | 6.1.2.8.3 | 6.1.2.8.4 |
| 6.1.3.1.1 | 6.1.3.1.2 | 6.1.3.1.3 | 6.1.3.1.4 | 6.1.3.2.1 | 6.1.3.2.2 | 6.1.3.2.3 | 6.1.3.2.4 |
| 6.1.3.3.1 | 6.1.3.3.2 | 6.1.3.3.3 | 6.1.3.3.4 | 6.1.3.4.1 | 6.1.3.4.2 | 6.1.3.4.3 | 6.1.3.4.4 |
| 6.1.3.5.1 | 6.1.3.5.2 | 6.1.3.5.3 | 6.1.3.5.4 | 6.1.3.6.1 | 6.1.3.6.2 | 6.1.3.6.3 | 6.1.3.6.4 |
| 6.1.3.7.1 | 6.1.3.7.2 | 6.1.3.7.3 | 6.1.3.7.4 | 6.1.3.8.1 | 6.1.3.8.2 | 6.1.3.8.3 | 6.1.3.8.4 |
| 6.1.4.1.1 | 6.1.4.1.2 | 6.1.4.1.3 | 6.1.4.1.4 | 6.1.4.2.1 | 6.1.4.2.2 | 6.1.4.2.3 | 6.1.4.2.4 |
| 6.1.4.3.1 | 6.1.4.3.2 | 6.1.4.3.3 | 6.1.4.3.4 | 6.1.4.4.1 | 6.1.4.4.2 | 6.1.4.4.3 | 6.1.4.4.4 |
| 6.1.4.5.1 | 6.1.4.5.2 | 6.1.4.5.3 | 6.1.4.5.4 | 6.1.4.6.1 | 6.1.4.6.2 | 6.1.4.6.3 | 6.1.4.6.4 |
| 6.1.4.7.1 | 6.1.4.7.2 | 6.1.4.7.3 | 6.1.4.7.4 | 6.1.4.8.1 | 6.1.4.8.2 | 6.1.4.8.3 | 6.1.4.8.4 |
| 6.2.1.1.1 | 6.2.1.1.2 | 6.2.1.1.3 | 6.2.1.1.4 | 6.2.1.2.1 | 6.2.1.2.2 | 6.2.1.2.3 | 6.2.1.2.4 |
| 6.2.1.3.1 | 6.2.1.3.2 | 6.2.1.3.3 | 6.2.1.3.4 | 6.2.1.4.1 | 6.2.1.4.2 | 6.2.1.4.3 | 6.2.1.4.4 |
| 6.2.1.5.1 | 6.2.1.5.2 | 6.2.1.5.3 | 6.2.1.5.4 | 6.2.1.6.1 | 6.2.1.6.2 | 6.2.1.6.3 | 6.2.1.6.4 |
| 6.2.1.7.1 | 6.2.1.7.2 | 6.2.1.7.3 | 6.2.1.7.4 | 6.2.1.8.1 | 6.2.1.8.2 | 6.2.1.8.3 | 6.2.1.8.4 |
| 6.2.2.1.1 | 6.2.2.1.2 | 6.2.2.1.3 | 6.2.2.1.4 | 6.2.2.2.1 | 6.2.2.2.2 | 6.2.2.2.3 | 6.2.2.2.4 |
| 6.2.2.3.1 | 6.2.2.3.2 | 6.2.2.3.3 | 6.2.2.3.4 | 6.2.2.4.1 | 6.2.2.4.2 | 6.2.2.4.3 | 6.2.2.4.4 |
| 6.2.2.5.1 | 6.2.2.5.2 | 6.2.2.5.3 | 6.2.2.5.4 | 6.2.2.6.1 | 6.2.2.6.2 | 6.2.2.6.3 | 6.2.2.6.4 |
| 6.2.2.7.1 | 6.2.2.7.2 | 6.2.2.7.3 | 6.2.2.7.4 | 6.2.2.8.1 | 6.2.2.8.2 | 6.2.2.8.3 | 6.2.2.8.4 |
| 6.2.3.1.1 | 6.2.3.1.2 | 6.2.3.1.3 | 6.2.3.1.4 | 6.2.3.2.1 | 6.2.3.2.2 | 6.2.3.2.3 | 6.2.3.2.4 |
| 6.2.3.3.1 | 6.2.3.3.2 | 6.2.3.3.3 | 6.2.3.3.4 | 6.2.3.4.1 | 6.2.3.4.2 | 6.2.3.4.3 | 6.2.3.4.4 |
| 6.2.3.5.1 | 6.2.3.5.2 | 6.2.3.5.3 | 6.2.3.5.4 | 6.2.3.6.1 | 6.2.3.6.2 | 6.2.3.6.3 | 6.2.3.6.4 |
| 6.2.3.7.1 | 6.2.3.7.2 | 6.2.3.7.3 | 6.2.3.7.4 | 6.2.3.8.1 | 6.2.3.8.2 | 6.2.3.8.3 | 6.2.3.8.4 |
| 6.2.4.1.1 | 6.2.4.1.2 | 6.2.4.1.3 | 6.2.4.1.4 | 6.2.4.2.1 | 6.2.4.2.2 | 6.2.4.2.3 | 6.2.4.2.4 |
| 6.2.4.3.1 | 6.2.4.3.2 | 6.2.4.3.3 | 6.2.4.3.4 | 6.2.4.4.1 | 6.2.4.4.2 | 6.2.4.4.3 | 6.2.4.4.4 |
| 6.2.4.5.1 | 6.2.4.5.2 | 6.2.4.5.3 | 6.2.4.5.4 | 6.2.4.6.1 | 6.2.4.6.2 | 6.2.4.6.3 | 6.2.4.6.4 |
| 6.2.4.7.1 | 6.2.4.7.2 | 6.2.4.7.3 | 6.2.4.7.4 | 6.2.4.8.1 | 6.2.4.8.2 | 6.2.4.8.3 | 6.2.4.8.4 |
| 6.3.1.1.1 | 6.3.1.1.2 | 6.3.1.1.3 | 6.3.1.1.4 | 6.3.1.2.1 | 6.3.1.2.2 | 6.3.1.2.3 | 6.3.1.2.4 |
| 6.3.1.3.1 | 6.3.1.3.2 | 6.3.1.3.3 | 6.3.1.3.4 | 6.3.1.4.1 | 6.3.1.4.2 | 6.3.1.4.3 | 6.3.1.4.4 |
| 6.3.1.5.1 | 6.3.1.5.2 | 6.3.1.5.3 | 6.3.1.5.4 | 6.3.1.6.1 | 6.3.1.6.2 | 6.3.1.6.3 | 6.3.1.6.4 |
| 6.3.1.7.1 | 6.3.1.7.2 | 6.3.1.7.3 | 6.3.1.7.4 | 6.3.1.8.1 | 6.3.1.8.2 | 6.3.1.8.3 | 6.3.1.8.4 |
| 6.3.2.1.1 | 6.3.2.1.2 | 6.3.2.1.3 | 6.3.2.1.4 | 6.3.2.2.1 | 6.3.2.2.2 | 6.3.2.2.3 | 6.3.2.2.4 |
| 6.3.2.3.1 | 6.3.2.3.2 | 6.3.2.3.3 | 6.3.2.3.4 | 6.3.2.4.1 | 6.3.2.4.2 | 6.3.2.4.3 | 6.3.2.4.4 |
| 6.3.2.5.1 | 6.3.2.5.2 | 6.3.2.5.3 | 6.3.2.5.4 | 6.3.2.6.1 | 6.3.2.6.2 | 6.3.2.6.3 | 6.3.2.6.4 |
| 6.3.2.7.1 | 6.3.2.7.2 | 6.3.2.7.3 | 6.3.2.7.4 | 6.3.2.8.1 | 6.3.2.8.2 | 6.3.2.8.3 | 6.3.2.8.4 |
| 6.3.3.1.1 | 6.3.3.1.2 | 6.3.3.1.3 | 6.3.3.1.4 | 6.3.3.2.1 | 6.3.3.2.2 | 6.3.3.2.3 | 6.3.3.2.4 |
| 6.3.3.3.1 | 6.3.3.3.2 | 6.3.3.3.3 | 6.3.3.3.4 | 6.3.3.4.1 | 6.3.3.4.2 | 6.3.3.4.3 | 6.3.3.4.4 |
| 6.3.3.5.1 | 6.3.3.5.2 | 6.3.3.5.3 | 6.3.3.5.4 | 6.3.3.6.1 | 6.3.3.6.2 | 6.3.3.6.3 | 6.3.3.6.4 |
| 6.3.3.7.1 | 6.3.3.7.2 | 6.3.3.7.3 | 6.3.3.7.4 | 6.3.3.8.1 | 6.3.3.8.2 | 6.3.3.8.3 | 6.3.3.8.4 |
| 6.3.4.1.1 | 6.3.4.1.2 | 6.3.4.1.3 | 6.3.4.1.4 | 6.3.4.2.1 | 6.3.4.2.2 | 6.3.4.2.3 | 6.3.4.2.4 |
| 6.3.4.3.1 | 6.3.4.3.2 | 6.3.4.3.3 | 6.3.4.3.4 | 6.3.4.4.1 | 6.3.4.4.2 | 6.3.4.4.3 | 6.3.4.4.4 |
| 6.3.4.5.1 | 6.3.4.5.2 | 6.3.4.5.3 | 6.3.4.5.4 | 6.3.4.6.1 | 6.3.4.6.2 | 6.3.4.6.3 | 6.3.4.6.4 |
| 6.3.4.7.1 | 6.3.4.7.2 | 6.3.4.7.3 | 6.3.4.7.4 | 6.3.4.8.1 | 6.3.4.8.2 | 6.3.4.8.3 | 6.3.4.8.4 |
| 6.4.1.1.1 | 6.4.1.1.2 | 6.4.1.1.3 | 6.4.1.1.4 | 6.4.1.2.1 | 6.4.1.2.2 | 6.4.1.2.3 | 6.4.1.2.4 |
| 6.4.1.3.1 | 6.4.1.3.2 | 6.4.1.3.3 | 6.4.1.3.4 | 6.4.1.4.1 | 6.4.1.4.2 | 6.4.1.4.3 | 6.4.1.4.4 |
| 6.4.1.5.1 | 6.4.1.5.2 | 6.4.1.5.3 | 6.4.1.5.4 | 6.4.1.6.1 | 6.4.1.6.2 | 6.4.1.6.3 | 6.4.1.6.4 |
| 6.4.1.7.1 | 6.4.1.7.2 | 6.4.1.7.3 | 6.4.1.7.4 | 6.4.1.8.1 | 6.4.1.8.2 | 6.4.1.8.3 | 6.4.1.8.4 |
| 6.4.2.1.1 | 6.4.2.1.2 | 6.4.2.1.3 | 6.4.2.1.4 | 6.4.2.2.1 | 6.4.2.2.2 | 6.4.2.2.3 | 6.4.2.2.4 |
| 6.4.2.3.1 | 6.4.2.3.2 | 6.4.2.3.3 | 6.4.2.3.4 | 6.4.2.4.1 | 6.4.2.4.2 | 6.4.2.4.3 | 6.4.2.4.4 |
| 6.4.2.5.1 | 6.4.2.5.2 | 6.4.2.5.3 | 6.4.2.5.4 | 6.4.2.6.1 | 6.4.2.6.2 | 6.4.2.6.3 | 6.4.2.6.4 |
| 6.4.2.7.1 | 6.4.2.7.2 | 6.4.2.7.3 | 6.4.2.7.4 | 6.4.2.8.1 | 6.4.2.8.2 | 6.4.2.8.3 | 6.4.2.8.4 |
| 6.4.3.1.1 | 6.4.3.1.2 | 6.4.3.1.3 | 6.4.3.1.4 | 6.4.3.2.1 | 6.4.3.2.2 | 6.4.3.2.3 | 6.4.3.2.4 |
| 6.4.3.3.1 | 6.4.3.3.2 | 6.4.3.3.3 | 6.4.3.3.4 | 6.4.3.4.1 | 6.4.3.4.2 | 6.4.3.4.3 | 6.4.3.4.4 |
| 6.4.3.5.1 | 6.4.3.5.2 | 6.4.3.5.3 | 6.4.3.5.4 | 6.4.3.6.1 | 6.4.3.6.2 | 6.4.3.6.3 | 6.4.3.6.4 |
| 6.4.3.7.1 | 6.4.3.7.2 | 6.4.3.7.3 | 6.4.3.7.4 | 6.4.3.8.1 | 6.4.3.8.2 | 6.4.3.8.3 | 6.4.3.8.4 |
| 6.4.4.1.1 | 6.4.4.1.2 | 6.4.4.1.3 | 6.4.4.1.4 | 6.4.4.2.1 | 6.4.4.2.2 | 6.4.4.2.3 | 6.4.4.2.4 |
| 6.4.4.3.1 | 6.4.4.3.2 | 6.4.4.3.3 | 6.4.4.3.4 | 6.4.4.4.1 | 6.4.4.4.2 | 6.4.4.4.3 | 6.4.4.4.4 |
| 6.4.4.5.1 | 6.4.4.5.2 | 6.4.4.5.3 | 6.4.4.5.4 | 6.4.4.6.1 | 6.4.4.6.2 | 6.4.4.6.3 | 6.4.4.6.4 |
| 6.4.4.7.1 | 6.4.4.7.2 | 6.4.4.7.3 | 6.4.4.7.4 | 6.4.4.8.1 | 6.4.4.8.2 | 6.4.4.8.3 | 6.4.4.8.4 |
| 6.5.1.1.1 | 6.5.1.1.2 | 6.5.1.1.3 | 6.5.1.1.4 | 6.5.1.2.1 | 6.5.1.2.2 | 6.5.1.2.3 | 6.5.1.2.4 |
| 6.5.1.3.1 | 6.5.1.3.2 | 6.5.1.3.3 | 6.5.1.3.4 | 6.5.1.4.1 | 6.5.1.4.2 | 6.5.1.4.3 | 6.5.1.4.4 |
| 6.5.1.5.1 | 6.5.1.5.2 | 6.5.1.5.3 | 6.5.1.5.4 | 6.5.1.6.1 | 6.5.1.6.2 | 6.5.1.6.3 | 6.5.1.6.4 |
| 6.5.1.7.1 | 6.5.1.7.2 | 6.5.1.7.3 | 6.5.1.7.4 | 6.5.1.8.1 | 6.5.1.8.2 | 6.5.1.8.3 | 6.5.1.8.4 |
| 6.5.2.1.1 | 6.5.2.1.2 | 6.5.2.1.3 | 6.5.2.1.4 | 6.5.2.2.1 | 6.5.2.2.2 | 6.5.2.2.3 | 6.5.2.2.4 |
| 6.5.2.3.1 | 6.5.2.3.2 | 6.5.2.3.3 | 6.5.2.3.4 | 6.5.2.4.1 | 6.5.2.4.2 | 6.5.2.4.3 | 6.5.2.4.4 |
| 6.5.2.5.1 | 6.5.2.5.2 | 6.5.2.5.3 | 6.5.2.5.4 | 6.5.2.6.1 | 6.5.2.6.2 | 6.5.2.6.3 | 6.5.2.6.4 |

TABLE 1-continued

| | | | | | | | |
|---|---|---|---|---|---|---|---|
| 6.5.2.7.1 | 6.5.2.7.2 | 6.5.2.7.3 | 6.5.2.7.4 | 6.5.2.8.1 | 6.5.2.8.2 | 6.5.2.8.3 | 6.5.2.8.4 |
| 6.5.3.1.1 | 6.5.3.1.2 | 6.5.3.1.3 | 6.5.3.1.4 | 6.5.3.2.1 | 6.5.3.2.2 | 6.5.3.2.3 | 6.5.3.2.4 |
| 6.5.3.3.1 | 6.5.3.3.2 | 6.5.3.3.3 | 6.5.3.3.4 | 6.5.3.4.1 | 6.5.3.4.2 | 6.5.3.4.3 | 6.5.3.4.4 |
| 6.5.3.5.1 | 6.5.3.5.2 | 6.5.3.5.3 | 6.5.3.5.4 | 6.5.3.6.1 | 6.5.3.6.2 | 6.5.3.6.3 | 6.5.3.6.4 |
| 6.5.3.7.1 | 6.5.3.7.2 | 6.5.3.7.3 | 6.5.3.7.4 | 6.5.3.8.1 | 6.5.3.8.2 | 6.5.3.8.3 | 6.5.3.8.4 |
| 6.5.4.1.1 | 6.5.4.1.2 | 6.5.4.1.3 | 6.5.4.1.4 | 6.5.4.2.1 | 6.5.4.2.2 | 6.5.4.2.3 | 6.5.4.2.4 |
| 6.5.4.3.1 | 6.5.4.3.2 | 6.5.4.3.3 | 6.5.4.3.4 | 6.5.4.4.1 | 6.5.4.4.2 | 6.5.4.4.3 | 6.5.4.4.4 |
| 6.5.4.5.1 | 6.5.4.5.2 | 6.5.4.5.3 | 6.5.4.5.4 | 6.5.4.6.1 | 6.5.4.6.2 | 6.5.4.6.3 | 6.5.4.6.4 |
| 6.5.4.7.1 | 6.5.4.7.2 | 6.5.4.7.3 | 6.5.4.7.4 | 6.5.4.8.1 | 6.5.4.8.2 | 6.5.4.8.3 | 6.5.4.8.4 |
| 6.6.1.1.1 | 6.6.1.1.2 | 6.6.1.1.3 | 6.6.1.1.4 | 6.6.1.2.1 | 6.6.1.2.2 | 6.6.1.2.3 | 6.6.1.2.4 |
| 6.6.1.3.1 | 6.6.1.3.2 | 6.6.1.3.3 | 6.6.1.3.4 | 6.6.1.4.1 | 6.6.1.4.2 | 6.6.1.4.3 | 6.6.1.4.4 |
| 6.6.1.5.1 | 6.6.1.5.2 | 6.6.1.5.3 | 6.6.1.5.4 | 6.6.1.6.1 | 6.6.1.6.2 | 6.6.1.6.3 | 6.6.1.6.4 |
| 6.6.1.7.1 | 6.6.1.7.2 | 6.6.1.7.3 | 6.6.1.7.4 | 6.6.1.8.1 | 6.6.1.8.2 | 6.6.1.8.3 | 6.6.1.8.4 |
| 6.6.2.1.1 | 6.6.2.1.2 | 6.6.2.1.3 | 6.6.2.1.4 | 6.6.2.2.1 | 6.6.2.2.2 | 6.6.2.2.3 | 6.6.2.2.4 |
| 6.6.2.3.1 | 6.6.2.3.2 | 6.6.2.3.3 | 6.6.2.3.4 | 6.6.2.4.1 | 6.6.2.4.2 | 6.6.2.4.3 | 6.6.2.4.4 |
| 6.6.2.5.1 | 6.6.2.5.2 | 6.6.2.5.3 | 6.6.2.5.4 | 6.6.2.6.1 | 6.6.2.6.2 | 6.6.2.6.3 | 6.6.2.6.4 |
| 6.6.2.7.1 | 6.6.2.7.2 | 6.6.2.7.3 | 6.6.2.7.4 | 6.6.2.8.1 | 6.6.2.8.2 | 6.6.2.8.3 | 6.6.2.8.4 |
| 6.6.3.1.1 | 6.6.3.1.2 | 6.6.3.1.3 | 6.6.3.1.4 | 6.6.3.2.1 | 6.6.3.2.2 | 6.6.3.2.3 | 6.6.3.2.4 |
| 6.6.3.3.1 | 6.6.3.3.2 | 6.6.3.3.3 | 6.6.3.3.4 | 6.6.3.4.1 | 6.6.3.4.2 | 6.6.3.4.3 | 6.6.3.4.4 |
| 6.6.3.5.1 | 6.6.3.5.2 | 6.6.3.5.3 | 6.6.3.5.4 | 6.6.3.6.1 | 6.6.3.6.2 | 6.6.3.6.3 | 6.6.3.6.4 |
| 6.6.3.7.1 | 6.6.3.7.2 | 6.6.3.7.3 | 6.6.3.7.4 | 6.6.3.8.1 | 6.6.3.8.2 | 6.6.3.8.3 | 6.6.3.8.4 |
| 6.6.4.1.1 | 6.6.4.1.2 | 6.6.4.1.3 | 6.6.4.1.4 | 6.6.4.2.1 | 6.6.4.2.2 | 6.6.4.2.3 | 6.6.4.2.4 |
| 6.6.4.3.1 | 6.6.4.3.2 | 6.6.4.3.3 | 6.6.4.3.4 | 6.6.4.4.1 | 6.6.4.4.2 | 6.6.4.4.3 | 6.6.4.4.4 |
| 6.6.4.5.1 | 6.6.4.5.2 | 6.6.4.5.3 | 6.6.4.5.4 | 6.6.4.6.1 | 6.6.4.6.2 | 6.6.4.6.3 | 6.6.4.6.4 |
| 6.6.4.7.1 | 6.6.4.7.2 | 6.6.4.7.3 | 6.6.4.7.4 | 6.6.4.8.1 | 6.6.4.8.2 | 6.6.4.8.3 | 6.6.4.8.4 |
| 6.7.1.1.1 | 6.7.1.1.2 | 6.7.1.1.3 | 6.7.1.1.4 | 6.7.1.2.1 | 6.7.1.2.2 | 6.7.1.2.3 | 6.7.1.2.4 |
| 6.7.1.3.1 | 6.7.1.3.2 | 6.7.1.3.3 | 6.7.1.3.4 | 6.7.1.4.1 | 6.7.1.4.2 | 6.7.1.4.3 | 6.7.1.4.4 |
| 6.7.1.5.1 | 6.7.1.5.2 | 6.7.1.5.3 | 6.7.1.5.4 | 6.7.1.6.1 | 6.7.1.6.2 | 6.7.1.6.3 | 6.7.1.6.4 |
| 6.7.1.7.1 | 6.7.1.7.2 | 6.7.1.7.3 | 6.7.1.7.4 | 6.7.1.8.1 | 6.7.1.8.2 | 6.7.1.8.3 | 6.7.1.8.4 |
| 6.7.2.1.1 | 6.7.2.1.2 | 6.7.2.1.3 | 6.7.2.1.4 | 6.7.2.2.1 | 6.7.2.2.2 | 6.7.2.2.3 | 6.7.2.2.4 |
| 6.7.2.3.1 | 6.7.2.3.2 | 6.7.2.3.3 | 6.7.2.3.4 | 6.7.2.4.1 | 6.7.2.4.2 | 6.7.2.4.3 | 6.7.2.4.4 |
| 6.7.2.5.1 | 6.7.2.5.2 | 6.7.2.5.3 | 6.7.2.5.4 | 6.7.2.6.1 | 6.7.2.6.2 | 6.7.2.6.3 | 6.7.2.6.4 |
| 6.7.2.7.1 | 6.7.2.7.2 | 6.7.2.7.3 | 6.7.2.7.4 | 6.7.2.8.1 | 6.7.2.8.2 | 6.7.2.8.3 | 6.7.2.8.4 |
| 6.7.3.1.1 | 6.7.3.1.2 | 6.7.3.1.3 | 6.7.3.1.4 | 6.7.3.2.1 | 6.7.3.2.2 | 6.7.3.2.3 | 6.7.3.2.4 |
| 6.7.3.3.1 | 6.7.3.3.2 | 6.7.3.3.3 | 6.7.3.3.4 | 6.7.3.4.1 | 6.7.3.4.2 | 6.7.3.4.3 | 6.7.3.4.4 |
| 6.7.3.5.1 | 6.7.3.5.2 | 6.7.3.5.3 | 6.7.3.5.4 | 6.7.3.6.1 | 6.7.3.6.2 | 6.7.3.6.3 | 6.7.3.6.4 |
| 6.7.3.7.1 | 6.7.3.7.2 | 6.7.3.7.3 | 6.7.3.7.4 | 6.7.3.8.1 | 6.7.3.8.2 | 6.7.3.8.3 | 6.7.3.8.4 |
| 6.7.4.1.1 | 6.7.4.1.2 | 6.7.4.1.3 | 6.7.4.1.4 | 6.7.4.2.1 | 6.7.4.2.2 | 6.7.4.2.3 | 6.7.4.2.4 |
| 6.7.4.3.1 | 6.7.4.3.2 | 6.7.4.3.3 | 6.7.4.3.4 | 6.7.4.4.1 | 6.7.4.4.2 | 6.7.4.4.3 | 6.7.4.4.4 |
| 6.7.4.5.1 | 6.7.4.5.2 | 6.7.4.5.3 | 6.7.4.5.4 | 6.7.4.6.1 | 6.7.4.6.2 | 6.7.4.6.3 | 6.7.4.6.4 |
| 6.7.4.7.1 | 6.7.4.7.2 | 6.7.4.7.3 | 6.7.4.7.4 | 6.7.4.8.1 | 6.7.4.8.2 | 6.7.4.8.3 | 6.7.4.8.4 |
| 6.8.1.1.1 | 6.8.1.1.2 | 6.8.1.1.3 | 6.8.1.1.4 | 6.8.1.2.1 | 6.8.1.2.2 | 6.8.1.2.3 | 6.8.1.2.4 |
| 6.8.1.3.1 | 6.8.1.3.2 | 6.8.1.3.3 | 6.8.1.3.4 | 6.8.1.4.1 | 6.8.1.4.2 | 6.8.1.4.3 | 6.8.1.4.4 |
| 6.8.1.5.1 | 6.8.1.5.2 | 6.8.1.5.3 | 6.8.1.5.4 | 6.8.1.6.1 | 6.8.1.6.2 | 6.8.1.6.3 | 6.8.1.6.4 |
| 6.8.1.7.1 | 6.8.1.7.2 | 6.8.1.7.3 | 6.8.1.7.4 | 6.8.1.8.1 | 6.8.1.8.2 | 6.8.1.8.3 | 6.8.1.8.4 |
| 6.8.2.1.1 | 6.8.2.1.2 | 6.8.2.1.3 | 6.8.2.1.4 | 6.8.2.2.1 | 6.8.2.2.2 | 6.8.2.2.3 | 6.8.2.2.4 |
| 6.8.2.3.1 | 6.8.2.3.2 | 6.8.2.3.3 | 6.8.2.3.4 | 6.8.2.4.1 | 6.8.2.4.2 | 6.8.2.4.3 | 6.8.2.4.4 |
| 6.8.2.5.1 | 6.8.2.5.2 | 6.8.2.5.3 | 6.8.2.5.4 | 6.8.2.6.1 | 6.8.2.6.2 | 6.8.2.6.3 | 6.8.2.6.4 |
| 6.8.2.7.1 | 6.8.2.7.2 | 6.8.2.7.3 | 6.8.2.7.4 | 6.8.2.8.1 | 6.8.2.8.2 | 6.8.2.8.3 | 6.8.2.8.4 |
| 6.8.3.1.1 | 6.8.3.1.2 | 6.8.3.1.3 | 6.8.3.1.4 | 6.8.3.2.1 | 6.8.3.2.2 | 6.8.3.2.3 | 6.8.3.2.4 |
| 6.8.3.3.1 | 6.8.3.3.2 | 6.8.3.3.3 | 6.8.3.3.4 | 6.8.3.4.1 | 6.8.3.4.2 | 6.8.3.4.3 | 6.8.3.4.4 |
| 6.8.3.5.1 | 6.8.3.5.2 | 6.8.3.5.3 | 6.8.3.5.4 | 6.8.3.6.1 | 6.8.3.6.2 | 6.8.3.6.3 | 6.8.3.6.4 |
| 6.8.3.7.1 | 6.8.3.7.2 | 6.8.3.7.3 | 6.8.3.7.4 | 6.8.3.8.1 | 6.8.3.8.2 | 6.8.3.8.3 | 6.8.3.8.4 |
| 6.8.4.1.1 | 6.8.4.1.2 | 6.8.4.1.3 | 6.8.4.1.4 | 6.8.4.2.1 | 6.8.4.2.2 | 6.8.4.2.3 | 6.8.4.2.4 |
| 6.8.4.3.1 | 6.8.4.3.2 | 6.8.4.3.3 | 6.8.4.3.4 | 6.8.4.4.1 | 6.8.4.4.2 | 6.8.4.4.3 | 6.8.4.4.4 |
| 6.8.4.5.1 | 6.8.4.5.2 | 6.8.4.5.3 | 6.8.4.5.4 | 6.8.4.6.1 | 6.8.4.6.2 | 6.8.4.6.3 | 6.8.4.6.4 |
| 6.8.4.7.1 | 6.8.4.7.2 | 6.8.4.7.3 | 6.8.4.7.4 | 6.8.4.8.1 | 6.8.4.8.2 | 6.8.4.8.3 | 6.8.4.8.4 |
| 7.1.1.1.1 | 7.1.1.1.2 | 7.1.1.1.3 | 7.1.1.1.4 | 7.1.1.2.1 | 7.1.1.2.2 | 7.1.1.2.3 | 7.1.1.2.4 |
| 7.1.1.3.1 | 7.1.1.3.2 | 7.1.1.3.3 | 7.1.1.3.4 | 7.1.1.4.1 | 7.1.1.4.2 | 7.1.1.4.3 | 7.1.1.4.4 |
| 7.1.1.5.1 | 7.1.1.5.2 | 7.1.1.5.3 | 7.1.1.5.4 | 7.1.1.6.1 | 7.1.1.6.2 | 7.1.1.6.3 | 7.1.1.6.4 |
| 7.1.1.7.1 | 7.1.1.7.2 | 7.1.1.7.3 | 7.1.1.7.4 | 7.1.1.8.1 | 7.1.1.8.2 | 7.1.1.8.3 | 7.1.1.8.4 |
| 7.1.2.1.1 | 7.1.2.1.2 | 7.1.2.1.3 | 7.1.2.1.4 | 7.1.2.2.1 | 7.1.2.2.2 | 7.1.2.2.3 | 7.1.2.2.4 |
| 7.1.2.3.1 | 7.1.2.3.2 | 7.1.2.3.3 | 7.1.2.3.4 | 7.1.2.4.1 | 7.1.2.4.2 | 7.1.2.4.3 | 7.1.2.4.4 |
| 7.1.2.5.1 | 7.1.2.5.2 | 7.1.2.5.3 | 7.1.2.5.4 | 7.1.2.6.1 | 7.1.2.6.2 | 7.1.2.6.3 | 7.1.2.6.4 |
| 7.1.2.7.1 | 7.1.2.7.2 | 7.1.2.7.3 | 7.1.2.7.4 | 7.1.2.8.1 | 7.1.2.8.2 | 7.1.2.8.3 | 7.1.2.8.4 |
| 7.1.3.1.1 | 7.1.3.1.2 | 7.1.3.1.3 | 7.1.3.1.4 | 7.1.3.2.1 | 7.1.3.2.2 | 7.1.3.2.3 | 7.1.3.2.4 |
| 7.1.3.3.1 | 7.1.3.3.2 | 7.1.3.3.3 | 7.1.3.3.4 | 7.1.3.4.1 | 7.1.3.4.2 | 7.1.3.4.3 | 7.1.3.4.4 |
| 7.1.3.5.1 | 7.1.3.5.2 | 7.1.3.5.3 | 7.1.3.5.4 | 7.1.3.6.1 | 7.1.3.6.2 | 7.1.3.6.3 | 7.1.3.6.4 |
| 7.1.3.7.1 | 7.1.3.7.2 | 7.1.3.7.3 | 7.1.3.7.4 | 7.1.3.8.1 | 7.1.3.8.2 | 7.1.3.8.3 | 7.1.3.8.4 |
| 7.1.4.1.1 | 7.1.4.1.2 | 7.1.4.1.3 | 7.1.4.1.4 | 7.1.4.2.1 | 7.1.4.2.2 | 7.1.4.2.3 | 7.1.4.2.4 |
| 7.1.4.3.1 | 7.1.4.3.2 | 7.1.4.3.3 | 7.1.4.3.4 | 7.1.4.4.1 | 7.1.4.4.2 | 7.1.4.4.3 | 7.1.4.4.4 |
| 7.1.4.5.1 | 7.1.4.5.2 | 7.1.4.5.3 | 7.1.4.5.4 | 7.1.4.6.1 | 7.1.4.6.2 | 7.1.4.6.3 | 7.1.4.6.4 |
| 7.1.4.7.1 | 7.1.4.7.2 | 7.1.4.7.3 | 7.1.4.7.4 | 7.1.4.8.1 | 7.1.4.8.2 | 7.1.4.8.3 | 7.1.4.8.4 |
| 7.2.1.1.1 | 7.2.1.1.2 | 7.2.1.1.3 | 7.2.1.1.4 | 7.2.1.2.1 | 7.2.1.2.2 | 7.2.1.2.3 | 7.2.1.2.4 |
| 7.2.1.3.1 | 7.2.1.3.2 | 7.2.1.3.3 | 7.2.1.3.4 | 7.2.1.4.1 | 7.2.1.4.2 | 7.2.1.4.3 | 7.2.1.4.4 |
| 7.2.1.5.1 | 7.2.1.5.2 | 7.2.1.5.3 | 7.2.1.5.4 | 7.2.1.6.1 | 7.2.1.6.2 | 7.2.1.6.3 | 7.2.1.6.4 |
| 7.2.1.7.1 | 7.2.1.7.2 | 7.2.1.7.3 | 7.2.1.7.4 | 7.2.1.8.1 | 7.2.1.8.2 | 7.2.1.8.3 | 7.2.1.8.4 |
| 7.2.2.1.1 | 7.2.2.1.2 | 7.2.2.1.3 | 7.2.2.1.4 | 7.2.2.2.1 | 7.2.2.2.2 | 7.2.2.2.3 | 7.2.2.2.4 |
| 7.2.2.3.1 | 7.2.2.3.2 | 7.2.2.3.3 | 7.2.2.3.4 | 7.2.2.4.1 | 7.2.2.4.2 | 7.2.2.4.3 | 7.2.2.4.4 |

TABLE 1-continued

| | | | | | | | |
|---|---|---|---|---|---|---|---|
| 7.2.2.5.1 | 7.2.2.5.2 | 7.2.2.5.3 | 7.2.2.5.4 | 7.2.2.6.1 | 7.2.2.6.2 | 7.2.2.6.3 | 7.2.2.6.4 |
| 7.2.2.7.1 | 7.2.2.7.2 | 7.2.2.7.3 | 7.2.2.7.4 | 7.2.2.8.1 | 7.2.2.8.2 | 7.2.2.8.3 | 7.2.2.8.4 |
| 7.2.3.1.1 | 7.2.3.1.2 | 7.2.3.1.3 | 7.2.3.1.4 | 7.2.3.2.1 | 7.2.3.2.2 | 7.2.3.2.3 | 7.2.3.2.4 |
| 7.2.3.3.1 | 7.2.3.3.2 | 7.2.3.3.3 | 7.2.3.3.4 | 7.2.3.4.1 | 7.2.3.4.2 | 7.2.3.4.3 | 7.2.3.4.4 |
| 7.2.3.5.1 | 7.2.3.5.2 | 7.2.3.5.3 | 7.2.3.5.4 | 7.2.3.6.1 | 7.2.3.6.2 | 7.2.3.6.3 | 7.2.3.6.4 |
| 7.2.3.7.1 | 7.2.3.7.2 | 7.2.3.7.3 | 7.2.3.7.4 | 7.2.3.8.1 | 7.2.3.8.2 | 7.2.3.8.3 | 7.2.3.8.4 |
| 7.2.4.1.1 | 7.2.4.1.2 | 7.2.4.1.3 | 7.2.4.1.4 | 7.2.4.2.1 | 7.2.4.2.2 | 7.2.4.2.3 | 7.2.4.2.4 |
| 7.2.4.3.1 | 7.2.4.3.2 | 7.2.4.3.3 | 7.2.4.3.4 | 7.2.4.4.1 | 7.2.4.4.2 | 7.2.4.4.3 | 7.2.4.4.4 |
| 7.2.4.5.1 | 7.2.4.5.2 | 7.2.4.5.3 | 7.2.4.5.4 | 7.2.4.6.1 | 7.2.4.6.2 | 7.2.4.6.3 | 7.2.4.6.4 |
| 7.2.4.7.1 | 7.2.4.7.2 | 7.2.4.7.3 | 7.2.4.7.4 | 7.2.4.8.1 | 7.2.4.8.2 | 7.2.4.8.3 | 7.2.4.8.4 |
| 7.3.1.1.1 | 7.3.1.1.2 | 7.3.1.1.3 | 7.3.1.1.4 | 7.3.1.2.1 | 7.3.1.2.2 | 7.3.1.2.3 | 7.3.1.2.4 |
| 7.3.1.3.1 | 7.3.1.3.2 | 7.3.1.3.3 | 7.3.1.3.4 | 7.3.1.4.1 | 7.3.1.4.2 | 7.3.1.4.3 | 7.3.1.4.4 |
| 7.3.1.5.1 | 7.3.1.5.2 | 7.3.1.5.3 | 7.3.1.5.4 | 7.3.1.6.1 | 7.3.1.6.2 | 7.3.1.6.3 | 7.3.1.6.4 |
| 7.3.1.7.1 | 7.3.1.7.2 | 7.3.1.7.3 | 7.3.1.7.4 | 7.3.1.8.1 | 7.3.1.8.2 | 7.3.1.8.3 | 7.3.1.8.4 |
| 7.3.2.1.1 | 7.3.2.1.2 | 7.3.2.1.3 | 7.3.2.1.4 | 7.3.2.2.1 | 7.3.2.2.2 | 7.3.2.2.3 | 7.3.2.2.4 |
| 7.3.2.3.1 | 7.3.2.3.2 | 7.3.2.3.3 | 7.3.2.3.4 | 7.3.2.4.1 | 7.3.2.4.2 | 7.3.2.4.3 | 7.3.2.4.4 |
| 7.3.2.5.1 | 7.3.2.5.2 | 7.3.2.5.3 | 7.3.2.5.4 | 7.3.2.6.1 | 7.3.2.6.2 | 7.3.2.6.3 | 7.3.2.6.4 |
| 7.3.2.7.1 | 7.3.2.7.2 | 7.3.2.7.3 | 7.3.2.7.4 | 7.3.2.8.1 | 7.3.2.8.2 | 7.3.2.8.3 | 7.3.2.8.4 |
| 7.3.3.1.1 | 7.3.3.1.2 | 7.3.3.1.3 | 7.3.3.1.4 | 7.3.3.2.1 | 7.3.3.2.2 | 7.3.3.2.3 | 7.3.3.2.4 |
| 7.3.3.3.1 | 7.3.3.3.2 | 7.3.3.3.3 | 7.3.3.3.4 | 7.3.3.4.1 | 7.3.3.4.2 | 7.3.3.4.3 | 7.3.3.4.4 |
| 7.3.3.5.1 | 7.3.3.5.2 | 7.3.3.5.3 | 7.3.3.5.4 | 7.3.3.6.1 | 7.3.3.6.2 | 7.3.3.6.3 | 7.3.3.6.4 |
| 7.3.3.7.1 | 7.3.3.7.2 | 7.3.3.7.3 | 7.3.3.7.4 | 7.3.3.8.1 | 7.3.3.8.2 | 7.3.3.8.3 | 7.3.3.8.4 |
| 7.3.4.1.1 | 7.3.4.1.2 | 7.3.4.1.3 | 7.3.4.1.4 | 7.3.4.2.1 | 7.3.4.2.2 | 7.3.4.2.3 | 7.3.4.2.4 |
| 7.3.4.3.1 | 7.3.4.3.2 | 7.3.4.3.3 | 7.3.4.3.4 | 7.3.4.4.1 | 7.3.4.4.2 | 7.3.4.4.3 | 7.3.4.4.4 |
| 7.3.4.5.1 | 7.3.4.5.2 | 7.3.4.5.3 | 7.3.4.5.4 | 7.3.4.6.1 | 7.3.4.6.2 | 7.3.4.6.3 | 7.3.4.6.4 |
| 7.3.4.7.1 | 7.3.4.7.2 | 7.3.4.7.3 | 7.3.4.7.4 | 7.3.4.8.1 | 7.3.4.8.2 | 7.3.4.8.3 | 7.3.4.8.4 |
| 7.4.1.1.1 | 7.4.1.1.2 | 7.4.1.1.3 | 7.4.1.1.4 | 7.4.1.2.1 | 7.4.1.2.2 | 7.4.1.2.3 | 7.4.1.2.4 |
| 7.4.1.3.1 | 7.4.1.3.2 | 7.4.1.3.3 | 7.4.1.3.4 | 7.4.1.4.1 | 7.4.1.4.2 | 7.4.1.4.3 | 7.4.1.4.4 |
| 7.4.1.5.1 | 7.4.1.5.2 | 7.4.1.5.3 | 7.4.1.5.4 | 7.4.1.6.1 | 7.4.1.6.2 | 7.4.1.6.3 | 7.4.1.6.4 |
| 7.4.1.7.1 | 7.4.1.7.2 | 7.4.1.7.3 | 7.4.1.7.4 | 7.4.1.8.1 | 7.4.1.8.2 | 7.4.1.8.3 | 7.4.1.8.4 |
| 7.4.2.1.1 | 7.4.2.1.2 | 7.4.2.1.3 | 7.4.2.1.4 | 7.4.2.2.1 | 7.4.2.2.2 | 7.4.2.2.3 | 7.4.2.2.4 |
| 7.4.2.3.1 | 7.4.2.3.2 | 7.4.2.3.3 | 7.4.2.3.4 | 7.4.2.4.1 | 7.4.2.4.2 | 7.4.2.4.3 | 7.4.2.4.4 |
| 7.4.2.5.1 | 7.4.2.5.2 | 7.4.2.5.3 | 7.4.2.5.4 | 7.4.2.6.1 | 7.4.2.6.2 | 7.4.2.6.3 | 7.4.2.6.4 |
| 7.4.2.7.1 | 7.4.2.7.2 | 7.4.2.7.3 | 7.4.2.7.4 | 7.4.2.8.1 | 7.4.2.8.2 | 7.4.2.8.3 | 7.4.2.8.4 |
| 7.4.3.1.1 | 7.4.3.1.2 | 7.4.3.1.3 | 7.4.3.1.4 | 7.4.3.2.1 | 7.4.3.2.2 | 7.4.3.2.3 | 7.4.3.2.4 |
| 7.4.3.3.1 | 7.4.3.3.2 | 7.4.3.3.3 | 7.4.3.3.4 | 7.4.3.4.1 | 7.4.3.4.2 | 7.4.3.4.3 | 7.4.3.4.4 |
| 7.4.3.5.1 | 7.4.3.5.2 | 7.4.3.5.3 | 7.4.3.5.4 | 7.4.3.6.1 | 7.4.3.6.2 | 7.4.3.6.3 | 7.4.3.6.4 |
| 7.4.3.7.1 | 7.4.3.7.2 | 7.4.3.7.3 | 7.4.3.7.4 | 7.4.3.8.1 | 7.4.3.8.2 | 7.4.3.8.3 | 7.4.3.8.4 |
| 7.4.4.1.1 | 7.4.4.1.2 | 7.4.4.1.3 | 7.4.4.1.4 | 7.4.4.2.1 | 7.4.4.2.2 | 7.4.4.2.3 | 7.4.4.2.4 |
| 7.4.4.3.1 | 7.4.4.3.2 | 7.4.4.3.3 | 7.4.4.3.4 | 7.4.4.4.1 | 7.4.4.4.2 | 7.4.4.4.3 | 7.4.4.4.4 |
| 7.4.4.5.1 | 7.4.4.5.2 | 7.4.4.5.3 | 7.4.4.5.4 | 7.4.4.6.1 | 7.4.4.6.2 | 7.4.4.6.3 | 7.4.4.6.4 |
| 7.4.4.7.1 | 7.4.4.7.2 | 7.4.4.7.3 | 7.4.4.7.4 | 7.4.4.8.1 | 7.4.4.8.2 | 7.4.4.8.3 | 7.4.4.8.4 |
| 7.5.1.1.1 | 7.5.1.1.2 | 7.5.1.1.3 | 7.5.1.1.4 | 7.5.1.2.1 | 7.5.1.2.2 | 7.5.1.2.3 | 7.5.1.2.4 |
| 7.5.1.3.1 | 7.5.1.3.2 | 7.5.1.3.3 | 7.5.1.3.4 | 7.5.1.4.1 | 7.5.1.4.2 | 7.5.1.4.3 | 7.5.1.4.4 |
| 7.5.1.5.1 | 7.5.1.5.2 | 7.5.1.5.3 | 7.5.1.5.4 | 7.5.1.6.1 | 7.5.1.6.2 | 7.5.1.6.3 | 7.5.1.6.4 |
| 7.5.1.7.1 | 7.5.1.7.2 | 7.5.1.7.3 | 7.5.1.7.4 | 7.5.1.8.1 | 7.5.1.8.2 | 7.5.1.8.3 | 7.5.1.8.4 |
| 7.5.2.1.1 | 7.5.2.1.2 | 7.5.2.1.3 | 7.5.2.1.4 | 7.5.2.2.1 | 7.5.2.2.2 | 7.5.2.2.3 | 7.5.2.2.4 |
| 7.5.2.3.1 | 7.5.2.3.2 | 7.5.2.3.3 | 7.5.2.3.4 | 7.5.2.4.1 | 7.5.2.4.2 | 7.5.2.4.3 | 7.5.2.4.4 |
| 7.5.2.5.1 | 7.5.2.5.2 | 7.5.2.5.3 | 7.5.2.5.4 | 7.5.2.6.1 | 7.5.2.6.2 | 7.5.2.6.3 | 7.5.2.6.4 |
| 7.5.2.7.1 | 7.5.2.7.2 | 7.5.2.7.3 | 7.5.2.7.4 | 7.5.2.8.1 | 7.5.2.8.2 | 7.5.2.8.3 | 7.5.2.8.4 |
| 7.5.3.1.1 | 7.5.3.1.2 | 7.5.3.1.3 | 7.5.3.1.4 | 7.5.3.2.1 | 7.5.3.2.2 | 7.5.3.2.3 | 7.5.3.2.4 |
| 7.5.3.3.1 | 7.5.3.3.2 | 7.5.3.3.3 | 7.5.3.3.4 | 7.5.3.4.1 | 7.5.3.4.2 | 7.5.3.4.3 | 7.5.3.4.4 |
| 7.5.3.5.1 | 7.5.3.5.2 | 7.5.3.5.3 | 7.5.3.5.4 | 7.5.3.6.1 | 7.5.3.6.2 | 7.5.3.6.3 | 7.5.3.6.4 |
| 7.5.3.7.1 | 7.5.3.7.2 | 7.5.3.7.3 | 7.5.3.7.4 | 7.5.3.8.1 | 7.5.3.8.2 | 7.5.3.8.3 | 7.5.3.8.4 |
| 7.5.4.1.1 | 7.5.4.1.2 | 7.5.4.1.3 | 7.5.4.1.4 | 7.5.4.2.1 | 7.5.4.2.2 | 7.5.4.2.3 | 7.5.4.2.4 |
| 7.5.4.3.1 | 7.5.4.3.2 | 7.5.4.3.3 | 7.5.4.3.4 | 7.5.4.4.1 | 7.5.4.4.2 | 7.5.4.4.3 | 7.5.4.4.4 |
| 7.5.4.5.1 | 7.5.4.5.2 | 7.5.4.5.3 | 7.5.4.5.4 | 7.5.4.6.1 | 7.5.4.6.2 | 7.5.4.6.3 | 7.5.4.6.4 |
| 7.5.4.7.1 | 7.5.4.7.2 | 7.5.4.7.3 | 7.5.4.7.4 | 7.5.4.8.1 | 7.5.4.8.2 | 7.5.4.8.3 | 7.5.4.8.4 |
| 7.6.1.1.1 | 7.6.1.1.2 | 7.6.1.1.3 | 7.6.1.1.4 | 7.6.1.2.1 | 7.6.1.2.2 | 7.6.1.2.3 | 7.6.1.2.4 |
| 7.6.1.3.1 | 7.6.1.3.2 | 7.6.1.3.3 | 7.6.1.3.4 | 7.6.1.4.1 | 7.6.1.4.2 | 7.6.1.4.3 | 7.6.1.4.4 |
| 7.6.1.5.1 | 7.6.1.5.2 | 7.6.1.5.3 | 7.6.1.5.4 | 7.6.1.6.1 | 7.6.1.6.2 | 7.6.1.6.3 | 7.6.1.6.4 |
| 7.6.1.7.1 | 7.6.1.7.2 | 7.6.1.7.3 | 7.6.1.7.4 | 7.6.1.8.1 | 7.6.1.8.2 | 7.6.1.8.3 | 7.6.1.8.4 |
| 7.6.2.1.1 | 7.6.2.1.2 | 7.6.2.1.3 | 7.6.2.1.4 | 7.6.2.2.1 | 7.6.2.2.2 | 7.6.2.2.3 | 7.6.2.2.4 |
| 7.6.2.3.1 | 7.6.2.3.2 | 7.6.2.3.3 | 7.6.2.3.4 | 7.6.2.4.1 | 7.6.2.4.2 | 7.6.2.4.3 | 7.6.2.4.4 |
| 7.6.2.5.1 | 7.6.2.5.2 | 7.6.2.5.3 | 7.6.2.5.4 | 7.6.2.6.1 | 7.6.2.6.2 | 7.6.2.6.3 | 7.6.2.6.4 |
| 7.6.2.7.1 | 7.6.2.7.2 | 7.6.2.7.3 | 7.6.2.7.4 | 7.6.2.8.1 | 7.6.2.8.2 | 7.6.2.8.3 | 7.6.2.8.4 |
| 7.6.3.1.1 | 7.6.3.1.2 | 7.6.3.1.3 | 7.6.3.1.4 | 7.6.3.2.1 | 7.6.3.2.2 | 7.6.3.2.3 | 7.6.3.2.4 |
| 7.6.3.3.1 | 7.6.3.3.2 | 7.6.3.3.3 | 7.6.3.3.4 | 7.6.3.4.1 | 7.6.3.4.2 | 7.6.3.4.3 | 7.6.3.4.4 |
| 7.6.3.5.1 | 7.6.3.5.2 | 7.6.3.5.3 | 7.6.3.5.4 | 7.6.3.6.1 | 7.6.3.6.2 | 7.6.3.6.3 | 7.6.3.6.4 |
| 7.6.3.7.1 | 7.6.3.7.2 | 7.6.3.7.3 | 7.6.3.7.4 | 7.6.3.8.1 | 7.6.3.8.2 | 7.6.3.8.3 | 7.6.3.8.4 |
| 7.6.4.1.1 | 7.6.4.1.2 | 7.6.4.1.3 | 7.6.4.1.4 | 7.6.4.2.1 | 7.6.4.2.2 | 7.6.4.2.3 | 7.6.4.2.4 |
| 7.6.4.3.1 | 7.6.4.3.2 | 7.6.4.3.3 | 7.6.4.3.4 | 7.6.4.4.1 | 7.6.4.4.2 | 7.6.4.4.3 | 7.6.4.4.4 |
| 7.6.4.5.1 | 7.6.4.5.2 | 7.6.4.5.3 | 7.6.4.5.4 | 7.6.4.6.1 | 7.6.4.6.2 | 7.6.4.6.3 | 7.6.4.6.4 |
| 7.6.4.7.1 | 7.6.4.7.2 | 7.6.4.7.3 | 7.6.4.7.4 | 7.6.4.8.1 | 7.6.4.8.2 | 7.6.4.8.3 | 7.6.4.8.4 |
| 7.7.1.1.1 | 7.7.1.1.2 | 7.7.1.1.3 | 7.7.1.1.4 | 7.7.1.2.1 | 7.7.1.2.2 | 7.7.1.2.3 | 7.7.1.2.4 |
| 7.7.1.3.1 | 7.7.1.3.2 | 7.7.1.3.3 | 7.7.1.3.4 | 7.7.1.4.1 | 7.7.1.4.2 | 7.7.1.4.3 | 7.7.1.4.4 |
| 7.7.1.5.1 | 7.7.1.5.2 | 7.7.1.5.3 | 7.7.1.5.4 | 7.7.1.6.1 | 7.7.1.6.2 | 7.7.1.6.3 | 7.7.1.6.4 |
| 7.7.1.7.1 | 7.7.1.7.2 | 7.7.1.7.3 | 7.7.1.7.4 | 7.7.1.8.1 | 7.7.1.8.2 | 7.7.1.8.3 | 7.7.1.8.4 |
| 7.7.2.1.1 | 7.7.2.1.2 | 7.7.2.1.3 | 7.7.2.1.4 | 7.7.2.2.1 | 7.7.2.2.2 | 7.7.2.2.3 | 7.7.2.2.4 |

TABLE 1-continued

| | | | | | | | |
|---|---|---|---|---|---|---|---|
| 7.7.2.3.1 | 7.7.2.3.2 | 7.7.2.3.3 | 7.7.2.3.4 | 7.7.2.4.1 | 7.7.2.4.2 | 7.7.2.4.3 | 7.7.2.4.4 |
| 7.7.2.5.1 | 7.7.2.5.2 | 7.7.2.5.3 | 7.7.2.5.4 | 7.7.2.6.1 | 7.7.2.6.2 | 7.7.2.6.3 | 7.7.2.6.4 |
| 7.7.2.7.1 | 7.7.2.7.2 | 7.7.2.7.3 | 7.7.2.7.4 | 7.7.2.8.1 | 7.7.2.8.2 | 7.7.2.8.3 | 7.7.2.8.4 |
| 7.7.3.1.1 | 7.7.3.1.2 | 7.7.3.1.3 | 7.7.3.1.4 | 7.7.3.2.1 | 7.7.3.2.2 | 7.7.3.2.3 | 7.7.3.2.4 |
| 7.7.3.3.1 | 7.7.3.3.2 | 7.7.3.3.3 | 7.7.3.3.4 | 7.7.3.4.1 | 7.7.3.4.2 | 7.7.3.4.3 | 7.7.3.4.4 |
| 7.7.3.5.1 | 7.7.3.5.2 | 7.7.3.5.3 | 7.7.3.5.4 | 7.7.3.6.1 | 7.7.3.6.2 | 7.7.3.6.3 | 7.7.3.6.4 |
| 7.7.3.7.1 | 7.7.3.7.2 | 7.7.3.7.3 | 7.7.3.7.4 | 7.7.3.8.1 | 7.7.3.8.2 | 7.7.3.8.3 | 7.7.3.8.4 |
| 7.7.4.1.1 | 7.7.4.1.2 | 7.7.4.1.3 | 7.7.4.1.4 | 7.7.4.2.1 | 7.7.4.2.2 | 7.7.4.2.3 | 7.7.4.2.4 |
| 7.7.4.3.1 | 7.7.4.3.2 | 7.7.4.3.3 | 7.7.4.3.4 | 7.7.4.4.1 | 7.7.4.4.2 | 7.7.4.4.3 | 7.7.4.4.4 |
| 7.7.4.5.1 | 7.7.4.5.2 | 7.7.4.5.3 | 7.7.4.5.4 | 7.7.4.6.1 | 7.7.4.6.2 | 7.7.4.6.3 | 7.7.4.6.4 |
| 7.7.4.7.1 | 7.7.4.7.2 | 7.7.4.7.3 | 7.7.4.7.4 | 7.7.4.8.1 | 7.7.4.8.2 | 7.7.4.8.3 | 7.7.4.8.4 |
| 7.8.1.1.1 | 7.8.1.1.2 | 7.8.1.1.3 | 7.8.1.1.4 | 7.8.1.2.1 | 7.8.1.2.2 | 7.8.1.2.3 | 7.8.1.2.4 |
| 7.8.1.3.1 | 7.8.1.3.2 | 7.8.1.3.3 | 7.8.1.3.4 | 7.8.1.4.1 | 7.8.1.4.2 | 7.8.1.4.3 | 7.8.1.4.4 |
| 7.8.1.5.1 | 7.8.1.5.2 | 7.8.1.5.3 | 7.8.1.5.4 | 7.8.1.6.1 | 7.8.1.6.2 | 7.8.1.6.3 | 7.8.1.6.4 |
| 7.8.1.7.1 | 7.8.1.7.2 | 7.8.1.7.3 | 7.8.1.7.4 | 7.8.1.8.1 | 7.8.1.8.2 | 7.8.1.8.3 | 7.8.1.8.4 |
| 7.8.2.1.1 | 7.8.2.1.2 | 7.8.2.1.3 | 7.8.2.1.4 | 7.8.2.2.1 | 7.8.2.2.2 | 7.8.2.2.3 | 7.8.2.2.4 |
| 7.8.2.3.1 | 7.8.2.3.2 | 7.8.2.3.3 | 7.8.2.3.4 | 7.8.2.4.1 | 7.8.2.4.2 | 7.8.2.4.3 | 7.8.2.4.4 |
| 7.8.2.5.1 | 7.8.2.5.2 | 7.8.2.5.3 | 7.8.2.5.4 | 7.8.2.6.1 | 7.8.2.6.2 | 7.8.2.6.3 | 7.8.2.6.4 |
| 7.8.2.7.1 | 7.8.2.7.2 | 7.8.2.7.3 | 7.8.2.7.4 | 7.8.2.8.1 | 7.8.2.8.2 | 7.8.2.8.3 | 7.8.2.8.4 |
| 7.8.3.1.1 | 7.8.3.1.2 | 7.8.3.1.3 | 7.8.3.1.4 | 7.8.3.2.1 | 7.8.3.2.2 | 7.8.3.2.3 | 7.8.3.2.4 |
| 7.8.3.3.1 | 7.8.3.3.2 | 7.8.3.3.3 | 7.8.3.3.4 | 7.8.3.4.1 | 7.8.3.4.2 | 7.8.3.4.3 | 7.8.3.4.4 |
| 7.8.3.5.1 | 7.8.3.5.2 | 7.8.3.5.3 | 7.8.3.5.4 | 7.8.3.6.1 | 7.8.3.6.2 | 7.8.3.6.3 | 7.8.3.6.4 |
| 7.8.3.7.1 | 7.8.3.7.2 | 7.8.3.7.3 | 7.8.3.7.4 | 7.8.3.8.1 | 7.8.3.8.2 | 7.8.3.8.3 | 7.8.3.8.4 |
| 7.8.4.1.1 | 7.8.4.1.2 | 7.8.4.1.3 | 7.8.4.1.4 | 7.8.4.2.1 | 7.8.4.2.2 | 7.8.4.2.3 | 7.8.4.2.4 |
| 7.8.4.3.1 | 7.8.4.3.2 | 7.8.4.3.3 | 7.8.4.3.4 | 7.8.4.4.1 | 7.8.4.4.2 | 7.8.4.4.3 | 7.8.4.4.4 |
| 7.8.4.5.1 | 7.8.4.5.2 | 7.8.4.5.3 | 7.8.4.5.4 | 7.8.4.6.1 | 7.8.4.6.2 | 7.8.4.6.3 | 7.8.4.6.4 |
| 7.8.4.7.1 | 7.8.4.7.2 | 7.8.4.7.3 | 7.8.4.7.4 | 7.8.4.8.1 | 7.8.4.8.2 | 7.8.4.8.3 | 7.8.4.8.4 |
| 8.1.1.1.1 | 8.1.1.1.2 | 8.1.1.1.3 | 8.1.1.1.4 | 8.1.1.2.1 | 8.1.1.2.2 | 8.1.1.2.3 | 8.1.1.2.4 |
| 8.1.1.3.1 | 8.1.1.3.2 | 8.1.1.3.3 | 8.1.1.3.4 | 8.1.1.4.1 | 8.1.1.4.2 | 8.1.1.4.3 | 8.1.1.4.4 |
| 8.1.1.5.1 | 8.1.1.5.2 | 8.1.1.5.3 | 8.1.1.5.4 | 8.1.1.6.1 | 8.1.1.6.2 | 8.1.1.6.3 | 8.1.1.6.4 |
| 8.1.1.7.1 | 8.1.1.7.2 | 8.1.1.7.3 | 8.1.1.7.4 | 8.1.1.8.1 | 8.1.1.8.2 | 8.1.1.8.3 | 8.1.1.8.4 |
| 8.1.2.1.1 | 8.1.2.1.2 | 8.1.2.1.3 | 8.1.2.1.4 | 8.1.2.2.1 | 8.1.2.2.2 | 8.1.2.2.3 | 8.1.2.2.4 |
| 8.1.2.3.1 | 8.1.2.3.2 | 8.1.2.3.3 | 8.1.2.3.4 | 8.1.2.4.1 | 8.1.2.4.2 | 8.1.2.4.3 | 8.1.2.4.4 |
| 8.1.2.5.1 | 8.1.2.5.2 | 8.1.2.5.3 | 8.1.2.5.4 | 8.1.2.6.1 | 8.1.2.6.2 | 8.1.2.6.3 | 8.1.2.6.4 |
| 8.1.2.7.1 | 8.1.2.7.2 | 8.1.2.7.3 | 8.1.2.7.4 | 8.1.2.8.1 | 8.1.2.8.2 | 8.1.2.8.3 | 8.1.2.8.4 |
| 8.1.3.1.1 | 8.1.3.1.2 | 8.1.3.1.3 | 8.1.3.1.4 | 8.1.3.2.1 | 8.1.3.2.2 | 8.1.3.2.3 | 8.1.3.2.4 |
| 8.1.3.3.1 | 8.1.3.3.2 | 8.1.3.3.3 | 8.1.3.3.4 | 8.1.3.4.1 | 8.1.3.4.2 | 8.1.3.4.3 | 8.1.3.4.4 |
| 8.1.3.5.1 | 8.1.3.5.2 | 8.1.3.5.3 | 8.1.3.5.4 | 8.1.3.6.1 | 8.1.3.6.2 | 8.1.3.6.3 | 8.1.3.6.4 |
| 8.1.3.7.1 | 8.1.3.7.2 | 8.1.3.7.3 | 8.1.3.7.4 | 8.1.3.8.1 | 8.1.3.8.2 | 8.1.3.8.3 | 8.1.3.8.4 |
| 8.1.4.1.1 | 8.1.4.1.2 | 8.1.4.1.3 | 8.1.4.1.4 | 8.1.4.2.1 | 8.1.4.2.2 | 8.1.4.2.3 | 8.1.4.2.4 |
| 8.1.4.3.1 | 8.1.4.3.2 | 8.1.4.3.3 | 8.1.4.3.4 | 8.1.4.4.1 | 8.1.4.4.2 | 8.1.4.4.3 | 8.1.4.4.4 |
| 8.1.4.5.1 | 8.1.4.5.2 | 8.1.4.5.3 | 8.1.4.5.4 | 8.1.4.6.1 | 8.1.4.6.2 | 8.1.4.6.3 | 8.1.4.6.4 |
| 8.1.4.7.1 | 8.1.4.7.2 | 8.1.4.7.3 | 8.1.4.7.4 | 8.1.4.8.1 | 8.1.4.8.2 | 8.1.4.8.3 | 8.1.4.8.4 |
| 8.2.1.1.1 | 8.2.1.1.2 | 8.2.1.1.3 | 8.2.1.1.4 | 8.2.1.2.1 | 8.2.1.2.2 | 8.2.1.2.3 | 8.2.1.2.4 |
| 8.2.1.3.1 | 8.2.1.3.2 | 8.2.1.3.3 | 8.2.1.3.4 | 8.2.1.4.1 | 8.2.1.4.2 | 8.2.1.4.3 | 8.2.1.4.4 |
| 8.2.1.5.1 | 8.2.1.5.2 | 8.2.1.5.3 | 8.2.1.5.4 | 8.2.1.6.1 | 8.2.1.6.2 | 8.2.1.6.3 | 8.2.1.6.4 |
| 8.2.1.7.1 | 8.2.1.7.2 | 8.2.1.7.3 | 8.2.1.7.4 | 8.2.1.8.1 | 8.2.1.8.2 | 8.2.1.8.3 | 8.2.1.8.4 |
| 8.2.2.1.1 | 8.2.2.1.2 | 8.2.2.1.3 | 8.2.2.1.4 | 8.2.2.2.1 | 8.2.2.2.2 | 8.2.2.2.3 | 8.2.2.2.4 |
| 8.2.2.3.1 | 8.2.2.3.2 | 8.2.2.3.3 | 8.2.2.3.4 | 8.2.2.4.1 | 8.2.2.4.2 | 8.2.2.4.3 | 8.2.2.4.4 |
| 8.2.2.5.1 | 8.2.2.5.2 | 8.2.2.5.3 | 8.2.2.5.4 | 8.2.2.6.1 | 8.2.2.6.2 | 8.2.2.6.3 | 8.2.2.6.4 |
| 8.2.2.7.1 | 8.2.2.7.2 | 8.2.2.7.3 | 8.2.2.7.4 | 8.2.2.8.1 | 8.2.2.8.2 | 8.2.2.8.3 | 8.2.2.8.4 |
| 8.2.3.1.1 | 8.2.3.1.2 | 8.2.3.1.3 | 8.2.3.1.4 | 8.2.3.2.1 | 8.2.3.2.2 | 8.2.3.2.3 | 8.2.3.2.4 |
| 8.2.3.3.1 | 8.2.3.3.2 | 8.2.3.3.3 | 8.2.3.3.4 | 8.2.3.4.1 | 8.2.3.4.2 | 8.2.3.4.3 | 8.2.3.4.4 |
| 8.2.3.5.1 | 8.2.3.5.2 | 8.2.3.5.3 | 8.2.3.5.4 | 8.2.3.6.1 | 8.2.3.6.2 | 8.2.3.6.3 | 8.2.3.6.4 |
| 8.2.3.7.1 | 8.2.3.7.2 | 8.2.3.7.3 | 8.2.3.7.4 | 8.2.3.8.1 | 8.2.3.8.2 | 8.2.3.8.3 | 8.2.3.8.4 |
| 8.2.4.1.1 | 8.2.4.1.2 | 8.2.4.1.3 | 8.2.4.1.4 | 8.2.4.2.1 | 8.2.4.2.2 | 8.2.4.2.3 | 8.2.4.2.4 |
| 8.2.4.3.1 | 8.2.4.3.2 | 8.2.4.3.3 | 8.2.4.3.4 | 8.2.4.4.1 | 8.2.4.4.2 | 8.2.4.4.3 | 8.2.4.4.4 |
| 8.2.4.5.1 | 8.2.4.5.2 | 8.2.4.5.3 | 8.2.4.5.4 | 8.2.4.6.1 | 8.2.4.6.2 | 8.2.4.6.3 | 8.2.4.6.4 |
| 8.2.4.7.1 | 8.2.4.7.2 | 8.2.4.7.3 | 8.2.4.7.4 | 8.2.4.8.1 | 8.2.4.8.2 | 8.2.4.8.3 | 8.2.4.8.4 |
| 8.3.1.1.1 | 8.3.1.1.2 | 8.3.1.1.3 | 8.3.1.1.4 | 8.3.1.2.1 | 8.3.1.2.2 | 8.3.1.2.3 | 8.3.1.2.4 |
| 8.3.1.3.1 | 8.3.1.3.2 | 8.3.1.3.3 | 8.3.1.3.4 | 8.3.1.4.1 | 8.3.1.4.2 | 8.3.1.4.3 | 8.3.1.4.4 |
| 8.3.1.5.1 | 8.3.1.5.2 | 8.3.1.5.3 | 8.3.1.5.4 | 8.3.1.6.1 | 8.3.1.6.2 | 8.3.1.6.3 | 8.3.1.6.4 |
| 8.3.1.7.1 | 8.3.1.7.2 | 8.3.1.7.3 | 8.3.1.7.4 | 8.3.1.8.1 | 8.3.1.8.2 | 8.3.1.8.3 | 8.3.1.8.4 |
| 8.3.2.1.1 | 8.3.2.1.2 | 8.3.2.1.3 | 8.3.2.1.4 | 8.3.2.2.1 | 8.3.2.2.2 | 8.3.2.2.3 | 8.3.2.2.4 |
| 8.3.2.3.1 | 8.3.2.3.2 | 8.3.2.3.3 | 8.3.2.3.4 | 8.3.2.4.1 | 8.3.2.4.2 | 8.3.2.4.3 | 8.3.2.4.4 |
| 8.3.2.5.1 | 8.3.2.5.2 | 8.3.2.5.3 | 8.3.2.5.4 | 8.3.2.6.1 | 8.3.2.6.2 | 8.3.2.6.3 | 8.3.2.6.4 |
| 8.3.2.7.1 | 8.3.2.7.2 | 8.3.2.7.3 | 8.3.2.7.4 | 8.3.2.8.1 | 8.3.2.8.2 | 8.3.2.8.3 | 8.3.2.8.4 |
| 8.3.3.1.1 | 8.3.3.1.2 | 8.3.3.1.3 | 8.3.3.1.4 | 8.3.3.2.1 | 8.3.3.2.2 | 8.3.3.2.3 | 8.3.3.2.4 |
| 8.3.3.3.1 | 8.3.3.3.2 | 8.3.3.3.3 | 8.3.3.3.4 | 8.3.3.4.1 | 8.3.3.4.2 | 8.3.3.4.3 | 8.3.3.4.4 |
| 8.3.3.5.1 | 8.3.3.5.2 | 8.3.3.5.3 | 8.3.3.5.4 | 8.3.3.6.1 | 8.3.3.6.2 | 8.3.3.6.3 | 8.3.3.6.4 |
| 8.3.3.7.1 | 8.3.3.7.2 | 8.3.3.7.3 | 8.3.3.7.4 | 8.3.3.8.1 | 8.3.3.8.2 | 8.3.3.8.3 | 8.3.3.8.4 |
| 8.3.4.1.1 | 8.3.4.1.2 | 8.3.4.1.3 | 8.3.4.1.4 | 8.3.4.2.1 | 8.3.4.2.2 | 8.3.4.2.3 | 8.3.4.2.4 |
| 8.3.4.3.1 | 8.3.4.3.2 | 8.3.4.3.3 | 8.3.4.3.4 | 8.3.4.4.1 | 8.3.4.4.2 | 8.3.4.4.3 | 8.3.4.4.4 |
| 8.3.4.5.1 | 8.3.4.5.2 | 8.3.4.5.3 | 8.3.4.5.4 | 8.3.4.6.1 | 8.3.4.6.2 | 8.3.4.6.3 | 8.3.4.6.4 |
| 8.3.4.7.1 | 8.3.4.7.2 | 8.3.4.7.3 | 8.3.4.7.4 | 8.3.4.8.1 | 8.3.4.8.2 | 8.3.4.8.3 | 8.3.4.8.4 |
| 8.4.1.1.1 | 8.4.1.1.2 | 8.4.1.1.3 | 8.4.1.1.4 | 8.4.1.2.1 | 8.4.1.2.2 | 8.4.1.2.3 | 8.4.1.2.4 |
| 8.4.1.3.1 | 8.4.1.3.2 | 8.4.1.3.3 | 8.4.1.3.4 | 8.4.1.4.1 | 8.4.1.4.2 | 8.4.1.4.3 | 8.4.1.4.4 |
| 8.4.1.5.1 | 8.4.1.5.2 | 8.4.1.5.3 | 8.4.1.5.4 | 8.4.1.6.1 | 8.4.1.6.2 | 8.4.1.6.3 | 8.4.1.6.4 |
| 8.4.1.7.1 | 8.4.1.7.2 | 8.4.1.7.3 | 8.4.1.7.4 | 8.4.1.8.1 | 8.4.1.8.2 | 8.4.1.8.3 | 8.4.1.8.4 |

TABLE 1-continued

| | | | | | | | |
|---|---|---|---|---|---|---|---|
| 8.4.2.1.1 | 8.4.2.1.2 | 8.4.2.1.3 | 8.4.2.1.4 | 8.4.2.2.1 | 8.4.2.2.2 | 8.4.2.2.3 | 8.4.2.2.4 |
| 8.4.2.3.1 | 8.4.2.3.2 | 8.4.2.3.3 | 8.4.2.3.4 | 8.4.2.4.1 | 8.4.2.4.2 | 8.4.2.4.3 | 8.4.2.4.4 |
| 8.4.2.5.1 | 8.4.2.5.2 | 8.4.2.5.3 | 8.4.2.5.4 | 8.4.2.6.1 | 8.4.2.6.2 | 8.4.2.6.3 | 8.4.2.6.4 |
| 8.4.2.7.1 | 8.4.2.7.2 | 8.4.2.7.3 | 8.4.2.7.4 | 8.4.2.8.1 | 8.4.2.8.2 | 8.4.2.8.3 | 8.4.2.8.4 |
| 8.4.3.1.1 | 8.4.3.1.2 | 8.4.3.1.3 | 8.4.3.1.4 | 8.4.3.2.1 | 8.4.3.2.2 | 8.4.3.2.3 | 8.4.3.2.4 |
| 8.4.3.3.1 | 8.4.3.3.2 | 8.4.3.3.3 | 8.4.3.3.4 | 8.4.3.4.1 | 8.4.3.4.2 | 8.4.3.4.3 | 8.4.3.4.4 |
| 8.4.3.5.1 | 8.4.3.5.2 | 8.4.3.5.3 | 8.4.3.5.4 | 8.4.3.6.1 | 8.4.3.6.2 | 8.4.3.6.3 | 8.4.3.6.4 |
| 8.4.3.7.1 | 8.4.3.7.2 | 8.4.3.7.3 | 8.4.3.7.4 | 8.4.3.8.1 | 8.4.3.8.2 | 8.4.3.8.3 | 8.4.3.8.4 |
| 8.4.4.1.1 | 8.4.4.1.2 | 8.4.4.1.3 | 8.4.4.1.4 | 8.4.4.2.1 | 8.4.4.2.2 | 8.4.4.2.3 | 8.4.4.2.4 |
| 8.4.4.3.1 | 8.4.4.3.2 | 8.4.4.3.3 | 8.4.4.3.4 | 8.4.4.4.1 | 8.4.4.4.2 | 8.4.4.4.3 | 8.4.4.4.4 |
| 8.4.4.5.1 | 8.4.4.5.2 | 8.4.4.5.3 | 8.4.4.5.4 | 8.4.4.6.1 | 8.4.4.6.2 | 8.4.4.6.3 | 8.4.4.6.4 |
| 8.4.4.7.1 | 8.4.4.7.2 | 8.4.4.7.3 | 8.4.4.7.4 | 8.4.4.8.1 | 8.4.4.8.2 | 8.4.4.8.3 | 8.4.4.8.4 |
| 8.5.1.1.1 | 8.5.1.1.2 | 8.5.1.1.3 | 8.5.1.1.4 | 8.5.1.2.1 | 8.5.1.2.2 | 8.5.1.2.3 | 8.5.1.2.4 |
| 8.5.1.3.1 | 8.5.1.3.2 | 8.5.1.3.3 | 8.5.1.3.4 | 8.5.1.4.1 | 8.5.1.4.2 | 8.5.1.4.3 | 8.5.1.4.4 |
| 8.5.1.5.1 | 8.5.1.5.2 | 8.5.1.5.3 | 8.5.1.5.4 | 8.5.1.6.1 | 8.5.1.6.2 | 8.5.1.6.3 | 8.5.1.6.4 |
| 8.5.1.7.1 | 8.5.1.7.2 | 8.5.1.7.3 | 8.5.1.7.4 | 8.5.1.8.1 | 8.5.1.8.2 | 8.5.1.8.3 | 8.5.1.8.4 |
| 8.5.2.1.1 | 8.5.2.1.2 | 8.5.2.1.3 | 8.5.2.1.4 | 8.5.2.2.1 | 8.5.2.2.2 | 8.5.2.2.3 | 8.5.2.2.4 |
| 8.5.2.3.1 | 8.5.2.3.2 | 8.5.2.3.3 | 8.5.2.3.4 | 8.5.2.4.1 | 8.5.2.4.2 | 8.5.2.4.3 | 8.5.2.4.4 |
| 8.5.2.5.1 | 8.5.2.5.2 | 8.5.2.5.3 | 8.5.2.5.4 | 8.5.2.6.1 | 8.5.2.6.2 | 8.5.2.6.3 | 8.5.2.6.4 |
| 8.5.2.7.1 | 8.5.2.7.2 | 8.5.2.7.3 | 8.5.2.7.4 | 8.5.2.8.1 | 8.5.2.8.2 | 8.5.2.8.3 | 8.5.2.8.4 |
| 8.5.3.1.1 | 8.5.3.1.2 | 8.5.3.1.3 | 8.5.3.1.4 | 8.5.3.2.1 | 8.5.3.2.2 | 8.5.3.2.3 | 8.5.3.2.4 |
| 8.5.3.3.1 | 8.5.3.3.2 | 8.5.3.3.3 | 8.5.3.3.4 | 8.5.3.4.1 | 8.5.3.4.2 | 8.5.3.4.3 | 8.5.3.4.4 |
| 8.5.3.5.1 | 8.5.3.5.2 | 8.5.3.5.3 | 8.5.3.5.4 | 8.5.3.6.1 | 8.5.3.6.2 | 8.5.3.6.3 | 8.5.3.6.4 |
| 8.5.3.7.1 | 8.5.3.7.2 | 8.5.3.7.3 | 8.5.3.7.4 | 8.5.3.8.1 | 8.5.3.8.2 | 8.5.3.8.3 | 8.5.3.8.4 |
| 8.5.4.1.1 | 8.5.4.1.2 | 8.5.4.1.3 | 8.5.4.1.4 | 8.5.4.2.1 | 8.5.4.2.2 | 8.5.4.2.3 | 8.5.4.2.4 |
| 8.5.4.3.1 | 8.5.4.3.2 | 8.5.4.3.3 | 8.5.4.3.4 | 8.5.4.4.1 | 8.5.4.4.2 | 8.5.4.4.3 | 8.5.4.4.4 |
| 8.5.4.5.1 | 8.5.4.5.2 | 8.5.4.5.3 | 8.5.4.5.4 | 8.5.4.6.1 | 8.5.4.6.2 | 8.5.4.6.3 | 8.5.4.6.4 |
| 8.5.4.7.1 | 8.5.4.7.2 | 8.5.4.7.3 | 8.5.4.7.4 | 8.5.4.8.1 | 8.5.4.8.2 | 8.5.4.8.3 | 8.5.4.8.4 |
| 8.6.1.1.1 | 8.6.1.1.2 | 8.6.1.1.3 | 8.6.1.1.4 | 8.6.1.2.1 | 8.6.1.2.2 | 8.6.1.2.3 | 8.6.1.2.4 |
| 8.6.1.3.1 | 8.6.1.3.2 | 8.6.1.3.3 | 8.6.1.3.4 | 8.6.1.4.1 | 8.6.1.4.2 | 8.6.1.4.3 | 8.6.1.4.4 |
| 8.6.1.5.1 | 8.6.1.5.2 | 8.6.1.5.3 | 8.6.1.5.4 | 8.6.1.6.1 | 8.6.1.6.2 | 8.6.1.6.3 | 8.6.1.6.4 |
| 8.6.1.7.1 | 8.6.1.7.2 | 8.6.1.7.3 | 8.6.1.7.4 | 8.6.1.8.1 | 8.6.1.8.2 | 8.6.1.8.3 | 8.6.1.8.4 |
| 8.6.2.1.1 | 8.6.2.1.2 | 8.6.2.1.3 | 8.6.2.1.4 | 8.6.2.2.1 | 8.6.2.2.2 | 8.6.2.2.3 | 8.6.2.2.4 |
| 8.6.2.3.1 | 8.6.2.3.2 | 8.6.2.3.3 | 8.6.2.3.4 | 8.6.2.4.1 | 8.6.2.4.2 | 8.6.2.4.3 | 8.6.2.4.4 |
| 8.6.2.5.1 | 8.6.2.5.2 | 8.6.2.5.3 | 8.6.2.5.4 | 8.6.2.6.1 | 8.6.2.6.2 | 8.6.2.6.3 | 8.6.2.6.4 |
| 8.6.2.7.1 | 8.6.2.7.2 | 8.6.2.7.3 | 8.6.2.7.4 | 8.6.2.8.1 | 8.6.2.8.2 | 8.6.2.8.3 | 8.6.2.8.4 |
| 8.6.3.1.1 | 8.6.3.1.2 | 8.6.3.1.3 | 8.6.3.1.4 | 8.6.3.2.1 | 8.6.3.2.2 | 8.6.3.2.3 | 8.6.3.2.4 |
| 8.6.3.3.1 | 8.6.3.3.2 | 8.6.3.3.3 | 8.6.3.3.4 | 8.6.3.4.1 | 8.6.3.4.2 | 8.6.3.4.3 | 8.6.3.4.4 |
| 8.6.3.5.1 | 8.6.3.5.2 | 8.6.3.5.3 | 8.6.3.5.4 | 8.6.3.6.1 | 8.6.3.6.2 | 8.6.3.6.3 | 8.6.3.6.4 |
| 8.6.3.7.1 | 8.6.3.7.2 | 8.6.3.7.3 | 8.6.3.7.4 | 8.6.3.8.1 | 8.6.3.8.2 | 8.6.3.8.3 | 8.6.3.8.4 |
| 8.6.4.1.1 | 8.6.4.1.2 | 8.6.4.1.3 | 8.6.4.1.4 | 8.6.4.2.1 | 8.6.4.2.2 | 8.6.4.2.3 | 8.6.4.2.4 |
| 8.6.4.3.1 | 8.6.4.3.2 | 8.6.4.3.3 | 8.6.4.3.4 | 8.6.4.4.1 | 8.6.4.4.2 | 8.6.4.4.3 | 8.6.4.4.4 |
| 8.6.4.5.1 | 8.6.4.5.2 | 8.6.4.5.3 | 8.6.4.5.4 | 8.6.4.6.1 | 8.6.4.6.2 | 8.6.4.6.3 | 8.6.4.6.4 |
| 8.6.4.7.1 | 8.6.4.7.2 | 8.6.4.7.3 | 8.6.4.7.4 | 8.6.4.8.1 | 8.6.4.8.2 | 8.6.4.8.3 | 8.6.4.8.4 |
| 8.7.1.1.1 | 8.7.1.1.2 | 8.7.1.1.3 | 8.7.1.1.4 | 8.7.1.2.1 | 8.7.1.2.2 | 8.7.1.2.3 | 8.7.1.2.4 |
| 8.7.1.3.1 | 8.7.1.3.2 | 8.7.1.3.3 | 8.7.1.3.4 | 8.7.1.4.1 | 8.7.1.4.2 | 8.7.1.4.3 | 8.7.1.4.4 |
| 8.7.1.5.1 | 8.7.1.5.2 | 8.7.1.5.3 | 8.7.1.5.4 | 8.7.1.6.1 | 8.7.1.6.2 | 8.7.1.6.3 | 8.7.1.6.4 |
| 8.7.1.7.1 | 8.7.1.7.2 | 8.7.1.7.3 | 8.7.1.7.4 | 8.7.1.8.1 | 8.7.1.8.2 | 8.7.1.8.3 | 8.7.1.8.4 |
| 8.7.2.1.1 | 8.7.2.1.2 | 8.7.2.1.3 | 8.7.2.1.4 | 8.7.2.2.1 | 8.7.2.2.2 | 8.7.2.2.3 | 8.7.2.2.4 |
| 8.7.2.3.1 | 8.7.2.3.2 | 8.7.2.3.3 | 8.7.2.3.4 | 8.7.2.4.1 | 8.7.2.4.2 | 8.7.2.4.3 | 8.7.2.4.4 |
| 8.7.2.5.1 | 8.7.2.5.2 | 8.7.2.5.3 | 8.7.2.5.4 | 8.7.2.6.1 | 8.7.2.6.2 | 8.7.2.6.3 | 8.7.2.6.4 |
| 8.7.2.7.1 | 8.7.2.7.2 | 8.7.2.7.3 | 8.7.2.7.4 | 8.7.2.8.1 | 8.7.2.8.2 | 8.7.2.8.3 | 8.7.2.8.4 |
| 8.7.3.1.1 | 8.7.3.1.2 | 8.7.3.1.3 | 8.7.3.1.4 | 8.7.3.2.1 | 8.7.3.2.2 | 8.7.3.2.3 | 8.7.3.2.4 |
| 8.7.3.3.1 | 8.7.3.3.2 | 8.7.3.3.3 | 8.7.3.3.4 | 8.7.3.4.1 | 8.7.3.4.2 | 8.7.3.4.3 | 8.7.3.4.4 |
| 8.7.3.5.1 | 8.7.3.5.2 | 8.7.3.5.3 | 8.7.3.5.4 | 8.7.3.6.1 | 8.7.3.6.2 | 8.7.3.6.3 | 8.7.3.6.4 |
| 8.7.3.7.1 | 8.7.3.7.2 | 8.7.3.7.3 | 8.7.3.7.4 | 8.7.3.8.1 | 8.7.3.8.2 | 8.7.3.8.3 | 8.7.3.8.4 |
| 8.7.4.1.1 | 8.7.4.1.2 | 8.7.4.1.3 | 8.7.4.1.4 | 8.7.4.2.1 | 8.7.4.2.2 | 8.7.4.2.3 | 8.7.4.2.4 |
| 8.7.4.3.1 | 8.7.4.3.2 | 8.7.4.3.3 | 8.7.4.3.4 | 8.7.4.4.1 | 8.7.4.4.2 | 8.7.4.4.3 | 8.7.4.4.4 |
| 8.7.4.5.1 | 8.7.4.5.2 | 8.7.4.5.3 | 8.7.4.5.4 | 8.7.4.6.1 | 8.7.4.6.2 | 8.7.4.6.3 | 8.7.4.6.4 |
| 8.7.4.7.1 | 8.7.4.7.2 | 8.7.4.7.3 | 8.7.4.7.4 | 8.7.4.8.1 | 8.7.4.8.2 | 8.7.4.8.3 | 8.7.4.8.4 |
| 8.8.1.1.1 | 8.8.1.1.2 | 8.8.1.1.3 | 8.8.1.1.4 | 8.8.1.2.1 | 8.8.1.2.2 | 8.8.1.2.3 | 8.8.1.2.4 |
| 8.9.1.3.1 | 8.8.1.3.2 | 8.8.1.3.3 | 8.8.1.3.4 | 8.8.1.4.1 | 8.8.1.4.2 | 8.8.1.4.3 | 8.8.1.4.4 |
| 8.8.1.5.1 | 8.8.1.5.2 | 8.8.1.5.3 | 8.8.1.5.4 | 8.8.1.6.1 | 8.8.1.6.2 | 8.8.1.6.3 | 8.8.1.6.4 |
| 8.8.1.7.1 | 8.8.1.7.2 | 8.8.1.7.3 | 8.8.1.7.4 | 8.8.1.8.1 | 8.8.1.8.2 | 8.8.1.8.3 | 8.8.1.8.4 |
| 8.8.2.1.1 | 8.8.2.1.2 | 8.8.2.1.3 | 8.8.2.1.4 | 8.8.2.2.1 | 8.8.2.2.2 | 8.8.2.2.3 | 8.8.2.2.4 |
| 8.8.2.3.1 | 8.8.2.3.2 | 8.8.2.3.3 | 8.8.2.3.4 | 8.8.2.4.1 | 8.8.2.4.2 | 8.8.2.4.3 | 8.8.2.4.4 |
| 8.8.2.5.1 | 8.8.2.5.2 | 8.8.2.5.3 | 8.8.2.5.4 | 8.8.2.6.1 | 8.8.2.6.2 | 8.8.2.6.3 | 8.8.2.6.4 |
| 8.8.2.7.1 | 8.8.2.7.2 | 8.8.2.7.3 | 8.8.2.7.4 | 8.8.2.8.1 | 8.8.2.8.2 | 8.8.2.8.3 | 8.8.2.8.4 |
| 8.8.3.1.1 | 8.8.3.1.2 | 8.8.3.1.3 | 8.8.3.1.4 | 8.8.3.2.1 | 8.8.3.2.2 | 8.8.3.2.3 | 8.8.3.2.4 |
| 8.8.3.3.1 | 8.8.3.3.2 | 8.8.3.3.3 | 8.8.3.3.4 | 8.8.3.4.1 | 8.8.3.4.2 | 8.8.3.4.3 | 8.8.3.4.4 |
| 8.8.3.5.1 | 8.8.3.5.2 | 8.8.3.5.3 | 8.8.3.5.4 | 8.8.3.6.1 | 8.8.3.6.2 | 8.8.3.6.3 | 8.8.3.6.4 |
| 8.8.3.7.1 | 8.8.3.7.2 | 8.8.3.7.3 | 8.8.3.7.4 | 8.8.3.8.1 | 8.8.3.8.2 | 8.8.3.8.3 | 8.8.3.8.4 |
| 8.8.4.1.1 | 8.8.4.1.2 | 8.8.4.1.3 | 8.8.4.1.4 | 8.8.4.2.1 | 8.8.4.2.2 | 8.8.4.2.3 | 8.8.4.2.4 |
| 8.8.4.3.1 | 8.8.4.3.2 | 8.8.4.3.3 | 8.8.4.3.4 | 8.8.4.4.1 | 8.8.4.4.2 | 8.8.4.4.3 | 8.8.4.4.4 |
| 8.8.4.5.1 | 8.8.4.5.2 | 8.8.4.5.3 | 8.8.4.5.4 | 8.8.4.6.1 | 8.8.4.6.2 | 8.8.4.6.3 | 8.8.4.6.4 |
| 8.8.4.7.1 | 8.8.4.7.2 | 8.8.4.7.3 | 8.8.4.7.4 | 8.8.4.8.1 | 8.8.4.8.2 | 8.8.4.8.3 | 8.8.4.8.4 |

The best mode of practicing the claimed invention is with compounds of Example numbers 48.6, 48.9, 48.15, and 48.20.

Preferred insulin sensitizers are compounds disclosed in the following publications and patents:

(1) Tamura et al. W09737688
(2) Nagao et al., Eur. Pat. Appl. EP-787727
(3) Kallam et al. Can. Pat. Appl. CA2173660 AA
(4) Inman et al. W09639401 A1
(5) Yanagisawa et al. W09638427
(6) Fujita et al., EP-745600 A1
(7) Ohara et al., W09626207 A1
(8) Ohara et al. W09611196 A1
(9) Malamas et al., U.S. Pat. No. 5,532,256 A
(10) Yanagisawa et al., EP-708098 A1
(11) Regnier et al., U.S. Pat. No. 5,478,853 A
(12) U.S. Pat. No. 5468762 A
(13) Ohara et al., W0952637 A1
(14) Antonucci et al. U.S. Pat. No. 5,457,109 A
(15) Yoshioka et al. JP07002852 A2
(16) Shibata et al., W09401433 A1
(17) Fujita et al., EP-543662 A2
(18) De Nanteuil et al., EP-559571 A1
(19) Zask et al., U.S. Pat. No. 5,236,941 A
(20) Ohnotaetal., W09214719
(21) Miyaoka et al., EP-489663 A1
(22) Arita et al., EP-506273 A2
(23) Hulin et al., J. Med. Chem. 35, 1853 (1992)
(24) Zask et al., J. Med. Chem. 33: 1418–1423 (1990)
(25) Clark U.S. Pat. No. 4,791,125A
(26) Iijima et al., EP-283035 A1
(27) Kees et al., U.S. Pat. No. 4,728,739 A
(28) Meguro et al., EP-177353 A2
(29) Hasler et al., EP-129747 A2
(30) Kawamatsu et al., EP-91761 A2
(31) Tontonez et al. Gene & Develop 8: 1224–1234 (1994)
(32) Tontonez et al. Cell 79: 1147–1156
(33) Lehmann et al., J. Biol. Chem. 270, 1–4, (1994)
(34) Amnri et al. J. Lipid Res. 32: 1449–1456 (1991)
(35) Grimaldi et al. Proc. Natl. Acad. Sci. USA 89: 10930 (1992)
(36) EP0745600

All references are incorporated by reference. While such disclosures constitute a large number of the insulin sensitizers, the instant invention is not so limited and can utilize any insulin sensitizer compound. The insulin sensitizers encompassed by the invention are compounds that improve insulin sensitivity as measured, for instance, by conducting standard assays such as those described in Examples H through M.

More preferred are the following insulin sensitizers:

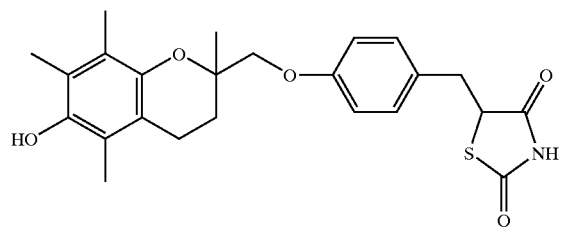

Troglitazone (1)

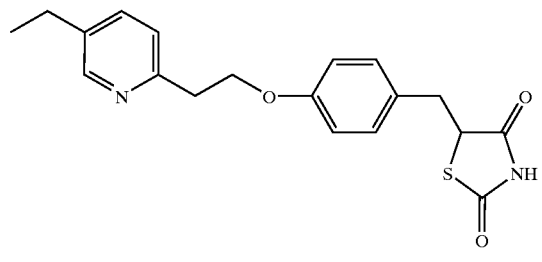

Pioglitazone (2)

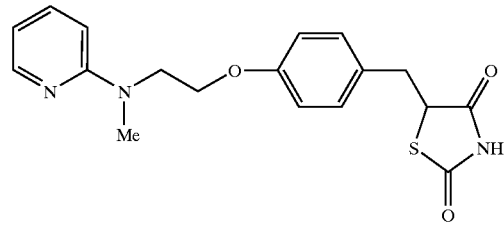

Rosiglitazone (3)

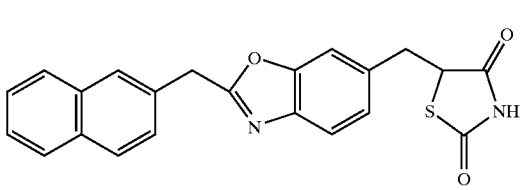

LY-282249
TA-174
Diabetologia, 36, Suppl., 1, A182, 1993
Diabetes, 42, Suppl., 1, 79A, 1993 (4)

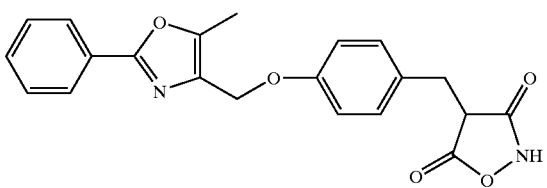

JTT-501 (5)

-continued (6)
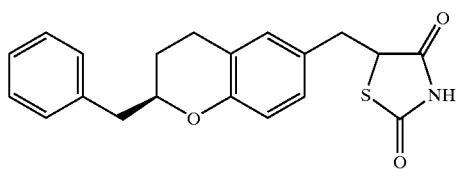
Englitazone
J. Med. Chem., 34, 319 (1991)

(7)
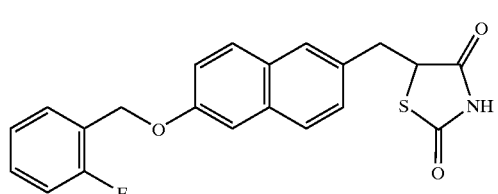
MCC-555
Diabetes, 45, Suppl. 2, 141A, 1996

(8)
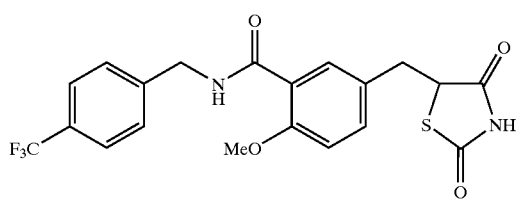
KRP-297
WO9638428-A1

(9)
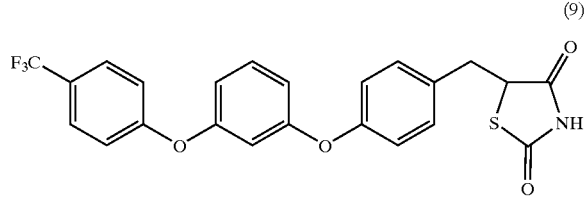
YM-440

(10)
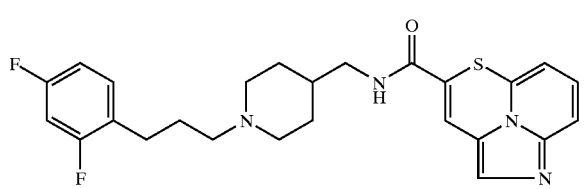
WO9740051

(11)
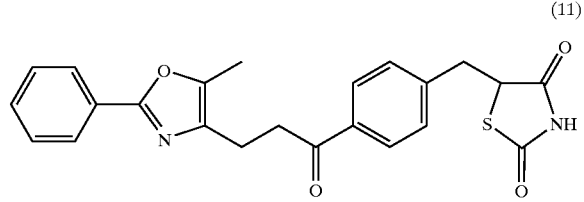
Darlitazone
CP-86325

(12)
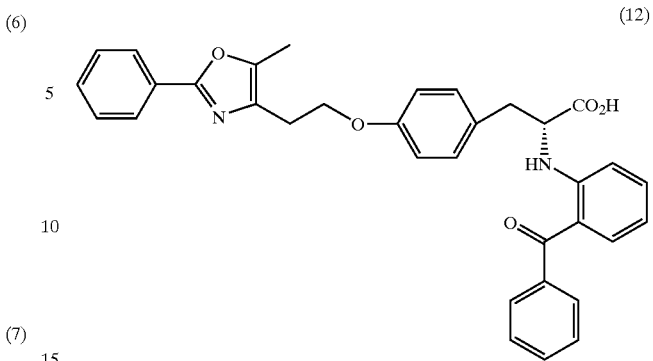
GI-262570

Especially preferred PPAR γ agonists are Troglitazone, Pioglitiazone, ciglitazone, WAY-120,744, englitazone, AD 5075, SB219994, SB219993, BRL49653, GI-262570, darglitazone and analogs thereof.

Preferred RXR ligands are described in e.g. Heyman et al., WO9710819 A1; Especially preferred RXR ligands are LG100268, LGD 1069, ALRT 1057 and analogs thereof Other classes of insulin sensitizers are within the scope of the invention and include non-thiazolidinediones) such as SB 236636 and SB 219994, which are 3-aryl-2-alkoxy propanoic acids, PKC inhibitors, angiotensin II antagonists, and angiotensin converting enzyme inhibitors.

As expected from their mechanism of action, insulin-sensitizers are primarily effective in the hyperinsulinemic, early stages of type 2 diabetes. Efficacy is considerably reduced in advanced diabetes which is associated with severely disturbed beta-cell function and hence diminished insulin levels. This drug profile has been observed both in animal models of the disease as well as in the clinic. Hyperglycemia in young, hyperinsulinemic ZDF rats, for instance, is completely reversed by treatment with Troglitazone. Sreenan et al. Am. J. Physiol. 271: E742–747. ZDF rats in a more advanced, hypoinsulinemic phase of the disease, however, respond poorly to insulin sensitizer treatment. Brown et al. Diabetes 48: 1415–1424 (1999). In addition, hypoinsulinemic, streptozotocin induced diabetic mice do not respond to Troglitazone treatment. Fujiwara et al. Diabetes 37: 1549–1558 (1988). Clinical trials with Troglitazone have brought to light similarly variable responses in type 2 diabetics, with the non-response rate ranging from 35–62%. Valiquett T. et al. Diabetes 44 (Suppl.1): 406A (1995). In these trials it was found that the best predictor of efficacy was fasting insulin C peptide levels; the higher the C-peptide level, the greater the glucose-lowering effect in patients. Maggs DG et al. Ann. Intern. Med 128:176–185 (1998). Patients with sufficient pancreatic insulin secretory function thus respond well to therapy, whereas patients with decreased pancreatic function, characteristic of more advanced diabetes, respond poorly or are non-responders to therapy.

Insulin sensitizer treatment in general falls short of restoring euglycemia or normalizing HbA1c levels in atients. In clinical trials with Pioglitazone, for example, average blood glucose lowering and HbA1c reductions were ~50 mg/dl and 0.6%, respectively. Mathisen et al. Diabetes 48 (Suppl.1): 441A (1998). In the patient populations treated, average reductions of >140 mg/dl and >3% would have been necessary to restore these parameters to normal values. A high rate of non-response and overall modest reductions in blood glucose levels have also been observed in clinical trials with Rosiglitazone. Patel et al. Diabetes, Obesity, and Metabolism 1: 165–172 (1999). There thus appears ample opportunity for agents such as the FBPase inhibitors to provide a benefit in combination with insulin sensitizers in the clinic.

FBPase inhibitors are likely to be efficacious both in early and advanced stages of type 2 diabetes. In animal studies they significantly lowered blood glucose in the hyperinsulinemic db/db mouse (a model of early type 2 diabetes, Examples S and T) as well as in a model of advanced type 2 diabetes: the insulinopenic streptozotocin-induced diabetic rat. In the ZDF rat, FBPase inhibitors were effective both in early diabetes (8–9 weeks of age, Examples N–R) as well as in advanced diabetes (16 weeks of age). Based on the pharmacological profile described above, the combination of FBPase inhibitors and insulin sensitizers will be effective across a broad patient population. In early stage diabetics, the insulin sensitizer and FBPase inhibitor are both likely to be fully effective, whereas in advanced diabetics, the response to insulin sensitizers may be partial whereas the FBPase inhibitor will maintain robust efficacy. The benefit of the combination in advanced diabetes will be a significant reduction in the number of non-responders to therapy (Example R). While the initial response of the combination may in large part be due to treatment with the FBPase inhibitor, blood glucose lowering may improve pancreatic function (Example P) and allow the insulin sensitizer to become more fully effective over time and in the long term provide enhanced glycemic control. In some cases, insulin sensitizers are best used in combination with agents that improve the actions of the insulin sensitizer, such as insulin, insulin analogs, RXR ligands, or insulin secretagogues (eg. the sulfonylureas). With the actions of the insulin sensitizer thus enhanced, combination treatment with an FBPase inhibitor will result in more effective glycemic control. Moreover, long term treatment will diminish the need for agents that enhance insulin levels.

FBPase inhibitors lower blood glucose both in the fasted (example T) and the fed state (examples N–S). This provides a broad opportunity for therapy in combination with insulin sensitizers. The combination could, for instance, be administered at mealtime and provide enhanced glycemic control over either agent alone by simultaneously enhancing glucose disposal and reducing the contribution of gluconeogenesis to hyperglycemia during the postprandial period. Meal time administration has the additional benefit of reducing the potential risk of hypoglycemia that could ensue from treatment with an FBPase inhibitor. Another possible dosing regimen may be the administation of the insulin sensitizer during the daytime, and administration of the FBPase inhibitor separately at bedtime. The insulin sensitizer will thus provide glycemic control by enhancing glucose disposal following daytime meals, whereas the FBPase inhibitor will control excessive glucose production by the liver known to occur to a greater extent during the overnight fast. There is precedent for the use of a hepatic glucose production suppressor during the overnight fast; insulin has been widely used in this application. Riddle, The Lancet 192–195 (1985).

An additional benefit of combination treatment is that it will allow a reduction in dose of both agents thereby reducing potential side effects. The most common side-effect of Troglitazone, for example, is hepatotoxicity which manifests itself as the elevation of liver enzymes (1% of patients). This side-effect has resulted in a recommendation for liver function monitoring every month for the first six months of treatment. In addition, an association between Troglitazone and increased heart weight in animals has led to recommendations that this drug be used cautiously in patients with congestive heart failure. Rosiglitazone treatment, although not reported to cause liver enzyme elevations, is known to significantly decrease haematocrit. All insulin sensitizers cause weight gain. As discussed above, in some cases efficacy with an insulin sensitizer can only be achieved with supplemental insulin or sulfonylurea administrations. Insulin has the undesirable side-effects of promoting weight gain, of exacerbating insulin resistance, and predisposing to hypoglycemia. Sulfonylureas also promote weight gain, increase the risk of hypoglycemia, and by overstimulating the pancreas can promote beta-cell degeneration. In certain animal models, FBPase inhibitors are known to elevate blood lactate and triglycerides and could therefore predispose to systemic acidosis and the vascular complication associated with hypertriglyceridemia. Combination treatment with an insulin sensitizer may suppress the potential lactate and triglyceride elevations associated with FBPase inhibitor treatment (Examples O and Q). Other side effects of FBPase inhibitors may manifest themselves in man. By treating patients with the combination of an insulin sensitizer and an FBPase inhibitor, the reduced dosages feasible are likely to significantly decrease the risks of the (potential) side-effects associated with the individual therapies.

While an insulin sensitizer-FBPase inhibitor combination is primarily envisaged for the treatment of type 2 diabetes and the associated renal, neuronal, retinal, micro- and macro-vascular and metabolic complications, treatment of other diseases that respond to improved glycemic control and improved insulin sensitivity is also possible. Patients with impaired glucose tolerance (IGT) are minimally hyperglycemic under ordinary circumstances but can become hyperglycemic following the ingestion of large glucose loads. IGT is a predictor of future diabetes and patients with this condition have become the target of diabetes prevention trials in recent years. Combination treatment of these patients, particularly at mealtime, restores a normal glucose response and reduces the risk of the development of diabetes. Another distinct group of subjects at high risk for the development of type 2 diabetes are women who suffer from polycystic ovary syndrome (POCS). Combination treatment is of benefit in these patients as well since they are typically, hyperinsulinemic, insulin resistant, and can suffer from IGT. Combination treatment is also useful for treating renal dysfunction and hypertension particularly in obese, insulin resistant, hyperinsulinemic patients with IGT. Other applications of combination treatment include gestational diabetes,.poorly controlled type 1 diabetes, obesity and dyslipidemia.

Formulations

For the purposes of this invention, the compounds may be administered by a variety of means including orally, parenterally, by inhalation spray, topically, or rectally in formulations containing pharmaceutically acceptable carriers, adjuvants and vehicles. The term parenteral as used here includes subcutaneous, intravenous, intramuscular, and intraarterial injections with a variety of infusion techniques. Intraarterial and intravenous injection as used herein includes administration through catheters. Oral administration is generally preferred.

Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating, and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Compounds of the invention may be administered as a daily dose or an appropriate fraction of the daily dose (e.g. bid). Administration of the FBPase inhibitor may occur at or near the time in which the insulin sensitizer active ingredient is administered or at a different time. Simultaneous administration of the active ingredients is achieved either by administration of the active ingredients in the same or different formulations. Formulations include time-release formulations intended to release either both of the active ingredients simultaneously or to stage the release of the active ingredients such that release, absorption and systemic exposure occurs with one of the ingredients before the other.

The amount of active ingredient that may be combined with the carrier material to produce a single dosage form will vary depending upon the host treated and the particular mode of administration. For example, a formulation intended for oral administration to humans may contain 20 to 2000 $\mu$mol (approximately 10 to 1000 mg) of active material compounded with an appropriate and convenient amount of carrier material which may vary from about 5 to about 95% of the total compositions.

As noted above, formulations of the present invention suitable for oral administration may be presented as discrete units such as capsules, cachets or tablets each containing a predetermined amount of the active ingredient; as a powder or granules; as a solution or a suspension in an aqueous or nonaqueous liquid; or as an oil-in-water liquid emulsion or a water in-oil liquid emulsion. The active ingredient may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made by molding in a'suitable machine a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and on-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, or an appropriate fraction thereof, a fructose-1,6-bisphosphatase inhibitor compound and an insulin sensitizer.

It will be understood, however, that the specific dose level for any particular patient will depend on a variety of factors including the activity of the specific compound employed; the age, body weight, general health, sex and diet of the individual being treated; the time and route of administration; the rate of excretion; other drugs which have previously been administered; and the severity of the particular disease undergoing therapy, as is well understood by those skilled in the art.

Capsules comprising FBPase inhibitors suitable for oral administration according to the methods of the present invention may be prepared as follows: (1) for a 10,000 capsule preparation: up to 5000 g of FBPase inhibitor is blended with other ingredients (as described above) and filled into capsules which are suitable for administration depending on dose, from about 1 capsules per day to about 8 capsules per day (2 capsules per 6 hours), to an adult human.

Capsules comprising insulin sensitizers suitable for oral administration according to the methods of the present invention may be prepared as follows: (1) for a 10,000 capsule preparation: up to 5000 g of insulin sensitizer is blended with other ingredients (as described above) and filled into capsules which are suitable for administration depending on dose, from about 1 capsules per day to about 8 capsules per day (2 capsules per 6 hours), to an adult human.

Capsules comprising FBPase inhibitors and insulin sensitizers suitable for oral administration according to the methods of the present invention may be prepared as follows: (1) for a 10,000 capsule preparation: up to 2500 g of FBPase inhibitor and up to 2500 g of insulin sensitizer are blended with other ingredients (as described above) and filled into capsules which are suitable for administration depending on dose, from about 1 capsules per day to about 8 capsules per day (2 capsules per 6 hours), to an adult human.

EXAMPLES

Compounds of formula VI are prepared according to the literature procedures with modifications and additions well understood by those skilled in the art. In general, these compounds are synthesized by the method of Srivastava, *J.Med. Chem.* (1976). Other methodology is described by Wood et al. *J. Med. Chem.* 28: 1198–1203 (1985); Sagi et al., *J. Med. Chem.*35: 4549–4556 (1992); Paul, Jr. *J. Med. Chem.* 28: 1704–1716 (1985); Cohen et al., *J. Am. Chem. Soc.* 95: 4619–4624 (1973).

Compounds of formulae II–IV are prepared according to the procedures described in PCT publication numbers WO 98/39344, WO 98/39343, and WO 98/39342.

Section 1.

Synthesis of Compounds of Formula I

Synthesis of compounds encompassed by the present invention typically includes some or all of the-following general steps: (1) preparation of a phosphonate prodrug; (2) deprotection of a phosphonate ester; (3) modification of a heterocycle; (4) coupling of a heterocycle with a phosphonate component; (5) construction of a heterocycle; (6) ring closure to construct a heterocycle with a phosphonate moiety present and (7) preparation of useful intermediates. These steps are illustrated in the following scheme for compounds of formula 2 wherein $R^5$ is a 5-membered heteroaromatic ring. Compounds of formula 2 wherein $R^5$ is a 6-member heteroaromatic ring or other heteroaromatic rings are prepared in an analogous manner.

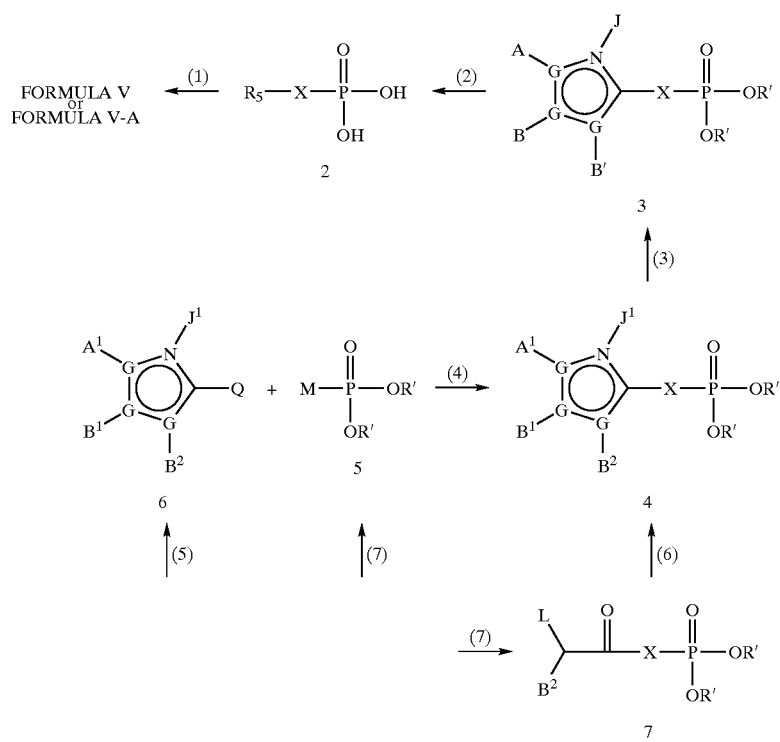

(1a) Preparation of a Phosphonate Prodrug

Prodrugs can be introduced at different stages of the synthesis. Most often these prodrugs are made from the phosphonic acids of formula 2, because of their lability. Advantageously, these prodrugs can be introduced at an earlier stage, provided that it can withstand the reaction conditions of the subsequent steps.

Compounds of formula 2, can be alkylated with electrophiles (such as alkyl halides, alkyl sulfonates, etc) under nucleophilic substitution reaction conditions to give phosphonate esters. For example, compounds of formula I, wherein $R^1$ is an acyloxyalkyl group can be synthesized through direct alkylation of compounds of formula 2 with an appropriate acyloxyalkyl halide (e.g. Cl, Br, I; Elhaddadi, et al *Phosphorus Sulfur*, 1990, 54(1–4): 143; Hoffmann, *Synthesis*, 1988, 62) in the presence of abase (e.g. N, N'-dicyclohexyl-4-morpholinecarboxamidine, Hunigs base, etc.) in suitable solvents such as 1,1-dimethyl formamide ("DMF") (Starrett, et al, *J. Med. Chem.*, 1994, 1857). The carboxylate component of these acyloxyalkyl halides includes but is not limited to acetate, propionate, isobutyrate, pivalate, benzoate, and other carboxylates. When appropriate, further modification are envisioned after the formation of these acyloxyalkyl phosphonate esters such as reduction of a nitro group. For example, compounds of formula 3 wherein A is a $NO_2$ group can be converted to compounds of formula 3 wherein A is an $H_2N$— group under suitable reduction conditions (Dickson, et al, *J. Med. Chem.*, 1996, 39: 661; Iyer, et al, *Tetrahedron Lett.*, 1989, 30: 7141; Srivastva, et al, *Bioorg. Chem.*, 1984, 12: 118). These methods can be extended to the synthesis of other types of prodrugs, such as compounds of formula I where $R^1$ is a 3-phthalidyl, a 2-oxo-4,5-didehydro-1,3-dioxolanemethyl, or a 2-oxotetrahydrofuran-5-yl group (Biller et al., U.S. Pat. No. 5,157,027; Serafinowska et al., *J. Med. Chem.* 1995,38: 1372; Starrett et al., *J. Med. Chem.* 1994, 3.7: 1857; Martin et al., *J. Pharm. Sci.* 1987, 76: 180; Alexander et al., *Collect. Czech. Chem. Commun*, 1994, 59: 1853; EPO 0632048A1). N,N-Dimethylformamide dialkyl acetals can also be used to alkylate phosphonic acids (Alexander, P., et al *Collect. Czech. Chem. Commun.*, 1994, 59, 1853).

Alternatively, these phosphonate prodrugs can also be synthesized by reactions of the corresponding dichlorophosphonates with an alcohol (Alexander et al, *Collect. Czech. Chem. Commun.*, 1994, 59: 1853). For example, reactions of a dichlorophosphonate with substituted phenols and aralkyl alcohols in the presence of base (e.g. pyridine, triethylamine, etc) yield compounds of formula V where $R^1$ is an aryl group (Khamnei et al., *J. Med. Chem.*, 1996, 39: 4109; Serafinowska et al., *J. Med. Chem.*, 1995, 38: 1372; De Lombaert et al., *J. Med. Chem.*, 1994, 37: 498) or an arylalkyl group (Mitchell et al., *J. Chem. Soc. Perkin Trans.* 1, 1992, 38: 2345). The disulfide-containing prodrugs (Puech et al., *Antiviral Res.*, 1993, 22: 155) can also be prepared from a dichlorophosphonate and 2-hydroxyethyl disulfide under standard conditions.

Such reactive dichlorophosphonates can be generated from the corresponding phosphonic acids with a chlorinating agent (e.g. thionyl chloride: Starrett et al., *J. Med. Chem.*, 1994, 1857, oxalyl chloride: Stowell et al., *Tetrahedron Lett.*, 1990, 31: 3261, and phosphorus pentachloride: Quast et al., *Synthesis*, 1974, 490). Alternatively, a dichlorophosphonate can also be generated from its corresponding disilyl phosphonate esters (Bhongle et al., *Synth. Commun.*, 1987, 17: 1071) or dialkyl phosphonate esters (Still et al., *Tetrahedron Lett.*, 1983, 24: 4405; Patois et al., *Bull. Soc. Chim. Fr.*, 1993, 130: 485).

Furthermore, these prodrugs can be prepared using Mitsunobu reactions (Mitsunobu, *Synthesis*, 1981, 1; Campbell, *J. Org. Chem.*, 1992, 52: 6331), and other coupling reactions (e.g. using carbodiimides: Alexander et al., *Collect. Czech. Chem. Commun.*, 1994, 59: 1853; Casara et al., *Bioorg.*

Mied. Chem. Lett., 1992, 2: 145; Ohashi et al., Tetrahedron Lett., 1988, 29: 1189, and benzotriazolyloxytris-(dimethylamino)phosphonium salts: Campagne et al., Tetrahedron Lett., 1993, 34: 6743). Compounds of formula I wherein $R^1$ is a cyclic carbonate, a lactone or a phthalidyl group can also be synthesized via direct alkylation of the free phosphonic acid with appropriate halides in the presence of a suitable base (e.g. NaH or diisopropylethylamine, Biller et al., U.S. Pat. No. 5,157,027; Serafinowska et al., J. Med. Chem. 1995, 38: 1372; Starrett et al., J. Med. Chem. 1994, 37: 1857; Martin et al., J. Pharm. Sci. 1987, 76: 180; Alexander et al., Collect. Czech. Chem. Commun, 1994, 59: 1853;EPO 0632048A1).

$R^1$ can also be introduced at an early stage of the synthesis provided that it is compatible with the subsequent reaction steps. For example, compounds of formula I where $R^1$ is an aryl group can be prepared by metalation of a 2-furanyl heterocycle (e.g. using LDA) followed by trapping the anion with a diaryl chlorophosphate.

It is envisioned that compounds of formula V can be mixed phosphonate esters (e.g. phenyl and benzyl esters, or phenyl and acyloxyalkyl esters) including the chemically combined mixed esters such as the phenyl and benzyl combined prodrugs reported by Meier, et al. Bioorg. Med. Chem. Lett., 1997, 7: 99.

(1b) Preparation of a Bisamidate Phosphonate

General synthesis of bis-phosphoroamidate prodrugs:

In general, the bis-phosphoroamidates of formula I, where both —$NR^{15}R^{16}$ and —$N(R^{18})$—$(CR^{12}R^{13})_n$—$C(O)$—$R^{14}$ are from the same amino acid residues can be prepared from the activated phosphonates for example, dichlorophosphonate, by coupling with an aminoacid ester for example, glycine ethylester with or without base for example, N-methylimidazole. The reactive dichloridates, can be prepared as described above in the general prodrug section Alternatively, these bis-phosphoroamidates can be prepared by reacting the corresponding phosphonic acid with an aminoacid ester for example, glycine ethylester in presence of $PPh_3$ and 2,2'-dipyridyl disulfide in pyridine as described in WO 95/07920 or Mukaiyama, T. et al, J Am. Chem. Soc., 1972, 94, 8528.

Synthesis of mixed bis-phosphoroamidates of formula IA, where —$NR^{15}R^{16}$ and —$N(R^{18})$—$(CR^{12}R^{13})_n C(O)$—$R^{14}$ are different aminoacid esters or a combination of an aminoacid ester and a substituted amine can be prepared by direct conversion via dichloridate as described above (sequential addition) followed by separation of the required product by column chromatography or HPLC. Alternatively, these mixed bis-phosphoroamidates can be prepared starting with an appropriate phosphonate monoester such as phenyl ester or benzyl ester to give the mixed phosphonoesteramide via the chloridate, followed by ester hydrolysis under conditions where the amide bond is stable. The resultant monoamide can be converted to a mixed bis-amide by condensation with a second amino ester or a substituted amine via the chloridate, as described above. Synthesis of such monoesters can be prepared using the reported procedure (EP 481 214).

The substituted cyclic propyl phosphonate esters can be synthesized by reactions of the corresponding dichlorophosphonate with a substituted 1,3-propanediol. Some of the methods useful for the preparation of a substituted 1,3-propanediol are discussed below.

Synthesis of a 1,3-Propanediol

Various synthetic methods can be used to prepare numerous types of 1,3-propanediols: (i) 1-substituted, (ii) 2-substituted, (iii) 1,2- or 1,3-annulated 1,3-propanediols. Substituents on the prodrug moiety of compounds of formula I (i.e. substituents on the 1,3-propanediol moiety) can be introduced or modified either during the synthesis of these diols or after the coupling of these diols to compounds of formula 2.

(i) 1-Substituted 1,3-Propanediols 1,3-Propanediols useful in the synthesis of compounds in the present invention can be prepared using various synthetic methods. Additions of a aryl Grignard to a 1-hydroxypropan-3-al give 1-aryl-substituted 1,3-propanediols (path a). This method is suitable for the conversion of various aryl halides to 1-arylsubstituted-1,3-propanediols (Coppi et. al., J. Org. Chem., 1988, 53, 911). Conversions of aryl halides to 1-substituted 1,3-propanediols can also be achieved using Heck reactions (e.g. couplings with a 1,3-diox-4-ene) followed by reductions and subsequent hydrolysis reactions (Sakamoto et. al., Tetrahedron Lett., 1992, 33, 6845). Various aromatic aldehydes can also be converted to 1-substituted-1,3-propanediols using alkenyl Grignard addition reactions followed by hydroboration reactions (path b). Additions of a metallated t-butyl acetate to aromatic aldehydes followed by reduction of the ester (path e) are also useful for the synthesis of 1,3-propanediols (Turner., J. Org. Chem., 1990, 55 4744). In another method, epoxidations of cinnamyl alcohols using known methods (e.g. Sharpless epoxidations and other asymmetric epoxidation reactions) followed by a reduction reaction (e.g. using Red-Al) give various 1,3-propanediols (path c). Alternatively, enantiomerically pure 1,3-propanediols can be obtained using chiral borane reduction reactions of hydroxyethyl aryl ketone derivatives (Ramachandran et. al., Tetrahedron Lett., 1997, 38 761). Propan-3-ols with a 1-heteroaryl substituent (e.g. a pyridyl, a quinolinyl or an isoquinolinyl) can be oxygenated to give 1-substituted 1,3-propanediols using N-oxide formation reactions followed by a rearrangement reaction in acetic anhydride conditions (path d) (Yamamoto et. al., Tetrahedron, 1981, 37, 1871).

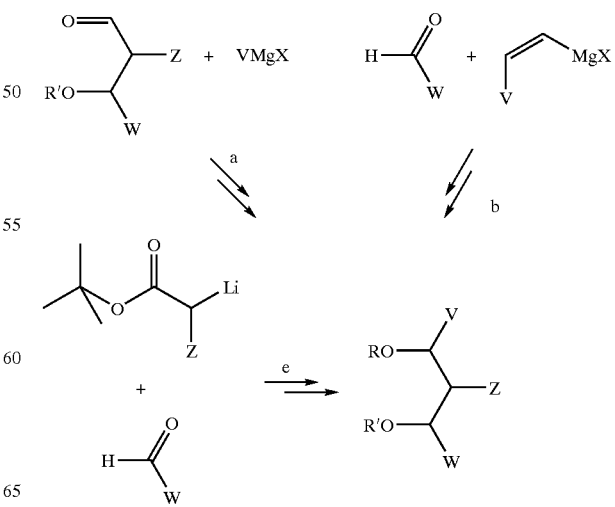

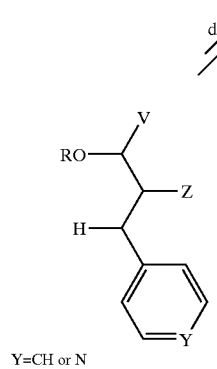

Y=CH or N

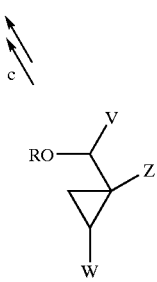

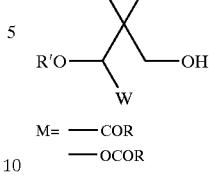

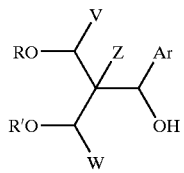

M= —COR
—OCOR (ii) 2-Substituted 1,3-Propanediols

A variety of 2substituted 1,3-propanediols usefull for the synthesis of compounds of formula I can be prepared from 2-(hydroxymethyl)-1,3-propanediols using known chemistry (Larock, *Comprehensive Organic Transformations*, VCH, New York, 1989). For example, reductions of a trialkoxycarbonylmethane under known conditions give a triol via complete reduction (path a) or a bis(hydroxymethyl) acetic acid via selective hydrolysis of one of the ester groups followed by reduction of the remaining two other ester groups. Nitrotriols are also known to give triols via reductive elimination (path b) (Latour et. al., *Synthesis*, 1987, 8, 742). Furthermore, a 2-(hydroxymethyl)-1,3-propanediol can be converted to a mono acylated derivative (e.g. acetyl, methoxycarbonyl) using an acyl chloride or an alkyl chloroformate (e.g. acetyl chloride or methyl chloroformate) (path d) using known chemistry (Greene et al., *Protective Groups In Organic Synthesis*; Wiley, N.Y., 1990). Other functional group manipulations can also be used to prepare 1,3-propanediols such as oxidation of one the hydroxylmethyl groups in a 2-(hydroxymethyl)-1,3-propanediol to an aldehyde followed by addition reactions with an aryl Grignard (path c). Aldehydes can also be converted to alkyl amines via reductive amination reactions (path e).

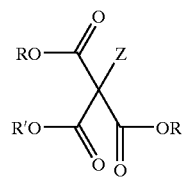

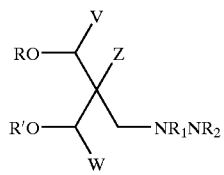

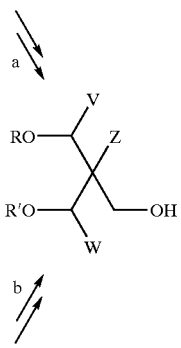

(iii) Annulated 1,3-Propane Diols

Compounds of formula I wherein V and Z or V and W are connected by four carbons to form a ring can be prepared from a 1,3-cyclohexanediol. For example, cis, cis-1,3,5-cyclohexanetriol can be modified as described for 2-substituted 1,3-propanediols. It is envisioned that these modifications can be performed either before or after formation of a cyclic phosphonate 1,3-propanediol ester. Various 1,3-cyclohexanediols can also be prepared using Diels-Alder reactions (e.g. using a pyrone as the diene: Posner et. al., *Tetrahedron Lett.*, 1991, 32, 5295). 1,3-Cyclohexanediol derivatives are also prepared via other cycloaddition reaction methodologies. For example, cycloadditon of a nitrile oxide to an olefin followed by conversion of the resulting cycloadduct to a 2-ketoethanol derivative can be converted to a 1,3-cylohexanediol using known chemistry (Curran, et. al., *J. Am. Chem. Soc.*, 1985, 107, 6023). Alternatively, precursors to 1,3-cyclohexanediol can be made from quinic acid (Rao, et. al., *Tetrahedron Lett.*, 1991, 32, 547.)

2) Deprotection of a Phosphonate Ester

Compounds of formula I wherein $R^1$ is H may be prepared from phosphonate esters using known phosphate and phosphonate ester cleavage conditions. Silyl halides are generally used to cleave various phosphonate esters, and subsequent mild hydrolysis of the resulting silyl phosphonate esters give the desired phosphonic acids. When required, acid scavengers (e.g. 1,1,1,3,3,3-hexamethyldisilazane, 2,6-lutidine, etc.) can be used for the synthesis of acid labile compounds. Such silyl halides include chlorotrimethylsilane (Rabinowitz, *J. Org. Chem.*, 1963, 28: 2975), and bromotrimethylsilane (McKenna, et al, *Tetrahedron Lett.*, 1977, 155), and iodotrimethylsilane (Blackburn, et al, *J. Chem. Soc., Chem. Commun.*, 1978, 870). Alternately, phosphonate esters can be cleaved under strong acidic conditions (e.g. HBr or HCl: Moffatt, et al, U.S. Pat. No. 3,524,846,1970). These esters can also be cleaved via dichlorophosphonates, prepared by treating the esters with halogenating agents (e.g. phosphorus pentachloride, thionyl chloride, $BBr_3$: Pelchowicz et al, *J. Chem. Soc.*, 1961, 238) followed by aqueous hydrolysis to give phosphonic acids. Aryl and benzyl phosphonate esters can be cleaved under hydrogenolysis conditions (Lejczak, et al, *Synthesis*, 1982, 412; Elliott, et al, *J. Med. Chem.*, 1985, 28: 1208; Baddiley, et al, *Nature*, 1953, 171: 76 ) or metal reduction conditions (Shafer, et al, *J. Am. Chem. Soc.*, 1977, 99: 5118). Electrochemical (Shono, et al, *J. Org. Chem.*, 1979, 44: 4508) and pyrolysis (Gupta, et al, *Synth; Commun.*, 1980, 10: 299) conditions have also been used to cleave various phosphonate esters.

(3) Modification of an Existing Heterocycle

Syntheses of the heterocycles encompassed in the disclosed compounds have been well, studied and described in numerous reviews (see section 4). Although it is advantageous to have the desired substituents present in these heterocycles before synthesis of compounds of formula 4, in some cases, the desired substituents are not compatible with .subsequent reactions, and therefore modifications of an existing heterocycle are required late in the synthetic scheme using conventional chemistry (Larock, *Comprehensive organic transformations*, VCH, New York, 1989; Trost, *Comprehensive organic synthesis*; Pergamon press, New York, 1991). For example, compounds of formula I wherein A, A", or B is a halo or a cyano group can be prepared from the corresponding amine group by conversion to the diazonium group and reaction with various copper (I) salts (e.g. CuI, CuBr, CuCl, CuCN). Halogens can also be introduced by direct halogenations of various heterocycles. For example, 5-unsubstituted-2-aminothiazoles can be converted to 2-amino-5-halothiazoles using various reagents (e.g. NIS, NBS, NCS). Heteroaryl halides are also useful intermediates and are often readily converted to other substituents (such as A, A", B, B", C", D, D", E and E") via transition metal assisted coupling reactions such as Suzuki, Heck or Stille reactions (Farina et al, *Organic Reactions, Vol.* 50; Wiley, N.Y., 1997; Mitchell, *Synthesis*, 1992, 808; Suzuki, *Pure App. Chem.*, 1991, 63, 419; Heck *Palladium Reagents in Organic Synthesis*; Academic Press: San Diego, 1985). Compounds of formula I wherein A is a carbamoyl group can be made from their corresponding alkyl carboxylate esters via aminolysis with various amines, and conventional functional group modifications of the alkyl carboxylate esters are useful for syntheses of compounds of formula I wherein A is a —CH$_2$OH group or a —CH$_2$-halo group. Substitution reactions of haloheterocycles (e.g. 2-bromothiazole, 5-bromothiazole) with various nucleophiles (e.g. HSMe, HOMe, etc.) represents still another method for introducing substituents such as A, A", B and B". For example, substitution of a 2-chlorothiazole with methanethiol gives the corresponding 2-methylthiothiazole.

It is envisioned that when necessary alkylation of nitrogen atoms in the heterocycles(e.g. imidazoles, 1,2,4-triazoles and 1,2,3,4-tetrazoles) can be readily performed using for example standard alkylation reactions (with an alkyl halide, an aralkyl halide, an alkyl sulfonate or an aralkyl sulfonate), or Mitsunobu reactions (with an alcohol).

(4) Coupling of a Heterocycle with a Phosphonate Component

When feasible compounds disclosed in the present invention are advantageously prepared via a convergent synthetic route entailing the coupling of a heterocycle with a phosphonate diester component.

Transition metal catalyzed coupling reactions such as Stille or Suzuki reactions are particularly suited for the synthesis of compounds of formula I. Coupling reactions between a heteroaryl halide or triflate (e.g. 2-bromopyridine) and a M-PO$_3$R' wherein M is a 2-(5-tributylstannyl)furanyl or a 2-(5-boronyl)furanyl group under palladium catalyzed reaction conditions (Farina et al, *Organic Reactions, Vol.* 50; Wiley, N.Y., 1997; Mitchell, *Synthesis*, 1992, 808; Suzuki, *Pure App. Chem.*, 1991, 63, 419) yield compounds of formula I wherein X is a furan-2,5-diyl group. It is envisioned that the nature of the coupling partners for these reactions can also be reversed (e.g. coupling of trialkylstannyl or boronyl heterocycles with a halo-X—P(O)(O-alkyl)$_2$). Other coupling reactions between organostannes and an alkenyl halide or an alkenyl triflate are also reported which may be used to prepared compounds of formula I wherein X is an alkenyl group. The Heck reaction may be used to prepare compounds of formula V wherein X is an alkynyl group (Heck *Palladium Reagents in Organic Synthesis*; Academic Press: San Diego, 1985).

These reactions are particularly suited for syntheses of various heteroaromatics as R$^5$ for compounds of formula I given the availability of numerous halogenated heterocycles, and these reactions are particularly suitable for parallel synthesis (e.g. combinatorial synthesis on solid phase (Bunin, B. A., *The Combinatorial Index*, Academic press: San Diego, 1998) or in solution phase (Flynn, D. L. et al., *Curr. Op. Drug. Disc. Dev.*, 1998, 1, 1367)) to generate large combinatorial libraries. For example, ethyl 5-iodo-2-furanylphosphonate can be coupled to Wang's resin under suitable coupling reaction conditions. The resin-coupled 5-iodo-2-[5-(O-ethyl-O-Wang's resin)phosphono]furan can then be subjected to transition metal catalyzed Suzuki and Stille reactions (as described above) with organoboranes and organotins in a parallel manner to give libraries of compounds of formula 3 wherein X is furan-2,5-diyl.

Substitution reactions are useful for the coupling of a heterocycle with a phosphonate diester component. For example, cyanuric chloride can be substituted with dialkyl mercaptoalkylphosphonates or dialkyl aminoalkylphosphonates to give compounds of formula 2 wherein R$^5$ is a 1,3,5-triazine, X is an alkylthio or an alkylamino group. Alkylation reactions are also used for the coupling of a heterocycle with a phosphonate diester component. For example, a heteroaromatic thiol (e.g. a 1,3,4-thiadiazole-2-thiol) can be alkylated with a dialkyl methylphosphonate derivative (e.g. ICH$_2$P(O)(OEt)$_2$, TsOCH$_2$P(O)(OEt)$_2$, TfOCH$_2$P(O)(OEt)$_2$) to lead to compounds of formula I wherein X is an alkylthio group. In another aspect, alkylation reactions of a heteroaromatic carboxylic acid (e.g. a thiazole-4-carboxylic acid) with a dialkyl methylphosphonate derivative,(e.g. ICH$_2$P(O)(OEt)$_2$, TsOCH$_2$P(O)(OEt)$_2$, TfOCH$_2$P(O)(OEt)$_2$) lead to compounds of formula I wherein X is an alkoxycarbonyl group, while alkylation reactions of a heteroaromatic thiocarboxylic acid (e.g. a thiazole-4-thiocarboxylic acid) with a dialkyl methylphosphonate derivative (e.g. ICH$_2$P(O)(OEt)$_2$, TsOCH$_2$P(O)(OEt)$_2$, TfOCH$_2$P(O)(OEt)$_2$) lead to compounds of formula I wherein X is an alkylthiocarbonyl group. Substitutions of haloalkyl heterocycles (e.g. 4-haloalkylthiazole) with nucleophiles containing the phosphonate group (diethyl hydroxymethylphosphonate) are useful for the preparation of compounds of formula I wherein X is an alkoxyalkyl or an alkylthioalkyl group. For example, compounds of formula I where X is a —CH$_2$OCH$_2$-group can be prepared from 2-chloromiethylpyridine or 4-chloromethylthiazole using dialkyl hydroxymethylphosphonates and a suitable base (e.g. sodium hydride). It is possible to reverse the nature of the nucleophiles and electrophiles for the substitution reactions, i.e. haloalkyl- and/or sulfonylalkylphosphonate esters can be substituted with heterocycles containing a nucleophile (e.g. a 2-hydroxyalkylpyridine, a 2-mercaptoalkylpyridine, or a 4-hydroxyalkyloxazole).

Known amide bond formation reactions (e.g. the acyl halide method, the mixed anhydride method, the carbodiimides method) can also be used to couple a heteroaromatic carboxylic acid with a phosphonate diester component leading to compounds of formula 4 wherein X is an alkylaminocarbonyl or an alkoxycarbonyl group. For example, couplings of a thiazole-4-carboxylic acid with a dialkyl aminoalkylphosphonate or a dialkyl hydroxyalkylphosphonate give compounds of formula 4 wherein R$^5$ is a thiazole, and X is an alkylaminocarbonyl or an alkoxycarbonyl group. Alternatively, the nature of the coupling partners can be reversed to give compounds of formula 4 wherein X is an alkylcarbonylamino group. For example, 2-aminothiazoles can be coupled with (RO)$_2$P(O)-alkyl-CO$_2$H (e.g. diethylphosphonoacetic acid) under these reaction conditions to give compounds of formula 4 wherein R$^5$ is a thiazole and X is an alkylcarbonylamino group. These reactions are also useful for parallel synthesis of compound libraries through combinatorial chemistry on solid phase or in solution phase. For example, $HOCH_2P(O)(OEt)(O\text{-resin})$, $H_2NCH_2P(O)(OEt)(O\text{-resin})$ and $HOOCCH_2P(O)(OEt)(O\text{-resin})$ (prepared using known methods) can be coupled to various heterocycles using the above described reactions to give libraries of compounds of formula 3 wherein X is a —C(O)OCH$_2$—, or a —C(O)NHCH$_2$—, or a —NHC(O)CH$_2$—.

Rearrangement reactions can also be used to prepare compounds covered in the present invention. For example, the Curtius's rearrangement of a thiazole-4-carboxylic acid in the presence of a dialkyl hydroxyalkylphosphonate or a dialkyl aminoalkylphosphonate lead to compounds of formula 4 wherein X is an alkylaminocarbonylamino or an alkoxycarbonylamino group. These reactions can also be adopted for combinatorial synthesis of various libraries of compounds of formula 3. For example, Curtius's rearrangement reactions between a heterocyclic carboxylic acid and $OCH_2P(O)(OEt)(O\text{-resin})$, or $H_2NCH_2P(O)(OEt)(O\text{-resin})$ can lead to libraries of compounds of formula I wherein X is a —NHC(O)OCH$_2$—, or a —NHC(O)NHCH$_2$—.

For compounds of formula V wherein X is an alkyl group, the phosphonate group can be introduced using other common phosphonate formation methods such as Michaelis-Arbuzov reaction (Bhattacharya et al., *Chem. Rev.*, 1981, 81: 415), Michaelis-Becker reaction (Blackburn et al., *J. Organomet. Chem.*, 1988, 348: 55), and addition reactions of phosphorus to electrophiles (such as aldehydes, ketones, acyl halides, imines and other carbonyl derivatives).

Phosphonate component can also be introduced via lithiation reactions. For example, lithiation of an 2-ethynylpyridine using a suitable base followed by trapping the thus generated anion with a dialkyl chlorophosphonate lead to compounds of formula 3 wherein R5 is a pyridyl, X is a 1-(2-phosphono)ethynyl group.

(5) Construction of a Heterocycle

Although existing heterocycles are useful for the synthesis of compounds of formula V, when required, heterocycles can also be constructed leading to compounds in the current invention, and in some cases may be preferred for the preparations of certain compounds. The construction of heterocycles have been well described in the literature using a variety of reaction conditions (Joule et al., *Heterocyclic Chemistry*; Chapman hall, London, 1995; Boger, Weinreb, *Hetero Diels-Alder Methodology In Organic Synthesis*; Academic press, San Diego, 1987; Padwa, *1,3-Dipolar Cycloaddition Chemistry*; Wiley, N.Y., 1984; Katritzsky et al., *Comprehensive Heterocyclic Chemistry*; Pergamon press, Oxford; Newkome et al., *Contemporary Heterocyclic Chemistry: Syntheses, Reaction and Applications*; Wiley, N.Y., 1982; *Syntheses of Heterocyclic Compounds*; Consultants Bureau, New York). Some of the methods which are useful to prepare compounds in the present invention are given as examples in the following discussion.

(i) Construction of a Thiazole Ring System

Thiazoles useful for the present invention can be readily prepared using a variety of well described ring-forming reactions (Metzger, *Thiazole and its derivatives, part* 1 and part 2; Wiley & Sons, New York, 1979). Cyclization reactions of thioamides (e.g. thioacetamide, thiourea) and alpha-halocarbonyl compounds (such as alpha-haloketones, alpha-haloaldehydes) are particularly useful for the construction of a thiazole ring system. For example, cyclization reactions between thiourea and 5-diethylphosphono-2-[(-2-bromo-1-oxo)alkyl]furans are useful for the synthesis of compounds of formula 2 wherein $R^5$ is a thiazole, A is an amino group and X is a furan-2,5-diyl group; cyclization reaction between thiourea and a bromopyruvate alkyl ester give a 2-amino-4-alkoxycarbonylthiazole which is useful for the preparations of compounds of formula 2 wherein R5 is a thiazole and X is an alkylaminocarbonyl, an alkoxycarbonyl, an alkylaminocarbonylamino, or an alkoxyacarbonylamino group. Thioamides can be prepared using reactions reported in the literature (Trost, *Comprehensive organic synthesis*, Vol. 6,; Pergamon press, New York, 1991, pages 419–434) and alpha-halocarbonyl compounds are readily accessible via conventional reactions (Larock, *Comprehensive organic transformations*, VCH, New York, 1989). For example, amides can be converted to thioamides using Lawesson's reagent or $P_2S_5$, and ketones can be halogenated using various halogenating reagents (e.g. NBS, $CuBr_2$).

(ii) Construction of an Oxazole Ring System

Oxazoles useful for the present invention can be prepared using various methods in the literature (Turchi, *Oxazoles*; Wiley & Sons, New York, 1986). Reactions between isocyanides (e.g. tosylmethylisocyanide) and carbonyl compounds (e.g. aldehydes and acyl chlorides) can be used to construct oxazole ring systems (van Leusen et al, *Tetrahedron Lett.*, 1972, 2369). Alternatively, cyclization reactions of amides (e.g. urea, carboxamides) and alpha-halocarbonyl compounds are commonly used for the construction of an oxazole ring system. For example, the reactions of urea and 5-diethylphosphono-2-[(-2-bromo-1-oxo)alkyl]furans are useful for the synthesis of compounds of formula 2 wherein $R^5$ is an oxazole, A is an amino group and X is a furan-2,5-diyl group. Reactions between amines and imidates are also used to construct the oxazole ring system (Meyers et al, *J. Org. Chem.*, 1986, 51(26), 5111).

(iii) Construction of a Pyridine Ring System

Pyridines useful for the synthesis of compounds of formula I can be prepared using various known synthetic methods (Klingsberg, Pyridine and Its Derivatives; Interscience Publishers, New York, 1960-1984). 1,5-Dicarbonyl compounds or their equivalents can be reacted with ammonia or compounds which can generate ammonia to produce 1,4-dihydropyridines which are easily dehydrogenated to pyridines. When unsaturated 1,5-dicarbonyl compounds, or their equivalents (e.g. pyrylium ions) are used to react with ammonia, pyridines can be generated directly. 1,5-Dicarbonyl compounds or their equivalents can be prepared using conventional chemistry. For example, 1,5-diketones are accessible via a number of routes, such as Michael addition of an enolate to an enone (or precursor Mannich base (Gill et al, *J. Am. Chem. Soc.*, 1952, 74, 4923)), ozonolysis of a cyclopentene precursor, or reaction of silyl enol ethers with 3-methoxyallylic alcohols (Duhamel et al, *Tetrahedron*, 1986, 42, 4777). When one of the carbonyl carbons is at the acid oxidation state, then this type of reaction produces 2-pyridones which can be readily converted to 2-halopyridines (Isler et al, *Helv. Chim. Acta*, 1955, 38, 1033) or 2-aminopyridines (Vorbruggen et al, *Chem. Ber.*, 1984, 117, 1523). Alternatively, a pyridine can be prepared from an aldehyde, a 1,3-dicarbonyl compound and ammonia via the classical Hantzsch synthesis (Bossart et al, *Angew. Chem. Int. Ed. Engl.*, 1981, 20, 762). Reactions of 1,3-dicarbonyl compounds (or their equivalents) with 3-amino-enones or 3-amino-nitriles have also been used to produce pyridines (such as the Guareschi synthesis, Mariella, *Org. Synth., Coll. Vol. IV*, 1963, 210). 1,3-Dicarbonyl compounds can be made via oxidation reactions on corresponding 1,3-diols or aldol reaction products (Mukaiyama, *Org, Reactions*, 1982, 28, 203). Cycloaddition reactions have also been used for the synthesis of pyridines, for example cycloaddition reactions between oxazoles and alkenes (Naito et al., *Chem. Pharm. Bull.*, 1965, 13, 869), and Diels-Alder reactions between 1,2,4-triazines and enamines (Boger et al., *J. Org. Chem.*, 1981, 46, 2179).

(iv) Construction of a Pyrimidine Ring System

Pyrimidine ring systems useful for the synthesis of compounds of formula V-2 are readily available (Brown, The pyrimidines; Wiley, N.Y., 1994). One method for pyrimidine synthesis involves the coupling of a 1,3-dicarbonyl component (or its equivalent) with an N—C—N fragment. The selection of the N—C—N component—urea (Sherman et al., *Org. Synth., Coll. Vol. IV*, 1963, 247), amidine (Kenner et al., *J. Chem. Soc.*, 1943, 125) or guanidine (Burgess, *J. Org. Chem.*, 1956, 21, 97; VanAllan, *Org. Synth., Coll. Vol. IV*, 1963, 245)—governs the substitution at C-2 in the pyrimidine products. This method is particular useful for the synthesis of compounds of formula V-2 with various A groups. In another method, pyrimidines can be prepared via cycloaddition reactions such as aza-Diels-Alder reactions between a 1,3,5-triazine and an enamine or an ynamine (Boger et al., *J. Org. Chem.*, 1992, 57, 4331 and references cited therein).

(v) Construction of an Imidazole Ring System

Imidazoles useful for the synthesis of compounds of formula V-1 are readily prepared using a variety of different synthetic methodologies. Various cyclization reactions are generally used to synthesize imidazoles such as reactions between amidines and alpha-haloketones (Mallick et al, *J. Am. Chem. Soc.*, 1984, 106(23), 7252) or alpha-hydroxyketones (Shi et al, *Synthetic Comm.*, 1993, 23(18), 2623), reactions between urea and alpha-haloketones, and reactions between aldehydes and 1,2-dicarbonyl compounds in the presence of amines.

(vi) Construction of an Isoxazole Ring System

Isoxazoles useful for the synthesis of compounds of formula V-1 are readily synthesized using various methodologies (such as cycliaddition reactions between nitrile oxides and alkynes or active methylene compounds, oximation of 1,3-dicarbonyl compounds or alpha, beta-acetylenic carbonyl compounds or alpha,beta-dihalocarbonyl compounds, etc.) can be used to synthesize an isoxazole ring system (Grunanger et al., *Isoxazoles*; Wiley & Sons, New York, 1991). For example, reactions between alkynes and 5-diethylphosphono-2-chlorooximidofuran in the presence of base (e.g. triethylamine, Hunig's base,. pyridine) are useful for the synthesis of compounds of formula 2 wherein $R^5$ is an isoxazole and X is a furan-2,5-diyl group.

(vii) Construction of a Pyrazole Ring System

Pyrazoles useful for the synthesis of compounds of formula V-1 are readily prepared using a variety of methods (Wiley, *Pyrazoles, Pyrazolines, Pyrazolidines, Indazoles, and Condensed Rings*; Interscience Publishers, New York, 1967) such as reactions between hydrazines and 1,3-dicarbonyl compounds or 1,3-dicarbonyl equivalents (e.g. one of the carbonyl group is masked as an enamine or ketal or acetal), and additions of hydrazines to acrylonitriles followed by cyclization reactions (Dorn et al, *Org. Synth.*, 1973, *Coll. Vol. V*, 39). Reaction of 2-(2-alkyl-3-N,N-dimethylamino)acryloyl-5-diethylphosphonofurans with hydrazines are useful for the synthesis of compounds of formula I wherein $R^5$ is a pyrazole, X is a furan-2,5-diyl group and B" is an alkyl group.

(viii) Construction of a 1,2.4-Triazole Ring System 1,2,4-Triazoles useful for the synthesis of compounds of formula V-1 are readily available via various methodologies (Montgomery, 1,2,4-Triazoles; Wiley, N.Y., 1981). For example, reactions between hydrazides and imidates or thioimidates (Sui et al, *Bioorg. Med. Chem. Lett.*, 1998, 8, 1929; Catarzi et al, *J. Med. Chem.*, 1995, 38(2), 2196), reactions between 1,3,5-triazine and hydrazines (Grundmann et al, *J. Org. Chem.*, 1956, 21, 1037), and reactions between aminoguanidine and carboxylic esters (Ried et al, *Chem. Ber.*, 1968, 101, 2117) are used to synthesize 1,2,4-triazoles.

(6) Ring Closure to Construct a Heterocycle with a Phosphonate

Compounds of formula 4 can also be prepared using a ring closure reaction to construct the heterocycle from precursors that contain the phosphonate component. For example, cyclization reactions between thiourea and 5-diethylphosphono-2-[(-2-bromo-1-oxo)alkyl]furans are useful for the synthesis of compounds of formula 2 wherein $R^5$ is a thiazole, A is an amino group and X is a furan-2,5-diyl group. Oxazoles of the present invention can also be prepared using a ring closure reaction. In this case, reactions of urea and 5-diethylphosphono-2-[(-2-bromo-1-oxo)alkyl] furans are useful for the synthesis of compounds of formula I wherein $R^5$ is an oxazole, A is an amino group and X is a furan-2,5-diyl group. Reactions between 5-diethylphosphono-2-furaldehyde, an alkyl amine, a 1,2-diketone and ammonium acetate are useful to synthesize compounds of formula 2 wherein $R^5$ is an imidazole and X is a furan-2,5-diyl group. These types of ring closure reactions can also be used for the synthesis of pyridines or pyrimidines useful in the present invention. For example, reaction of 5-diethylphosphono-2-[3-dimethylamino-2-alkyl)acryloyl]furans and cyanoacetamide in the presence of base gives 5-alkyl-3-cyano-6-[2-(5-diethylphosphono) furanyl]-2-pyridones (Jain et al., *Tetrahedron Lett.*, 1995, 36, 3307). Subsequent conversion of these 2-pyridones to the corresponding 2-halopyridines (see references cited in section 3 for the modifications of heterocycles) will lead to compounds of formula I wherein $R^5$ is a pyridine, A is a halo group, X is a furan-2,5-diyl group, and B is an alkyl group. Reactions of 5-diethylphosphono-2-[3-dimethylamino-2-alkyl)acryloyl]furans and amidines in the presence of base give 5-alkyl-6-[2-(5-diethylphosphono)-furanyl] pyrimidines which will lead to compounds of formula 2 wherein $R^5$ is a pyrimidine, X is a furan-2,5-diyl group and B is an alkyl group.

(7) Preparation of Various Precursors useful for Cyclization Reactions

Intermediates required for the synthesis of compounds in the present invention are generally prepared using either an existing method in the literature or a modification of an existing method. Syntheses of some of the intermediates useful for the synthesis of compounds in the present invention are described herein.

Various aryl phosphonate dialkyl esters are particularly useful for the synthesis of compounds of formula I. For example, compounds of formula 3 wherein X is a furan-2, 5-diyl group can be prepared from a variety of furanyl precursors. It is envisioned that synthesis of other precursors may follow some or all of these reaction steps, and some modifications of these reactions may be required for different precursors. 5-Dialkylphosphono-2-furancarbonyl compounds (e.g. 5-diethylphosphono-2-furaldehyde, 5-diethylphosphono-2-acetylfuran) are well suited for the synthesis of compounds of formula I wherein X is a furan-2,5-diyl group. These intermediates are prepared from furan or furan derivatives using conventional chemistry such as lithiation reactions, protection of carbonyl groups and deprotection of carbonyl groups. For example, lithiation of furan using known methods (Gschwend *Org. React.* 1979, 26: 1) followed by addition of phosphorylating agents (e.g.

ClPO$_3$R$_2$) gives 2-dialkylphosphono-furans (e.g. 2-diethylphosphonofuran). This method can also be applied to a 2-substituted furan (e.g. 2-furoic acid) to give a 5-dialkylphosphono-2-substituted furan (e.g. 5-diethylphosphono-2-furoic acid). It is envisioned that other aryl phosphonate esters can also be prepared using this approach or a modification of this approach. Alternatively, other methods such as transition metal catalyzed reactions of aryl halides or triflates (Balthazar et al. *J. Org. Chem.*, 1980, 45: 5425; Petrakis et al. *J. Am. Chem. Soc.*, 1987, 109: 2831; Lu et al. *Synthesis*, 1987, 726) are used to prepare aryl phosphonates. Aryl phosphonate esters can also be prepared from aryl phosphates under anionic rearrangement conditions (Melvin, *Tetrahedron Lett.*, 1981, 22: 3375; Casteel et al. *Synthesis*, 1991, 691). N-Alkoxy aryl salts with alkali metal derivatives of dialkyl phosphonate provide another general synthesis for heteroaryl-2-phosphonate esters (Redmore *J. Org. Chem.*, 1970, 35: 4114).

A second lithiation step can be used to incorporate a second group on the aryl phosphonate dialkyl ester such as an aldehyde group, a trialkylstannyl or a halo group, although other methods known to generate these functionalities (e.g. aldehydes) can be envisioned as well (e.g. Vilsmeier-Hack reaction or Reimar-Teimann reaction for aldehyde synthesis). In the second lithiation step, the lithiated aromatic ring is treated with reagents that either directly generate the desired functional group (e.g. for an aldehyde using DMF, HCO$_2$R, etc.) or with reagents that lead to a group that is subsequently transformed into the desired functional group using known chemistry (e.g. alcohols, esters, nitriles, alkenes can be transformed into aldehydes). For example, lithiation of a 2-dialkylphosphonofuran (e.g. 2-diethylphosphonofuran) under normal conditions (e.g. LDA in THF) followed by trapping of the thus generated anion with an electrophile (e.g. tributyltin chloride or iodine) produces a 5-functionalized-2-dialkylphosphonofuran (e.g. 5-tributylstannyl-2-diethylphosphonofuran or 5-iodo-2-diethylphosphonofuran). It is also envisioned that the sequence of these reactions can be reversed, i.e. the aldehyde moiety can be incorporated first followed by the phosphorylation reaction. The order of the reaction will be dependent on reaction conditions and protecting groups. Prior to the phosphorylation, it is also envisioned that it may be advantageous to protect some of these functional groups using a number of well-known methods (e.g. protection of aldehydes as acetals, aminals; protection of ketones as ketals). The protected functional group is then unmasked after phosphorylation. (*Protective groups in Organic Synthesis*, Greene, T. W., 1991, Wiley, N.Y.). For example, protection of 2-furaldehyde as 1,3-propanediol acetal followed by a lithiation step (using for example LDA) and trapping the anion with a dialkyl chlorophosphate (e.g. diethyl chlorophosphate), and subsequent deprotection of the acetal functionality under normal deprotection conditions produces the 5-dialkylphosphono-2-furaldehyde (e.g. 5-diethylphosphono-2-furaldehyde). Another example is the preparation of 5-keto-2-dialkylphosphonofurans which encompass the following steps: acylations of furan under Friedel-Crafts reaction conditions give 2-ketofuran, subsequent protection of the ketone as ketals (e.g. 1,3-propanediol cyclic ketal) followed by a lithiation step as described above gives the 5-dialkylphosphono-2-furanketone with the ketone being protected as a 1,3-propanediol cyclic ketal, and final deprotection of the ketal under, for example, acidic conditions gives 2-keto-5-dialkylphosphonofurans (e.g. 2-acetyl-5-diethylphosphonofuran). Alternatively, 2-ketofurans can be synthesized via a palladium catalyzed reaction between 2-trialkylstannylfurans (e.g. 2-tributylstannylfuran) and an acyl chloride (e.g. acetyl chloride, isobutyryl chloride). It is advantageous to have the phosphonate moiety present in the 2-trialkylstannylfurans (e.g. 2-tributylstannyl-5-diethylphosphonofuran). 2-Keto-5-dialkylphosphonofurans can also be prepared from a 5-dialkylphosphono-2-furoic acid (e.g. 5-diethylphosphono-2-furoic acid) by conversion of the acid to the corresponding acyl chloride and followed by additions of a Grignard reagent.

Some of the above described intermediates can also be used for the synthesis of other useful intermediates. For example, a 2-keto-5-dialkylphosphonofuran can be further converted to a 1,3-dicarbonyl derivative which is useful for the preparation of pyrazoles, pyridines or pyrimidines. Reaction of a 2-keto-5-dialkylphosphonofuran (e.g. 2-acetyl-5-diethylphosphonofuran) with a dialkylformamide dialkyl acetal (e.g. dimethylformamide dimethyl acetal) gives a 1,3-dicarbonyl equivalent as a 2-(3-dialkylamino-2-alkyl-acryloyl)-5-dialkylphosphonofuran (e.g. 2-(3-dimethylaminoacryloyl)-5-diethylphosphonofuran).

It is envisioned that the above described methods for the synthesis of furan derivatives can be either directly or with some modifications applied to syntheses of various other useful intermediates such as aryl phosphonate esters (e.g. thienyl phosphonate esters, phenyl phosphonate esters or pyridyl phosphonate esters).

It is conceivable that when applicable the above described synthetic methods can be adopted for parallel synthesis either on solid phase or in solution to provide rapid SAR (structure activity relationship) exploration of FBPase inhibitors encompassed in the current invention, provided method development for these reactions are successful.

Section 2.

Synthesis of Compounds of Formula X

Synthesis of the compounds encompassed by the present invention typically includes some or all of the following general steps: (1) preparation of a phosphonate prodrug ; (2) deprotection of a phosphonate ester; (3) construction of a heterocycle; (4) introduction of a phosphonate component; (5) synthesis of an aniline derivative. Step (1) and step (2) were discussed in section 1, and discussions of step (3), step (4) and step (5) are given below. These methods are also generally applicable to compounds of Formula X.

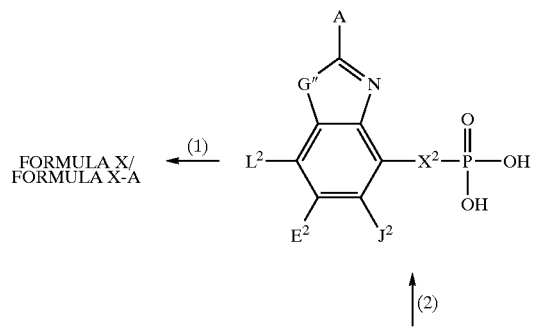

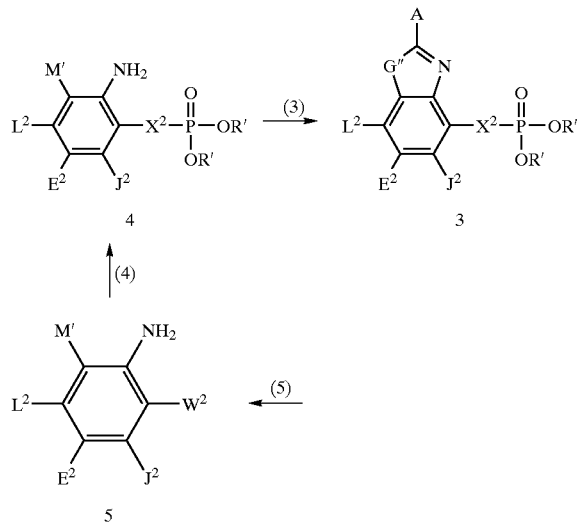

(3) Construction of a Heterocycle
  (i) Benzothiazole Ring System
  Compounds of formula 3 wherein G"=S, i.e. benzothiazoles, can be prepared using various synthetic methods reported in the literature. Two of these methods are given as examples as discussed below. One method is the modification of commercially available benzothiazole derivatives to give the appropriate functionality on the benzothiazole ring. Another method is the annulation of various anilines (e.g. compounds of formula 4) to construct the thiazole portion of the benzothiazole ring. For example, compounds of formula 3 wherein G"=S, A=NH$_2$, L$^2$,E$^2$,J$^2$=H, X$^2$=CH$_2$O, and R'=Et can be prepared from the commercially available 4-methoxy-2-amino thiazole via a two-step sequence: conversion 4-methoxy-2-aminobenzothiazole to 4-hydroxy-2-aminobenzothiazole with reagents such as BBr$_3$ (Node, M.; et al J. Org. Chem. 45, 2243–2246, 1980) or AlCl$_3$ in presence of a thiol (e.g. EtSH) (McOmie, J. F. W.; et al. Org. Synth., Collect. Vol. V, 412, 1973) followed alkylation of the phenol group with diethylphosphonomethyl trifluoromethylsulfonate (Phillion, D. P.; et al. Tetrahedron Lett. 27, 1477–1484, 1986) in presence of a suitable base (e.g. NaH) in polar aprotic solvents (e.g. DMF) provide the required compound.

Several methods can be used to convert various anilines to benzothiazoles (Sprague, J. M.; Land, A. H. Heterocycle. Compd. 5, 506–13, 1957). For example, 2-aminobezothiazoles (formula 3 wherein A=NH2) can be prepared by annulation of compounds of formula 4 wherein W$^2$=H, using various common methods. One method involves the treatment of a suitably substituted aniline with a mixture of KSCN and CuSO$_4$ in methanol to give a substituted 2-aminobenzothiazole (Ismail, I. A.; Sharp, D. E; Chedekel, M. R. J. Org. Chem. 45, 2243–2246, 1980). Alternatively, a 2-aminobenzothiazole can also be prepared by the treatment of Br$_2$ in presence of KSCN in acetic acid (Patil, D. G.; Chedekel, M. R. J. Org. Chem. 49, 997–1000, 1984). This reaction can also be done in two step sequence. For example treatment of substituted phenylthioureas with Br$_2$ in CHCl$_3$ gives substituted 2-aminobenzothiazoles (Patil, D. G.; Chedekel, M. R. J. Org. Chem. 49, 997–1000, 1984). 2-Aminobenzothiazoles can also be made by condensation of ortho iodo anilines with thiourea in presence of Ni catalyst (NiCl$_2$ (PPh$_3$)$_2$) (Takagi, K. Chem. Lett. 265–266, 1986).

Benzothiazoles can undergo electrophilic aromatic substitution to give 6-substituted benzothiazoles (Sprague, J. M.; Land, A. H. Heterocycle. Compd. 5, 606–13, 1957). For example bromination of formula 3 wherein G"=S, A=NH$_2$, L$^2$,E$^2$,J$^2$=H, X$^2$=CH$_2$O and R'=Et with bromine in polar solvents such as AcOH gave compound of formula 3 wherein E$^2$=Br.

Furthermore, compounds of formula 3 wherein A is a halo, H, alkoxy, alkylthio or an alkyl can be prepared from the corresponding amino compound (Larock, Comprehensive organic transformations, VCH, New York, 1989; Trost, Comprehensive organic synthesis; Pergamon press, New York, 1991).

(ii) Benzoxazoles
  Compounds of formula 3 wherein G"=O, i.e. benzoxazoles, can be prepared by the annulation of ortho aminophenols with suitable reagent (e.g. cyanogen halide (A=NH$_2$; Alt, K. O.; et al J. Heterocyclic., Chem. 12, 775, 1975) or acetic acid (A=CH3; Saa, J. M.; J. Org. Chem. 57, 589–594, 1992) or trialkyl orthoformate (A=H; Org. Prep. Proced. Int., 22, 613,1990)).

(4) Introduction of a Phosphonate Component
  Compounds of formula 4 (wherein X$^2$=CH$_2$O and R'=alkyl) can made in different ways (e.g. using alkylation and nucleophilic substitution reactions). Typically, compounds of formula 5 wherein M'=OH is treated with a suitable base (e.g. NaH) in polar aprotic solvent (e.g. DMF, DMSO) and the resulting phenoxide anion can be alkylated with a suitable electrophile preferably with a phosphonate component present (e.g. diethyl iodomethylphosphonate, diethyl trifluoromethylsulphonomethyl phosphonate, diethyl p-methyltoluenesulphonomethylphosphonate). The alkylation method can also be applied to the precursor compounds to compounds of formula 5 wherein a phenol moiety is present and it can be alkylated with a phosphonate containing component. Alternately, compounds of formula 4 can also be made from the nucleophilic substitution of the precursor compounds to compounds of formula 5 (wherein a halo group, preferably a fluoro or a chloro, is present ortho to a nitro group). For example, a compound of formula 4 (wherein X$^2$=CH2O and R'=Et) can be prepared from a 2-chloro-1-nitrobenzene derivative by treatment with NaOCH$_2$P(O)(OEt)$_2$ in DMF. Similarly, compounds of formula 4 where X$^2$=-alkyl-S— or -alkyl-N— can also be made.

(5) Synthesis of an Aniline Derivative
  Numerous synthetic methods have been reported for the synthesis of aniline derivatives, these methods can be applied to the synthesis of useful intermediates which can lead to compounds of formula X. For example, various alkenyl or aryl groups can be introduced on to a benzene ring via transition metal catalyzed reactions (Kasibhatla, S. R., et al. WO 98/39343 and the references cited in); anilines can be prepared from their corresponding nitro derivatives via reduction reactions (e.g. hydrogenation reactions in presence of 10% Pd/C, or reduction reactions using SnCl$_2$ in HCl (Patil, D. G.; Chedekel, M. R. J. Org. Chem. 49, 997–1000, 1984)).

EXAMPLES

Example 1

Preparation of 5-diethylphosphono-2-furaldehyde (1).

Step A. A solution of 2-furaldehyde diethyl acetal (1 mmole) in THF (tetrahydrofuran) was treated with nBuLi (1 mmole) at −78° C. After 1 h, diethyl chlorophosphate (1.2 mmole) was added and the reaction was stirred for 40 min. Extraction and evaporation gave a brown oil.

Step B. The resulting brown oil was treated with 80% acetic acid at 90° C. for 4 h. Extraction and chromatography gave compound 1 as a clear yellow oil. Alternatively this aldehyde can be prepared from furan as described below.

Step C. A solution of furan (1 mmole) in diethyl ether was treated with TMEDA (N,N,N'N'-tetramethylethylenediamine) (1 mmole) and nBuLi (2 mmole) at −78° C. for 0.5 h. Diethyl chlorophosphate (1.2 mmole) was added to the reaction mixture and stirred for another hour. Extraction and distillation gave diethyl 2-furanphosphonate as a clear oil.

Step D. A solution of diethyl 2-furanphosphonate (1 mmole) in THF was treated with LDA (1.12 mmole, lithium N,N-diisopropylamide) at −78° C. for 20 min. Methyl formate (1.5 mmole) was added and the reaction was stirred for 1 h. Extraction and chromatography gave compound 1 as a clear yellow oil. Preferably this aldehyde can be prepared from 2-furaldehyde as described below.

Step E. A solution of 2-furaldehyde (1 mmole) and N,N'-dimethylethylene diamine (1 mmole) in toluene was refluxed while the resulting water being collected through a Dean-Stark trap. After 2 h the solvent was removed in vacuo and the residue was distilled to give furan-2-(N,N'-dimethylimidazolidine) as a clear colorless oil. bp 59–61° C. (3 mm Hg).

Step F. A solution of furan-2-(N,N'-dimethylimidazolidine) (1 mmole) and TMEDA (1 mmole) in THF was treated with nBuLi (1.3 mmole) at −40 to −48° C. The reaction was stirred at 0° C. for 1.5 h and then cooled to −55° C. and treated with a solution of diethylchlorophosphate (1.1 mmole) in THF. After stirring at 25° C. for 12 h the reaction mixture was evaporated and subjected to extraction to give 5-diethylphosphono-furan-2-(N,N'-dimethylimidazolidine) as a brown oil.

Step G. A solution of 5-diethylphosphonofuran-2-(N,N'-dimethyl-imidazolidine) (1 mmole) in water was treated with concentrated sulfuric acid until pH=1. Extraction and chromatography gave compound 1 as a clear yellow oil.

Example 2

Preparation of 5-diethylphosphono-2-[(1-oxo)alkyl]furans and 6-diethylphosphono2-[(1-oxo)alkyl]pyridines.

Step A. A solution of furan (1.3 mmole) in toluene was treated with 4-methyl pentanoic acid (1 mmole), trifluoroacetic anhydride (1.2 mmole) and boron trifluoride etherate (0.1 mmole) at 56° C. for 3.5 h. The cooled reaction mixture was quenched with aqueous sodium bicarbonate (1.9 mmole), filtered through a celite pad. Extraction, evaporation and distillation gave 2-[(4-methyl-1-oxo)pentyl)furan as a brown oil (bp 65–77° C., 0.1 mmHg).

Step B. A solution of 2-[(4-methyl-1-oxo)pentyl]furan (1 mmole) in benzene was treated with ethylene glycol (2.1 mmole) and p-toluenesulfonic acid (0.05 mmole) at reflux for 60 h while removing water via a Dean-Stark trap. Triethyl orthoformate (0.6 mmole) was added and resulting mixture was heated at reflux for an additional hour. Extraction and evaporation gave 2-(2-furanyl)-2-[(3-methyl)butyl]-1,3-dioxolane as an orange liquid.

Step C. A solution of 2-(2-furanyl)-2-[(3-methyl)butyl]-1,3-dioxolane (1 mmole) in THF was treated with TMEDA (1 mmole) and nBuLi (1.1 mmole) at −45° C., and the resulting reaction mixture was stirred at −5 to 0° C. for 1 h. The resulting reaction mixture was cooled to −45° C., and cannulated into a solution of diethyl chlorophosphate in THF at −45° C. The reaction mixture was gradually warmed to ambient temperature over 1.25 h. Extraction and evaporation gave 2-[2-(5-diethylphosphono)furanyl]-2-[(3-methyl)butyl]-1,3-dioxolane as a dark oil.

Step D. A solution of 2-[2-(5-diethylphosphono)furanyl]-2-[(3-methyl)butyl]-1,3-dioxolane (1 mmole) in methanol was treated with 1 N hydrochloric acid (0.2 mmole) at 60° C. for 18 h. Extraction and distillation gave 5-diethylphosphono-2-[(4-methyl-1-oxo)pentyl]furan (2.1) as a light orange oil (bp 152–156° C., 0.1 mmHg).

The following compounds were prepared according to this procedure:

(2.2) 5-diethylphosphono-2-acetylfuran: bp 125–136° C., 0.1 mmHg.

(2.3) 5-diethylphosphono-2-[(1-oxo)butyl]furan: bp 130–145° C., 0.08 mmHg.

Alternatively these compounds can be prepared using the following procedures:

Step E. A solution of 2-[(4-methyl-1-oxo)pentyl]furan (1 mmole, prepared as in Step A) in benzene was treated with N,N-dimethyl hydrazine (2.1 mmole) and trifluoroacetic acid (0.05 mmole) at reflux for 6 h. Extraction and evaporation gave 2-[(4-methyl-1-oxo)pentyl]furan N,N-dimethyl hydrazone as a brown liquid.

Step F. 2-[(4-Methyl-1-oxo)pentyl]furan N,N-dimethyl hydrazone was subjected to the procedures of Step C to give 2-[(4-methyl-1-oxo)pentyl]-5-diethylphosphonofuran N,N-dimethyl hydrazone as a brown liquid which was treated with copper (II) chloride (1.1 equivalent) in ethanol-water at 25° C. for 6 h. Extraction and distillation gave compound 2.1 as a light orange oil.

Some of 5-diethylphosphono-2-[(1-oxo)alkyl]furans are prepared using the following procedures:

Step G. A solution of compound 1(1 (mmole) and 1,3-propanedithiol (1.1 mmole) in chloroform was treated with borontrifluoride etherate (0.1 mmole) at 25° C. for 24 h. Evaporation and chromatography gave 2-(2-(5-diethylphosphono)furanyl)-1,3-dithiane as a light yellow oil.

A solution of 2-(2-(5-diethylphosphono)furanyl)-1,3-dithiane (1 mmole) in THF was cooled to −78° C. and treated with nBuLi (1.2 mmole). After 1 h. at −78° C. the reaction mixture was treated with cyclopropanemethyl bromide and reaction was stirred at −78° C. for another hour. Extraction and chromatography gave 2-(2-(5-diethylphosphono)furanyl)-2-cyclopropanemethyl-1,3-dithiane as an oil.

A solution of 2-(2-(5-diethylphosphono)furanyl)-2-cyclopropanemethyl-1,3-dithiane (1 mmole) in acetonitrile—water was treated with [bis(trifluoroacetoxy)iodo]benzene,(2 mmole) at 25° C. for 24 h. Extraction and chromatography gave 5-diethylphosphono-2-(2-cyclopropylacetyl)furan as a light orange oil.

The following compounds were prepared according to this procedure: (2.4) 5-Diethylphosphono-2-(2-ethoxycarbonylacetyl)furan (2.5) 5-Diethylphosphono-2-(2-methylthioacetyl)furan (2.6) 6-Diethylphosphono-2-acetylpyridine Example 3

Preparation of 4-[2-(5-phosphono)furanyl]thiazoles, 4-[2-(6-phosphono)pyridyl]thiazoles and 4-[2-(5-phosphono)furanyl]selenazoles Step A. A solution of compound 2.1 (1 mmole) in ethanol was treated with copper (II) bromide (2.2 mmole) at reflux for 3 h. The cooled reaction mixture was filtered and the filtrate was evaporated to dryness. The resulting dark oil was purified by chromatography to give 5-diethylphosphono-2-[(2-bromo-4-methyl-1-oxo)pentyl]furan as an orange oil.

Step B. A solution of 5-diethylphosphono-2-[(2-bromo-4-methyl-1-oxo)pentyl]furan (1 mmole) and thiourea (2 mmole) in ethanol was heated at reflux for 2 h. The cooled reaction mixture was evaporated to dryness and the resulting yellow foam was suspended in saturated sodium bicarbonate and water (pH=8). The resulting yellow solid was collected through filtration to give 2-amino-5-isobutyl-4-[2-(5-diethylphosphono)furanyl]thiazole.

Step C. A solution of 2-amino-5-isobutyl-4-[2-(5-diethylphosphono)-furanyl]thiazole (1 mmole) in methylene chloride was treated with bromotrimethylsilane (10 mmole) at 25° C. for 8 h. The reaction mixture was evaporated to dryness and the residue was suspended in water. The resulting solid was collected through filtration to give 2-amino-5-isobutyl-4-[2-(5-phosphono)furanyl]thiazole (3.1) as an off-white solid. mp>250° C. Anal. calcd. for $C_{11}H_{15}N_2O_4PS+1.25HBr$: C: 32.75; H: 4.06; N: 6.94. Found: C: 32.39; H: 4.33; N: 7.18.

According to the above procedures or in some cases with minor modifications of these procedures using conventional chemistry the following compounds were prepared:

(3.2) 2-Methyl-5-isobutyl-4-[2-(5-phosphono)furanyl]thiazole. Anal. calcd. for $C_{12}H_{16}NO_4PS+HBr+0.1CH_2Cl_2$: C: 37.20; H: 4.44; N: 3.58. Found: C: 37.24; H: 4.56; N: 3.30.

(3.3) 4-[2-(5-Phosphono)furanyl]thiazole. Anal. calcd. for $C_7H_6NO_4PS+0.65$ HBr: C: 29.63; H: 2.36; N: 4.94. Found: C: 29.92; H: 2.66; N: 4.57.

(3.4) 2-Methyl-4-[2-(5-phosphono)furanyl]thiazole. mp 235–236° C. Anal. calcd. for $C_8H_8NO_4PS+0.25H_2O$: C: 38.48; H: 3.43; N: 5.61. Found: C: 38.68; H: 3.33; N: 5.36.

(3.5) 2-Phenyl-5-isobutyl-4-[2-(5-phosphono)furanyl]thiazole. Anal. calcd. for $C_{17}H_{18}NO_4PS+HBr$: C: 45.96; H: 4.31; N: 3.15. Found: C: 45.56; H: 4.26; N: 2.76.

(3.6) 2-Isopropyl-4-[2-(5-phosphono)furanyl]thiazole. mp 194–197° C. Anal. calcd. for $C_{10}H_{12}NO_4PS$: C: 43.96; H: 4.43; N: 5.13. Found: C: 43.70; H: 4.35; N: 4.75.

(3.7) 5-Isobutyl-4-[2-(5-phosphono)furanyl]thiazole. mp 164–166° C. Anal. calcd. for $C_{11}H_{14}NO_4PS$: C: 45.99; H: 4.91; N: 4.88. Found: C: 45.63; H: 5.01; N: 4.73.

(3.8) 2-Aminothiocarbonyl-4-[2-(5-phosphono)furanyl]thiazole. mp 189–191° C. Anal. calcd. for $C_8H_7N_2O_4PS_2$: C: 33.10; H: 2.43; N: 9.65. Found: C: 33.14; H: 2.50; N: 9.32.

(3.9) 2-(1-Piperidyl)-5-isobutyl-4-[2-(5-phosphono)furanyl]thiazole. Anal. calcd. for $C_{16}H_{23}N_2O_4PS+1.3HBr$: C: 40.41; H: 5.15; N: 5.89. Found: C: 40.46; H: 5.36; N: 5.53.

(3.10) 2-(2-Thienyl)-5-isobutyl-4-[2-(5-phosphono)furanyl]thiazole. Anal. calcd. for $C_{15}H_{16}NO_4PS_2+0.75H_2O$: C: 47.05; H: 4.61; N: 3.66. Found: C: 47.39; H: 4.36; N: 3.28.

(3.11) 2-(3-Pyridyl)-5-isobutyl-4-[2-(5-phosphono)furanyl]thiazole. Anal. calcd. for $C_{16}H_{17}N_2O_4PS+3.75HBr$: C: 28.78; H: 3.13; N: 4.20. Found: C: 28.73; H: 2.73; N: 4.53.

(3.12) 2-Acetamido-5-isobutyl-4-[2-(5-phosphono)furanyl]thiazole. mp 179–181° C. Anal. calcd. for $C_{13}H_{17}N_2O_5PS+0.25H_2O$: C: 44.76; H: 5.06; N: 8.03. Found: C: 44.73; H: 5.07; N: 7.89.

(3.13) 2-Amino-4-[2-(5-phosphono)furanyl]thiazole. Anal. calcd. for $C_7H_7N_2O_4PS$: C: 34.15; H: 2.87; N: 11.38. Found: C: 33.88; H: 2.83; N: 11.17.

(3.14) 2-Methylamino-5-isobutyl-4-[2-(5-phosphono)furanyl]thiazole. mp 202–205° C. Anal. calcd. for $C_{12}H_{17}N_2O_4PS+0.5H_2O$: C: 44.30; H: 5.58; N: 8.60. Found: C: 44.67; H: 5.27; N: 8.43.

(3.15) 2-(N-amino-N-methyl)amino-5-isobutyl-4-[2-(5-phosphono)furanyl]thiazole. mp 179–181° C. Anal. calcd. for $C_{12}H_{18}N_3O_4PS+1.25HBr$: C: 33.33; H: 4.49; N: 9.72. Found: C: 33.46; H: 4.81; N: 9.72.

(3.16) 2-Amino-5-methyl-4-[2-(5-phosphono)furanyl]thiazole. mp 200–220° C. Anal. calcd. for $C_8H_9N_2O_4PS+0.65HBr$: C: 30.72; H: 3.11; N: 8.96. Found: C: 30.86; H: 3.33; N: 8.85.

(3.17) 2,5-Dimethyl-4-[2-(5-phosphono)furanyl]thiazole. mp 195° C. (decomp). Anal. calcd. for $C_9H_{10}NO_4PS+0.7HBr$: C: 34.22; H: 3.41; N: 4.43. Found: C: 34.06; H: 3.54; N: 4.12.

(3.18) 2-Aminothiocarbonyl-5-isobutyl-4-[2-(5-phosphono)furanyl]thiazole. Anal. calcd. for $C_{12}H_{15}N_2O_4PS_2+0.1HBr+0.3EtOAc$: C: 41.62; H: 4.63; N: 7.35. Found: C: 41.72; H: 4.30; N: 7.17.

(3.19) 2-Ethoxycarbonyl-4-[2-(5-phosphono)furanyl]thiazole. mp 163–165° C. Anal. calcd. for $C_{10}H_{10}NO_6PS+0.5H_2O$: C: 38.47; H: 3.55; N: 4.49. Found: C: 38.35; H: 3.30; N: 4.42.

(3.20) 2-Amino-5-isopropyl-4-[2-(5-phosphono)furanyl]thiazole. Anal. calcd. for $C_{10}H_{13}N_2O_4PS+1HBr$: C: 32.53; H: 3.82; N: 7.59. Found: C: 32.90; H: 3.78; N: 7.65.

(3.21) 2-Amino-5-ethyl-4-[2-(5-phosphono)furanyl]thiazole. mp>250° C. Anal. calcd. for $C_9H_{11}N_2O_4PS$: C: 39.42; H: 4.04; N: 10.22. Found: C: 39.02; H: 4.15; N: 9.92.

(3.22) 2-Cyanomethyl-4-[2-(5-phosphono)furanyl]thiazole. mp 204–206° C. Anal. calcd. for $C_9H_7N_2O_4PS$: C: 40.01; H: 2.61; N: 10.37. Found: C: 39.69; H: 2.64; N: 10.03.

(3.23) 2-Aminothiocarbonylamino-5-isobutyl-4-[2-(5-phosphono)furanyl]thiazole. mp 177–182° C. Anal. calcd. for $C_{12}H_{16}N_3O_4PS_2+0.2hexane+0.3HBr$: C: 39.35; H: 4.78; N: 10.43. Found: C: 39.61; H: 4.48; N: 10.24.

(3.24) 2-Amino-5-propyl-4-[2-(5-phosphono)furanyl]thiazole. mp 235–237° C. Anal. calcd. for $C_{10}H_{13}N_2O_4PS+0.3H_2O$: C: 40.90; H: 4.67; N: 9.54. Found: C: 40.91; H: 4.44; N: 9.37.

(3.25) 2-Amino-5-ethoxycarbonyl-4-[2-(5-phosphono)furanyl]thiazole. mp 248–250° C. Anal. calcd. for $C_{10}H_{11}N_2O_6PS+0.1HBr$: C: 36.81; H: 3.43; N: 8.58. Found: C: 36.99; H: 3.35; N: 8.84.

(3.26) 2-Amino-5-methylthio-4-[2-(5-phosphono)furanyl]thiazole. mp 181–184° C. Anal. calcd. for $C_8H_9N_2O_4PS_2+0.4H_2O$: C: 32.08; H: 3.30; N: 9.35. Found: C: 33.10; H: 3.80, N: 9.15.

(3.27) 2-Amino-5-cyclopropyl-4-[2-(5-phosphono)furanyl]thiazole. Anal. calcd. for $C_{10}H_{11}N_2O_4PS+1H_2O+0.75HBr$: C: 32.91; H: 3.80; N: 7.68. Found: C: 33.10; N: 7.34.

(3.28) 2-Amino-5-methanesulfinyl-4-[2-(5-phosphono)furanyl]thiazole. mp>250° C. Anal. calcd. for $C_8H_9N_2O_5PS_2+0.35NaCl$: C: 29.23; H: 2.76; N: 8.52. Found: C: 29.37; H: 2.52; N: 8.44.

(3.29) 2-Amino-5-benzyloxycarbonyl-4-[2-(5-phosphono)furanyl]thiazole. Anal. calcd for $C_{15}H_{13}N_2O_6PS+0.2H_2O$: C: 46.93; H: 3.52; N: 7.30. Found: C: 46.64; H: 3.18; N: 7.20.

(3.30) 2-Amino-5-cyclobutyl-4-[2-(5-phosphono)furanyl]thiazole. Anal. calcd for $C_{11}H_{13}N_2O_4PS+0.15$ HBr+0.15H_2O: C: 41.93; H: 4.30; N: 8.89. Found: C: 42.18; H: 4.49; N: 8.53.

(3.31) 2-Amino-5-cyclopropyl-4-[2-(5-phosphono)furanyl]thiazole hydrobromide. Anal. calcd for $C_{10}H_{11}N_2O_4PSBr+0.73HBr+0.15MeOH+0.5H_2O$: C: 33.95; H: 3.74; N: 7.80; S: 8.93; Br: 16.24. Found: C: 33.72; H: 3.79; N: 7.65; S: 9.26; Br: 16.03.

(3.32) 2-Amino-5-[(N,N-dimethyl)aminomethyl]-4-[2-(5-phosphono)furanyl]thiazole dihydrobromide. Anal. calcd for $C_{10}H_{16}N_3O_4Br_2PS+0.8CH_2Cl_2$: C: 24.34; H: 3.33; N: 7.88. Found: C: 24.23; H: 3.35; N: 7.64.

(3.33) 2-Amino-5-methoxycarbonyl-4-[2-(5-phosphono)furanyl]thiazole. Mp 227° C. (decomp). Anal. calcd for $C_9H_9N_2O_6PS+0.1H_2O+0.2HBr$: C: 33.55; H: 2.94; N: 8.69. Found: C: 33.46; H: 3.02; N: 8.49.

(3.34) 2-Amino-5-ethylthiocarbonyl-4-[2-(5-phosphono)furanyl]thiazole. Mp 245° C. (decomp). Anal. calcd for $C_{10}H_{11}N_2O_5PS_2$: C: 35.93; H: 3.32; N: 8.38. Found: C: 35.98; H: 3.13; N: 8.17.

(3.35) 2-Amino-5-propyloxycarbonyl-4-[2-(5-phosphono)furanyl]thiazole. Mp 245° C. (decomp). Anal. calcd for $C_{11}H_{13}N_2O_6PS$: C: 39.76; H: 3.94; N: 8.43. Found: C: 39.77; H: 3.72; N: 8.19.

(3.36) 2-Amino-5-benzyl-4-[2-(5-phosphono)furanyl]thiazole. Anal. calcd for $C_{14}H_{13}N_2O_4PS+H_2O$: C: 47.46; H: 4.27; N: 7.91. Found: C: 47.24; H: 4.08;

(3.37) 2-Amino-5-[(N,N-diethyl)aminomethyl]-4-[2-(5-phosphono)furanyl]thiazole dihydrobromide. Anal. calcd for $C_{12}H_{20}N_3O_4Br_2PS+0.1HBr+1.4$ MeOH: C: 29.47; H: 4.74; N: 7.69. Found: C: 29.41; H: 4.60; N: 7.32.

(3.38) 2-Amino-5-[(N,N-dimethyl)carbamoyl]-4-[2-(5-phosphono)furanyl]thiazole. Anal. calcd for $C_{10}H_{12}N_3O_5PS+1.3HBr+1.0H_2O+0.3$ Acetone: C: 28.59; H: 3.76; N: 9.18. Found: C: 28.40; H: 3.88; N: 9.01.

(3.39) 2-Amino-5-carboxyl-4-[2-(5-phosphono)furanyl]thiazole. Anal. calcd for $C_8H_7N_2O_6PS+0.2HBr+0.1 H_2O$: C: 31.18; H: 2.42; N: 9.09. Found: C: 31.11; H: 2.42; N: 8.83.

(3.40) 2-Amino-5-isopropyloxycarbonyl-4-[2-(5-phosphono)furanyl]thiazole. Mp 240° C. (decomp). Anal. calcd for $C_{11}H_{13}N_2O_6PS$: C: 39.76; H: 3.94; N: 8.43. Found: C: 39.42; H: 3.67; N: 8.09.

(3.41) 2-Methyl-5-ethyl-4-[2-(5-phosphono)furanyl]thiazole. Anal. calcd for $C_{10}H_{12}O_4PNS+0.75HBr+0.35H_2O$: C: 36.02; H: 4.13; N: 4.06. Found: C: 36.34; H: 3.86; N: 3.69.

(3.42) 2-Methyl-5-cyclopropyl-4-[2-(5-phosphono)furanyl]thiazole. Anal. calcd for $C_{11}H_{12}NO_4PS+0.3HBr+0.5CHCl_3$: C: 37.41; H: 3.49; N: 3.79. Found: C: 37.61; H: 3.29; N: 3.41.

(3.43) 2-Methyl-5-ethoxycarbonyl-4-[2-(5-phosphono)furanyl]thiazole. Anal. calcd for $C_{11}H_{12}NO_6PS$: C: 41.64; H: 3.81; N: 4.40. Found: C: 41.61; H: 3.78; N: 4.39.

(3.44) 2-[(N-acetyl)amino]-5-methoxymethyl-4-[2-(5-phosphono)furanyl]thiazole. Anal. calcd for $C_{11}H_{13}N_2O_6PS+0.15HBr$: C: 38.36; H: 3.85; N: 8.13. Found: C: 38.74; H: 3.44; N: 8.13.

(3.45) 2-Amino-5-(4-morpholinyl)methyl-4-[2-(5-phosphono)furanyl]thiazole dihydrobromide. Anal. calcd for $C_{12}H_{18}Br_2N_3O_5PS+0.25HBr$: C: 27.33; H: 3.49; N: 7.97. Found: C: 27.55; H: 3.75; N: 7.62.

(3.46) 2-Amino-5-cyclopropylmethoxycarbonyl-4-[2-(5-phosphono)furanyl]thiazole. Mp 238° C. (decomp). Anal. calcd for $C_{12}H_{13}N_2O_6PS$: C: 41.86; H: 3.81; N: 8.14. Found: C: 41.69; H: 3.70; N: 8.01.

(3.47) 2-Amino-5-methylthio-4-[2-(5-phosphono)furanyl]thiazole N,N-dicyclohexylammonium salt. Mp>250° C. Anal. calcd for $C_8H_9N_2O_4PS_2+1.15 C_{12}H_{23}N$: C: 52.28; H: 7.13; N: 8.81. Found: C: 52.12; H: 7.17; N: 8.81

(3.48) 2-[(N-Dansyl)amino]-5-isobutyl-4-[2-(5-phosphono)furanyl]thiazole. Anal. calcd for $C_{23}H_{26}N_3O_6PS_2+0.5HBr$: C: 47.96; H: 4.64; N: 7.29. Found: C: 48.23; H: 4.67; N: 7.22.

(3.49) 2-Amino-5-(2,2,2-trifluoroethyl)-4-[2-(5-phosphono)furanyl]thiazole. Anal. calcd for $C_9H_8N_2F_3O_4PS$: C: 32.94, H: 2.46, N: 8.54. Found: C: 32.57, H: 2.64, N: 8.14.

(3.50) 2-Methyl-5-methylthio-4-[2-(5-phosphono)furanyl]thiazole. Anal. calcd for $C_9H_{10}NO_4PS_2$: C: 37.11; H: 3.46; N: 4.81. Found: C: 36.72; H: 3.23; N: 4.60.

(3.51) 2-Amino-5-methylthio-4-[2-(5-phosphono)furanyl]thiazole ammonium salt. Anal. calcd for $C_8H_{12}N_3O_4PS_2$: C: 31.07; H: 3.91; N: 13.59. Found: C: 31.28; H: 3.75; N: 13.60.

(3.52) 2-Cyano-5-ethyl-4-[2-(5-phosphono)furanyl]thiazole. Anal. calcd for $C_{10}H_9N_2O_4PS$: C: 42.26; H: 3.19; N: 9.86. Found: C: 41.96; H: 2.95; N: 9.76.

(3.53) 2-Amino-5-hydroxymethyl-4-[2-(5-phosphono)furanyl]thiazole. Anal. calcd for $C_8H_9N_2O_5PS$: C: 34.79; H: 3.28; N: 10.14. Found: C: 34.57; H: 3.00; N: 10.04.

(3.54) 2-Cyano-5-isobutyl-4-[2-(5-phosphono)furanyl]thiazole. Anal. calcd for $C_{12}H_{13}N_2O_4SP+0.09HBr$: C: 46.15; H: 4.20; N: 8.97. Found: C: 44.81; H: 3.91; N: 8.51.

(3.55) 2-Amino-5-isopropylthio-4-[2-(5-phosphono)furanyl]thiazole hydrobromide. Anal. calcd for $C_{10}H_{14}BrN_2O_4PS_2$: C: 29.94; H: 3.52; N: 6.98. Found: C: 30.10; H: 3.20; N: 6.70.

(3.56) 2-Amino-5-phenylthio-4-[2-(5-phosphono)furanyl]thiazole. Anal. calcd for $C_{13}H_{11}N_2O_4PS_2$: C: 44.07; H: 3.13; N: .91. Found: C: 43.83; H: 3.07; N: 7.74.

(3.57) 2-Amino-5-tert-butylthio-4-[2-(5-phosphono)furanyl]thiazole. Anal. calcd for $C_{11}H_{15}N_2O_4PS_2+0.6CH_2Cl_2$: C: 36.16; H: 4.24; N: 7.27. Found: C: 36.39; H: 3.86; N: 7.21.

(3.58) 2-Amino-5-propylthio-4-[2-(5-phosphono)furanyl]thiazole hydrobromide. Anal. calcd for $C_{10}H_{14}BrN_2O_4PS_2$: C: 29.94; H: 3.52; N: 6.98. Found: C: 29.58; H: 3.50; N: 6.84.

(3.59) 2-Amino-5-ethylthio-4-[2-(5-phosphono)furanyl]thiazole. Anal. calcd for $C_9H_{11}N_2O_4PS_2+0.25HBr$: C: 33.11; H: 3.47; N: 8.58. Found: C: 33.30; H: 3.42; N: 8.60.

(3.60) 2-[(N-tert-butyloxycarbonyl)amino]-5-methoxymethyl-4-[2-(5-phosphono)furanyl]thiazole. Anal. calcd for $C_{14}H_{19}N_2O_7PS$: C: 43.08; H: 4.91; N: 7.18. Found: C: 42.69; H: 4.58; N: 7.39.

(3.61) 2-Hydroxyl-4-[2-(5-phosphono)furanyl]thiazole. Anal. calcd for $C_7H_6NO_5PS$: C: 34.02; H: 2.45; N: 5.67. Found: C: 33.69; H: 2.42; N: 5.39.

(3.62) 2-Hydroxyl-5-ethyl-4-[2-(5-phosphono)furanyl]thiazole. Anal. calcd for $C_9H_{10}NO_5PS$: C: 39.28; H: 3.66; N: 5.09. Found: C: 39.04; H: 3.44; N: 4.93.

(3.63) 2-Hydroxyl-5-isopropyl-4-[2-(5-phosphono)furanyl]thiazole. Anal. calcd for $C_{10}H_{12}NO_5PS+0.1HBr$: C: 40.39; H: 4.10; N: 4.71. Found: C: 40.44; H: 4.11; N: 4.68.

(3.64) 2-Hydroxyl-5-isobutyl-4-[2-(5-phosphono)furanyl]thiazole. Anal. calcd for $C_{11}H_{14}NO_5PS$: C: 43.57; H: 4.65; N: 4.62. Found: C: 43.45; H: 4.66; N: 4.46.

(3.65) 5-Ethoxycarbonyl-4-[2-(5-phosphono)furanyl]thiazole. Anal. calcd for $C_{10}H_{10}NO_6PS$: C: 39.61; H: 3.32; N: 4.62. Found: C: 39.60; H: 3.24; N: 4.47.

(3.66) 2-Amino-5-vinyl-4-[2-(5-phosphono)furanyl]thiazole. Anal. calcd for $C_9H_9N_2O_4PS+0.28HCl$: C: 37.66; H: 3.26; N: 9.46. Found: C: 37.96; H: 3.37; N: 9.10.

(3.67) 2-Amino-4-[2-(6-phosphono)pyridyl]thiazole hydrobromide.

(3.68) 2-Methylthio-5-isobutyl-4-[2-(5-phosphono)furanyl]thiazole. Anal. calcd for $C_{12}H_{16}NO_4PS_2$: C: 43.24; H: 4.84; N: 4.20. Found: C: 43.55; H: 4.63; N: 4.46.

(3.69) 2-Amino-5-isobutyl-4-[2-(3-phosphono)furanyl]thiazole. Anal. calcd for $C_{11}H_{15}N_2O_4PS+0.1\ H_2O$: C: 43.45; H: 5.04; N: 9.21. Found: C: 43.68; H: 5.38; N: 8.98.

(3.70) 2-Amino-5-isobutyl-4-[2-(5-phosphono)furanyl]selenazole. Anal. calcd for $C_{11}H_{15}N_2O_4PSe+0.14\ HBr+0.6\ EtOAc$: C: 38.93; H: 4.86; N: 6.78. Found: C: 39.18; H: 4.53; N: 6.61.

(3.71) 2-Amino-5-methylthio-4-[2-(5-phosphono)furanyl]selenazole. Anal. calcd for $C_8H_9N_2O_4PSSe+0.7\ HBr+0.2\ EtOAc$: C: 25.57; H: 2.75; N: 6.78. Found: C: 25.46; H: 2.49; N: 6.74.

(3.72) 2-Amino-5-ethyl-4-[2-(5-phosphono)furanyl]selenazole. Anal. calcd for $C_9H_{11}N_2O_4PSe+HBr$: C: 26.89; H: 3.01; N: 6.97. Found: C: 26.60; H: 3.16; N: 6.81.

Example 4

Preparation of 5-halo-4-[2-(5-phosphono)furanyl]thiazoles

Step A. A solution of 2-amino-4-[2-(5-diethylphosphono)furanyl]thiazole (prepared as in Step B of Example 3) (1 mmole) in chloroform was treated with N-bromo succinimide (NBS) (1.5 mmole) at 25° C. for 1 h. Extraction and chromatography gave 2-amino-5-bromo-4-[2-(5-diethylphosphono)furanyl]-thiazole as a brown solid.

Step B. 2-Amino-5-bromo-4-[2-(5-diethylphosphono)furanyl]thiazole was subjected to Step C of Example 3 to give 2-amino-5-bromo-4-[2-(5-phosphono)-furanyl]thiazole (4.1) as a yellow solid. mp>230° C. Anal. calcd. for $C_7H_6N_2O_4PSBr$: C: 25.86; H: 1.86; N: 8.62. Found: C: 25.93; H: 1.64; N: 8.53.

The following compounds were prepared according to this procedure:

(4.2) 2-Amino-5-chloro-4-[2-(5-phosphono)furanyl]thiazole. Anal. calcd. for $C_7H_6N_2O_4PSCl$: C: 29.96; H: 2.16; N: 9.98. Found: C: 29.99; H: 1.97; N: 9.75.

(4.3) 2-Amino-5-iodo-4-[2-(5-phosphono)furanyl]thiazole. Anal. calcd. for $C_7H_6N_2O_4PSI$: C: 22.42; H: 2.28; N: 6.70. Found: C: 22.32; H: 2.10; N: 6.31.

(4.4) 2,5-Dibromo-4-[2-(5-phosphono)furanyl]thiazole. Anal. calcd. for $C_7H_4NO_4PSBr_2$: C: 21.62; H: 1.04; N: 3.60. Found: C: 21.88; H: 0.83; N: 3.66.

Examples 5

Preparation of 2-halo-4-[2-(5-phosphono)furanyl]thiazoles

Step A. A solution of 2-amino-5-isobutyl-4-[2-(5-diethylphosphono)-furanyl]thiazole (prepared as in Step B of Example 3) (1 mmole) in acetonitrile was treated with copper (II) bromide (1.2 mmole) and isoamyl nitrite (1.2 mmole) at 0° C. for 1 h. Extraction and chromatography gave 2-bromo-5-isobutyl-4-[2-(5-diethylphosphono)furanyl]thiazole as a brown solid.

Step B. 2-Bromo-5-isobutyl-4-[2-(5-diethylphosphono)furanyl]thiazole was subjected to Step C of Example 3 to give 2-bromo-5-isobutyl-4-[2-(5-phosphono)furanyl]thiazole (5.1) as a yellow hygroscopic solid. Anal. calcd. for $C_{11}H_{13}NO_4PSBr$: C: 36.08; H: 3.58; N: 3.83. Found: C: 36.47; H: 3.66; N: 3.69.

The following compound was prepared according to this procedure:

(5.2) 2-Chloro-5-isobutyl-4-[2-(5-phosphono)furanyl]thiazole: Anal. calcd. for $C_{11}H_{13}NO_4PSCl$: C: 41.07; H: 4.07; N: 4.35. Found: C: 40.77; H: 4.31; N: 4.05.

(5.3) 2-Bromo-5-methylthio-4-[2-(5-phosphono)furanyl]thiazole: Anal. calcd. for $C_8H_7NO_4PS_2Br$: C: 26.98; H: 1.98; N: 3.93. Found: C: 27.21; H: 1.82; N: 3.84.

Example 6

Preparation of Various 2- and 5-substituted 4-[2-(5-phosphono)furanyl]thiazoles

Step A. A solution of 2-bromo-5-isobutyl-4-[2-(5-diethylphosphono)-furanyl]thiazole (1 mmole, prepared as in the Step A of Example 5) in DMF was treated with tributyl(vinyl)tin (5 mmole) and palladium bis (triphenylphosphine) dichloride (0.05 mmole) at 100° C. under nitrogen. After 5 h the cooled reaction mixture was evaporated and the residue was subjected to chromatography to give 2-vinyl-5-isobutyl-4-[2-(5-diethylphosphono)furanyl]thiazole as a yellow solid.

Step B. 2-Vinyl-5-isobutyl-4-[2-(5-diethylphosphono)furanyl]thiazole was subjected to Step C of Example 3 to give 2-vinyl-5-isobutyl-4-[2-(5-phosphono)-furanyl]thiazole (6.1) as a yellow solid. Anal. calcd. for $C_{13}H_{16}NO_4PS+1HBr+0.1H_2O$: C: 39.43; H: 4.38; N: 3.54. Found: C: 39.18; H: 4.38; N: 3.56.

This method can also be used to prepare various 5-substituted 4-[2-(5-phosphono)furanyl]thiazoles from their corresponding halides.

Step C. 2-Amino-5-bromo-4-[2-(5-diethylphosphono)furanyl]thiazole was subjected to Step A using 2-tributylstannylfuran as the coupling partner to give 2-amino-5-(2-furanyl)-4-[2-(5-diethylphosphono)furanyl]thiazole.

Step D. 2-Amino-5-(2-furanyl)-4-[2-(5-diethylphosphono)furanyl]thiazole was subjected to Step C of Example 3 to give 2-amino-5-(2-furanyl)-4-[2-(5-phosphono)furanyl]thiazole (6.2). mp 190–210° C. Anal. calcd. for $C_{11}H_9N_2O_5PS+0.25HBr$: C: 39.74; H: 2.80; N: 8.43. Found: C: 39.83; H: 2.92; N: 8.46.

The following compound was prepared according to this procedure:

(6.3) 2-Amino-5-(2-thienyl)-4-[2-(5-diethylphosphono)furanyl]thiazole. Anal. calcd. for $C_{11}H_9N_2O_4PS_2+0.3EtOAc+0.11HBr$: C: 40.77; H: 3.40; N: 7.79. Found: C: 40.87; H: 3.04; N: 7.45.

Example 7

Preparation of 2-ethyl-4-[2-(5-phosphono)furanyl]thiazoles

Step A. A solution of 2-vinyl-5-isobutyl-4-[2-(5-diethylphosphono)furanyl]-thiazole (1 mmole, prepared as in the Step A of Example 6) in ethanol was treated with palladium on carbon (0.05 mmole) under 1 atmosphere of hydrogen for 12 h. The reaction mixture was filtered, the filtrate was evaporated and the residue was purified by chromatography to give 2-ethyl-5-isobutyl-4-[2-(5-diethylphosphono)furanyl]thiazole as a yellow foam.

Step B. 2-Ethyl-5-isobutyl-4-[2-(5-diethylphosphono)furanyl]thiazole was subjected to Step C of Example 3 to give 2-ethyl-5-isobutyl-4-[2-(5-phosphono)-furanyl]thiazole (7.1) as a yellow solid. Anal. calcd. for $C_{13}H_{18}NO_4PS+1HBr$: C: 39.41; H: 4.83; N: 3.53. Found: C: 39.65; H: 4.79; N: 3.61.

Example 8

Preparation of 4-phosphonomethoxymethylthiazoles

Step A. A solution of diethyl hydroxymethylphosphonate (1 mmole) in DMF was treated with sodium hydride (1.2 mmole) followed by 2-methyl-4-chloromethylthiazole (1 mmole) at 0° C. and stirred at 25° C. for 12 h. Extraction and chromatography gave 2-methyl-4-(diethylphosphonomethoxymethyl)thiazole.

Step B. 2-Methyl-4-diethylphosphonomethoxymethylthiazole was subjected to Step C of Example 3 to give 2-methyl-4-phosphonomethoxymethylthiazole (8.1). Anal. calcd. for $C_6H_{10}NO_4PS+0.5HBr+0.5H_2O$: C: 26.43; H: 4.25; N: 5.14. Found: C: 26.52; H: 4.22; N: 4.84.

Step C. 2-Methyl-4-diethylphosphonomethoxymethylthiazole was subjected to Step A of Example 4 and followed by Step C of Example 3 to give 5-bromo-2-methyl-4-phosphonomethoxymethylthiazole (8.2). Anal. calcd. for $C_6H_9NO_4PSBr+0.5HBr$: C: 21.04; H: 2.80; N: 4.09. Found: C: 21.13; H: 2.69; N: 4.01.

Step D. A solution of ethyl 2-[(N-Boc)amino]-4-thiazolecarboxylate (1 mmole) in $CH_2Cl_2$ (10 mL) was cooled to −78° C., and treated with DIBAL-H (1M, 5 ML). The reaction was stirred at −60° C. for 3 h, and quenched with a suspension of $NaF/H_2O$ (1 g/1 mL). The resulting mixture was filtered and the filtrate was concentrated to give 2-[(N-Boc)amino]-4-hydroxymethylthiazole as a solid.

Step E. A solution of 2-[(N-Boc)amino]-4-hydroxymethylthiazole (1 mmole) in DMF (10 mL) was cooled to 0C, and treated with NaH (1.1 mmole). The mixture was stirred at room temperature for 30 min, then phosphonomethyl trifluoromethanesulfonate (1.1 mmole) was added. After stirring at room temperature for 4 h, the reaction was evaporated to dryness. Chromatography of the residue gave 2-[(N-Boc)amino]-4-diethylphosphonomethoxylmethylthiazole as a solid.

Step F. 2-[(N-Boc)amino]-4-diethylphosphonomethoxylmethylthiazole was subjected to Step C of Example 3 to give 2-amino-4-phosphonomethoxymethylthiazole (8.3) as a solid. Anal. calcd. for $C_5H_9N_2O_4PS+0.16 HBr+0.1 MeOH$: C: 25.49; H: 4.01; N: 11.66. Found: C: 25.68; H: 3.84; N: 11.33.

Example 9

Preparation of 2-carbamoyl-4-[2-(5-phosphono)furanyl]thiazoles

Step A. A solution of 2-ethoxycarbonyl-5-isobutyl-4-[2-(5-diethylphosphono)furanyl]thiazole (1 mmole) in saturated methanolic ammonia solution at 25° C. for 12 h. Evaporation and chromatography gave 2-carbamoyl-5-isobutyl-4-[2-(5-diethylphosphono)furanyl]thiazole as a white solid.

Step B. 2-Carbamoyl-5-isobutyl-4-[2-(5-diethylphosphono)furanyl]thiazole was subjected to Step C of Example 3 to give 2-carbamoyl-5-isobutyl-4-[2-(5-phosphono)furanyl]thiazole (9.1) as a solid. mp 185–186° C. Anal. calcd. for $C_{12}H_{15}N_2O_5PS$: C: 43.64; H: 4.58; N: 8.48. Found: C: 43.88; H: 4.70; N: 8.17.

The following compound was prepared according to this procedure:

(9.2) 2-Carbamoyl-4-[2-(5-phosphono)furanyl]thiazole. mp 195–200° C. Anal. calcd. for $C_8H_7N_2O_5PS+0.25H_2O$: C: 34.48; H: 2.71; N: 10.05. Found: C: 34.67; H: 2.44; N: 9.84.

2-Ethoxycarbonyl-4-[2-(5-diethylphosphono)furanyl] thiazoles can also be converted to other 2-substituted 4-[2-(5-phosphono)furanyl]thiazoles.

Step C. A solution of 2-ethoxycarbonyl-4-[2-(5-diethylphosphono)furanyl]thiazole (1 mmole) in methanol was treated with sodium borohydride (1.2 mmole) at 25° C. for 12 h. Extraction and chromatography gave 2-hydroxymethyl-4-[2-(5-diethylphosphono)furanyl] thiazole.

Step D. 2-Hydroxymethyl-4-[2-(5-diethylphosphono)furanyl]-thiazole was subjected to Step C of Example 3 to give 2-hydroxymethyl-4-[2-(5-phosphono)furanyl]thiazole (9.3). mp 205–207° C. Anal. calcd. for $C_8H_8NO_5PS+0.25H_2O$: C: 36.16; H: 3.22; N: 5.27. Found: C: 35.98; H: 2.84; N: 5.15.

The following compound was prepared according to this procedure:

(9.4) 2-Hydroxymethyl-5-isobutyl-4-[2-(5-phosphono)furanyl]thiazole. mp 160–170° C. Anal. calcd. for $C_{12}H_{16}NO_5PS+0.75HBr$: C: 38.13; H: 4.47; N: 3.71. Found: C: 37.90; H: 4.08; N: 3.60.

Step E. A solution of 2-hydroxymethyl-5-isobutyl-4-[2-(5-diethylphosphono)furanyl]thiazole (1 mmole) in methylene chloride was treated with phosphorus tribromide (1.2 mmole) at 25° C. for 2 h. Extraction and chromatography gave 2-bromomethyl-5-isobutyl-4-[2-(5-diethylphosphono)furanyl]thiazole.

Step F. 2-Bromomethyl-5-isobutyl-4-[2-(5-diethylphosphono)furanyl]-thiazole was subjected to Step C of Example 3 to give 2-bromomethyl-5-isobutyl-4-[2-(5-phosphono)furanyl]thiazole (9.5). mp 161–163° C. Anal. calcd. for $C_{12}H_{15}BrNO_4PS+0.25HBr$: C: 35.99; H: 3.84; N: 3.50. Found: C: 36.01; H: 3.52; N: 3.37.

The following compound was prepared according to this procedure:

(9.6) 2-Bromomethyl-4-[2-(5-phosphono)furanyl]thiazole. mp>250° C. Anal. calcd. for $C_8H_7BrNO_4PS$: C: 29.65; H: 2.18; N: 4.32. Found: C: 29.47; H: 1.99; N: 4.16.

Step G. A solution of 2-hydroxymethyl-5-isobutyl-4-[2-(5-diethylphosphono)furanyl]thiazole (1 mmole) in methylene chloride was treated with thionyl chloride (1.2 mmole) at 25° C. for 2 h. Extraction and chromatography gave 2-chloromethyl-5-isobutyl-4-[2-(5-diethylphosphono)furanyl]thiazole.

Step H. 2-Chloromethyl-5-isobutyl-4-[2-(5-diethylphosphono)furanyl]-thiazole was subjected to Step C of Example 3 to give 2-chloromethyl-5-isobutyl-4-[2-(5-phosphono)furanyl]thiazole (9.7). mp 160–162° C. Anal. calcd. for $C_{12}H_{15}ClNO_4PS+0.45HBr$: C: 38.73; H: 4.18; N: 3.76. Found: C: 38.78; H: 4.14; N: 3.73.

Step I. A solution of 2-bromomethyl-5-isobutyl-4-[2-(5-diethylphosphono)furanyl]thiazole (1 mmole) in DMF was treated with potassium phthalimide (1.2 mmole) at 25° C. for 12 h. Extraction and chromatography gave 2-phthalimidomethyl-5-isobutyl-4-[2-(5-diethylphosphono)furanyl]thiazole.

Step J. 2-Phthalimidomethyl-5-isobutyl-4-[2-(5-diethylphosphono)furanyl]-thiazole (1 mmole) in ethanol was treated with hydrazine (1.5 mmole) at 25° C. for 12 h.

Filtration, evaporation and chromatography gave 2-aminomethyl-5-isobutyl-4-[2-(5-diethylphosphono)furanyl]thiazole.

Step K. 2-Aminomethyl-5-isobutyl-4-[2-(5-diethylphosphono)furanyl]-thiazole was subjected to Step C of Example 3 to give 2-aminomethyl-5-isobutyl-4-[2-(5-phosphono)furanyl]thiazole (9.8). mp 235–237° C. Anal. calcd. for $C_{12}H_{17}N_2O_4PS+0.205HBr$: C: 43.30; H: 5.21; N: 8.41. Found: C: 43.66; H: 4.83; N: 8.02.

According to the above procedures or in some cases with some minor modifications of the above procedures, the following compounds were prepared: (9.9) 2-Carbamoyl-5-cyclopropyl-4-[2-(5-phosphono)furanyl]thiazole. Anal. calcd for $C_{11}H_{11}N_2O_5PS+0.15HBr$: C: 40.48; H: 3.44; N: 8.58. Found: C: 40.28; H: 3.83; N: 8.34.

(9.10) 2-Carbamoyl-5-ethyl-4-[2-(5-phosphono)furanyl]thiazole. Anal. calcd for $C_{10}H_{11}N_2O_5PS+0.75H_2O$: C: 38.04; H: 3.99; N: 8.87. Found: C: 37.65; H: 3.93; N: 8.76.

Example 10

Preparation of 4-[2-(5-phosphono)furanyl]oxazoles and 4-[2-(5-phosphono)furanyl]imidazoles Step A. A solution of 5-diethylphosphono-2-[(2-bromo-4-methyl-1-oxo)pentyl]furan (1 mmole) in t-BuOH was treated with urea (10 mmole) at reflux for 72 h. Filtration, evaporation and chromatography gave 2-amino-5-isobutyl-4-[2-(5-diethylphosphono)furanyl]oxazole, and 2-hydroxy-5-isobutyl-4-[2-(5-diethylphosphono)furanyl]imidazole.

Step B. 2-Amino-5-isobutyl-4-[2-(5-diethylphosphono)furanyl]oxazole was subjected to Step C of Example 3 to give 2-amino-5-isobutyl-4-[2-(5-phosphono)furanyl]oxazole (10.1). mp 250° C. (decomp.). Anal. Calcd. for $C_{11}H_{15}N_2O_5P$: C: 46.16; H: 5.28; N: 9.79. Found: C: 45.80; H: 5.15; N: 9.55.

Step C. 2-Hydroxy-5-isobutyl-4-[2-(5-diethylphosphono)furanyl]imidazole was subjected to Step C of Example 3 to give 2-hydroxy-5-isobutyl-4-[2-(5-phosphono)furanyl]imidazole (10.14). mp 205° C. (decomp). Anal. Calcd. for $C_{11}H_{15}N_2O_5P$: C: 46.16; H: 5.28; N: 9.79. Found: C: 45.80; H: 4.90 N: 9.73.

Alternatively 4-[2-(5-phosphono)furanyl]oxazoles and 4-[2-(5-phosphono)furanyl]imidazoles can be prepared as following:

Step D. A solution of 5-diethylphosphono-2-[(2-bromo-4-methyl-1-oxo)pentyl]furan (1 mmole) in acetic acid was treated with sodium acetate (2 mmole) and ammonium acetate (2 mmole) at 100° C. for 4 h. Evaporation and chromatography gave 2-methyl-5-isobutyl-4-[2-(5-diethylphosphono)furanyl]-oxazole, 2-methyl-4-isobutyl-5-[2-(5-diethylphosphono)furanyl]oxazole and 2-methyl-5-isobutyl-4-[2-(5-diethylphosphono)furanyl]imidazole.

Step E. 2-Methyl-5-isobutyl-4-[2-(5-diethylphosphono)furanyl]oxazole, 2-methyl-4-isobutyl-5-[2-(5-diethylphosphono)furanyl]oxazole and 2-methyl-5-isobutyl-4-[2-(5-diethylphosphono)furanyl]imidazole were subjected to Step C of Example 3 to give the following compounds:

(10.18) 2-Methyl-4-isobutyl-5-[2-(5-phosphono)furanyl]oxazole hydrogen bromide. mp>230° C.; Anal. Calcd. for $C_{12}H_{17}BrNO_5P+0.4H_2O$: C: 38.60; H: 4.81; N: 3.75. Found: C: 38.29; H: 4.61; N: 3.67.

(10.19) 2-Methyl-5-isobutyl-4-[2-(5-phosphono)furanyl]oxazole hydrogen bromide. Anal. Calcd. for $C_{12}H_{17}BrNO_5P$: C: 39.36; H: 4.68; N: 3.83. Found: C: 39.33; H: 4.56; N: 3.85.

(10.21) 2-Methyl-5-isobutyl-4-[2-(5-phosphono)furanyl]imidazole hydrogen bromide. Anal. Calcd. for $C_{12}H_{18}BrN_2O_4P+0.2NH_4Br$: C: 37.46; H: 4.93; N: 8.01. Found: C: 37.12; H: 5.11; N: 8.28.

Alternatively 4-[2-(5-phosphono)furanyl]imidazoles can be prepared as following:

Step F. A solution of 5-diethylphosphono-2-(bromoacetyl)furan (1 mmole) in ethanol was treated with trifluoroacetamidine (2 mmole) at 80° C. for 4 h. Evaporation and chromatography gave 2-trifluoromethyl-4-[2-(5-diethylphosphono)furanyl]imidazole as an oil.

Step G. 2-Trifluoromethyl-4-[2-(5-diethylphosphono)furanyl]imidazole was subjected to Step C of Example 3 to give 2-trifluoromethyl-4-[2-(5-phosphono)-furanyl]imidazole (10.22). mp 188° C. (dec.); Anal. Calcd. for $C_8H_6F_3N_2O_4P+0.5HBr$: C: 29.79; H: 2.03; N: 8.68. Found: C: 29.93; H: 2.27; N: 8.30.

Alternatively 4,5-dimethyl-1-isobutyl-2-[2-(5-phosphono)furanyl]-imidazole can be prepared as following:

Step H. A solution of 5-diethylphosphono-2-furaldehyde (1 mmole), ammonium acetate (1.4 mmole), 3,4-butanedione (3 mmole) and isobutylamine (3 mmole) in glacial acetic acid was heated at 100° C. for 24 h. Evaporation and chromatography gave 4,5-dimethyl-1-isobutyl-2-[2-(5-diethylphosphono)furanyl]imidazole as an yellow solid.

Step I. 4,5-Dimethyl-1-isobutyl-2-[2-(5-diethylphosphono)furanyl]-imidazole was subjected to Step C of Example 3 to give 4,5-dimethyl-1-isobutyl-2-[2-(5-phosphono)furanyl]imidazole (10.23); Anal. Calcd. for $C_{13}H_{19}N_2O_4P+1.35HBr$: C: 38.32; H: 5.03; N: 6.87. Found: C: 38.09; H: 5.04; N: 7.20.

According to the above procedures or in some cases with some minor modifications of the above procedures, the following compounds were prepared:

(10.2) 2-Amino-5-propyl-4-[2-(5-phosphono)furanyl]oxazole. mp 250° C. (decomp.); Anal. Calcd. for $C_{10}H_{13}N_2O_5P$: C: 44.13; H: 4.81; N: 10.29. Found: C: 43.74; H: 4.69; N: 9.92.

(10.3) 2-Amino-5-ethyl-4-[2-(5-phosphono)furanyl]oxazole. Anal. Calcd. for $C_9H_{11}N_2O_5P+0.4H_2O$: C: 40.73; H: 4.48; N: 10.56. Found: C: 40.85; H: 4.10; N: 10.21.

(10.4) 2-Amino-5-methyl-4-[2-(5-phosphono)furanyl]oxazole. Anal. Calcd. for $C_8H_9N_2O_5P+0.1H_2O$: C: 39.07; H: 3.77; N: 11.39. Found: C: 38.96; H: 3.59; N: 11.18.

(10.5) 2-Amino-4-[2-(5-phosphono)furanyl]oxazole. Anal. Calcd. for $C_7H_7N_2O_5P+0.6H_2O$: C: 34.90; H: 3.43; N: 11.63. Found: C: 34.72; H: 3.08; N: 11.35.

(10.6) 2-Amino-5-isobutyl-4-[2-(5-phosphono)furanyl]oxazole hydrogen bromide. Anal. Calcd. for $C_{11}H_{16}N_2OSBrP+0.4H_2O$: C: 35.29; H: 4.52; N: 7.48. Found: C: 35.09; H: 4.21; N: 7.34.

(10.7) 2-Amino-5-phenyl-4-[2-(5-phosphono)furanyl]oxazole. Anal. Calcd. for $C_{13}H_{11}N_2O_5P$: C: 50.99; H: 3.62; N: 9.15. Found: C: 50.70; H: 3.43; N: 8.96.

(10.8) 2-Amino-5-benzyl-4-[2-(5-phosphono)furanyl]oxazole. Anal. Calcd. for $C_{14}H_{13}N_2O_5P+1.1H_2O$: C: 49.45; H: 4.51; N: 8.24. Found: C: 49.35; H: 4.32; N: 8.04.

(10.9) 2-Amino-5-cyclohexylmethyl-4-[2-(5-phosphono)furanyl]oxazole. Anal. Calcd. for $C_{14}H_{19}N_2O_5P+0.3H_2O$: C: 50.70; H: 5.96; N: 8.45. Found: C: 50.60; H: 5.93; N: 8.38.

(10.10) 2-Amino-5-allyl-4-[2-(5-phosphono)furanyl]oxazole. Anal. Calcd. for $C_{10}H_{11}N_2O_5P+0.4HBr+0.3H_2O$: C: 39.00; H: 3.93; N: 9.10. Found: C: 39.31; H: 3.83; N: 8.76.

(10.11) 5-Isobutyl-4-[2-(5-phosphono)furanyl]oxazole. Anal. Calcd. for $C_{11}H_{14}NO_5P$: C: 48.72; H: 5.20; N: 5.16. Found: C: 48.67; H: 5.02; N: 5.10.

(10.12) 2-Amino-5-butyl-4-[2-(5-phosphono)furanyl]oxazole. Anal. Calcd. for $C_{11}H_{15}N_2O_5P+0.2H_2O$: C: 45.59; H: 5.36; N: 9;67. Found: C: 45.32; H: 5.29; N: 9.50.

(10.13) 5-Isobutyl-4-[2-(5-phosphono)furanyl]oxazole-2-one. Anal. Calcd. for $C_{11}H_{14}NO_6P+0.39HBr$: C: 41.45; H: 4.55; N: 4.39. Found: C: 41.79; H: 4.22; N: 4.04.

(10.15) 5-Cyclohexylmethyl-2-hydroxy-4-[2-(5-phosphono)furanyl]imidazole. Anal. Calcd. for $C_{14}H_{19}N_2O_5P+0.05HBr$: C: 50.90; H: 5.81; N: 8.48. Found: C: 51.06; H: 5.83; N: 8.25.

(10.16) 5-Butyl-2-hydroxy-4-[2-(5-phosphono)furanyl]. Anal. Calcd. for $C_{11}H_{15}N_2O_5P+0.2H_2O$: C: 45.59; H: 5.36; N: 9.67. Found: C: 45.77; H: 5.34; N: 9.39.

(10.17) 5-Benzyl-2-hydroxy-4-[2-(5-phosphono)furanyl]imidazole. Anal. Calcd. for $C_{14}H_{13}N_2O_5P$: C: 52.51; H: 4.09; N: 8.75. Found: C: 52.29; H: 4.15; N: 8.36.

(10.20) 2-Methyl-5-propyl-4-[2-(5-phosphono)furanyl]imidazole hydrogen bromide. Anal. Calcd. for $C_{11}H_{16}BrN_2O_4P+0.5H_2O$: C: 36.69; H: 4.76; N: 7.78. Found: C: 36.81; H: 4.99; N: 7.42.

(10.24) 2-Amino-5-(2-thienylmethyl)-4-[2-(5-phosphono)furanyl]oxazole. Anal. calcd for $C_{12}H_{11}N_2O_5PS+0.9HBr$: C: 36.12; H: 3.01; N: 7.02. Found: C: 36.37; H: 2.72; N: 7.01.

(10.25) 2-Dimethylamino-5-isobutyl-4-[2-(5-phosphono)furanyl]oxazole hydrogen bromide. Anal. Calcd for $C_{13}H_2OBrN_2O_5P+0.05HBr$: C: 39.11; H: 5.06; N: 7.02. Found: C: 39.17; H: 4.83; N: 6.66

(10.26) 2-Isopropyl-5-isobutyl-4-[2-(5-phosphono)furanyl]oxazole. Anal. Calcd for $C_{14}H_{20}NO_5P+0.8HBr$: C: 44.48; H: 5.55; N: 3.71. Found: C: 44.45; H: 5.57; N: 3.73.

(10.27) 2-Amino-5-ethoxycarbonyl-4-[2-(5-phosphono)furanyl]oxazole. mp 245° C. (decomp.). Anal. Calcd for $C_{10}H_{11}N_2O_7P$: C: 39.75; H: 3.67; N: 9.27. Found: C: 39.45; H: 3.71; N: 8.87

(10.28) 2-Methylamino-5-isobutyl-4-[2-(5-phosphono)furanyl]oxazole hydrogen bromide. Anal. Calcd for $C_{12}H_{18}BrN_2O_5P+0.7H_2O$: C: 36.60; H: 4.97; N: 7.11. Found: C: 36.50; H: 5.09; N: 7.04.

(10.29) 2-Ethyl-5-isobutyl-4-[2-(5-phosphono)furanyl]oxazole hydrogen bromide. Anal. Calcd for $C_{13}H_{19}BrNO_5P$: C: 41.07; H: 5.04; N: 3.68. Found: C: 41.12; H: 4.84; N: 3.62.

(10.30) 2-Ethylamino-5-isobutyl-4-[2-(5-phosphono)furanyl]oxazole hydrogen bromide. Anal. Calcd for $C_{13}H_{20}BrN_2O_5P$: C: 39.51; H: 5.10; N: 7.09. Found: C: 39.03; H: 5.48; N: 8.90.

(10.31) 2-Vinyl-5-isobutyl-4-[2-(5-phosphono)furanyl]oxazole. Anal. Calcd for $C_{13}H_{16}NO_5P+0.25HBr$: C: 49.18; H: 5.16; N: 4.41. Found: C: 48.94; H: 5.15; N: 4.40.

(10.32) 2-Amino-5-pentyl-4-[2-(5-phosphono)furanyl]oxazole. Anal. Calcd for $C_{12}H_{17}N_2O_5P+0.5H_2O$: C: 46.61; H: 5.87; N: 9.06. Found: C: 46.38; H: 5.79; N: 9.07.

(10.33) 5-Pentyl-2-hydroxy-4-[2-(5-phosphono)furanyl]imidazole. Anal. Calcd. for $C_{12}H_{17}N_2O_5P$: C: 48.00; H: 5.71; N: 9.33. Found: C: 48.04; H: 5.58; N: 9.26.

(10.45) 2-Amino-5-methylthio-4-[2-(5-phosphono)furanyl]oxazole. mp 196° C. (decomp). Anal. calcd. for $C_8H_9N_2O_5PS$: C: 34.79; H: 3.28; N: 10.14. Found: C: 34.60; H: 2.97; N: 10.00.

(10.35) 2-Amino-5-benzyloxycarbonyl-4-[2-(5-phosphono)furanyl]oxazole. mp 230° C. (decomp). Anal. calcd for $C_{15}H_{13}N_2O_7P+0.7H_2O$: C: 47.81; H: 3.85; N: 7.43. Found: C: 47.85; H: 3.88; N: 7.21.

(10.36) 2-Amino-5-isopropyloxycarbonyl-4-[2-(5-phosphono)furanyl]oxazole. mp 221° C. (decomp). Anal. calcd for $C_{11}H_{13}N_2O_7P+0.9H_2O$: C: 39.75; H: 4.49; N: 8.43. Found: C: 39.72; H: 4.25; N: 8.20.

(10.37) 2-Amino-5-methoxycarbonyl-4-[2-(5-phosphono)furanyl]oxazole. mp 240° C. (decomp). Anal. calcd for $C_9H_9N_2O_7P+0.3H_2O+0.1Acetone$: C: 37.31; H: 3.43; N: 9.36. Found: C: 37.37; H: 3.19; N: 9.01.

(10.38) 2-Amino-5-[(N-methyl)carbamoyl]-4-[2-(5-phosphono)furanyl]oxazole. mp 235° C. (decomp). Anal. calcd for $C_9H_{10}N_3O_6P$: C: 37.64; H: 3.51; N: 14.63. Found: C: 37.37; H: 3.22; N: 14.44.

(10.39) 2-Amino-5-ethylthiocarbonyl-4-[2-(5-phosphono)furanyl]oxazole. mp 225° C. (decomp). Anal. calcd for $C_{10}H_{11}N_2O_6PS$: C: 37.74; H: 3.48; N: 8.80. Found: C: 37.67; H: 3.27; N: 8.46.

(10.40) 2-Amino-5-isopropylthio-4-[2-(5-phosphono)furanyl]oxazole. Anal. calcd for $C_{10}H_{13}N_2O_5PS+0.2HBr$: C: 37.48; H: 4.15; N: 8.74. Found: C: 37.39; H: 4.11; N: 8.56.

(10.41) 2-Amino-5-phenylthio-4-[2-(5-phosphono)furanyl]oxazole. Anal. calcd for $C_{13}H_{11}N_2O_5PS+0.25 HBr$: C: 43.55; H: 3.16; N: 7.81. Found: C: 43.82 H: 3.28; N: 7.59.

(10.42) 2-Amino-5-ethylthio-4-[2-(5-phosphono)furanyl]oxazole. Anal. calcd for $C_9H_{11}N_2O_5PS+0.85HBr$: C: 30.11; H: 3.33; N: 7.80. Found: C: 30.18; H: 3.44; N: 7.60.

(10.43) 2-Amino-5-propylthio-4-[2-(5-phosphono)furanyl]oxazole. Anal. calcd for $C_{10}H_{13}N_2O_5+H_2O$: C: 37.27; H: 4.69; N: 8.69; $H_2O$: 5.59. Found: C: 37.27; H: 4.67; N: 8.60; $H_2O$: 5.66.

(10.44) 2-Amino-5-tert-butylthio-4-[2-(5-phosphono)furanyl]oxazole. Anal. calcd for $C_{11}H_{15}N_2O_5PS+0.25HBr$: C: 39.03; H: 4.54; N: 8.28. Found: C: 39.04; H: 4.62; N: 8.06.

(10.34) 4,5-Dimethyl-2-[2-(5-phosphono)furanyl]imidazole. Anal. Calcd. for $C_9H_{11}N_2O_4P+1.25 H_2O$: C: 40.84; H: 5.14; N: 10.58. Found: C: 41.02; H: 5.09; N: 10.27.

Example 11

Preparation of N-alkylated 4-[2-(5-phosphono)furanyl]imidazoles and 4-[2-(5-phosphono)furanyl]oxazoles Step A. A suspension of cesium carbonate (1.5 mmole) and 2-methyl-5-isobutyl-4-[2-(5-diethylphosphono)furanyl]imidazole (1 mmole) in DMF was treated with iodomethane (1.5 mmole) at 25° C. for 16 h. Extraction and chromatography gave 1,2-dimethyl-4-isobutyl-5-[2-(5-diethylphosphono)-furanyl]imidazole and 1,2-dimethyl-5-isobutyl-4-[2-(5-diethylphosphono)-furanyl]imidazole.

Step B. 1,2-Dimethyl-4-isobutyl-5-[2-(5-diethylphosphono)furanyl]-imidazole and 1,2-dimethyl-5-isobutyl-4-[2-(5-diethylphosphono)furanyl]-imidazole were subjected to Step C of Example 3 to give the following compounds:

(11.1) 1,2-Dimethyl-5-isobutyl-4-[2-(5-phosphono)furanyl]imidazole hydrogen bromide. Anal. Calcd. for $C_{13}H_2ON_2O_4PBr+0.8H_2O$: C: 39.67; H: 5.53; N: 7.12. Found: C: 39.63; H: 5.48; N: 7.16.

Example 12

Preparation of 2-[2-(6-phosphono)pyridyl]pyridine

Step A. A solution of 2,2'-bipyridyl (1 mmole) in dichloromethane was treated with m-chloroperoxybenzoic acid (2 mmole) at 0° C., and the reaction mixture was stirred at 25° C. for 2 h. Extraction and chromatography gave 2,2'-bipyridyl-N-oxide.

Step B. (Redmore, D., *J. Org. Chem.*, 1970, 35, 4114) A solution of 2,2'-bipyhdyl-N-oxide methyl ether (1 mmole, prepared from dimethyl sulfate and 2,2'-bipyridyl-N-oxide in diethyl phosphite) was added slowly at −30° C. to a solution of n-butyl lithium (1 mmole) in diethyl phosphite at −30° C. The resulting reaction mixture was stirred at 25° C. for 12 h. Extraction and chromatography gave 2-[2-(6-diethylphosphono)pyridyl]pyridine.

Step C. 2-[2-(6-Diethylphosphono)pyridyl]pyridine was subjected to Step C of Example 3 to give 2-[2-(6-phosphono)pyridyl]pyridine (12.1). mp 158–162° C. Anal. Calcd. for $C_{10}H_9N_2O_3P+0.5H_2O+0.1HBr$: C: 47.42; H: 4.02; N: 11.06. Found: C: 47.03; H: 3.67; N: 10.95.

Example 13

Preparation of 4.6-dimethyl-2-(phosphonomethoxymethyl)pyridine

Step A. A solution of 2,4,6-collidine (1 mmole) in carbon tetrachloride was treated with NBS (5 mmole) and dibenzoyl peroxide (0.25 mmole) at 80° C. for 12 h. The reaction mixture was cooled to 0° C. and the precipitate was filtered. The filtrate was concentrated under vacuum. Chromatography gave 2-bromomethyl-4,6-dimethylpyridine.

Step B. A solution of diethyl hydroxymethylphosphonate (1 mmole)in toluene was treated with sodium hydride (1.1 mmole) at 0° C., and after 15 min 2-bromomethyl-4,6-dimethylpyridine (1 mmole) was added. After 3 h the reaction mixture was subjected to extraction and chromatography to give 2-diethylphosphonomethyl-4,6-dimethylpyridine.

Step C. 2-Diethylphosphonomethyl-4,6-dimethylpyridine was subjected to Step C of Example 3 to give 4,6-dimethyl-2-(phosphonomethoxymethyl)pyridine (13.1). mp 109–112° C. Anal. Calcd for $C_9H_{14}NO_4P+1.0H_2O+0.5HBr$: C: 37.32; H: 5.74; N: 4.84. Found: C: 37.18; H: 5.38; N: 4.67.

The following compound was prepared similarly:

(13.2) 2-Amino-4-methyl-5-propyl-6-phosphonomethoxymethylpyrimidine. mp 153–156° C. Anal. Calcd. for $C_{10}H_{18}N_3O_4P+1.25H_2O+1.6HBr$: C: 28.11; H: 5.21; N: 9.84. Found: C: 28.25; H: 4.75; N: 9.74.

Example 14

Preparation of diethyl 5-tributylstannyl-2-furanphosphonate (14)

A solution of diethyl 2-furanphosphonate (1 mmole, prepared as in Step C of Example 1) in THF was cooled at −78° C. and cannulated to a solution of lithium N-isopropyl-N-cyclohexylamide in THF at −78° C. over 15 min. The resulting mixture was stirred at −78° C. for 2 h and cannulated into a solution of tributyltin chloride (1 mmole) in THF at −78° C. over 20 min. The mixture was then stirred at −78° C. for 1 h, and at 25° C. for 12 h. Extraction and chromatography gave compound (14) as a light yellow oil.

Example 15

Preparation of 6-[2-(5-phosphono)furanyl]pyridines

Step A. A solution of 2,6-dichloropyridine (120 mmol) in ethanol was treated with aqueous ammonia solution (28%, excess) at 160–165° C. for 60 h in a sealed tube. Extraction and chromatography gave 2-amino-6-chloropyridine as a white solid.

Step B. A solution of 2-amino-6-chloropyridine (1 mmole) and compound 14 (1 mmole) in p-xylene was treated with tetrakis(triphenylohosphine) palladium (0.05 mmole) at reflux for 12 h. Extraction and chromatography gave 2-amino-6-[2-(5-diethylphosphono)furanyl]pyridine as a light yellow solid.

Step C. 2-Amino-6-[2-(5-diethylphosphono)furanyl] pyridine was subjected to Step C of Example 3 to give 2-amino-6-[2-(5-phosphono)furanyl]pyridine (15.1). mp 186–187° C. Anal. Calcd. for $C_9H_9N_2O_4P+0.4HBr$: C: 39.67; H: 3.48; N: 10.28. Found: C: 39.95; H: 3.36; N: 10.04.

Step D. A solution of 2-amino-6-[2-(5-diethylphosphono) furanyl]pyridine (1 mmole) in acetic acid was treated with a solution of bromine in acetic acid (1N, 1 mmole) at 25° C. for 0.5 h. Evaporation and chromatography gave 2-amino-5-bromo-6-[2-(5-diethylphosphono)furanyl]pyridine and 2-amino-3,5-dibromo-6-[2-(5-diethylphosphono)furanyl] pyridine.

Step E. 2-Amino-5-bromo-6-[2-(5-diethylphosphono) furanyl]pyridine and 2-amino-3,5-dibromo-6-[2-(5-diethylphosphono)furanyl]pyridine were subjected to Step C of Example 3 to give the following compounds:

(15.2) 6-Amino-3-bromo-2-[2-(5-phosphono)furanyl] pyridine. Anal. Calcd. for $C_9H_8BrN_2O_4P+0.7H_2O+0.9HBr+0.12PhCH_3$: C: 28.44; H: 2.73; N: 6.74. Found: C: 28.64; H: 2.79; N: 6.31.

(15.3) 6-Amino-3,5-dibromo-2-[2-(5-phosphono)furanyl] pyridine. mp 233–235° C. Anal. Calcd. for $C_9H_7Br_2N_2O_4P+1.2HBr$: C: 21.84; H: 1.67; N: 5.66. Found: C: 21.90; H: 1.52; N: 5.30.

Step F. A solution of 2-amino-3,5-dibromo-6-[2-(5-diethylphosphono)-furanyl]pyridine (1 mmole) in DMF was treated with tributyl(vinyl)tin (1.2 mmole) and tetrakis (triphenylphosphine) palladium (0.2 mmole) at 85° C. for 4 h. Evaporation and chromatography gave 2-amino-3,5-bis (vinyl)-6-[2-(5-diethylphosphono)furanyl]pyridine.

Step G. A solution of 2-amino-3,5-bis(vinyl)-6-[2-(5-diethylphosphono)-furanyl]pyridine (1 mmole) in ethyl acetate was treated with palladium on carbon (10%) at 25° C. under 1 atmosphere of hydrogen for 12 h. Filtration, evaporation and chromatography gave 2-amino-3,5-diethyl-6-[2-(5-diethylphosphono)furanyl]pyridine.

Step H. 2-Amino-3,5-diethyl-6-[2-(5-diethylphosphono) furanyl]pyridine was subjected to Step C of Example 3 to give 2-amino-3,5-diethyl-6-[2-(5-phosphono)furanyl] pyridine (15.4). mp 217–218° C. Anal. Calcd. for $C_{13}H_{17}N_2O_4P+0.7H_2O+1.0HBr$: C: 40.06; H: 5.02; N: 7.19. Found: C: 40.14; H: 4.70; N: 6.87.

Step I. A solution of 2-amino-6-picoline (1 mmole) in 48% hydrobromic acid (4.4 mmole) was treated with bromine (3 mmole) at 0° C. for 1 h. An aqueous solution of sodium nitrite (2.5 mmole) was then added and the reaction mixture was stirred at 0° C. for 0.5 h. An aqueous solution of sodium hydroxide (9.4 mmole) was then added and the reaction mixture was stirred at 25° C. for 1 h. Extraction and chromatography gave 2,3-dibromo-6-picoline and 2,3,5-tribromo-6-picoline.

Step J. 2,3-Dibromo-6-picoline was subjected to Step B of Example 15 and followed by Step C of Example 3 to give 5-bromo-2-methyl-6-[2-(5-phosphono)furanyl]pyridine (15.5). mp 207–208° C. Anal. Calcd. for $C_{10}H_9BrNO_4P+0.6HBr$: C: 32.76; H: 2.64; N: 3.88. Found: C: 32.62; H: 2.95; N: 3.55.

Following compounds were prepared according to the above described procedures or with some minor modifications of these procedures using conventional chemistry.

(15.6) 2-[2-(5-Phosphono)furanyl]pyridine. mp 220–221° C. Anal. Calcd. for $C_9H_8NO_4P+0.1H_2O+0.45HBr$: C: 41.05; H: 3.31; N: 5.32. Found: C: 41.06; H: N: 5.10.

(15.7) 2-Amino-3-nitro-6-[2-(5-phosphono)furanyl] pyridine. mp 221–222° C. Anal. Calcd. for $C_9H_8N_3O_6P+0.55HBr+0.02PhCH_3$: C: 33.12; H: 2.65; N: 12.68. Found: C: 33.22; H: 2.43; N: 12.26.

(15.8) 2,3-Diamino-6-[2-(5-phosphono)furanyl]pyridine. mp 150–153° C. Anal. Calcd for $C_9H_{10}N_3O_4P+1.5HBr+0.05PhCH_3$: C: 29.46; H: 3.15; N: 11.02. Found: C: 29.50; H: 3.29; N: 10.60.

(15.9) 2-Chloro-6-[2-(5-phosphono)furanyl]pyridine. mp 94–96° C. Anal. Calcd. for $C_9H_7ClNO_4P+0.25HBr$: C: 38.63; H: 2.61; N: 5.01. Found: C: 38.91; H: 3.00; N: 5.07.

(15.10) 3,5-Dichloro-2-[2-(5-phosphono)furanyl] pyridine. mp 180–181° C. Anal. Calcd. for $C_9H_6Cl_2NO_4P+0.7HBr$: C: 31.61; H: 2.01; N: 3.94. Found: C: 31.69; H: 2.09; N: 3.89.

(15.11) 3-Chloro-5-trifluoromethyl-2-[2-(5-phosphono) furanyl]pyridine. mp 253–254° C. Anal. Calcd. for $C_{10}H_6ClF3NO_4P$: C: 36.67; H: 1.85; N: 4.28. Found: C: 36.69; H: 1.89; N: 4.30.

(15.12) 2-Amino-3-ethyl-6-[2-(5-phosphono)furanyl] pyridine. mp 220–221° C. Anal. Calcd. for $C_{11}H_{13}N_2O_4P+0.6HBr+0.2H_2O$: C: 41.24; H: 4.40; N: 8.74. Found: C: 41.02; H: 4.57; N: 8.68.

(15.13) 6-Amino-3-ethyl-2-[2-(5-phosphono)furanyl] pyridine. Anal. Calcd. for $C_{11}H_{13}N_2O_4P+1.0HBr+0.3H_2O$: C: 37.27; H: 4.15; N: 7.90. Found: C: 37.27; H: 4.19; N: 7.51.

(15.14) 6-Amino-3-propyl-2-[2-(5-phosphono)furanyl] pyridine. mp 252–253° C. Anal. Calcd. for $C_{12}H_{15}N_2O_4P+1.0HBr+1.0H_2O+0.32PhCH_3$: C: 41.65; H: 5.05; N: 6.82. Found: C: 41.97; H: 5.19; N: 6.83.

(15.15) 2,4-Dimethyl-3-bromo-6-[2-(5-phosphono) furanyl]pyridine. mp 232–233° C. Anal. Calcd. for $C_{11}H_{11}BrNO_4P+0.45HBr$: C: 35.85; H: 3.13; N: 3.80. Found: C: 35.98; H: 3.10; N: 3.71.

(15.16) 2-Chloro-4-amino-6-[2-(5-phosphono)furanyl] pyridine. Anal. Calcd. for $C_9H_8N_2O_4PCl+HBr+0.5 H_2O+MeOH$: C: 30.99; H: 3.38; N: 7.23. Found: C: 31.09; H: 3.21; N: 6.96.

(15.17) 3-Hydroxyl-2-[2-(5-phosphono)furanyl]pyridine. Anal. Calcd. for $C_9H_8NO_5P+1.1HBr+0.3 CH_3Ph$: C: 37.26; H: 3.24; N: 3.91. Found: C: 37.66; H: 3.55; N: 3.84.

(15.19) 2-Amino-3-cyclopropyl-6-[2-(5-phosphono) furanyl]pyridine. Anal. Calcd. for $C_{12}H_{13}N_2O_4PCl+HBr+0.4 H_2O$: C: 39.13; H: 4.05; N: 7.61. Found: C: 39.06; H: 3.85; N: 7.37.

(15.20) 2-Amino-5-cyclopropyl-6-[2-(5-phosphono) furanyl]pyridine. Anal. Calcd. for $C_{12}H_{13}N_2O_4P+HBr+0.7 CH_3Ph$: C: 47.69; H: 4.64; N: 6.58. Found: C: 47.99; H: 4.62; N: 6.91.

(15.21) 5-Amino-2-methoxy-6-[2-(5-phosphono)furanyl] pyridine. Anal. Calcd. for $C_{10}H_{11}N_2O_5P+0.2 H_2O$: C: 43.87; H: 4.20; N: 10.23. Found: C: 43.71; H: 3.77; N: 9.77.

(15.22) 2-Methyl-5-cyano-6-[2-(5-phosphono)furanyl] pyridine. Anal. Calcd. for $C_{11}H_9N_2O_4P+0.75 HBr+0.5 H_2O+0.5 MePh$: C: 45.84; H: 3.91; N: 7.37. Found: C: 45.93; H: 3.56; N: 7.36.

(15.23) 2-Amino-3,5-bis(cyano)-4-methyl-6-[2-(5-phosphono)furanyl]pyridine. Anal. Calcd. for $C_{12}H_9N_4O_4P+0.7 H_2O$: C: 45.49; H: 3.31; N: 17.68. Found: C: 45.48; H: 3.06; N: 17.51.

(15.24) 2-Chloro-4-cyano-6-[2-(5-phosphono)furanyl] pyridine. Anal. Calcd. for $C_{10}H_6N_2O_4PCl$: C: 42.20; H: 2.13; N: 9.84. Found: C: 41.95; H: 2.10; N: 9.47;

Example 16

Preparation of 2-[2-(5-phosphono)furanyl] pyrimidines and 4-[2-(5-phosphono)furanyl] pyrimidines Step A. A solution of 5-diethylphosphono-2-[(1-oxo) pentyl]furan in N,N-dimethylformamide dimethyl acetal was heated at reflux for 12 h. Evaporation and chromatography gave diethyl 5-(2-propyl-3-N,N-dimethylamino) acryloyl-2-furanphosphonate.

Step B. A solution of diethyl 5-(2-propyl-3-N,N-dimethylamino)acryloyl-2-furanphosphonate (1 mmole) in ethanol was treated with guanidine hydrogen chloride (1.2 mmole) and sodium ethoxide (1 mmole) at 80° C. for 12 h. The reaction mixture was evaporated, and residue was dissolved in water. The aqueous solution was neutralized with HCl (2 N), and concentrated under reduced pressure. The residue was co-evaporated with toluene to give 2-amino-5-propyl-4-[2-(5-ethylphosphono)-furanyl] pyrimidine as a yellow solid.

Step C. 2-Amino-5-propyl-4-[2-(5-ethylphosphono) furanyl]pyrimidine (1 mmole) and thionyl chloride was heated at reflux for 2 h. The reaction mixture was evaporated to dryness and the residue was dissolved in methylene chloride, and treated with excess pyridine and ethanol at 25° C. for 12 h. Evaporation and chromatography gave 2-amino-5-propyl-4-[2-(5-diethylphosphono)furanyl]pyrimidine.

Step D. 2-Amino-5-propyl-4-[2-(5-diethylphosphono) furanyl]pyrimidine was subjected to Step C of Example 3 to give 2-amino-5-propyl-4-[2-(5-phosphono)furanyl] pyrimidine (16.1). mp 258–259° C. Anal. Calcd. for $C_{11}H_{14}N_3O_4P+1.33H_2O$: C: 43.01; H: 5.47; N: 13.68. Found: C: 43.18; H: 5.31; N: 13.30.

The following compound was prepared according to this procedure:

(16.2) 2-Amino-5-isobutyl-4-[2-(5-phosphono)furanyl] pyrimidine. mp 218–220° C. Anal. Calcd. for $C_{12}H_{16}N_3O_4P+0.75HBr+0.3PhCH_3$: C: 43.92; H: 5.01; N: 10.90. Found: C: 44.02; H: 4.62; N: 10.69.

Alternatively other 4-[2-(5-phosphono)furanyl] pyrimidines can be prepared according to the following procedures:

Step E. Compound 2.2 was subjected to Step A of Example 16 to give diethyl 5-(3-N,N-dimethylamino) acryloyl-2-furanphosphonate as an orange solid.

Step F. A solution of diethyl 5-(3-N,N-dimethylamino) acryloyl-2-furanphosphonate (1 mmole), sodium ethoxide ethanol solution (2 mmole) and guanidine hydrochloride (1.1 mmole) was heated at 55° C. for 2 h. The reaction mixture was cooled in an ice bath and was neutralized with 1N HCl. Evaporation and chromatography gave 2-amino-4-[2-(5-diethylphosphono)-furanyl]pyrimidine as a yellow solid.

Step G. 2-Amino-4-[2-(5-diethylphosphono)furanyl] pyrimidine was subjected to Step C of Example 3 to give 2-amino-4-[2-(5-phosphono)furanyl]-pyrimidine (16.3). mp>230° C. Anal. Calcd. for $C_8H_8N_3O_4P+0.75H_2O+0.2HBr$: C: 35.48; H: 3.61; N: 15.51. Found: C: 35.42; H: 3.80; N: 15.30.

Step H. A solution of 2-amino-4-[2-(5-diethylphosphono) furanyl]pyrimidine (1 mmole) in methanol and chloroform was treated with NBS (1.5 mmole) at 25° C. for 1 h. Extraction and chromatography gave 2-amino-5-bromo-4-[2-(5-diethylphosphono)furanyl]pyrimidine as a yellow solid.

Step I. 2-Amino-5-bromo-4-[2-(5-diethylphosphono) furanyl]pyrimidine was subjected to Steps F and G of Example 15 followed by Step C of Example 3 to give 2-amino-5-ethyl-4-[2-(5-phosphono)furanyl]pyrimidine (16.4). mp>225° C. Anal. Calcd. for $C_{10}H_{12}N_3O_4P+1.4H_2O+0.2HBr+0.25PhCH_3$: C: 42.30; H: 5.14; N: 12.59. Found: C: 42.74; H: 4.94; N: 12.13.

The following compounds were prepared according to the above described procedures or with some minor modifications using conventional chemistry:

(16.5) 2-[2-(5-Phosphono)furanyl]pyrimidine. mp 194–196° C. Anal. Calcd. for $C_8H_7N_2O_4P+0.1H_2O+0.55HBr$: C: 35.27; H: 2.87; N: 10.28. Found: C: 35.26; H: 2.83; N: 9.89.

(16.6) 2-Amino-6-methyl-4-[2-(5-phosphono)furanyl]pyrimidine. mp 238–239° C. Anal. Calcd. for $C_9H_{10}N_3O_4P+0.9HBr$: C: 32.96; H: 3.35; N: 12.81. Found: C: 33.25; H: 3.34; N: 12.46.

(16.7) 2-Methylthio-4-[2-(5-phosphono)furanyl]pyrimidine. mp 228–229° C. Anal. Calcd. for $C_9H_9N_2O_4PS+0.5H_2O$: C: 38.44; H: 3.58; N: 9.96. Found: C: 38.19; H: 3.25; N: 9.66.

(16.8) 2-Methyl-4-[2-(5-phosphono)furanyl]pyrimidine. mp 206–212° C. Anal. Calcd. for $C_9H_9N_2O_4P+0.9H_2O+0.25HBr$: C: 34.05; H: 3.30; N: 8.82. Found: C: 34.02; H: 3.06; N: 8.75.

(16.9) 4,6-Dimethyl-5-bromo-2-[2-(5-phosphono)furanyl]pyrimidine. mp 251–252° C. Anal. Calcd. for $C_{10}H_{10}BrN_2O_4P$: C: 36.06; H: 3.03; N: 8.41. Found: C: 35.89; H: 2.82; N: 8.11.

(16.10) 2-Amino-5-chloro-4-[2-(5-phosphono)furanyl]pyrimidine. Anal. Calcd. for $C_8H_7ClN_3O_4P+0.5H_2O$: C: 33.76; H: 2.83; N: 14.76. Found: C: 33.91; H: 2.86; N: 14.20.

(16.11) 2-Amino-6-methylthio-4-[2-(5-phosphono)furanyl]pyrimidine. Anal. Calcd. for $C_9H_{10}N_3O_4PS+HBr$: C: 29.36; H: 3.01; N: 11.41. Found: C: 29.63; H: 3.02; N: 11.27.

(16.12) 2-Amino-5-bromo-6-methylthio-4-[2-(5-phosphono)furanyl]pyrimidine. Anal. Calcd. for $C_9H_9N_3O_4PSBr+0.8 HBr+0.2 MePh$: C: 27.80; H: 2.56; N: 9.35. Found: C: 27.74; H: 2.40; N: 8.94.

(16.13) 2-Amino-(4-morpholino)-4-[2-(5-phosphono)furanyl]pyrimidine. Mp>230° C. Anal. Calcd. for $C_{12}H_{15}N_4O_5P+HBr+0.05 MePh$: C: 36.02; H: 4.01; N: 13.61. Found: C: 35.98; H: 4.04; N: 13.33.

(16.14) 6-Amino-4-chloro-2-[2-(5-phosphono)furanyl]pyrimidine. Mp>230° C. Anal. Calcd. for $C_8H_7N_3O_4PCl+0.5 H_2O$: C: 33.76; H: 2.83; N: 14.76. Found: C: 33.83; H: 2.54; N: 14.48.

Example 17

Preparation of 2-[2-(5-phosphono)furanyl]pyrazines and 2-[2-(5-phosphono)furanyl]triazines Step A. The procedures described in Example 16 can also be applied to the synthesis of 2-[2-(5-phosphono)furanyl]pyrazine and 2-[2-(5-phosphono)furanyl]triazine analogs and in some cases with minor modifications of these procedures using conventional chemistry methods. The following compounds were prepared accordingly:

(17.1) 2,5-Dimethyl-3-[2-(5-phosphono)furanyl]pyrazine. mp 212–213° C. Anal. Calcd. for $C_{10}H_{11}N_2O_4P+0.75HBr$: C: 38.15; H: 3.76; N: 8.90. Found: C: 38.41; H: 3.93; N: 8.76.

(17.2) 2-Chloro-6-[2-(5-phosphono)furanyl]pyrazine. mp 204–205° C. Anal. Calcd. for $C_8H_6ClN_2O_4P+0.3HBr+0.02PhCH_3$: C: 34.10; H: 2.27; N: 9.77. Found: C: 34.36; H: 2.07; N: 9.39.

(17.3) 2-Amino-3-propyl-6-[2-(5-phosphono)furanyl]pyrazine. mp 227–228° C. Anal. Calcd. for $C_{11}H_{14}N_3O_4P+0.7HBr$: C: 38.87; H: 4.36; N: 12.36. Found: C: 39.19; H: 4.36; N: 11.92.

(17.4) 2-Amino-6-[2-(5-phosphono)furanyl]pyrazine. mp 235–236 IC. Anal. calcd. for $C_8H_8N_3O_4P+1.15H_2O+0.03PhCH_3$; C: 37.26; H: 4.01; N: 15.88. Found: C: 37.09; H: 3.67; N: 15.51.

(17.5) 2-Amino-3-bromo-6-[2-(5-phosphono)furanyl]pyrazine. Anal. calcd. for $C_8H_7N_3O_4PBr+1HBr$: C: 23.97; H: 2.01; N: 10.48. Found: C: 24.00; H: 2.00; N: 10.13.

(17.6) 3-Methylthio-2-[2-(5-phosphono)furanyl]pyrazine. Anal. calcd. for $C_9H_9N_2O_4PS+0.3 H_2O$: C: 38.94; H: 3.49; N: 10.09. Found: C: 38.99; H: 3.11; N: 9.67.

(17.7) 6-Amino-3-methylthio-2-[2-(5-phosphono)furanyl]pyrazine. Anal. calcd. for $C_9H_{10}N_3O_4PS+1.5 H_2O+1.7 HBr+0.25 MePh$: C: 27.19; H: 3.54; N: 8.85. Found: C: 27.10; H: 3.85; N: 8.49.

(17.8) 6-Amino-5-methylthio-2-[2-(5-phosphono)furanyl]pyrazine. Anal. calcd. for $C_9H_{10}N_3O_4PS+1.1 HBr+0.05 MePh$: C: 29.49; H: 3.04; N: 11.03. Found: C: 2923; H: 2.79; N: 10.87.

(17.9) 6-Amino-5-methoxycarbonyl-3-chloro-2-[2-(5-phosphono)furanyl]pyrazine. Anal. calcd. for $C_{10}H_9N_3O_6PCl+0.3 HBr+0.04 MePh$: C: 34.15; H: 2.68; N: 11.62. Found: C: 34.20; H: 2.90; N: 11.21.

(17.10) 6-Amino-3-methylthio-2-[2-(5-phosphono)furanyl]pyrazine ammonium salt. Anal. calcd. for $C_9H_{13}N_4O_4PS+0.8 HBr$: C: 29.30; H: 3.77; N: 15.18. Found: C: 29.03; H: 3.88; N: 15.08.

(17.11) 2-Amino-4-phenyl-6-[2-(5-phosphono)furanyl]triazine. Anal. calcd. for $C_{13}H_{11}N_4O_4P+HBr+0.1 EtOAc$: C: 39.45; H: 3.16; N: 13.73. Found: C: 39.77; H: 3.26; N: 13.48.

Example 18

Preparation of Analogs with X Being Methoxycarbonyl, Methylthiocarbonyl, Methylaminocarbonyl and Methylcarbonylamino Preparations of 4-phosphonomethoxycarbonylthiazoles and 4-phosphonomethoxycarbonyloxazoles Step A. A solution of 2-amino-4-ethoxycarbonylthiazole (1 mmole) in 1,4-dioxane (5 mL) was treated with di-tert-butyl dicarbonate (1.2 mmole), TMEDA (0.1 mmole) and DMAP (0.1 mmole) at room temperature. After the reaction was stirred for 20 h, it was evaporated to dryness. The residue was subjected to extraction to give 2-[N-Boc(amino)]-4-ethoxycarbonyl thiazole as a yellow solid.

Step B. A solution of 2-[N-Boc(amino)]-4-ethoxycarbonylthiazole (1 mmole) in a 2:1 mixture of EtOH:H$_2$O (10 mL) was treated with NaOH (3N, 3 mmole) and the reaction was stirred at 60° C. for 4 h. The reaction was cooled to 0° C. and neutralized to pH 5 with 3 N HCl, and the resulting solid was collected via filtration to give 2-[N-Boc(amino)]-4-carboxylthiazole as a white solid.

Step C. A suspension of 2-[N-Boc(amino)]-4-carboxylthiazole (1 mmole) in CH$_2$Cl$_2$ (5 mL) was treated with thionyl chloride (4 mmole) at room temperature. After stirring for 4 h the reaction was evaporated to dryness. The residue was dissolved in $CH_2Cl_2$ (5 mL) and added to a solution of diethyl (hydroxymethyl)phosphonate (1.5 mmole) and pyridine (2 mmole) in $CH_2Cl_2$ (5 mL) at 0° C. The reaction was warmed to room temperature and stirred for 4 h. The reaction was quenched with water and the mixture was subjected to extraction to give 2-[N-Boc(amino)]-4-diethylphosphonomethoxycarbonylthiazole as a thick yellow oil.

Alternatively the ester linkage can be formed using a mixed anhydride method as exemplified in the following procedures:

A solution of 2-[N-Boc(amino)]-4-carboxylthiazole (1 mmole) in pyridine (5 mL) was treated with para-toluenesulfonyl chloride (2 mmole) followed by diethyl (hydroxymethyl)phosphonate (2 mmole) at room temperature for 4 h. Evaporation, extraction and chromatography gave 2-[N-Boc(amino)]-4-diethylphosphonomethoxycarbonylthiazole as a thick yellow oil.

Step D. A solution of 2-[N-Boc(amino)]-4-diethylphosphonomethoxycarbonylthiazole (1 mmole) and anisole (0.1 mmole) in methylene chloride (5 mL) and trifluoroacetic acid (5 mL) was stirred at 0° C. for 1 h, and at room temperature for 1 h. Evaporation, extraction and chromatography gave 2-amino-4-diethyllphosphonomethoxycarbonylthiazole as a solid.

Step E. 2-Amino-4-diethyllphosphonomethoxycarbonylthiazole was subjected to Step C of Example 3 to give 2-amino-4-phosphonomethoxycarbonylthiazole (18.1) as a solid. Mp>240° C. (decomp). Anal. Calcd. for $C_5H_7N_2O_5PS$: C: 25.22; H: 2.96; N: 11.76. Found: C: 25.30; H: 2.86; N: 11.77.

Step F. A solution of 2-[N-Boc(amino)]-4-diethylphosphonomethoxycarbonylthiazole (1 mmole) in $CH_2Cl_2$ (5 mL) was treated with bromine (2 mmole) at room temperature for 4 h. Evaporation and extraction gave 2-[N-Boc(amino)]-5-bromo-4-diethylphosphonomethoxycarbonylthiazole as an orange oil which was subjected to Step D of Example 18 followed by Step C of Example 3 to give 2-amino-5-bromo-4-phosphonomethoxycarbonylthiazole (18.2) as a solid. Mp>230° C. (decomp). Anal. Calcd. for $C_5H_6N_2O_5PSBr$: C: 18.94; H: 1.91; N: 8.84. Found: C: 19.08; H: 1.76; N: 8.67.

Step G. A solution of 2-[N-Boc(amino)]-5-bromo-4-diethylphosphonomethoxycarbonylthiazole (1 mmole) and dichlorobis(triphenylphosphine)palladium(II) (0.1 mmole) in DMF (5 mL) was treated with tributyl(vinyl)tin (2.5 mmole) and the reaction was stirred at 60° C. for 2 h. The solvent was removed and the residue taken up in EtOAc and stirred with 2 mmol NaF in 5 ml water for 1 h. Extraction and chromatography gave 2-[N-Boc(amino)]-5-vinyl-4-diethylphosphonomethoxycarbonylthiazole as a yellow solid.

Step H. A suspension of 2-[N-Boc(amino)]-5-vinyl-4-diethylphosphonomethoxycarbonyl thiazole (1 mmole) and 10% Pd/C (0.5 mmole) in MeOH (5 mL) was stirred under an atmosphere of $H_2$ (balloon) at room temperature for 15 h. Filtration and evaporation gave 2-[N-Boc(amino)]-5-ethyl-4-diethylphosphonomethoxycarbonylthiazole as a yellow solid, which was subjected to Step D of Example 18 followed by Step C of Example 3 to give 2-amino-5-ethyl-4-phosphonomethoxycarbonylthiazole (18.3) as a solid. Mp>230° C. (decomp). Anal. Calcd. for $C_7H_{11}N_2O_5PS$: 31.58; H: 4.16; N: 10.52. Found: C: 31.80; H: 4.04; N: 10.18.

Step I. A solution of N-[Bis(methylthio)methylene] glycine methyl ester (1 mmole) in anhydrous THF (2 mL) was added to a solution of t-BuOK (1.4 mmole) in anhydrous THF (10 mL) at −78° C. and the mixture was stirred for 30 min. Then a solution of ethyl isothiocyanate (1 mmole) in anhydrous THF (2 mL) was added and the reaction was stirred at −78° C. for 30 min and at room temperature for 2 h. The reaction was quenched with water. Extraction and chromatography gave 2-methylthio-5-(N-ethylamino)-4-methoxycarbonylthiazole as a yellow solid, which was subjected to Step B and C of Example 18 followed by Step C of Example 3 to give 2-methylthio-5-(N-ethylamino)-4-phosphonomethoxycarbonylthiazole (18.4) as a solid. Mp>200° C. (decomp). Anal. Calcd. for $C_8H_{13}N_2O_5PS_2$+0.1 HBr: C: 29.99; H: 4.12; N: 8.74. Found: C: 29.71; H: 4.10; N: 8.60.

I. Preparation of 4-phosphonomethylthiocarbonylthiazole

Step J. A solution of 1 mmol of 2-[N-Boc(amino)]-4-thiazolecarboxylate acid chloride (1 mmole) and pyridine (2 mmole) in $CH_2Cl_2$ (5 mL), was cooled to −78° C. and $H_2S(g)$ was bubbled through the solution for 10 min. The reaction was stirred at −78° C. for 30 min and then warmed to room temperature. The mixture was washed with 3 N HCl. The organic phase was separated, dried and concentrated to give 2-[N-Boc(amino)]-4-thiazolethiocarboxylic acid as a yellow solid.

Step K. A solution of give 2-[N-Boc(amino)]-4-thiazolethiocarboxylic acid (1 mmole) in THF (5 mL) was cooled to −78° C. and treated with NaH (2 mmole) in small portions. After 10 min the reaction was treated with a solution of diethylphosphonomethyl triflate in THF (5 mL). The reaction was stirred at −78° C. for 1 h, and then quenched with $H_2O$. Extraction and chromatography gave 2-[N-Boc(amino)]-4-diethylphosphonomethylthiocarbonylthiazole as a thick oil, which was subjected to Step D of Example 18 followed by Step C of Example 3 to give 2-amino-4-phosphonomethylthiocarbonylthiazole (18.5) as a solid. Mp>230° C. (decomp). Anal. Calcd. for $C_5H_7N_2O_4PS_2$: C: 23.62; H: 2.78; N: 11.02. Found: C: 23.77; H: 2.61; N: 10.73.

Preparation of 4-[(N-phosphonomethyl)carbamoyl]thiazole, 3-[N-phosphonomethyl)-carbamoyl]isbthiazole and 2-[N-phosphonomethyl)carbamoyl]pyridine Step L. A solution of 2-[N-Boc(amino)]-4-thiazolecarboxylic acid (1 mmole) in DMF (5 mL) was treated with 1-(3-dimethylaminopropyl)-3-ethylcarbodiimide hydrochloride (EDCI, 1.5 mmole) and 1-hydroxylbenzotriazole hydrate (HOBt, 1.5 mmole) followed by addition of diethyl aminomethylphosphonate (1.5 mmole) at room temperature for 24 h. The reaction was subjected to evaporation, extraction and chromatography to give 2-[N-Boc(amino)]-4-[(N-diethylphosphonomethyl)carbamoyl]thiazole as a white solid, which was subjected to Step D of Example 18 followed by Step C of Example 3 to give 2-amino-4-[(N-phosphonomethyl)carbamoyl]thiazole (18.6) as a light brown solid. Mp>245° C. (decomp). Anal. Calcd. for $C_5H_8N_3O_4PS$+1.05 HBr: C: 18.64; H: 2.83; N: 13.04. Found: C: 18.78; H: 2.43; N: 12.97.

Preparation of 2-[(N-phosphonoacetyl)amino]thiazole and 2-[(N-phosphonoacetyl)amino]pyridine Step M. A solution of 2-amino-4,5-dimethylthiazole hydrochloride (2 mmole) and diethyl phosphonoacetica acid (1 mmole) in DMF (5 mL) was treated with EDCI (1.5 mmole), HOBt (1.5 mmole) and triethylamine (2 mmole) at room temperature for 24 h. The reaction was subjected to evaporation, extraction and chromatography to give 2-[(N- diethylphosphonoacetyl)amino]-4,5-dimethylthiazole as a yellow solid, which was subjected to Step D of Example 18 followed by Step C of Example 3 to give 4,5-dimethyl-2-[(N-phosphonoacetyl)amino]thiazole (18.7) as a light brown solid. Mp>250° C. Anal. Calcd. for $C_7H_{11}N_2O_4PS$: C: 33.60; H: 4.43; N: 11.20. Found: C: 33.62; H: 4.29; N: 10.99.

The following compounds were prepared using some of the above described procedures or some of the above procedures with some minor modifications using conventional chemistry:

(18.8) 2-[(N-phosphonomethyl)carbamoyl]pyridine. Anal. Calcd. for $C_7H_9N_2O_4P+HBr+0.67\ H_2O$: C: 27.20; H: 3.70; N: 9.06. Found: C: 27.02; H: 3.71; N: 8.92.

(18.9) 2-[(N-phosphonoacetyl)amino]pyridine. Anal. Calcd. for $C_7H_9N_2O_4P+HBr+0.67\ H_2O$: C: 27.20; H: 3.70; N: 9.06. Found: C: 27.05; H: 3.59; N: 8.86.

(18.10) 4-Ethoxycarbonyl-2-[(N-phosphonoacetyl)amino]thiazole. Anal. Calcd. for $C_8H_{11}N_2O_6PS$: C: 32.66; H: 3.77; N: 9.52. Found: C: 32.83; H: 3.58; N: 9.20.

(18.11) 2-Amino-5-bromo-4-[(N-phosphonomethyl)carbamoyl]thiazole. Mp 232° C. (decomp). Anal. Calcd. for $C_5H_7N_3O_4PSBr+0.15HBr+0.1$ hexane: C: 19.97; H: 2.56; N: 12.48. Found: C: 19.90; H: 2.29; N: 12.33.

(18.12) 2-Amino-5-(2-thienyl)-4-[(N-phosphonomethyl)carbamoyl]thiazole. Mp 245° C. (decomp). Anal. Calcd. for $C_9H_{10}N_3O_4PS_2+HBr+0.1$ EtOAc: C: 27.60; H: 2.91; N: 10.27. Found: C: 27.20; H: 2.67; N: 9.98.

(18.13) 4,5-Dichloro-3-[(N-phosphonomethyl)carbamoyl]isothiazole. Mp 189–191° C. Anal. Calcd. for $C_5H_5N_2O_4PSCl_2$: C: 20.63; H: 1.73; N: 9.62. Found: C: 20.43; H: 1.54; N: 9.51.

(18.14) 2-Amino-5-bromo-4-{[N-(1-phosphono-1-phenyl)methyl]carbamoyl}thiazole. Mp>250° C. Anal. Calcd. for $C_{11}H_{11}N_3O_4PSBr$: C: 33.69; H: 2.83; N: 10.71. Found: C: 33.85; H: 2.63; N: 10.85.

(18.15) 2-Amino-5-(2-thienyl)-4-phosphonomethoxycarbonylthiazole. Mp>230° C. (decomp). Anal. Calcd. for $C_9H_9N_2O_5PS_2$: C: 33.75; H: 2.83; N: 8.75. Found: C: 33.40; H: 2.74; N: 8.51.

(18.16) 2-Amino-5-benzyl-4-phosphonomethoxycarbonylthiazole. Mp>230° C. (decomp). Anal. Calcd. for $C_{12}H_{13}N_2O_5PS$: C: 43.91; H: 3.99; N: 8.53. Found: C: 43.77; H: 4.03; N: 8.25.

(18.17) 2-Methylthio-5-methylamino-4-phosphonomethoxycarbonylthiazole. Anal. Calcd. for $C_7H_{11}N_2O_5PS_2+0.2\ HBr$: C: 26.74; H: 3.59; N: 8.91. Found: C: 26.79; H: 3.89; N: 8.89.

(18.18) 2-Amino-5-ethyl-4-[(N-phosphonomethyl)carbamoyl]thiazole. Mp 180° C. (decomp). Anal. Calcd. for $C_7H_{12}N_3O_4PS+HBr+0.4\ CH_2Cl_2$: C: 23.49; H: 3.67; N: 11.18. Found: C: 23.73; H: 3.29; N: 11.42.

(18.19) 2-Amino-5-isopropyl-4-[(N-phosphonomethyl)carbamoyl]thiazole. Mp 247–250° C. Anal. Calcd. for $C_8H_{14}N_3O_4PS$: C: 34.41; H: 5.05; N: 15.05. Found: C: 34.46; H: 4.80; N: 14.68.

(18.20) 2-Amino-5-isopropyl-4-phosphonomethoxycarbonylthiazole. Mp>230° C. Anal. Calcd. for $C_8H_{13}N_2O_5PS$: C: 34.29; H: 4.68; N: 10.00. Found: C: 33.97; H: 4.49; N: 9.70.

(18.21) 2-Amino-5-phenyl-4-phosphonomethoxycarbonylthiazole. Mp>230° C. Anal. Calcd. for $C_{11}H_{11}N_2O_5PS$: C: 42.04; H: 3.53; N: 8.91. Found: C: 42.04; H: 3.40; N: 8.72.

(18.22) 2-Amino-4-phosphonomethoxycarbonyloxazole. Anal. Calcd. for $C_5H_7N_2O_6P+0.09\ HBr$: C: 26.18; H: 3.12; N: 12.21. Found: C: 26.29; H: 3.04; N: 11.90.

(18.23) 2-Amino-6-[(N-phosphonoacetyl)amino]pyridine. Anal. Calcd. for $C_7H_{10}N_3O_4P+1.1\ HBr+0.25$ MeOH: C: 26.54; H: 3.72; N: 12.80. Found: C: 26.79; H: 3.63; N: 12.44.

(18.24) 2-Amino-5-methyl-4-[(N-phosphonomethyl)carbamoyl]thiazole. Mp>250° C. Anal. Calcd. for $C_6H_{10}N_3O_4PS+0.06$ EtOAc: C: 29.22; H: 4.12; N: 16.38. Found: C: 29.03; H: 3.84; N: 16.01.

(18.25) 2-Amino-3-bromo-6-[(N-phosphonoacetyl)amino]pyridine. Anal. Calcd. for $C_7H_9N_3O_4PBr+1.25\ HBr+0.8$ EtOAc: C: 25.43; H: 3.48; N: 8.72. Found: C: 25.58; H: 3.71; N: 8.56.

(18.26) 2-Amino-3,5-dibromo-6-[(N-phosphonoacetyl)amino]pyridine. Anal. Calcd. for $C_7H_8N_3O_4PBr_2+HBr+0.5$ EtOAc: C: 21.03; H: 2.55; N: 8.18. Found: C: 21.28; H: 2.55; N: 7.91.

(18.27) 2-Amino-5-methyl-4-phosphonomethoxycarbonylthiazole. Mp 230° C. (decomp). Anal. Calcd. for $C_6H_9N_2O_5PS$: C: 28.58; H: 3.60; N: 11.11. Found: C: 28.38; H: 3.49; N: 11.10.

(18.28) 2-Amino-3,5-diethyl-6-[(N-phosphonoacetyl)amino]pyridine. MS calcd. for $C_{11}H_{18}N_3O_4P+H$: 288, found 288.

(18.29) 2-Amino-3,5-dibromo-6-{[N-(2,2-dibromo-2-phosphono)acetyl]amino}pyridine. Anal. Calcd. for $C_7H_6N_3O_4PBr_4+0.5\ HBr+EtOAc$: C: 19.56; H: 2.16; N: 6.22. Found: C: 19.26; H: 2.29; N: 5.91.

(18.30) 2-Amino-5-isopropyl-4-phosphonomethoxycarbonyloxazole. Anal. Calcd. for $C_8H_{13}N_2O_6P+0.2\ HBr$: C: 34.27; H: 4.75; N: 9.99. Found: C: 34.47; H: 4.84; N: 9.83.

(18.31) 2-Amino-5-[1-(2-cyclohexylmethyl)ethynyl]-4-phosphonomethoxycarbonylthiazole. Mp 230° C. (decomp). Anal. Calcd. for $C_{14}H_{19}N_2O_5PS+0.1\ HBr$: C: 45.89; H: 5.25; N: 7.64. Found: C: 45.85; H: 4.96; N: 7.44.

(18.32) 2-Amino-5-[1-(4-cyano)butynyl]-4-phosphonomethoxycarbonylthiazole. Mp 230° C. (decomp). Anal. Calcd. for $C_{10}H_{10}N_3O_5PS+0.25\ HBr$: C: 35.80; H: 3.08; N: 12.53. Found: C: 35.92; H: 2.99; N: 12.20.

(18.33) 2-Amino-5-methyl-4-phosphonomethoxycarbonyloxazole. Anal. Calcd. for $C_6H_9N_2O_6P+0.15\ HBr$: C: 29.03; H: 3.71; N: 11.28. Found: C: 28.98; H: 3.66; N: 11.21.

(18.34) 2-Amino-5-[1-(4-cyano)butyl]-4-phosphonomethoxycarbonylthiazole. Mp 230° C. (decomp). Anal. Calcd. for $C_{10}H_{14}N_3O_5PS$: C: 37.62; H: 4.42; N: 13.16. Found: C: 37.23; H: 4.18; N: 12.79.

(18.35) 2-Amino-5-pentyl-4-phosphonomethoxycarbonyloxazole. Anal. Calcd. for $C_{10}H_{17}N_2O_6P$: C: 41.10; H: 5.86; N: 9.59. Found: C: 41.16; H: 5.75; N: 9.50.

(18.36) 2-[N-Boc(amino)]-4-[(2-phosphono)ethoxycarbonyl]thiazole. Anal. Calcd. for $C_{11}H_{17}N_2O_7PS$: C: 37.50; H: 4.86; N: 7.95. Found: C: 37.10; H: 4.59; N: 7.84.

(18.37) 2-Amino-4-[(2-phosphono)ethoxycarbonyl]thiazole hydrobromide. Anal. Calcd. for $C_6H_9N_2O_5PS+HBr$: C: 21.63; H: 3.03; N: 8.41. Found: C: 22.01; H: 2.99; N: 8.15.

(18.38) 2-Amino-5-butyl-4-phosphonomethoxycarbonyloxazole. Anal. Calcd. for $C_9H_{15}N_2O_6P$: C: 38.86; H: 5.43; N: 10.07. Found: C: 38.59; H: 5.43; N: 9.96.

(18.39) 2-Amino-5-[1-(1-oxo-2,2-dimethyl)propyl]-4-phosphonomethoxycarbonylthiazole. Anal. Calcd. for $C_{10}H_{15}N_2O_6PS$: C: 37.27; H: 4.69; N: 8.69. Found: C: 37.03; H: 4.69; N: 8.39.

(18.40) 2-Amino-5-propyl-4-phosphonomethoxycarbonyloxazole. Anal. Calcd. for $C_8H_{13}N_2O_6P$+0.35 EtOAc+0.05 HBr: C: 37.75; H: 5.34; N: 9.37. Found: C: 37.69; H: 5.21; N: 9.03.

(18.41) 2-Amino-5-propyl-4-phosphonomethoxycarbonylthiazole. Mp 134° C. (decomp). Anal. Calcd. for $C_8H_{13}N_2O_5PS$: C: 34.29; H: 4.68; N: 10.00. Found: C: 33.90; H: 4.30; N: 9.61.

(18.42) 2-Amino-5-pentyl-4-phosphonomethoxycarbonylthiazole. Mp 130° C. (decomp). Anal. Calcd. for $C_{10}H_{17}N_2O_5PS$: C: 38.96; H: 5.56; N: 9.09. Found: C: 38.69; H: 5.25; N: 8.85.

(18.43) 2-Amino-5-bromo-4-phosphonomethylthiocarbonylthiazole. Mp 230° C. (decomp). Anal. Calcd. for $C_5H_6N_2O_5PS_2Br$: C: 18.03; H: 1.82; N: 8.41. Found: C: 18.40; H: 1.93; N: 8.18.

(18.44) 2-Amino-5-(2-furanyl)-4-phosphonomethoxycarbonylthiazole. Mp 230° C. (decomp). Anal. Calcd. for $C_9H_9N_2O_6PS$: C: 35.53; H: 2.98; N: 9.21. Found: C: 35.78; H: 3.05; N: 8.11.

(18.45) 2-Amino-5-ethyl-4-phosphonomethoxycarbonyloxazole. Mp 141° C. (decomp). Anal. Calcd. for $C_7H_{11}N_2O_6P$: C: 33.61; H: 4.43; N: 11.20. Found: C: 33.79; H: 4.47; N: 11.09.

(18.46) 5-Methyl-4-[(N-phosphonomethyl)carbamoyl]imidazole. Anal. calcd. for $C_6H_{10}N_3O_4P$: C: 32.89; H: 4.60; N: 19.18. Found; C: 33.04; H: 4.65; N: 18.84.

Example 19

Preparation of Various Phosphonate Diesters as Prodrugs

A suspension of 2-methyl-5-isobutyl-4-[2-(5-phosphono)furanyl]thiazole (1 mmole) in thionyl chloride (5 mL) was warmed at reflux for 4 h. The cooled reaction mixture was evaporated to dryness and the resulting yellow residue was dissolved in methylene chloride and treated with a solution of the corresponding benzyl alcohol (4 mmole) and pyridine (2.5 mmole) in methylene chloride. After stirring at 25° C. for 24 h the reaction mixture was subjected to extraction and chromatography to give the titled compounds. The following compounds were prepared according to this procedure:

(19.1) 2-Methyl-5-isobutyl-4-{2-[5-bis(4-pivaloyloxybenzyl)phosphono]furanyl}thiazole. Anal. Calcd. for $C_{36}H_{44}NO_8PS$+0.4H$_2$O: C: 62.76; H: 6.55; N: 2.03. Found: C: 62.45; H: 6.44; N: 2.04.

(19.2) 2-Methyl-5-isobutyl-4-{2-[5-bis(3,4-diacetoxybenzyl)phosphono]furanyl} thiazole. Anal. Calcd. for $C_{34}H_{36}NO_{12}PS$+0.8H$_2$O: C: 56.09; H: 5.21; N: 1.92. Found: C: 55.90; H: 4.98; N: 1.94.

(19.3) 2-Methyl-5-isobutyl-4-{2-[5-bis(4-acetoxy-3-methoxybenzyl)phosphono]furanyl}thiazole. Anal. Calcd. for $C_{32}H_{36}NO_{10}PS$: C: 58.44; H: 5.52; N: 2.13. Found: C: 58.16; H: 5.34; N: 2.13.

(19.4) 2-Methyl-5-isobutyl-4-{2-[5-bis(4-acetoxy-3-methylbenzyl)phosphono]furanyl}thiazole. Anal. Calcd. for $C_{32}H_{36}NO_8PS$: C: 61.43; H: 5.80; N: 2.24. Found: C: 61.34; H: 5.89; N: 2.25.

(19.5) 2-Amino-5-isobutyl-4-{2-[5-bis(3,4-diacetoxybenzyl)phosphono]furanyl}thiazole. Anal. Calcd. for $C_{33}H_{35}N_2O_{12}PS$: C: 55.46; H: 4.94; N: 3.92. Found: C: 55.06; H: 4.96; N: 3.79.

(19.6) 2-Amino-5-isobutyl-4-{2-[5-bis(4-acetoxybenzyl)phosphono]furanyl}thiazole. Anal. Calcd. for $C_{29}H_{31}N_2O_8PS$: C: 58.19; H: 5.22; N: 4.68. Found: C: 57.82; H: 4.83; N: 4.50.

This method is also useful for the preparation of phenyl phosphonate esters as prodrugs, and the following compound was prepared:

(19.7) 2-Methyl-5-isobutyl-4-[2-(5-diphenylphosphono)furanyl]thiazole. Anal. Calcd. for $C_{24}H_{24}NO_4PS$+0.1H$_2$O: C: 63.31; H: 5.36; N: 3.08. Found: C: 63.22; H: 5.34; N: 3.14.

(19.63) 2-Amino-5-isobutyl-4-[2-(5-diphenylphosphono)furanyl]thiazole. Mp 128–129 0° C. Anal. Calcd. for $C_{23}H_{23}N_2O_4PS$: C: 60.78; H: 5.10; N: 6.16. Found: C: 60.68; H: 4.83; N: 6.17.

(19.64) 2-Amino-5-isobutyl-4-[2-(5-phenylphosphono)furanyl]thiazole. Mp>250 0° C. Anal. Calcd. for $C_{17}H_{19}N_2O_4PS$: C: 53.96; H: 5.06; N: 7.40. Found: C: 53.81; H: 4.87; N: 7.41.

(19.65) 2-Amino-5-isobutyl-4-[2-(5-bis(3-chlorophenyl)phosphono)furanyl]thiazole. Anal. Calcd. for $C_{23}H_{21}N_2O_4PSCl_2$+0.5 H$_2$O: C: 51.89; H: 4.17; N: 5.26. Found C: 51.55; H: 3.99; N: 5.22.

(19.67) 2-Amino-5-isobutyl-4-[2-(5-bis(4-methoxyphenyl)phosphono)furanyl]thiazole. Anal. Calc. for $C_{25}H_{27}N_2O_6PS$+0.5 H$_2$O: C: 57.35; H: 5.39; N: 5.35. Found C: 57.11; H: 5.36; N: 5.75.

This method is also useful for the preparation of some thio-containing phosphonate esters as prodrugs, and the following compounds were prepared:

(19.8) 2-Methyl-5-isobutyl-4-{2-[5-bis(2-methylcarbonylthioethyl)phosphono]furanyl}thiazole. Anal. Calcd. for $C_{20}H_{28}NO_6PS_3$: C: 47.51; H: 5.58; N: 2.77. Found: C: 47.32; H: 5.56; N: 2.77.

(19.9) 2-Methyl-5-isobutyl-4-{2-[5-bis(thiobenzoylmethyl)phosphono]furanyl}thiazole. Anal. Calcd. for $C_{28}H_{28}NO_6PS_3$: C: 55.89; H: 4.69; N: 2.33. Found: C: 55.73; H: 4.72; N: 2.28.

This method is also useful for the preparation of cyclic phosphonate esters (e.g. cyclic 1,3-propanediol phosphonate esters) as prodrugs by coupling of phosphonic acids with various diols (e.g. 1,3-propanediols see Example 21 for the synthesis of some 1,3-propanediols), and the following compounds were made:

(19.10) 5-Isobutyl-2-methyl-4-{2-[5-(1-hydroxy-3,5-cyclohexyl)phosphono]furanyl}thiazole (minor isomer). Anal. Calcd. for $C_{18}H_{24}NO_5PS$+0.33H$_2$O: C: 53.60; H: 6.16; N: 3.47. Found: C: 53.75; H: 6.53; N: 3.45.

(19.11) 5-Isobutyl-2-methyl-4-{2-[5-(1-hydroxy-3,5-cyclohexyl)phosphono]furanyl}thiazole (major isomer). Anal. Calcd. for $C_{18}H_{24}NO_5PS$: C: 54.40; H: 6.09; N: 3.52. Found: C: 54.44; H: 6.11; N: 3.63.

(19.12) 5-Isobutyl-2-methyl-4-{2-[5-(2-hydroxymethyl-1,3-propyl)phosphono]furanyl}thiazole. Anal. Calcd. for $C_{16}H_{22}NO_5PS$+0.3CH$_2$Cl$_2$+0.5H$_2$O: C: 48.24; H: 5.86; N: 3.45. Found: C: 47.94; H: 5.59; N: 3.57.

(19.13) 5-Isobutyl-2-methyl-4-{2-[5-(1-phenyl-1,3-propyl)phosphono]furanyl}thiazole, (minor isomer). Anal. Calcd. for $C_{21}H_{24}NO_4PS$+0.25H$_2$O: C: 59.77; H: 5.85; N: 3.32. Found: C: 59.76; H: 5.69; N: 3.38.

(19.14) 5-Isobutyl-2-methyl-4-{2-[5-(1-phenyl-1,3-propyl)phosphono]furanyl}thiazole, (major isomer). Anal. Calcd. for $C_{21}H_{24}NO_4PS$+0.5 H$_2$O: C: 59.14; H: 5.91; N: 3.28. Found: C: 59.27; H: 5.85; N: 3.38.

(19.15) 2-Amino-5-isobutyl-4-[2-(5-[2-(methoxycarbonyloxymethyl)-propan-1,3-yl]phosphono)furanyl]thiazole (minor isomer). mp 170–173° C. Anal. Calcd. for $C_{17}H_{23}N_2O_7PS$: C: 47.44; H: 5.39; N: 6.51. Found: C: 47.28; H: 5.27; N: 6.47.

(19.16) 2-Amino-5-isobutyl-4-[2-(5-[2-(methoxycarbonyloxymethyl)-propan-1,3-yl]phosphono)furanyl]thiazole (major isomer). Anal. Calcd. for $C_{17}H_{23}N_2O_7PS+0.5\ H_2O$: C: 46.47; H: 5.51; N: 6.38. Found: C: 46.38; H: 5.29; N: 6.20.

(19.17) 5-Isobutyl-2-methyl-4-{2-[5-(1-(4-pyridyl)-1,3-propyl)phosphono]furanyl}-thiazole. Anal. Calcd. for $C_{20}H_{23}N_2O_4PS+2H_2O+0.4CH_2Cl_2$: C: 50.16; H: 5.74; N: 5.74. Found: C: 50.36; H: 5.36; N: 5.80.

(19.18) 2-Amino-5-isobutyl-4-(2-{5-[1-(4-pyridyl)-propan-1,3-yl]phosphono}furanyl)-thiazole. mp 101–106° C. Anal. Calcd. for $C_{19}H_{22}N_3O_4PS+0.75H_2O$: C: 52.71; H: 5.47; N: 9.71. Found: C: 52.59; H: 5.49; N: 9.65.

(19.20) 2-Amino-5-isobutyl-4-{2-[5-(1-phenyl-1,3-propyl)phosphono]furanyl}thiazole (minor isomer). Anal. Calcd. for $C_{20}H_{23}N_2O_4PS+0.33HCl$: C: 55.80; H: 5.46; N: 6.51. Found: C: 55.95; H: 5.36; N: 6.46.

(19.21) 2-Amino-5-isobutyl-4-{2-[5-(1-phenyl-1,3-propyl)phosphono] furanyl} thiazole (major isomer). Anal. Calcd. for $C_{20}H_{23}N_2O_4PS+0.33HCl$: C: 55.80; H: 5.46; N: 6.51. Found: C: 55.77; H: 5.19; N: 6.44.

(19.22) 2-Amino-5-ethyl-4-{2-[5-(1-phenyl-1,3-propyl)phosphono]furanyl} thiazole (less polar isomer). Anal. Calcd. for $C_{18}H_{19}N_2O_4PS+0.2HCl+0.25\ H_2O$: C: 53.75; H: 4.94; N: 6.97. Found: C: 53.86; H: 4.70; N: 6.87.

(19.23) 2-Amino-5-ethyl-4-{2-[5-(1-phenyl-1,3-propyl)phosphono]furanyl}-thiazole (more polar isomer). Anal. Calcd. for $C_{18}H_{19}N_2O_4PS+0.2HCl+0.25\ H_2O$: C: 53.75; H: 4.94; N: 6.97. Found: C: 53.92; H: 4.82; N: 6.92.

(19.24) 2-Amino-5-ethyl-4-{2-[5-(1-{4-pyridyl}-1,3-propyl)phosphono]furanyl}thiazole. Anal. Calcd. for $C_{17}H_{18}N_3O_4PS+0.1HCl+0.5\ H_2O$: C: 50.54; H: 4.76; N: 10.40. Found: C: 50.38; H: 4.53; N: 10.25.

(19.25) 2-Methyl-4-{2-[5-(2-acetoxymethylpropan-1,3-diyl)phosphono]furanyl}thiazole. Anal. calcd. for $C_{14}H_{16}NO_6PS+0.5H_2O$: C: 45.90; H: 4.68; N: 3.82. Found C: 45.50; H: 4.55; N: 3.45.

(19.26) 2-Methyl-4-(2-{5-[1-(4-pyridyl)propan-1,3-diyl]phosphono}furanyl)thiazole. Anal. calcd. for $C_{16}H_{15}N_2O_4PS+0.75H_2O$: C: 51.13; H: 4.42; N: 7.45. Found: C: 50.86; H: 4.72; N: 7.11.

(19.27) 2-Amino-5-methylthio-4-(2-{5-[1-(4-pyridyl)propan-1,3-diyl]phosphono}furanyl)thiazole. Anal. calcd. for $C_{16}H_{16}N_3O_4PS_2+0.4\ HCl$: C: 45.32; H: 3.90; N: 9.91. Found: C: 45.29; H: 3.80; N: 9.83.

(19.28) 2-Amino-5-isobutyl-4-{2-[5-(1-(3-bromophenyl)propan-1,3-diyl)phosphono]furanyl}thiazole, major isomer. Anal. calcd. for $C_{20}H_{22}N_2O_4PBrS$: C: 48.30; H: 4.46; N: 5.63. Found: C: 48.51; H: 4.21; N: 5.33.

(19.29) 2-Amino-5-methylthio-4-{2-[5-(1-(R)-phenyl-1,3-propyl)phosphono]furanyl}thiazole. Anal. Calcd. for $C_{17}H_{17}N_2O_4PS+HCl$: C: 49.46; H: 4.39; N: 6.79. Found: C: 49.77; H: 4.13; N: 6.54.

(19.30) 2-Amino-5-isobutyl-4-{2-[5-(1-(3-bromophenyl)-1,3-propyl)phosphono]furanyl}thiazole, minor isomer. Anal. Calcd. for $C_{20}H_{22}N_2O_4PSBr+0.25HCl$: C: 47.43; H: 4.43; N: 5.53. Found: C: 47.58; H: 4.16; N: 5.31.

(19.31) 2-Amino-5-isobutyl-4-{2-[5-(2-benzyl-1,3-propyl)phosphono]furanyl}thiazole. Anal. Calcd. for $C_{21}H_{25}N_2O_4PS$: C: 58.32; H: 5.83; N: 6.48. Found: C: 57.98; H: 5.65; N: 6.47.

(19.32) 2-Amino-5-cyeloproyl-4-{2-[5-(1-(4-pyridyl)-1,3-propyl)phosphono]furanyl}thiazole. Anal. Calcd. for $C_{18}H_{18}N_3O_4PS+0.5H_2O$: C: 52.42; H: 4.64; N: 10.19. Found: C: 52.62; H: 4.51; N: 9.89.

(19.33) 2-Methyl-5-isobutyl-4-{2-[5-(1-(S)-phenyl-1,3-propyl)phosphono]furanyl}thiazole, minor isomer. Anal. Calcd. for $C_{21}H_{24}NO_4PS$: C: 60.42; H: 5.79; N: 3.36. Found: C: 60.10; H: 5.58; N: 3.32.

(19.34) 2-Methyl-5-isobutyl-4-{2-[5-(1-(S)-phenyl-1,3-propyl)phosphono]furanyl}thiazole, major isomer. Anal. Calcd. for $C_{21}H_{24}NO_4PS+0.33\ H_2O$: C: 59.57; H: 5.87; N: 3.31. Found: C: 59.45; H: 5.83; N: 3.30.

(19.35) 2-Azido-5-ethyl-4-{2-[5-(1-phenyl-1,3-propyl)phosphono]furanyl}thiazole, major isomer. Anal. Calcd. for $C_{18}H_{17}N_4O_4PS+0.25H_2O+0.1$ isoamyl alcohol $(C_5H_{12}O)$: C: 51.71; H: 4.39; N: 13.04. Found: C: 51.80; H: 4.20; N: 12.78.

(19.36) 2-Azido-5-ethyl-4-{2-[5-(1-phenyl-1,3-propyl)phosphono]furanyl}thiazole, minor isomer. Anal. Calcd. for $C_{18}H_{17}N_4O_4PS+0.15$ isoamyl alcohol $(C_5H_{12}O)$: C: 52.42; H: 4.41; N: 13.04. Found: C: 52.27; H: 4.47; N: 12.76.

(19.37) 2-Amino-5-isobutyl-4-{2-[5-(1-(1-naphthyl)-1,3-propyl)phosphono]furanyl}thiazole. Anal. Calcd. for $C_{24}H_2N_2O_4PS$: C: 61.53; H: 5.38; N: 5.98. Found: C: 61.40; H: 5.12; N: 6.11.

(19.38) 2-Amino-5-isobutyl-4-{2-[5-(1-(2-bromophenyl)-1,3-propyl)phosphono]furanyl}thiazole. Anal. Calcd. for $C_{20}H_{22}N_2O_4PSBr+0.1\ C_5H_5N$: C: 48.73; H: 4.49; N: 5.82. Found: C: 48.63; H: 4.26; N: 5.70.

(19.39) 2-Amino-5-isobutyl-4-{2-[5-(1-(4-bromophenyl)-1,3-propyl)phosphono]furanyl}thiazole, minor isomer. Anal. Calcd. for $C_{20}H_{22}N_2O_4PSBr$: C: 48.30; H: 4.46; N: 5.63. Found: C: 48.23; H: 4.30; N: 5.77.

(19.40) 2-Amino-5-isobutyl-4-{2-[5-(1-(4-bromophenyl)-1,3-propyl)phosphono]furanyl}thiazole, major isomer. Anal. Calcd. for $C_{20}H_{22}N_2O_4PSBr$: C: 48.30; H: 4.46; N: 5.63. Found: C: 48.20; H: 4.63; N: 5.41.

(19.41) 2-Amino-5-isobutyl-4-{2-[5-(1-(4-fluoro-3-bromophenyl)-1,3-propyl)phosphono]furanyl}thiazole, minor isomer. Anal. Calcd. for $C_{20}H_{21}N_2O_4PSBrF+0.1\ C_5H_5N$: C: 47.06; H: 4.14; N: 5.62. Found: C: 47.00; H: 3.84; N: 5.48.

(19.42) 2-Amino-5-isobutyl-4-{2-[5-(1-(4-fluoro-3-bromophenyl)-1,3-propyl)phosphono]furanyl}thiazole, major isomer. Anal. Calcd. for $C_{20}H_{21}N_2O_4PSBrF$: C: 46.61; H: 4.11; N: 5.44; P: 6.01. Found: C: 46.81; H: 4.23; N: 5.65; P: 5.65.

(19.43) 2-Amino-5-isobutyl-4-{2-[5-(1-(4-trifluoromethylphenyl)-1,3-propyl)phosphono]furanyl}thiazole, minor isomer. Anal. Calcd. for $C_{21}H_{22}N_2O_4PSF_3+0.1\ H_2O$: C: 51.66; H: 4.58; N: 5.74. Found: C: 51.54; H: 4.28; N: 5.46.

(19.44) 2-Amino-5-isobutyl-4-{2-[5-(1-(4-trifluoromethylphenyl)-1,3-propyl)phosphono]furanyl}thiazole, major isomer. Anal. Calcd. for $C_{21}H_{22}N_2O_4PSF_3+0.1\ H_2O$: C: 51.66; H: 4.58; N: 5.74. Found: C: 51.48; H: 4.62; N: 5.81.

(19.45) 2-Amino-5-isobutyl-4-{2-[5-(1-(3-chlorophenyl)-1,3-propyl)phosphono]furanyl}thiazole, minor isomer. Anal. Calcd. for $C_{20}H_{22}N_2O_4PSCl+0.5\ H_2O$: C: 52.01; H: 5.02; N: 6.06. Found: C: 52.10; H: 4.92; N: 5.82.

(19.46) 2-Amino-5-isobutyl-4-{2-[5-(1-(3-chlorophenyl)-1,3-propyl)phosphono]furanyl}thiazole, major isomer. Anal. Calcd. for $C_{20}H_{22}N_2O_4PSCl+0.25\ H_2O$: C: 52.52; H: 4.96; N: 6.12. Found: C: 52.70; H: 4.79; N: 5.91.

(19.47) 2-Amino-5-isobutyl-4-{2-[5-(1-(3,5-dichlorophenyl)-1,3-propyl)phosphono]furanyl}thiazole, minor isomer. Anal. Calcd. for $C_{20}H_{21}N_2O_4PSCl_2$: C: 49.29; H: 4.34; N: 5.75. Found: C: 49.47; H: 4.60; N: 5.89.

(19.48) 2-Amino-5-isobutyl-4-{2-[5-(1-(3,5-dichlorophenyl)-1,3-propyl)phosphono]furanyl}thiazole, major isomer. Anal. Calcd. for $C_{20}H_{21}N_2O_4PSCl_2$: C: 49.29; H: 4.34; N: 5.75; Cl: 14.55. Found: C: 49.26; H: 4.36; N: 5.71; Cl: 14.66.

(19.49) 2-Amino-5-isobutyl-4-{2-[5-(2-(4-methoxybenzyl)-1,3-propyl)phosphono]furanyl}thiazole. Mp 185–188° C. Anal. Calcd. for $C_{22}H_{27}N_2O_5PS$: C: 57.13; H: 5.88; N: 6.06. Found: C: 56.86; H: 5.71; N: 5.73.

(19.50) 2-Amino-5-isobutyl-4-{2-[5-(2-methanesulfonyloxymethyl-1,3-propyl)phosphono]furanyl}thiazole. Anal. Calcd. for $C_{16}H_{23}N_2O_7PS_2+0.2 H_2O$: C: 42.32; H: 5.19; N: 6.17. Found: C: 42.15; H: 4.94; N: 5.95.

(19.51) 2-Amino-5-isobutyl-4-{2-[5-(2-azidomethyl-1,3-propyl)phosphono]furanyl}thiazole. Mp 187–189° C. Anal. Calcd. for $C_{15}H_{20}N_5O_4PS$: C: 45.34; H: 5.07; N: 17.62. Found: C: 45.09; H: 4.82; N: 17.72.

(19.52) 2-Amino-5-isobutyl-4-{2-[5-(2-aminomethyl-1,3-propyl)phosphono]furanyl}thiazole. Anal. Calcd. for $C_{15}H_{22}N_3O_4PS+0.3 H_2O+0.1 HCl$: C: 47.36; H: 6.01; N: 11.04. Found: C: 47.55; H: 5.62; N: 10.64.

(19.53) 2-Amino-5-isobutyl-4-{2-[5-(1-(4-tert-butylphenyl)-1,3-propyl)phosphono]furanyl}thiazole, minor isomer. Mp 141–143° C. Anal. Calcd. for $C_{24}H_{31}N_2O_4PS+1.5 HCl$: C: 54.47; H: 6.19; N: 5.29. Found: C: 54.44; H: 5.85; N: 4.92.

(19.54) 2-Amino-5-isobutyl-4-{2-[5-(1-(4-tert-butylphenyl)-1,3-propyl)phosphono]furanyl}thiazole, major isomer. Mp 178° C. (decomp). Anal. Calcd. for $C_{24}H_{31}N_2O_4PS+H_2O$: C: 58.52; H: 6.75; N: 5.69. Found: C: 58.20; H: 6.31; N: 5.29.

(19.55) 2-Amino-5-isobutyl-4-{2-[5-(1-(4-chlorophenyl)-1,3-propyl)phosphono]furanyl}thiazole, major isomer. Mp 102–104° C. Anal. Calcd. for $C_{20}H_{22}N_2O_4PSCl+H_2O+0.2EtOAc$: C: 51.14; H: 5.28; N: 5.73. Found: C: 51.67; H; 5.09; N: 5.34.

(19.56) 2-Amino-5-isobutyl-4-{2-[5-(1-(2,4-dichlorophenyl)-1,3-propyl)phosphono]furanyl}thiazole, major isomer. Mp 173–174° C. Anal. Calcd. for $C_{20}H_{21}N_2O_4PSCl_2$: C: 49.29; H: 4.34; N: 5.75. Found: C: 49.55; H: 4.32; N: 5.46.

(19.57) 2-Amino-5-isobutyl-4-{2-[5-(1,3-(S,S)-diphenyl)-1,3-propyl)phosphono]furanyl}thiazole. Mp 105–107° C. Anal. Calcd. for $C_{26}H_{27}N_2O_4PS+0.5H_2O+0.5HCl$: C: 59.85; H: 5.51; N: 5.37. Found: C: 59.83; H: 5.18; N: 5.27.

(19.58) 2-Amino-5-isobutyl-4-{2-[5-(1-(4-chlorophenyl)-1,3-propyl)phosphono]furanyl}thiazole, minor isomer. Mp 102–104° C. Anal. Calcd. for $C_{20}H_{22}N_2O_4PSCl$: C: 53.04; H: 4.90; N: 6.19. Found: C: 52.80; H: 4.70; N: 6.07.

(19.59) 2-Amino-5-isobutyl-4-{2-[5-(1-(3,5-difluorophenyl)-1,3-propyl)phosphono]furanyl}thiazole, minor isomer. Mp 152–154° C. Anal. Calcd. for $C_{20}H_{21}N_2O_4PSF_2+0.5 H_2O+0.3 EtOAc$: C: 51.98; H: 5.02; N: 5.72. Found: C: 51.67; H: 4.77; N: 5.42.

(19.60) 2-Amino-5-isobutyl-4-{2-[5-(1-(3,5-difluorophenyl)-1,3-propyl)phosphono]furanyl}thiazole, major isomer. Mp 94–95° C. Anal. Calcd. for $C_{20}H_{21}N_2O_4PSF_2$: C: 52.86; H: 4.66; N: 6.16. Found: C: 52.68; H: 4.73; N: 5.90.

(19.61) 2-Amino-5-isobutyl-4-{2-[5-(1-(3,5-dibromophenyl)-1,3-propyl)phosphono]furanyl}thiazole, major isomer. Mp 113–115° C. Anal. Calcd. for $C_{20}H_{21}N_2O_4PSBr_2+0.3 EtOAc$: C: 42.25; H: 3.91; N: 4.65. Found: C: 42.52; H: 3.91; N: 4.96.

(19.62) 2-Amino-5-isobutyl-4-{2-[5-(1-(3,5-dibromophenyl)-1,3-propyl)phosphono]furanyl}thiazole, minor isomer. Mp 209–210° C. Anal. Calcd. for $C_{20}H_{21}N_2O_4PSBr_2$: C: 41.69; H: 3.67; N: 4.86. Found: C: 41.93; H: 3.71; N: 4.74.

(19.66) 2-Amino-5-isobutyl-4-{2-[5-(1-(3-pyridyl)-1,3-propyl)phosphono]furanyl}thiazole dihydrochloride. Anal. Calcd. for $C_{19}H_{22}N_3O_4PS+2HCl+2H_2O$: C: 43.19; H: 5.34; N: 7.95. Found: C: 43.10; H: 5.25; N: 7.85.

(19.68) 2-Amino-5-isobutyl-4-{2-[5-(1-oxo-1-phospha-2,5,8-trioxa-3,4-benzo)cyclooctan-1-yl]furanyl}thiazole. Anal. Calcd. for $C_{19}H_{21}N_2O_5PS+0.75 H_2O$: C: 52.59; H: 5.23; N: 6.46. Found: C: 52.38; H: 4.85; N: 6.08.

Preferably the cyclic 1,3-propanediol phosphonate esters were prepared using 1,3-dicyclohexylcarbodiimide (DCC) coupling reaction conditions as following.

A suspension of 2-amino-5-isobutyl-4-[2-(5-phosphono)furanyl]thiazole (1 mmole) in DMF:pyridine (5:1, 10 mL) was treated with DCC (2 mmole) followed by 3-(3,5-dichloro)phenyl-1,3-propanediol (1.1 mmole). The resulting mixture was heated at 80° C. for 8 h. Evaporation followed by column chromatography gave 2-amino-5-isobutyl-4-{2-[5-(1-(3,5-dichlorophenyl)-1,3-propyl)phosphono]furanyl}thiazole, major isomer. (19.48) as a solid.

This method is also useful for the preparation of (5-substituted 2-oxo-1,3-dioxolen-4-yl)methyl and (5-substituted 2-thiocarbonyl-1,3-dioxolen-4-yl)methyl phosphonate prodrugs by coupling of phosphonic acids with 5-methyl-4-hydroxymethyl-2-oxo-1,3-dioxolene and 5-methyl-4-hydroxymethyl-2-thiocarbonyl-1,3-dioxolene (prepared from 4,5-dimethyl-2-oxo-1,3-dioxolene as described in Example 23). The following compound was made using this method.

(19.19) 2-Methyl-5-isobutyl-4-{2-[5-(bis(5-methyl-2-thioxo-1,3-dioxolen-4-yl phosphono]furanyl}thiazole. Anal. Calcd. for $C_{22}H_{24}NO_8PS_3$: C: 47.39; H: 4.34; N: 2.51. Found: C: 47.42; H: 4.30; N: 2.52.

Alternatively, these compounds can be prepared according to reported procedures (*Chem. Pharm. Bull.* 1984, 32(6), 2241) by reaction of phosphonic acids with 5-methyl-4-bromomethyl-2-oxo-1,3-dioxolene in DMF in the presence of sodium hydride at 25° C. 2-Amino-5-isobutyl-4-{2-[5-bis(3-phthalidyl-2-ethyl)phosphono]furanyl}-thiazole is also prepared following the above described procedures using 2-(3-phthalidyl)ethanol which was prepared from phthalide-3-acetic acid in Example 22.

Example 20

Preparation of Acyloxyalkyl and Alkyloxycarbonyloxyalkyl Phosphonate Diesters as Prodrugs A solution of 2-methyl-4-[2-(5-phosphono)furanyl]thiazole (1 mmole) in acetonitrile and N,N,N-diisopropylethylamine (5 mmole) was treated with pivaloyloxymethyl iodide (4 mmole) at 0° C. for 24 h. Extraction and chromatography gave 2-methyl-4-[2-(5-dipivaloyloxymethylphosphono)furanyl]-thiazole (20.1). Anal. Calcd. for $C_{20}H_{28}NO_8PS$: C: 50.59; H: 6.03; N: 2.65. Found: C: 50.73; H: 5.96; N: 2.96.

The following compounds were prepared according to this procedure: (20.2) 2-Methyl-5-isobutyl-4-{2-[5-(0-isobutyryloxymethyl-O-pivaloyloxymethyl)-phosphono]furanyl}thiazole. Anal. Calcd. for $C_{23}H_{34}NO_8PS$: C: 53.58; H: 6.65; N: 2.72. Found: C: 53.81; H: 6.83; N: 2.60.

(20.3) 2-Methyl-5-isobutyl-4-{2-[5-(dipivaloyloxymethyl)phosphono]furanyl}thiazole. Anal. Calcd. for $C_{24}H_{36}NO_8PS$: C: 54.43; H: 6.85; N: 2.64. Found: C: 54.46; H: 7;04; N: 2.55.

(20.4) 2-Amino-5-isobutyl-4-{2-[5-(dipivaloyloxymethyl)phosphono]furanyl}thiazole. Anal. Calcd. for $C_{23}H_{35}N_2O_8PS$: C: 52.07; H: 6.65; N: 5.28. Found: C: 52.45; H: 6.78; N: 5.01.

(20.5) 2-Bromo-5-isobutyl-4-{2-[5-(dipivaloyloxymethyl)phosphono]furanyl}thiazole. Anal. Calcd. for $C_{23}H_{33}NO_8PSBr$: C: 47.00; H: 5.75; N: 2.32. Found: C: 47.18; H: 5.46; N: 2.30.

The cyclic acyloxyalkyl phosphonate esters can also be prepared in a similar manner according to Farquhar's procedure (Farquhar, D. et al, *Tetrahedron Lett*. 1995, 36, 655).

(20.13) 2-Amino-5-isobutyl-4-{2-[5-(1-benzoyloxypropane-1,3-diyl)phosphono]furanyl}thiazole, more polar isomer. MS calcd for $C_{21}H_{23}N_2O_6PS+H$: 463, found 463.

(20.14) 2-Amino-5-isobutyl-4-{2-[5-(1-benzoyloxypropane-1,3-diyl)phosphono]furanyl}thiazole, less polar isomer. MS calcd for $C_{21}H_{23}N_2O_6PS+H$: 463, found 463.

Alkyloxycarbonyloxyalkyl phosphonate esters were also prepared according to the above procedures with slight modifications described below:

A solution of 2-methyl-5-isobutyl-4-[2-(5-phosphono)furanyl]thiazole (1 mmole) in DMF was treated with N,N'-dicyclohexyl-4-morpholinecarboxamidine (5 mmole) and ethylpropyloxycarbonyloxymethyl iodide (5 mmole) which was prepared from chloromethyl chloroformate according to the reported procedure (Nishimura et al. *J. Antibiotics*, 1987, 40(1), 81–90). The reaction mixture was stirred at 25° C. for 24 h, and evaporation followed by chromatography gave 2-methyl-5-isobutyl-4-{-2-[5-bis(ethoxycarbonyloxymethyl)phosphono]furanyl}thiazole (20.6). Anal. Calcd. for $C_{20}H_{28}NO_{10}PS$: C: 47.52; H: 5.58; N: 2.77. Found: C: 47.52; H: 5.67; N: 2.80.

The following compounds were prepared according to this procedure: (20.7) 2-Methyl-5-isobutyl-4-{-2-[5-bis(isopropyloxycarbonyloxymethyl)phosphono]furanyl}thiazole. Anal. Calcd. for $C_{22}H_{32}NO_{10}PS$: C: 49.53; H: 6.05; N: 2.63. Found: C: 49.58; H: 6.14; N: 2.75.

(20.8) 2-Amino-5-isobutyl-4-{-2-[5-bis(phenoxycarbonyloxymethyl)phosphono]-furanyl}thiazole. Anal. Calcd. for $C_{27}H_{27}N_2O_{10}PS$: C: 53.82; H: 4.52; N: 4.65. Found: C: 54.03; H: 4.16; N: 4.30.

(20.9) 2-Amino-5-isobutyl-4-{-2-[5-bis(ethoxycarbonyloxymethyl)phosphono]-furanyl}thiazole. Anal. Calcd. for $C_{19}H_{27}N_2O_{10}PS$: C: 45.06; H: 5.37; N: 5.53. Found: C: 45.1 1; H: 5.30; N: 5.43.

(20.10) 2-Methyl-5-isobutyl-4-{-2-[5-bis(isopropylthiocarbonyloxymethyl)-phosphono]furanyl}thiazole. Anal. Calcd. for $C_{22}H_{32}NO_8PS_3+0.2$ EtOAc: C: 46.95; H: 5.81; N: 2.40. Found: C: 47.06; H: 5.86; N: 2.73.

(20.11) 2-Amino-5-isobutyl-4-{2-[5-bis(isopropyloxycarbonyloxymethyl)phosphono]furanyl}thiazole. Anal. calcd. for $C_{21}H_{31}N_2O_{10}PS$: C: 47.19; H: 5.85; N: 5.24. Found: C: 47.33; H: 5.66; N: 5.57.

(20.12) 2-Methyl-5-isobutyl-4-{2-[5-bis(benzoyloxymethyl)phosphono]furanyl}thiazole. Anal. calcd. for $C_{28}H_{28}NO_8PS+0.2CH_2Cl_2$: C: 59.31; H: 5.40; N: 2.64. Found: C: 59.25; H: 5.27; N: 2.44.

(20.15) 2-Amino-5-isobutyl-4-{2-[5-bis(1-(1-ethoxycarbonyloxy)ethyl)phosphono]-furanyl}thiazole. Mp 76–78° C. Anal. calcd. for $C_{21}H_{31}N_2O_{10}PS$: C: 47.19; H: 5.85; N: 5.42. Found C: 48.06; H: 5.80; N: 5.16.

2-Amino-5-isobutyl-4-{2-[5-bis(3-(5,6,7-trimethoxy)phthalidyl)-phosphono]furanyl}thiazole is also synthesized following this procedure using 3-bromo-5,6,7-trimethoxyphthalide as the alkylating reagent.

Example 21

Preparation of 3-(2-pyridyl)propan-1,3-diol

Step A. (*J. Org. Chem.*, 1957, 22, 589) A solution of 3-(2-pyridyl)propanol in acetic acid was treated with 30% hydrogen peroxide at 80° C. for 16 h. The reaction was concentrated under vacuum and the residue was dissolved in acetic anhydride and heated at 110° C. for 12 h. Evaporation and chromatography gave 3-(2-pyridyl)-1,3-propanediol diacetate.

Step B. A solution of 3-(2-pyridyl)-1,3-propanediol diacetate (1 mmole) in methanol-water (3:1) was treated with potassium carbonate (5 mmole) at 25° C. for 3 h. Evaporation and chromatography gave 3-(2-pyridyl)-1,3-propanediol as a solid.

Example 22

Preparation of 3-(2-hydroxyethyl)phthalide

A solution of phthalide-3-acetic acid (1 mmole) in THF was treated with borane dimethylsulfide (1.5 mmole) at 0° C. for 1 h, and at 25° C. for 24 h. Extraction and chromatography gave 2-(3-phthalidyl)ethanol as a light yellow oil: Rf=0.25, 50% EtOAc-hexane.

Example 23

Preparation of 5-methyl-4-hydroxymethyl-2-oxo-1,3-dioxolene

A solution of 4,5-dimethyl-2-oxo-1,3-dioxolene (1 mmole) and selenium dioxide (2.5 mmole) in dioxane was heated at reflux for 1 h. Evaporation, extraction and chromatography gave 5-methyl-4-hydroxymethyl-2-oxo-1,3-dioxolene as a yellow oil. TLC: RPf=0.5, 5% MeOH-dichloromethane.

A solution of 5-methyl-4-hydroxymethyl-2-oxo-1,3-dioxolene (1 mmole) in DMF was treated with tert-butyldimethylsilane (1.2 mmole) and imidazole (2.2 mmole) at 25° C. for 24 h. Extraction and chromatography gave 5-methyl-4-tert-butyldimethylsilyloxymethyl-2-oxo-1,3-dioxolene.

A solution of 5-methyl-4-tert-butyldimethylsilyloxymethyl-2-oxo-1,3-dioxolene (1 mmole) and Lawesson's reagent (1.2 mmole) in toluene was heated to 120° C. for 12 h. Extraction and chromatography gave 5-methyl-4-tert-butyldimethylsilyloxymethyl-2-thio-1,3-dioxolene.

A solution of 5-methyl-4-tert-butyldimethylsilyloxymethyl-2-thio-1,3-dioxolene in methanolic hydrogen chloride was stirred at 0° C. for 1 h and 25° C. for 12 h. Extraction and chromatography gave 5-methyl-4-hydroxymethyl-2-thio-1,3-dioxolene.

Example 24

Preparation of Hydroxyethyldisulfidylethylphosphonate Diester

A suspension of 2-methyl-5-isobutyl-4-[2-(5-phosphono) furanyl]thiazole (1 mmole) in thionyl chloride (5 mL) is warmed at reflux for 4 h. The cooled reaction mixture is evaporated to dryness and the resulting yellow residue is treated with a solution of 2-hydroxyethyl disulfide (4 mmole), pyridine (2.5 mmole) in methylene chloride. After stirring at 25° C. for 4 h. the reaction is subjected to extraction and chromatography to give two compounds: 2-methyl-5-isobutyl-4-{2-[5-bis(6'-hydroxy-3',4'-disulfide) hexylphosphono]furanyl}thiazole and 2-methyl-5-isobutyl-4-{2-[5-(3',4'-disulfide)nonacyclicphosphono]-furanyl}thiazole.

Example 25

Preparation of 3-[2-(5-phosphono)furanyl]pyrazoles

Step A. A solution of diethyl 5-(2-isobutyl-3-N,N-dimethylamino)acryloyl-2-furanphosphonate (1 mmole, prepared according to Step A of Example 17) in ethanol was treated with hydrazine (1.2 mmole) 80° C. for 12 h. Evaporation and chromatography gave 4-isobutyl-3-[2-(5-diethylphosphono)furanyl]pyrazole.

Step B. 4-Isobutyl-3-[2-(5-diethylphosphono)furanyl] pyrazole was subjected to Step C of Example 3 to give 4-isobutyl-3-[2-(5-phosphono)furanyl]pyrazole (25.1). mp 210–215° C. Anal. Calcd. for $C_{11}H_{15}N_2O_4P$: C: 48.89; H: 5.60; N: 10.37. Found: C: 48.67; H: 5.55; N: 10.20.

Step C. 4-Isobutyl-3-[2-(5-diethylphosphono)furanyl] pyrazole was subjected to Step A of Example 11 to give 1-methyl-4-isobutyl-3-[2-(5-diethylphosphono)furanyl] pyrazole.

Step D. 1-Methyl-4-isobutyl-3-[2-(5-diethylphosphono) furanyl]pyrazole was subjected to Step C of Example 3 to give 1-methyl-4-isobutyl-3-[2-(5-phosphono)furanyl] pyrazole (25.2). Anal. Calcd. for $C_{12}H_{17}N_2O_4P+0.85HBr+0.75 H_2O$: C: 39.32; H: 5.32; N: 7.64. Found: C: 39.59; H: 5.30; N: 7.47.

Example 26

Preparation of 3-[2-(5-phosphono)furanyl] isoxazoles

Step A. A solution of 5-diethylphosphono-2-furaldehyde (1 mmole) in ethanol was treated with hydroxylamine (1.1 mmole) and sodium acetate (2.2 mmole) at 25° C. for 12 h. Extraction and chromatography gave 5-diethylphosphono-2-furaldehyde oxime.

Step B. A solution of 5-diethylphosphono-2-furaldehyde oxime (1 mmole) in DMF was treated with N-chlorosuccinimide (1.1 mmole) at 25° C. for 12 h. Extraction gave 5-diethylphosphono-2-chlorooximidofuran.

Step C. A solution of 5-diethylphosphono-2-chlorooximidofuran (1 mmole) and ethyl propiolate (5 mmole) in diethyl ether was treated with triethylamine (2 mmole) at 25° C. for 12 h. Extraction and chromatography gave 5-ethoxycarbonyl-3-{2-(5-diethylphosphono)furanyl} isoxazole.

Step D. 5-Ethoxycarbonyl-3-{2-(5-diethylphosphono) furanyl]isoxazole was subjected to Step A of Example 9 followed by Step C of Example 3 to give 5-carbamoyl-3-[2-(5-phosphono)furanyl]isoxazole (26.1). mp 221–225° C. Anal. Calcd. for $C_8H_7N_2O_6P+0.25EtOH$: C: 37.86; H: 3.18; N: 10.39. Found: C: 37.90; H: 3.02; N: 10.05.

The following compound was prepared according to this procedure:

(26.2) 5-Ethoxycarbonyl-4-methyl-3-[2-(5-phosphono) furanyl]isoxazole. mp 150–152° C. Anal. Calcd. for $C_{11}H_{12}NO_7P+0.25H_2O+0.15HBr$: C: 41.57; H: 4.01; N: 4.41. Found: C: 41.57; H: 4.20; N: 4.54.

(26.3) 4,5-Bis(ethoxycarbonyl)-3-[2-(5-phosphono) furanyl]isoxazole. Anal. calcd for $C_{13}H_{14}NO_9P$: C: 43.47; H: 3.93; N: 3.90. Found: C: 43.26; H: 3.92; N: 3.97.

(26.4) 5-Amino-4-ethoxycarbonyl-3-[2-(5-phosphono) furanyl]isoxazole. mp 190° C. (decomp). Anal. calcd for $C_{10}H_{11}N_2O_7P+0.25HBr$: C: 37.25; H: 3.52; N: 8.69. Found: C: 37.56; H: 3.50; N: 8.85.

(26.5) 4,5-bis(carbamoyl)-3-[2-(5-phosphono)furanyl] isoxazole. mp>220° C. Anal. calcd for $C_9H_8N_3O_7P$: C: 35.90; H: 2.68; N: 13.95. Found: C: 35.67; H: 2.55; N: 13.62.

(26.6) 4-Ethoxycarbonyl-5-trifluoromethyl-3-[2-(5-phosphono)furanyl]isoxazole. Anal. calcd for $C_{11}H_9F_3NO_7P+0.25HBr$: C: 35.20; H: 2.48; N: 3.73. Found: C: 35.25; H: 2.34; N: 3.98.

(26.7) 5-Amino-4-(2-furyl)-3-[2-(5-phosphono)furanyl] isoxazole. mp>220° C. Anal. calcd for $C_{12}H_9N_2O_7P+0.1AcOEt$: C: 44.73; H: 2.97; N: 8.41. Found: C: 45.10; H: 2.58; N: 8.73.

(26.8) 4-Amino-5-cyano-3-[2-(5-phosphono)furanyl] isoxazole. Anal. calcd for $C_8H_6N_3O_5P+0.1H_2O+0.2HBr$: C: 35.18; H: 2.36; N: 15.39. Found: C: 35.34; H: 2.50; N: 15.08.

(26.9) 4-Cyano-5-phenyl-3-[2-(5-phosphono)furanyl] isoxazole. Anal. calcd for $C_{14}H_9N_2O_5P+0.15HBr$: C: 51.21; H: 2.81; N: 8.53. Found: C: 51.24; H: 3.09; N: 8.33.

Example 27

Preparation of 2-[2-(5-phosphono)furanyl]thiazoles

Step A. Diethyl 5-tributylstannyl-2-furanphosphonate (14) and 2-bromo-4-ethoxycarbonylthiazole was subjected to Step A of Example 6 to give 4-ethoxycarbonyl-2-[2-(5-diethylphosphono)furanyl]thiazole.

Step B. 4-Ethoxycarbonyl-2-[2-(5-diethylphosphono) furanyl]thiazole was subjected to Step A of Example 9 followed by Step C of Example 3 to give 4-carbamoyl-2-[2-(5-phosphono)furanyl]thiazole (27.1). mp 239–240° C. Anal. Calcd. for $C_8H_7N_2O_5PS+0.2H_2O$: C: 34.59; H: 2.68; N: 10.08. Found: C: 34.65; H: 2.69; N: 9.84.

Example 28

Preparation of 4-(3,3-difluoro-3-phosphono-1-propyl)thiazoles

Step A. A solution of 3-(tert-butyl-diphenylsilyloxy)-1-propanol (1 mmole) in methylene chloride (7 mL) was treated with powder molecular sieves (4 A, 0.5 equiv. wt/wt) and pyridinium chlorochromate (1.5 mmole) at 0° C. The resulting mixture was stirred at room temperature for 2 h, and diluted with diethyl ether (7 mL) and stirred at room temperature for another 30 min. Filtration, evaporation and chromatography gave 3-(tert-butyldiphenylsilyloxy)-1-propanal as a clear oil.

Step B. A solution of LDA (1.06 mmole) in THF was treated with a solution of. diethyl difluoromethylphosphonate (1 mmole) at −78° C. for 45 min. The reaction was then treated with a THF solution of 3-(tert-butyldiphenylsilyloxy)-1-propanal (1.07 mmole) and the resulting soultion was stirred at −78° C. for another 4 h. The reaction was quenched with phenyl chlorothioformate (2.14 mmole), and the reaction mixture was subjected to extraction and chromatography to give diethyl 4-(tert-butyldiphenylsilyloxy)-3-phenoxythiocarbonyloxy-2,2-difluorobutylphosphonate as a clear oil.

Step C. A solution of diethyl 4-(tert-butyldiphenylsilyloxy)-3-phenoxythiocarbonyloxy-2,2-difluorobutylphosphonate (1 mmole) in toluene (1 mL) was treated with tri-n-butyltin hydride (1.5 mmole) and AIBN (0.1 mmole), and the resulting reaction mixture was heated to reflux for 2 h. Evaporation and chromatography gave diethyl 4-(tert-butyldiphenylsilyloxy)-2,2-difluorobutylphosphonate as a clear oil.

Step D. A solution of diethyl 4-(tert-butyldiphenylsilyloxy)-2,2-difluorobutylphosphonate (1 mmole) in methanol (1 mL) was treated with hydrochloric acid (4 N, 4 mmole) at 0° C., and the resulting reaction was stirred at room temperature for 2 h. Evaporation and chromatography gave diethyl 4-hydroxy-2,2-difluorobutylphosphonate as a clear oil.

Step E. A solution of gave diethyl 4-hydroxy-2,2-difluorobutylphosphonate (1 mmole) in acetone (10 mL) was treated with Jones's reagent (10 mmole) at 0° C. for 30 min. The reaction was quenched with 2-propanol (10 mL), and the resulting mixture was filtered through a Celite pad. Evaporation of the filtrate followed by extraction gave diethyl 3-carboxyl-2,3-difluoropropylphosphonate as an oil.

Step F. A solution of diethyl 3-carboxyl-2,3-difluoropropylphosphonate (1 mmole) in thionyl chloride (3 mL) was heated to reflux for 2 h. The reaction was evaporated to dryness, and the residue was dissolved in diethyl ether (1 mL) was treated with an etheral solution of diazomethane (10 mmole) at 0° C. for 30 min. A solution of HBr in acetic acid (30%, 1 mL) was added to the reaction, and the resulting solution was stirred at room temperature for 1 h. The reaction was evaporated to dryness and the residue was dissolved in THF-EtOH (1:1, 5 mL) and treated with thiourea (1 mmole). The resulting reaction mixture was heated to 75° C. for 1 h. Evaporation followed by extraction and chromatography gave 2-amino-4-[1-(3-diethylphosphono-3,3-difluoro)propyl]thiazole as a solid, which was subjected to Step C of Example 3 to give gave 2-amino-4-[1-(3-phosphono-3,3-difluoro)propyl]thiazole (28.1) as a solid. Anal. Calcd. for $C_6H_9N_2O_3PS_{F2}$+HBr: C: 21.25; H: 2.97; N: 8.26. Found: C: 21.24; H: 3.25; N: 8.21.

The following compound was prepared in a similar manner: 2-Amino-5-methylthio-4-[1-(3-phosphono-3,3-difluoro)propyl]thiazole (28.2). MS m/e 305 (M+H).

Example 29

Preparation of 2-methylthio-5-phosphonomethylthio-1,34-thiadiazole and 2-phospbhonomethylthiopyridine Step A. A solution of 2-methylthio-1,3,4-thiadiazole-5-thiol (1 mmole) in THF (5 mL) was treated with sodium hydride (60%, 1.1 mmole) at 0° C. and the resulting mixture was stirred at room temperature for 30 min. The reaction was then cooled to 0° C. and treated with diethylphosphonomethyl trifluoromethanesulfonate (1.1 mmole). After stirring at room temperature for 12 h, the reaction was quenched with saturated ammonium chloride. Extraction and chromatography gave 2-methylthio-5-diethylphosphonomethylthio-1,3,4-thiadiazole as an oil.

Step B. 2-Methylthio-5-diethylphosphonomethylthio-1,3,4-thiadiazole was subjected to Step C of Example 3 to give 2-methylthio-5-phosphonomethylthio-1,3,4-thiadiazole (29.1) as a yellow solid. Anal. Calcd. for $C_4H_7N_2O_3PS_3$+0.2 HBr: C: 17.50; H: 2.64; N: 10.21. Found: C: 17.64; H: 2.56; N: 10.00.

Alternatively, phosphonomethylthio substituted heteroaromatics are made using the following method as exemplified by the synthesis of 2-phosphonomethylthiopyridine:

Step C. A solution of 2,2'-dipyridyl disulfide (1 mmole) in THF was treated with tri-n-butylphosphine (1 mmole) and diethyl hydroxymethylphosphonate at 0° C. The resulting reaction solution was stirred at room temperature for 18 h. Extraction and chromatography gave 2-diethylphosphonomethylthiopyridine as a yellow oil.

Step D. 2-Diethylphosphonomethylthiopyridine was subjected to Step C of Example 3 to give 2-phosphonomethylthiopyridine (29.2) as a yellow solid. Anal. Calcd. for $C_6H_8NO_3PS$+0.62 HBr: C: 28.22; H: 3.40; N: 5.49. Found: C: 28.48; H: 3.75; N: 5.14.

Example 30

Preparation of 2-[(2-phosphono)ethynyl]pyridine

Step A. A solution of 2-ethynylpyridine (1 mmole) in THF (5 mL) was treated with LDA (1.2 mmole) at 0° C. for 40 min. Diethyl chlorophosphate (1.2 mmole) was added to the reaction and the resulting reaction solution was stirred at room temperature for 16 h. The reaction was quenched with saturated ammonium chloride followed by extraction and chromatography to give 2-[(2-diethylphosphono)ethynyl] pyridine as a yellow oil.

Step B. 2-[(2-Diethylphosphono)ethynyl]pyridine was subjected to Step C of Example 3 to give 2-[1-(2-phosphono)ethynyl]pyridine (30.1) as a brown solid. Mp 160° C. (decomp). MS m/e 184 (M+H).

Example 31

A. Preparation of Various Phosphoramides as Prodrugs

Step A. A solution of 2-methyl-5-isopropyl-4-[2-(5-phosphono)furanyl]thiazole dichloridate (generated as in Example 19) (1 mmole) in dichloromethane (5 mL) was cooled to 0° C. and treated with a solution of benzyl alcohol (0.9 mmole) in dichloromethane (0.5 mL) and pyridine (0.3 mL). The resulting reaction solution was stirred at 0° C. for 1 h, and then added a solution of ammonia (excess) in THF. After stirring at room temperature for 16 h, the reaction was evaporated to dryness and the residue was purified by chromatography to give 2-methyl-5-isopropyl-4-[2-(5-phosphonomonoamido)furanyl]thiazole (31.1) as a yellow hard gum and 2-methyl-5-isopropyl-4-[2-(5-phosphorodiamido)furanyl]thiazole (31.2) as a yellow hard gum.

(31.1) 2-Methyl-5-isopropyl-4-[2-(5-phosphonomonoamido)furanyl]thiazole: MS m/e 299 (M−H).

(31.2) 2-Methyl-5-isopropyl-4-[2-(5-phosphorodiamido) furanyl]thiazole: MS m/e 298 (M−H).

Alternatively, a different method was used to prepare other phosphoramides as exemplified in the following procedure:

Step B. A suspension of 2-amino-5-methylthio-4-[2-(5-phosphono)furanyl]thiazole dichloridate (generated as in Example 15) (1 mmole) in dichloromethane (5 mL) was cooled to 0° C. and ammonia (excess was bubbled through the reaction for 10 min. After stirring at room temperature for 16 h, the reaction was evaporated to dryness and the residue was purified by chromatography to give 2-amino-5-methylthio-4-[2-(5-phosphorodiamido)furanyl]thiazole (31.3) as a foam. Anal. Calcd for $C_8H_{11}N_4O_2PS_2$+1.5 HCl+ 0.2 EtOH: C: 28.48; H: 3.90; N: 15.82. Found: C: 28.32; H: 3.76; N: 14.21.

The following compounds were prepared according to the above described procedures or in some cases with minor modifications of these procedures:

(31.4) 2-Amino-5-isobutyl-4-[2-(5-phosphonomonoamido)furanyl]thiazole. Mp 77–81° C. Anal. Calcd for $C_{11}H_{16}N_3O_3PS$+$H_2O$+0.8 $Et_3N$: C: 47.41; H: 7.55; N: 13.30. Found: C: 47.04; H: 7.55; N: 13.67.

(31.5) 2-Amino-5-isobutyl-4-[2-(5-phosphorodiamido) furanyl]thiazole. Anal. Calcd for $C_{11}H_{17}N_4O_2PS$+0.5$H_2O$+ 0.75 HCl: C: 39.24; H: 5.61; N: 16.64. Found: C: 39.05; H: 5.43; N: 15.82.

(31.28) 2-Amino-5-isobutyl-4-{2-[5-(N,N'-diisobutyl) phosphoroadiamido]furanyl}-thiazole. Mp 182–183° C. Anal. Calcd. for $C_{19}H_{33}N_4O_2PS$: C: 55.32; H: 8.06; N: 13.58. Found: C: 54.93; H: 7.75; N: 13.20.

(31.29) 2-Amino-5-isobutyl-4-{2-[5-(N,N'-(1,3-bis (ethoxycarbonyl)-1-propyl)phosphoro)diamido] furanyl}thiazole. Anal. Calcd for $C_{29}H_{45}N_4O_{10}PS$: C: 51.78: H: 6.74; N: 8.33. Found: C: 51.70; H: 6.64; N: 8.15.

(31.30) 2-Amino-5-isobutyl-4-{2-[5-(N,N'-(1-benzyloxycarbonyl) 1-ethyl)phosphorodiamido] furanyl}thiazole. Anal. Calcd for $C_{31}H_{37}N_4O_6PS$: C: 59.60; H: 5.97; N: 8.97. Found C: 59.27; H: 5.63; N: 8.74.

(31.31) 2-Amino-5-isobutyl-4-{2-[5-bis(2-methoxycarbonyl-1-azirdinyl)phosphorodiamido] furanyl}thiazole. Anal. Calcd for $C_{19}H_{25}N_4O_6PS$+ 0.3$CH_2Cl_2$: C: 46.93; H: 5.22; N: 11.34. Found: C: 58.20; H: 5.26; N: 9.25.

(31.39) 2-Amino-5-isobutyl-4-{2-[5-(N,N'-2-(1-ethoxycarbonyl)propyl)phosphorodiamido] furanyl}thiazole. Anal. Calcd for $C_{23}H_{37}N_4O_6PS$+ 0.6EtOAc+0.1 $CH_2Cl_2$: C: 51.91; H: 7.18; N: 9.50. Found: C: 51.78; H: 7.17; N: 9.26.

The monophenyl-monophosphonamide derivatives of compounds of formula I can also be prepared according to the above described procedures:

Step C. A solution of 2-amino-5-isobutyl-4-[2-(5-diphenylphosphono)furanyl]thiazole (prepared according to the procedures of Example 19) (1 mmole) in acetonitrile (9 mL) and water (4 mL) was treated with lithium hydroxide (1N, 1.5 mmole) at room temperature for 4 h. The reaction solution was evaporated to dryness, and the residue was dissolved in water (10 mL), cooled to 0° C. and the pH of the solution was adjusted to 4 by addition of 6 N HCl. The resulting white solid was collected through filtration to give 2-amino-5-isobutyl-4-[2-(5-phenylphosphono)furanyl] thiazole (19.64).

Step D. A suspension of 2-amino-5-isobutyl-4-[2-(5-phenylphosphono)furanyl]thiazole (1 mmole) in thionyl chloride (3 mL) was heated to reflux for 2 h. The reaction solution was evaporated to dryness, and the residue was dissolved in anhydrous dichloromethane (2 mL) and the resulting solution was added to a solution of L-alanine methyl ester hydrochloride (1.2 mmole) in pyridine (0.8 mL) and dichloromethane (3 mL) at 0° C. The resulting reaction solution was stirred at room temperature for 14 h. Evaporation and chromatography gave 2-amino-5-isobutyl-4-{2-[5-(O-phenyl-N-(1-methoxycarbonyl)ethyl)phosphonanido] furanyl}thiazole (31.6) as an oil. Anal. calcd. for $C_{21}H_{26}N_3O_5PS$: C: 54.42; H: 5.65; N: 9.07. Found: C: 54.40; H: 6.02; N: 8.87.

The following compounds were prepared according to the above described procedures:

(31.7) 2-amino-5-isobutyl-4-{2-[5-(O-phenylphosphonamido)]furanyl}thiazole. mp 205° C. (decomp). Anal. calcd. for $C_{17}H_{20}N_3O_3PS$+0.3 $H_2O$+0.3 HCl: C: 51.86; H: 5.35; N: 10.67. Found: C: 51.58; H: 4.93; N: 11.08.

(31.8) 2-amino-5-isobutyl-4-{2-[5-(O-phenyl-N-ethoxycarbonylmethyl)phosphonamido]furanyl}thiazole. Anal. calcd. for $C_{21}H_{26}N_3O_5PS$: C: 54.42; H: 5.65; N: 9.07. Found: C: 54.78; H: 5.83; N: 8.67.

(31.9) 2-amino-5-isobutyl-4-{2-[5-(O-phenyl-N-isobutyl)phosphonamido]furanyl}thiazole. mp 151–152° C. Anal. calcd. for $C_{21}H_{28}N_3O_3PS$: C: 58.18; H: 6.51; N: 9.69. Found: C: 58.12; H: 6.54; N: 9.59.

(31.18) 2-amino-5-isobutyl-4-{2-[5-(O-phenyl-N-(1-(1-ethoxycarbonyl-2-phenyl)ethyl)phosphonamido)] furanyl}thiazole. Anal. calcd. for $C_{28}H_{32}N_3O_5PS$: C: 60.75; H: 5.83; N: 7.59. Found: C: 60.35; H: 5.77; N: 7.37.

(31.19) 2-amino-5-isobutyl-4-{2-[5-(O-phenyl-N-(1-(1-ethoxycarbonyl-2-methyl)propyl)phosphonamido)] furanyl}thiazole. Anal. calcd. for $C_{23}H_{30}N_3O_5PS$: C: 56.20; H: 6.15; N: 8.55. Found: C: 55.95; H: 5.80; N: 8.35.

(31.20) 2-amino-5-isobutyl-4-{2-[5-(O-phenyl-N-(1-(1, 3-bis(ethoxycarbonyl) propyl)phosphonamido)] furanyl}thiazole. Anal. calcd. for $C_{26}H_{34}N_3O_7PS$+0.2 $CH_2Cl_2$: C: 54.20; H: 5.97; N: 7.24. Found C: 54.06; H: 5.68; N: 7.05.

(31.21) 2-amino-5-isobutyl-4-{2-[5-(O-(3-chlorophenyl)-N-(1-(1-methoxycarbonyl)ethyl) propyl)phosphonamido)] furanyl}thiazole. Anal. calcd. for $C_{21}H_{25}N_3O_5PSCl$: C: 50.65; H: 5.06; N: 8.44. Found: C: 50.56; H: 4.78; N: 8.56.

(31.22) 2-amino-5-isobutyl-4-{2-[5-(O-(4-chlorophenyl)-N-(1-(1-methoxycarbonyl)ethyl)phosphonamido)] furanyl}thiazole. Anal. calcd. for $C_{21}H_{25}N_3O_5PSCl$+1HCl+ 0.2 $H_2O$: C: 46.88; H: 4.95; N: 7.81. Found: C: 47.33; H: 4.71; N: 7.36.

(31.23) 2-amino-5-isobutyl-4-{2-[5-(O-phenyl-N-(1-(1-bis(ethoxycarbonyl)methyl) phosphonamido)] furanyl}thiazole. Anal. calcd. for $C_{24}H_{30}N_3O_7PS$: C: 53.83; H: 5.65; N: 7.85. Found: C: 53.54 H: 5.63; N: 7.77

(31.24) 2-amino-5-isobutyl-4-{2-[5-(O-phenyl-N-(1-morpholinyl) phosphonamido)]furanyl}thiazole. Anal. calcd. for $C_{21}H_{26}N_3O_4PS$: C: 56.37; H: 5.86; N: 9.39. Found: C: 56.36; H: 5.80; N: 9.20.

(31.25) 2-amino-5-isobutyl-4-{2-[5-(O-phenyl-N-(1-(1-benzyloxycarbonyl)ethyl)phosphonamido)] furanyl}thiazole. Anal. calcd. for $C_{27}H_{30}N_3O_5PS$: C: 60.10; H: 5.60; N: 7.79. Found: C: 59.80; H: 5.23; N: 7.53.

(31.32) 2-amino-5-isobutyl-4-{2-[5-(O-phenyl-N-benzyloxycarbonylmethyl)phosphonamido)] furanyl}thiazole. Anal. calcd. for $C_{26}H_{28}N_3O_5PS$: C: 59.42; H: 5.37; N: 8.00. Found: C: 59.60; H: 5.05; N: 7.91.

(31.36) 2-amino-5-isobutyl-4-{2-[5-(O-(4-methyoxyphenyl)-N-(1-(1-methoxycarbonyl)ethyl) phosphonamido)]furanyl}thiazole. Anal. calcd. for $C_{22}H_{28}N_3O_6PS$+0.1 $CHCl_3$+0.1 MeCN: C: 52.56; H: 5.62; N: 8.52. Found: C: 52.77; H: 5.23: N: 8.87.

(31.37) 2-amino-5-isobutyl-4-{2-[5-(O-phenyl-N-2-methoxycarbonyl) propyl)phosphonamido)]furanyl}thiazole. Anal. calcd. for $C_{22}H_{28}N_3O_5PS+0.6\ H_2O$: C: 54.11; H: 6.03; N: 8.60. Found: C: 53.86; H: 5.97; N: 8.61.

31.38) 2-amino-5-isobutyl-4-{2-[5-(O-phenyl-N-(2-(1-ethoxycarbonyl)propyl)phosphonamido)]furanyl}thiazole. Anal. calcd. for $C_{23}H_{30}N_3O_5PS$: C: 56.20; H: 6.15; N: 8.55. Found: C: 55.90; H: 6.29; N: 8.46.

The reaction of a dichlorophosphonate with a 1-amino-3-propanol in the presence of a suitable base (e.g. pyridine, triethylamine) can also be used to prepare cyclic phosphoramidates as prodrugs of phosphonates. The following compounds were prepared in this manner:

(31.10) 2-Methyl-5-isobutyl-4-{2-[5-(1-phenyl-1,3-propyl)phosphonamido]furanyl}thiazole minor isomer. Anal. calcd. for $C_{21}H_{25}N_2O_3PS+0.25\ H_2O+0.1\ HCl$: C: 59.40; H: 6.08; N: 6.60. Found: C: 59.42; H: 5.72; N: 6.44.

(31.11) 2-Methyl-5-isobutyl-4-{2-[5-(1-phenyl-1,3-propyl)phosphonamido]furanyl}thiazole major isomer. Anal. calcd. for $C_{21}H_{25}N_2O_3PS+0.25\ H_2O$: C: 59.91; H: 6.11; N: 6.65. Found: C: 60.17; H: 5.81; N: 6.52.

(31.12) 2-Amino-5-isobutyl-4-{2-[5-(1-phenyl-1,3-propyl)phosphonamido]furanyl}thiazole major isomer. Anal. calcd. for $C_{20}H_{24}N_3O_3PS+0.25\ H_2O+0.1\ CH_2Cl_2$: C: 55.27; H: 5.72; N: 9.57. Found: C: 55.03; H: 5.42; N: 9.37.

(31.13) 2-Amino-5-isobutyl-4-{2-[5-(1-phenyl-1,3-propyl)phosphonamido]furanyl}thiazole minor isomer. Anal. calcd. for $C_{20}H_{24}N_3O_3PS+0.15\ CH_2Cl_2$: C: 56.26; H: 5.69; N: 9.77. Found: C: 56.36; H: 5.46; N: 9.59.

(31.14) 2-Amino-5-methylthio-4-{2-[5-(1-phenyl-1,3-propyl)phosphonamido]furanyl}thiazole less polar isomer. Anal. calcd. for $C_{17}H_{18}N_3O_3PS_2+0.4\ HCl$: C: 48.38; H: 4.39; N: 9.96. Found: C: 48.47; H: 4.21; N: 9.96.

(31.15) 2-Amino-5-methylthio-4-{2-[5-(1-phenyl-1,3-propyl)phosphonamido]furanyl}thiazole more polar isomer. Anal. calcd. for $C_{17}H_{18}N_3O_3PS_2$: C: 50.11; H: 4.45; N: 10.31. Found: C: 49.84; H: 4.19; N: 10.13.

(31.16) 2-Amino-5-methylthio-4-{2-[5-(N-methyl-1-phenyl-1,3-propyl)phosphonamido]furanyl}thiazole. Anal. calcd. for $C_{18}H_{20}N_3O_3PS_2+0.25\ HCl$: C: 50.21; H: 4.74; N: 9.76. Found: C: 50.31; H: 4.46; N: 9.79.

(31.17) 2-Amino-5-methylthio-4-{2-[5-(1-phenyl-1,3-propyl)-N-acetylphosphonamido]furanyl}thiazole. Anal. calcd. for $C_{22}H_{26}N_3O_4PS+1.25\ H_2O$: C: 54.82; H: 5.96; N: 8.72. Found: C: 55.09; H: 5.99; N: 8.39.

(31.26) 2-amino-5-isobutyl-4-{2-[5-(1-oxo-1-phospha-2-oxa-7-aza-3,4-benocycloheptan-1-yl)]furanyl}thiazole, major isomer. Mp 233–234° C. Anal. calcd. for $C_{21}H_{24}N_3O_5PS+0.2\ CHCl_3$: C: 52.46; H: 5.03; N: 8.66. Found C: 52.08; H: 4.65; N: 8.58.

(31.27) 2-amino-5-isobutyl-4-{2-[5-(1-oxo-1-phospha-2-oxa-7-aza-3,4-benocycloheptan-1-yl)]furanyl}thiazole, minor isomer. MS calcd. for $C_{21}H_{24}N_3O_5PS+H$: 462, found 462.

(31.34) 2-amino-5-isobutyl-4-{2-[5-(3-(3,5-dichlorophenyl)-1,3-propyl)phosphonamido]furanyl}thiazole. Anal. calcd. for $C_{20}H_{22}N_3O_3PSCl_2$: C: 49.39; H: 4.56; N: 8.64. Found: C: 49.04; H: 4.51; N: 8.37.

(31.35) 2-amino-5-isobutyl-4-{2-[5-(4,5-benzo-1-oxo-1-phospha-2-oxa-6-oxa)cyclohexan-1-yl]furanyl}thiazole. Anal. calcd. for $C_{18}H_{20}N_3O_3PS+0.7\ H_2O$: C; 53.78; H: 5.37; N: 10.45. Found C: 53.63; H: 5.13; N: 10.36.

Example 32

Preparation of 5-[2-(5-phosphono)furanyl]tetrazole

Step A. To a mixture of tetrazole (1 mmole) and powdered $K_2CO_3$ (1.5 mmole) in 1 mL DMF cooled to 0° C. was added benzyl chloromethyl ether (1.2 mmole) and the resulting mixture stirred for 30 min at 0° C. and then for 16 h at rt. The mixture was diluted with water and ether. Extraction and chromatography provided 2-benzyloxymethyltetrazole as a colorless oil.

Step B. To a solution of 2-benzyloxymethyltetrazole (1 mmole) and TMEDA (2 mmole) in 3 mL diethyl ether at −78° C. was added n-BuLi in hexanes (1 mmole). This was let stir for 5 min at −78° C. and then it was added to a precooled (−78° C.) solution of $(n-Bu)_3SnCl$ (1 mmole) in 2 mL of diethyl ether. After stirring at −78° C. for 30 min it was diluted with water and diethyl ether. Extraction and chromatography provided 2-benzyloxymethyl-5-(tributylstannyl)tetrazole as a colorless oil.

Step C. A mixture of 5-iodo-2-diethylphosphonofuran (1 mmole), 2-benzyloxymethyl-5-(tributylstannyl)tetrazole (1.05 mmole), tetrakis(triphenylphosphine) palladium(0) (0.03 mmole) and copper(I) iodide (0.07 mmole) in 3 mL of toluene was refluxed at 110° C. for 20 h. Evaporation and chromatography provided 2-benzyloxymethyl-5-[2-(5-diethylphosphono)furanyl]tetrazole as an oil.

Step D. A mixture of 2-benzyloxymethyl-5-[2-(5-diethylphosphono)furanyl]tetrazole (1 mmole) and 6 M HCl (1 mL) in 10 mL ethanol was heated at 70° C. for 20 h and then the solvent concentrated by evaporation, made basic with 1 N NaOH and extracted with EtOAc. The aqueous layer was made acidic and extracted with EtOAc. This EtOAc extract was evaporated to provide 5-[2-(5-diethylphosphono)furanyl]tetrazole as a solid, which was subjected to Step C of Example 3 to give 5-[2-(5-phosphono)furanyl]tetrazole (32.1) as a solid: mp 186–188° C. Anal. calcd. for $C_5H_5N_4O_4P+1.5\ H_2O$: C, 24.70; H, 3.32; N, 23.05. Found: C, 24.57; N: 23.05.

Step E.

Step 1. A mixture of 5-[2-(5-diethylphosphono)furanyl]tetrazole (1 mmole), 1-iodo-2-methylpropane (2 mmole) and powdered $K_2CO_3$ (2 mmole) in 5 mL DMF was stirred at 80° C. for 48 h and then diluted with $CH_2Cl_2$ and water and the layers separated. The $CH_2Cl_2$ layer was evaporated and combined with the product of the following reaction for chromatography.

Step 2. The aqueous layer of Step 1 was made acidic and extracted with EtOAc. This extract was evaporated and the residue heated at 80° C. in 2 mL of $SOCl_2$ for 3 h and then the solvent evaporated. The residue was dissolved in 5 mL $CH_2Cl_2$ and 0.3 mL $NEt_3$ and 0.5 mL of EtOH was added. After stirring for 1 h at rt the mixture was diluted with $CH_2Cl_2$ and water. This organic extract was combined with that kept from Step 1 and chromatography provided 1-isobutyl-5-[2-(5-diethylphosphono)furanyl]tetrazole and 2-isobutyl-5-[2-(5-diethylphosphono)furanyl]tetrazole each as an oil.

Step 3. 1-Isobutyl-5-[2-(5-diethylphosphono)furanyl]tetrazole was subjected to Step C of Example 3 to give 1-isobutyl-5-[2-(5-phosphono)furanyl]tetrazole (32.2) as a solid: mp 200–202° C. Anal. calcd. for $C_9H_{13}N_4O_4P$: C: 39.71; H: 4.81; N: 20.58. Found: C: 39.64; H: 4.63; N: 20.21.

Step F. A mixture of 2-isobutyl-5-[2-(5-diethylphosphono)furanyl]tetrazole (1 mmole) and TMSBr (10 mmole) in 10 mL of $CH_2Cl_2$ was stirred at room temperature for 16 h. The solvent was evaporated and the residue dissolved in 10:1 $CH_3CN$:water, the solvent evaporated and the residue precipitated from acetone by addition of dicyclohexylamine (2 mmole) to provide 2-isobutyl-5-[2-(5-phosphono)furanyl]tetrazole N,N-dicyclohexyl ammonium salt.

(32.3) as a solid: mp 226–228° C. Anal. calcd. for $C_9H_{13}N_4O_4P+C_{12}H_{23}N$: C: 55.62; H: 8.00; N: 15.44. Found: C: 55.55; H: 8.03; N: 15.07.

Example 33

High Throughput Synthesis of Various 2-(5-phosphono)furanyl Substituted Heteroaromatic Compounds Step A. Various 2-(5-diethylphosphono)furanyl substituted heteroaromatic compounds were prepared in a similar manner as Step B of Example 15, and some of these compounds were used for the high throughput synthesis of compounds listed in Table 33.1 and Table 33.2

Step B. A mixture of 2-chloro-6-[2-(5-diethylphosphono)furanyl]pyridine (0.01 mmole) and TMSBr (0.1 mL) in $CH_2Cl_2$ (0.5 mL) was stirred at room temperature for 16 h and then evaporated and diluted with 0.5 mL of 9:1 $CH_3CN$:water. Evaporation provided 2-chloro-6-[2-(5-phosphono)furnayl]pyridine.

Step C. A mixture of 2-chloro-6-[2-(5-diethylphosphono)furanyl]pyridine (0.01 mmole) and a solution of freshly prepared sodium propoxide in propanol (0.25 M, 0.4 mL) was let sit at 85° C. for 14 h. The reaction mixture was evaporated and the residue was subjected to Step B of Example 33 to give 2-propyloxy-6-[2-(5-phosphono)furanyl]pyridine.

Step D. A mixture of 2-chloro-6-[2-(5-diethylphosphono)furanyl]pyridine (0.01 mmol) and 1-methylpiperazine (0.2 mL) in ethylene glycol (0.2 mL) was heated at 145° C. for 24 h. The mixture was further diluted with 0.5 mL of $CH_3CN$ and 0.1 mL of water and then 150 mg of Dowex 1 2–100 formate resin was added. After stirring this mixture 30 min it was filtered and the resin washed with DMF (2 1 0 min), $CH_3CN$ (2 1 0 min) and then 9:1 $CH_3CN$:water (1 1 0 min). Finally the resin was stirred with 9:1 TFA:water for 30 min, filtered and the filtrate evaporated. The residue obtained subjected to Step B of example to give 2-[1-(4-methyl)piperazinyl]-6-[2-(5-phosphono)furanyl]pyridine.

Step E. A mixture of 3-chloro-5-[2-(5-diethylphosphono)furanyl]pyrazine (0.01 mmole), 5-tributylstannylthiophene (0.04 mmole), $Pd(PPh_3)_4$ (0.001 mmole) and CuI (0.002 mmole) in dioxane (0.5 mL) was heated at 85° C. for 16 h then the solvent was evaporated. The resulting residue and TMSBr (0.1 mL) in 0.5 mL $CH_2Cl_2$ was stirred at rt for 16 h and then evaporated and diluted with 0.5 mL of 9:1 $CH_3CN$:water. To this solution 150 mg of Dowex 12–100 formate resin was added and after stirring 30 min it was filtered and the resin washed with DMF (2 10 min), $CH_3CN$ (2 10 min) and then 9:1 $CH_3CN$:water (1 10 min). Finally the resin was stirred with 9:1 TFA:water for 30 min, filtered and the filtrate evaporated to give 3-(2-thienyl)-5-[2-(5-phosphono)furnayl]pyrazine.

Step F. A mixture of 3-chloro-5-[2-(5-diethylphosphono)furanyl]pyrazine (0.01 mmole), 1-hexyne (0.04 mmole), diisopropylethylamine (0.1 mmole), $Pd(PPh_3)_4$ (0.001 mmole) and CuI (0.002 mmole) in dioxane (0.5 mL) was heated at 85° C. for 16 h then the solvent was evaporated. The resulting residue was subjected to Step B to give 3-(1-hexyn-1-yl)-5-[2-(5-phosphono)furanyl]pyrazine.

Preparation of the Carboxymethylphosphonate Resin

Step G. A solution of trimethylphosphonoacetate (30.9 mmol), 2-(trimethylsiyl) ethanol (10.4 mmol) and DMAP (3.1 mmol) in toluene (25 mL) was refluxed for 48 h under $N_2$. After cooling, the solution was diluted with EtOAc and washed with 1N HCl followed by water. The organic solution was dried over sodium sulfate and concentrated under vacuum to give an oil. The residue was treated with LiI (10.4 mmol) in 2-butanone (30 mL), and refluxed overnight under $N_2$. The solution was diluted with EtOAc, washed with 1N HCl, dried over $Na_2SO_4$ and concentrated under vacuum to afford the SEM protected carboxy monomethylphosphonate as a colorless oil.

Step H. Hydroxymethylpolystyrene (2.35 mmol) was prepared for coupling by combining with anhyrous THF (40 mL), gently skaking for 20 min. and then removing the excess solvent by cannula. This procedure was repeated 3 times. The swollen resin was then suspended in THF (40 mL) and DIPEA (21.2 mmol). To this mixture was added, by cannula, a solution of the SEM protected carboxy monomethylphosphonate (prepared in Step G) (7.1 mmol), DIAD (7.1 mmol) and tris(4-chlorophenyl)phosphine (7.1 mmol) in THF (15 mL) which had been stirred for 15 min. prior to addition. After shaking the mixture overnight under a blanket of $N_2$, the resin was filtered, rinsed with THF (3×40 mL), DMF (3×40 mL), and THF again (3×40 mL) before drying under vacuum to afford 3.8 g of the coupled phosphonate resin.

Step I. To coupled phosphonate resin (2.41 mmol) in THF (100 mL) was added 1M TBAF in THF solution (12 mL). The mixture was shaken overnight before being filtered and the resin rinsed with THF (3×40 mL) to afford the desired carboxymethylphosphonate resin as the tetrabutylammonium salt.

Coupling of the Carboxymethylphosphonate Resin to a Heteroaromatic Amine

Step J. In a 2 mL well, aheteroaromatic amine (0.14 mmol), resin (0.014 mmol), PyBOP (0.14 mmol) and TEA (0.36 mmol) in DMF (1.45 mL) were combined and shaken for 48 h at room temperature. The treated resin was then filtered, washed with DMF (3×) and $CH_2Cl_2$ (3×). The isolated resin was resuspended in $CH_2Cl_2$ (900 L), combined with TMSBr (100 L) and mixed for 6 h. The mixture was filtered, the resin washed with anhydrous $CH_2Cl_2$ (500 L) and the filtrate concentrated under vacuum. To the isolated residue was added a solution of $CH_3CN/H_2O$ (9:1, 300 L). After shaking for 30 min. the solvents were removed to provide the desired [{N-(phosphono)acetyl]amino} substituted heteroaromatic analogs. Compounds 33.97–33.119 and 33.146–33.164 were synthesized according to these procedures and they are listed in Table 33.1 and Table 33.2.

Preparation of the Aminomethylphosphonate Resin

Step K. To a solution of dimethyl phthalimidomethylphosphonate (37 mmole) in 2-butanone (150 mL) was added LiI (38.9 mmol). After refluxing overnight under $N_2$, the solution was diluted with EtOAc, washed with 1N HCl, dried over $MgSO_4$ and concentrated under vacuum to afford monomethyl phthalimidomethylphosphonate as a white solid.

Step L. As described above in Step H. monomethyl phthalimidomethyl-phosphonate was coupled to hydroxymethylpolystyrene to give the resin-coupled phthalimidomethylphosphonate monomethyl ester.

Step M. To the resin-coupled phthalimidomethylphosphonate monomethyl ester (6.8 mmol) in DMF (7 mL) was added anhydrous hydrazine (3 mL). After shaking at room temperature for 24 h the resin was filtered, rinsed with DMF (3×10 mL), $CH_2Cl_2$ (3×10 mL) and then dried under vacuum to afford 832 mg the desired resin-coupled aminomethylphosphonate monomethyl ester.

Coupling of Various Heteroaromatic Carboxylic Acids to the Resin-coupled Aminomethylphosl)honate Monomethyl Ester.

Step N. In a 2 mL well, a heteroaromatic carboxylic acid (0.2 mmol), resin (0.02 mmol), EDC (0.2 mmol) and HOBT (0.2 mmol) in DMF (0.5 mL) were combined and shaken for 24 h at room temperature. The treated resin was then filtered, washed with DMF (3×) and $CH_2Cl_2$ (3×). The isolated resin was resuspended in $CH_2Cl_2$ (500 L), combined with TMSBr (50 L) and mixed for 6 h. The mixture was filtered, the resin washed with anhydrous $CH_2Cl_2$ (500 L) and the filtrate concentrated under vacuum. To the isolated residue was added a solution of $CH_3CN/H_2O$ (9:1, 300 L). After shaking for 30 min the solvents were evaporated to provide the desired (N-phosphonomethyl)carbamoyl substituted heteroaromatic analogs. Compounds 33.120–33.145 were synthesized according to these procedures and they are listed in Table 33.2.

The following compounds were prepared according to some or all of the above described procedures. These compounds were characterized by HPLC (as described below) and mass spectroscopy (APCI negative ion), and these characterization data are listed in Table 33.1 and Table 33.2.

HPLC was performed using a YMC ODS-Aq, Aq-303-5, 250 4.6 mm ID, S-5 μm, 120 A column with the UV detector set at 280 nm.

| HPLC Elution Program: 1.5 mL/min flow rate | | |
|---|---|---|
| Time (min) | % Acetonitrile (A) | % Buffer[a] (B) |
| 0 | 10 | 90 |
| 7.5 | 90 | 10 |
| 12.4 | 90 | 10 |
| 12.5 | 10 | 90 |
| 15 | 10 | 90 |

[a]Buffer = 95:5:0.1 water:methanol:acetic acid

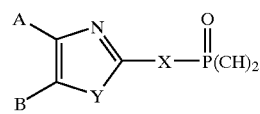

| synthetic example number | A | B | X | Y' | HPLC Rt (min.) | M-1 found |
|---|---|---|---|---|---|---|
| 33.146 | H | Br | NHC(O)CH2 | S | 6.58 | 299/301 |
| 33.147 | H | Ph | NHC(O)CH2 | S | 6.57 | 297 |
| 33.148 | Ph | H | NHC(O)CH2 | S | 6.06 | 297 |
| 33.149 | Ph | Et | NHC(O)CH2 | O | | 309 |
| 33.150 | H | H | NHC(O)CH2 | S | 4.22 | 221 |
| 33.151 | adamantyl | Me | NHC(O)CH2 | S | 6.59 | 369 |
| 33.152 | Bu-t | Br | NHC(O)CH2 | S | 6.62 | 355/357 |
| 33.153 | H | Ph(-4-Br) | NHC(O)CH2 | S | 6.62 | 375/377 |

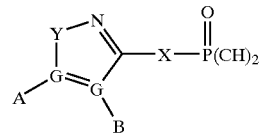

| synthetic example number | A* | B* | X | Y' | HPLC Rt (min.) | M-1 found |
|---|---|---|---|---|---|---|
| 33.154 | H | H | NHC(O)CH2 | O | 6.68 | 205 |
| 33.155 | null | NH2 | NHC(O)CH2 | O | 6.6 | 221 |
| 33.156 | NHMe | null | NHC(O)CH2 | S | 3.82 | 251 |
| 33.157 | Me | H | NHC(O)CH2 | NH | | |
| 33.158 | H | H | NHC(O)CH2 | NH | | |
| 33.159 | OH | H | NHC(O)CH2 | NH | | |
| 33.160 | Bu-t | H | NHC(O)CH2 | O | 6.62 | 261 |
| 33.161 | null | 3-pyridyl | NHC(O)CH2 | O | 6.58 | 283 |
| 33.162 | CH2Ph(2,6-dichloro) | null | NHC(O)CH2 | O | | |
| 33.163 | Br | null | furan-2,5-diyl | NH | 4.46 | 292/294 |
| 33.164 | Br | null | furan-2,5-diyl | S | 5.96 | 309/311 |

*when A or B is null, then the corresponding G is N.

65

TABLE 33.2

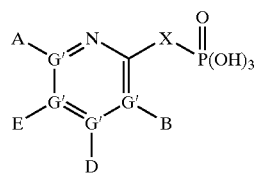

| synthetic example number | A* | B* | X | D* | E* | HPLC Rt (min.) | M-1 found |
|---|---|---|---|---|---|---|---|
| 33.1 | NH2 | Cl | furan-2,5-diyl | Me | null | 11.06 | 288 |
| 33.2 | H | OC(O)(Ph-2,6-dichloro) | furan-2,5-diyl | H | H | 3.99 | 413 |
| 33.3 | OMe | H | furan-2,5-diyl | CH2OH | H | 8.34 | 284 |
| 33.4 | OMe | H | furan-2,5-diyl | C(O)NH2 | H | 8.23 | 297 |
| 33.5 | OMe | H | furan-2,5-diyl | CO2H | H | 9.54 | 298 |
| 33.6 | OH | H | furan-2,5-diyl | CF3 | C(O)NH2 | 3.91 | 351 |
| 33.7 | OMe | H | furan-2,5-diyl | CF3 | C(O)NH2 | 9.14 | 365 |
| 33.8 | null | H | furan-2,5-diyl | H | OMe | 9.72 | 255 |
| 33.9 | null | H | furan-2,5-diyl | H | OH | 4.52 | 241 |
| 33.10 | OH | H | furan-2,5-diyl | Me | null | 3.79 | 255 |
| 33.11 | OMe | H | furan-2,5-diyl | Me | null | 6.44 | 269 |
| 33.12 | NH2 | null | furan-2,5-diyl | OH | H | 3.96 | 256 |
| 33.13 | NH2 | null | furan-2,5-diyl | OMe | H | 8.02 | 270 |
| 33.14 | H | OMe | furan-2,5-diyl | null | H | 7.22 | 255 |
| 33.15 | H | OH | furan-2,5-diyl | null | H | 4.82 | 241 |
| 33.16 | OMe | H | furan-2,5-diyl | null | H | 7.48 | 255 |
| 33.17 | OEt | H | furan-2,5-diyl | H | H | 9.72 | 268 |
| 33.18 | OEt | H | furan-2,5-diyl | CH2OH | H | 5.26 | 298 |
| 33.19 | null | H | furan-2,5-diyl | Me | OEt | 7.80 | 283 |
| 33.20 | null | H | furan-2,5-diyl | Me | OH | 3.80 | 255 |
| 33.21 | OH | H | furan-2,5-diyl | Me | null | 3.77 | 255 |
| 33.22 | OEt | H | furan-2,5-diyl | Me | null | 7.33 | 283 |
| 33.23 | NH2 | null | furan-2,5-diyl | OH | H | 3.94 | 256 |
| 33.24 | NH2 | null | furan-2,5-diyl | OEt | H | 5.66 | 284 |
| 33.25 | NH2 | H | furan-2,5-diyl | OEt | null | 5.90 | 284 |
| 33.26 | NH2 | H | furan-2,5-diyl | OH | null | 3.78 | 256 |
| 33.27 | H | OEt | furan-2,5-diyl | null | H | 9.74 | 269 |
| 33.28 | H | OH | furan-2,5-diyl | null | H | 4.81 | 241 |
| 33.29 | OEt | H | furan-2,5-diyl | null | H | 9.78 | 269 |
| 33.30 | Br | H | furan-2,5-diyl | H | NO2 | 7.78 | 347/ |
| 33.31 | Cl | H | furan-2,5-diyl | H | C(O)OEt | 9.69 | 330 |
| 33.32 | Br | H | furan-2,5-diyl | H | C(O)OEt | 9.69 | 374/376 |
| 33.33 | Cl | H | furan-2,5-diyl | Me | C(O)NH2 | 3.72 | 315 |
| 33.34 | Cl | CF3 | furan-2,5-diyl | H | CF3 | 9.04 | 394 |
| 33.35 | Cl | H | furan-2,5-diyl | NH2 | H | 4.89 | 273 |
| 33.36 | Cl | H | furan-2,5-diyl | CN | H | 7.93 | 283 |
| 33.37 | Cl | H | furan-2,5-diyl | CH2OH | H | 5.38 | 288 |
| 33.38 | Cl | H | furan-2,5-diyl | C(O)NH2 | H | 5.57 | 301 |
| 33.39 | Cl | H | furan-2,5-diyl | C(O)OEt | H | 8.54 | 330 |
| 33.40 | Cl | 1-triazinyl(3-amino-5-methylthio) | furan-2,5-diyl | H | H | 8.91 | 398 |
| 33.41 | Cl | H | furan-2,5-diyl | Me | CN | 8.22 | 297 |
| 33.42 | Cl | H | furan-2,5-diyl | CF3 | NH2 | 8.60 | 341 |
| 33.43 | Cl | H | furan-2,5-diyl | CF3 | CN | 8.66 | 351 |
| 33.44 | null | CH3 | furan-2,5-diyl | Me | Br | 9.25 | 331/333 |
| 33.45 | null | CH3 | furan-2,5-diyl | Me | Cl | 9.25 | 287 |
| 33.46 | Br | CH3 | furan-2,5-diyl | H | null | 5.62 | 317/319 |
| 33.47 | Br | Br | furan-2,5-diyl | H | null | 3.54 | 381/383/385 |
| 33.48 | Br | H | furan-2,5-diyl | Me | null | 5.55 | 317/319 |
| 33.49 | H | NH2 | furan-2,5-diyl | Br | null | 4.78 | 318/320 |
| 33.50 | Br | Cl | furan-2,5-diyl | Br | null | 8.38 | 417/419 |
| 33.51 | SMe | Ph | furan-2,5-diyl | Br | null | 9.26 | 425/427 |
| 33.52 | NH2 | H | furan-2,5-diyl | Br | null | 4.87 | 318/320 |
| 33.53 | NH2 | H | furan-2,5-diyl | OH | null | 3.70 | 256 |
| 33.54 | Br | H | furan-2,5-diyl | Br | null | 9.64 | 381/383/385 |
| 33.55 | Br | H | furan-2,5-diyl | Cl | null | 9.64 | 337/339 |
| 33.56 | H | Br | furan-2,5-diyl | null | H | 5.08 | 303/305 |
| 33.57 | NH2 | Cl | furan-2,5-diyl | null | C(O)OMe | 3.34 | 332 |
| 33.58 | OPr-n | H | furan-2,5-diyl | Me | null | 8.14 | 297 |
| 33.59 | H | OPr-n | furan-2,5-diyl | null | H | 8.45 | 283 |
| 33.60 | H | O(CH2)2OEt | furan-2,5-diyl | null | H | 7.82 | 313 |
| 33.61 | NH2 | null | furan-2,5-diyl | OH | H | 3.97 | 256 |
| 33.62 | NH2 | null | furan-2,5-diyl | OPr-n | H | 7.84 | 298 |

TABLE 33.2-continued

| synthetic example number | A* | B* | X | D* | E* | HPLC Rt (min.) | M-1 found |
|---|---|---|---|---|---|---|---|
| 33.63 | OPr-n | H | furan-2,5-diyl | CH2OH | H | 4.36 | 312 |
| 33.64 | OBu-n | H | furan-2,5-diyl | CH2OH | H | 8.58 | 326 |
| 33.65 | O(CH2)2OEt | H | furan-2,5-diyl | CH2OH | H | 4.13 | 342 |
| 33.66 | NH2 | H | furan-2,5-diyl | OPr-n | null | 7.96 | 298 |
| 33.67 | NH2 | H | furan-2,5-diyl | OBu-n | null | 3.86 | 312 |
| 33.68 | H | OBu-i | furan-2,5-diyl | null | H | 8.80 | 297 |
| 33.69 | H | O(CH2)2OEt | furan-2,5-diyl | null | H | 7.14 | 299 |
| 33.70 | H | O(CH2)2NMe2 | furan-2,5-diyl | null | H | 4.57 | 312 |
| 33.71 | NH2 | null | furan-2,5-diyl | OBu-i | H | 8.06 | 312 |
| 33.72 | NH2 | null | furan-2,5-diyl | O(CH2)2OMe | H | 4.84 | 314 |
| 33.73 | NH2 | H | furan-2,5-diyl | OBu-i | null | 8.70 | 312 |
| 33.74 | Br | H | furan-2,5-diyl | C(O)NH2 | H | 7.68 | 346/348 |
| 33.75 | NH2 | null | furan-2,5-diyl | Cl | H | 4.77 | 274 |
| 33.76 | NH(CH2)2OH | H | furan-2,5-diyl | Me | null | 4.56 | 298 |
| 33.77 | H | NH(CH2)2OH | furan-2,5-diyl | null | H | 4.55 | 284 |
| 33.78 | NH2 | null | furan-2,5-diyl | NH(CH2)2OH | H | 4.58 | 299 |
| 33.79 | NH(CH2)2OH | H | furan-2,5-diyl | NH2 | null | 4.58 | 299 |
| 33.80 | NH(CH2)2OH | H | furan-2,5-diyl | CH2OH | H | 4.44 | 313 |
| 33.81 | NH2 | H | furan-2,5-diyl | NH(CH2)2OH | null | 4.33 | 299 |
| 33.82 | NHCH2CH(OH)Me | H | furan-2,5-diyl | CH3 | H | 4.65 | 312 |
| 33.83 | NH2 | H | furan-2,5-diyl | NHCH2CH(OH)Me | H | 4.63 | 313 |
| 33.84 | NHCH2CH(OH)Me | H | furan-2,5-diyl | NH2 | null | 4.63 | 313 |
| 33.85 | NHCH2CH(OH)Me | H | furan-2,5-diyl | CH2OH | H | 4.52 | 327 |
| 33.86 | NH2 | H | furan-2,5-diyl | NHCH2CH(OH)Me | null | 4.65 | 313 |
| 33.87 | NH(CH2)3OH | H | furan-2,5-diyl | Me | null | 4.62 | 312 |
| 33.88 | NH2 | null | furan-2,5-diyl | NH(CH2)3OH | H | 4.48 | 313 |
| 33.89 | NH(CH2)3OH | H | furan-2,5-diyl | NH2 | null | 4.48 | 313 |
| 33.90 | NH2 | NH(CH2)3OH | furan-2,5-diyl | null | C(O)NH(CH2)3OH | 4.76 | 414 |
| 33.91 | H | 4-morpholinyl | furan-2,5-diyl | null | H | 6.46 | 310 |
| 33.92 | 4-morpholinyl | H | furan-2,5-diyl | Me | null | 6.53 | 324 |
| 33.93 | NH2 | null | furan-2,5-diyl | 4-morpholinyl | H | 6.15 | 325 |
| 33.94 | 4-morpholinyl | H | furan-2,5-diyl | NH2 | null | 4.84 | 325 |
| 33.95 | NH2 | 4-morpholinyl | furan-2,5-diyl | null | C(O)(4-morpholinyl) | 7.47 | 438 |
| 33.96 | NH2 | H | furan-2,5-diyl | 4-morpholinyl | null | 5.30 | 325 |
| 33.97 | Me | H | NHC(O)CH2 | H | H | 6.58 | 229 |
| 33.98 | H | Me | NHC(O)CH2 | H | H | 6.60 | 229 |
| 33.99 | NH2 | H | NHC(O)CH2 | H | Cl | 6.63 | 264 |
| 33.100 | NH2 | H | NHC(O)CH2 | H | H | 6.63 | 264 |
| 33.101 | H | OH | NHC(O)CH2 | H | H | 6.54 | 231 |
| 33.102 | Me | H | NHC(O)CH2 | Me | H | 6.59 | 243 |
| 33.103 | H | H | NHC(O)CH2 | H | Cl | 7.02 | 249 |
| 33.104 | H | H | NHC(O)CH2 | H | Br | 8.01 | 293/295 |
| 33.105 | Me | H | NHC(O)CH2 | H | Br | 6.64 | 307/309 |
| 33.106 | H | H | NHC(O)CH2 | H | H | 6.72 | 215 |
| 33.107 | H | H | NHC(O)CH2 | H | Me | 6.54 | 229 |
| 33.108 | H | H | NHC(O)CH2 | Me | H | 6.53 | 229 |
| 33.109 | Me | Cl | NHC(O)CH2 | Me | null | 3.93 | 279 |
| 33.110 | Cl | H | NHC(O)CH2 | null | H | 4.20 | 251 |
| 33.111 | H | Br | NHC(O)CH2 | H | Me | 6.44 | 307/309 |
| 33.112 | NH2 | H | NHC(O)CH2 | NH(Ph-4-Br) | null | 4.42 | 401/403 |
| 33.113 | NH2 | Bn | NHC(O)CH2 | H | Bn | 6.49 | 410 |
| 33.114 | H | H | NHC(O)CH2 | Et | H | 6.57 | 243 |
| 33.115 | Me | Et | NHC(O)CH2 | H | H | 6.54 | 257 |
| 33.116 | Me | H | NHC(O)CH2 | H | Br | 6.55 | 307/309 |
| 33.117 | H | Br | NHC(O)CH2 | H | Me | 6.51 | 307/309 |
| 33.118 | H | Me | NHC(O)CH2 | H | Br | 6.52 | 307/309 |
| 33.119 | Me | Br | NHC(O)CH2 | H | Br | 6.19 | 385/387/389 |
| 33.120 | H | H | C(O)NHCH2 | H | H | 3.74 | 215 |
| 33.121 | Me | H | C(O)NHCH2 | H | H |  | 229 |
| 33.122 | OH | H | C(O)NHCH2 | H | H | 3.72 | 231 |
| 33.123 | Br | H | C(O)NHCH2 | H | H | 5.02 | 293/295 |
| 33.124 | Cl | H | C(O)NHCH2 | H | H | 4.60 | 249/251 |
| 33.125 | H | H | C(O)NHCH2 | Cl | H | 5.18 | 249/251 |
| 33.126 | H | Br | C(O)NHCH2 | OH | H | 3.60 | 310/312 |

TABLE 33.2-continued

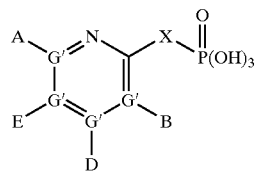

| synthetic example number | A* | B* | X | D* | E* | HPLC Rt (min.) | M-1 found |
|---|---|---|---|---|---|---|---|
| 33.127 | H | H | C(O)NHCH2 | null | H | 3.70 | 216 |
| 33.128 | H | H | C(O)NHCH2 | NO2 | H | 5.00 | 260 |
| 33.129 | H | H | C(O)NHCH2 | H | Bu-n | 8.35 | 271 |
| 33.130 | H | OPr-n | C(O)NHCH2 | H | H | 7.46 | 273 |
| 33.131 | Cl | Cl | C(O)NHCH2 | H | H | 4.23 | 283/285/287 |
| 33.132 | Cl | CF3 | C(O)NHCH2 | H | H | 8.05 | 317/319 |
| 33.133 | H | Cl | C(O)NHCH2 | H | CF3 | 6.49 | 317/319 |
| 33.134 | H | Cl | C(O)NHCH2 | Cl | Cl | 7.20 | 318/320/322 |
| 33.135 | H | C(O)Ph | C(O)NHCH2 | H | H | 7.00 | 319 |
| 33.136 | H | OEt | C(O)NHCH2 | H | CF3 | 6.65 | 327 |
| 33.137 | SMe | Cl | C(O)NHCH2 | H | null | 5.82 | 296/298 |
| 33.138 | SMe | Br | C(O)NHCH2 | H | null | 5.40 | 340/342 |
| 33.139 | H | O(Ph-3-CF3) | C(O)NHCH2 | null | H | | 376 |
| 33.140 | H | H | C(O)NHCH2 | null | Me | 3.75 | 230 |
| 33.141 | H | Me | C(O)NHCH2 | H | H | 4.96 | 229 |
| 33.142 | Cl | Cl | C(O)NHCH2 | Cl | Cl | 9.18 | 351/353/355/357 |
| 33.143 | H | F | C(O)NHCH2 | OH | null | | 250 |
| 33.144 | Me | F | C(O)NHCH2 | OH | null | | 264 |
| 33.145 | OH | F | C(O)NHCH2 | OH | null | 3.93 | 266 |

*When A, B, D or E is null, then the corresponding G' is N.

Section 2

Synthesis of Compounds of Formula X

Example 34

Preparation of 2-Amino-4-phosphonomethyloxy-6-bromobenzothiazole

Step A. A solution of AlCl$_3$ (5 mmole) in ETSH (10 mL) was cooled to 0° C. and treated with 2-amino-4-methoxybenzothiazole (1 mmole). The mixture was stirred at 0–5° C. for 2 h. Evaporation and extraction gave 2-amino-4-hydroxybenzothiazole as white solid.

Step B. A mixture of 2-amino-4-hydroxybenzothiazole (1 mmole) and NaH (1.3 mmole) in DMF (5 mL) was stirred at 0° C. for 10 min, and then treated with diethylphosphonomethyl trifluoromethylsulfonate (1.2 mmole). After being stirred at room temperature for 8 h, the reaction was subjected to extraction and chromatography to give 2-amino-4-diethylphosphonomethyloxybenzothiazole as an oil.

Step C. A solution of 2-amino-4-(diethylphosphonomethyloxy)benzothiazole (1 mmole) in AcOH (6 mL) was cooled to 10° C. and treated with bromine (1.5 mmole) in AcOH (2 mL). After 5 min the mixture was stirred at room temperature for 2.5 h. The yellow precipitate was collected via filtration and washed with CH$_2$Cl$_2$ to give 2-amino-4-diethylphosphonomethyloxy-6-bromobenzothiazole.

Step D. A solution of 2-amino-4-diethylphosphonomethyloxy-6-bromobenzothiazole (1 mmole) in CH$_2$Cl$_2$ (4 mL) was treated with TMSBr (10 mmole) at 0° C. After stirred for 8 h at room temperature the reaction was evaporated to dryness and the residue was taken into water (5 mL). The resulting precipitate was collected via filtration and washed with water to give 2-amino-4-phosphonomethyloxy-6-bromobenzothiazole (34.1) as white solid. mp >220° C. (dec.). Anal. Calcd. for C$_9$H$_8$N$_2$O$_4$PSBr: C:28.34; H:2.38; N:8.26. Found: C:28.32; H:2.24; N:8.06.

Similarly, the following compounds were prepared according to the above described procedures:

(34.2) 2-Amino-4-phosphonomethyloxybenzothiozole. mp >250° C. Anal. Calcd. for C$_8$H$_9$N$_2$O$_4$PS+0.4 H$_2$O: C:35.93; H:3.69; N:10.48. Found: C:35.90; H:3.37; N:10.37.

Example 35

Preparation of 2-Amino-4-phosphonomethyloxy-6-bromo-7-chlorobenzothiazole

Step A. A solution of 1-(2-methoxy-5-chlorophenyl)-2-thiourea (1 mmole) in chloroform (10 mL) was cooled to 10° C. and treated with bromine (2.2 mmole) in chloroform (10 mL). The reaction was stirred at 10° C. for 20 mm and at room temperature for 0.5 h. The resulting suspension was heated at reflux for 0.5 h. The precipitate was collected via filtration (washed with CH$_2$Cl$_2$) to give 2-amino-4-methoxy-7-chlorobenzothiazole which was subjected to Steps A, B, C and D of Example 34 to give 2-amino-4-phosphonomethoxy-6-bromo-7-chloro benzothiazole (35.1). mp >220° C. (dec.). Anal. Calcd. for C$_8$H$_7$N$_2$O$_4$PSClBr: C:25.72; H: 1.89; N:7.50. Found: C:25.66; H:1.67; N:7.23.

Similarly, the following compounds were prepared according to the above described procedures:

(35.2) 2-Amino-4-phosphonomethoxy-6-bromo-7-methyl benzothiazole. mp >220° C. (dec.). Anal. Calcd. for $C_9H_{10}N_2O_4PSBr$: C:30.61; H:2.85; N:7.93 Found: C:30.25; H:2.50; N:7.77.

(35.3) 2-Amino-4-phosphonomethoxy-7-methylbenzothiazole. mp >220° C. (dec.). Anal. Calcd. for $C_9H11N_2O_4PS+1.0\ H_2O$: C:36.99; H:4.48; N:9.59. Found: C:36.73; H:4.23; N:9.38.

(35.4) 2-Amino-4-phosphonomethoxy-7-chlorobenzothiazole. mp >220° C.(dec.). Anal. Calcd. for $C_8H8N_2O_4PSCI+0.1H_2O$: C:32.41; H:2.79; N:9.45. Found: C:32.21; H:2.74; N:9.22.

Example 36

Preparation of 2-Amino-4-phosphonomethoxy-5.6.7,8-tetrahydronaphtho-[1.2-d]thiazole Step A. 3-Amino-2-hydroxy-5,6,7,8-tetrahydronaphthalene was subjected to Step B of Example 34 to give 3-amino-2-diethylphosphonomethyloxy-5,6,7,8-tetrahydronaphthlene.

Step B. A solution of KSCN (16 mmole) and $CuSO_4$ (7.7 mmole) in MeOH (10 mL) was treated with a solution of 3-amino-2-diethylphosphonomethyloxy-5,6,7,8-tetrahydronaphthalene (1 mmole) in MeOH (5 mL) at room temperature. The mixture was heated at reflux for 2 h. Filtration, extraction and chromatography provided 2-amino-4-diethylphosphonomethyloxy-5,6,7,8-tetrahydronaphtho[1,2-d]thiazole as light brown solid.

Step C. 2-Amino-4-diethylphosphonomethyloxy-5,6,7,8-tetrahydronaphtho[1,2-d]thiazole was subjected to Step D of Example 34 to give 2-Amino-4-phosphonomethoxy-5,6,7,8-tetrahydronaphtho[1,2-d]thiazole (36.1). mp >220° C. (dec.). Anal. Calcd. for $C_{12}H_{15}N_2O_4PS+0.5\ H_2O$: C:45.86; H:4.81; N:8.91 Found: C:44.68; H:4.77; N:8.73.

The following compounds were also prepared according to above procedures:

(36.2) 2-Amino-4-phosphonomethoxy-[1,2d]naphthothiazole. mp >240° C.(dec.). Anal. Calcd. for $C_{12}H_{11}N_2O_4PS+0.2HBr$: C:44.15; H:3.46; N:8.58. Found: C:44.13; H:3.46; N:8.59.

(36.3) 2-Amino-5,7-dimethyl-6-thiocyanato-4-phosphonomethoxybenzothiazole. mp >240° C. (dec.). Anal. Calcd. for $C_{11}H_{12}N_3O_4PS_2+0.2CH_2Cl_2$: C:37.13; H:3.45; N: 11.60. Found: C:37.03; H:3.25; N:11.65.

Example 37

Preparation of 2-Amino-7-methoxy-6thiocyanato-4-phosphonometxy-benzothiazole

Step A. 2-Hydroxy-5-methoxynitrobenzene was subjected to Step B of Example 34 to give 2-diethylphosphonomethyloxy-5-methoxynitrobenzene.

Step B. A solution of $SnCl_2$ (4 mmole) in freshly prepared methonolic HCl (10 mL) was added to a cold (0° C.) solution of 2-diethylphosphonomethyloxy-5-methoxynitrobenzene (1 mmole) in MeOH (5 mL). The mixture was warmed to room temperature and stirred for 3 h. Evaporation, extraction and chromatography provided 2-diethylphosphonomethyloxy-5-methoxyaniline.

Step C. 2-Diethylphosphonomethyloxy-5-methoxyaniline was subjected to Step B of Example 36 to give 2-amino-4-diethylphosphonomethyloxy-6-thiocyano-7-methoxybenzothiazole, which was subjected to Step D of Example 34 to give 2-amino-7-methoxy-6-thiocyanato-4-phosphonomethoxybenzothiazole (37.1). mp >170° C.(dec.). Anal. Calcd. for $C_{10}H_{10}N_3O_5PS_2$: C:34.58; H:2.90; N:12.10. Found: C:34.23; H:2.68; N:11.77.

Similarly, the following compounds were prepared according to above procedures:

(37.2) 2-Amino-5,6-difluoro-4-phosphonomethoxybenzothiazole. mp >240° C.(dec.). Anal. Calcd. for $C_8H_7N_2O_4PSF_2$: C:32.44; H:2.38; N:9.46. Found: C:32.30; H:2.26; N:9.17.

(37.3) 2-Amino-5-fluoro-7-bromo-4-phosphonomethoxybenzothiazole. mp >190° C.(dec.). Anal. Calcd. for $C_8H_7N_2O_4PSBrF$: C:26.91; H:1.98; N:7.84. Found: C:27.25; H:1.92; N:7.54.

(37.4) 2-Amino-7-ethoxycarbonyl-4-phosphonomethoxybenzothiazole. mp >240° C.(dec.). Anal. Calcd. for $C_1H_{13}N_2O_6PS+0.2HBr+0.1$ DMF: C:38.15; H:3.94; N:8.27. Found: C:38.51; H:3.57; N:8.66.

Example 38

Preparation of 2-Amino-7-bromo-6-thiocyanato-4-phosphonomethoxy benzothiazole

Step A. A solution of 2-fluoro-5-bromonitrobenzene (1 mmole) in DMF (5 mL) was cooled to 0° C., and treated with a solution of freshly prepared sodium salt of diethylhydroxymethylphosphonate (1.2 mmole) in DMF (5 mL). The mixture was stirred at room temperature for 16 h. Evaporation, extraction and chromatography provided 2-diethylphosphonomethyloxy-5-bromonitrobenzene.

Step B. 2-Diethylphosphonomethyloxy-5-bromonitrobenzene was subjected to Step B of Example 37, Step B of Example 36, and Step D of Example 34 to give 2-amino-7-bromo-6-thiocyanato-4-phosphonomethoxybenzothiazole (38.1). mp >250° C.(dec.). Anal. Calcd. for $C_9H_7N_3O_4PS_2$ Br: C:27.29; H:1.78; N:10.61. Found: C:26.90; H:1.58; N:10.54.

Similarly, the following compound was prepared according to above procedures: (38.2) 2-Amino-7-fluoro-6-thiocyanato-4-phosphonomethoxybenzothiazole. mp >136° C.(dec.). Anal. Calcd. for $C_9H_7N_3O_4PFS_2+0.3HBr$: C:30.07; H:2.05; N Found: C:30.27; H:2.01; N:11.38.

Example 39

Preparation of 2-Amino-7-hydroxymetbyl-6-thiocyano-4-phosphonomethoxy benzothiazole Step A. 2-Chloro-5-formylnitrobenzene was subjected to Step A of Example 38 to give 2-diethylphosphonomethyloxy-5-formylnitrobenzene.

Step B. A solution of 2-diethylphosphonomethyloxy-5-fornylnitrobenzene (1 mmole) in methanol (5 mL) was treated with 10% palladium on carbon (0.05 mmole) under 1 atmosphere of hydrogen at room temperature for 12 h. Filtration followed by evaporation gave 2-diethylphosphonomethyloxy-5-hydroxymethylaniline which was subjected to Step B of Example 36 followed by Step D of Example 34 to give 2-amino-7-hydroxymethyl-6-thiocyanato-4-phosphonomethoxybenzothiazole (39.1). mp 181–184° C. Anal. Calcd. for $C_{10}H_{10}N_3O_5PS_2+0.35H_2O$: C:33.97; H:3.05; N:11.88. Found C:33.76; H:2.66; N:11.61.

Example 40

Preparation of 2-Amino-6-bromo-7-fluoro-4-phosphonomethoxybenzothiazole

Step A. A solution of 2-diethylphosphonomethyloxy-4-bromo-5-fluoroaniline (1 mmole, prepared as in Example 4, Step B) and KSCN (2 mmole) in AcOH (8 mL) was cooled to 10° C., and treated with a solution of bromine (2 mmole) in AcOH (5 mL). After being stirred at room temperature for 0.5 h, the reaction mixture was evaporated to dryness and the residue was purified by chromatography to provide 2-amino-7-fluoro1-6-bromo-4-diethylphosphonomethyloxybenzothiazole which was subjected to Step D of Example 34 to give 2-amino-6-bromo-7-fluoro-4-phosphonomethoxybenzothiazole (40.1). Anal. Calcd. for $C_8H_7N_2O_4PSBrF+0.1HBr$: C:26.31; H:1.96; N:7.67. Found: C:25.96; H:1.94; N:7.37.

Example 41

Preparation of 2-Amino-7-ethyl-6-thiocyano-4-phosphonomethoxy Benzothiazole

Step A. A solution of 2-diethylphosphonomethyloxy-5-bromonitrobenzene (1 mmole, prepared as in Example 37, Step A) in DMF (5 mL) was treated with tributyl(vinyl)tin (1.2 mmole) and palladium bis(triphenylphosphine) dichloride (0.1 mmole), and the mixture was heated at 60° C. under nitrogen for 6 h. Evaporation and chromatography gave 2-diethylphosphonomethyloxy-5-vinylnitrobenzene as an oil which was subjected to Step B of Example 38, Step B of Example 36, and Step D of Example 34 to give 2-amino-7-ethyl-6-thiocyano-4-phosphonomethoxybenzothiazole (41.1). mp >167° C.(dec.). Anal. Calcd. for $C_{11}H_{12}N_3O_4PS_2$: C:38.26; H:3.50; N:12.17. Found: C:37.87; H:3.47; N: 11.93.

Example 42

Preparation of 2-Amino-7-cyclooropyl-6-thiocyanato-4-phosphonomethoxy benzothiazole Step A. A suspension of 2-diethylphosphonomethyloxy-5-vinylnitrobenzene (1 mmole, prepared as in Step A of Example 40) and Pd(OAc)$_2$ (0.1 mmole) in ether (8 mL) was treated with a solution of diazomethane (generated from 3.0 g of 1-methyl-3-nitro-1-nitrosoguanidine) in ether at 0° C. After being stirred at room temperature for 20 h the reaction was evaporated to dryness and the residue was chromatographed to give 2-diethylphosphonomethyloxy-5-cyclopropylnitrobenzene which was subjected to Step B of Example 37, Step B of Example 36, and Step D of Example 34 to give 2-amino-7-cyclopropyl-6-thiocyanato-4-phosphonomethoxybenzothiazole hydrogen bromide (42.1). Anal. Calcd. for $C_{12}H_{13}N_3O_4PS_2Br+0.1HBr$: C:27.76; H:2.72; N:8.09. Found: C:27.54; H:3.05; N:7.83.

Example 43

Preparation of 2-Amino-4-phosphonomethoxy-6-chloro-7-methyl benzothiazole

Step A. 2-Methoxy-4-chloro-5-methylaniline was subjected to Steps A and B of Example 34, Step B of Example 36, and Step D of Example 34 to give 2-amino-4-phosphonomethoxy-6-chloro-7-methyl benzothiazole (43.1). mp >250° C.(dec.). Anal. Calcd. for $C_9H_{10}N_2O_4PS_2Cl+0.3H_2O+0.4$ HBr: C:31.20; H:3.20; N:8.09. Found: C:31.37: H:2.87; N:7.89.

Similarly, the following compounds were prepared according to above procedures:

(43.2) 2-Amino-7-phenyl-6thiocyanato-4-phosphonomethoxybenzothiazole. mp >250° C.(dec.). Anal. Calcd. for $C_{15}H_{12}N_3O_4PS_2+0.2H_2O$: C:45.38; H:3.15: N10.58. Found: C:45.25; H:3.21; N:10.53.

Example 44

Preparation of 2-bromo-4-diethylphosphonomethoxy-5.6.7,8-tetrahydronaphtho[1,2-d]thiazole Step A. A solution of 2-amino-4-diethylphosphonomethoxy-5,6,7,8-tetrahydronaphtho[1,2-d]thiazole (1 mmole) in CH$_3$CN (4 mL) was cooled to 0° C., and treated with CuBr$_2$ (1.2 mmole) followed by isoamylnitrite (1.5 mmole) dropwisely. The resulting dark mixture was stirred for 3.5 h. Evaporation and chromatography gave 2-bromo-4-diethylphosphonomethoxy-5,6,7,8-tetrahydrpnaphtho[1,2-d]thiazole as an oil.

Step B. 2-Bromo-4-diethylphosphonomethoxy-5,6,7,8-tetrahydronaphtho[1,2-d]thiazole was subjected to Step D of Example 34 to give 2-bromo-4-phosphonomethoxy-5,6,7,8-tetrahydronaphtho[1,2-d]thiazole (44.1) as a solid. Mp 220–230° C. Anal. Calcd. for $C_{12}H_{13}NO_4PSBr$: C:38.11; H:3.46; N:3.70. Found: C:37.75; H:3.26; N:3.69.

Example 45

Preparation of 4-diethylphosphonomethoxy-5,6,7,8-tetrahydronaphtho-[1,2-d]thiazole Step A. A solution of isoamylnitrite (1.5 mmole) in DMF (1 mL) at 65° C. was treated with 2-amino-4-diethylphosphonomethoxy-5,6,7,8-tetrahydronaphtho[1,2-d]thiazole (1 mmole) in DMF (3 mL). After 30 min, the cooled reaction solution was subjected to evaporation and chromatography to provide 4-diethylphosphonomethoxy-5,6,7,8-tetrahydronaphtho[1,2-d]thiazole as an oil, which was subjected to Step D of Example 34 to give 4-phosphonomethoxy-5,6,7,8-tetrahydronaphtho[1,2-d]thiazole (45.1) as a solid. Mp 215–220° C. Anal. Calcd. for $C_{12}H_{14}NO_4PS+1.3HBr$: C:35.63; H:3.81; N:3.46. Found: C:35.53; H:3.46; N:3.40.

Example 46

Preparation of 2-Amino-4-phosphonomethythio benzothiazole

Step A. 2-Diethylphosphonomethylthioaniline, prepared according to Step B of Example 34, was subjected to Step B of Example 36 to give 2-amino-4-diethylphosphonomethythiobenzothiazole.

Step B. 2-Amino-4-diethylphosphonomethythiobenzothiazole was subjected to Step D of Example 34 to give 2-amino-4-phosphonomethythiobenzothiazole (46.1) as a foam. Anal. Calcd. for $C_8H_{10}N_2O_3PS_2+0.4H_2O$: C:35.63; H:3.81; N:3.46. Found: C:35.53; H:3.46; N:3.40.

Example 47

Preparation of Various Prodrugs of Benzothiazoles

Step A. A suspension of 2-amino-4-phosphonomethoxy-5,6,7,8-tetrahydronaphtho[1,2-d]thiazole (1 mmole) in DMF (10 mL) was treated with DCC (3 mmole) followed by 3-(3,5-dichloro)phenyl-1,3-propanediol (1.1 mmole). The resulting mixture was heated at 80° C. for 8 h. Evaporation followed by column chromatography gave 2-amino-4-{[3-(3,5-dichlorophenyl)propane-1,3-diyl] phosphonomethoxy}-5,6,7,8-tetrahydronaphtho[1,2-d] thiazole (47.1) as solid. mp >230° C. Anal. Calcd. for $C_{21}H_{21}N_2O_4PSCl_2$: C:50.51; H:4.24; N:5.61. Found: C:50.83; H:4.34; N:5.25.

Step B. A solution of 4-phosphonomethoxy-5,6,7,8-tetrahydronaphtho[1,2-d]thiazole dichloridate (generated as in Example 19) (1 mmole) in dichloromethane (5 mL) is cooled to 0° C. and treated with a solution of benzyl alcohol (0.9 mmole) in dichloromethane (0.5 mL) and pyridine (0.3 mL). The resulting reaction solution is stirred at 0° C. for 1 h, and then added a solution of ammonia (excess) in THF. After stirring at room temperature for 16 h, the reaction is evaporated to dryness and the residue is purified by chromatography to give of 4-phosphonomonoamidomethoxy-5,6,7,8-tetrahydronaphtho[1,2-d]thiazole.

Alternatively, a different method is used to prepare other phosphoramides as exemplified in the following procedure:.

Step C. A suspension of 4-phosphonomethoxy-5,6,7,8-tetrahydronaphtho[1,2-d]thiazole dichloridate (generated as in Example 19) (1 mmole) in dichloromethane (5 mL) is cooled to 0° C. and ammonia (excess) is bubbled through the reaction for 10 min. After stirring at room temperature for 16 h the reaction is evaporated to dryness and the residue is purified by chromatography to give 4-(phosphorodiamido) methoxy-5,6,7,8-tetrahydronaphtho[1,2-d]thiazole.

The monophenyl-monophosphonamide derivatives of compounds of formula X can also be prepared according to the above described procedures:

Step D. A solution of 4-diphenylphosphonomethoxy-5,6,7,8-tetrahydronaphtho[1,2-d]thiazole (prepared according to the procedures of Example 19) (1 mmole) in acetonitrile (9 mL) and water (4 mL) is treated with lithium hydroxide (1N, 1.5 mmole) at room temperature for 24 h. The reaction solution is evaporated to dryness, and the residue is dissolved in water (10 mL), cooled to 0° C. and the pH of the solution is adjusted to 4 by addition of 6 N HCl. The resulting white solid is collected through filtration to give 4-phenylphosphonomethoxy-5,6,7,8-tetrahydronaphtho[1,2-d]thiazole.

Step E. A suspension of 4-phenylphosphonomethoxy-5,6,7,8-tetrahydronaphtho[1,2-d]thiazole (11 mmole) in thionyl chloride (3 mL) is heated to reflux for 2 h. The reaction solution is evaporated to dryness, and the residue is dissolved in anhydrous dichloromethane (2 mL) and the resulting solution is added to a solution of L-alanine ethyl ester hydrochloride (1.2 mmole) in pyridine (0.8 mL) and dichloromethane (3 mL) at 0° C. The resulting reaction solution is stirred at room temperature for 14 h. Evaporation and chromatography give 4-[O-phenyl-N-(1-ethoxycarbonyl) ethylphosphonamido]methoxy-5,6,7,8-tetrahydronaphtho [1,2-d]thiazole.

Step F. A solution of 4-phosphnomethoxy-5,6,7,8-tetrahydronaphtho[1,2-d]thiazole (1 mmole) in DMF is treated with N,N'-dicyclohexyl-4-morpholinecarboxamidine (5 mmole) and ethylpropyloxycarbonyloxymethyl iodide (5 mmole) which was prepared from chloromethyl chloroformate according to the reported procedure (Nishimura et al. J Antibiotics, 1987, 40, 81). The reaction mixture is stirred at 25° C. for 24 h. Evaporation and chromatography give 4-bis(ethoxycarbonyloxymethyl)phosphonomethoxy-5,6,7,8-tetrahydronaphtho[1,2-d]thiazole.

4-(Dipivaloyloxymethyl)phosphonomethoxy-5,6,7,8-tetrahydronaphtho[1,2-d]thiazole and 4-bis (isobutyryloxymethyl)phosphonomethoxy-5,6,7,8-tetrahydronaphtho[1,2-d]thiazole are also prepared in a similar manner.

Example 48

General Procedure for bis-phosphoroamide Prodrugs Dichloridate Formation

To a suspension of 1 mmol of phosphonic acid in 5 mL of dichloroethane was added 0.1 mmol of pyridine (or 0.1 mmol of DMF) followed by 6 mmol of thionyl chloride and was heated to reflux for 2.5 h. Solvent and excess thionyl chloride were removed under reduced pressure and dried to give the dichloridate. Coupling reaction:

Method A: The crude dichloridate was taken into 5 mL of dry $CH_2Cl_2$, and was added 8 mmol of amino acid ester at 0° C. The resultant mixture was allowed to come to rt where it was stirred for 16 h. The reaction mixture was subjected to aq. work up and chromatography.

Method B: The crude dichloridate was taken into 5 mL of dry $CH_2Cl_2$, and was added a mixture of 4 mmol of aminoacid ester and 4 mmol of N-methylimidazole at 0° C. The resultant mixture was allowed to come to rt where it was stirred for 16 h. The reaction mixture was subjected to aq. work up and chromatography.

The following compounds were prepared in this manner.

(48.1) 2-Amino-5-isobutyl-4-[2-(5-N,N-bis(L-glutamic acid diethylester) phosphonoamido)furanyl]thiazole. Anal. cald. For $C_{29}H_{45}N_4O10PS$: C: 51.78; H: 6.74; N: 8.33. Found: C: 51.70; H: 6.64; N: 8.15.

(48.2) 2-Amino-5-isobutyl-4-[2-(5-N,N-bis(L-alanine acid dibenzyl ester)phosphonoamido)furanyl]thiazole. Anal. cald. For $C_{31}H_{37}N_4O_6PS$: C: 59.60; H: 5.97; N: 8.97. Found: C: 59.27; H: 5.63; N: 8.74.

(48.3) 2-Amino-5-isobutyl-4-{2-[5-(N,Nbis (benzyloxycarbonylmethyl) phosphonodiamido] furanyl}thiazole. Anal. cald. for $C_{19}H_{25}N_4O_6PS+0.3$ $CH_2Cl_2$: C: 46.93; H: 5.22; N: 11.34. Found: C: 46.92; H: 5.00; N: 11.22.

(48.4) 2-Amino-5-isobutyl-4-{2-[5-(N,N-bis (benzyloxycarbonylmethyl) phosphonodiamido] furanyl}thiazole. Anal. cald. For $C_{29}$ $H_{33}$ $N_4$ $O_6$ P S: C: 58.38; H: 5.57; N:.9.39. Found: C: 58.20; H: 5.26; N: 9.25.

(48.5) 2-Amino-5-isobutyl-4-{2-[5-(N,N'-bis((R)-1-methoxycarbonyl)ethyl) phosphonamido]furanyl}thiazole. Anal. cald. for $C_{19}H_{29}N_4O_6PS+0.6$ $CH_2Cl_2$: C: 44.97; H: 5.82; N: 10.70. Found: C: 44.79; H: 5.46; N: 10.48.

(48.6) 2-Amino-5-isobutyl-4-{2-[5-(N,N'-bis((S)-1-ethoxycarbonyl)ethyl) phosphonamido]furanyl}thiazole. mp. 164–165° C.: Anal. cald. for $C_{21}H_{33}N_4O_6PS+0.61$ $CH_2Cl_2$: C: 46.99; H: 6.24; N: 10.14. Found: C: 47.35; H: 5.85; N: 9.85.

(48.7) 2-Amino-5-isobutyl-4-{2-[5-(N,N'-bis((t-butoxycarbonyl)methyl) phosphonamido]furanyl}thiazole. Anal. cald. for $C_{23}H_{37}N_4O_6PS+0.15$ $CH_2Cl_2$: C: 51.36; H: 6.94; N: 10.35. Found: C: 51.34; H 6.96; N: 10.06.

(48.8) 2-Amino-5-isobutyl-4-{2-[5-(N,N'-bis (ethoxycarbonyl) methyl)phosphonamido)] furanyl}thiazole. Anal. cald. for $C_{19}H_{29}N_4O_6PS+0.1$ EtOAc+0.47 $CH_2Cl_2$: C: 45.79; H: 5.94; N: 10.75. Found: C: 46.00; H: 5.96; N: 10.46.

(48.9) 2-Amino-5-isobutyl-4-{2-[5-(O-(2-bis(N-(1-methyl-ethoxycarbonyl)ethyl)phosphonamido] furanyl}thiazole. mp. 142–145° C.:; Anal. cald. for $C_{23}H_{37}N_4O_6PS$: C: 52.26; 7.06; 10.60. Found: C: 52.21; 6.93; 10.62.

(48.10) 2-Amino-5-isobutyl-4-{2-[5-(N,N'-bis(ethoxycarbonylmethyl)-N,N'-dimethylphosphonamido]furanyl}thiazole. Anal. cald. for $C_{21}H_{33}N_4O_6PS$: C: 50.39; H: 6.65; N: 11.19. Found: C: 50.57; H: 6.56; N: 11.06.

(48.11) 2-Amino-5-isobutyl-4-{2-[5-(N,N'-bis((S)-1-benzyloxycarbonyl-2-methyl)propyl) phosphonamido]furanyl}thiazole. Anal. cald. for $C_{35}H_{45}N_4O_6PS+0.5H_2O$: C: 60.94; H: 6.72; N: 8.12. Found: C: 61.01: H: 6.48; N: 7.82.

(48.12) 2-Amino-5-isobutyl-4-{2-[5-(N,N'-bis((S)-1-methoxycarbonyl-3-methyl)butyl) phosphonamido]furanyl}thiazole. Anal. cald. for $C_{25}H_{41}N_4O_6PS$: C: 53.94; H: 7.42; N: 10.06. Found: C: 54.12; H: 7.62; N: 9.82.

(48.13) 2-Amino-5-isobutyl-4-{2-[5-(N,N'-bis((R)-1-ethoxycarbonyl-2-(S-benzyl))ethyl) phosphonamido]furanyl}thiazole. Anal. cald. for $C_{35}H_{45}N_4O_6PS3+0.4$ toluene: C: 58.07; H: 6.21; N: 7.17. Found: C: 57.87; H: 6.14; N: 6.81.

(48.14) 2-Amino-5-isobutyl-4-{2-[5-(N,N'-bis((S)-1-ethoxycarbonyl-3-(S-methyl))butyl)phosphonamido]furanyl}thiazole. Anal. cald. for $C_{23}H_{37}N_4O_6PS3$: C: 46.61; H: 6.92; N: 9.45. Found: C: 46.26; H: 6.55; N: 9.06.

(48.15) 2-Amino-5-propylthio-4-{2-[5-(N,N'-(1-(S)-ethoxycarbonyl)ethyl)phosphonamido]furanyl}thiazole. Anal. cald. for $C_{20}H_{31}N_4O_6PS_2$: C: 46.32; H: 6.03; N: 10.80. Found: C: 46.52; H: 6.18; H: 10.44.

(48.16) 2-Amino-5-isobutyl-4-{2-[5-(N,N'-bis((S)-1-benzyloxycarbonyl-2-methyl)isobutyl)phosphonamido]furanyl}thiazole. Anal. cald. for $C_{37}H_{49}N_4O_6PS$: C: 62.69; H: 6.97; H: 7.90. Found: C: 62.85; h 7.06, 7.81.

(48.17) 2-Amino-5-isobutyl-4-{2-[5-(N,N'-bis((S)-1-ethoxycarbonyl-3-methyl)butyl) phosphonamido]furanyl}thiazole. Anal. cald. for $C_{27}H_{45}N_4O_6PS$: C: 55.46; H: 7.76; N: 9.58. Found: C: 55.35; H: 7.94; N: 9.41.

(48.18) 2-Amino-5-isobutyl-4-{2-[5-(N,N'-bis((S)-ethoxycarbonyl-2-methyl)propyl) phosphonamido]furanyl}thiazole. Anal. cald. for $C_{25}H_{41}N_4O_6PS$: C: 53.94; H: 7.42; N: 10.06. Found: C: 54.01; H: 7.58; N: 9.94.

(48.19) 2-Amino-5-isobutyl-4-{2-[5-(N,N'-bis((S)-1-ethoxycarbonyl-2-phenyl)ethyl) phosphonamido]furanyl}thiazole. Anal. cald. for $C_{33}H_{41}N_4O_6PS+0.15 CH_2Cl_2$: C: 59.83; H: 6.26; H: 8.42. Found: C: 59.88; H: 6.28; H: 8.32.

(48.20) 2-Amino-5-propylthio-4-{2-[5-(N,N'-(-methyl-1ethoxycarbonyl)ethyl) phosphonamido]furanyl}thiazole. mp. 110–115° C.: Anal. cald. for $C_{22}H_{35}N_4O_6PS_2+0.4HCl+0.5Et2O$: C: 48.18; H: 6.81; N: 9.36. Found: C: 48.38; H: 6.60; H: 8.98.

(48.21) 2-Amimo-5-methylthio-4-{2-[5-(N,N'-bis(1-methyl-1-ethoxycarbonyl)ethyl) phosphonamido]furanyl}thiazole. Anal. cald. for $C_{20}H_{31}N_4O_6PS_2+0.5H_2O$: C: 45.53; H: 6.11; N: 10.62. Found: C: 45.28; H: 5.85; N: 10.56.

Example 49

General Procedure for Mixed bis-phosphoroamidate Prodrugs

To a solution of crude dichloridate (1 mmol, prepared as described in Example 40) in 5 mL of dry $CH_2Cl_2$ was added amine (1 mmol) followed by 4-dimethylaminopyridine (3mmol) at 0° C. The resulting mixture was allowed to warm to room temperature and stirred for 1 h. The reaction was cooled back to 0° C. before adding aminoacid ester (2 mmol) and left at room temperature for 16 h. The reaction mixture was subjected to aq. work up and the mixed bis-phosphoroamidate prodrug was purified by column chromatography.

The following compounds were prepared in this manner.

(49.1) 2-Amino-5-isobutyl-4-{2-[5-(1-morpholino-N'-(1-methyl-1-ethoxycarbonyl)ethyl)phosphonamido]furanyl}thiazole. mp. 182–183° C.: Anal. cald. for $C_{21}H_{33}N_4O_5PS$: C: 52.05; H: 6.86; N: 11.56. Found: C: 51.66; H:6.68; N: 11.31.

(49.2) 2-Amino-5-isobutyl-4-{2-[5-(N-pyrrolidino-N'-(1-methyl-1-ethoxycarbonyl)ethyl)phosphonamido]furanyl}thiazole. ip. 189–190° C.: Anal. cald. for $C_{21}H_{33}N_4O_4PS$: C: 53.83; H: 7.10; N: 11.96. Found: C: 54.15; H: 7.48; N: 12.04.

Biologicals Examples

The following examples may be useful for identifying compounds which 1) inhibit FBPase and gluconeogenesis in cellular and animal models of diabetes; or 2) enhance insulin sensitivity in cell culture or animal models of diabetes; or 3) exhibit superior pharmacological activity as combinations of FBPase inhibitors and insulin sensitizers relative to either agent alone.

The following compounds A–K are used in some of the Biological Examples which follow:

Compound A
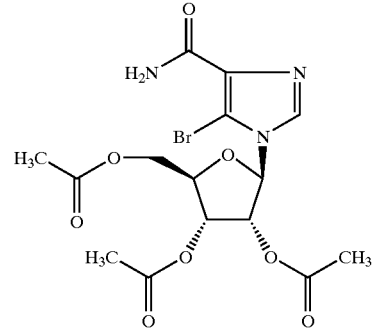

Compound B
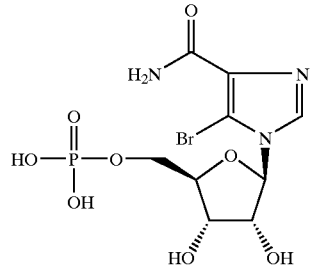

Compound C
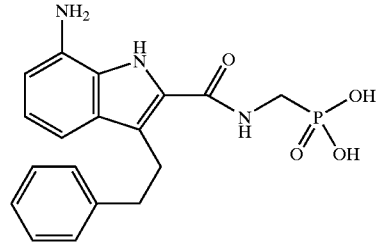

-continued

Compound D

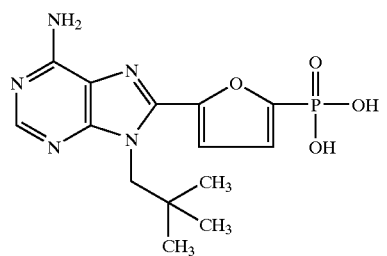

Compound E

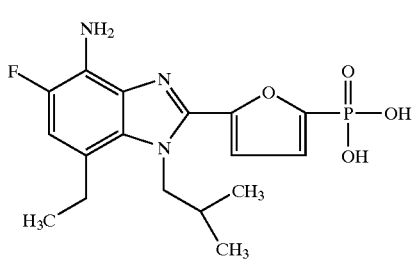

Compound F

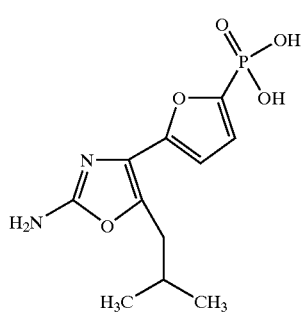

Compound G

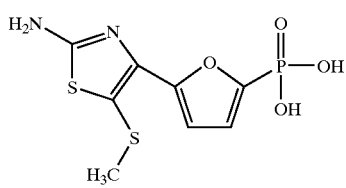

Compound H

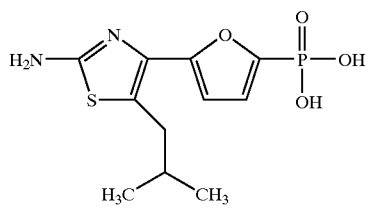

Compound I

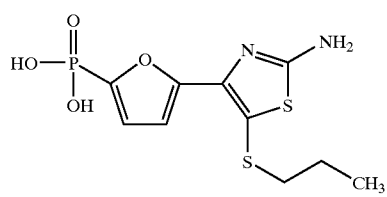

-continued

Compound J

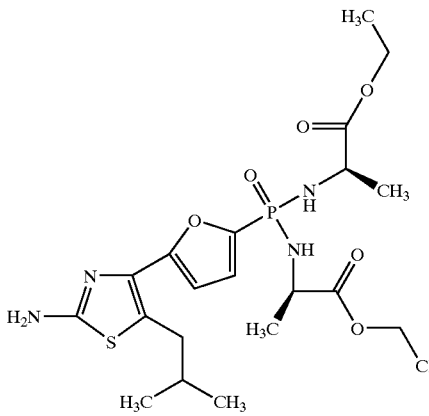

Compound K

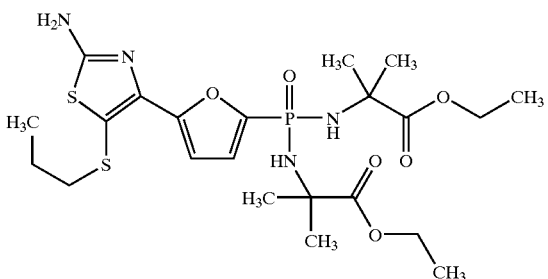

Compound F is prepared in Example 10.6, Compound G is prepared in example 3.26, compound H is prepared in Example 3.68, Compound I is prepared in Example 3.58, Compound J is prepared in Example 48.6, and Compound K is prepared in Example 48.2.

Example A

Inhibition of Human Liver FBPase

E. coli strain BL21 transformed with a human liver FBPase-encoding plasmid was obtained from Dr. M. R. El-Maghrabi at the State University of New York at Stony Brook. hlFBPase was typically purified from 10 liters of E. coli culture as described by M. Gidh-Jain et al. J. Biol Chem. 269, 27732–27738 (1994). Enzymatic activity was measured spectrophotometrically in reactions that coupled the formation of product (fructose 6-phosphate) to the reduction of dimethylthiazoldiphenyltetrazolium bromide (MTT) via NADP and phenazine methosulfate (PMS), using phosphoglucose isomerase and glucose 6-phosphate dehydrogenase as the coupling enzymes. Reaction mixtures (200 μl) were made up in 96-well microtitre plates, and consisted of 50 mM Tris-HCl, pH 7.4–100 mM KCl, 5 mM EGTA, 2 mM MgCl$_2$, 0.2 mM NADP, 1 mg/ml BSA, 1 mM MTT, 0.6 mM PMS, 1 unit/ml phosphoglucose isomerase, 2 units/ml glucose 6-phosphate dehydrogenase, and 0.150 mM substrate (fructose 1,6-bisphosphate). Inhibitor concentrations were varied from 0.01 μM to 10 μM. Reactions were started by the addition of 0.002 units of pure hlFBPase and were monitored for 7 minutes at 590 nm in a Molecular Devices Plate Reader (37° C.).

The potencies of select compounds against human liver FBPase are shown in the table below:

TABLE 1

| Compound | IC50, $\mu$M |
|---|---|
| AMP | 1.3 |
| E | 0.055 |
| D | 1.0 |
| B | 5.0 |
| C | 30 |
| F | 0.12 |
| G | 0.015 |
| H | 0.025 |
| I | 0.018 |
| Troglitazone | >100 |

Example B

Inhibition of Rat Liver and Mouse Liver FBPase

*E. coli* strain BL21 transformed with a rat liver FBPase-encoding plasmid was obtained from Dr. M. R. El-Maghrabi at the State University of New York at Stony Brook, and purified as described (El-Maghrabi, M. R., and Pilkis, S. J. (1991) *Biochem. Biophys. Res. Commun.* 176: 137–144). Mouse liver FBPase was obtained by homogenizing freshly isolated mouse liver in 100 mM Tris-HCl buffer, pH 7.4, containing 1 mM EGTA, and 10% glycerol. The homogenate was clarified by centrifugation, and the 45–75% ammonium sulfate fraction prepared. This fraction was redissolved in the homogenization buffer and desalted on a PD-10 gel filtration column (Biorad) eluted with same. This partially purified fraction was used for enzyme assays. Both rat liver and mouse liver FBPase were assayed as described for human liver FBPase in Example A. Generally, as reflected by higher $IC_{50}$ values, the rat and mouse liver enzymes are less sensitive to inhibition by the compounds tested than the human liver enzyme.

The following Table depicts the $IC_{50}$ values for several compounds prepared in the Examples:

TABLE 2

| Compound | $IC_{50}$ Rat Liver ($\mu$M) | $IC_{50}$ Mouse Liver ($\mu$M) |
|---|---|---|
| AMP | 25 | 15 |
| B | 140 | 33 |
| D | 1.25 | 55 |
| C | >100 | >100 |
| E | 0.4 | 1.1 |
| F | 2.0 | |
| G | 0.25 | |
| H | 0.175 | |
| I | 0.05 | |

Example C

Inhibition of Gluconeogenesis in Rat Hepatocytes

Hepatocytes were prepared from fed Sprague-Dawley rats. (250–300 g) according to the procedure of Berry and Friend (Berry, M. N., Friend, D. S., 1969, J Cell. Biol. 43, 506–520) as-modified by Groen (Groen, A. K., Sips, H. J., Vervoom, R. C., Tager, J. M., 1982, Eur. J. Biochem. 122, 87–93). Hepatocytes (75 mg wet weight/ml) were-incubated in 1 ml Krebs-bicarbonate buffer containing 10 mM Lactate, 1 mM pyruvate, 1 mg/ml BSA, and test compound concentrations from 0 to 500 $\mu$M. Incubations were carried out in a 95% oxygen, 5% carbon dioxide atmosphere in closed, 50-ml Falcon tubes submerged in .a rapidly shaking water bath (37° C.). After 1 hour, an aliquot (0.25 ml) was removed, transferred to an Eppendorf tube and centrifuged. 50 $\mu$l of supernatant was then assayed for glucose content using a Sigma Glucose Oxidase kit as per the manufacturer's instructions.

The following Table depicts the $IC_{50}$ values for several compounds prepared in the Examples:

TABLE 3

| Compound | IC50 ($\mu$M) |
|---|---|
| Compound A | 50 |
| Compound D | 4.5 |
| Compound E | 2.5 |
| Compound C | >100 |
| Compound F | 15 |
| Compound G | 10 |
| Compound H | 2.5 |
| Compound I | 2.0 |
| Compound J | 2.0 |
| Compound K | 2.1 |
| Troglitazone | >100 |

FBPase from rat liver is less sensitive to AMP than that from human liver. $IC_{50}$ values are consequently higher in rat hepatocytes than would be expected in human hepatocytes.

It is particularly advantageous to screen compounds of formula I on hepatocytes such as described in Examples C and D because these compounds are phosphorylated by the hepatocytes and thereby become FBPase inhibitors.

Example D

Inhibition of Glucose Production and Elevation of Fructose-1,6-Bisphosphate Levels in Rat Hepatocytes Treated with FBPase Inhibitors Rat hepatocytes were isolated and incubated as described in Example C. Cell extracts, were analyzed for glucose content as described in Example C, and also for fructose 1,6-bisphosphate. Fructose 1,6-bisphosp hate was assayed spectrophotometrically by coupling its enzymatic conversion to glycerol 3-phosphate to the oxidation of NADH, which was monitored at 340 nm. Reaction mixtures (1 ml) consisted of 200 nM Tris-HCl, pH 7.4, 0.3 mM NADH, 2 units/ml glycerol 3-phosphate dehydrogenase, 2 units/ml triosephosphate isomerase, and 50–100 ml cell extract. After a 30 minute preincubation at 37C, 1 unit/ml of aldolase was added and the change in absorbance measured until a stable value was obtained. 2 moles of NADH are oxidized in this reaction per mole of fructose 1,6-bisphosphate present in the cell extract.

Compound A and Compound E inhibited glucose production in a dose-dependent manner with $IC_{50}$'s of 50 and 2.5 $\mu$M, respectively. Consistent with the inhibition of FBPase, dose-dependent elevation of intracellular fructose 1,6-bisphosphate was observed with both compounds.

Example E

Analysis of Hepatic and Plasma Drug Metabolite Levels, Blood Glucose, and Hepatic Fructose 1,6-bisphosphate Levels After Administration of Compound A p.o. to Normal Fasted Rats Compound A was administered by oral gavage to freely-feeding SpragueDawley rats (250–300g). The compound was prepared as a suspension in carboxymethylcellulose, and administered at a dose of 250 mg/kg. For the determination of liver metabolites, rats were serially sacrificed over the course of 24 hours after drug administration. Livers were freeze-clamped, homogenized in perchloric acid, neutralized, and then analyzed for Compound B by anion exchange HPLC.

For the determination of plasma metabolites, rats were instrumented with carotid catheters prior to oral dosing. Blood samples were withdrawn via the catheters at appropriate time points over the course of 8 hours post drug administration. Plasma was prepared from the blood samples by centrifugation, and plasma protein precipitated by the addition of methanol to 60%. Compound A metabolites were quantitated by reverse phase HPLC in the deproteinated plasma samples. A $C_{18}$ column (1.4 cm×250 mm) was equilibrated with 10 mM sodium phosphate, pH 5.5 and eluted with a gradient from this buffer to acetonitrile. Detection was at 254 nm.

The effect of Compound A on blood glucose and hepatic fructose. 1,6-bisphosphate levels was determined in 18-hour fasted Sprague-Dawley rats (250–300 g). Animals were dosed as described above. At appropriate time points post drug administration, rats were anesthetized with halothane and a liver biopsy (approx. 1 g) was taken, as well as a blood sample (2 ml) from the posterior vena cava. A heparin flushed syringe and needle was used for blood collection. The liver sample was immediately homogenized in ice-cold 10% perchloric acid (3 ml), centrifuged, and the supernatant neutralized with 1/3rd volume of 3' M KOH/3 M $KH_2CO3$. Following centrifugation and filtration,the neutralized extract was analyzed for fructose 1,6-bisphosphate content as decribed for isolated hepatocytes in Example C. Blood glucose was measured by means of a Hemocue analyzer (Hemocue Inc, Mission Viejo, Calif.).

Analysis of liver metabolites revealed that Compound A was efficiently converted to Compound B, with intrahepatic levels of the latter reaching 3 μmoles/g tissue within 1 hour. Although levels declined slowly over time, Compound B was measurable out to the final, 24 hour time point. In plasma 5-bromo-1-βD-ribofuranosyl-imidazole-carboxamide but not Compound A was detectable, suggesting that Compound A was rapidly deacetylated at all three positions.

The single 250 mg/kg dose of Compound A markedly lowered blood glucose for approximately 8 hours, at which time levels in the treated animals rebounded slowly to those of the vehicle-treated controls. Drug treatment resulted in the elevation of hepatic fructose 1,6-bisphosphate levels. The time course of elevation of this gluconeogeneic intermediate correlated well with the time course of glucose lowering. Peak elevation was observed at near maximal glucose lowering, and as blood glucose levels rebounded, fructose 1,6-bisphosphate levels slowly returned to normal. The latter observations are consistent with the inhibition of gluconeogenesis by Compound A at the level of fructose 1,6-bisphosphatase.

Example F

Analysis of Hepatic and Plasma Drug Levels After Administration Compounds D and E Intraperitoneally to Normal Fasted Rats Sprague-Dawley rats (250–300 g) were fasted for 18 hours and then dosed intraperitoneally either with saline or FBPase inhibitor. The vehicle used for drug administration was 10 mM-bicarbonate. One hour post injection, rats were anesthetized with halothane, and liver and blood samples were taken and processed as described in Example E. The neutralized liver extracts were analyzed for FBPase inhibitor content by HPLC. A reverse phase YMC ODS AQ column (250×4.6 cm) was used and eluted with a gradient from 10 mM sodium phosphate pH 5.5 to 75% acetonitrile. Absorbance was monitored at 310 nm. Glucose was measured in the blood sample as described in Example C. Plasma was prepared by centrifugation and extracted by addition of methanol to 60% (v/v). The methanolic extract was clarified by centrifugation and filtration and then analyzed by HPLC as described above.

Results for select compounds prepared in the examples are shown in the table below.

TABLE 4

| Compound | Glucose Lowering, % | Plasma con. (μM) | Liver conc. (nmoles/g) |
|---|---|---|---|
| D | 31 | 8.8 | 27.2 |
| E | 44.4 | 79.2 | 38.4 |
| F | 51 | 18 | 35 |
| G | 73 | 56.1 | |

Example G

Oral Bioavailability Determination

The oral bioavailability of prodrugs and parent compounds was determined by the urinary excretion method in the rat. Prodrugs were dissolved in 10% ethanol/90% polyethylene glycol (mw 400) and administered by oral gavage at doses of 10 to 40 mg/kg parent compound equivalents to 6-hour fasted, Sprague Dawley rats (220–240 g). Parent compounds were typically dissolved in deionized water, neutralized with sodium hydroxide, and then administered orally at 10–40 mg/kg or intravenously at 10 mg/kg. The rats were subsequently placed in metabolic cages and urine was collected for 24 hours. The quantity of parent compound excreted into urine was determined by HPLC analysis as described in Example F. Analysis was performed as described in Example F. For prodrugs, the percentage oral bioavajlability was estimated by comparison of the recovery in urine of the parent compound generated from the prodrug administered orally, to that recovered in urine following intravenous administration of the corresponding parent compound. For parent compounds, the percentage oral bioavailability was estimated by comparison of the recovery in urine of the parent compound when administered orally to that recovered when administered intravenously.

The estimated % oral bioavailability of select prodrugs and parent compounds is shown below.

| Compound | Oral bioavailability, % |
|---|---|
| G | 18 |
| H | 4 |
| I | 5 |
| J | 21 |

Example H

PPAR γ Binding

Human PPAR γ g extracts, obtained from Sf9 insect cells expressing the cloned human gene incorporated into a baculovirus expression vector using procedures described in Mangelsdorf et al. *Cell* 54: 199–207 (1991), are used for saturation binding analysis. Extracts are incubated at 4 C for 3 h in buffer containing 10 mM Tris (pH 8.0), 50 mM KCl, 10 mM dithiothreitol with [$^3$H]-BRL-49653 in the presence or absence of the insulin sensitizer. Bound is separated from free radioactivity by elution through 1-mL Sephadex G-25 desalting columns. Bound radioactivity is eluted in the column void volume and is quantitated by liquid scintillation counting. Insulin sensitizer treatment displaces [3H]-BRL-49653 from the PPAR γ receptor, and results in reduced recovery of radioactivity in the bound fraction. The tighter the affinity of the insulin sensitizer for the receptor, the more radioactivity is displaced.

Example I

Adipocyte Binding

Adipocytes are prepared from adipose tissue obtained from mammary gland by collagenase digestion (2 mg/ml collagenase; 4 ml/g tissue) by the method of Rodbell. Krebs-Henseleit medium is used (NaCl; 123 mM, NaHCO$_3$; 26 mM, KCl; 5 mM, MgSO$_4$; 1.2 mM, KH$_2$PO$_4$; 1.25 mM, glucose 5.6 mM, pH 7.4) gassed with 95% O$_2$/5% CO$_2$. The medium includes 4% BSA and is supplemented with p-aminoclonidine (100 nM) and adenosine (200 nM) to inhibit lipolysis. Binding studies are performed by rinsing the adipocytes in Dulbecco's modified Eagles medium/Hams F-12 nutrient mix medium containing 15 mM HEPES, pH 7.4, supplemented with 200 nM adenosine. After three washes to remove collagenase and BSA, 0.5 ml of cells are added (in triplicate) tubes containing radiolabelled insulin sensitizer. Final concentration of insulin sensitizer in all incubations is 30 pM. Tubes are incubated at 37 C for 1 h in a shaking bath and cell-associated radioactivity is assessed by separation of cells from medium by centrifugation (200 µl of incubation medium, in duplicate) through silicone oil (Dow Corning 200/200 cs) for 20 s at 10000 g in a Beckman microfuge. Cell pellets are counted for $^{125}$I content after cutting the microfuge tube. Non-specific binding is estimated in the presence of 3 µM RBL 49653. Affinity of the insulin sensitizer for adipocyte receptor is indicated by an increase in specific $^{125}$I content in the cell pellets.

Example J

Triglyceride Formation by Differentiated Adipocytes

The pre-adipocyte cell line, 3T3-L1 fibroblasts, are obtained from ATCC. The cells are grown to confluence and differentiated with insulin, dexamethasone and IBMX. Adipocyte differentiation is observed by oil red O staining which stains the lipid droplets within the cytoplasm red. The extent of adipocyte differentiation is then monitored by microscope observation. Mature, lipid-filled adipocytes are used 8–10 days post-differentiation. Treatment of cells with insulin, a thiazolidinedione, or RXR ligands induces triglyceride accumulation.

Example K

Glucose Uptake

The pre-adippcyte cell line, 3T3-L1 fibroblasts are grown to confluence and differentiated with insulin, dexamethasone and IBMX. Mature, lipid-filled adipocytes are used 8–10 days post-differentiation. Glucose transport is assessed after treatment of differentiated cells with insulin sensitizers for 48 h. Compounds are added freshly each day. 2-deoxyglucose transport is determined by addition of 1 µC of 25 µM 2-deoxy-D-[2,6-$^3$H] glucose. After 10 minutes, cells are freed of tracer by extensive washing with ice-cold PBS and cell-associated radioactivity determined by liquid scintillation counting of alkali-solubilized extracts. Glucose uptake rates are normalized for protein content. Insulin sensitizer treatment increases the rate of glucose transport into the cells as indicated by higher levels of cell-associated radioactivity.

Example L

Activation of PPARγ/RXR Heterodimers

CV-1 cells are co-transfected with plasmids containing the genes encoding PPARγ, RXR, and a luciferase-based reporter plasmid containing one or more PPRE's. Cells are treated with a range of doses of ligand. A concentration-dependent increase in luciferase induction is observed with ligands of RXR or of PPARγ.

Example M

Insulin Sensitivity Measured by Euglycemic-hyperinsulinemic Clamp Technique

ZDF Diabetic rats are treated with vehicle or an insulin sensitizer for 7 or more days, and then instrumented with jugular and carotid catheters. After a recovery period, animals are fasted overnight, and a constant infusion of insulin is initiated. Blood glucose levels are maintained at baseline with a variable rate glucose infusion. Samples for plasma glucose are drawn every 10 minutes for the duration of the 4-hour protocol. Steady state glucose infusion rates are higher in the insulin-sensitizer treated group, indicating improved glucose disposal/insulin sensitivity.

Example N

Combination Treatment With Troglitazone and an FBPase Inhibitor (Compound G), and With Troglitazone and a Prodrug of an FBPase Inhibitor (Compound J) in the ZDF rat -Effects on Blood Glucose The Zucker Diabetic Fatty (ZDF) rat is widely used as a model for human type 2 diabetes as the progression of the disease in these rodents is similar to that described for human patients (Clark and Palmer 1982, Terrettaz and Jeanrenaud 1983). The mature ZDF rat not only displays obesity, hyperglycemia, insulin resistance and accelerated. hepatic glucose production, but also develops some of the common macro-and micro-vascular complications associated with type 2 diabetes.

Clark J B, Palmer C J (1982) Diabetes 30: 126A Terrettaz J, Jeanrenaud B (1983) Endocrinology 112: 1346–1351.

The purpose of this study was to determine whether combination treatment with Troglitazone-Compound G or Troglitazone-Compound J results in improved glycemic control in the ZDF rat relative to either agent administered alone, and thus establish whether combination therapy will be of clinical benefit.

(a) Troglitazone-Compound G Protocol: Male ZDF rats were purchased at 8 weeks of age from Genetics Models Inc. (Indianapolis, Indiana). The rats were maintained under standard vivarium conditions (25° C., 12-hour light, 12-hour dark cycle) and received powdered Purina 5008 chow and water ad libitum. At 11 weeks of age, animals with blood glucose >500 mg/dl were selected and divided into 4 treatment groups (n=8/group). The treatments were control, Troglitazone; Compound G, and the combination of Troglitazone and Compound G. Drugs were administered as 0.2% food admixtures for 15 days. The dose of Troglitazone selected (0.2%) is a maximal dose, which in pilot studies was found to normalize blood glucose levels in 10-week old ZDF rats. It is higher than the dose reported to prevent the onset of hyperglycemia in prediabetic ZDF rats (Sreenan et al 1996). In animals with established diabetes such as those selected for this study, the effects of Troglitazone better approximate those in man, where modest glucose lowering effects are generally observed (Inzucchi et al 1998). The dose of Compound G selected (0.2%) is also a maximal dose; a pilot study in the ZDF rat revealed that higher doses were of no additional benefit (blood glucose lowering at 0.5% was equivalent to that at 0.2%). Blood glucose levels were measured in tail vein samples by means of a HemoCue glucose analyzer (HemoCue Inc., Mission Viejo, Calif.). Values are expressed as the mean plus or minus the standard error of the mean. Differences between groups were evaluated by analysis of variance with the Tukey-Kramer post hoc test. Results are considered significant with $p<0.05$.

(b) Troglitazone-Compound J Protocol: This study was carried out exactly as described in the Troglitazone-Compound G section above with two modifications: the treatment period was 21 days and the dose of Compound J used was 0.4%. In a pilot study, Compound J showed a trend (not significant) towards more pronounced blood glucose lowering at 0.4% than at 0.2%. The 0.4% dose was therefore chosen to ensure a maximal drug response.

Combination treatment with Troglitazone and Compound G resulted in significantly greater reductions in blood glucose levels than treatment with either agent alone (see table below). At the end of the treatment period, blood glucose levels in the combination group (~200 mg/dl) approximated those of normal fed rats (~150 mg/dl).

|             | Blood Glucose, mg/dl | |
| --- | --- | --- |
| Treatment | Day 0 | Day 14 |
| Control | 655 ± 39 | 762 ± 31* |
| Compound G | 653 ± 55 | 530 ± 48 |
| Troglitazone | 655 ± 33 | 431 ± 73 |
| Combination | 661 ± 39 | 222 ± 39** |

*p < 0.05 versus all groups
**p < 0.05 versus all groups

Similar results were observed in the Troglitazone-Compound J study:

|             | Blood Glucose, mg/dl | |
| --- | --- | --- |
| Treatment | Day 0 | Day 21 |
| Control | 678 ± 19 | 815 ± 34* |
| Compound J | 674 ± 20 | 452 ± 40 |
| Troglitazone | 669 ± 23 | 514 ± 135 |
| Combination | 675 ± 31 | 232 ± 39** |

*p < 0.05 versus all groups
**p < 0.05 versus all groups

The data suggest that the combination of an insulin sensitizer (Troglitazone) ;and an FBPase inhibitor (Compound G) or a prodrug of an FBPa'se inhibitor (Compound J) may provide better glycemic control than either agent alone in the treatment of type 2 diabetes.

Example O

Combination Treatment With Troglitazone and an FBPase Inhibitor (Compound G), and With Troglitazone and a Prodrug of an FBPase Inhibitor (Compound J) in the ZDF rat—Effects on Plasma Triglycerides Troglitazone treatment is known to reduce circulating triglycerides both in animal models of diabetes and in man. Triglyceride lowering is generally regarded as beneficial in Type 2 diabetics as these patients often suffer from hypertriglycen demia and are at risk of the associated cardiovascular complications. The purpose of this study was to determine the effects of combination treatment on plasma triglycerides.

On the final day of treatment in the study described in Example N, blood samples were taken from the posterior vena cava of each rat while under halothne anesthesia. Plasma was prepared by centrifugation and triglyceride levels then measured by means of a standard assay kit according to the instructions of the manufacturer (Sigma Chemical Company). Differences between groups were evaluated by analysis of variance with the Trukey-Kramer post hoc test. Results are considered significant with $p<0.05$.

As illustrated in the tables below, troglitazone treatment had the expected effect of significantly reducing plasmia triglyceride levels. In contrast, treatment with Compound G or Compound J resulted in an approximate 2-fold elevation of plasma triglycerides. Surprisingly, combination treatment resulted in the same degree of triglyceride lowering as treatment with Troglitazone alone (a) Troglitazone-Compound G

| Treatment | Plasma Triglycerides, mg/dl (Mean ± SEM) |
| --- | --- |
| Control | 352 ± 26 |
| Compound G | 795 ± 88** |
| Troglitazone | 131 ± 16* |
| Combination | 102 ± 14* |

*p < 0.05 vs Control
**p < 0.05 vs all groups (b) Troglitazone-Compound J

| Treatment | Plasma Triglycerides, mg/dl (Mean ± SEM) |
| --- | --- |
| Control | 421 ± 58 |
| Compound J | 759 ± 76** |
| Troglitazone | 249 ± 60* |
| Combination | 188 ± 45* |

*p < 0.05 vs Control
**p < 0.05 vs all groups

This study indicates that the beneficial triglycride lowering effects of Troglitazone are maintained in combination with Compound G or Compound J. Remarkably, the increase in triglycerides elicited by FBPase inhibitor monotherapy was suppressed in combination with the insulin sensitizer.

Example P

Combination Treatment With Troglitazone and an FBPase Inhibitor (Compound G), and With Troglitazone and a Prodrug of an FBPase Inhibitor (Compound J) in the ZDF rat—Effects on Plasma Insulin Severe type 2 diabetes in man is often associated with the deterioration of pancreatic beta-cell function and eventually the inability of the pancreas to secrete the amount of insulin appropriate for the degree of hyperglycemia. This progression is also evident in the ZDF rat. Animals initially go through a hyperinsulinemic phase to compensate for elevated blood glucose levels but eventually overstimulation of the pancreas results in diminished insulin secretion and hypoinsulinemia can ensue (Pickavance L et al 1998). The purpose of this study was to determine whether the improved glycemic control afforded by combination treatment with an insulin sensitizer and an FBPase inhibitor can attenuate the deterioration of pancreatic beta-cell function.

On the final day of treatment in the study described in Example N, blood samples were taken from the posterior vena cava of each rat while under halothane anesthesia. Plasma was prepared by centrifugation and insulin levels then measured by means of an enzyme-linked immunoassay kit according to the instructions of the manufacturer (Amersham Life Sciences). Differences between groups were evaluated by analysis of variance with the Tukey-Kramer post hoc test. Results are considered significant with $p<0.05$.

There was no significant difference in plasma insulin levels between control rats and those on either Troglitazone or Compound G monotherapy (see tables below). Combination treatment, however, resulted in a significant increase in plasma insulin levels relative to all other groups, and in fact restored them to levels similar to those observed in non diabetes prone, lean ZDF rats (Pickavance et al 1998).

| Treatment | Plasma Insulin, ng/ml (Mean ± SEM) |
| --- | --- |
| Control | 1.88 ± 0.3 |
| Compound G | 1.94 ± 0.21 |
| Troglitazone | 3.61 ± 1.03 |
| Combination | 8.23 ± 2.67* |

*$p < 0.05$ vs all groups

The data show that combination treatment synergistically improves pancreatic endocrine function; insulin levels were increased significantly over those in controls only in the combination therapy group. This increase in plasma insulin could potentially be due to a reversal of lipotoxicity (Unger, 1997) and glucotoxicity (Leahy, 1990) in pancreatic islet cells. Attenuation of lipotoxicity may result from the triglyceride lowering effects of Troglitazone (Example O), while the attenuation of glucotoxicity may result from the combined glucose lowering effects of Trolitazone and Compound G (Example N).

Example Q

Combination Treatment With Troglitazone and an FBPase Inhibitor (Compound G), and With Troglitazone and a Prodrug of an FBPase Inhibitor (Compound J) in the ZDF rat—Effects on Blood Lactate The aim of this study was to determine the effects of combination treatment on blood lactate levels.

Blood samples were taken from the tail vein on days 0, 3, 7, 10 and 14 of the Troglitazone-Compound G combination study and on days 0,7,14, and 21 of the Troglitazone-Compound J combination study (study protocols are described in Example N). Following their acidification with perchloric acid and clarification by centrifugation, lactate was measured by means of a standard kit according to the instructions of the manufacturer (Sigma Chemical Company).

Baseline blood lactate levels for the Compound G and Compound J monotherapy groups were 1.98±0.17 mM and 2.24±0.08 mM, respectively. The maximal blood lactate elevations over baseline observed during the course of the studies were 2.5-fold for Compound G monotherapy and 3-fold for Compound J monotherapy. Blood lactate was typically elevated 2-fold over baseline in these groups. Blood lactate was not elevated above baseline (2 mM) in the control or combination groups on any of the measurement days.

Combination treatment with Troglitazone suppressed the blood lactate elevations observed in the FBPase inhibitor or FBPase inhibitor prodrug monotherapy groups. Combination treatment may thus have the unexpected benefit of improving the safety profile of FBPase inhibitors and their prodrugs.

Example R

Combination Treatment With Rosiglitazone and an FR Pase Inhibitor (Compound G), in the ZDF rat—Effects on Blood Glucose This study addressed whether combination treatment with Rosiglitazone and Compound G results in improved glycemic control in the Zucker Diabetic Fatty (ZDF) rat relative to either agent administered alone.

The protocol for this study was identical to the one described for the Troglitazone-Compound G combination in Example N with the following changes: (a) rats with blood glucose levels >600 mg/dl were includedtin the study, (b) the dose of Rosiglitazone used was 0.0045% based on a literature report that this dose prevented the onset of diabetes in the ZDF rat (Smith et al 1997), and (c) the length of the study was 25 days.

Blood glucose levels were significantly reduced in all treatment groups relative to the control group. Blood glucose lowering in the combination group tended to be more pronounced but was not significantly different than that in the Rosiglitazone or Compound G monotherapy groups. As illustrated in the table below, the response to Rosiglitazone was highly variable and was likely a factor in the less than expected efficacy of combination treatment. However, there was a clear benefit of adding Compound G treatment on top of Rosiglitazone treatment; whereas only 6 out of 10 rats responded to therapy in the Rosiglitazone monotherapy group, 10 out of 10 rats responded in the combination group.

| Treatment | Change in Blood glucose, mg/dl (day 25 vs day 0) | Responders[a] |
| --- | --- | --- |
| Control | +113 ± 52 | 2/9 |
| Compound G | −120 ± 34* | 8/9 |

-continued

| Treatment | Change in Blood glucose, mg/dl (day 25 vs day 0) | Responders[a] |
|---|---|---|
| Rosiglitazone | −107 ± 78* | 6/10 |
| Combination | −207 ± 44* | 10/10 |

[a]Rats whose blood glucose levels were lower on day 25 than on day 0
*p < 0.05 compared to control The variable response to Rosiglitazone observed in the ZDF rat in this study has also been encountered in the clinic where reductions in fasting plasma glucose observed have ranged from less than 45 mg/dl (60% of patients) to greater than 140 mg/dl (25% of patienits) (Patel et al 1999). Based on the trend towards improved glycemic control as well as the higher response rate of rats in the combination versus other treatment groups, this study suggests that co-treatment with an FBPase inhibitor could benefit patients on Rosiglitazone monotherapy.

Example S

Combination Treatment With Troglitazone and an FBPase Inhibitor (Compound G), in the db/db Mouse—Effects on Blood Glucose The db/db mouse, like the ZDF rat, is a standard model of type 2 diabetes which displays many of the characteristics of human diabetes, including obesity, increased hepatic glucose output, insulin resistance, and hyperglycemia (Coleman and Hummel 1967). The purpose of this study was to determine whether combination treatment with an insulin sensitizer (Troglitazone) and an FBPase inhibitor (Compound G) could provide better antihyperglycemic activity than treatment with either agent alone.

Male db/db mice were purchased at 8 weeks of age from Jackson Labs (Bar Harbor, Maine). The mice were maintained under standard vivarium conditions (25° C., 12-hour light, 12-hour dark cycle) and received powdered Purina 5008 chow and water ad libitum. At 10 weeks of age, animals with blood glucose >400 mg/dl and <900 mg/dl were selected and divided into 4 treatment groups (n=5–6/group). The treatments were control, Troglitazone, Compound G, and the combination of Troglitazone and Compound G. Troglitazone was administered as an 0.1% food admixture and Compound G as an 0.4% food admixture. Treatment was for 18 days. The dose of Troglitazone selected (0.1%) is reported to exert the maximal glucose lowering possible in this model (Fujiwara et al., 1995). The dose of Compound G selected (0.4%) is also a maximal dose; a 6-day pilot study revealed that a higher dose (0.6%) was of no additional benefit. Blood glucose levels were measured in tail vein samples by means of a HemoCue glucose analyzer (HemoCue Inc., Mission Viejo, Calif.). Values are expressed as the mean plus or minus the standard error of the mean. Differences between groups were evaluated by analysis of variance with the Tukey-Krarmer post hoc test. Results are considered significant with p<0.05.

As shown in the table below, on the last treatment day (day 18), blood glucose levels in the combination group were significantly lower than those in the control, as well as the Troglitazone and Compound G monotherapy groups.

| Treatment | Blood Glucose, mg/dl | |
|---|---|---|
| | Day 0 | Day 18 |
| Control | 707 ± 65 | 870 ± 32* |
| Compound G | 708 ± 55 | 646 ± 37 |
| Troglitazone | 710 ± 44 | 509 ± 70 |
| Combination | 709 ± 42 | 263 ± 49** |

*p < 0.05 versus all groups
**p < 0.05 versus all groups

Combination treatment with Troglitazone and Compound G profoundly reduced hyperglycemia in the db/db mouse and was significantly more efficacious than treatment with either agent alone. The data suggest that combination treatment with an insulin sensitizer and an FBPase inhibitor may be of clinical benefit in the treatment of type 2 diabetes.

Example T

Combination Treatment With Troglitazone and an FBPase Inhibitor (Compound A), in the db/db Mouse—Effects on Blood Glucose Treatment of mature db/db mice with maximal doses of Troglitazone results in a partial reduction of the hyperglycemia characteristic of this animal model of type 2 diabetes (Fujiwara et al, 1995). The aim of this study was to determine whether treatment with the FBPase inhibitor Compound A could further improve the glycemic control of db/db mice treated with a maximal dose of Troglitazone.

Male $C_{57}BL/KsJ$-db/db mice were obtained from Jackson Laboratories (Bar Harbor, Maine) at 9 weeks of age. The mice were maintained under standard vivarium conditions (25° C., 12-hour light, 12-hour dark cycle) and received Harlan-Teklad mouse chow and water ad libitum. At approximately 11 weeks of age, mice with levels between 340 and'450 mg/dl were selected and divided into three statistically equivalent groups (n=6/group). Group 1 (controls) received powdered Purina 5008 chow alone. Troglitazone was given as a powdered Purina 5008 admixture (01%) for 7 days to Groups 2and 3. This dose is reported to elicit the maximal hypoglycemic effect of Troglitazone in this model (Fujiwara et al 1995). Compound A was administered orally in polyethlene glycol (PEG 400) to Group 3 at a dose of 250 mg/kg on the 4th and 7th day of the study Blood glucose levels were measured in tail vein samples by means of a HemoCue glucose. analyzer (HemoCue Inc., Mission Viejo, Calif.). Values are expressed as the mean plus or minus the standard error of the mean. Differences between groups were evaluated by analysis of variance with the Tukey-Kramer post hoc test. Results are considered significant with p<0.05.

On the fourth day of the study, the Troglitazone-treated groups (2 and 3), as expected, showed significantly lower fed blood glucose values than the untreated-controls (Group 1):

| Group | Treatment | Blood glucose, mg/dl (8 am day 4) |
|---|---|---|
| 1 | Control | 336.5 ± 13.4 |
| 2 | Troglitazone | 240 ± 21.3* |
| 3 | Troglitazone | 237.5 ± 18.5* |

*p < 0.05 vs Group 1

Following the above measurements, Group 3 was treated with a single oral dose of Compound A and Groups 1 and 2 with an equivalent volume of vehicle. Nine hours post administration, blood glucose levels were found to have increased in the control group (Group 1), to have stayed essentially the same in Group 2, but to have significantly decreased by 30% in the Compound A-treated group (Group 3):

| Group | Treatment | Blood glucose, mg/dl (5 pm day 4) |
|---|---|---|
| 1 | Control | 376.5 ± 8.4 |
| 2 | Troglitazone | 232.5 ± 17* |
| 3 | Troglitazone/Compound A | 167 ± 10.3** |

*p < 0.05 vs Group 1
*p < 0.05 vs Groups 1 and 2

On the 7th day of the study, a second dose of Compound A (Group 3) or vehicle (Groups 1 and 2) was administered. Food was withheld for 6 hours post drug/vehicle administration. As shown in the table below, the mice in Group 3 (combination therapy) achieved blood glucose levels which were on average 44% lower than those of Group 2 (Troglitazone monotherapy) during the treatment period.

| | | Blood glucose, mg/dl | |
|---|---|---|---|
| Group | Treatment | 8 am, day 7 | 2 pm, day 7 |
| 1 | control) | 392   13.3 | 279.5 ± 19 |
| 2 | Troglitazone | 237   25.5 | 195 ± 12.1* |
| 3 | Troglitazone/Compound A | 243   20.4 | 109.5 ± 10.7** |

*p < 0.05 vs Group 1
**p < 0.05 vs Groups 1 and 2

Combination treatment of Troglitazone and Compound A resulted in significantly lower blood glucose levels both in the fed and fasted state than when Troglitazone was administered alone. This study suggests that the addition of an FBPase inhibitor to the treatment regimen of patients on insulin sensitizer therapy could provide significantly improved glycemic control.

References

Coleman D L, Humel K P (1967) Diabetologia 3: 238–248

Fujiwara T et al (1995) Metabolism 44:.486–490

Inzucchi S E, Maggs D G, Spollett G R et al (1998) N. Engl. J. Med. 338: 867–872

Leahy J L (1990) Diabetes Care 13: 992–1010

Patel J, Anderson R J, Rappaport E B (1999) Diabetes, Obesity & Metabolism 1: 165–172

Pickavance L, Widdowson P S, King P, Ishii S, Tanaka H, Williams G.(1998) Br. J. Pharmacol. 125: 767–770

Smith S, Lister C, Hughes M, Buckingham R (i997) Diabetes 46, supplement 1, abstract 577

Sreenan S, Sturis J, Pugh W et al (1996) Am. J. Physiol. 271: E742–747

Unger RH (1997) Trends Endocrinol. Metab. 8: 276–281

We Claim:

1. A pharmaceutical composition comprising a pharmaceutically effective amount of an insulin sensitizer agent and a pharmaceutically effective amount of an FBPase inhibitor, or prodrugs or salts thereof.

2. The pharmaceutical composition of claim 1 wherein said insulin sensitizer is a thiazolidinedione.

3. The pharmaceutical composition of claim 2 wherein said thiazolidinedione is selected from the group consisting of BRL 49653, troglitazone, pioglitazone, ciglitazone, WAY-120,744, englitazone, AD 5075, GI-262570, SB219994, SB219993, and darglitazone.

4. The pharmaceutical composition of claim 1 wherein said FBPase inhibitor is a compound selected from the group consisting of formulae I and IA:

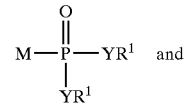

(I)

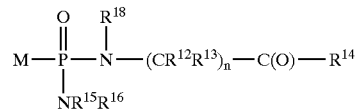

(IA)

wherein in vivo or in vitro compounds of formulae I and IA are converted to $M\text{-}PO_3^{2-}$ which inhibits FBPase and wherein Y is independently selected from the group consisting of —O—, and —NR$^6$;

when Y is —O—, then R$^1$ attached to —O— is independently selected from the group consisting of —H, alkyl, optionally substituted aryl, optionally substituted alicyclic where the cyclic moiety contains a carbonate or thiocarbonate, optionally substituted -alkylaryl, —C(R$^2$)$_2$OC(O)NR$^2$$_2$, —NR$^2$—C(O)—R$^3$, —C(R$^2$)$_2$—OC(O)R$^3$, —C(R$^2$)$_2$O—C(O)OR$^3$, —C(R$^2$)$_2$OC(O)SR$^3$, -alkyl-S-C(O)R$^3$, -alkyl-S—S-alkylhydroxy, and -alkyl-S—S—S-alkylhydroxy, when Y is —NR$^6$—, then R$^1$ attached to —NR$^6$— is independently selected from the group consisting of —H, —[C(R$^2$)$_2$]$_q$—COOR$^3$, —C(R$^4$)$_2$COOR$^3$, —[C(R$^2$)2]$_q$—C(O)SR, and -cycloalkylene-COOR$^3$;

or when either Y is independently selected from —O— and —NR$^6$-, then together R$^1$ and R$^1$ are -alkyl-S—S-alkyl-to form a cyclic group, or together R$^1$ and R$^1$ are

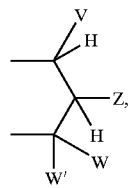

wherein

V, W, and W' are independently selected from the group consisting of —H, alkyl, aralkyl, alicyclic, aryl, substituted aryl, heteroaryl, substituted heteroaryl, 1-alkenyl, and 1-alkynyl; or together V and Z are connected via an additional 3–5 atoms to form a cyclic group containing 5–7 atoms, optionally 1 heteroatom, substituted with hydroxy, acyloxy, alkoxycarbonyloxy, or aryloxycarbonyloxy attached to a carbon atom that is three atoms from both Y groups attached to the phosphorus; or together V and Z are connected via an additional 3–5 atoms to form a cyclic group, optionally containing 1 heteroatom, that is fused to an aryl group at the beta and gamma position to the Y attached to the phosphorus;

together V and W are connected via an additional 3 carbon atoms to form an optionally substituted cyclic group containing 6 carbon atoms and substituted with one substituent selected from the group consisting of hydroxy, acyloxy, alkoxycarbonyloxy, alkylthiocarbonyloxy, and aryloxycarbonyloxy, attached to one of said carbon atoms that is three atoms from a Y attached to the phosphorus;

together Z and W are connected via an additional 3–5 atoms to form a cyclic group, optionally containing one heteroatom, and V must be aryl, substituted aryl, heteroaryl, or substituted heteroaryl;

together W and W' are connected via an additional 2–5 atoms to form a cyclic group, optionally containing 0–2 heteroatoms, and V must be aryl, substituted aryl, heteroaryl, or substituted heteroaryl;

Z is selected from the group consisting of —CHR$^2$OH, —CHR$^2$OC(O)R$^3$, —CHR$^2$OC(S)R$^3$, —CHR$^2$OC(S)OR$^3$, —CHR$^2$OC(O)SR$^3$, —CHR$^2$OCO$_2$R$^3$, —OR$^2$, —SR$^2$, —CHR$^2$N$_3$, —CH$_2$aryl, —CH(aryl)OH, —CH(CH=C$^2{}_2$)OH, —CH(C≡CR$^2$)OH, —R$^2$, —NR$^2{}_2$, —OCOR$^3$, —OCO$_2$R$^3$, —SCOR$^3$, —SCO$_2$R$^3$, —NHCOR$^2$, —NHCO$_2$R$^3$, —CH$_2$NHaryl, —(CH$_2$)$_p$—OR$^2$, and —(CH$_2$)$_p$—SR$^2$;

p is an integer 2 or 3;

q is an integer 1 or 2;

with the provisos that:

a) V, Z, W, W' are not all —H; and b) when Z is —R$^2$, then at least one of V, W, and W' is not —H, alkyl, aralkyl, or alicyclic;

R$^2$ is selected from the group consisting of R$^3$ and —H;

R$^3$ is selected from the group consisting of alkyl, aryl, alicyclic, and aralkyl;

each R$^4$ is independently selected from the group consisting of —H, and alkyl, or together R$^4$ and R$^4$ form a cyclic alkyl group;

R$^6$ is selected from the group consisting of —H, lower alkyl, acyloxyalkyl, alkoxycarbonyloxyalkyl, and lower acyl;

n is an integer from 1 to 3;

R$^{18}$ is independently selected from the group consisting of H, lower alkyl, aryl, aralkyl, or together with R$^{12}$ is connected via 1–4 carbon atoms to form a cyclic group;

each R$^{12}$ and R$^{13}$ is independently selected from the group consisting of H, lower alkyl, lower aryl, lower aralkyl, all optionally substituted, or R$^{12}$ and R$^{13}$ together are connected via 2–6 carbon atoms to form a cyclic group;

each R$^{14}$ is independently selected from the group consisting of —OR$^{17}$, —N(R$^{17}$)$_2$, —NHR$^7$, and —SR$^{17}$;

R$^{15}$ is selected from the group consisting of —H, lower alkyl, lower aryl, lower arakyl, or together with R$^{16}$ is connected via 2–6 atoms, optionally including 1 heteroatom selected from the group consisting of O, N, and S;

R$^{16}$ is selected from the group consisting of —(CR$^{12}$R$^{13}$)$_n$—C(O)—R$^4$, lower alkyl, lower aryl, lower aralkyl, or together with R$^{15}$ is connected via 2–6 atoms, optionally including 1 heteroatom selected from the group consisting of O, N, and S;

each R$^{17}$ is independently selected from the group consisting of lower alkyl, lower aryl, and lower aralkyl, or together R$^{17}$ and R$^{17}$ on N is connected via 2–6 atoms, optionally including 1 heteroatom selected from the group consisting of O, N, and S;

with the proviso that when only one Y is —O—, and it is not part of a cyclic group containing the other Y, then the other Y must be —N(R$^{18}$)—(CR$^{12}$R$^{13}$)—C(O)—R$^{14}$.

and pharmaceutically acceptable prodrugs and salts thereof.

5. The pharmaceutical composition of claim 4 wherein M is R$^5$—X—:

wherein R$^5$ is selected from the group consisting of:

and wherein:

each G is independently selected from the group consisting of C, N, O, S and Se, and wherein only one G may be O, S, or Se, and at most one G is N;

each G' is independently selected from the group consisting of C and N and wherein no more than two G' groups are N;

A is selected from the group consisting of —H, —NR$^4{}_2$, —CONR$^4{}_2$, —CO$_2$R$^3$, halo, —S(O)R$^3$, —SO$_2$R$^3$, alkyl, alkenyl, alkynyl, perhaloalkyl, haloalkyl, aryl, —CH$_2$OH, —CH$_2$NR$^4{}_2$, —CH$_2$CN, —CN, —C(S)NH$_2$, —OR$^3$, —SR$^3$, —N$_3$, —NHC(S)NR$^4{}_2$, —NHAc, and null;

each B and D are independently selected from the group consisting of —H, alkyl, alkenyl, alkynyl, aryl, alicyclic, aralkyl, alkoxyalkyl, —C(O)R$^{11}$, —C(O)SR$^3$, —SO$_2$R$^{11}$, —S(O)R$^3$, —CN, —NR$^9{}_2$, —OR$^3$, —SR$^3$, perhaloalkyl, halo, —NO$_2$, and null, all except —H, —CN, perhaloalkyl, —NO$_2$, and halo are optionally substituted;

E is selected from the group consisting of —H, alkyl, alkenyl, alkynyl, aryl, alicyclic, alkoxyalkyl, —C(O)OR$^3$, —CONR$^4{}_2$, —CN, —NR$^9{}_2$, —NO$_2$, —OR$^3$, —SR$^3$, perhaloalkyl, halo, and null, all except —H, —CN, perhaloalkyl, and halo are optionally substituted;

J is selected from the group consisting of —H and null;

X is an optionally substituted linking group that links R$^5$ to the phosphorus atom via 2–4 atoms, including 0–1 heteroatoms selected from N, O, and S, except that if X is urea or carbamate there is 2 heteroatoms, measured by the shortest path between R5 and the phosphorus atom, and wherein the atom attached to the phosphorus is a carbon atom, and wherein X is selected from the group consisting of -alkyl(hydroxy)-, -alkynyl-, -heteroaryl-, -carbonylalkyl-, -1,1-dihaloalkyl-, -alkoxyalkyl-, -alkyloxy-, -alkylthioalkyl-, -alkylthio-, -alkylaminocarbonyl-, -alkylcarbonylamino-, -alkoxycarbonyl-, -carbonyloxyalkyl-, -alkoxycarbonylarnino-, and -alkylaminocarbonylamino-, all optionally substituted; with the proviso that X is not substituted with —COOR$^2$, —SO$_3$H, or —PO$_3$R$^2{}_2$;

R$^2$ is selected from the group consisting of R$^3$ and —H;

R$^3$ is selected from the group consisting of alkyl, aryl, alicyclic, and aralkyl;

each R$^4$ is independently selected from the group consisting of —H, and alkyl, or together R$^4$ and R$^4$ form a cyclic alkyl group;

each R$^9$ is independently selected from the group consisting of —H, alkyl, aralkyl, and alicyclic, or together R$^9$ and R$^9$ form a cyclic alkyl group;

R$^{11}$ is selected from the group consisting of alkyl, aryl, —NR$^2{}_2$, and —OR$^2$;

and with the proviso that:
1) when G' is N, then the respective A, B, D, or E is null;
2) at least one of A and B, or A, B, D, and E is not selected from the group consisting of —H or null;
3) when R$^5$ is a six-membered ring, then X is not any 2 atom linker, an optionally substituted -alkyloxy-, organ optionally substituted -alkylthio-;
4) when G is N, then the respective A or B is not halogen or a group directly bonded to G via a heteroatom;
5) when X is not a -heteroaryt- group, then R$^5$ is not substituted with two or more aryl groups;

and pharmaceutically acceptable prodrugs and salts thereof.

6. The compounds of claim 5 wherein when R$^5$ is 2-thiazolyl, 2-oxazolyl, or 2-selenazolyl, and X is -alkoxyalkyl-, -alkylthioalkyl-, -alkyloxy-, or -alkylthio-, then A is not —CONH$_2$ and B is not —H.

7. The compounds of claim 5 wherein when R$^5$ is 2-thiazolyl, 2-oxazolyl, or 2-selenazolyl, then X is not -alkyloxyalkyl-, -alkylthioalkyl-, -alkyloxy-, or -alkylthio-.

8. The compounds of claim 6 wherein said compound of formula I or formula IA has an IC$_{50}$ of ≦50 μM on glucose production in isolated rat hepatocytes.

9. The compounds of claim 8 wherein R$^5$ is selected from the group consisting of pyrrolyl, imidazolyl, oxazolyl, thiazolyl, isothiazolyl, 1,2,4-thiadiazolyl, pyrazolyl, isoxazolyl, 1,2,3-oxadiazolyl, 1,2,4-oxadiazolyl, 1,2,5-oxadiazolyl, 1,3,4-oxadiazolyl, 1,2,4-thiadiazolyl, 1,3,4-thiadiazolyl, pyridinyl, pyrimidinyl, pyrazinyl, pyridazinyl, 1,3,5-triazinyl, 1,2,4-triazinyl, and 1,3-selenazolyl, all of which contain at least one substituent.

10. The compounds of claim 9 wherein R$^5$ is not 2-thiazolyl, or 2-oxazolyl.

11. The compounds of claim 10 wherein

A is selected from the group consisting of —H, —NR$^4{}_2$, —CONR$^4{}_2$, —CO$_2$R$^3$, halo, C1–C6 alkyl, C2–C6 alkenyl, C2–C6 alkynyl, C1–C6 perhaloalkyl, C1–C6 haloalkyl, aryl, 13 CH$_2$OH, —CH$_2$NR$^4{}_2$, —CH$_2$CN, —CN, —C(S)NH$_2$, —OR$^4$, —SR$^4$, —N$_3$, —NHC(S)NR$^4{}_2$, —NHAc, and null;

each B and D are independently selected from the group consisting of —H, alkyl, alkenyl, alkynyl, aryl, alicyclic, aralkyl, alkoxyalkyl, —C(O)R$^{11}$, —C(O)SR$^3$, —SO$_2$R$^{11}$, —S(O)R$^3$, —CN, —NR$^2{}_2$, —OR$^3$, —SR$^3$, perhaloalkyl, halo, and null, all except —H, —CN, perhaloalkyl, and halo are optionally substituted;

E is selected from the group consisting of —H, C1–C6 alkyl, C2–C6 alkenyl, C2–C6 alkynyl, aryl, C4–C6 alicyclic, alkoxyalkyl, —C(O)OR$^3$, —CONR$^4{}_2$, —CN, —NR$^9{}_2$, —OR$^3$, SR$^3$, C1–C6 perhaloalkyl, halo, and null, all except —H, —CN, perhaloalkyl, and halo are optionally substituted; and each R$^4$ is independently selected from the group consisting of —H, and C1–C2 alkyl.

12. The compounds of claim 10 wherein R$^5$ is:

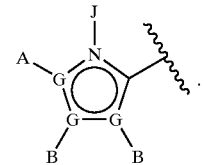

13. The compounds of claim 10 wherein R$^5$ is:

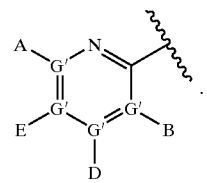

14. The compounds of claim 10 wherein R$^5$ is selected from the group consisting of:

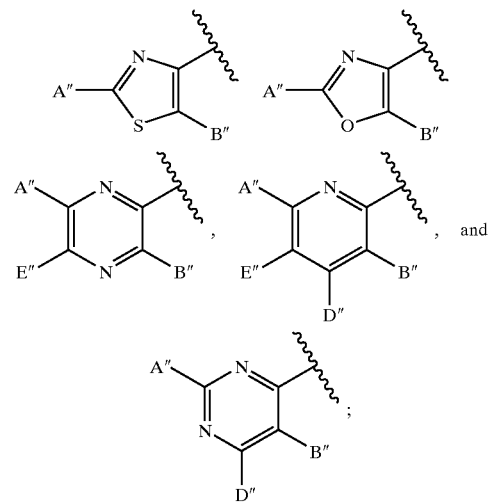

wherein

A" is selected from the group, —H, —NR$^4{}_2$, —CONR$^4{}_2$, —CO$_2$R$^3$, halo, C1–C6 alkyl, C2–C6 alkenyl, C2–C6 alkynyl, C1–C6 perhaloalkyl, C1–C6 haloalkyl, aryl, —CH$_2$OH, —CH$_2$NR$^4{}_2$, —CH$_2$CN, —CN, —C(S)NH$_2$, —OR$^3$, —SR$^3$, —N$_3$, —NHC(S)NR$^4{}_2$, and —NHAc;

B" and D" are independently selected from the group consisting of —H, alkyl, alkenyl, alkynyl, aryl alicyclic, aralkyl, alkoxyalkyl, —(O)R$^{11}$, —C(O)SR$^3$, —SO$_2$R$^{11}$, —S(O)R$^3$, —CN, —NR$^9{}_2$, —OR$^3$, —SR$^3$, perhaloalkyl, and halo, all except —H, —CN, perhaloalkyl, and halo are optionally substituted;

E" is selected from the group consisting of —H, C1–C6alkyl, C2–C6 alkenyl, C2–C6 alkynyl, C4–C6 alicyclic, alkoxyalkyl, —C(O)OR$^3$, —CONR$^4{}_2$, —CN, —NR$^9{}_2$, —OR$^3$, —SR$^3$, C1–C6 perhaloalkyl, and halo, all except H, —CN, perhaloalkyl, and halo are optionally substituted; and each R$^4$ is independently selected from the group consisting of —H and C1–C2 alkl.

15. The compounds of claim 14 wherein R$^5$ is selected from the group consisting of:

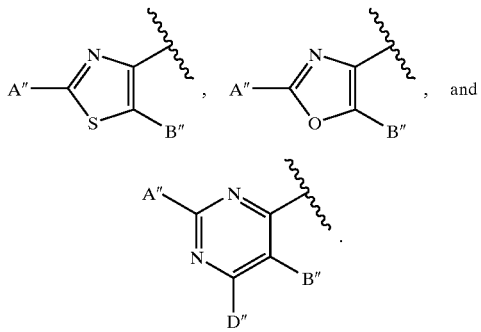

16. The compounds of claim 14 wherein R$^5$ is selected from the group consisting of

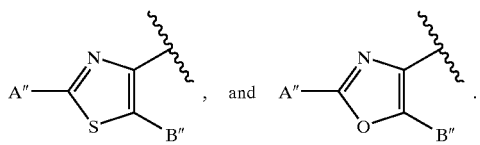

17. The compounds of claim 14 wherein R$^5$ is selected from the group consisting of:

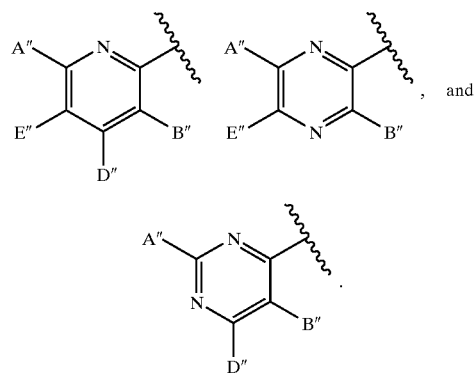

18. The compounds of claim 11 wherein X is selected from the group consisting of -heteroaryl-, -alkylcarbonylamino-, -alkylaminocarbonyl-, and -alkoxycarbonyl-.

19. The compounds of claim 18 wherein X is selected from the group consisting of -heteroaryl-, and -alkoxycarbonyl-.

20. The compounds of claim 11 wherein said compound is a compound of formulae VII, VIII, or IX:

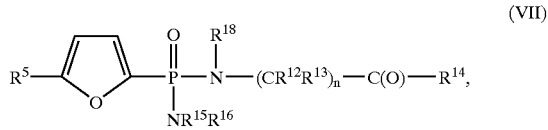
(VII)

(VIII)

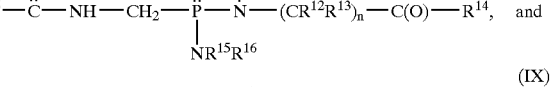
(IX)

21. The compounds of claim 14 wherein X is selected from the group consisting of —heteroaryl-, -alkylcarbonylamino alkylaminocarbonyl-, and -alkoxycarbonyl-.

22. The compounds of claim 20 wherein said compound is a compound of formulae VII or IX:

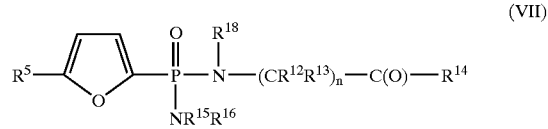
(VII)

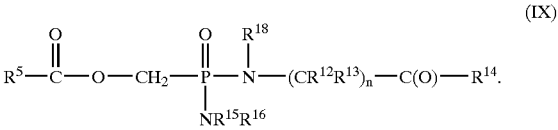
(IX)

23. The compounds of claim 21 wherein A" is selected from the group consisting of —NH$_2$, —CONH$_2$, halo, —CH$_3$, —CF$_3$, —CH$_2$-halo, —CN, —OCH$_3$, —SCH$_3$, and —H.

24. The compounds of claim 23 wherein A" is selected from the group consisting of —NH$_2$, —Cl, —Br, and —CH$_3$.

25. The compounds of claim 21 wherein each B" is selected from the group consisting of —H, —C(O)R$^{11}$, —C(O)SR$^3$, alkyl aryl, alicyclic, halo, —CN, —SR$^3$, —NR$^9{}_2$, and —OR$^3$.

26. The compounds of claim 25 wherein each B" is selected from the group consisting of —H, C(O)OR$^3$, —C(O)SR$^3$, C1–C6 alkyl, alicyclic, halo, heteroaryl, and —SR$^3$.

27. The compounds of claim 21 wherein D" is selected from the group consisting of —H, —C(O)R$^{11}$, —C(O)SR$^3$, alkyl aryl, alicyclic, halo, —NR$^9{}_2$, and —SR$^3$.

28. The compounds of claim 27 wherein D" is selected from the group consisting of —H, —C(O)OR$^3$, lower alkyl alicyclic, and halo.

29. The compounds of claim 21 wherein E" is selected from the group consisting of —H, C1–C6 alkyl, lower alicyclic, halogen, —CN, —C(O)OR$^3$, —SR$^3$ and —CONR$^4{}_2$.

30. The compounds of claim 29 wherein E" is selected from the group consisting of —H, —Br, and —Cl.

31. The compounds of claim 10 wherein R$^{18}$ is selected from the group consisting of —H, methyl, and ethyl.

32. The compounds of claim 31 wherein R$^{18}$ is selected from the group consisting of —H and methyl.

33. The compounds of claim 32 wherein $R^{18}$ is —H.

34. The compounds of claim 10 wherein each $R^{12}$ and $R^{13}$ is independently selected from the group consisting of —H, methyl, ethyl, n-propyl, i-propyl, n-butyl, i-butyl, —CH$_2$CH$_2$—SCH$_3$, phenyl, and benzyl, or together $R^{12}$ and $R^{13}$ are connected via 2–5 carbon atoms to form a cycloalkyl group.

35. The compounds of claim 34 wherein each $R^{12}$ and $R^{13}$ is independently selected from the group consisting of —H, methyl, i-propyl, i-butyl, and benzyl, or together $R^{12}$ and $R^{13}$ are connected via 2–5 carbon atoms to form a cycloalkyl group.

36. The compounds of claim 35 wherein each $R^{12}$ and $R^{13}$ is independently selected from the group consisting of —H, methyl, i-propyl, and benzyl, or together $R^{12}$ and $R^{13}$ are connected via 4 carbon atoms to form a cyclopentyl group.

37. The compounds of claim 36 wherein $R^{12}$ and $R^{13}$ are both —H, both methyl, or $R^{12}$ is H and $R^{13}$ is selected from the group consisting of methyl, i-propyl, and benzyl.

38. The compounds of claim 37 wherein n is 1, and $R^{12}$ is —H, then the carbon attached to $R^{12}$ and $R^{13}$ has S stereochemistry.

39. The compounds of claim 10 wherein n is an integer of from 1–2.

40. The compounds of claim 39 wherein n is 1.

41. The compounds of claim 10 wherein each $R^{14}$ is independently selected from the group consisting of —OR$^{17}$ and —SR$^{17}$; and $R^{17}$ is selected from the group consisting of optionally substituted methyl, ethyl, propyl, t-butyl, and benzyl.

42. The compounds of claim 41 wherein each $R^{14}$ is independently selected from the group consisting of —OR$^{17}$; and $R^{17}$ is selected from the group consisting of methyl, ethyl, propyl, and benzyl.

43. The compounds of claim 42 wherein $R^{17}$ is selected from the group consisting of ethyl, and benzyl.

44. The compounds of claim 10 wherein $R^{15}$ is not H.

45. The compounds of claim 44 wherein $R^{15}$ and $R^{16}$ are independently selected from the group consisting of lower alkyl, and lower aralkyl, or together $R^{15}$ and $R^{16}$ are connected via 2–6 atoms, optionally including 1 heteroatom selected from the group consisting of O, N, and S.

46. The compounds of claim 45 wherein $R^{15}$ and $R^{16}$ are independently selected from the group consisting of C1–C6 alkyl, or together $R^{15}$ and $R^{16}$ are connected via 2–6 atoms, optionally including 1 heteroatom selected from the group consisting of O, N, and S.

47. The compounds of claim 46 wherein —NR$^{15}$R$^{16}$ is a cyclic amine.

48. The compounds of claim 47 wherein —NR$^{15}$R$^{16}$ is selected from the group consisting of morpholinyl and pyrrolidinyl.

49. The compounds of claim 10 wherein $R^{16}$ is —(CR$^{12}$R$^{13}$)$_n$—C(O)—R$_{14}$.

50. The compounds of claim 40 wherein $R^{18}$ is selected from the group consisting of —H, methyl, and ethyl;

$R^{12}$ and $R^{13}$ are independently selected from the group consisting of —H, methyl, i-propyl, i-butyl, and benzyl, or together are connected via 2–5 carbon atoms to form a cycloalkyl group;

$R^{14}$ is —OR$^7$;

$R^{17}$ is selected from the group consisting of methyl, ethyl, propyl, t-butyl, and benzyl; and $R^{15}$ and $R^{16}$ are independently selected from the group consisting of lower alkyl, and lower aralkyl, or together $R^{15}$ and $R^{16}$ are connected via 2–6 atoms, optionally including 1 heteroatom selected from the group consisting of O, and N.

51. The compounds of claim 49 that are of the formula:

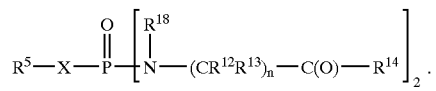

52. The compounds of claim 51 wherein n is 1.

53. The compounds of claim 52 wherein when $R^{12}R^{13}$ are not the same, then H$_2$N—CR$^{12}$R$^{13}$—C(O)—R$^{14}$ is an ester, or thioester of a naturally occurring amino acid; and $R^{14}$ is selected from the group consisting of —OR$^{17}$ and 'SR$^{17}$.

54. The compounds of claim 14 wherein

A" is selected from the group consisting of —NH$_2$, —CONH$_2$, halo, —CH$_3$, —CF$_3$, —CH$_2$-halo, —CN, —OCH$_3$, —SCH$_3$, and —H;

B" is selected from the group consisting of —H, —C(O)R$^{11}$, —C(O)SR$^3$, alkyl, aryl, alicyclic, halo, —CN, —SR$^3$, OR$^3$ and —NR$^9{}_2$;

D" is selected from the group consisting of —H, —C(O)R$^{11}$, —C(O)SR$^3$; —NR$^9{}_2$, alkyl, aryl, alicyclic, halo, and —SR$^3$;

E" is selected from the group consisting of —H, C1–C6 alkyl, lower alicyclic, halo, —CN, —C(O)OR$^3$, and —SR$^3$.

X is selected from the group consisting of —heteroaryl-, -alkoxycarbonyl-, and -alkylaminocarbonyl-, all optionally substituted;

$R^{18}$ and $R^{15}$ are selected from the group consisting of H, and methyl;

$R^2$ is selected from the group consisting of $R^3$ and —H;

$R^3$ is selected from the group consisting of alkyl, aryl, alicyclic, and aralkyl;

each $R^{12}$ and $R^{13}$ is independently selected from the group consisting of —H, methyl, i-propyl, i-butyl, and benzyl, or together $R^{12}$ and $R^{13}$ are connected via 2–5 carbon atoms to form a cycloalkyl group;

n is 1;

$R^{14}$ is —OR$^{17}$;

$R^{16}$ is —(CR$^{12}$R$^{13}$)$_n$—C(O)—R$^{14}$; and $R^{17}$ is selected from the group consisting of methyl, ethyl, propyl, phenyl, and benzyl.

55. The compounds of claim 54 wherein

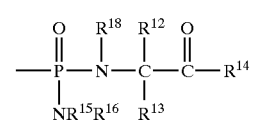

is selected from the group consisting of

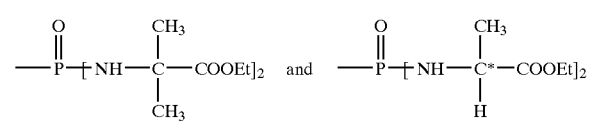

wherein C* has S stereochemistry.

56. The compounds of claim 54 wherein R⁵ is

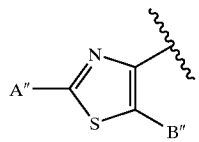

X is selected from the group consisting of methylenoxycarbonyl, and furan-2,5-diyl, and pharmaceutically acceptable salts thereof.

57. The compounds of claim 56 wherein A" is —NH₂, X is furan-2,5-diyl, and B" is —S(CH₂)₂CH₃.

58. The compounds of claim 56 wherein A" is —NH₂, X is furan-2,5-diyl, and B" is —CH₂—CH(CH₃)₂.

59. The compounds of claim 56 wherein A" is —NH₂, X is furan-2,5-diyl, and B" is —COOEt.

60. The compounds of claim 56 wherein A" is —NH₂, X is furan-2,5-diyl, and B" is —SMe.

61. The compounds of claim 56 wherein A" is —NH₂, X is methyleneoxycarbonyl, and B" is —CH(CH₃)₂.

62. The compounds of claim 57 wherein

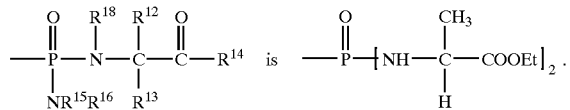

63. The compounds of claim 57 wherein

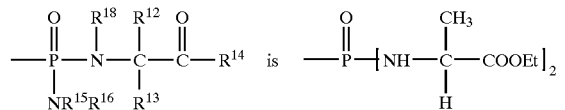

wherein C* has S stereochemistry.

64. The compounds of claim 57 wherein

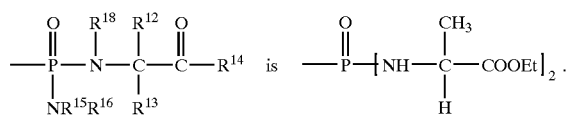

65. The compounds of claim 57 wherein

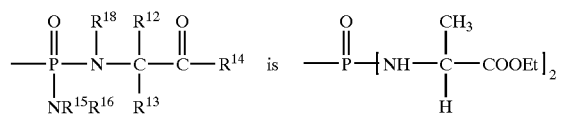

wherein C* has S stereochemistry.

66. The compounds of claim 54 wherein R⁵ is

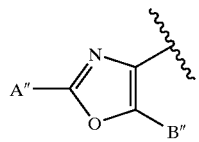

X is selected from the group consisting of furan-2,5-diyl, and methyleneoxycarbonyl, A" is —NH₂, and pharmaceutically acceptable salts thereof.

67. The compounds of claim 66 wherein X is furan-2,5-diyl, and B" is —SCH₂CH₂CH₃.

68. The compounds of claim 54 wherein R⁵ is

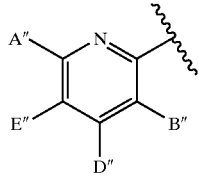

A" is —NH₂, E" and D" are —H, B" is selected from the group consisting of cyclopropyl, and n-propyl, X is selected from the group consisting of methyleneoxycarbonyl, and furan-2,5-diyl, and pharmaceutically acceptable salts thereof.

69. The compounds of claim 54 wherein R⁵ is

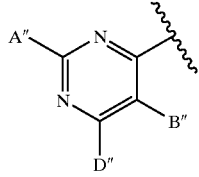

A" is —NH₂, D" is —H, B" is selected from the group consisting of n-propyl, and cyclopropyl, X is selected from the group consisting of furan-2,5-diyl, and methyleneoxycarbonyl, and pharmaceutically acceptable salts thereof.

70. The pharmaceutical composition of claim 5 wherein said insulin sensitizer is a thiazolidinedione.

71. The pharmaceutical composition of claim 1 wherein said combination is administered orally.

72. The pharmaceutical composition of claim 1 wherein said insulin sensitizer is a PPAR γ agonist.

73. The pharmaceutical composition of claim 72 wherein said PPAR γ agonist is select from the group consisting of BRL 49653, troglitazone, pioglitazone, ciglitazone, WAY-120,744, englitazone, AD 5075, darglitazone, GI-262570, SB 217092, SB 236636, SB 219994, and SB 219993.

74. The pharmaceutical composition of claim 5 wherein said insulin sensitizer is a PPAR γ agonist.

* * * * *

UNITED STATES PATENT AND TRADEMARK OFFICE
CERTIFICATE OF CORRECTION

PATENT NO.        : 6,756,360 B1                                             Page 1 of 7
APPLICATION NO. : 09/470649
DATED               : June 29, 2004
INVENTOR(S)       : Mark D. Erion and Paul D. van Poelje It is certified that error appears in the above-identified patent and that said Letters Patent is hereby corrected as shown below:

Cover Page,
(60), Related U.S. Application Data
"Provisional application No. 60/114,718, filed on Dec. 23, 1998." should read
--Provisional application No. 60/114,718, filed on Dec. 24, 1998.--.

Column 1,
Line 8, "Application Serial No. 60/114,718, filed Dec. 23, 1998 and" should read
--Application Serial No. 60/114,718, filed Dec. 24, 1998 and--.

Column 28,
Line 29, ""A" is –NH2" should read --A" is $-NH_2$--.

Column 32,
Lines 55-56, "—OC(O)— —OCH$_2$—" should read -- —OC(O)—, —OCH$_2$— --.

Column 37,
Line 61, "NHSO$_2$R$^3$" should read -- —NHSO$_2$R$^3$--.

Column 42,
Line 48, "—NO$^2$" should read -- —NO$_2$--.

Column 54,
Line 57, "—SO$^2$NR$^4_2$" should read -- —SO$_2$NR$^4_2$--.

Column 56,
Lines 45-46, "—OC(O)— —OCH$_2$—" should read -- —OC(O)—, —OCH$_2$— --.

Column 58,
Line 60, "—C(O)NR$_{42}$" should read -- —C(O)NR$^4_2$--.

Column 60,
Line 64, "has,S" should read --has S--.

Column 65,
Line 46, "CH$_2$CH(OCOR$^3$)—CH2—" should read --CH$_2$CH(OCOR$^3$)—CH$_2$— --.
Line 61, "—(CH$_{2p}$—OR$^2$" should read-- —(CH$_2$)$_p$OR$^2$--.

Column 70,
Line 26, "(—P(O)(OPh)(NH—CH2CO2Me)" should read
          --(—P(O)(OPh)(NH—CH$_2$CO$_2$Me)--.

UNITED STATES PATENT AND TRADEMARK OFFICE
CERTIFICATE OF CORRECTION

PATENT NO. : 6,756,360 B1
APPLICATION NO. : 09/470649
DATED : June 29, 2004
INVENTOR(S) : Mark D. Erion and Paul D. van Poelje It is certified that error appears in the above-identified patent and that said Letters Patent is hereby corrected as shown below:

Column 72,
Lines 26-27, "(—P(O)(OPh—2—Cl)(NH—CH$_2$C02Et)" should read --(—P(O)(OPh—2—Cl)(NH—CH$_2$CO$_2$Et)--.

Column 73,
Line 40, "NH2" should read --NH$_2$--.
Line 50, "—SCH3" should read -- —SCH$_3$--.
Line 50, "—CH2cPr" should read -- —CH$_2$cPr --.

Column 73,
Lines 58-66,
"Group 1:                             should read     --Group 1:
Q$^1$andQ$^2$                                                 Q$^1$ and Q$^2$
1. —NH—CH2—C(O)R14                              1. —NH—CH$_2$—C(O)R$^{14}$
2. —NH—CH(CH3)—C(O)R14                          2. —NH—CH(CH$_3$)—C(O)R$^{14}$
3. —NH—C(CH3)2—C(O)R14                          3. —NH—C(CH$_3$)$_2$—C(O)R$^{14}$
4. —NH—C(CH3)2CH2—C(O)R14                       4. —NH—C(CH$_3$)$_2$CH$_2$—C(O)R$^{14}$
5. —NH—CH(CH(CH3)2))—C(O)Rl4                    5. —NH—CH(CH(CH$_3$)$_2$ ))—C(O)R$^{14}$
6. —NH—CH(CH2(CH(CH3)2)))—C(O)R14  6. —NH—CH(CH$_2$(CH(CH$_3$)$_2$))—C(O)R$^{14}$
7. —NH—CH(CH2CH2SCH3)—C(O)R14                   7. —NH—CH(CH$_2$CH$_2$SCH$_3$)—C(O)R$^{14}$
8. —NH—CH(CH2SCH2Ph)—C(O)R14"                   8. —NH—CH(CH$_2$SCH$_2$Ph)—C(O)R$^{14}$--.

Column 74,
Lines 35-65,
"Group 2:                             should read     --Group 2:
Q$^1$ and Q$^2$                                               Q$^1$ and Q$^2$
1. —NH—CH2CH2—C(O)R14                           1. —NH—CH$_2$CH$_2$—C(O)R$^{14}$
2. —NH—CH(CH2CH2COR14)—C(O)R14                  2. —NH—CH(CH$_2$CH$_2$COR$^{14}$)—C(O)R$^{14}$
3. —NH—CH(CH2COR14)—C(O)R14                     3. —NH—CH(CH$_2$COR$^{14}$)—C(O)R$^{14}$
4. —NH—CH(CH2CONH2)—C(O)R14                     4. —NH—CH(CH$_2$CONH$_2$)—C(O)R$^{14}$
5. —NH—CH(COR14)CH2-C(O)R:4                     5. —NH—CH(COR$^{14}$)CH$_2$—C(O)R$^{14}$
6. —NH—CH(CH2OR17)—C(O)R14                      6. —NH—CH(CH$_2$OR$^{17}$)—C(O)R$^{14}$
7. —NH—CH(CH2CH2COR14)—C(O)R14                  7. —NH—CH(CH$_2$CH$_2$COR$^{14}$)—C(O)R$^{14}$
8. —NH—CH(CH2OH)—C(O)R14                        8. —NH—CH(CH$_2$OH)—C(O)R$^{14}$

UNITED STATES PATENT AND TRADEMARK OFFICE
CERTIFICATE OF CORRECTION

PATENT NO. : 6,756,360 B1
APPLICATION NO. : 09/470649
DATED : June 29, 2004
INVENTOR(S) : Mark D. Erion and Paul D. van Poelje It is certified that error appears in the above-identified patent and that said Letters Patent is hereby corrected as shown below:

Column 74,
Lines 35-65, (cont'd)

Group 3:
$Q^1$ and $Q^2$
1. —NH—CH(CH2—C6H5OH)—C(O)R14
2. —NH—C(c-propyl)—C(O)R14
3. —NH—C(c-pentyl)—C(O)R14
4. —NH—C(c-hexyl)—C(O)R14
5. —NH—CH(CH2Ph)—C(O)R14
6. —N(CH3)—CH2CO)—C(O)R14
7.  COR14
8. —NR18R19"

Group 3:
$Q^1$ and $Q^2$
1. —NH—CH(CH$_2$—C$_6$H$_5$OH)—C(O)R$^{14}$
2. —NH—C(c-propyl)—C(O)R$^{14}$
3. —NH—C(c-pentyl)—C(O)R$^{14}$
4. —NH—C(c-hexyl)—C(O)R$^{14}$
5. —NH—CH(CH$_2$Ph)—C(O)R$^{14}$
6. —N(CH$_3$)—CH$_2$CO)—C(O)R$^{14}$
7. 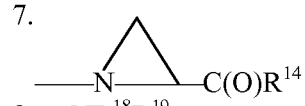
8. —NR$^{18}$R$^{19}$--.

Column 75,
Line 2, "R19" should read --R$^{19}$--.
Lines 2-3, "R18 and R19" should read --R$^{18}$ and R$^{19}$--.
Lines 64-67,
"$Q^1$ and $Q^2$ should read --$Q^1$ and $Q^2$
1. —NH—CH2—C(O)R14
2. —NH—CH(CH3)—C(O)R14
3. —NH—C(CH3)2—C(O)R14"

1. —NH—CH$_2$—C(O)R$^{14}$
2. —NH—CH(CH$_3$)—C(O)R$^{14}$
3. —NH—C(CH$_3$)$_2$—C(O)R$^{14}$--.

Column 76,
Lines 1-6,
"4. —NH—C(CH3)2CH2—C(O)R14
5. —NH—CH(CH(CH3)2))—C(O)R14
6. —NH—CH(CH2(CH(CH3)2)))—C(O)R14
7. —NH—CH(CH2CH2SCH3)—C(O)R14
8. —NH—CH(CH2SCH2Ph)—C(O)R14"

should read

--4. —NH—C(CH$_3$)$_2$CH$_2$—C(O)R$^{14}$
5. —NH—CH(CH(CH$_3$)$_2$))—C(O)R$^{14}$
6. —NH—CH(CH$_2$(CH(CH$_3$)$_2$)))—C(O)R$^{14}$
7. —NH—C(CH$_2$CH$_2$SCH$_3$)—C(O)R$_{14}$
8. —NH—CH(CH$_2$SCH$_2$Ph)—C(O)R$_{14}$--.

UNITED STATES PATENT AND TRADEMARK OFFICE
CERTIFICATE OF CORRECTION

PATENT NO. : 6,756,360 B1
APPLICATION NO. : 09/470649
DATED : June 29, 2004
INVENTOR(S) : Mark D. Erion and Paul D. van Poelje It is certified that error appears in the above-identified patent and that said Letters Patent is hereby corrected as shown below:

Column 76,
Lines 10-48,
"Group 2:                                should read    --Group 2:
$Q^1$ and $Q^2$                                                $Q^1$ and $Q^2$
1. —NH—CH2CH2—C(O)R14                    1. —NH—$CH_2CH_2$—C(O)$R^{14}$
2. —NH—CH(CH2CH2COR14)—C(O)R14           2. —NH—CH($CH_2CH_2COR^{14}$)—C(O)$R^{14}$
3. —NH—CH(CH2COR14)—C(O)R14              3. —NH—CH($CH_2COR^{14}$)—C(O)$R^{14}$
4. —NH—CH(CH2CONH2)—C(O)R14              4. —NH—CH($CH_2CONH_2$)—C(O)$R^{14}$
5. —NH—CH(COR14)CH2—C(O)R14              5. —NH—CH($COR^{14}$)$CH_2$—C(O)$R^{14}$
6. —NH—CH(CH2OR17)—C(O)R14               6. —NH—CH($CH_2OR^{17}$)—C(O)$R^{14}$
7. —NH—CH(CH2CH2COR14)—C(O)R14           7. —NH—CH($CH_2CH_2COR^{14}$)—C(O)$R^{14}$
8. —NH—CH(CH2OH)—C(O)R14                 8. —NH—CH($CH_2OH$)—C(O)$R^{14}$ Group 3:                                                 Group 3:
$Q^1$ and $Q^2$                                                $Q^1$ and $Q^2$
1. —NH—CH(CH2—C6H5OH)—C(O)R14            1. —NH—CH($CH_2$—$C_6H_5OH$)—C(O)$R^{14}$
2. —NH—C(c-propyl)—C(O)R14               2. —NH—C(c-propyl)—C(O)$R^{14}$
3. —NH—C(c-pentyl)—C(O)R14               3. —NH—C(c-pentyl)—C(O)$R^{14}$
4. —NH—C(c-hexyl)—C(O)R14                4. —NH—C(c-hexyl)—C(O)$R^{14}$
5. —NH—CH(CH2Ph)—C(O)R14                 5. —NH—CH($CH_2Ph$)—C(O)$R^{14}$
6. —N(CH3)—CH2—C(O)R14                   6. —N($CH_3$)—$CH_2$—C(O)$R^{14}$
7.                                       7.

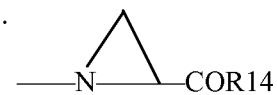                     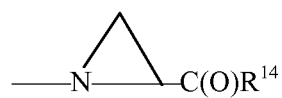

8. —NR18R19"                             8. —$NR^{18}R^{19}$--.

Column 77,
Line 45, "—N(Me)2" should read -- —N(Me)$^2$--.
Line 46, "R17" should read --$R^{17}$--.
Line 46, "R18" should read --$R^{18}$--.
Line 47, "Ph and R19" should read --Ph and $R^{19}$--.
Line 48, "R18 and R19" should read --$R^{18}$ and $R^{19}$--.

Column 130,
Line 19, "(A=CH3;" should read (A=$CH_3$;--.
Line 41, "$X^2$=CH2O" should read --$X^2$=$CH_2$O--.

Column 134,
Line 52, "Found: C:33.10; N:" should read --Found: C: 33.10; H: 3.80; N:--.

UNITED STATES PATENT AND TRADEMARK OFFICE
CERTIFICATE OF CORRECTION

PATENT NO. : 6,756,360 B1
APPLICATION NO. : 09/470649
DATED : June 29, 2004
INVENTOR(S) : Mark D. Erion and Paul D. van Poelje It is certified that error appears in the above-identified patent and that said Letters Patent is hereby corrected as shown below:

Column 135,
Line 23, "H: 4.08;" should read --H: 4.08; N: 7.85.--.

Column 139,
Line 37, "0C" should read --0°C--.

Column 165,
Line 51, "$C_6H_9N_2O_3PS_{F2}$" should read --$C_6H_9N_2O_3PSF_2$--.

Column 170,
Line 40, "Found: C, 24.57; N: 23.05" should read --Found: C, 24.57; H: 2.57; N: 23.05--.

Column 182,
Line 37, "$C_9H_7N_3O_4PS_2$ Br:" should read --$C_9H_7N_3O_4PS_2Br$:--.
Line 44, "H:2.05; N Found:" should read --H:2.05; N: 11.69. Found:--.

Column 184,
Line 6, "N10.58." should read --N:10.58.--.

Column 186,
Lines 66-67, "C:52.26; 7.06; 10.60. Found: C: 52.21; 6.93; 10.62" should read
    --C:52.26; H:7.06; N:10.60. Found: C:52.21; H:6.93; N:10.62.--.

Column 187,
Line 7, "$C_{35} H_{45} N_4 O_6 P S+0.5$" should read --$C_{35}H_{45}N_4O_6PS+0.5$--.
Line 12, "$C_{25} H_{41} N_4 O_6 P S$: C:" should read --$C_{25}H_{41}N_4O_6PS$:C:--.
Line 17, "$C_{35} H_{45} N_4 O_6 P S_3+0.4$" should read --$C_{35}H_{45}N_4O_6PS_3+0.4$--.
Line 22, "$C_{23} H_{37} N_4 O_6 P S_3$:" should read --$C_{23}H_{37}N_4O_6 PS_3$:--.
Line 27, "H: 10.44." should read --N: 10.44.--.
Line 31, "H: 7.90. Found: C: 62.85; h 7.06, 7.81." should read
    --N: 7.90. Found: C: 62.85; H: 7.06; N: 7.81.--.
Lines 44-45, "H: 8.42. Found: C: 59.88; H: 6.28; H: 8.32." should read
    --N: 8.42. Found: C: 59.88; H: 6.28; N: 8.32.--.
Line 50, "H: 8.98." should read --N: 8.98.--.

Column 188,
Line 19, "Biologicals Examples" should read --Biological Examples--.

UNITED STATES PATENT AND TRADEMARK OFFICE
CERTIFICATE OF CORRECTION

PATENT NO.      : 6,756,360 B1
APPLICATION NO. : 09/470649
DATED           : June 29, 2004
INVENTOR(S)     : Mark D. Erion and Paul D. van Poelje It is certified that error appears in the above-identified patent and that said Letters Patent is hereby corrected as shown below:

Column 205,
Lines 33-34, "—CH(CH=C$^2_2$)OH" should read -- —CH(CH=CR$^2_2$)OH--.
Line 38, "aninteger" should read --an integer--.
Line 65, "—NHR$^7$" should read -- —NHR$^{17}$--.

Column 206,
Lines 4-5, "—(CR$^{12}$R$^{13}$)$_n$—C(O)—R$^4$" should read -- —(CR$^{12}$R$^{13}$)$_n$—C(O)—R$^{14}$--.
Line 66, "R5" should read --R$^5$--.

Column 207,
Line 7, "-alkoxycarbonylarnino-" should read -- -alkoxycarbonylamino- --.
Line 62, "aryl, 13, CH$_2$OH" should read --aryl, CH$_2$OH--.

Column 208,
Line 64, "—(O)R$^{11}$" should read-- —C(O)R$^{11}$--.

Column 209,
Line 2, "Cl-C6alkyl" should read --C1-C6 alkyl--.
Line 9, "alkl" should read --alkyl--.

Column 210,
Line 12,
"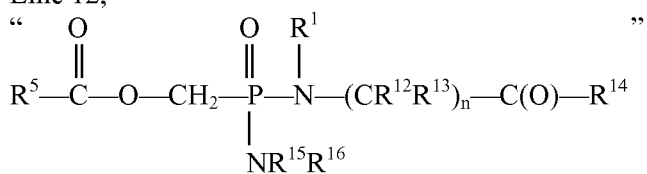"
should read
--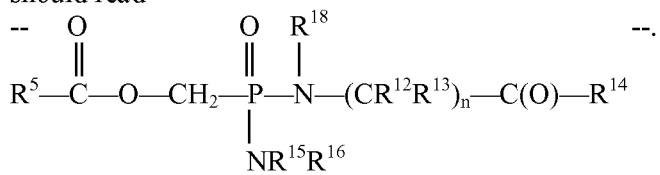--.

Column 211,
Line 54, "—(CR$^{12}$R$^{13}$)$_n$—C(O)—R$_{14}$" should read -- —(CR$^{12}$R$^{13}$)$_n$—C(O)—R$^{14}$--.
Line 63, "—OR$^7$" should read-- —OR$^{17}$--.

UNITED STATES PATENT AND TRADEMARK OFFICE
CERTIFICATE OF CORRECTION

PATENT NO. : 6,756,360 B1
APPLICATION NO. : 09/470649
DATED : June 29, 2004
INVENTOR(S) : Mark D. Erion and Paul D. van Poelje It is certified that error appears in the above-identified patent and that said Letters Patent is hereby corrected as shown below:

Column 212,
Line 16, "'SR$^{17}$'" should read-- —SR$^{17}$--.

Signed and Sealed this

Eighth Day of May, 2007

JON W. DUDAS
*Director of the United States Patent and Trademark Office*